US009040538B2

(12) United States Patent
Attardo et al.

(10) Patent No.: US 9,040,538 B2
(45) Date of Patent: May 26, 2015

(54) PYRIMIDINES AS NOVEL THERAPEUTIC AGENTS

(75) Inventors: Giorgio Attardo, Laval (CA); Sasmita Tripathy, Pierre Fonds (CA); Martin Gagnon, Montreal (CA)

(73) Assignee: Universite Laval, Laval (CA)

( * ) Notice: Subject to any disclaimer, the term of this patent is extended or adjusted under 35 U.S.C. 154(b) by 384 days.

(21) Appl. No.: 12/784,975

(22) Filed: May 21, 2010

(65) Prior Publication Data

US 2010/0298336 A1 Nov. 25, 2010

Related U.S. Application Data

(60) Provisional application No. 61/180,253, filed on May 21, 2009, provisional application No. 61/285,003, filed on Dec. 9, 2009, provisional application No. 61/289,628, filed on Dec. 23, 2009.

(51) Int. Cl.
| | |
|---|---|
| A61K 31/497 | (2006.01) |
| A61K 31/506 | (2006.01) |
| A61K 31/435 | (2006.01) |
| C07D 239/38 | (2006.01) |
| C07D 403/14 | (2006.01) |
| C07D 213/02 | (2006.01) |
| C07D 239/56 | (2006.01) |
| C07D 401/12 | (2006.01) |
| C07D 403/12 | (2006.01) |
| C07D 409/12 | (2006.01) |
| C07D 413/12 | (2006.01) |
| C07D 417/12 | (2006.01) |
| C07D 471/04 | (2006.01) |
| C07D 487/04 | (2006.01) |
| C07D 513/04 | (2006.01) |

(52) U.S. Cl.
CPC ............ *C07D 239/38* (2013.01); *C07D 239/56* (2013.01); *C07D 401/12* (2013.01); *C07D 403/12* (2013.01); *C07D 403/14* (2013.01); *C07D 409/12* (2013.01); *C07D 413/12* (2013.01); *C07D 417/12* (2013.01); *C07D 471/04* (2013.01); *C07D 487/04* (2013.01); *C07D 513/04* (2013.01)

(58) Field of Classification Search
USPC ............. 514/252.18, 274, 277; 544/316, 296, 544/295; 546/339
See application file for complete search history.

(56) References Cited

U.S. PATENT DOCUMENTS

| | | | | |
|---|---|---|---|---|
| 5,025,016 | A | 6/1991 | Ahrens et al. | |
| 5,037,830 | A | 8/1991 | Zolyomi et al. | |
| 5,472,967 | A * | 12/1995 | Hoornaert et al. | 514/269 |
| 5,753,651 | A | 5/1998 | dePadova | |
| 5,981,537 | A | 11/1999 | Nugent et al. | |
| 6,043,248 | A | 3/2000 | Nugent et al. | |
| 2003/0032642 | A1 * | 2/2003 | Bonnert et al. | 514/234.5 |
| 2004/0186114 | A1 | 9/2004 | Cirillo et al. | |
| 2005/0124637 | A1 * | 6/2005 | Cheng et al. | 514/263.2 |
| 2006/0058308 | A1 | 3/2006 | Norman et al. | |
| 2006/0211645 | A1 | 9/2006 | Scott et al. | |
| 2007/0135437 | A1 | 6/2007 | Benjamin et al. | |
| 2007/0197537 | A1 | 8/2007 | Blake et al. | |
| 2010/0022538 | A1 | 1/2010 | Boebel et al. | |
| 2011/0160206 | A1 | 6/2011 | Kawanishi et al. | |
| 2011/0166135 | A1 | 7/2011 | Morimoto et al. | |

FOREIGN PATENT DOCUMENTS

| | | |
|---|---|---|
| CA | 1260938 | 9/1989 |
| EP | 391254 A2 | 10/1990 |
| JP | 06-206805 A1 | 7/1994 |
| JP | 2003206230 A | 7/2003 |
| JP | 2005082486 A | 3/2005 |
| WO | WO 95/13267 | 5/1995 |
| WO | WO 96/11902 | 4/1996 |
| WO | WO 96/35678 | 11/1996 |
| WO | WO 98/28299 | 7/1998 |
| WO | WO 00/39094 | 7/2000 |
| WO | WO 01/94339 | 12/2001 |
| WO | WO 02/083628 | 10/2002 |

(Continued)

OTHER PUBLICATIONS

Gutpa et al., "Synthesis and biological activity of 2,6-disubstituted 3-aryl-4(3H)-pyrimidinones as potential CNS agents," *Indian Journal of Chemistry, Section B: Organic Chemistry Including Medicinal Chemistry* 22B:789-794, 1983 (Abstract only).

Nawrozkij et al., "5-Alkyl-6-benzyl-2-(2-oxo-2-phenylethylsulfanyl)pyrimidin-4(3H)-ones, a Series of Anti-HIV-1 Agents of the Dihydro-alkoxy-benzyl-oxopyrimidine Family with Peculiar Structure-Activity Relationship Profile," *J. Med. Chem.* 51(15):4641-4652, 2008.

Schickaneder et al., "2-[(3-Pyridinylmethyl)thio]pyrimidine Derivatives: New Bronchosecretolytic Agents," *J. Med. Chem.* 30:547-551, 1987.

Wilimowski et al., "Central action of 2-amino- and 2-amino-5-aryltetrahydropyrimidine-4,6-diones," *Inst. Physiol. Pharmacol., Med. Acad., Wroclaw, Pol. Archivum Immunologiae et Therapiae Experimentalis* 23(4):569-579, 1975 (Abstract only).

(Continued)

*Primary Examiner* — Kristin Vajda

(74) *Attorney, Agent, or Firm* — Clark & Elbing LLP

(57) ABSTRACT

The present invention features compounds having the Formula (Ia) and (Ib) (e.g., a compound of any of Formulas ((Ia-2)-(Ia-21)), including other tautomers, stereoisomers, E/Z stereoisomers, prodrugs, pharmaceutically acceptable salts, and compositions thereof. The invention also features methods for treating or preventing pain (e.g., neuropathic pain), inflammation, or epilepsy in a patient by administering an effective amount of a compound of Formula (Ia) or (Ib). The invention also features a method for treating or preventing pain (e.g., neuropathic pain), inflammation, or epilepsy in a patient that includes administering to a patient in need thereof an effective amount of a compound of Formula (IIa) or (IIb) (e.g., a compound of any of Formulas ((IIa-2)-(IIa-6)). The compounds described herein (e.g., a compound of Formulas (Ia), (Ib), (IIa), or (IIb)) can also be used as anti-convulsants.

13 Claims, No Drawings

(56) References Cited

FOREIGN PATENT DOCUMENTS

| WO | WO 02/092576 | 11/2002 | |
| WO | WO-02094795 A1 | 11/2002 | |
| WO | WO 02/098869 | 12/2002 | |
| WO | WO 03/044021 | 5/2003 | |
| WO | WO 2004/014870 | 2/2004 | |
| WO | WO 2004/078729 | 9/2004 | |
| WO | WO-2005026133 A1 | 3/2005 | |
| WO | WO 2006/024823 | 3/2006 | |
| WO | WO 2006040558 A1 * | 4/2006 | ......... A61K 31/7076 |
| WO | WO 2006/059245 | 6/2006 | |
| WO | WO 2006/107257 A1 | 10/2006 | |
| WO | WO 2006/107258 A1 | 10/2006 | |
| WO | WO 2006/133353 A2 | 12/2006 | |
| WO | WO 2009094442 A2 * | 7/2009 | ........... C07D 239/47 |
| WO | WO-2010027097 A1 | 3/2010 | |

OTHER PUBLICATIONS

Wilimowski et al., "Central action of new derivatives of tetrahydropyrimidine-4,6-dione," *Inst. Physiol. Pharmacol., Med. Acad., Wroclaw, Pol. Archivum Immunologiae et Therapiae Experimentalis* 27(3):397-405, 1979 (Abstract only).

Zimon et al., "Synthesis of 2-benzylaminotetrahydropyrimidine-4,6-dione derivatives," *Dep. Pharm. Chem., Sch. Med., Krakow, Pol. Acta Poloniae Pharmaceutica* 37(4): 415-418, 1980 (Abstract only).

International Search Report from International Application No. PCT/CA2010/000779 dated Aug. 6, 2010 (date of completion of search) and Aug. 30, 2010 (date of mailing of report).

UKrOrgSynthesis Building Blocks Catalogue, Order # BBV-29375345, Aug. 21, 2009, STN CHEMACATS Accession No. 2096227445, STN Registry No. 1183309-67-2.

Written Opinion from International Application No. PCT/CA2010/000779, mailed Aug. 30, 2010.

Communication from European Patent Office enclosing extended and Supplementary European Search Report for European Patent Application No. 10777279.0, dated Sep. 25, 2012 (11 pages).

English Translation of a Search Report issued for Taiwanese Patent Application No. 099116454, completed Apr. 8, 2014 (1 page).

* cited by examiner

PYRIMIDINES AS NOVEL THERAPEUTIC AGENTS

CROSS-REFERENCE TO RELATED APPLICATIONS

This application claims benefit of U.S. Provisional Application Nos. 61/180,253, filed May 21, 2009, 61/285,003, filed Dec. 9, 2009, and 61/289,628, filed Dec. 23, 2009, each of which is hereby incorporated by reference.

BACKGROUND OF THE INVENTION

The present invention relates to pharmaceutical compositions and methods for treating or preventing pain, inflammation, and epilepsy.

Pain is a common form of physical suffering and distress and is one of the most common reasons patients report to physicians. It may be categorized in terms of form (nociceptive or neuropathic), duration (chronic or acute), and degree (mild, moderate or severe). Typically, nociceptive pain is acute, and results from injury, such as burns, sprains, fractures, or inflammation (inflammatory pain, including from osteo- and rheumatoid arthritis). Neuropathic pain, on the other hand, is defined by the International Association for the Study of Pain as a form of chronic pain that is caused by a lesion or dysfunction of the nervous system. Commonly, neuropathic pain results from diabetic neuropathy, HIV infections, or post-herpetic neuralgia. Other disorders that are associated with neuropathic pain include complex regional pain syndromes, trigeminal neuralgia, low back pain, sciatica, phantom limb pain, blast pain, fibromyalgia, and other conditions that result in chronic pain. Few therapeutics are approved by the U.S. Food and Drug Administration and other regulatory agencies for the treatment of neuropathic pain. Those that are approved exhibit, at best, a modest efficacy in terms of pain reduction (see Jensen, *Eur. J. Pain* 2002; 6 Suppl A:61-68).

SUMMARY OF THE INVENTION

The present invention features compounds having the Formula (Ia) and (Ib):

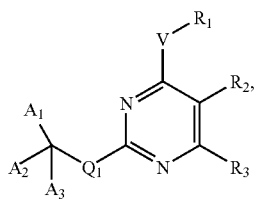

(Ia)

and its tautomer

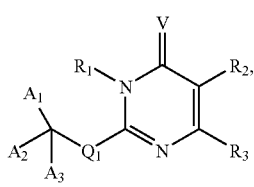

(Ib)

including other tautomers, stereoisomers, E/Z stereoisomers, prodrugs, and pharmaceutically acceptable salts thereof, wherein:

$Q_1$ is —O—, —S—, —SO—, —SO$_2$—, —CH$_2$—, —CH$_2$CH$_2$—, —CH═CH—, —OCH$_2$—, —SCH$_2$—, —SOCH$_2$—, or —SO$_2$CH$_2$—;

V is O, S, NH, or NZ, or N-terminal linked amino acid, halogen, or H when $R_1$ is absent;

$R_1$ is absent, —H, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, —(CR$_{2A}$R$_{2B}$)$_{r3}$PO(OZ)$_2$, or C-terminal linked amino acid;

each $R_{1A}$, $R_{1B}$, $R_{2A}$, and $R_{2B}$ is, independently, H or C$_{1-5}$ alkyl;

each Z is, independently, —H, —C$_1$-C$_8$ alkyl, —C$_4$-C$_{12}$ alkcycloalkyl, —C$_3$-C$_9$ alkheterocyclyl, wherein the heterocyclyl is 3 to 9 membered, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —C$_2$-C$_8$ alkenyl, or —C$_2$-C$_8$ alkynyl, or two Z, together with the atom(s) to which each is attached, join to form a 3- to 7-membered aromatic or non aromatic heterocycle;

each n is 1 or 2;

each r2 is an integer between 1-3;

each r3 is an integer between 0-2;

$R_2$ and $R_3$ are each, independently, —H, -D, —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$, or $R_2$ and $R_3$, together with the atom to which each is attached, join to form a 5- or 6-membered aromatic or non aromatic carbocycle or heterocycle;

$A_1$ and $A_2$ are each, independently, —H, -D, -halogen, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, or —C$_7$-C$_{14}$ arylalkyl;

$A_3$ is an aromatic heterocyclic ring selected from the group consisting of:

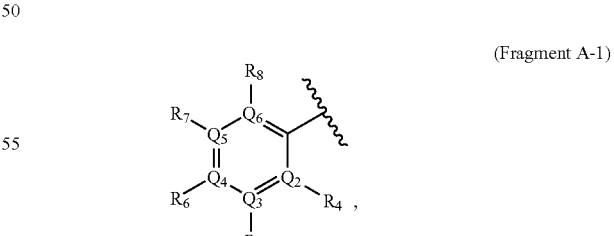

(Fragment A-1)

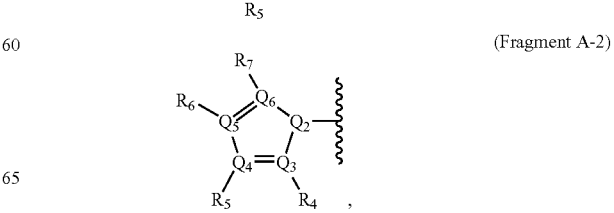

(Fragment A-2)

-continued (Fragment A-3)

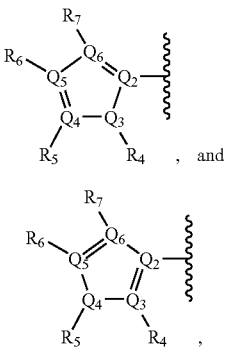

, and (Fragment A-4)

R_7
R_6—Q_5—Q_6—Q_2
    Q_4—Q_3
R_5    R_4    , $Q_2$, $Q_5$, and $Q_6$ are each, independently, N, N$^+$—O$^-$, or C;
$Q_3$ and $Q_4$ are each, independently, N, N$^+$—O$^-$, C, O, or S, wherein only one of $Q_3$ and $Q_4$ can be O or S;
wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and
$R_4$, $R_5$, $R_6$, $R_7$, and $R_8$ are each, independently, absent, —H, -D, —OH, —O$^-$, -halogen, —CN, —NO$_2$, —SH, —C$_1$-C$_8$ alkyl, —C$_2$-C$_8$ alkenyl, —C$_2$-C$_8$ alkynyl, —C$_3$-C$_{12}$ cycloalkyl, C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle provided that the resulting ring system is not substituted or unsubstituted benzimidazole, unsubstituted benzothiazole, unsubstituted imidazo[1,2-a]pyridine, 5- or 6-chloro-imidazo[1,2-a] pyridine, indole when $R_2$ is C(O)OCH$_2$CH$_3$, unsubstituted quinoline, 8-substituted quinoline, unsubstituted quinoxaline, 2- or 4-chloro-quinoline, 2-chloro-7-methyl-quinoline or 2-piperidin-1-yl-quinoline when $R_3$ is NH$_2$, or 4-hydroxy-1,3-quinazoline,
wherein when $A_3$ is unsubstituted pyridine-2-yl, and $A_1$ and $A_2$ are each —H, $R_3$ is not —H, —OH, —NH$_2$, —CF$_3$, —C$_1$-C$_3$ alkyl, phenyl, difluorobenzyl, —NHC(O)furan, —NHC(O)CH$_3$, or —NHC(O)CH$_2$CH$_3$;
wherein when $A_3$ is unsubstituted pyridine-4-yl, and $A_1$ and $A_2$ are each —H, $R_3$ is not —H, —OH, —NH$_2$, —CH$_3$, —CH$_2$CH$_3$, or difluorobenzyl;
wherein when $A_3$ is unsubstituted, 6-chloro, or 2,6-dichloro pyridine-3-yl, and $A_1$ and $A_2$ are each —H, $R_3$ is not —H, —OH, —NH$_2$, —CF$_3$, —C$_1$-C$_3$ alkyl, phenyl, —C(O)OCH$_2$CH$_3$, or —NHC(O)CH$_3$;
wherein when $A_3$ is substituted or unsubstituted pyrazol-1-yl, $R_3$ is not —OH; and wherein $A_3$ is not 4-NO$_2$-imidazol-2-yl.

In certain embodiments, $A_3$ is not substituted imidazo[1,2-a]pyridine, unsubstituted or substituted quinoline, unsubstituted or substituted quinoxaline, unsubstituted or substituted quinazoline, unsubstituted or substituted benzothiazole, imidazole, or indole.

In other embodiments, $Q_1$ is —O—, —S—, —SO—, —SO$_2$—, or —C$_2$—;
V is O;
$R_1$ is —H, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, —(CH$_2$)$_n$OZ, —C(O)Z, —C(O)OZ, —C(O)NH(Z), or —C(O)N(Z)$_2$;

$R_2$, and $R_3$ are each, independently, —H, -D, —OH, halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and
$A_1$ and $A_2$ are each, independently, —H, -D, -halogen, or —C$_1$-C$_8$ alkyl. For example, $Q_1$ is —S—, —SO—, or —SO$_2$—;
$R_1$ is —H, —(CH$_2$)OZ, —C(O)Z, —C(O)OZ, —C(O)NHZ, or —C(O)N(Z)$_2$;
each Z is, independently, —H, —C$_1$-C$_5$ alkyl, —C$_4$-C$_{12}$ alkcycloalkyl, —C$_3$-C$_9$ alkheterocyclyl, wherein the heterocyclyl is 3 to 9 membered, —C$_3$-C$_8$ cycloalkyl, —C$_6$-C$_{12}$ aryl, —C$_7$-C$_{14}$ arylalkyl, 3 to 9-membered aromatic or non aromatic heterocycle, —C$_2$-C$_8$ alkenyl, or —C$_2$-C$_8$ alkynyl, or two Z, together with the atom to which each is attached, join to form a 3- to 7-membered aromatic or non aromatic heterocycle;
$R_2$, and $R_3$ are each, independently, —H, -D, —CF$_3$, —C$_1$-C$_5$ alkyl, —C$_2$-C$_5$ alkenyl, —C$_2$-C$_5$ alkynyl, CN, —N(Z)$_2$, —C(NH)N(Z)$_2$, —C(O)Z, —C(O)N(Z)$_2$, —C(O)OZ, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;
$A_1$ and $A_2$ are each, independently, —H, -halogen, or —C$_1$-C$_5$ alkyl; and
$R_4$, $R_5$, $R_6$, $R_7$, and $R_8$ are each, independently, —H, -D, —OH, -halogen, —CN, —NO$_2$, —SH, —C$_1$-C$_5$ alkyl, —C$_2$-C$_5$ alkenyl, —C$_2$-C$_5$ alkynyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle. In another example, $Q_1$ is —S—;
V is O
$R_1$ is —H, —C(O)Z, —C(O)OZ, —C(O)NHZ, or —C(O)N(Z)$_2$;
each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;
$R_2$, and $R_3$ are each, independently, —H, -D, —CF$_3$, —C$_1$-C$_5$ alkyl, —C$_2$-C$_5$ alkenyl, —C$_2$-C$_5$ alkynyl, CN, or —N(Z)$_2$;
$A_1$ and $A_2$ are each, independently, —H, -D, —F, or —C$_1$-C$_4$ alkyl; and
$R_4$, $R_5$, $R_6$, $R_7$, and $R_8$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle.

In other embodiments, V is O, for example when $Q_1$ is —S—; and $R_1$ and $R_2$ are each —H; $R_2$ is —H; and/or $A_1$ and A₂ are —H or -D. Alternatively, Q₁ is —S—; R₁, R₂, A₁, and A₂ are each —H; and R₃ is —CH₃ or —CF₃.

The compound of formula (Ia) may have the following structure:

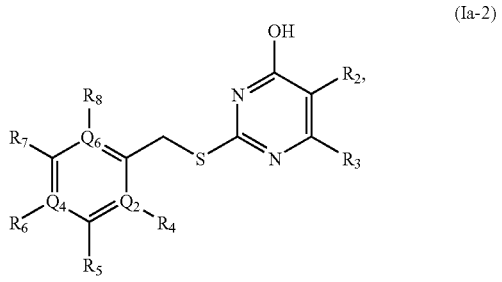

(Ia-2)

wherein:

R₂ and R₃ are each, independently, —H, -D, —CF₃, —C₁-C₅ alkyl, —C₂-C₅ alkenyl, —C₂-C₅ alkynyl, or —CN;

R₄, R₅, R₆, R₇, and R₈ are each, independently, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₅ and R₆, or R₆ and R₇, or R₇ and R₈, together with the atoms to which each is attached, join to form a 5- to 6-membered aromatic or non aromatic carbocycle or heterocycle;

each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-C₅ alkynyl, or two Z, together with the atom to which each is attached, join to form a 3- to 7-membered aromatic or non aromatic heterocycle; and Q₂, Q₄, and Q₆ are each, independently, N, N⁺—O⁻, or C, wherein Q₂, Q₄, and Q₆ are not simultaneously C.

In particular, the compound of formula (Ia-2) may have the following structure:

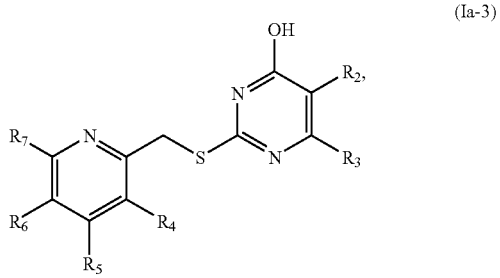

(Ia-3)

wherein:

R₂ and R₃ are each, independently, —H, -D, —CF₃, —C₁-C₅ alkyl, —C₂-C₅ alkenyl, —C₂-C₅ alkynyl, or —CN;

R₄, R₅, R₆, and R₇ are each, independently, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₅ and R₆, or R₆ and R₇, together with the carbon atoms to which each is attached, join to form a 5- to 6-membered aromatic or non aromatic carbocycle or heterocycle; and each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-O₅ alkynyl, or two Z, together with the atom to which each is attached, join to form a 3- to 7-membered aromatic or non aromatic heterocycle.

The compound of formula (Ia) may have the following structure:

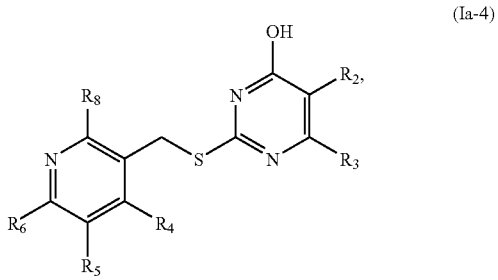

(Ia-4)

wherein:

R₂ and R₃ are each, independently, —H, -D, —CF₃, —C₁-C₅ alkyl, —C₂-C₅ alkenyl, —C₂-C₅ alkynyl, or —CN;

R₄, R₅, R₆, and R₈ are each, independently, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₅ and R₆, together with the carbon atoms to which each is attached, join to form a 5- to 6-membered aromatic or non aromatic carbocycle or heterocycle; and each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-C₅ alkynyl, or two Z, together with the atom to which each is attached, join to form a 3- to 7-membered aromatic or non aromatic heterocycle.

The compound of formula (Ia) may have the following structure:

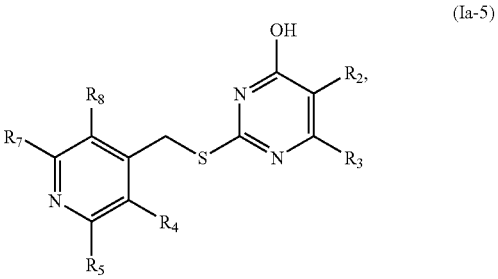

(Ia-5)

wherein:

R₂ and R₃ are each, independently, —H, -D, —CF₃, —C₁-C₅ alkyl, —C₂-C₅ alkenyl, —C₂-C₅ alkynyl, or —CN;

R₄, R₅, R₇, and R₈ are each, independently, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC (O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or R$_4$ and R$_5$, or R$_7$ and R$_8$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

The compound of formula (Ia) may have the following structure:

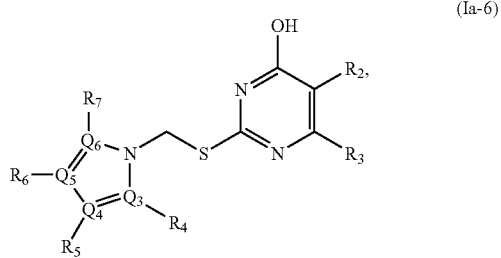

(Ia-6)

wherein:
R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;
R$_4$, R$_5$, R$_6$, and R$_7$, are each, independently, —H, -D, —OH, halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or R$_4$ and R$_5$, or R$_5$ and R$_6$, or R$_6$ and R$_7$, together with the atoms to which each is attached, join to form a 5- to 6-membered aromatic or non aromatic carbocycle or heterocycle;

each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle; and Q$_3$, Q$_4$, Q$_5$, and Q$_6$ are each, independently, N, N$^+$—O$^-$, or C.

In particular, the compound of formula (Ia-6) may have the following structure:

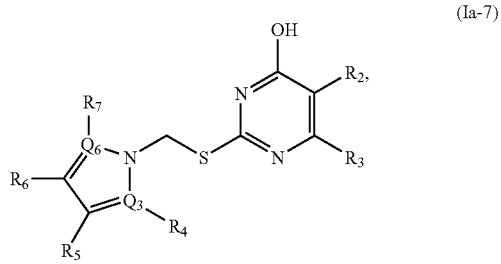

(Ia-7)

wherein:
R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;
R$_4$, R$_5$, R$_6$, and R$_7$, are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or R$_4$ and R$_5$, or R$_5$ and R$_6$, or R$_6$ and R$_7$, together with the atoms to which each is attached, join to form a 5- to 6-membered aromatic or non aromatic carbocycle or heterocycle;

each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle; and Q$_3$ and Q$_6$ are each, independently, N, N$^+$—O$^-$, or C.

The compound of formula (Ia) may have the following structure:

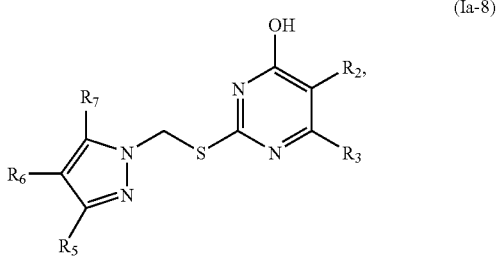

(Ia-8)

wherein:
R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;
R$_5$, R$_6$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or R$_4$ and R$_5$, or R$_5$ and R$_6$, or R$_6$ and R$_7$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

The compound of formula (Ia) may have the following structure:

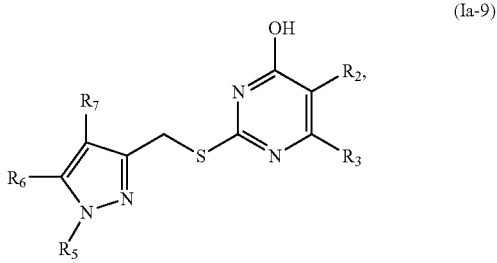

(Ia-9)

wherein:
R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;

R$_5$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_6$ and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_5$ and R$_6$, or R$_6$ and R$_7$, together with the atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

The compound of formula (Ia) may have the following structure:

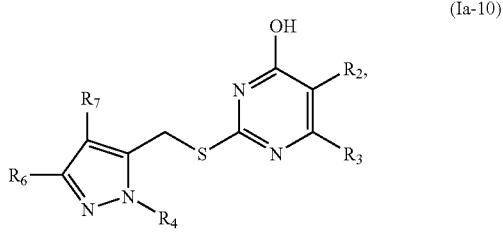

(Ia-10)

wherein:

R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;

R$_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_6$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_6$ and R$_7$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

The compound of formula (Ia) may have the following structure:

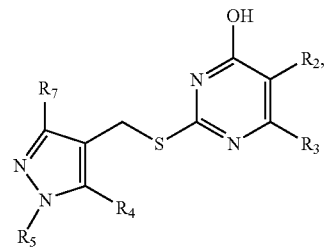

(Ia-11)

wherein:

R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;

R$_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_5$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_4$ and R$_5$, together with the atoms to which each is attached, join to form a 5- to 6-membered aromatic or non aromatic heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

The compound of formula (Ia) may have the following structure:

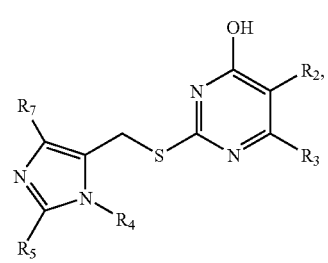

(Ia-12)

wherein:

R$_2$ and R$_3$ are each, independently, —H, -D, —CF$_3$, —C$_1$-C$_5$ alkyl, —C$_2$-C$_5$ alkenyl, —C$_2$-C$_5$ alkynyl, or —CN;

R$_4$, R$_5$ and R$_7$ are each, independently, —H, -D, —OH, halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_4$ and R$_5$, together with the carbon atoms to which each is attached, join to form a 5- to 6-membered aromatic or non aromatic carbocycle or heterocycle; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

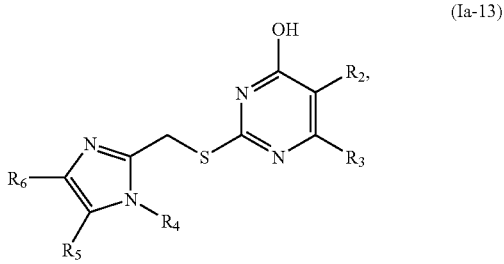

(Ia-13)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_4$ is —H, —OH, —CN, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —$N(Z)_2$, —$C(NH)N(Z)_2$, —C(O)Z, —$C(O)N(Z)_2$, —C(O)OZ, —$S(O)_2Z$, —NHC(O)Z, —$NHS(O)_2Z$, —$NHC(NH)N(Z)_2$, —$NZC(NH)N(Z)_2$, —$NHC(NCN)N(Z)_2$, or —$NZC(NCN)N(Z)_2$;

$R_5$ and $R_6$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —$N(Z)_2$, —$C(NH)N(Z)_2$, —C(O)Z, —OC(O)Z, —OC(O)OZ, —$OC(O)N(Z)_2$, —$C(O)N(Z)_2$, —C(O)OZ, —SZ, —SOZ, —$S(O)_2Z$, —NHC(O)Z, —$NHS(O)_2Z$, —$NHC(NH)N(Z)_2$, —$NZC(NH)N(Z)_2$, —$NHC(NCN)N(Z)_2$, —$NZC(NCN)N(Z)_2$, or $R_4$ and $R_5$, or $R_5$ and $R_6$, together with the carbon atoms to which each is attached, join to form a 5- to 6-membered aromatic or non aromatic carbocycle or heterocycle wherein $R_5$ is not —$NO_2$ when $R_6$ is —H; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

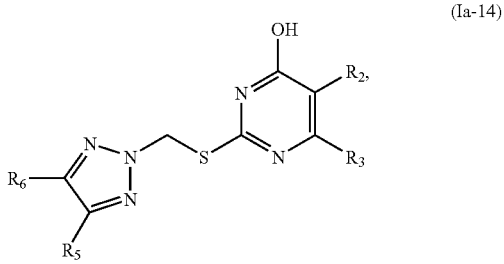

(Ia-14)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_5$ and $R_6$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —$N(Z)_2$, —$C(NH)N(Z)_2$, —C(O)Z, —OC(O)Z, —OC(O)OZ, —$OC(O)N(Z)_2$, —$C(O)N(Z)_2$, —C(O)OZ, —SZ, —SOZ, —$S(O)_2Z$, —NHC(O)Z, —$NHS(O)_2Z$, —$NHC(NH)N(Z)_2$, —$NZC(NH)N(Z)_2$, —$NHC(NCN)N(Z)_2$, or —$NZC(NCN)N(Z)_2$, or $R_5$ and $R_6$, together with the carbon atoms to which each is attached, join to form a 5- to 6-membered aromatic or non aromatic carbocycle or heterocycle; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

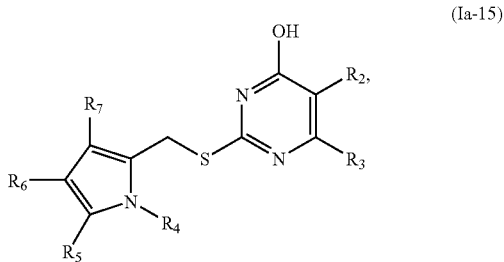

(Ia-15)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_4$ is —H, —OH, —CN, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —$N(Z)_2$, —$C(NH)N(Z)_2$, —C(O)Z, —$C(O)N(Z)_2$, —C(O)OZ, —$S(O)_2Z$, —NHC(O)Z, —$NHS(O)_2Z$, —$NHC(NH)N(Z)_2$, —$NZC(NH)N(Z)_2$, —$NHC(NCN)N(Z)_2$, or —$NZC(NCN)N(Z)_2$;

$R_5$, $R_6$, and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —$N(Z)_2$, —$C(NH)N(Z)_2$, —C(O)Z, —OC(O)Z, —OC(O)OZ, —$OC(O)N(Z)_2$, —$C(O)N(Z)_2$, —C(O)OZ, —SZ, —SOZ, —$S(O)_2Z$, —NHC(O)Z, —$NHS(O)_2Z$, —$NHC(NH)N(Z)_2$, —$NZC(NH)N(Z)_2$, —$NHC(NCN)N(Z)_2$, —$NZC(NCN)N(Z)_2$, or $R_5$ and $R_6$, or $R_6$ and $R_7$, together with the carbon atoms to which each is attached, join to form a 5- to 6-membered aromatic or non aromatic carbocycle or heterocycle provided that the resulting ring system is not indole when $R_2$ is $C(O)OCH_2CH_3$; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

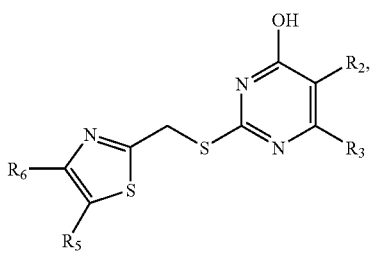

(Ia-16)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_5$ and $R_6$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or $R_5$ and $R_6$, together with the carbon atoms to which each is attached, join to form a 5- to 6-membered aromatic or non aromatic carbocycle or heterocycle provided that the resulting ring system is not unsubstituted benzothiazole; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

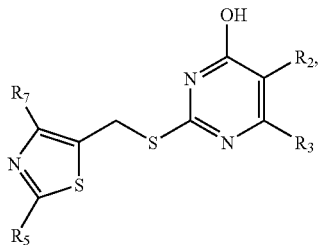

(Ia-17)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_5$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

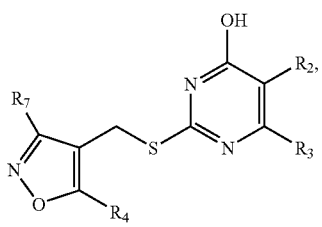

(Ia-18)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_4$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

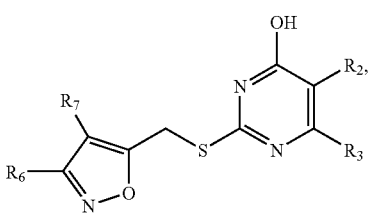

(Ia-19)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_6$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or $R_6$ and $R_7$, together with the carbon atoms to which each is attached, join to form a 5- to 6-membered aromatic or non aromatic carbocycle or heterocycle; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

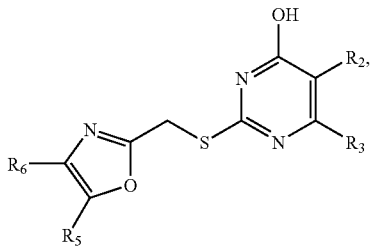

(Ia-20)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_5$ and $R_6$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —$N(Z)_2$, —$C(NH)N(Z)_2$, —C(O)Z, —OC(O)Z, —OC(O)OZ, —OC(O)$N(Z)_2$, —C(O)$N(Z)_2$, —C(O)OZ, —SZ, —SOZ, —$S(O)_2Z$, —NHC(O)Z, —NHS(O)$_2$Z, —NHC(NH)$N(Z)_2$, —NZC(NH)$N(Z)_2$, —NHC(NCN)$N(Z)_2$, —NZC(NCN)$N(Z)_2$, or $R_5$ and $R_6$, together with the carbon atoms to which each is attached, join to form a 5- to 6-membered aromatic or non aromatic carbocycle or heterocycle; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

The compound of formula (Ia) may have the following structure:

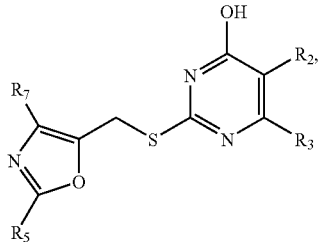

(Ia-21)

wherein:

$R_2$ and $R_3$ are each, independently, —H, -D, —$CF_3$, —$C_1$-$C_5$ alkyl, —$C_2$-$C_5$ alkenyl, —$C_2$-$C_5$ alkynyl, or —CN;

$R_5$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —$N(Z)_2$, —$C(NH)N(Z)_2$, —C(O)Z, —OC(O)Z, —OC(O)OZ, —OC(O)$N(Z)_2$, —C(O)$N(Z)_2$, —C(O)OZ, —SZ, —SOZ, —$S(O)_2Z$, —NHC(O)Z, —NHS(O)$_2$Z, —NHC(NH)$N(Z)_2$, —NZC(NH)$N(Z)_2$, —NHC(NCN)$N(Z)_2$, or —NZC(NCN)$N(Z)_2$; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle.

In some embodiments, the hydrogens that correspond to $A_1$ and $A_2$ in any of Formulas (Ia-2)-(Ia-21) can be replaced, independently, with deuterium.

In certain embodiments, when present, Z is either —H or —$CH_3$; two Z, together with the atom to which each is attached, join to form a 5-, 6-, or 7-membered non aromatic heterocycle; or two Z, together with the atom to which each is attached, join to form a 3- to 7-membered aromatic or non aromatic heterocycle. In some embodiments, the heterocycle is substituted with any of the substituent groups described herein for $R_4$-$R_8$. The heterocycle formed by two Z may be substituted with 1, 2, 3, 4, 5, 6, or 7 substituents, e.g., an amino group.

In other embodiments, $R_2$ and $R_3$, together with the atom to which each is attached, join to form a 5- or 6-membered aromatic or non aromatic carbocycle or heterocycle.

In other embodiments, when present, each Z is, independently, —H, —$C_{1-3}$ alkyl, or two Z combine to form a 5-, 6-, or 7-membered ring. For example, each Z is, independently, —H, —$CH_3$, or —$CH_2CH_3$ or both Z are either —H or —$CH_3$. In another example, two Z, together with the atom to which each is attached, join to form a 5-, 6-, or 7-membered non aromatic heterocycle.

In some embodiments, the carbocycle or the heterocycle formed by $R_4$ and $R_5$, $R_5$ and $R_6$, $R_6$ and $R_7$, or $R_7$ and $R_8$, is substituted with 1, 2, 3, 4, 5, 6, or 7 substituents.

In other embodiments, $Q_1$ is —S—, and/or $R_1$ and $R_2$ are both —H.

In some embodiments, the compound of Formula (Ia) or I(b) is one of the following compounds, or is a stereoisomer, tautomer, prodrug, or pharmaceutically acceptable salt thereof:

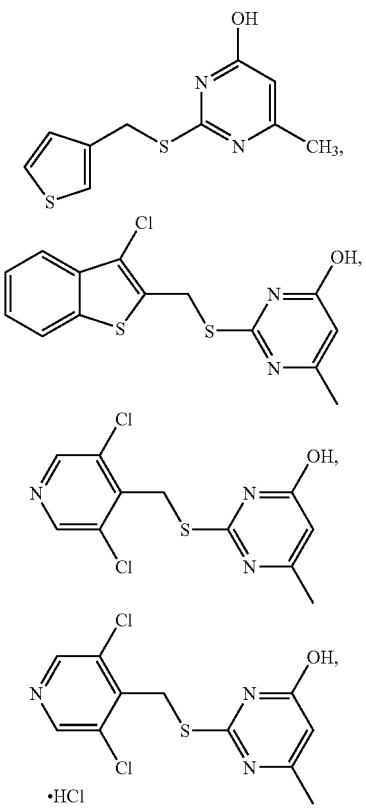

-continued
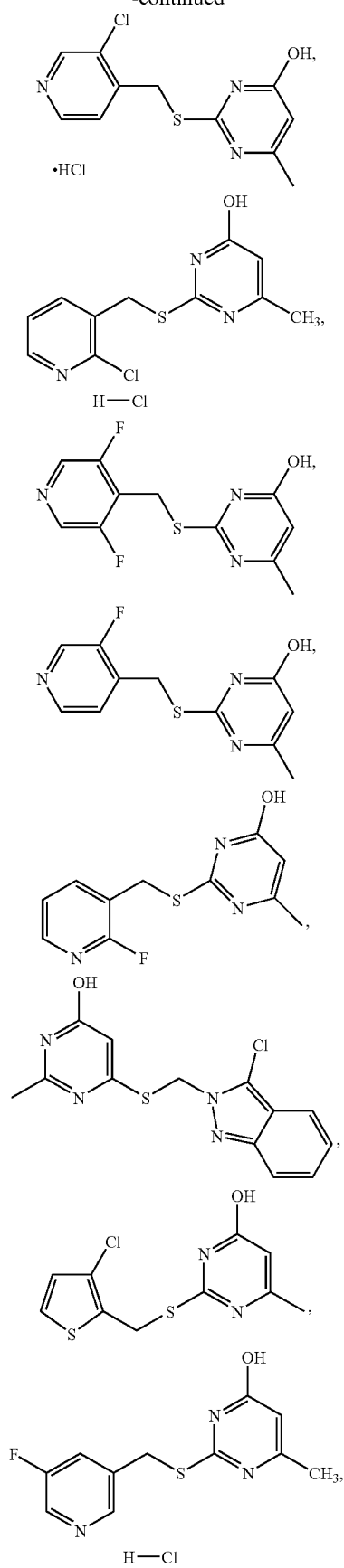
-continued
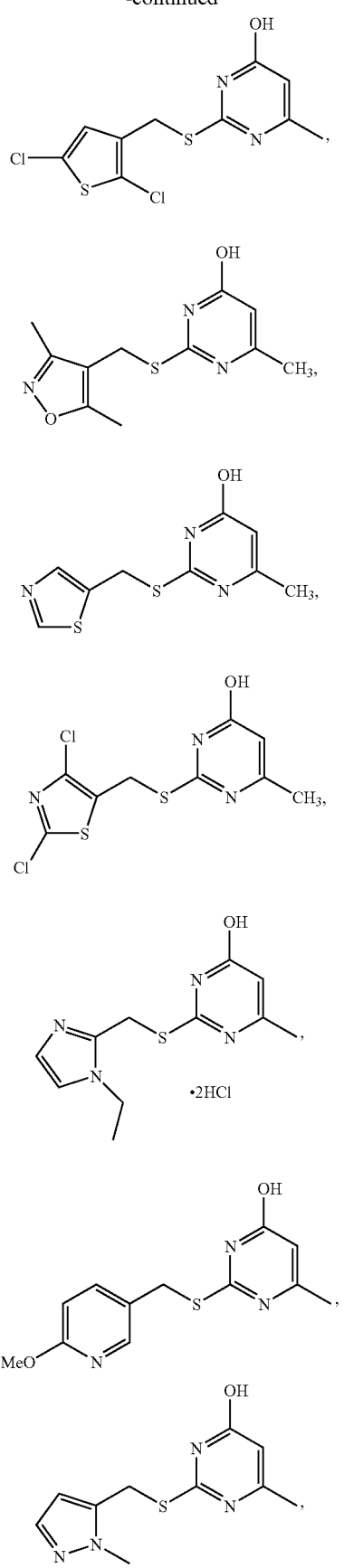

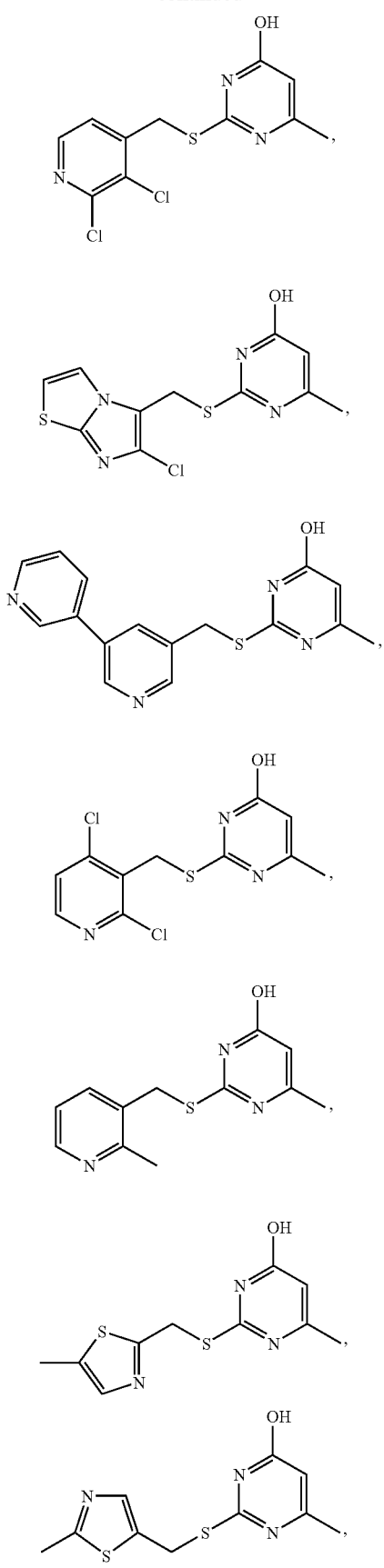
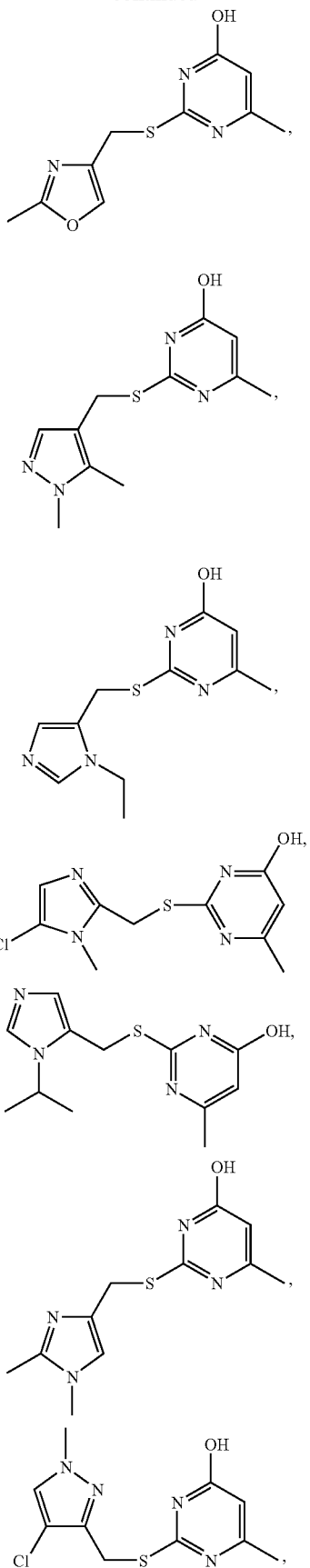

21
-continued
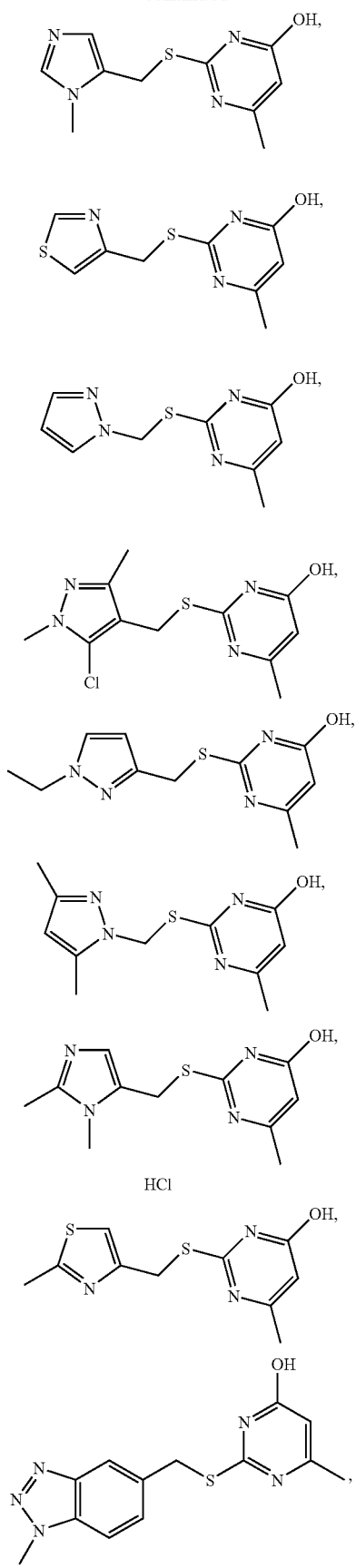
22
-continued
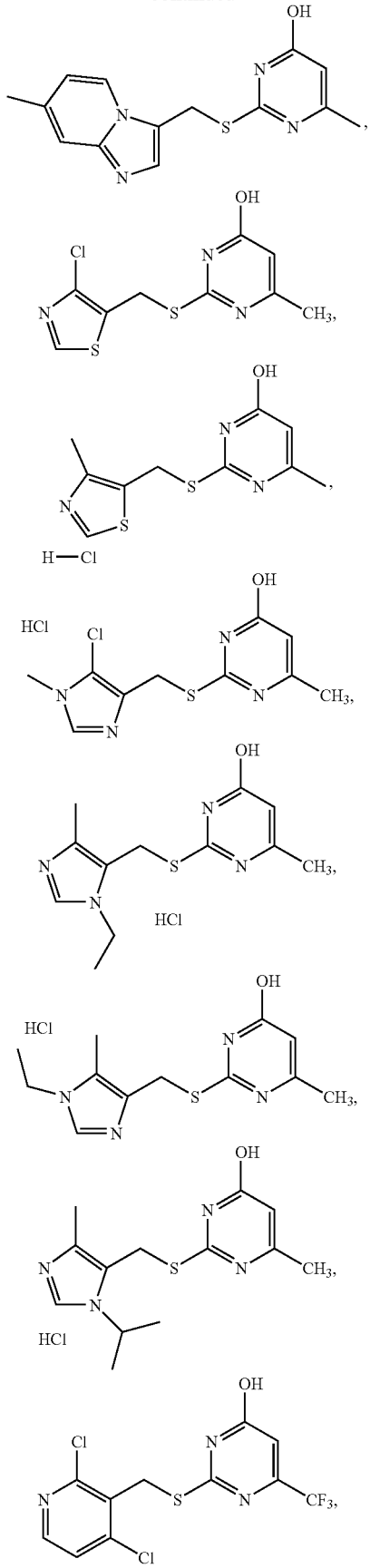

-continued
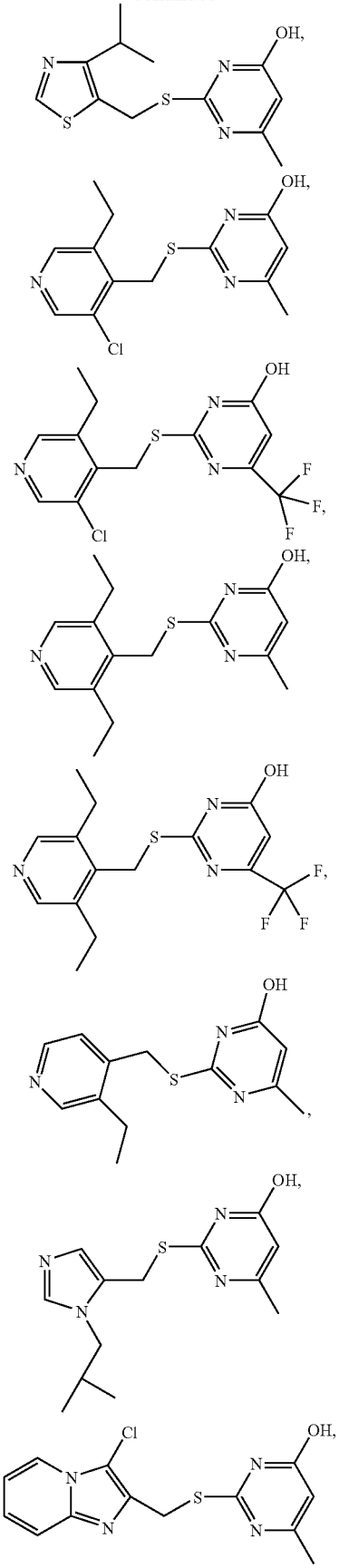
-continued
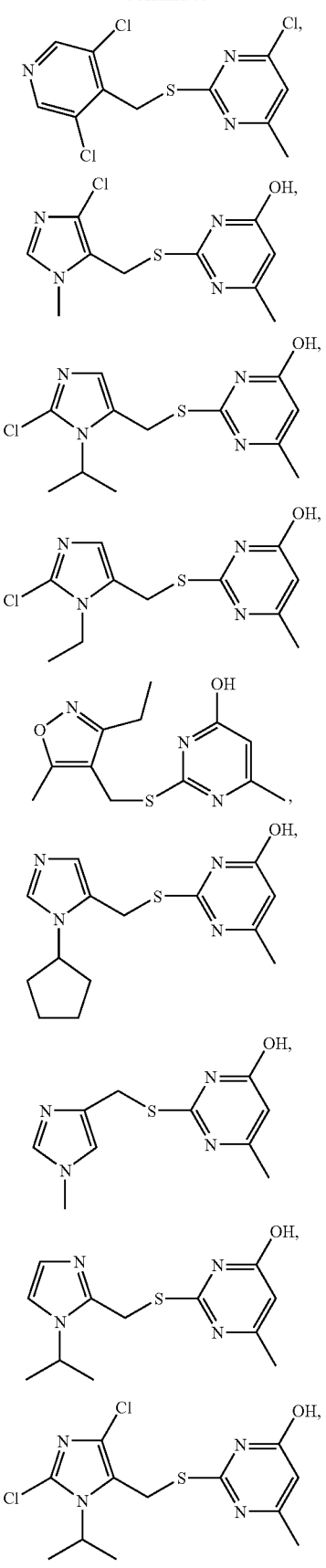

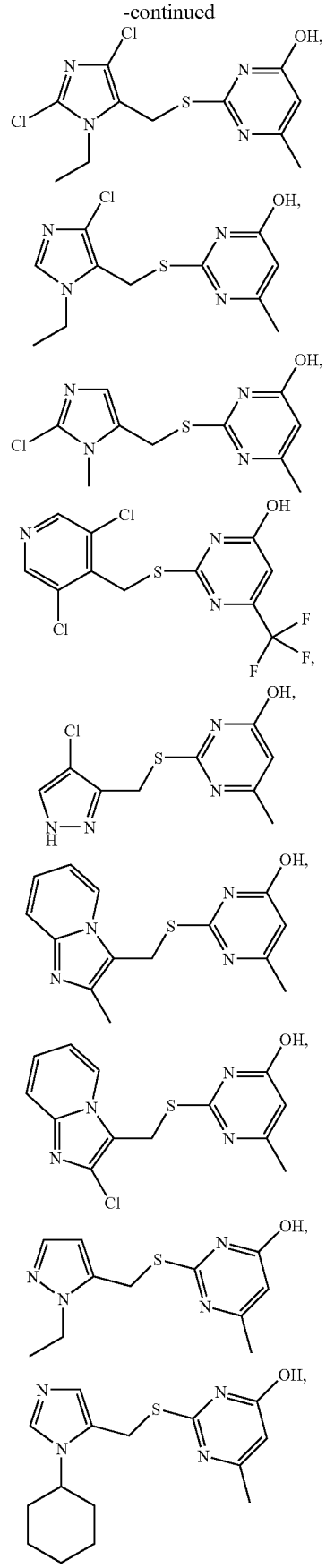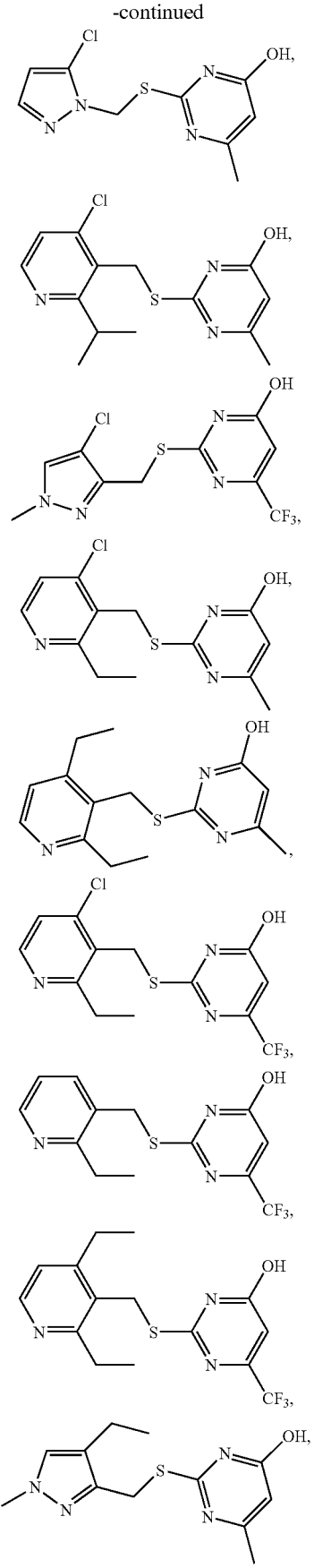

-continued
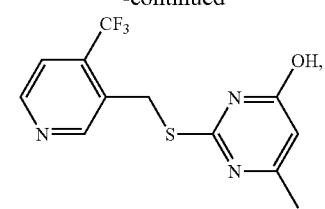
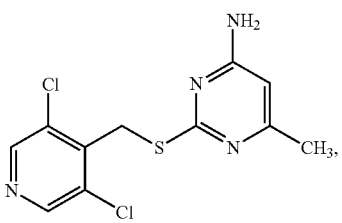
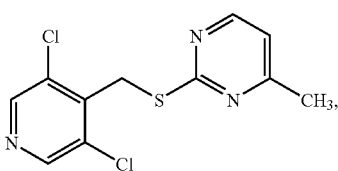
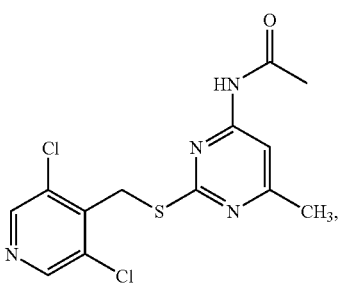
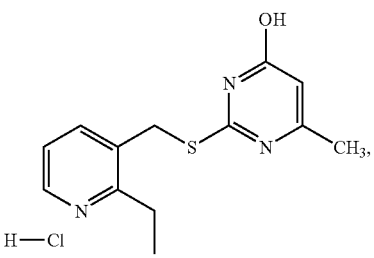
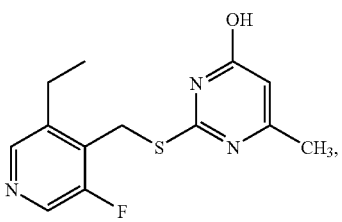
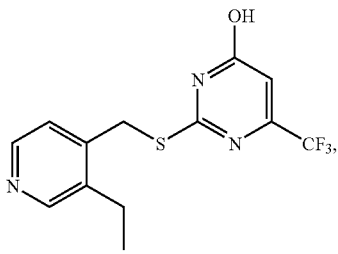
-continued
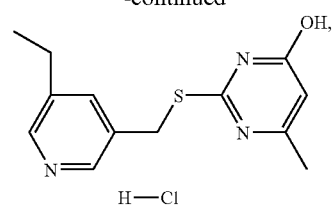
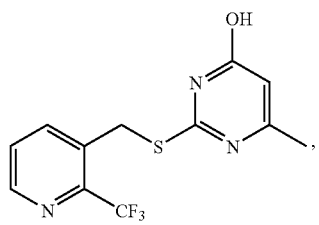
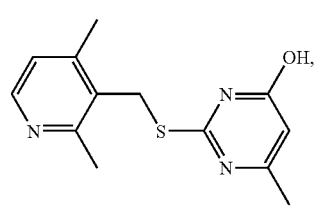
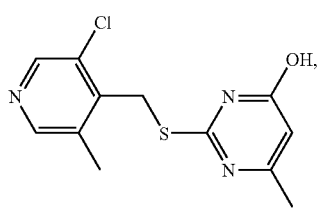
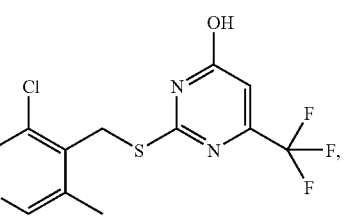
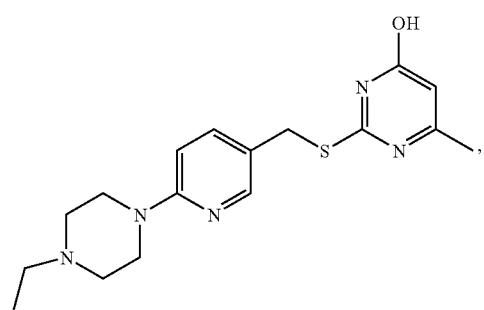

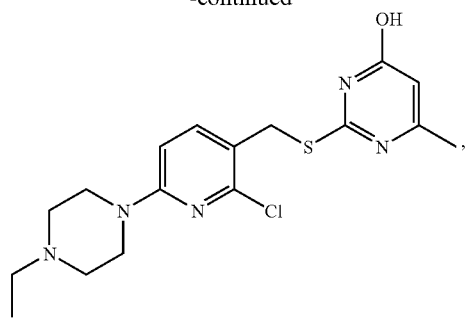
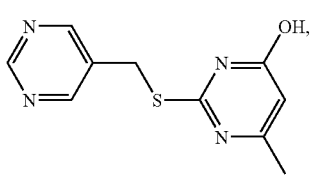
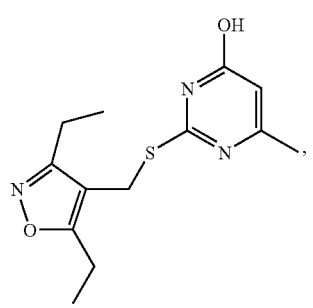
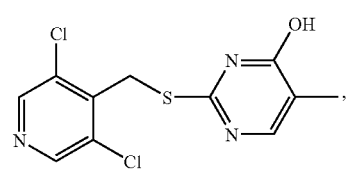
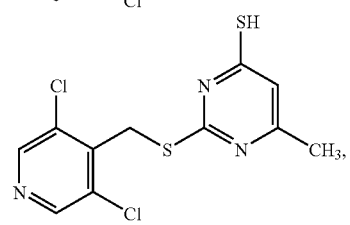
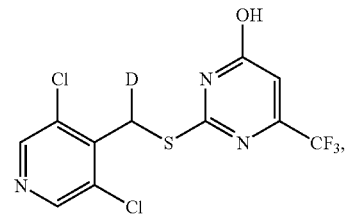
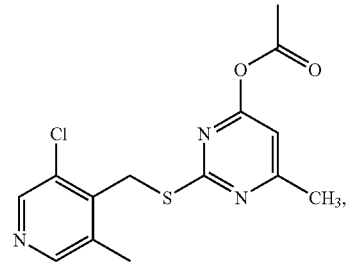
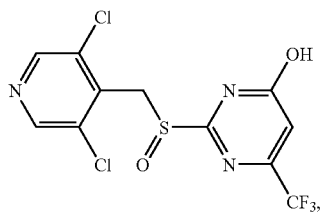
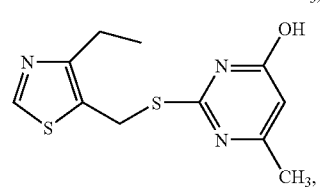
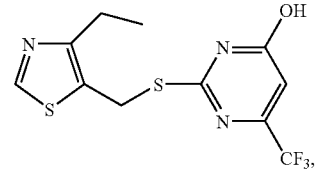
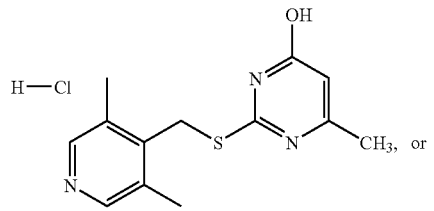
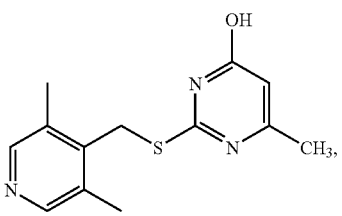
or a stereoisomer, tautomer, prodrug, or pharmaceutically acceptable salt thereof.
In other embodiments, the compound of Formula (Ia) is one of the following compounds, or is a stereoisomer, tautomer, prodrug, or pharmaceutically acceptable salt thereof:
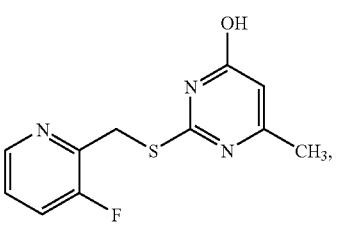
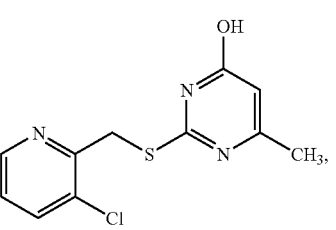

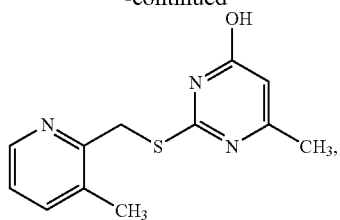
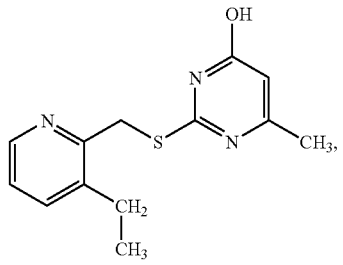
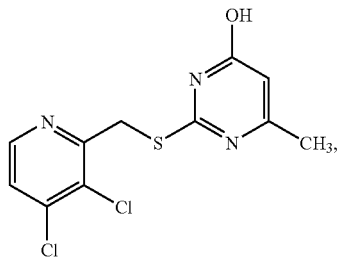
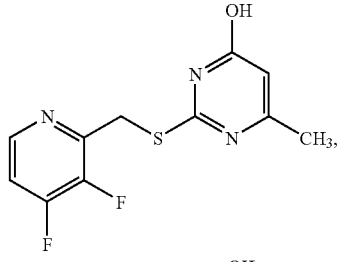
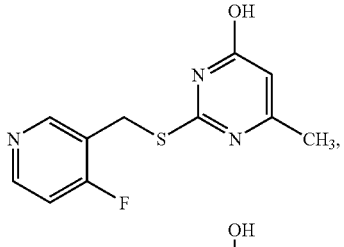
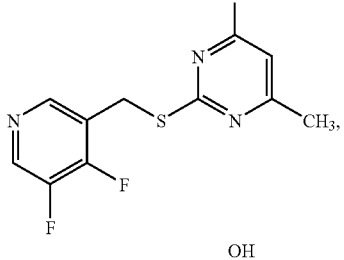
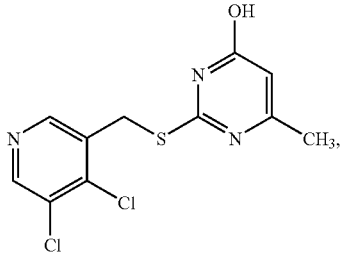
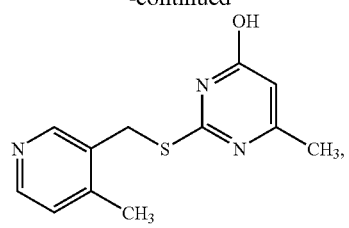
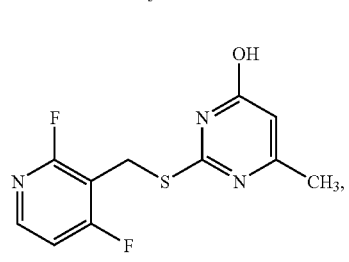
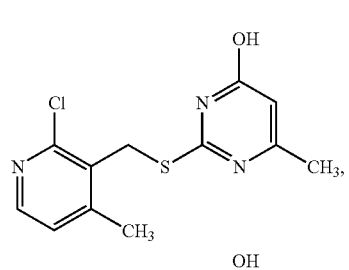
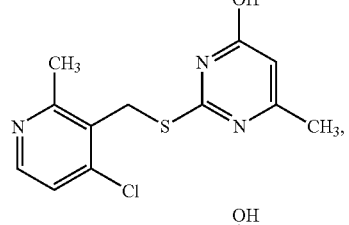
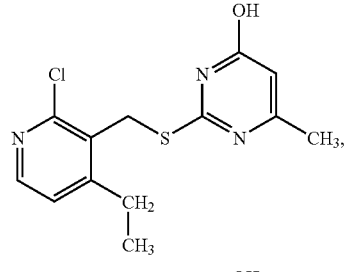
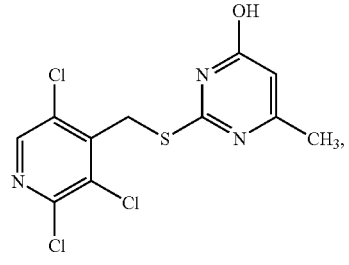
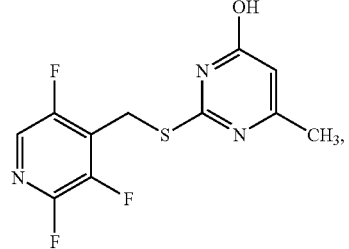

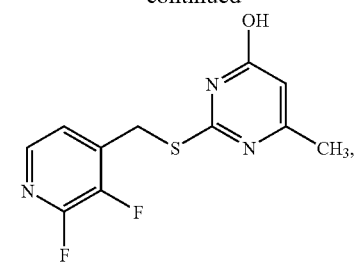
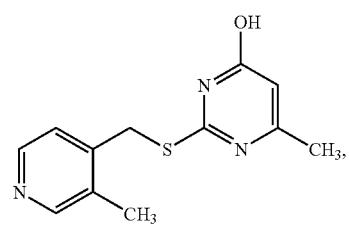
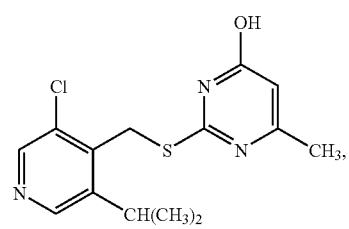
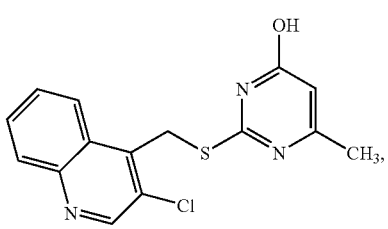
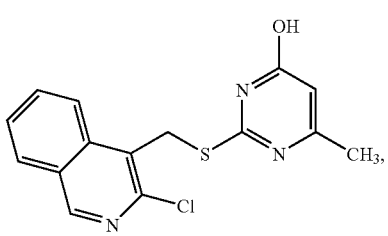
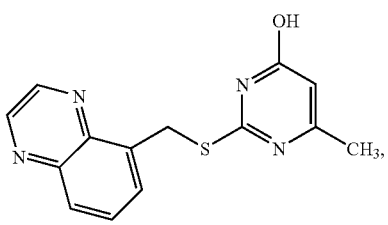
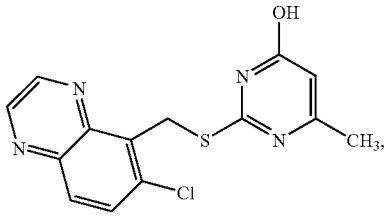
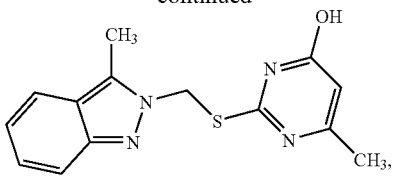
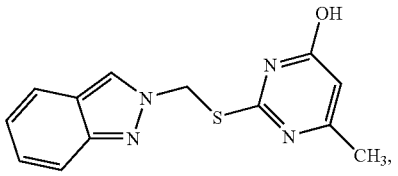
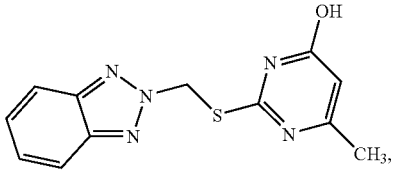
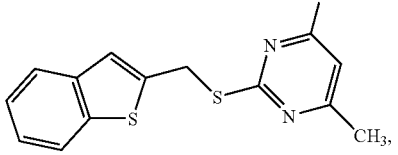
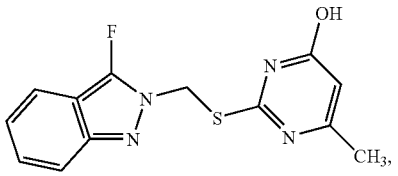
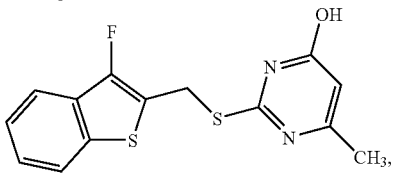
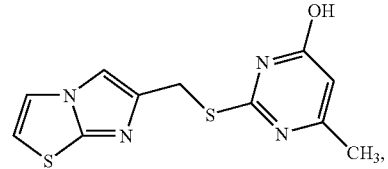
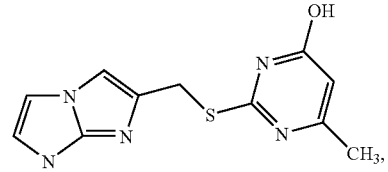
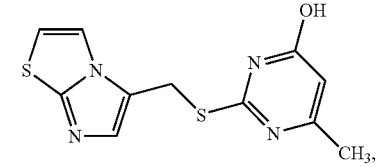
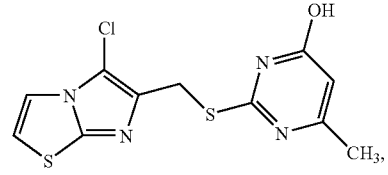

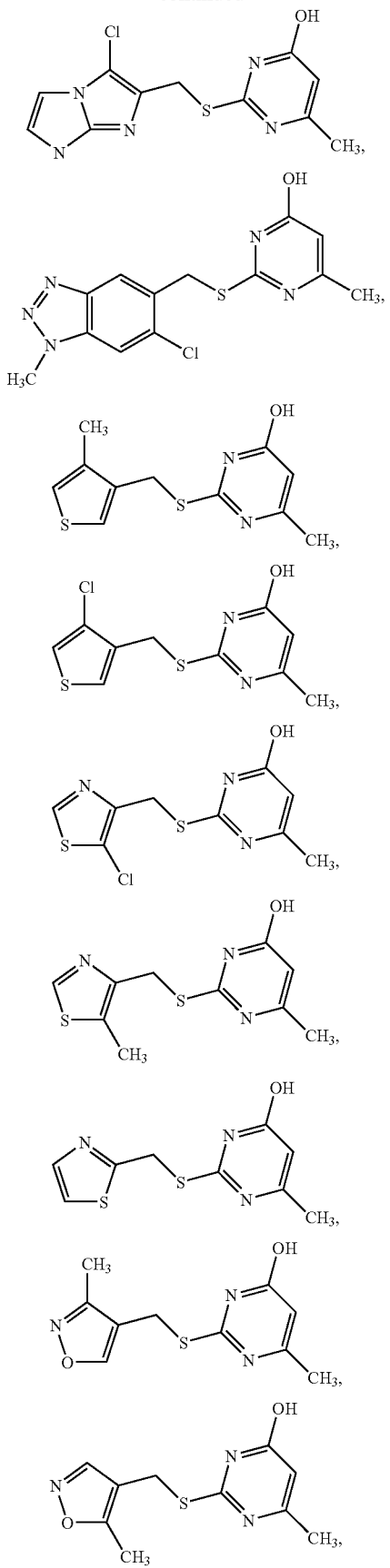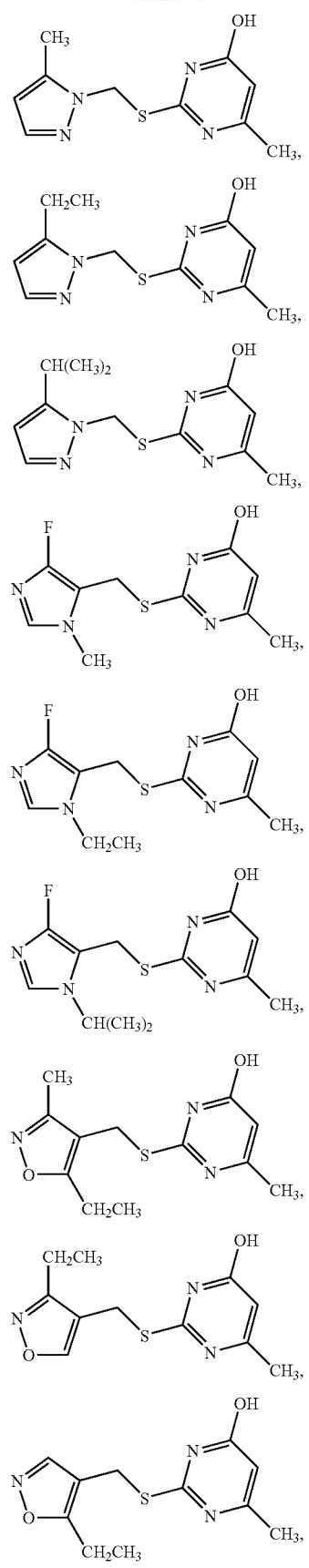

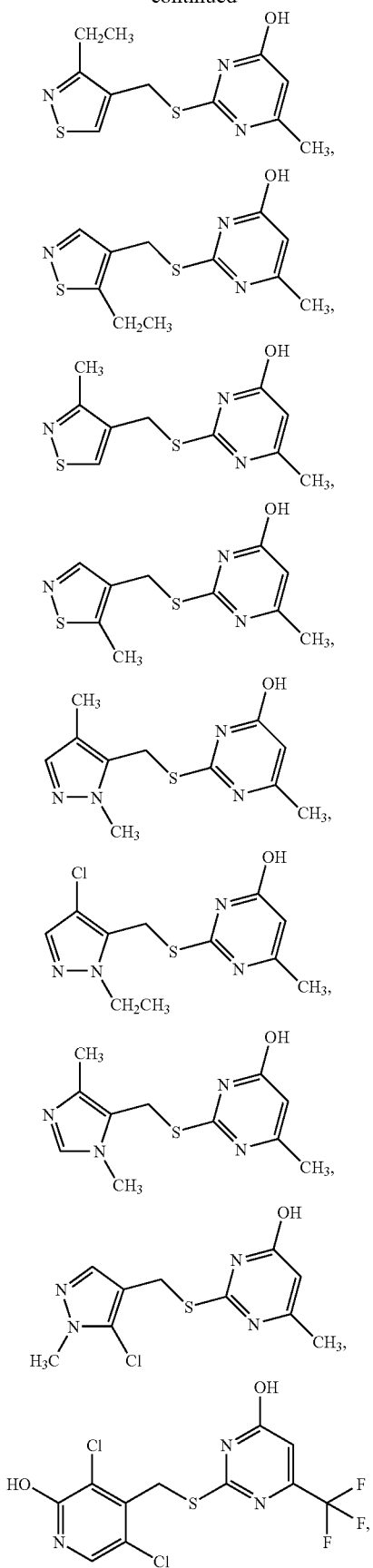
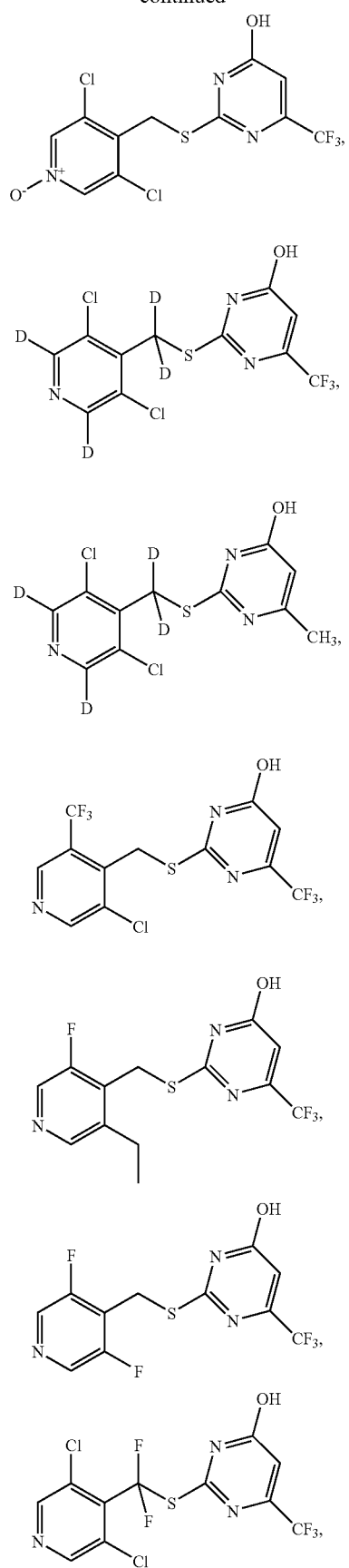

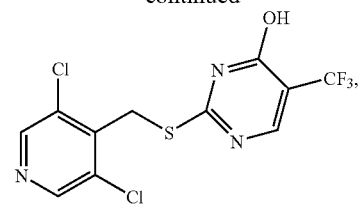
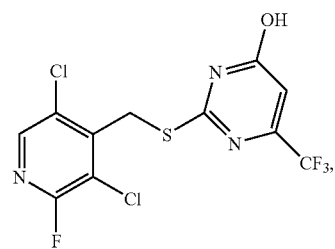
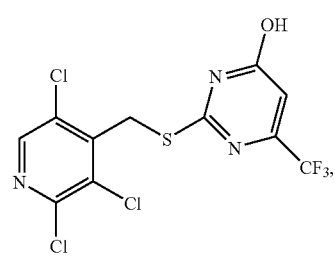
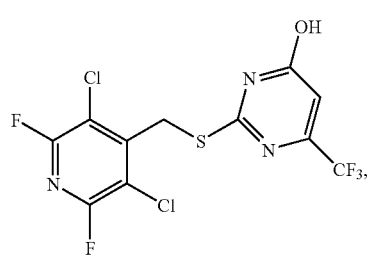
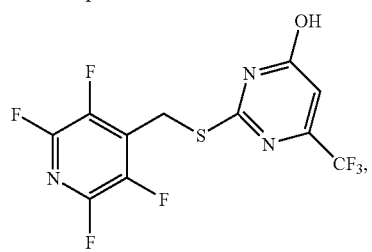
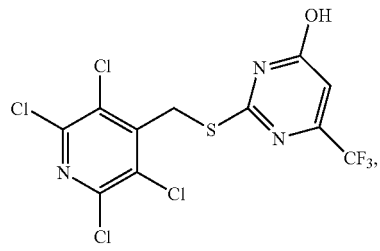
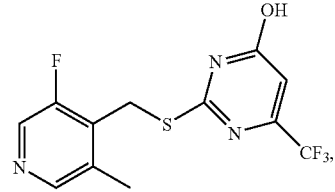
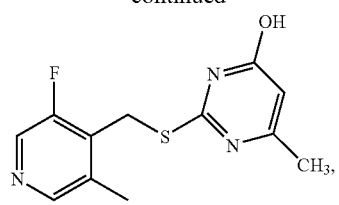
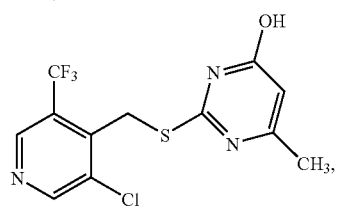
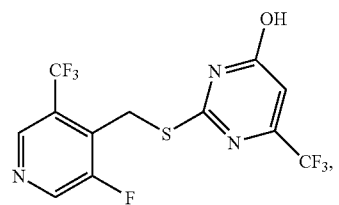
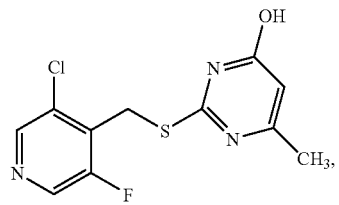
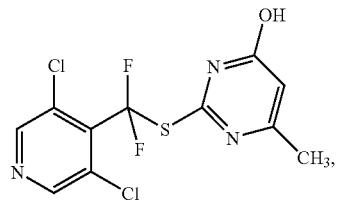
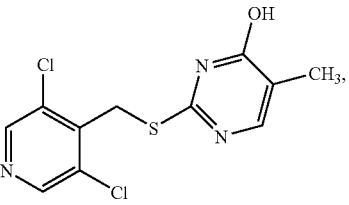
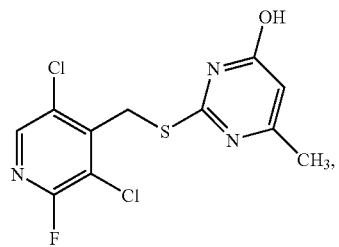
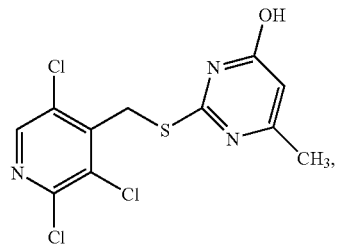

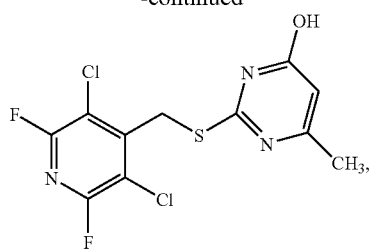
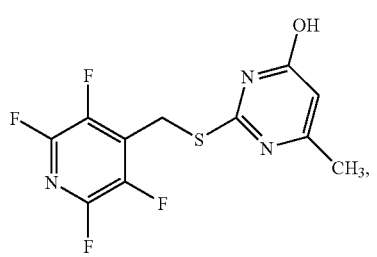
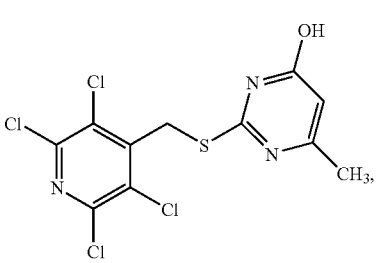
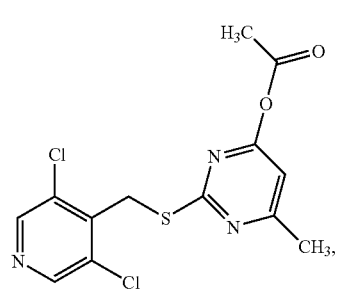
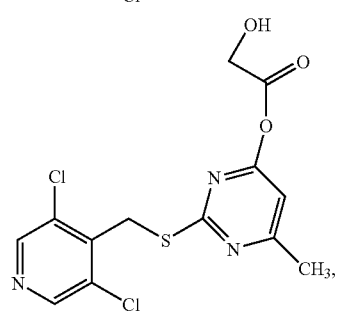
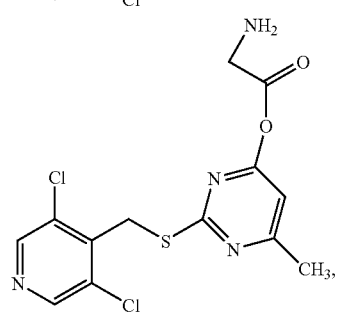
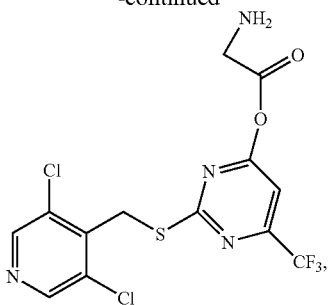
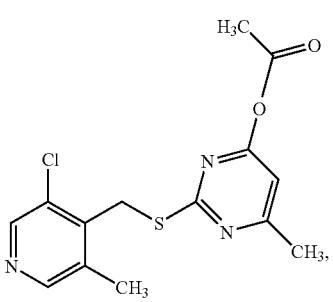
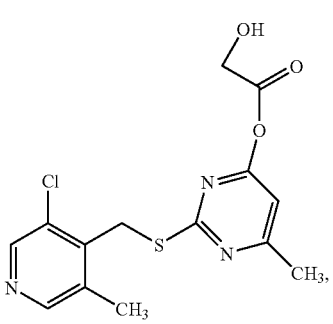
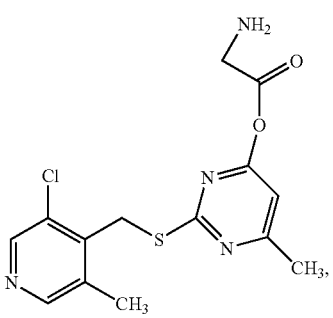
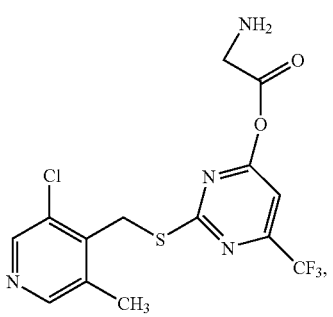

-continued
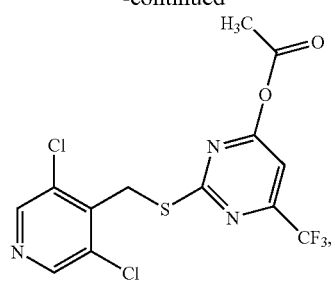
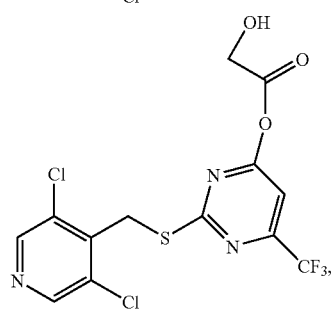
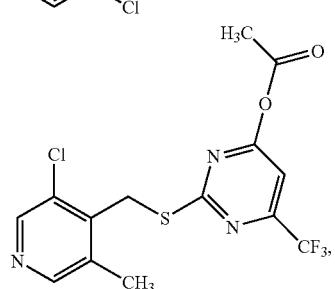
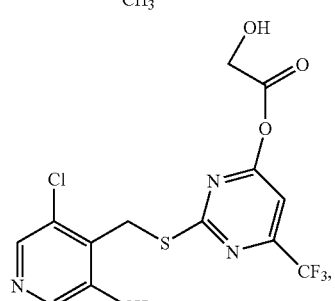
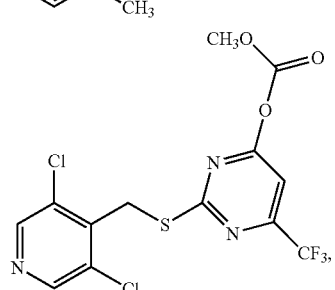
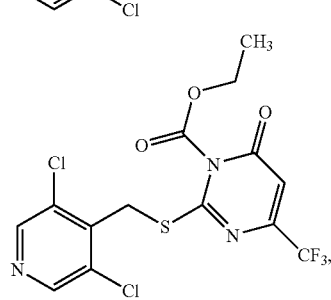
-continued
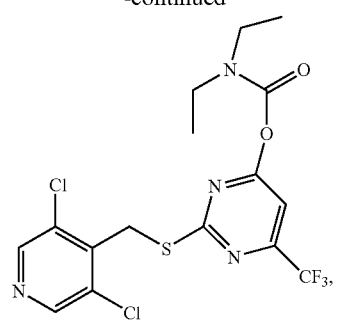
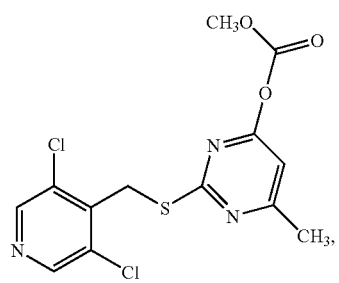
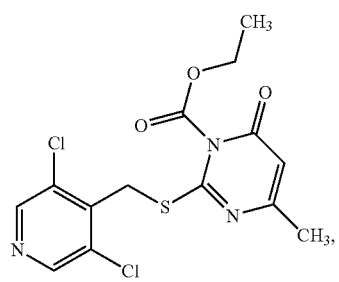
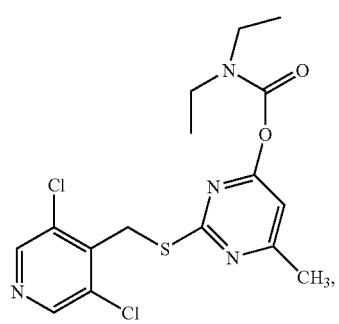
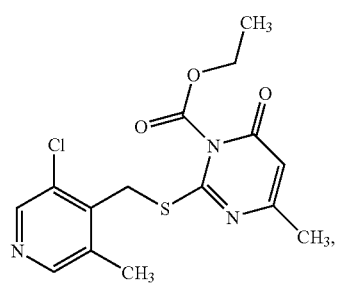

-continued
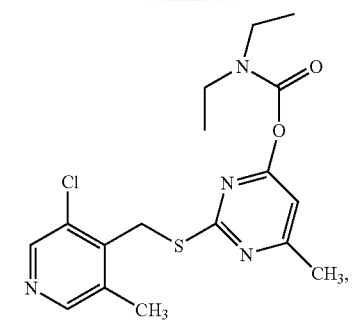
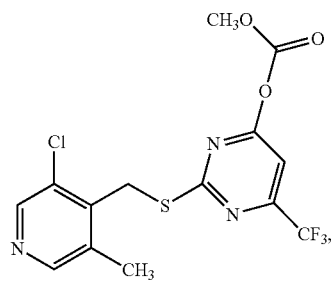
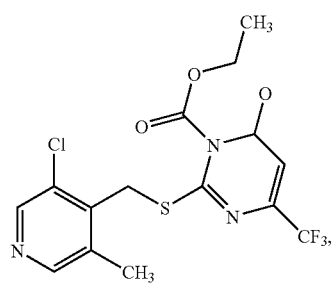
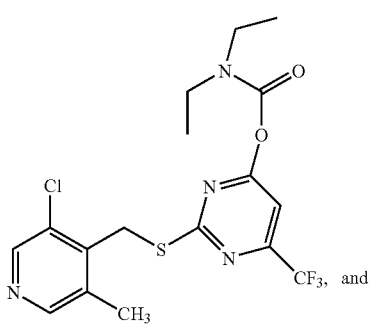
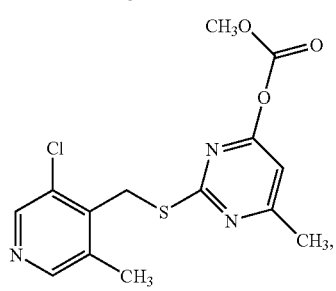
or a stereoisomer, tautomer, prodrug, or pharmaceutically acceptable salt thereof.
In other embodiments, the compound of Formula (Ia) or (Ib) is one of the following compounds, or is a stereoisomer, tautomer, prodrug, or pharmaceutically acceptable salt thereof:
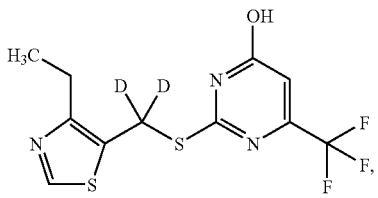
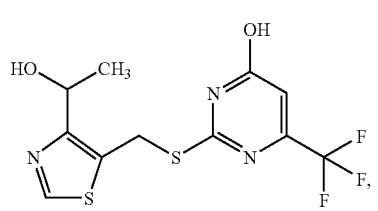
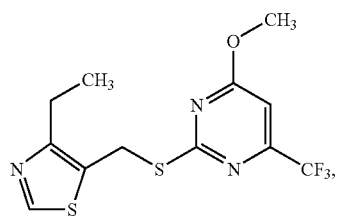
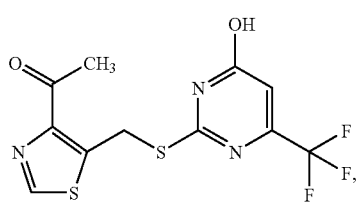
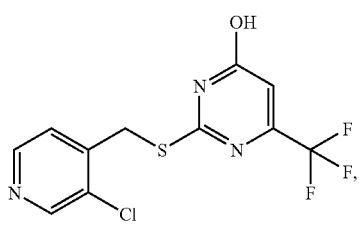
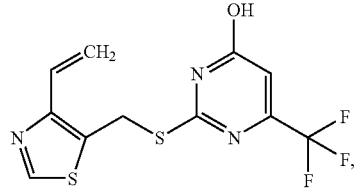
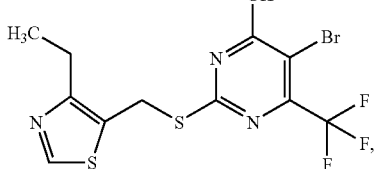
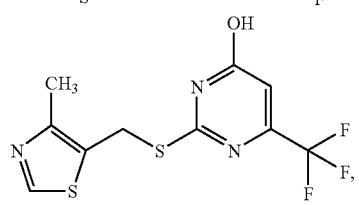

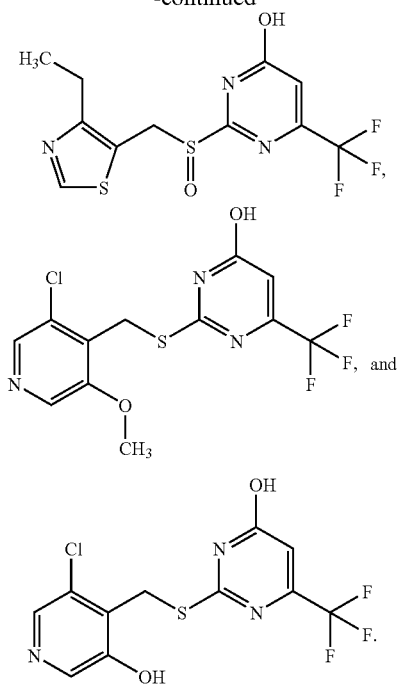

In a second aspect, the invention provides compositions including a pharmaceutically acceptable carrier or vehicle and an effective amount of a compound having the Formula (Ia).

In a third aspect, the invention provides methods for treating or preventing pain (e.g., neuropathic pain) in a patient by administering to the patient in need thereof an effective amount of a compound of Formula (Ia).

In a fourth aspect, the invention provides methods for treating or preventing inflammation in a patient by administering to the patient in need thereof an effective amount of a compound of Formula (Ia).

In all of the compositions and methods of the invention, it is understood that stereoisomers, tautomers, and prodrugs of the structures of Formula (Ia), and pharmaceutically acceptable salts thereof, are encompassed by the invention.

In a fifth aspect, the invention features a method for treating or preventing pain (e.g., neuropathic pain) in a patient that includes administering to a patient in need thereof an effective amount of a compound of Formula (IIa), In another aspect, the invention features a method for treating inflammation in a patient, by administering to the patient in need thereof an effective amount of a compound of Formula (IIa) as described herein, including stereoisomers, tautomers, E/Z stereoisomers, prodrugs, and pharmaceutically acceptable salts thereof.

Compounds of formula (II) have the structure:

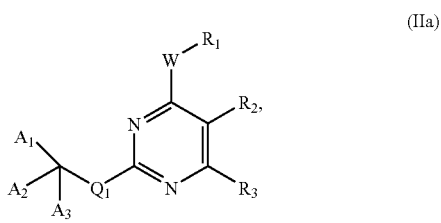
(IIa)

or its tautomer

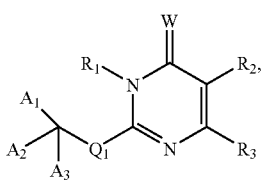
(IIb)

including other tautomers, stereoisomers, E/Z stereoisomers, prodrugs and pharmaceutically acceptable salts thereof, wherein:

W is O, S, NH, N-terminal linked amino acid, or $CH_2$;

$Q_1$ is —O—, —NH—, —S—, —SO—, —$SO_2$—, —$CH_2$, —$CH_2CH_2$—, —CH=CH—, —$OCH_2$—, —$SCH_2$—, —$SOCH_2$—, or —$SO_2CH_2$—, wherein $Q_1$ is not —O— when W is O or S;

$R_1$ is —H, OH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, —$(CH_2)_nOZ$, —C(O)Z, —C(O)OZ, —C(O)NHZ, —$C(O)N(Z)_2$, —$(CR_{1A}R_{1B})_{r2}OPO(OZ)_2$, —$(CR_{2A}R_{2B})_{r3}PO(OZ)_2$, or C-terminal linked amino acid;

each $R_{1A}$, $R_{1B}$, $R_{2A}$, and $R_{2B}$ is, independently, —H or —$C_{1-5}$ alkyl;

$R_2$ and $R_3$ are each, independently, —H, -D, —OH, -halogen, —CN, —$NO_2$, —SH, —$C_1$-$C_8$ alkyl, —$CF_3$, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —OZ, —$N(Z)_2$, —$C(NH)N(Z)_2$, —$O(CH_2)_nOZ$, —C(O)Z, —OC(O)Z, —OC(O)OZ, —OC(O)N(Z)_2, —C(O)N(Z)_2, —C(O)OZ, —SZ, —SOZ, —$S(O)_2$Z, —NHC(O)Z, —$NHS(O)_2$Z, —$NHC(NH)N(Z)_2$, —$NZC(NH)N(Z)_2$, —$NHC(NCN)N(Z)_2$, —$NZC(NCN)N(Z)_2$, or —$PO(OZ)_2$, or $R_2$ and $R_3$, together with the carbon atoms to which each is attached, join to form a 5- to 6-membered aromatic or non aromatic carbocycle or heterocycle;

each Z is, independently, —H, —$C_1$-$C_8$ alkyl, —$C_4$-$C_{12}$ alkcycloalkyl, —$C_3$-$C_9$ alkheterocyclyl, wherein the heterocyclyl is 3 to 9 membered, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, or two Z, together with the atom to which each is attached, join to form a 3- to 7-membered aromatic or non aromatic heterocycle;

each n is 1 or 2;

each r2 is an integer between 1-3;

each r3 is an integer between 0-2;

$A_1$ and $A_2$ are each, independently, —H, -D, -halogen, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, or —$C_7$-$C_{14}$ arylalkyl; and $A_3$ is a 3- to 9-membered aromatic or non aromatic carbocycle or heterocycle.

In certain embodiments, W is O, S, or NH; e.g., W is O.

The compound of Formula (IIa) may have the following structure:

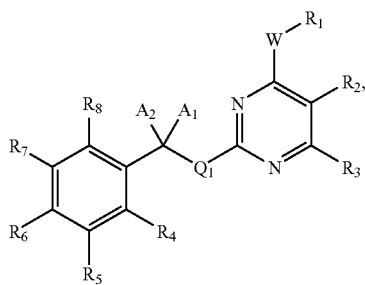

(IIa-2)

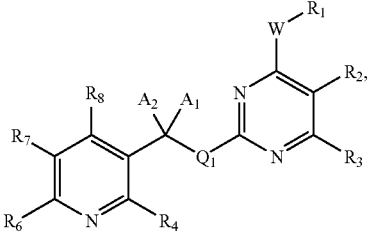

(IIa-4)

wherein $R_4$, $R_5$, $R_6$, $R_7$, and $R_8$ are each, independently, —H, -D, —OH, -halogen, —CN, —NO$_2$, —SH, $C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$, or $R_4$ and $R_5$, or $R_5$ and $R_6$, or $R_6$ and $R_7$, or $R_7$ and $R_8$, together with the carbon atoms to which each is attached, join to form a 5- to 6-membered aromatic or non aromatic carbocycle or heterocycle.

The compound of Formula (IIa) may have the following structure:

wherein $R_4$, $R_6$, $R_7$, and $R_8$ are each, independently, —H, -D, —OH, -halogen, —CN, —NO$_2$, —SH, $C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$, or $R_6$ and $R_7$, or $R_7$ and $R_8$, together with the carbon atoms to which each is attached, join to form a 5- to 6-membered aromatic or non aromatic carbocycle or heterocycle.

The compound of Formula (IIa) may have the following structure:

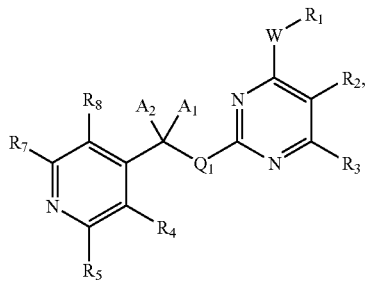

(IIa-3)

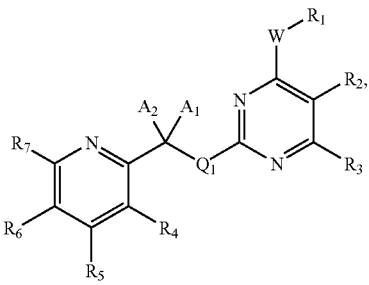

(IIa-5)

wherein $R_4$, $R_5$, $R_7$, and $R_8$ are each, independently, —H, -D, —OH, -halogen, —CN, —NO$_2$, —SH, $C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NHC(NCN)N(Z)$_2$, —NZC(NCN)N(Z)$_2$, or —PO(OZ)$_2$, or $R_4$ and $R_5$, or $R_7$ and $R_8$, together with the carbon atoms to which each is attached, join to form a 5- to 6-membered aromatic or non aromatic carbocycle or heterocycle.

The compound of Formula (IIa) may have the following structure:

wherein $R_4$, $R_5$, $R_6$, and $R_7$ are each, independently, —H, -D, —OH, -halogen, —CN, —NO$_2$, —SH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —(CH$_2$)$_n$C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$, or $R_4$ and $R_5$, or $R_5$ and $R_6$, or $R_6$ and $R_7$, together with the carbon atoms to which each is attached, join to form a 5- to 6-membered aromatic or non aromatic carbocycle or heterocycle.

The compound of Formula (IIa) may have a structure according to the formula

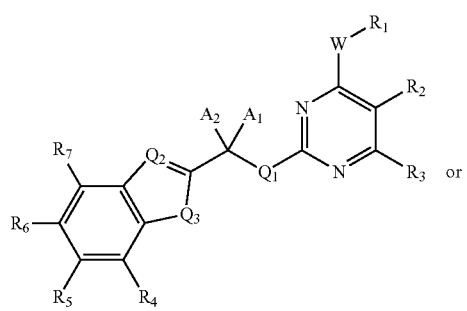

(IIa-6-1)

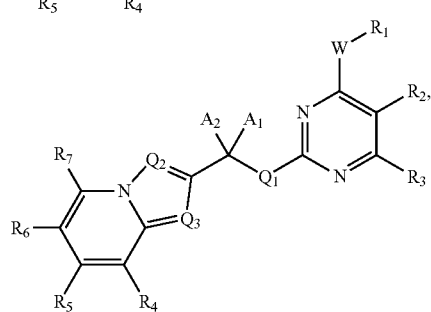

wherein $Q_2$ is $CR_8$ or $NR_9$;

$Q_3$ is $CR_8$, $NR_9$, O, or S;

$R_4$, $R_5$, $R_6$, $R_7$, and $R_8$ are each, independently, —H, -D, —OH, -halogen, —CN, —NO$_2$, —SH, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocycle, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$, or $R_4$ and $R_5$, or $R_5$ and $R_6$, or $R_6$ and $R_7$, together with the carbon atoms to which each is attached, join to form a 5- to 6-membered aromatic or non aromatic carbocycle or heterocycle;

$R_9$ is absent, —H, —CN, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocycle, —NHZ, or NZ$_2$.

In some embodiments, the hydrogens that correspond to $A_1$ and $A_2$ in any of Formulas (IIa-2)-(IIa-6) can be replaced, independently, with deuterium.

In any of the methods described herein, the compound of Formula (IIa) is one of the following compounds, or is a stereoisomer, tautomer, prodrug, or pharmaceutically acceptable salt thereof:

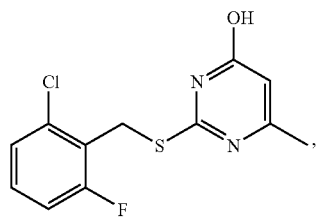

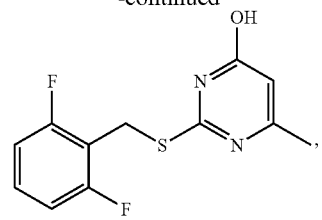

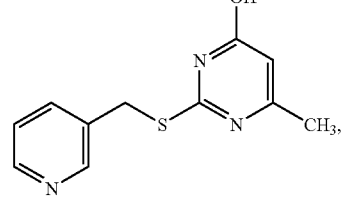

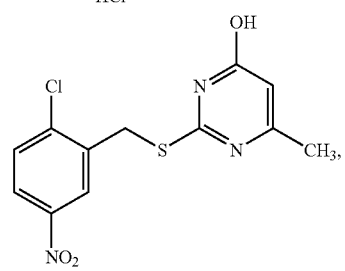

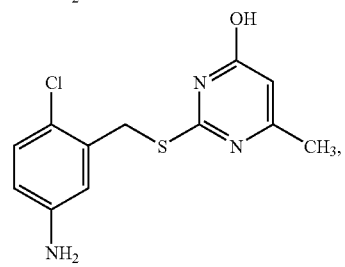

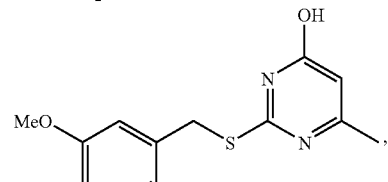

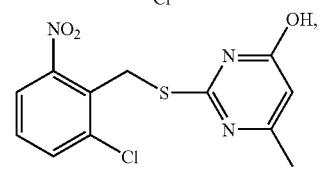

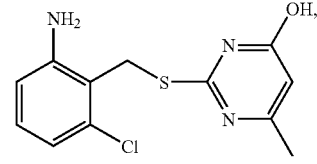

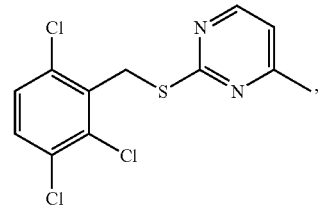

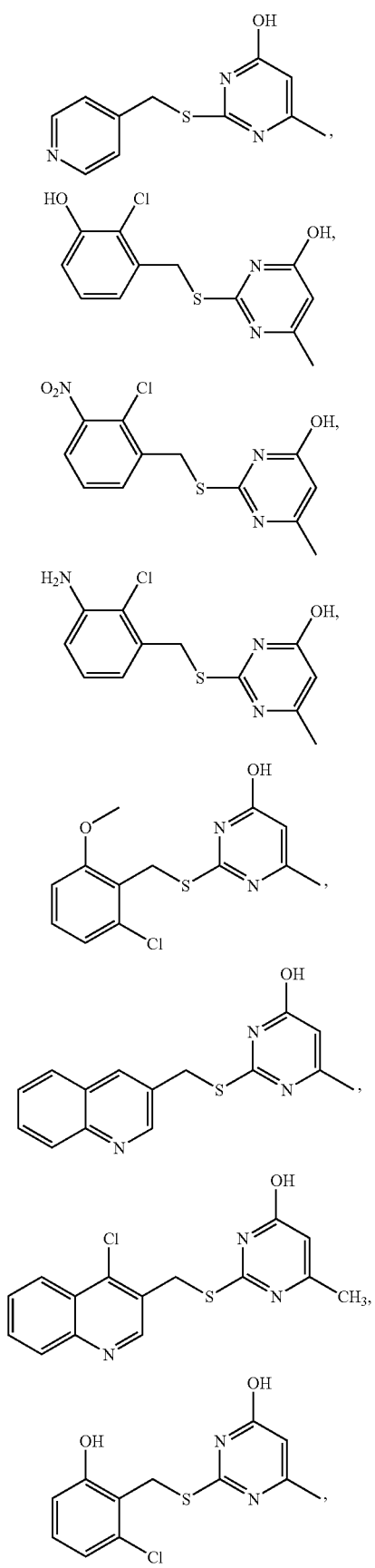
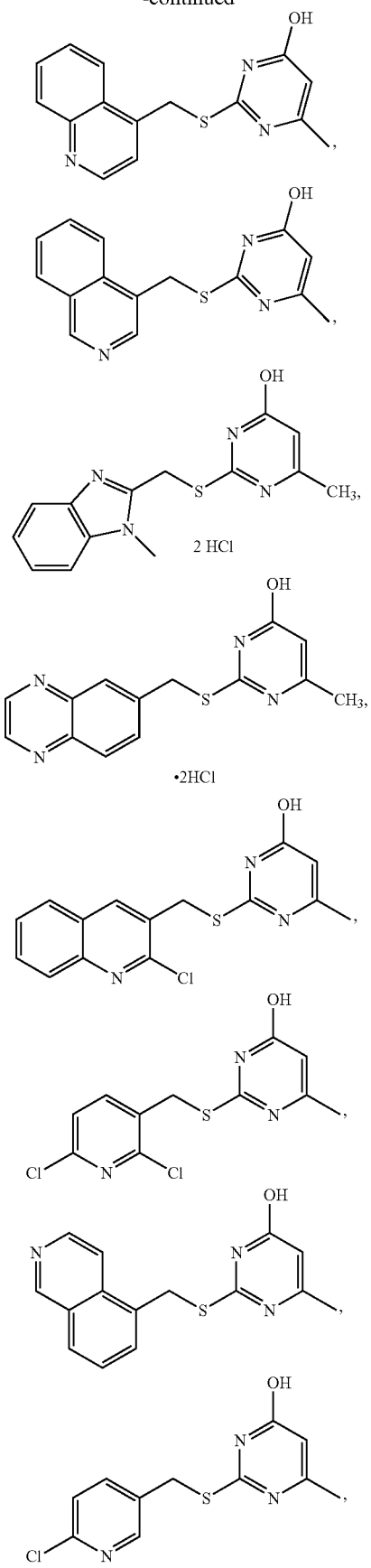

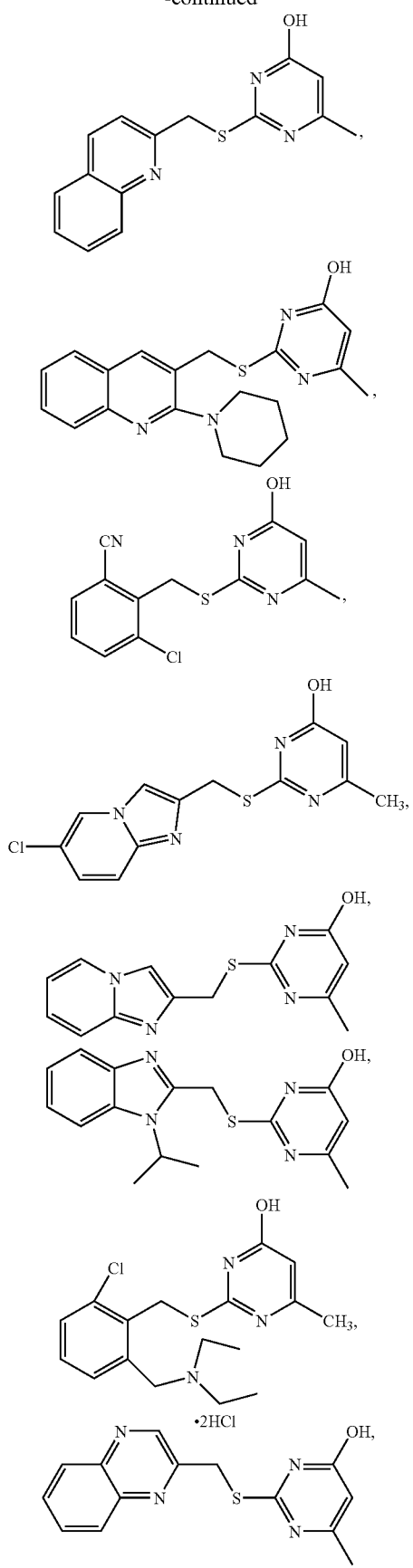
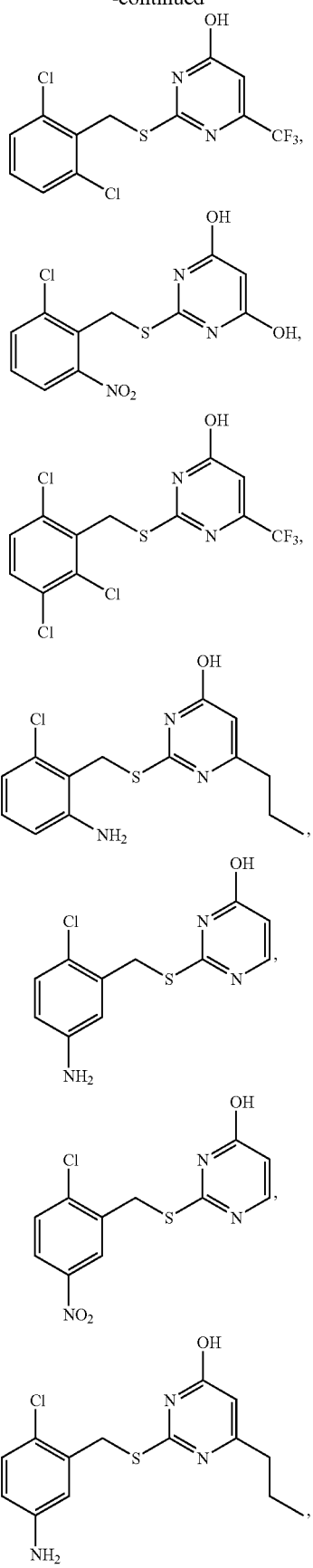

-continued
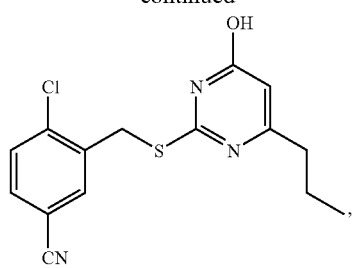
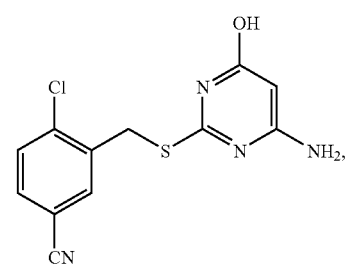
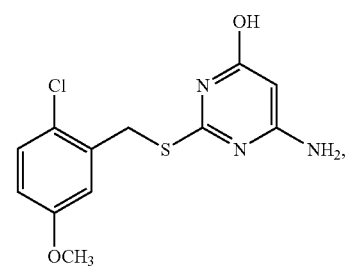
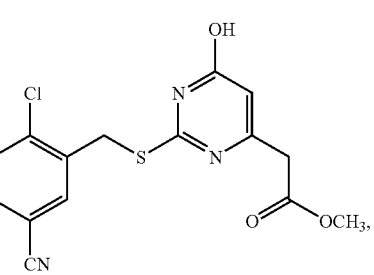
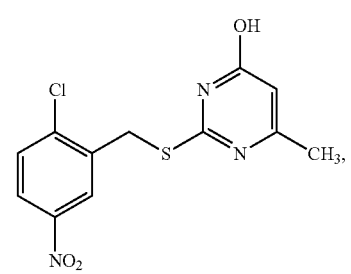
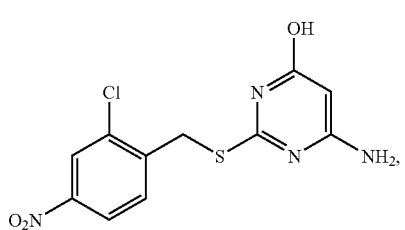
-continued
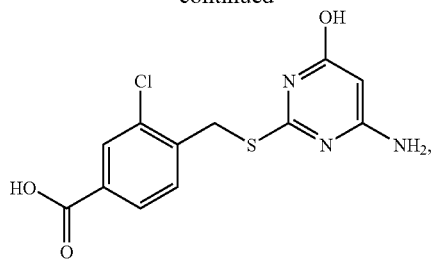
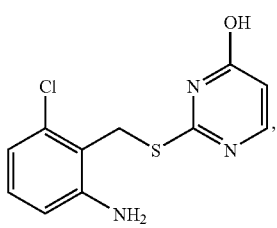
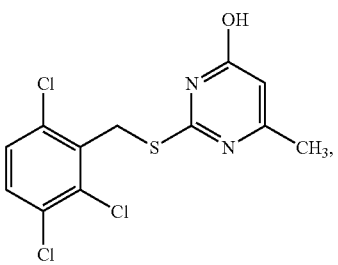
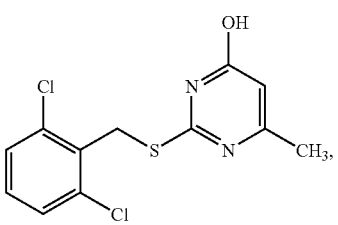
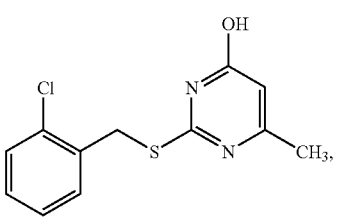
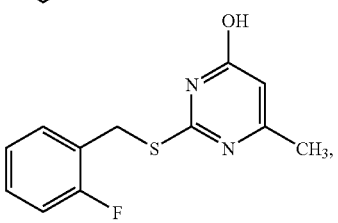
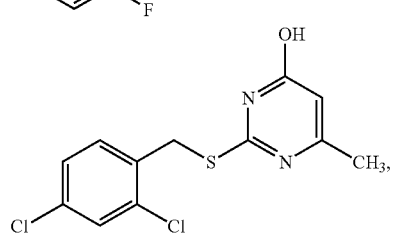

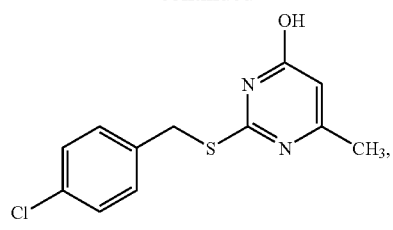
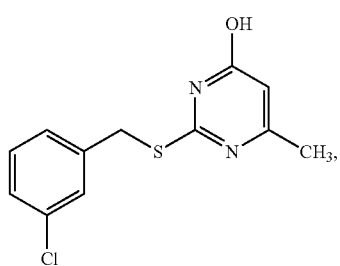
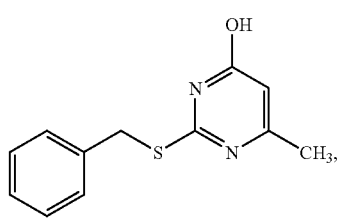
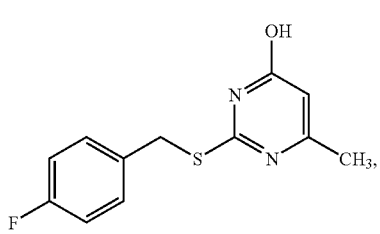
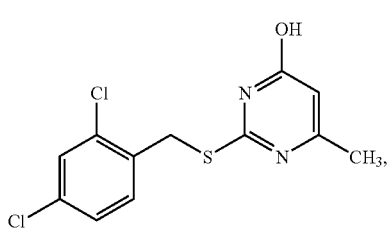
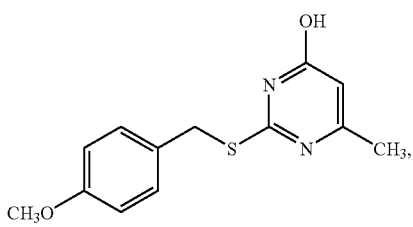
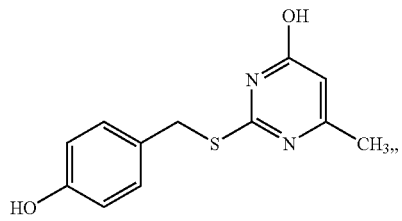
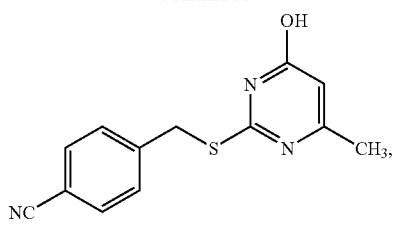
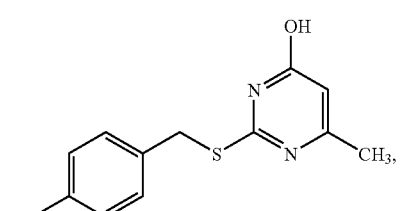
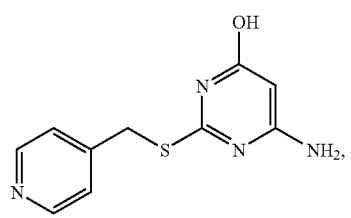
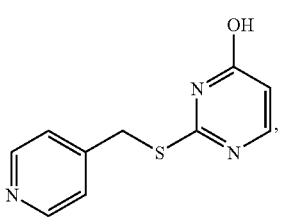
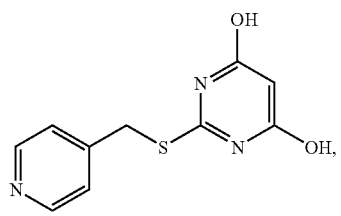
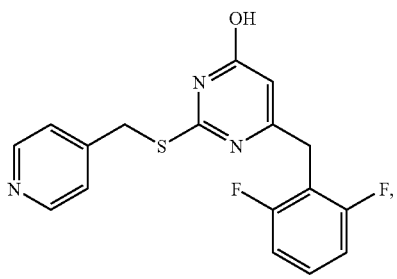
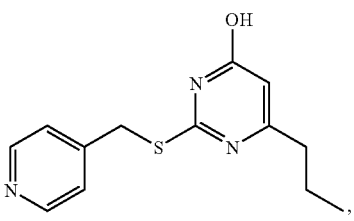

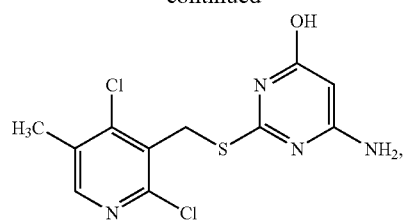
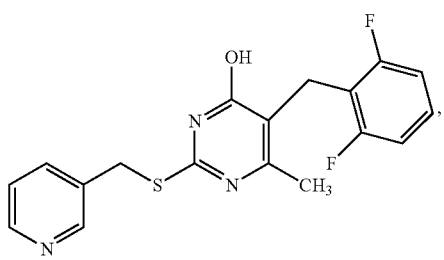
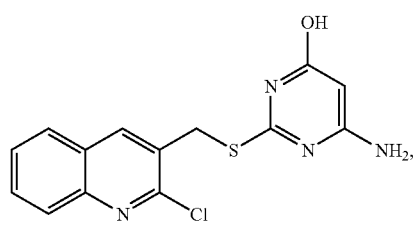
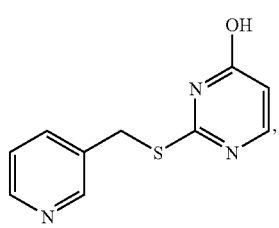
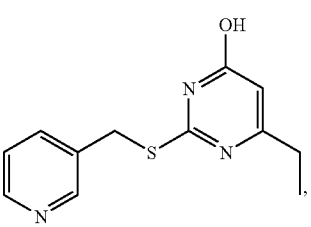
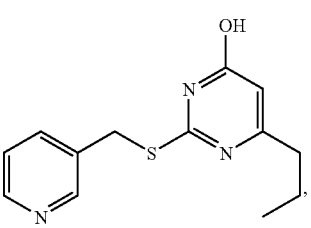
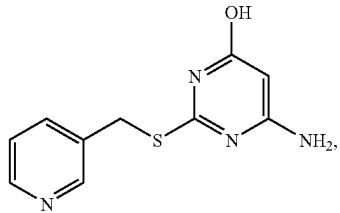
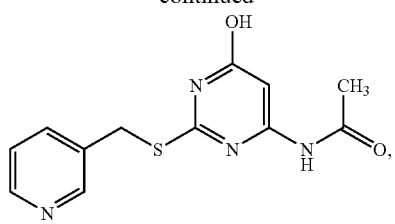
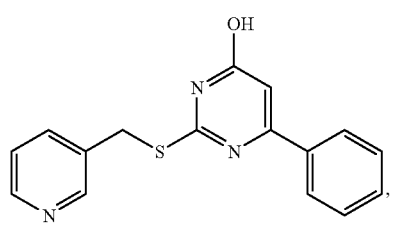
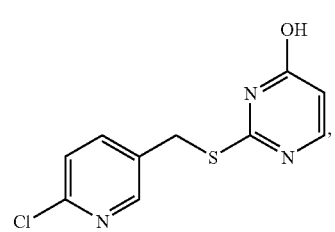
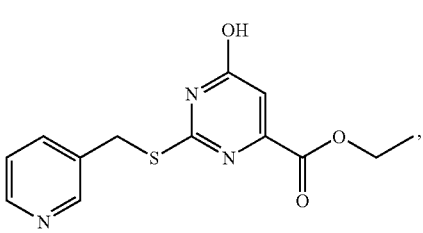
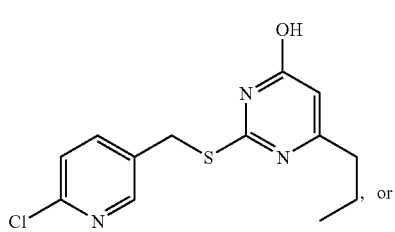
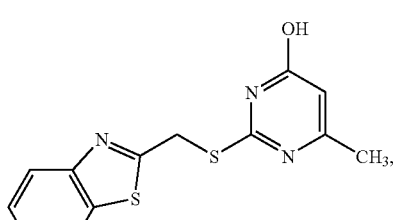
or a stereoisomer, tautomer, prodrug, or pharmaceutically acceptable salt thereof.
In other embodiments, the compound of Formula (IIa) or (IIb) is one of the following compounds, or is a stereoisomer, tautomer, prodrug, or pharmaceutically acceptable salt thereof:

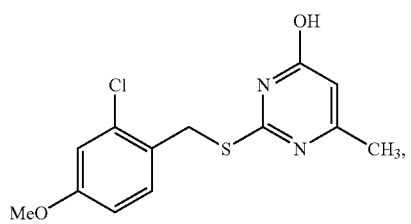
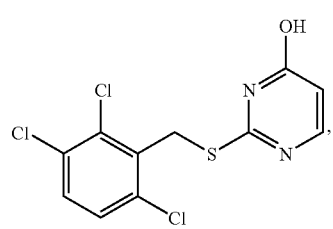
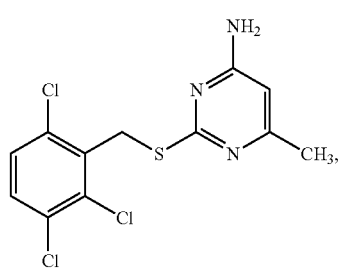
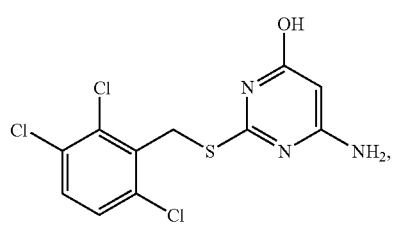
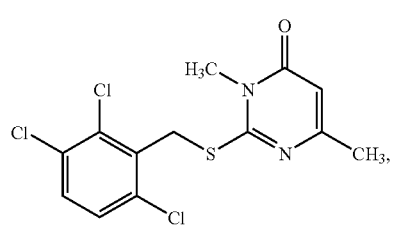
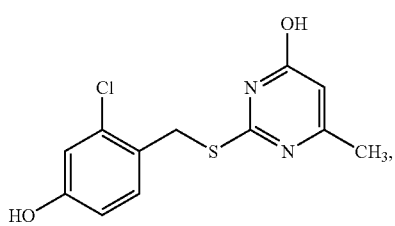
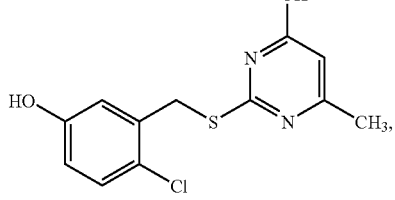
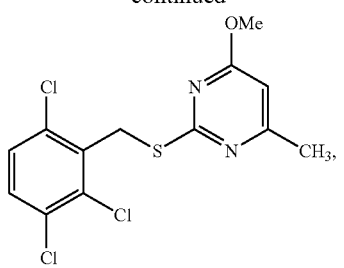
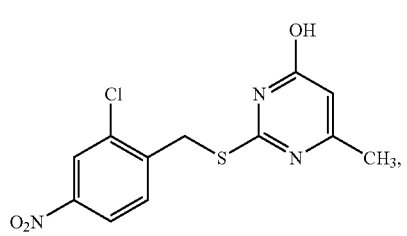
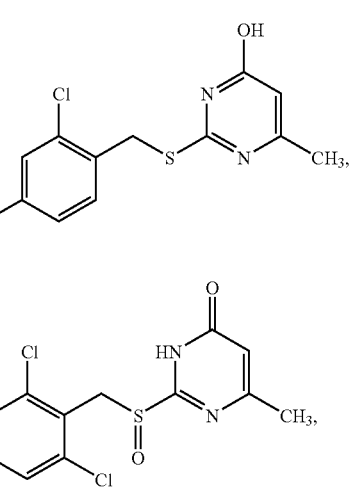
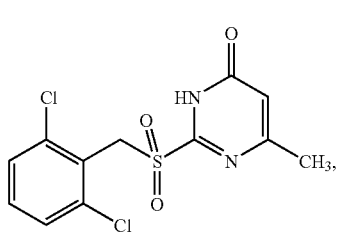
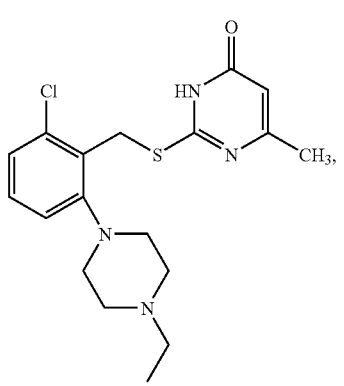
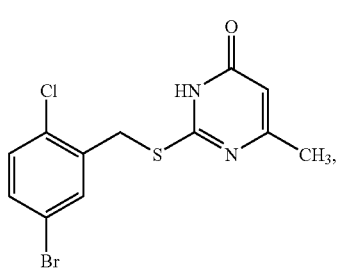

-continued

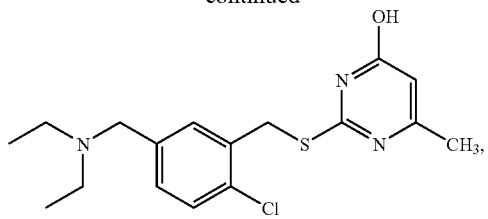

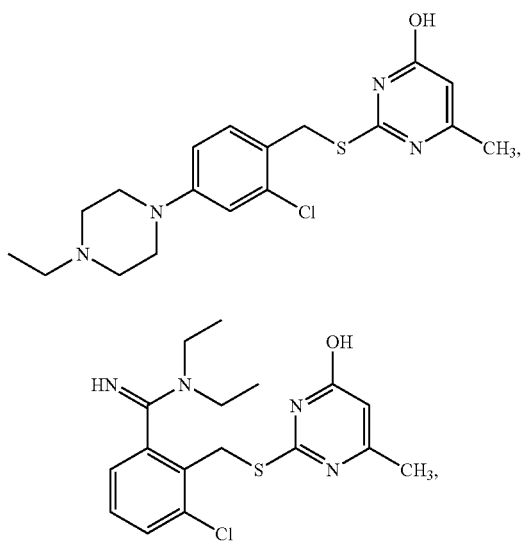

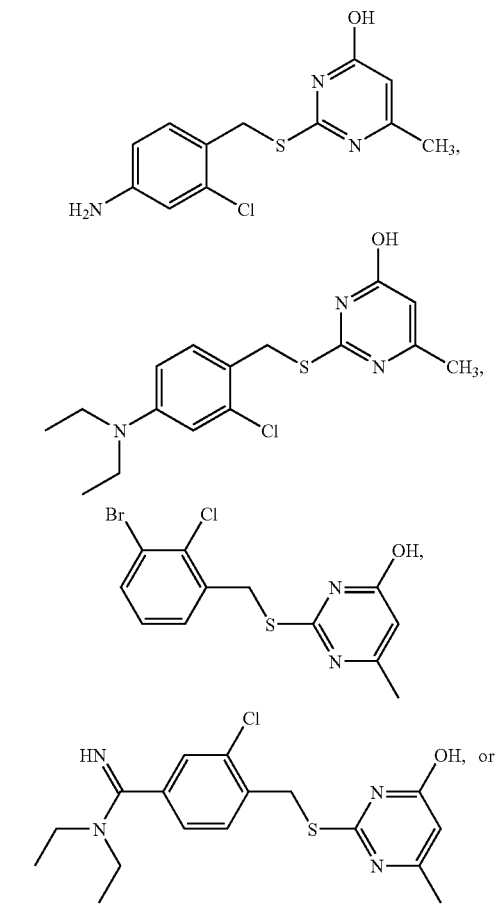

-continued

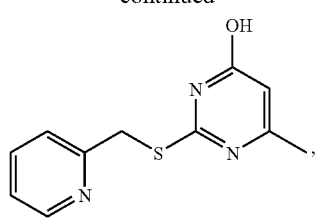

or a stereoisomer, tautomer, prodrug, or pharmaceutically acceptable salt thereof.

As used herein, it is understood that stereoisomers, tautomers, and prodrugs of the structures of Formula (IIa), and pharmaceutically acceptable salts thereof, are encompassed by the invention. In some embodiments, the compound of Formula (IIa) has the keto tautomeric configuration (i.e., Formula (IIb)).

In any of the compounds, compositions, and methods of the invention, where a compound, e.g., a compound of Formula (Ia) or (IIa), is depicted as a salt, the invention also includes the free acid or base, and vice versa.

In another aspect, the invention features a method of treating or preventing pain (e.g., neuropathic pain) or inflammation in a patient that includes administering to a patient in need thereof an effective amount of a compound of any of Formulas (Ia), (Ib), (IIa), or (IIb), or a compound having the structure:

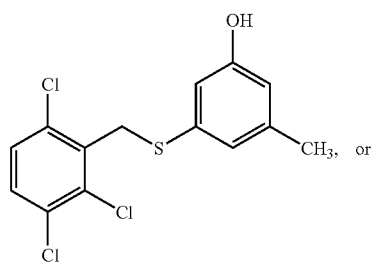

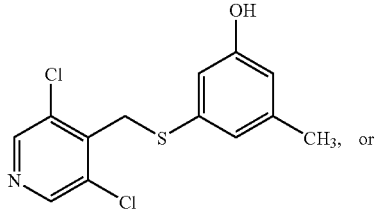

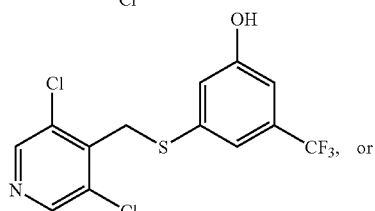

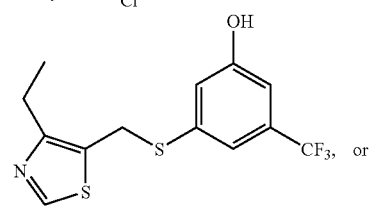

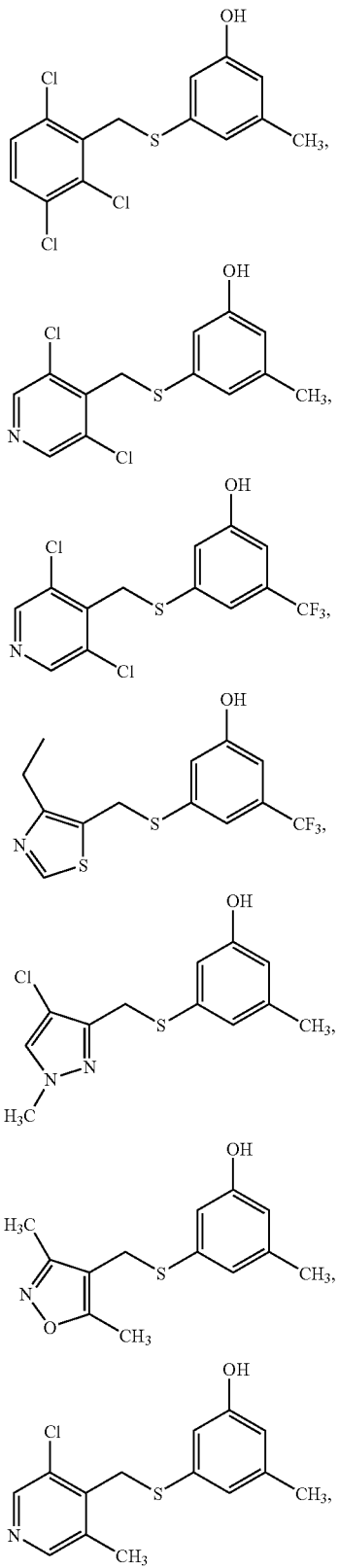

or a stereoisomer, tautomer, prodrug, or pharmaceutically acceptable salt thereof.

The compounds described herein (e.g., a compound of Formulas (Ia), (Ib), (IIa), or (IIb)) can also be used as anticonvulsants, such as for treating epilepsy. In another aspect, the invention features a method of treating epilepsy in a patient by administering to the patient in need thereof an effective amount of a compound of any of Formulas (Ia), (Ib), (IIa), or (IIb), or a compound having the structure:

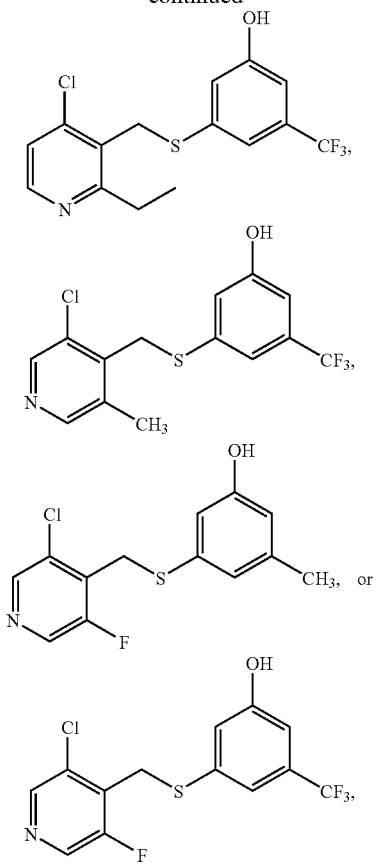

or, or a stereoisomer, tautomer, prodrug, pharmaceutically acceptable salt, or composition thereof.

It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates.

Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

In one embodiment, when administered to a patient, e.g., a mammal for veterinary use or a human for clinical use, the compounds are administered in isolated form. In another embodiment, via conventional techniques, the compounds are purified.

Compositions of the invention may also be substantially anhydrous.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

Compounds may be in acid, base, or salt form.

As used herein, "D" refers to deuterium.

As used herein "aldehyde" refers to a carboxyl group having the structure represented by —CH(O).

As used herein, "alkcycloalkyl" refers to a cycloalkyl group attached to the parent molecular group through an alkylene group.

As used herein, "alkenyl" or "$C_2$-$C_8$ alkenyl" refers to an optionally substituted unsaturated, straight or branched chain hydrocarbon group containing 2-8 carbon atoms and at least one carbon-carbon double bond that can be optionally substituted (e.g., with a phenyl or naphthyl group).

As used herein, "$C_2$-$C_8$ alkenylene" refers to an optionally substituted $C_2$-$C_8$ alkenyl group in which one of the $C_2$-$C_8$ alkenyl group's hydrogen atoms has been replaced with a bond to another group (e.g., aryl, heteroaryl, cycloalkyl, or heterocyclyl).

As used herein, "alkheterocyclyl" refers to a heterocyclic group attached to the parent molecular group through an alkylene group.

As used herein, "alkoxy" refers to a group having the structure —OR, wherein R is selected from —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, or —$C_7$-$C_{14}$ arylalkyl, each of which is optionally substituted.

As used herein, "alkyl" or the prefix "alk" refers to an optionally substituted straight or branched chain saturated hydrocarbon group containing 1-8 carbon atoms. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl, and 1-octyl. A substituted alkyl can be substituted with one or more (e.g., 2, 3, 4, 5, 6, or 7) substituent groups such as -halogen, —$NH_2$, —$NH(C_1$-$C_8$ alkyl), —$N(C_1$-$C_8$ alkyl)$_2$, —OH, —O—($C_1$-$C_8$ alkyl), or $C_6$-$C_{10}$ aryl groups, such as phenyl or naphthyl groups, or any other substituent group described herein.

As used herein, "alkylene" or "$C_1$-$C_8$ alkylene" refers to an optionally substituted $C_1$-$C_8$ alkyl group in which one of the $C_1$-$C_8$ alkyl group's hydrogen atoms has been replaced with a bond to another group (e.g., aryl, heteroaryl, cycloalkyl, or heterocyclyl).

As used herein, "alkynyl" or "$C_2$-$C_8$ alkynyl" refers to an optionally substituted unsaturated, straight or branched chain hydrocarbon group containing 2-8 carbon atoms and at least one carbon-carbon triple bond that can be unsubstituted or optionally substituted. Exemplary substituents on the carbon-carbon triple bond are phenyl or naphthyl.

As used herein, "$C_2$-$C_8$ alkynylene" refers to an optionally substituted $C_2$-$C_8$ alkynyl group in which one of the $C_2$-$C_8$ alkynyl group's hydrogen atoms has been replaced with a bond to another group (e.g., aryl, heteroaryl, cycloalkyl, or heterocyclyl).

As used herein, "amido" refers to a group having a structure selected from —$N(Z)_2$, wherein each Z is selected, independently, from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, —$C_2$-$C_8$ alkynyl, —$C(O)Z_a$, —$C(O)NZ_aR_{7a}$, and —$C(O)OZ_a$, wherein at least one Z is —$C(O)Z_a$, —$C(O)NZ_aR_{7a}$, or —$C(O)OZ_a$, and wherein $Z_a$ and $R_{7a}$ are selected, independently, from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, —$C_2$-$C_8$ alkynyl, each of which is optionally substituted, or Z and $R_{7a}$, or $Z_a$ and $R_{7a}$, together with the atom to which each is attached, join to form an optionally substituted 3- to 7-membered aromatic or non aromatic heterocycle As used herein, "amino" refers to a group having the structure —$NZR_7$, wherein Z and $R_7$ are selected, independently, from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted.

As used herein, "amino acid" refers to a molecular fragment having an amino functional group and a carboxylic functional group. Amino acids include natural amino acids and unnatural amino acids, as defined herein. Types of amino acids include "α-amino acids," wherein the amino and carboxylic groups are attached to the same carbon. In "β-amino acids," the carbon to which the amino group is attached is adjacent to the carbon to which the carboxylic group is attached, and in "γ-amino acids," there is an additional intervening carbon. Amino acids can have the L-configuration (for example, natural amino acids have the L-configuration) or the D-configuration. An amino acid can be attached to a compound of the invention through a covalent attachment to, for example, the carboxylic functional group ("C-terminal linked") or through the amino functional group ("N-terminal linked").

As used herein, "aromatic" refers to a cyclic ring system having $(4n+2)\pi$ electrons in conjugation, where n is 1, 2, or 3.

As used herein, "aromatic carbocyclic" refers to an aryl group.

As used herein, "aryl" or "$C_6$-$C_{12}$ aryl" refers to an optionally substituted monocyclic or bicyclic structure wherein all rings are aromatic and the rings are formed by carbon atoms. Exemplary aryl groups include phenyl and naphthyl. Where an aryl group is substituted, substituents can include any substituent group described herein (e.g., one or more groups selected from F, Cl, Br, I, alkyl groups, alkoxy groups, or a phosphorus (V) containing group). Exemplary phosphorus (V) containing groups include —$(CH_2)_nPO(OZR_7)$, wherein n is 0 to 3, —$(CHR')_nPO(OZR_7)$, wherein n is 0 to 3, and —$(C(R')_2)_nPO(OZR_7)$, wherein n is 0 to 3.

As used herein, "arylalkyl" or "$C_7$-$C_{14}$ arylalkyl" refers to an optionally substituted group having the formula —$(C_x$-alkyl)-$(C_y$-aryl) wherein (x+y) is an integer between 7 and 14 and x is at least 1. Exemplary arylalkyls include benzyl and phenethyl. Where an arylalkyl group is substituted, substituents can include any substituent group described herein (e.g., one or more groups selected from F, Cl, Br, I, alkyl groups, alkoxy groups, or a phosphorus (V) containing group). Exemplary phosphorus (V) containing groups include —$(CH_2)_nPO(OZR_7)$, wherein n is 0 to 3, —$(CHR')_nPO(OZR_7)$, wherein n is 0 to 3, and —$(C(R')_2)_nPO(OZR_7)$, wherein n is 0 to 3.

As used herein, "carbocycle" refers to an optionally substituted $C_3$-$C_{12}$ monocyclic, bicyclic, or tricyclic structure in which the rings are formed by carbon atoms. Carbocycles may be aromatic or may be non-aromatic.

As used herein, "carboxyl" refers to a group having a structure selected from —$C(O)Z$, —$OC(O)Z$, —$OC(O)OZ$, —$OC(O)NZR_7$, —$C(O)NZR_7$, or —$C(O)OZ$, wherein Z and $R_7$ are independently selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, —$C_2$-$C_8$ alkynyl, each of which is optionally substituted, or Z and $R_7$, together with the atom to which each is attached, join to form an optionally substituted 3- to 7-membered aromatic or non aromatic heterocycle.

As used herein, "carrier" or "pharmaceutical carrier" refers to a diluent, adjuvant, excipient, or vehicle with which a compound of the invention is administered. Such pharmaceutical carriers can be liquids, such as water and oils, including those of petroleum, animal, vegetable, or synthetic origin, such as peanut oil, soybean oil, mineral oil, sesame oil, and the like. Saline solutions and aqueous dextrose and glycerol solutions can also be employed as liquid carriers, particularly for injectable solutions. The pharmaceutical carriers can be gum acacia, gelatin, starch paste, talc, keratin, colloidal silica, urea, and the like. In addition, auxiliary, stabilizing, thickening, lubricating, and coloring agents may be used. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, methylcellulose, propylene, glycol, polyethylene glycol 300, water, ethanol, polysorbate 20, wetting or emulsifying agents, or pH buffering agents.

As used herein, "cyano" refers to a group having the structure —CN.

As used herein, "cycloalkyl" or "$C_3$-$C_{12}$ cycloalkyl" refers to an optionally substituted, non-aromatic, saturated or unsaturated monocyclic or polycyclic (e.g., bicyclic or tricyclic) hydrocarbon ring system containing 3-12 carbon atoms. Polycyclic cycloalkyls may be linear, fused, bridged, or spirocyclic. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

An "effective amount" is an amount of a compound of the invention that is effective for treating or preventing pain (e.g., neuropathic pain), inflammation, or epilepsy.

As used herein, "ester" refers to a group having the structure —$C(O)OZ$, wherein Z is selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted.

A "5- to 6-membered ring" is an optionally substituted 5- to 6-membered aromatic or nonaromatic carbocycle or an optionally substituted 5- to 6-membered aromatic or nonaromatic heterocycle. Examples of 5- to 6-membered rings include, but are not limited to, cyclopentyl, cyclopentenyl, cyclopentadienyl, cyclohexyl, cyclohexenyl, cyclohexadienyl, phenyl, diazinanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, purinyl, isoxazolyl, furanyl, furazanyl, pyridinyl, oxazolyl, thiazolyl, thiophenyl, pyrazolyl, triazolyl, and pyrimidinyl, each of which may be substituted or unsubstituted.

As used herein, "haloalkyl" refers to an alkyl group wherein at least one substituent is a halogen. Haloalkyls may also be perhalogenated (e.g., —$CF_3$) or include other substituent groups as described herein.

As used herein, "halogen" refers to —F, —Cl, —Br, or —I.

As used herein, "heteroaryl" or "heteroaromatic" refers to a 3-9 membered heterocycle that is aromatic.

As used herein, a "heterocycle," "heterocyclyl," or "3- to 9-membered heterocycle" is an optionally substituted 3- to 9-membered aromatic or nonaromatic monocyclic or bicyclic ring system that includes one or more carbon atoms and 1 to 4 (e.g., 1, 2, 3, or 4) heteroatoms selected from oxygen, nitrogen, and sulfur. Non-aromatic heterocycles may have one or more double bonds. Examples of double bonds include carbon-carbon double bonds (C=C), carbon-nitrogen double bonds (C=N), and nitrogen-nitrogen double bonds (N=N). Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, diazinanyl, piperidinyl, tetrahydropyridinyl, piperazinyl, morpholinyl, azepinyl or any partially or fully saturated derivatives thereof, diazepinyl or any partially or fully saturated derivatives thereof, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl, and indazolyl. Where a heterocycle group is substituted, substituents include, for example, one or more alkyl groups or a phosphorus (V) containing group.

As used herein, "hydroxy" refers to a group having the structure —OH.

As used herein, "imine" refers to a group having the structure —C(NZ), wherein Z is selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted.

As used herein, "isolated" means that the compounds of the invention are separated from other components of either (a) a natural source, such as a plant or cell, preferably bacterial culture, or (b) a synthetic organic chemical reaction mixture. An isolated compound can be, for example, 10%, 20%, 30%, 40%, 50%, 60%, 70%, 80%, 85%, 90%, 95%, 97%, 98%, or 99% pure.

By "isomer" is meant any tautomer, stereoisomer, enantiomer, or diastereomer of any compound of the invention. Representative isomers include tautomeric isomers, such as compounds having the following structures:

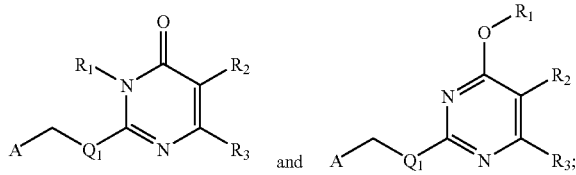

see, e.g., *IUPAC Compendium of Chemical Terminology*, 2nd ed. (Eds. A. D. McNaught and A. Wilkinson, Blackwell Scientific Publications, Oxford, 1997).

As used herein, "ketone" refers to a carboxyl group that has the structure —C(O)Z, wherein Z is selected from —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted.

As used herein, "natural amino acid" refers to an amino acid that is naturally produced or found in a mammal. Natural amino acids can be encoded by the standard genetic code or may result from, for example, post-translational modifications. Natural amino acids include the twenty proteinogenic L-amino acids (Alanine (A), Cysteine (C), Serine (S), Threonine (T), Aspartic Acid (D), Glutamic Acid (E), Asparagine (N), Glutamine (Q), Histidine (H), Arginine (R), Lysine (K), Isoleucine (I), Leucine (L), Methionine (M), Valine (V), Phenylalanine (F), Tyrosine (Y), Tryptophan (W), Glycine (G), and Proline (P)). Other natural amino acids include gamma-aminobutyric acid (GABA; a γ-amino acid), 3,4-dihydroxy-L-phenylalanine (L-DOPA), carnitine, ornithine, citrulline, homoserine, lanthionine, 2-aminoisobutyric acid, and dehydroalanine.

As used herein, "nitro" refers to a group having the structure —$NO_2$.

As used herein, "non-aromatic carbocycle" refers to an optionally substituted monocyclic or polycyclic (e.g., bicyclic, or tricyclic) structure wherein the atoms that form the ring are all carbons and at least one ring does not have 4 n+2π electrons. Carbocycles contain 3-12 carbon atoms. Carbocycles include cycloalkyls, partially unsaturated cycloalkyls (e.g., cycloalkenyls or cyclodienyls), or an aromatic ring fused to a cycloalkyl or partially unsaturated cycloalkyl. In addition to cycloalkyls and partially unsaturated cycloalkyls, exemplary non-aromatic carbocycles include tetrahydronaphthyl.

By "oxo" is meant a group having a structure =O, wherein an oxygen atom makes a double bond to another element such as C, S, or P.

As used herein, "partially unsaturated cycloalkyl" refers to an optionally substituted $C_3$-$C_{12}$ cycloalkyl that has at least one carbon-carbon double bond. Exemplary partially unsaturated cycloalkyls include cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, and cyclooctadienyl.

As used herein, "pharmaceutically acceptable" means approved by a regulatory agency of the federal or a state government or listed in the U.S. Pharmacopeia or other generally recognized pharmacopeia for use in animals, and more particularly in humans. As used herein, "pharmaceutically acceptable salt(s)," includes but are not limited to salts of acidic or basic groups that may be present in compounds used in the present compositions. Exemplary pharmaceutically acceptable salts are described in Berge et al., *J. Pharm. Sci.* 1977; 66:1-19 and in *Pharmaceutical Salts: Properties, Selection, and Use*, (Eds. P. H. Stahl and C. G. Wermuth, Wiley-VCH, 2008). Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, mesylate, hydroxymethylsulfonate, hydroxyethyl sulfonate, and pamoate (i.e., 1,1'-methylene-bis-(2-hydroxy-3-naphthoate)) salts. Similarly, compounds of the invention that include ionizable hydrogens can be combined with various inorganic and organic bases to form salts. Representative alkali or alkaline earth metal salts include sodium, lithium, potassium, calcium, magnesium and the like, as well as nontoxic ammonium, quaternary ammonium, and amine cations, including, but not limited to, ammonium, tetramethylammonium, tetraethylammonium, methylamine, dimethylamine, trimethylamine, triethylamine, ethylamine, and the like.

As used herein, "phosphine" refers to a group having the structure —P($Z_a$)$_3$, wherein each $Z_a$ is selected, independently, from —H, —$C_1$-$C_8$ alkyl, —$C_3$-$C_{12}$ cycloalkyl, —$C_6$-$C_{12}$aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, or any two $Z_a$, together with the atom to which each is attached, join to form a 3- to 7-membered aromatic or non aromatic heterocycle As used herein, "phosphonato" refers to a group having the structure —P(=O)(OZ)$_2$, wherein each Z is, independently, —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, —$C_2$-$C_8$ alkynyl, or two Z, together with the atom to which each is attached, join to form a 3- to 7-membered aromatic or non aromatic heterocycle.

As used herein, a "phosphorus (V) containing group" refers to a group having the structure —(CR'R")$_n$OP(=O)(OZ)(OR$_7$) or —(CR'R")$_n$P(=O)(OZ)(OR$_7$), wherein each R' and R" is, independently, —H or —$C_{1-5}$ alkyl, Z and $R_7$ are independently —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, —$C_2$-$C_8$ alkynyl or two Z, together with the atom to which each is attached, join to form a 3- to 7-membered aromatic or non aromatic heterocycle, and n is 0, 1, 2, or 3. An exemplary phosphorus (V) containing group is a phosphonato group, as described herein. Still other exemplary phosphorus (V) containing groups include —(CH$_2$)$_n$PO(OZR$_7$), wherein n is 0 to 3, —(CHR')$_n$PO(OZR$_7$), wherein n is 0 to 3, and —(C(R')$_2$)$_n$PO(OZR$_7$), wherein n is 0 to 3.

As used herein, the term "prevent" refers to prophylactic treatment or treatment that prevents one or more symptoms or conditions of a disease, disorder, or conditions described herein (e.g., pain such as neuropathic pain or inflammation). Preventative treatment can be initiated, for example, prior to ("pre-exposure prophylaxis") or following ("post-exposure prophylaxis") an event that precedes the onset of the disease, disorder, or conditions (e.g., exposure to a headache trigger, to another cause of pain or inflammation, or to a pathogen). Preventive treatment that includes administration of a compound of the invention, or a pharmaceutical composition thereof, can be acute, short-term, or chronic. The doses administered may be varied during the course of preventative treatment.

As used herein, a "prodrug" is a compound that is rapidly transformed in vivo to the parent compound of the compounds of the invention, for example, by hydrolysis in blood. Prodrugs of the compounds of the invention may be esters, carbamates, phosphorus (III) esters, or phosphorus (V) esters. Some common esters that have been utilized as prodrugs are phenyl esters, aliphatic ($C_7$-$C_8$ or $C_8$-$C_{24}$) esters, cholesterol esters, acyloxymethyl esters, and amino acid esters. Compounds of the invention (e.g., compounds of Formula (Ia) or (IIa)) can be converted to their corresponding prodrugs according to methods known in the art. For example, the phenol group of (Ia) or (IIa) can be treated with an electrophile (e.g., an acid chloride, an anhydride, a carboxylic ester, a carbonate, a carbamyl chloride, or a phosphorus (III) or (V) electrophile) to prepare the corresponding prodrug. Exemplary methods for the preparation of prodrugs are described herein. A thorough discussion is provided in Higuchi & Stella, Pro-drugs as Novel Delivery Systems, in *Bioreversable Carriers in Drug Design*, vol. 14 of the A.C.S. Symposium Series (Ed. Edward B. Roche, American Pharmaceutical Association and Pergamon Press, 1987), and Judkins et al., *Synthetic Commun.* 1996; 26(23):4351-4367, each of which is incorporated herein by reference.

As used herein, "purified" means that when isolated, the isolate contains at least 95%, preferably at least 98%, of a single compound by weight of the isolate.

As used herein and unless otherwise indicated, the term "stereomerically pure" means a composition that includes one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

Any group described herein may be substituted or unsubstituted. When substituted, a group may be substituted with any desired substituent or substituents selected from the following group: halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino (primary, secondary, or tertiary); nitro; thiol; thioether; imine; cyano; amido; carbamoyl; phosphonato; phosphine; a phosphorus (V) containing group; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or non-aromatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups includes benzyloxy; —N(CH$_3$)$_2$; O-alkyl; O-aryl; aryl; aryl-lower alkyl; —CO$_2$CH$_3$; —OCH$_2$CH$_3$; methoxy; —CONH$_2$; —OCH$_2$CONH$_2$; —SO$_2$NH$_2$; —OCHF$_2$; —CF$_3$; and —OCF$_3$. A substituted group may have 1, 2, 3, 4, 5, 6, 7, or 8 substituent groups. These substituent groups may optionally be further substituted with a substituent listed herein. Substituents may also be optionally substituted by a fused-ring structure or bridge, for example —OCH$_2$O—. In other embodiments, these substituents are not further substituted.

The phrase "substantially anhydrous," as used herein in connection with a reaction mixture or an organic solvent, means that the reaction mixture or organic solvent comprises less than about 1 percent of water by weight; in one embodiment, less than about 0.5 percent of water by weight; and in another embodiment, less than about 0.25 percent of water by weight of the reaction mixture or organic solvent.

As used herein, "sulfonamide" refers to a group having a structure selected from —S(O)N(Z)$_2$ or —S(O)$_2$N(Z)$_2$, wherein each Z is, independently, —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted, or two Z, together with the atom to which each is attached, join to form an optionally substituted 3- to 7-membered aromatic or non aromatic heterocycle.

As used herein, "sulfonyl" refers to a group having a structure selected from —S(O)Z, and —S(O)$_2$Z, wherein Z is selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted.

As used herein, "thiocarbonyl" refers to a group having a structure selected from —C(S)Z, —O—C(S)Z, —O—C(S)OZ, —O—C(S)N(Z)$_2$, —C(S)N(Z)$_2$, —C(S)OZ, wherein each Z is, independently, selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_8$ alkynyl, each of which is optionally substituted, or two Z, together with the atom to which each is attached, join to form an optionally substituted 3- to 7-membered aromatic or non aromatic heterocycle.

As used herein, "thioether" refers to a group having the structure —SZ, wherein Z is selected from —H, —$C_1$-$C_8$ alkyl, —$C_3$-$C_{12}$ cycloalkyl, —$C_6$-$C_{12}$ aryl, —$C_7$-$C_{14}$ arylalkyl, 3 to 9-membered aromatic or non aromatic heterocycle, —$C_2$-$C_8$ alkenyl, or —$C_2$-$C_3$ alkynyl, each of which is optionally substituted.

As used herein, "thiol" refers to a group having the structure —SH.

As used herein, and as well understood in the art, "treatment" is an approach for obtaining beneficial or desired results, such as clinical results. Beneficial or desired results can include, but are not limited to, alleviation or amelioration of one or more symptoms or conditions (e.g., pain such as neuropathic pain or inflammation); diminishment of extent of disease, disorder, or condition; stabilization (i.e., not worsening) of state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened as compared to the extent or time course in the absence of treatment.

As used herein, "unnatural amino acid" is an amino acid that is not naturally produced (e.g., encoded by the genetic code or resulting from a posttranslational modification) or naturally found in a mammal. Unnatural amino acids include amino acids that normally do not occur in proteins (e.g., an α-amino acid having the D-configuration, or a (D,L)-isomeric mixture thereof), homologues of naturally occurring amino acids (e.g., β- or γ-amino acid analogue), an α,α-disubstituted analogue of a naturally occurring amino acid, or an α-amino acid wherein the amino acid side chain has been shortened by one or two methylene groups or lengthened to up to 10 carbon atoms. Other unnatural amino acids include γ-amino acids that are GABA analogues, such as (S)-3-(aminomethyl)-5-methylhexanoic acid (pregabalin), 2-[1-(aminomethyl)cyclohexyl]acetic acid (gabapentin), or those described in Yogeeswari et al., *Recent Patents on CNS Drug Discovery* 2006; 1:113-118, herein incorporated by reference.

The following abbreviations and their definitions, unless defined otherwise, are used in this specification:

| Abbreviation | Definition |
|---|---|
| ACN | acetonitrile |
| BOC | —C(O)OC(CH$_3$)$_3$ |
| dba | dibenzylideneacetone |
| DBU | 1,8-diazabicyclo[5.4.0]undec-7-ene |
| DCM | dichloromethane |
| DEF | N,N-diethylformamide |
| DIPEA | N,N-diisopropylethylamine |
| DMAP | 4-dimethylaminopyridine |
| DMF | N,N-dimethylformamide |
| DMSO | dimethylsulfoxide |
| EtOAc | ethyl acetate |
| EtOH | ethanol |
| MTBE | methyl tert-butyl ether |
| MeOH | methanol |
| MeOd$_4$ | CD$_3$OD |
| NBS | N-bromosuccinimide |
| NCS | N-chlorosuccinimide |
| Ph | phenyl |
| TBDMSCl | tert-butyldimethylsilyl chloride |
| TEA | triethylamine |
| TFA | trifluoroacetic acid |
| THF | tetrahydrofuran |
| Tf | —SO$_2$CF$_3$ |

DETAILED DESCRIPTION OF THE INVENTION

The present invention features compounds having the Formula (Ia) and use of these compounds in pharmaceutical compositions and methods of treatment or prevention of disease:

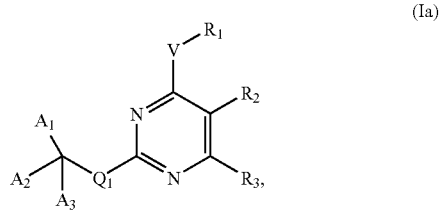

(Ia)

including tautomers, stereoisomers, prodrugs, and pharmaceutically acceptable salts thereof.

In some embodiments, the compounds of (Ia) have structures according to the following formulas:

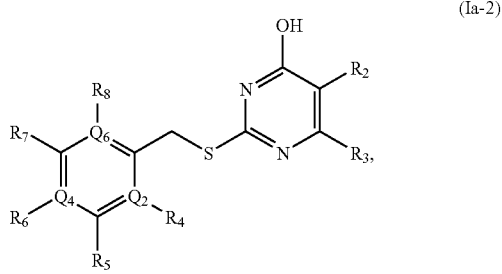

(Ia-2)

(Ia-3)
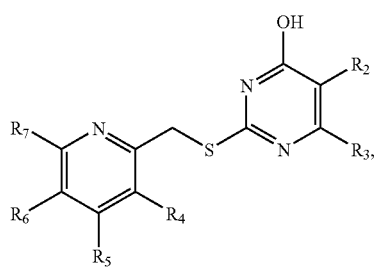
(Ia-4)
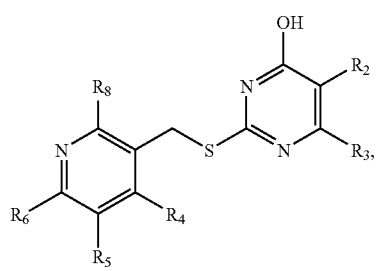
(Ia-5)
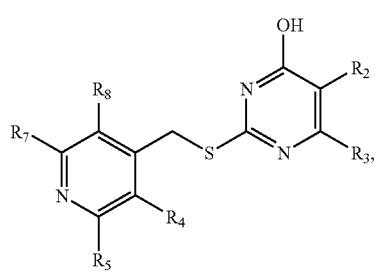
(Ia-6)
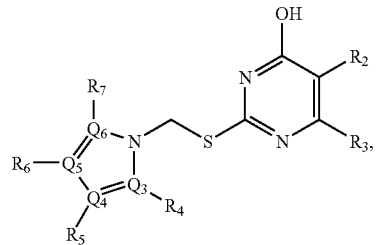
(Ia-7)
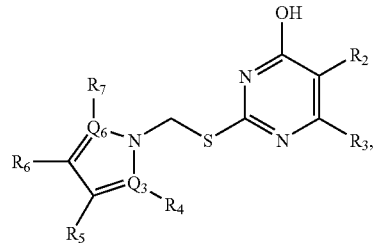
(Ia-8)
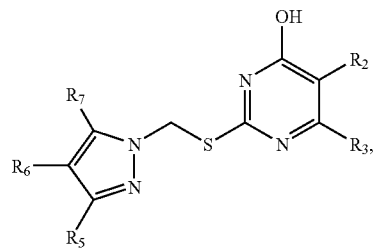
(Ia-9)
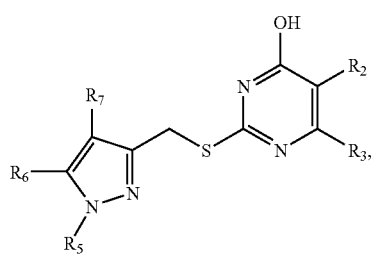
(Ia-10)
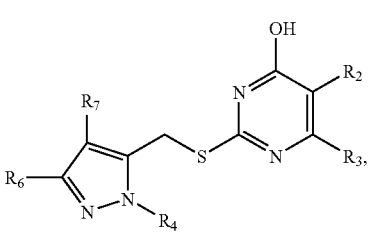
(Ia-11)
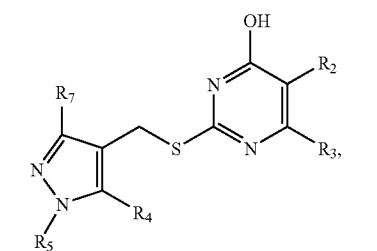
(Ia-12)
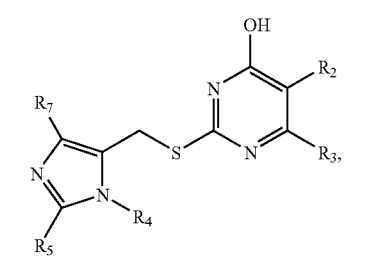
(Ia-13)
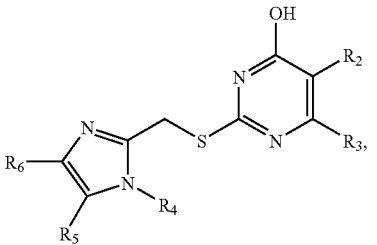
(Ia-14)
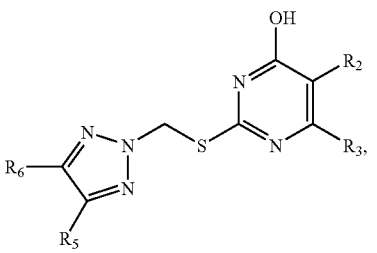

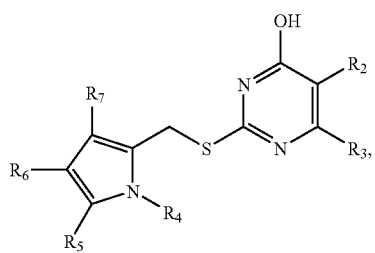
(Ia-15)

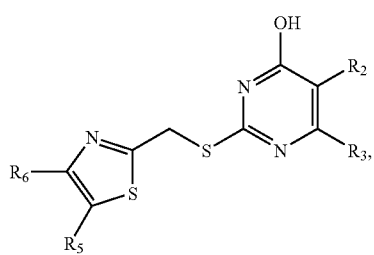
(Ia-16)

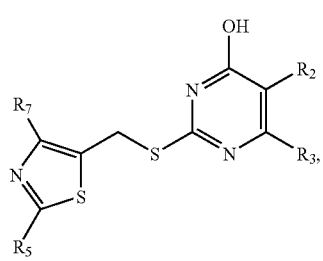
(Ia-17)

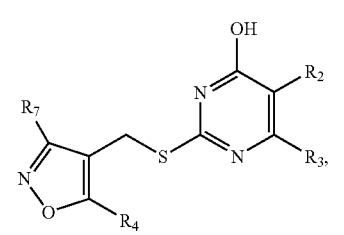
(Ia-18)

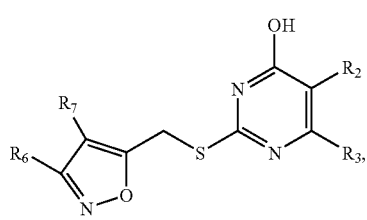
(Ia-19)

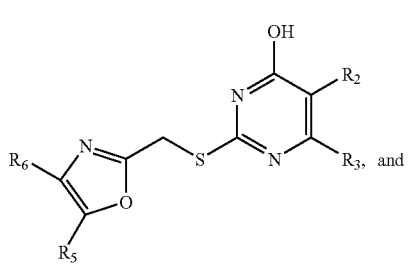
(Ia-20), and

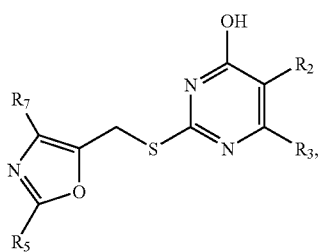
(Ia-21)

including stereoisomers, tautomers, prodrugs, and pharmaceutically acceptable salts thereof.

The invention further provides methods for treating disease by administering a compound having the Formula (IIa), depicted below,

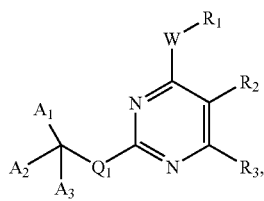
(IIa)

including stereoisomers, tautomers, prodrugs, and pharmaceutically acceptable salts thereof.

In some embodiments, the compound of Formula (IIa) has a structure according to the following formulas

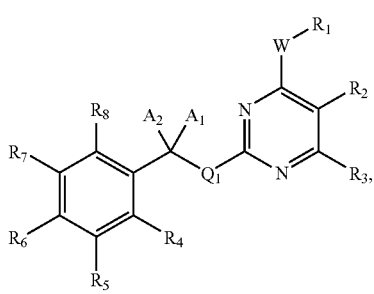
(IIa-2)

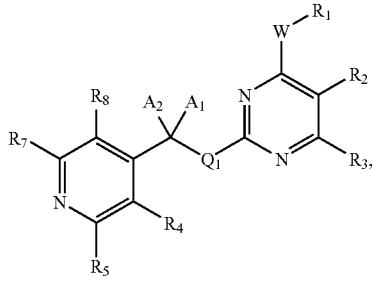
(IIa-3)

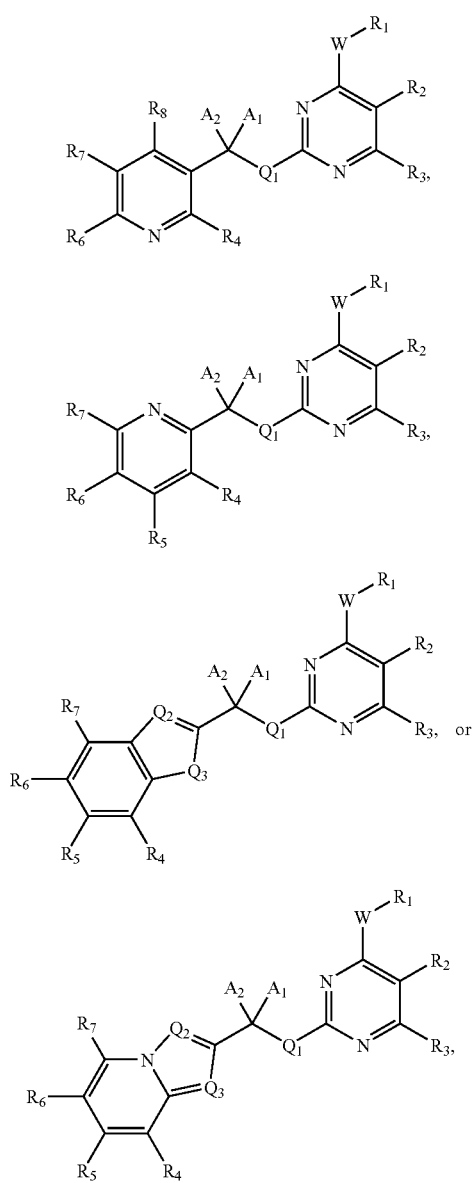

(IIa-4)

(IIa-5)

(IIa-6-1)

(IIa-6-2)

including stereoisomers, tautomers, prodrugs, and pharmaceutically acceptable salts thereof.

Exemplary compounds of the invention are shown herein.

Synthesis

In general, the compounds of the invention can be obtained via standard, well-known synthetic methodology (e.g., March's Advanced Organic Chemistry: Reactions, Mechanisms, and Structure, 6$^{th}$ ed., 2007). Illustrative methods are described below. Starting materials useful for preparing the compounds of the invention and intermediates therefore, are commercially available or can be prepared from commercially available materials using known synthetic methods and reagents. It is understood that the methods of synthesis provided below also encompass the synthesis of isomers and tautomers (e.g., compounds having structures according to Formulas (Ib) and (IIb)).

An example of a synthetic pathway useful for making the compounds is set forth below and generalized in Scheme 1. The compounds of Formula (Ia) or (IIa) can be obtained via conventional organic synthesis, e.g., as described below. Scheme 1 indicates a general method by which the compounds can be obtained, wherein $Q_1$, W (which is V for Ia), $A_{1-3}$, and $R_{1-3}$ are defined above for the compounds of Formula (Ia) and (IIa).

Scheme 1

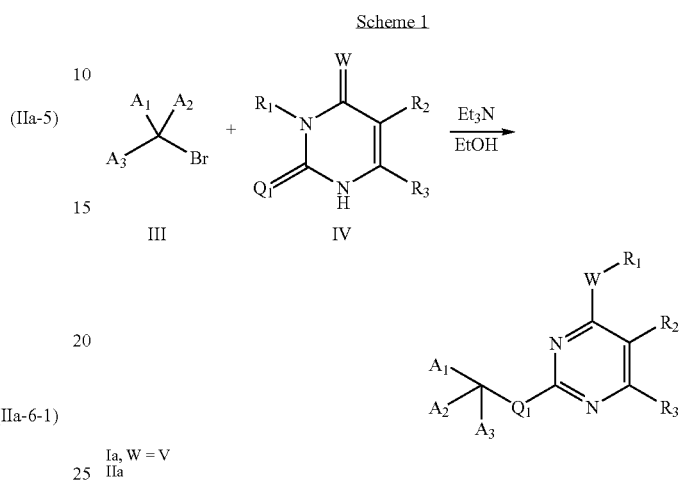

Ia, W = V
IIa

For example, a commercially available or synthetically prepared compound of Formula (IV) is subjected to alkylation reaction with a commercially available or synthetically prepared compound of Formula (III) under basic conditions in a polar solvent such as ethanol.

A second example of a synthetic pathway useful for making the compounds is set forth below and generalized in Scheme 2. The compounds of Formula (Ia) or (IIa) can be obtained via conventional organic synthesis, e.g., as described below. Scheme 2 provides a second general method by which the compounds can be obtained, wherein $Q_1$, W (which is V for Ia), $A_{1-3}$, and $R_{1-3}$ are defined above for the compounds of Formula (Ia) and (IIa).

Scheme 2

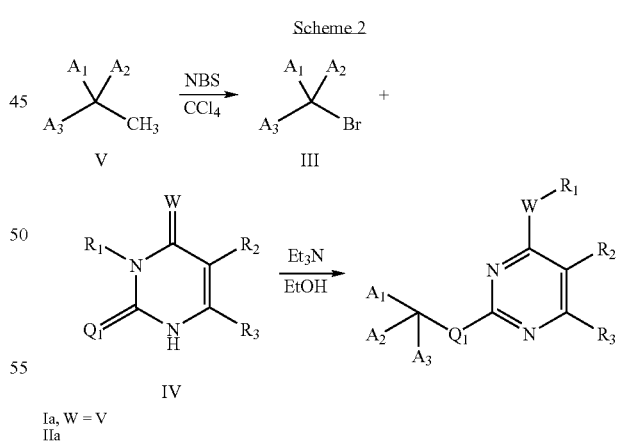

Ia, W = V
IIa

For example, a commercially available or synthetically prepared compound of Formula (IV) is subjected to alkylation reaction with a compound of Formula (III), which itself is obtained from free radical bromination of a suitably functionalized compound of Formula (V) with, for example, NBS in a solvent such as $CCl_4$.

Scheme 3 provides a variation of scheme 2 for the preparation of compounds of Formula (Ia) and (IIa) when $A_1$ and $A_2$ are both —H, wherein $Q_1$, Z, W (which is V for Ia), $A_3$, and $R_{1-3}$ are defined above for the compounds of Formula (Ia) and (IIa). Hence, the prerequisite intermediate of Formula (III) is obtained following treatment with a Lewis acid, such as $BBr_3$, of a compound of Formula (VI), which itself was obtained via reduction of a commercially available or synthetically prepared compound of Formula (VII) with a reducing agent, such as $NaBH_4$, in a solvent, such as methanol.

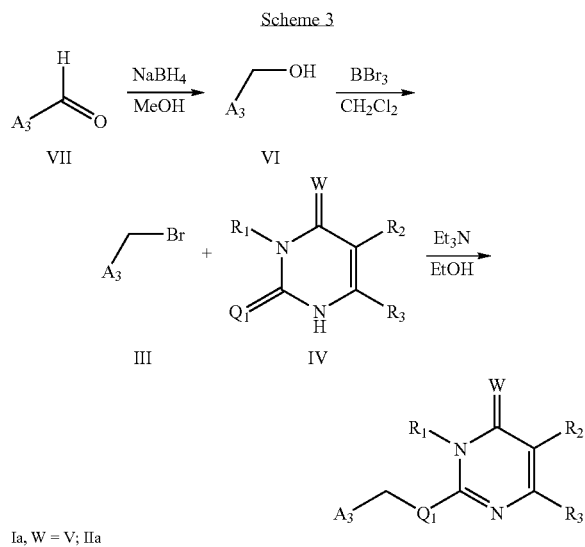

The formation of a compound of Formula (Ia) or (IIa) can be monitored using conventional analytical techniques, including, but not limited to, thin-layer chromatography, high-performance liquid chromatography, gas chromatography, and nuclear magnetic resonance spectroscopy, such as $^1H$ or $^{13}C$ NMR.

Therapeutic/Prophylactic Use

Because of their activity, the compounds of the invention are advantageously useful in veterinary and human medicine. For example, the compounds described herein are useful for the treatment or prevention of pain, inflammation, or epilepsy.

The invention provides methods of treatment and prophylaxis by administration to a patient of an effective amount of a compound described herein. The patient is an animal, including, but not limited to, a human, mammal (e.g., cow, horse, sheep, pig, cat, dog, mouse, rat, rabbit, mouse, or guinea pig), or other animal, such as a chicken, turkey, or quail.

The present compositions, which include an effective amount of a compound of the invention, can be administered by any convenient route, for example by infusion or bolus injection, by absorption through epithelial or mucocutaneous linings (e.g., oral mucosa, rectal and intestinal mucosa, etc.) and can be administered alone or together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or filters. In one embodiment, administration can be by direct injection at the site (or former site) of an injury. In another embodiment, administration can be by direct injection at the site (or former site) of an infection, tissue or organ transplant, or autoimmune response.

In certain embodiments, it may be desirable to introduce one or more compounds of the invention into the central nervous system by any suitable route, including intraventricular or intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulating with an aerosolizing agent, or via perfusion in a fluorocarbon or synthetic pulmonary surfactant. In certain embodiments, the compounds of the invention can be formulated as a suppository, with traditional binders and carriers, such as triglycerides.

In another embodiment, the compounds of the invention can be delivered in a vesicle, in particular a liposome (see Langer, *Science* 1990; 249:1527-1533; Treat et al., in *Liposomes in the Therapy of Infectious Disease and Cancer*, pp. 353-365 (Eds. Lopez-Berestein and Fidler, Liss, New York, (1989); Lopez-Berestein, ibid., pp. 317-327; see generally ibid.).

In yet another embodiment, the compounds of the invention can be delivered in a controlled-release system. In one embodiment, a pump may be used (see Langer, supra; Sefton, *CRC Crit. Ref Biomed. Eng.* 1987; 9:201; Buchwald et al., *Surgery* 1980; 88:507; and Saudek et al., *N. Engl. J. Med.* 1989; 321:574). In another embodiment, polymeric materials can be used (see *Medical Applications of Controlled Release* (Eds. Langer and Wise, CRC Press, Boca Raton, Fla., 1974); *Controlled Drug Bioavailability, Drug Product Design and Performance* (Eds. Smolen and Ball, Wiley, New York, 1984); and Ranger and Peppas, *J. Macromol. Sci. Rev. Macromol. Chem.* 1983; 23:61; see also Levy et al., *Science* 1985; 228: 190; During et al., *Ann. Neurol.* 1989; 25:351; and Howard et al., *J. Neurosurg.* 1989; 71:105). In yet another embodiment, a controlled-release system can be placed in proximity of the target of the compounds of the invention, e.g., the brain, thus requiring only a fraction of the systemic dose (see, e.g., Goodson in *Medical Applications of Controlled Release*, vol. 2, pp. 115-138, supra). Other controlled-release systems discussed in the review by Langer (*Science* 1990; 249:1527-1533) may be used.

Pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. In addition, auxiliary, stabilizing, thickening, lubricating, and coloring agents may be used. When administered to a patient, the compounds of the invention and pharmaceutically acceptable carriers can be sterile. In one embodiment, water is a carrier when the compound is administered intravenously. Saline solutions and aqueous dextrose and glycerol solutions can also be employed as liquid carriers, particularly for injectable solutions. Suitable pharmaceutical carriers also include excipients, such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, methylcellulose, water, ethanol, polysorbate 20, and the like. The present compositions, if desired, can also contain minor amounts of wetting or emulsifying agents, or pH buffering agents.

In one embodiment, compounds described herein (e.g., a compound of Formula (Ia) or (IIa)), or a tautomer, stereoisomer, prodrug, or a pharmaceutically acceptable salt thereof, are formulated in 10 to 40% of a sulfobutylether β-cyclodextrin (Captisol®) or in 10 to 40% hydroxypropyl-β-cyclodextrin, optionally with precipitation inhibitors, such as hydroxypropylmethylcellulose.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in *Remington's Pharmaceutical Sciences* by E. W. Martin.

Compounds of the invention included in the present compositions that include an amino moiety may form pharmaceutically acceptable salts with various amino acids, in addition to the acids mentioned above. Compounds included in the present compositions that are acidic in nature are capable of forming base salts with various pharmacologically or cosmetically acceptable cations. Examples of such salts include alkali metal or alkaline earth metal salts and, particularly, calcium, magnesium, sodium, lithium, zinc, potassium, and iron salts.

In another embodiment, the compounds of the invention are formulated in accordance with routine procedures as a pharmaceutical composition adapted for intravenous administration to human beings. Typically, compounds for intravenous administration are solutions in sterile isotonic aqueous buffer. Where necessary, the compositions may also include a solubilizing agent. Compositions for intravenous administration may optionally include a local anesthetic, such as lignocaine to ease pain at the site of the injection. Generally, the ingredients are supplied either separately or mixed together in unit dosage form, for example, as a dry lyophilized powder or water free concentrate in a hermetically sealed container, such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents, such as fructose, aspartame or saccharin; flavoring agents, such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material, such as glycerol monostearate or glycerol stearate, may also be used. Oral compositions can include standard carriers, such as mannitol, lactose, starch, magnesium stearate, sodium saccharine, cellulose, or magnesium carbonate. Such carriers can be of pharmaceutical grade.

The amount of the compound of the invention that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable effective dosage ranges for intravenous (i.v.) administration are generally about 0.001 to about 5 g, preferably about 0.001 to about 1 g of the compound per kilogram body weight. In specific embodiments, the i.v. dose is about 0.001 to about 0.5 g/kg, about 0.01 to about 0.3 g/kg, about 0.025 to about 0.25 g/kg, about 0.04 to about 0.20 g/kg, or about 0.05 to about 0.20 g/kg (or the equivalent doses expressed per square meter of body surface area). Alternatively, a suitable dose range for i.v. administration may be obtained using doses of about 1 to about 2000 mg, without adjustment for a patient's body weight or body surface area. Suitable dosage ranges for intranasal administration are generally about 0.01 pg/kg body weight to 10 mg/kg body weight. Suppositories generally contain 0.5% to 20% by weight of one or more compounds of the invention alone or in combination with another therapeutic agent. Oral compositions can contain about 10% to about 95% by weight of one or more compounds alone or in combination with another therapeutic agent. In specific embodiments of the invention, suitable dose ranges for oral administration are generally about 0.1 to about 200 mg, preferably about 0.5 to about 100 mg, and more preferably about 1 to about 50 mg of pyrimidine heterocycle per kilogram body weight or their equivalent doses expressed per square meter of body surface area. In specific embodiments, the oral dose is about 0.25 to about 75 mg/kg, about 1.0 to about 50 mg/kg, about 2.0 to about 25 mg/kg, about 2.5 to about 15 mg/kg, or about 5.0 to about 20 mg/kg (or the equivalent doses expressed per square meter of body surface area). In another embodiment, a suitable dose range for oral administration is from about 10 to about 4000 mg, without adjustment for a patient's body weight or body surface area. Other effective doses may be extrapolated from dose-response curves derived from in vitro or animal model test systems. Such animal models and systems are well known in the art.

The invention also provides pharmaceutical packs or kits comprising one or more containers containing one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In certain embodiments, e.g., when administered for the treatment or prevention of pain, the kit may also contain one or more analgesic agents useful for treating pain to be administered in combination with a pyrimidine heterocycle. The compounds of the invention are preferably assayed in vivo, for the desired therapeutic or prophylactic activity, prior to use in humans. For example, in vivo assays can be used to determine whether administration of a specific compound or combination of compounds is preferred.

Inhibition of Pain

Pain can be treated or prevented by administration of an effective amount of a compound of the invention. The compounds may be demonstrated to inhibit pain by using the procedures described by Decosterd & Woolf (*Pain* 2000; 87(2):149-58). Experimental details are provided in the Examples section.

Exemplary pain conditions that can be treated or prevented include, but are not limited to: musculoskeletal pain (e.g., back and leg pain, neck, shoulder and arm pain, whiplash injuries, motor vehicle, work-related and sports injuries, pre- or postoperative pain syndromes, cervicogenic headache, pain due to arthritis, myofascial pain, or fibromyalgia), cancer pain (e.g., primary or metastatic cancer pain or medication side effect management), vascular pain, Raynaud's disease, psychogenic pain, trigeminal neuralgia, spinal cord injury, spasticity, post dural puncture headache, pelvic pain, or neuropathic pain (e.g., Complex Regional Pain Syndrome (RSD), postherpetic neuralgia (shingles), peripheral neuralgia, nerve injuries, phantom limb pain, or AIDS-related pain). Pain can be acute or chronic. The compounds of the invention can be used to treat or prevent acute or chronic pain associated with any of the following conditions: musculoskeletal disorders (e.g., osteoarthritis/degenerative joint disease/spondylosis, rheumatoid arthritis, Lyme disease, Reiter syndrome, disk herniation/facet osteoarthropathy, fractures/compression fracture of lumbar vertebrae, faulty or poor posture, fibromyalgia, polymyalgia rheumatica, mechanical low back pain, chronic coccygeal pain, muscular strains and sprains, pelvic floor myalgia (levator ani spasm), Piriformis syndrome, rectus tendon strain, hernias (e.g., obturator, sciatic, inguinal, femoral, spigelian, perineal, or umbilical), abdominal wall myofascial pain (trigger points), chronic overuse syndromes (e.g., tendinitis, bursitis)), neurological disorders (e.g., brachial plexus traction injury, cervical radiculopathy, thoracic outlet syndrome, spinal stenosis, arachnoiditis, metabolic deficiency myalgias, polymyositis, neoplasia of spinal cord or sacral nerve, cutaneous nerve entrapment in surgical scar, postherpetic neuralgia (shingles), neuralgia (e.g., iliohypogastric, ilioinguinal, or genitofemoral nerves), polyneuropathies, polyradiculoneuropathies, mononeuritis multiplex, chronic daily headaches, muscle tension headaches, migraine headaches, temporomandibular joint dysfunction, temporalis tendonitis, sinusitis, atypical facial pain, trigeminal neuralgia, glossopharyngeal neuralgia, nervus intermedius neuralgia, sphenopalatine neuralgia, referred dental or temporomandibular joint pain, abdominal epilepsy, or abdominal migraine), urologic disorders (e.g., bladder neoplasm, chronic urinary tract infection, interstitial cystitis, radiation cystitis, recurrent cystitis, recurrent urethritis, urolithiasis, uninhibited bladder contractions (detrusor-sphincter dyssynergia), urethral diverticulum, chronic urethral syndrome, urethral carbuncle, prostatitis, urethral stricture, testicular torsion, or Peyronie disease)), gastrointestinal disorders (e.g., chronic visceral pain syndrome, gastroesophageal reflux, peptic ulcer disease, pancreatitis, chronic intermittent bowel obstruction, colitis, chronic constipation, diverticular disease, inflammatory bowel disease, or irritable bowel syndrome), reproductive disorders (e.g., adenomyosis, endometriosis, adhesions, adnexal cysts, atypical dysmenorrhea or ovulatory pain, cervical stenosis, chlamydial endometritis or salpingitis, chronic ectopic pregnancy, chronic endometritis, endometrial or cervical polyps, endosalpingiosis, from a intrauterine contraceptive device, leiomyomata, ovarian retention syndrome (residual ovary syndrome), ovarian remnant syndrome, ovarian dystrophy or ovulatory pain, pelvic congestion syndrome, postoperative peritoneal cysts, residual accessory ovary, subacute salpingo-oophoritis, symptomatic pelvic relaxation (genital prolapse), or tuberculous salpingitis), psychological disorders (e.g., bipolar personality disorders, depression, porphyria, or sleep disturbances), cardiovascular disease (e.g., angina), peripheral vascular disease, or from chemotherapeutic, radiation, or surgical complications.

Treatment or Prevention of Pain Further Comprising Administering Other Pain Control Agents Methods may include the administration of one or more additional pain control agent, including, but not limited to, gababentin, morphine, oxycodone, fentanyl, pethidine, methadone, propoxyphene, hydromorphone, hydrocodone, codeine, meperidine, gabapentin, pregabalin, lidocaine, ketamine, or capsaicin; anticonvulsants, such as valproate, oxcarbazepine, or carbamazepine; tricyclic antidepressants, such as amitriptyline, duloxetine, venlafaxine, or milnacipran; or serotonin-norepinephrine reuptake inhitors (SNRIs), such as bicifadine, desipramine, desvenlafaxine, duloxetine, milnacipran, nefazodone, sibutramine, or venlafaxine.

Treatment or Prevention of Inflammation

Inflammation can be treated or prevented by administration of an effective amount of a compound of the invention. The compounds of the invention can also be used to treat or prevent pain that results from inflammation. Inflammatory pain can be acute or chronic. Exemplary conditions associated with inflammatory pain include, but are not limited to: osteoarthritis, rheumatoid arthritis, autoimmune conditions, burns, extreme cold, excessive stretching, fractures, infections, pancreatitis, penetration wounds, and vasoconstriction.

Treatment or Prevention of Seizures

Seizures can be treated or prevented by administration of an effective amount of a compound of the invention. The compounds may be demonstrated to inhibit seizures by using the procedures described by Barton et al., *Epilepsy Res.* 2001; 47(3):217-27). Experimental details are provided in the Examples section.

Exemplary pain conditions that can be treated or prevented include, but are not limited to: seizures, seizure disorders, epilepsy, status epilepticus, chronic epilepsy, and episodic seizures.

Treatment or Prevention of Seizures Further Comprising Administering Other Seizure Control Agents Methods may include the administration of one or more additional seizure control agent, including, but not limited to, carbamazepine, clorazepate, clonazepam, ethosuximide, felbamate, fosphenyloin, gabapentin, lacosamide, lamotrigine, levetiracetam, oxcarbazepine, phenobarbital, phenyloin, pregabalin, primidone, tiagabine, topiramate, valproate semisodium, valproic acid, zonisamide, clobazam, vigabatrin, retigabine, brivaracetam, seletracetam, diazepam, lorazepam, paraldehyde, midazolam, pentobarbital, acetazolamide, progesterone, adrenocorticotropic hormone, corticotropic steroid hormones, and bromide.

Prodrugs

The present invention also provides prodrugs of the compounds of the invention. Prodrugs include derivatives of compounds that can hydrolyze, oxidize, or otherwise react under biological conditions (in vitro or in vivo) to provide an active compound of the invention. Examples of prodrugs include, but are not limited to, derivatives and metabolites of a compound of the invention that include biohydrolyzable moieties, such as biohydrolyzable amides, biohydrolyzable esters, biohydrolyzable carbamates, biohydrolyzable carbonates, and biohydrolyzable phosphate analogues. In certain embodiments, prodrugs of the compounds of the invention with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Ed. Donald J. Abraham, Wiley, 2001) and *Design and Application of Prodrugs* (Ed. H. Bundgaard, Harwood Academic Publishers Gmfh, 1985). Biohydrolyzable moieties of a compound of the invention either do not interfere with the biological activity of the compound but can confer upon that compound advantageous property in vivo, such as uptake, duration of action, or onset of action or are biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

EXAMPLES

Synthesis of Representative Compounds of Formula (Ia) and (IIa)

Compounds of Formula (Ia) and (IIa) can be prepared by using the general procedures described earlier in Scheme 1-3 and further exemplified below.

Example 1

2-{[(2-chloro-4-methoxyphenyl)methyl]sulfanyl}-6-methylpyrimidin-4-ol

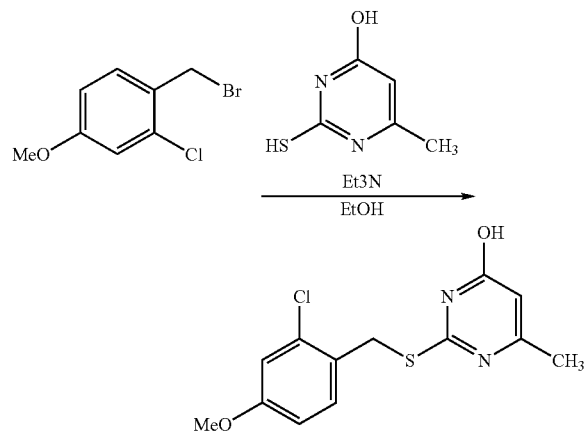

A mixture of 1-(bromomethyl)-2-chloro-4-methoxybenzene (1.0 g, 4.2 mmol), 6-methyl-2-sulfanylpyrimidin-4-ol (550 mg, 3.9 mmol), and triethylamine (585 μL, 4.2 mmol) in absolute ethanol (20 mL) was stirred at room temperature overnight. The product was recovered by filtration, washed with water (2×20 mL) and diethyl ether (2×20 mL), and dried in vacuo, affording the title compound (929 mg, 81% yield); $^1$H NMR (400 MHz, DMSO-$d_6$): δ 2.07 (s, 3H), 3.76 (s, 3H), 4.41 (s, 2H), 6.00 (s (br), 1H), 6.89 (dd, 1H, J=2.5 Hz, 8.6 Hz), 7.07 (d, 1H, J=8.6 Hz), 7.52 (d, 1H, J=8.6 Hz); M+ 297.

Example 2

2-{[(2-chloro-6-fluorophenyl)methyl]sulfanyl}-6-methylpyrimidin-4-ol

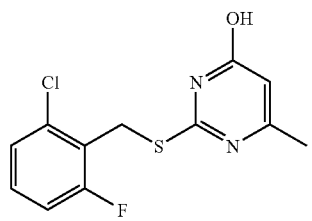 [SMILES: Cc1cc(O)nc(SCc2c(F)cccc2Cl)n1]

As per procedure from Example 1, 2-(bromomethyl)-1-chloro-3-fluorobenzene and 6-methyl-2-sulfanylpyrimidin-4-ol were reacted together to provide the title compound as a white solid (1.04 g, 82% yield); $^1$H NMR (400 MHz, DMSO-$d_6$): δ 2.19 (s, 3H), 4.53 (s, 2H), 6.01 (bs, 1H), 7.26 (m, 1H), 7.38 (m, 2H); M+ 282.06.

Example 3

2-{[(2,6-difluorophenyl)methyl]sulfanyl}-6-methylpyrimidin-4-ol

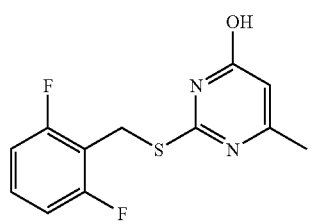 [SMILES: Cc1cc(O)nc(SCc2c(F)cccc2F)n1]

As per procedure from Example 1, the title compound was prepared from 2-(bromomethyl)-1,3-difluorobenzene and 6-methyl-2-sulfanylpyrimidin-4-ol to provide the title compound as a white solid (1.02 g, 79% yield); $^1$H NMR (400 MHz, DMSO-$d_6$): δ 2.04 (s, 3H), 4.42 (s, 2H), 6.01 (bs, 1H), 7.12 (m, 2H), 7.38 (m, 1H), 12.29 (2 bs); M+ 268.8.

Example 4

2-{[(2,3,6-trichlorophenyl)methyl]sulfanyl}pyrimidin-4-ol

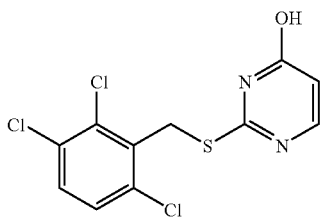 [SMILES: Oc1ccnc(SCc2c(Cl)ccc(Cl)c2Cl)n1]

As per procedure from Example 1, this compound was prepared from 2-(bromomethyl)-1,3,4-trichlorobenzene and 2-sulfanylpyrimidin-4-ol to provide the title compound as a white solid (1.04 g, 89% yield); $^1$H NMR (400 MHz, DMSO-d$_o$): δ 4.72 (s, 2H), 6.21 (bs, 1H), 7.58 (d, J=8.8 Hz 1H), 7.68 (d, J=8.8 Hz 1H), 8.02 (bs, 1H); M+ 322.8.

Example 5

6-methyl-2-{[(2,3,6-trichlorophenyl)methyl]sulfanyl}pyrimidin-4-amine

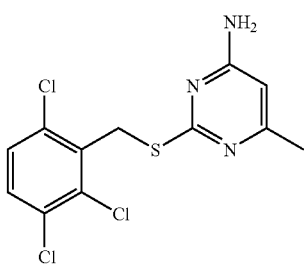 [SMILES: Cc1cc(N)nc(SCc2c(Cl)ccc(Cl)c2Cl)n1]

In a 100 mL round bottom flask, 2-(bromomethyl)-1,3,4-trichlorobenzene (550 mg, 2.0 mmol), 4-amino-6-methylpyrimidine-2-thiol (282 mg, 2.0 mmol), and triethylamine (0.28 mL, 2.0 mmol) were mixed in ethanol (10 mL). The reaction mixture was stirred at room temperature for 2 hours. The solvent was evaporated. To the crude solid, water (50 mL) was added. The suspension was filtered and washed with water and ethyl acetate to provide a white solid (530 mg, 95% yield); $^1$H NMR (400 MHz, DMSO-d$_6$): δ 2.18 (s, 3H), 4.65 (s, 2H), 6.03 (s, 1H), 6.90 (br, 1H), 7.55 (d, 1H), 7.64 (d, 1H); M+ 334, 336.

Example 6

6-methyl-2-[(pyridin-2-ylmethyl)sulfanyl]pyrimidin-4-ol

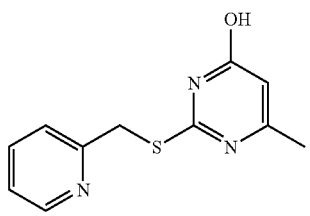 [SMILES: Cc1cc(O)nc(SCc2ccccn2)n1]

As per procedure from Example 1, 2-(bromomethyl)pyridine hydrobromide and 6-methyl-2-sulfanylpyrimidin-4-ol were combined to provide the title compound as a white solid (86% yield); $^1$H NMR (400 MHz, DMSO-d$_6$): δ 2.68 (s, 3H), 4.47 (s, 2H), 6.00 (s, 1H), 7.25 (dd, 1H), 7.47 (d, 1H), 7.72 (dd, 1H), 8.50 (d, 1H); M+ 234.

Example 7

6-amino-2-{[(2,3,6-trichlorophenyl)methyl]sulfanyl}pyrimidin-4-ol

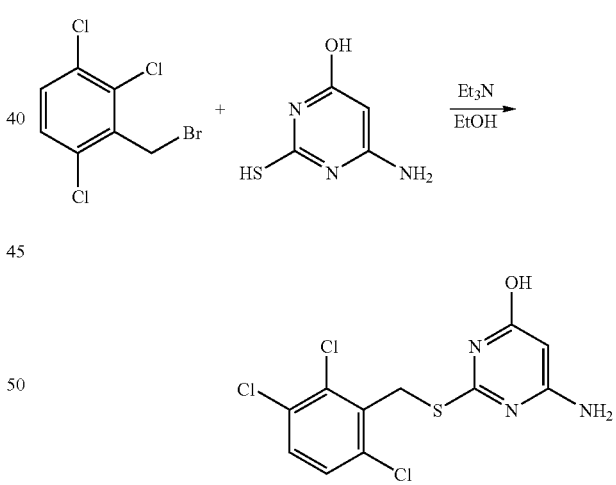

A mixture of 2-(bromomethyl)-1,3,4-trichlorobenzene (580 mg, 2.1 mmol), 6-amino-2-sulfanylpyrimidin-4-ol (290 mg, 1.8 mmol), and triethylamine (280 μL, 2.0 mmol) in absolute ethanol (10 mL) was stirred at room temperature overnight. The solvent was evaporated under reduced pressure. The solid product was suspended in water (50 mL). The solid material was recovered by filtration, washed with water (1×20 mL) and diethyl ether (2×20 mL), and dried in vacuo, affording the title compound (325 mg, 54% yield); $^1$H NMR (400 MHz, DMSO-d$_6$): δ 4.64 (s, 2H), 5.03 (s, 1H), 6.57 (s (br), 2H), 7.54 (d, 1H, J=8.8 Hz), 7.64 (d, 1H, J=8.8 Hz); M+ 337; HPLC purity: 95.5%.

Example 8

3,6-dimethyl-2-{[(2,3,6-trichlorophenyl)methyl]sulfanyl}-3,4-dihydropyrimidin-4-one

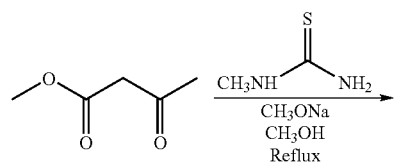

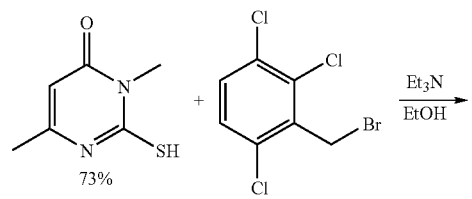

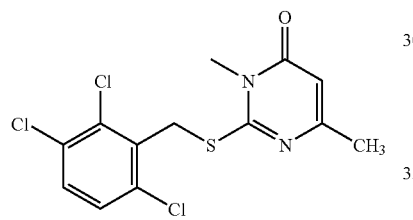

Methyl 3-oxobutanoate (2 mL, 18.5 mmol) was added dropwise to a solution of sodium methoxide (25% wt in MeOH, 5 mL) and anhydrous MeOH (20 mL). N-methyl thiourea (1.67 g, 18.5 mmol) was added to the reaction mixture. The resulting solution was stirred at reflux for 5 hours. After cooling to room temperature, the solvent was evaporated. The residue was dissolved in water (25 mL), and the solution was acidified to pH 2-3 with concentrated HCl. The solid material was recovered by filtration, washed with water (2×20 mL) and diethyl ether (1×30 mL), and dried in vacuo, affording 3,6-dimethyl-2-sulfanyl-3,4-dihydropyrimidin-4-one (2.16 g, 73% yield). The product was used without further purification.

A mixture of 2-(bromomethyl)-1,3,4-trichlorobenzene (576 mg, 2.1 mmol), 3,6-dimethyl-2-sulfanyl-3,4-dihydropyrimidin-4-one (300 mg, 1.9 mmol), and triethylamine (280 μL, 2.0 mmol) in absolute ethanol (10 mL) was stirred at room temperature overnight. The solvent was evaporated under reduced pressure. The solid product was suspended in water (30 mL). The solid material was recovered by filtration, washed with water (2×10 mL) and hexanes (2×20 mL), and dried in vacuo, affording the title compound (475 mg, 72% yield); $^1$H NMR (400 MHz, DMSO-$d_6$): δ 2.20 (s, 3H), 3.31 (s, 3H), 4.77 (s, 2H), 6.08 (s, 1H), 7.57 (d, 1H, J=8.8 Hz), 7.68 (d, 1H, J=8.8 Hz); M+ 350; HPLC purity: 95.8%.

Example 9

6-methyl-2-[(pyridin-3-ylmethyl)sulfanyl]pyrimidin-4-ol hydrochloride

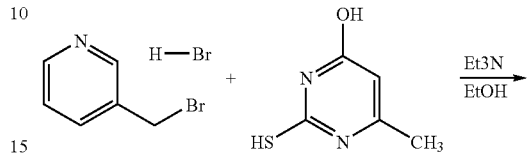

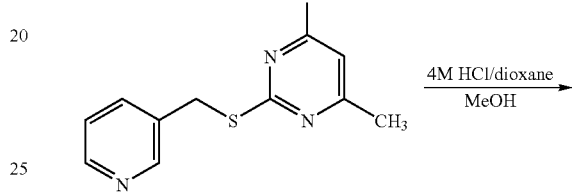

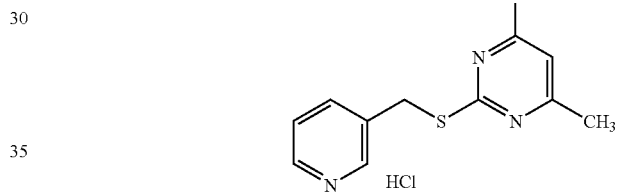

A mixture 3-(bromomethyl)pyridin-1-ium bromide (550 mg, 2.5 mmol), 6-methyl-2-sulfanylpyrimidin-4-ol (285 mg, 2.0 mmol), and triethylamine (1.1 mL, 8.0 mmol) in absolute ethanol (10 mL) was stirred at room temperature overnight. The solid residue was removed by filtration. The filtrate was recovered and evaporated under reduced pressure. The solid product was suspended in acetone (50 mL). The solid material was removed by filtration. The filtrate was recovered and evaporated to dryness. The residue was suspended in water (50 mL). The product was recovered by filtration, washed with diethyl ether (2×20 mL), and dried in vacuo, affording 6-methyl-2-[(pyridin-3-ylmethyl)sulfanyl]pyrimidin-4-ol (181 mg, 39% yield); $^1$H NMR (400 MHz, DMSO-$d_6$): δ 2.19 (s, 3H), 4.36 (s, 2H), 6.00 (s (br), 1H), 7.32 (td, 1H, J=0.8 Hz, 7.8 Hz), 7.82 (dd, 1H, J=0.8 Hz, 7.8 Hz), 8.42 (dd, 1H, J=0.8 Hz, 4.7 Hz), 8.61 (d, 1H, J=1.8 Hz); M+ 234; HPLC purity: 98.1%.

To a solution of 6-methyl-2-[(pyridin-3-ylmethyl)sulfanyl]pyrimidin-4-ol (153 mg, 0.66 mmol) in MeOH (3 mL) was added 4 M HCl/dioxane (1 mL, 4.0 mmol). The mixture was evaporated and dried in vacuo, affording the title compound (176 mg, 99% yield); $^1$H NMR (400 MHz, DMSO-$d_6$): δ 2.23 (s, 3H), 4.52 (s, 2H), 6.09 (s (br), 1H), 8.03 (td, 1H, J=5.9 Hz, 8.0 Hz), 8.68 (d, 1H, J=8.2 Hz), 8.81 (d, 1H, J=5.3 Hz), 9.05 (s, 1H); M+ 234.

Example 10

6-methyl-2-[(thiophen-3-ylmethyl)sulfanyl]pyrimidin-4-ol

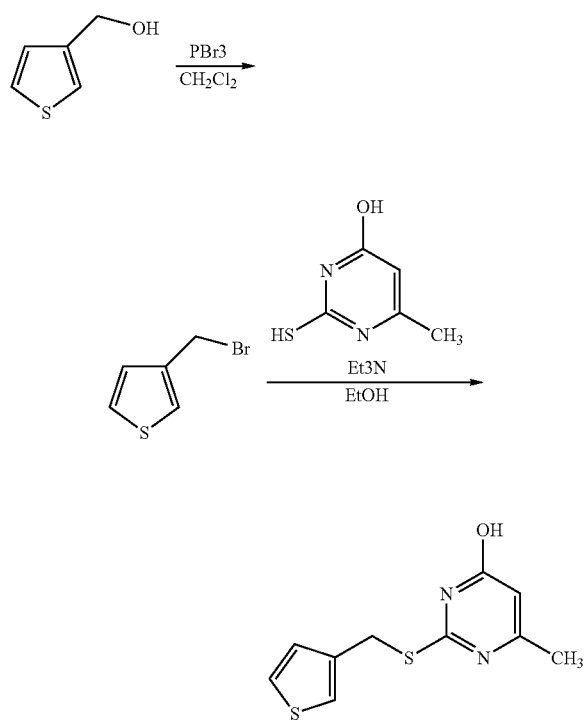

To a solution of thiophen-3-ylmethanol (1.0 g, 8.8 mmol) in anhydrous dichloromethane (80 mL) was added a phosphorus tribromide (1.7 mL, 17.9 mmol). The solution was stirred at room temperature overnight. Dichloromethane was evaporated. The residue was treated slowly with a saturated aqueous sodium bicarbonate solution (50 mL). The mixture was extracted with dichloromethane (3×50 mL). The organic extracts were combined, dried over MgSO$_4$, filtered, evaporated, and dried in vacuo. The crude product was purified by flash chromatography (0-20% EtOAc/hexanes), affording 3-(bromomethyl)thiophene (360 mg, 23% yield).

A mixture of 3-(bromomethyl)thiophene (360 mg, 2.0 mmol), 6-methyl-2-sulfanylpyrimidin-4-ol (242 mg, 1.7 mmol), and triethylamine (280 µL, 2.0 mmol) in absolute ethanol (10 mL) was stirred at room temperature for 2 days. The solid residue was removed by filtration. The filtrate was recovered and evaporated under reduced pressure. The solid product was suspended in water (20 mL). The solid material was recovered by filtration, washed with water (2×15 mL) and hexanes (3×15 mL), and dried in vacuo, affording the title compound (80 mg, 20% yield); $^1$H NMR (400 MHz, DMSO-d$_6$): δ 2.21 (s, 3H), 4.39 (s, 2H), 6.02 (s (br), 1H), 7.12 (dd, 1H, J=1.3 Hz, 3.5 Hz), 7.47 (m, 2H); M+ 239; HPLC purity: 96.1%.

Example 11

2-{[(2-chloro-4-hydroxyphenyl)methyl]sulfanyl}-6-methylpyrimidin-4-ol

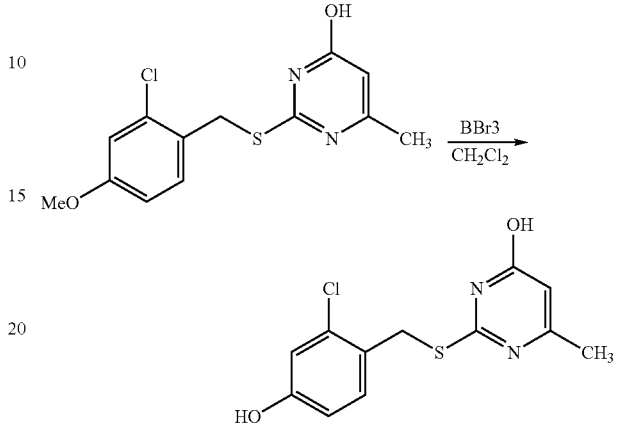

To a 0° C. mixture of 2-{[(2-chloro-4-methoxyphenyl)methyl]sulfanyl}-6-methyl-pyrimidin-4-ol (500 mg, 1.7 mmol) in anhydrous dichloromethane (20 mL) was added a solution of boron tribromide (1 M in THF, 2 mL, 2 mmol). The solution was stirred at room temperature overnight. Water (20 mL) and more dichloromethane (50 mL) were added to the mixture. The undissolved solid material was recovered by filtration, washed with diethyl ether (2×25 mL), and dried in vacuo. The crude product was purified by flash chromatography (0-10% MeOH/CH$_2$Cl$_2$), affording the title compound (65 mg, 13% yield); $^1$H NMR (400 MHz, DMSO-d$_6$): δ 2.22 (s, 3H), 4.37 (s, 2H), 6.00 (s (br), 1H), 6.70 (dd, 1H, J=2.3 Hz, 8.4 Hz), 6.84 (d, 1H, J=2.3 Hz), 7.40 (d, 1H, J=8.6 Hz), 9.96 (s, 1H); M+ 283; HPLC purity: 98.0%.

Example 12

2-{[(2-chloro-5-nitrophenyl)methyl]sulfanyl}-6-methylpyrimidin-4-ol

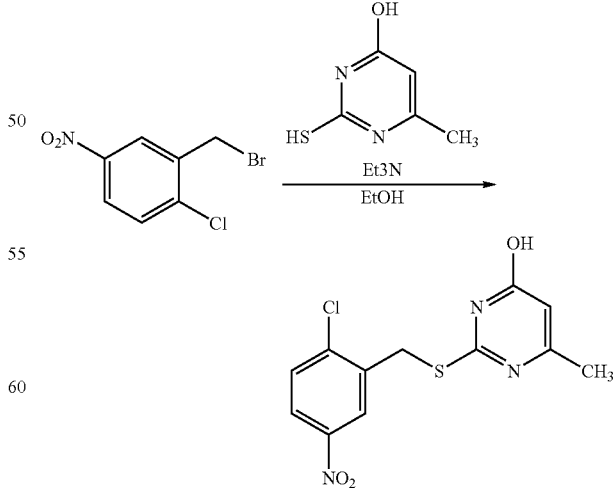

A mixture of 2-(bromomethyl)-1-chloro-4-nitrobenzene (1.0 g, 4.0 mmol), 6-methyl-2-sulfanylpyrimidin-4-ol (512 mg, 3.6 mmol), and triethylamine (560 µL, 4.0 mmol) in absolute ethanol (20 mL) was stirred at room temperature overnight. The product was recovered by filtration, washed with EtOH (2×15 mL) and diethyl ether (3×25 mL), and dried in vacuo, affording the title compound (1.0 g, 90% yield); $^1$H NMR (400 MHz, DMSO-d$_6$): δ 2.26 (s, 3H), 4.53 (s, 2H), 6.00 (s (br), 1H), 7.78 (d, 1H, J=8.8 Hz), 8.15 (dd, 1H, J=2.9 Hz, 8.8 Hz), 8.59 (d, 1H, J=2.7 Hz); M+ 312.

Example 13

2-{[(5-amino-2-chlorophenyl)methyl]sulfanyl}-6-methylpyrimidin-4-ol hydrochloride

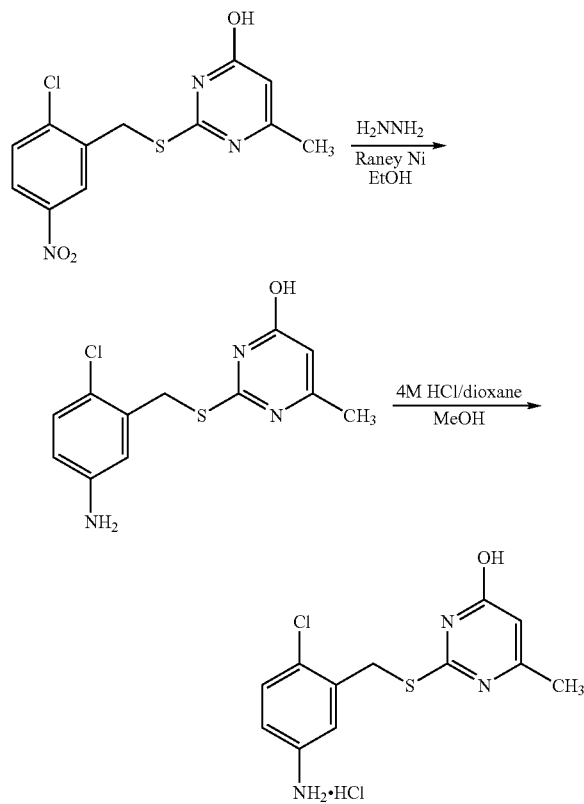

To a mixture of 2-{[(2-chloro-5-nitrophenyl)methyl]sulfanyl}-6-methylpyrimidin-4-ol (500 mg, 1.6 mmol) in absolute EtOH (15 mL) was added hydrazine hydrate (1 mL, 32 mmol) and Raney nickel. The reaction mixture was stirred at room temperature overnight. The solid material was filtered on Celite. The pad was recovered and suspended in a mixture of MeOH/EtOAc/CH$_2$Cl$_2$ (100 mL). The mixture was filtered. The filtrate was recovered, evaporated, and dried in vacuo, affording the 2-{[(5-amino-2-chlorophenyl)methyl]sulfanyl}-6-methylpyrimidin-4-ol (45 mg, 10% yield). The product was used without further purification.

To a solution of 2-{[(5-amino-2-chlorophenyl)methyl]sulfanyl}-6-methylpyrimidin-4-ol (45 mg, 0.16 mmol) in MeOH (2 mL) was added 4 M HCl/dioxane (1 mL, 4.0 mmol). The mixture was evaporated and dried in vacuo, affording the title compound (50 mg, 98% yield); $^1$H NMR (400 MHz, DMSO-d$_6$): δ 2.23 (s, 3H), 4.50 (s, 2H), 6.01 (s, 1H), 7.19 (d, 1H, J=7.4 Hz), 7.50 (m, 2H); M+ 282.

Example 14

2-{[(2-chloro-5-methoxyphenyl)methyl]sulfanyl}-6-methylpyrimidin-4-ol

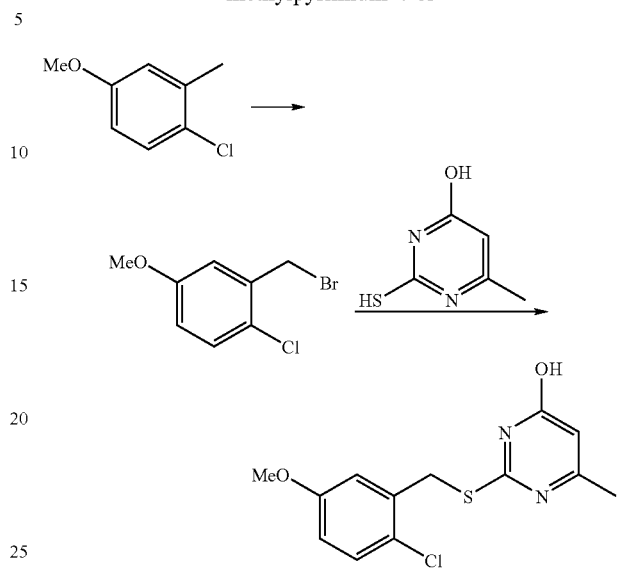

To a solution of the 1-chloro-4-methoxy-2-methylbenzene (2.0 g, 12.77 mmol) in anhydrous carbon tetrachloride (50 mL), NBS (2.29 g, 12.98 mmol) and benzoyl peroxide (0.154 g, 0.64 mmol) was added. The reaction mixture was heated to reflux overnight. Then, the reaction mixture was cooled to room temperature and filtered. The filtrate was evaporated to provide crude 2-(bromomethyl)-1-chloro-4-methoxybenzene, which was used for the next step without any further purification; $^1$H NMR (400 MHz, DMSO-d$_6$): δ 3.74 (s, 3H), 4.66 (s, 2H), 7.01 (d, J=8.9 Hz, 1H), 7.19 (s, 1H), 7.38 (d, J=8.9 Hz, 1H).

To the 2-(bromomethyl)-1-chloro-4-methoxybenzene (3.79 g, 16.09 mmol) in anhydrous ethanol (30 mL) at room temperature, 6-methyl-2-sulfanylpyrimidin-4-ol (2.28 g, 16.09 mmol) was added. Triethylamine (1.79 g, 17.7 mmol) was then added. The reaction mixture was stirred overnight at room temperature. The reaction progress was monitored by LCMS. The solvent was evaporated, and the crude residue was suspended in water and sonicated. The white precipitated product was filtered off and washed with water, ether, and ethyl acetate to provide the 2-{[(2-chloro-5-methoxyphenyl)methyl]sulfanyl}-6-methylpyrimidin-4-ol as a white solid (4.05 g, 85% yield); $^1$H NMR (400 MHz, DMSO-d$_6$): δ 2.20 (s, 3H), 3.71 (s, 3H), 4.39 (s, 2H), 5.99 (bs, 1H), 6.88 (d, J=8.9 Hz, 1H), 7.19 (s, 1H), 7.38 (d, J=8.9 Hz, 1H).

Example 15

2-{[(2-chloro-5-hydroxyphenyl)methyl]sulfanyl}-6-methylpyrimidin-4-ol

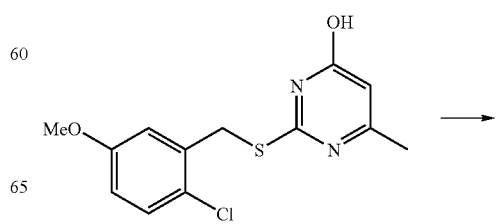

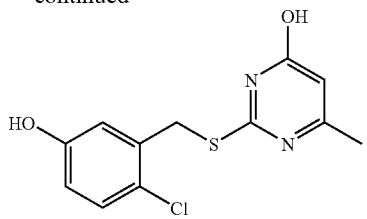

To a solution of the 2-{[(2-chloro-5-methoxyphenyl)methyl]sulfanyl}-6-methylpyrimidin-4-ol (1.0 g, 3.36 mmol) compound in anhydrous dichloromethane at 0° C., 1 M solution of boron tribromide (0.844 g, 3.36 mmol) was added. The reaction mixture was stirred at room temperature overnight. Then, the reaction mixture was quenched with sodium bicarbonate solution and the solid was filtered. The crude solid was purified by using dichloromethane and methanol (1:10) to provide the product 2-{[(2-chloro-5-hydroxyphenyl)methyl]sulfanyl}-6-methylpyrimidin-4-ol as a white solid (0.62 g, 65% yield); $^1$H NMR (400 MHz, DMSO-$d_6$): δ 2.20 (s, 3H), 4.34 (s, 2H), 5.98 (bs, 1H), 6.66 (d, J=8.8 Hz, 1H), 6.97 (s, 1H), 7.20 (d, J=8.8 Hz, 1H); M+ 283.06.

Example 16

2-{[(2-chloro-6-nitrophenyl)methyl]sulfanyl}-6-methylpyrimidin-4-ol

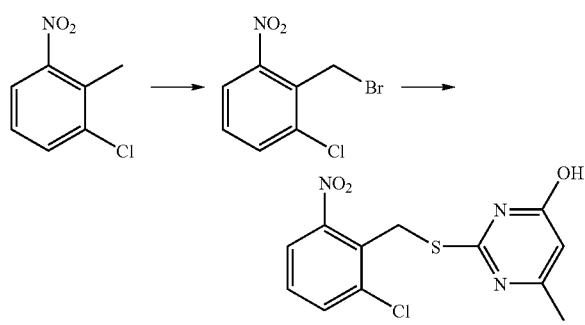

To a solution of the 1-chloro-2-methyl-3-nitrobenzene (2.0 g, 11.66 mmol) in anhydrous carbon tetrachloride 50 mL, NBS (2.07 g, 11.66 mmol) and benzoyl peroxide (0.141 g, 0.583 mmol) was added. The reaction mixture was heated to reflux overnight. Then, the reaction mixture was cooled to room temperature and filtered. The filtrate was evaporated to provide crude 2-(bromomethyl)-1-chloro-3-nitrobenzene, which was used for the next step without any further purification (2.93 g); $^1$H NMR (400 MHz, DMSO-$d_6$): δ 4.77 (s, 2H), 7.60 (t, J=6.2, 8.2 Hz, 1H), 7.90 (d, J=8.2 Hz, 1H), 8.00 (d, J=8.2 Hz, 1H).

To the 2-(bromomethyl)-1-chloro-4-nitrobenzene (2.93 g, 11.67 mmol) in anhydrous ethanol (30 mL) at room temperature, 6-methyl-2-sulfanylpyrimidin-4-ol (1.66 g, 11.67 mmol) was added. Triethylamine (1.30 g, 12.87 mmol) was then added. The reaction mixture was stirred overnight at room temperature. The reaction progress was monitored by LCMS. The solvent was evaporated, and the crude residue was suspended in water and was sonicated. The white precipitated product was filtered off and washed with water, ether, and ethyl acetate to provide the titled product (2.99 g, 82% yield); $^1$H NMR (400 MHz, DMSO-$d_6$): δ 2.16 (s, 3H), 4.73 (s, 2H), 6.01 (bs, 1H), 7.56 (t, J=8.3 Hz, 16.5 Hz, 1H), 7.90 (m, 2H); M+ 311.8.

Example 17

2-{[(2-amino-6-chlorophenyl)methyl]sulfanyl}-6-methylpyrimidin-4-ol

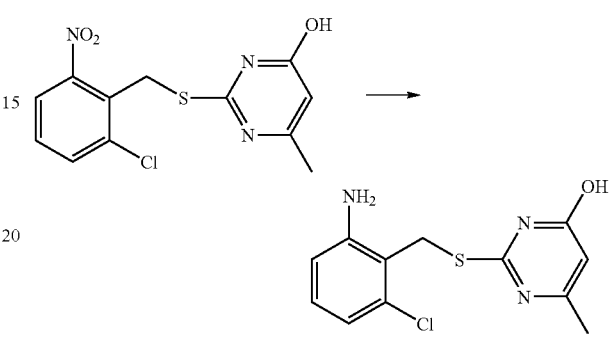

To a suspension of the 2-{[(2-chloro-6-nitrophenyl)methyl]sulfanyl}-6-methylpyrimidin-4-ol (1.0 g, 3.20 mmol) in ethanol (30 mL), a water mixture of iron powder (1.07 g, 19.24 mmol) and equivalent NH$_4$Cl (0.741 g, 9.6 mmol) was added. The reaction mixture was stirred at room temperature for 48 hours. The reaction mixture was filtered over Celite and washed with methanol, and the solvent was evaporated. The precipitated solid was filtered off and washed with ether to provide the titled amine (0.316 g, 35% yield); $^1$H NMR (400 MHz, DMSO-$d_6$): δ 2.20 (s, 3H), 4.42 (s, 2H), 6.01 (bs, 1H), 6.60 (m, 2H), 6.95 (t, J=8.0, 16.1 Hz, 1H); M+ 282.06.

Example 18

4-methoxy-6-methyl-2-{[(2,3,6-trichlorophenyl)methyl]sulfanyl}pyrimidine

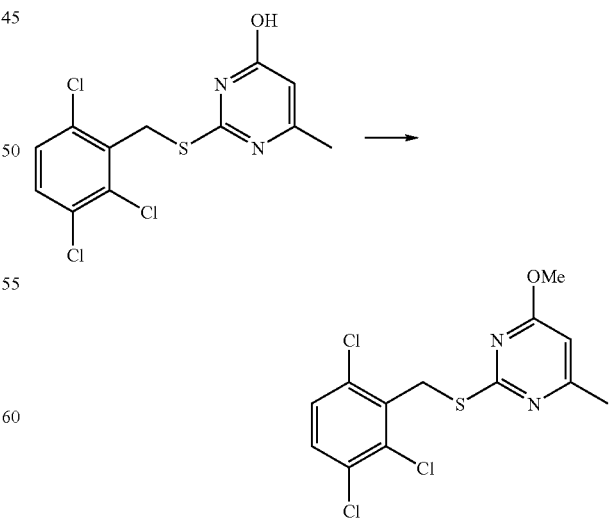

2-{[(3,5-dichloropyridin-4-yl)methyl]sulfanyl}-6-methylpyrimidin-4-ol (200 mg, 600 µmol) was suspended in anhydrous methanol (3 mL). A solution of sodium methoxide (25% in methanol, 140 μL, 660 μmol) was added at 0° C., and the mixture was heated at reflux for 1.5 hours. Neat iodomethane (45 μL, 720 μmol) was added, and the mixture was heated at reflux for 5 hours. After overnight stirring at room temperature, the precipitate was filtered, washed with water, and dried in vacuo, affording 4-methoxy-6-methyl-2-{[(2,3,6-trichlorophenyl)methyl]sulfanyl}pyrimidine as a white solid (70 mg, 33% yield); $^1$H NMR (400 MHz, DMSO-$d_6$): δ 2.20 (s, 3H), 3.31 (s, 3H), 4.77 (s, 2H), 6.09 (s, 1H), 7.58 (d, J=8.7 Hz, 1H), 7.69 (d, J=8.7 Hz, 1H).

Example 19

4-methyl-2-{[(2,3,6-trichlorophenyl)methyl]sulfanyl}pyrimidine

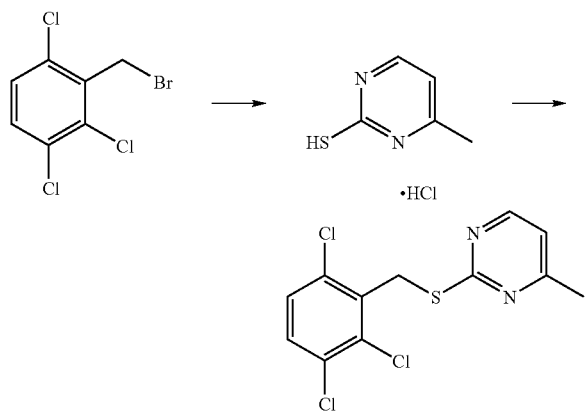

4-methylpyrimidine-2-thiol hydrochloride (200 mg, 1.2 mmol) and potassium carbonate (357 mg, 2.6 mmol) was stirred for 30 minutes in anhydrous DMF (4 mL) at room temperature. Then, 2-(bromomethyl)-1,3,4-trichlorobenzene (345 mg, 1.3 mmol) in anhydrous DMF (1 mL) was added, and the mixture was stirred overnight at room temperature. The solid was removed by filtration and filtrate evaporation. The residue was dissolved in DCM and purified on silica gel using 5% DCM/MeOH to afford, after trituration with diethyl ether, 4-methyl-2-{[(2,3,6-trichlorophenyl)methyl]sulfanyl}pyrimidine as a white solid (88 mg, 22% yield); $^1$H NMR (400 MHz, DMSO-$d_6$): δ 2.44 (s, 3H), 4.75 (s, 2H), 6.09 (s, 1H), 7.17 (d, J=5.1 Hz, 1H), 7.58 (d, J=8.7 Hz, 1H), 7.67 (d, J=8.7 Hz, 1H), 8.54 (d, J=5.1 Hz, 1H); LRMS (ES$^+$) m/z 319 (100%, M+1), 321 (100%, M+3), 323 (35%, M+5).

Example 20

6-methyl-2-[(pyridin-4-ylmethyl)sulfanyl]pyrimidin-4-ol hydrochloride

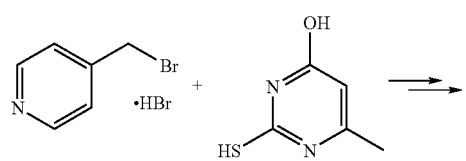

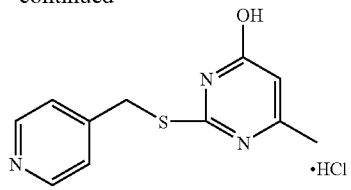

6-methyl-2-sulfanylpyrimidin-4-ol (300 mg, 2.1 mmol) was dissolved in absolute ethanol (10 mL), then triethylamine (650 μL, 4.6 mmol) and 4-(bromomethyl)pyridin-1-ium bromide (587 mg, 2.3 mmol) were added. The mixture was stirred overnight at room temperature, and the solvent was evaporated. The residue was dissolved in DCM and purified on silica gel using 10% DCM/MeOH to afford, after washing with water, 6-methyl-2-[(pyridin-4-ylmethyl)sulfanyl]pyrimidin-4-ol as white solid (128 mg, 26% yield); $^1$H NMR (400 MHz, MeOd$_4$): δ 2.24 (s, 3H), 4.47 (s, 2H), 6.00 (s, 1H), 7.52 (dd, J=4.5 Hz, J=1.6 Hz, 2H), 8.45 (dd, J=4.5 Hz, J=1.6 Hz, 2H).

6-methyl-2-[(pyridin-4-ylmethyl)sulfanyl]pyrimidin-4-ol (100 mg, 429 μmol) was stirred in methanol (10 mL) and a solution of HCl 4N in dioxane (160 μL, 643 mmol) was added dropwise at 0° C. The mixture was stirred for 30 minutes at room temperature. The solvent was removed, and the residue was washed 3 times with diethyl ether and dried in vacuo to afford to 6-methyl-2-[(pyridin-4-ylmethyl)sulfanyl]pyrimidin-4-ol hydrochloride (109 mg, 94% yield); $^1$H NMR (400 MHz, MeOd$_4$): δ 2.42 (s, 3H), 4.82 (s, 2H), 6.48 (s, 1H), 8.26 (bs, 2H), 8.82 (bs, 2H); LRMS (ES$^+$) m/z 234 (100%, M+1).

Example 21

2-{[(3-chloro-1-benzothiophen-2-yl)methyl]sulfanyl}-6-methylpyrimidin-4-ol

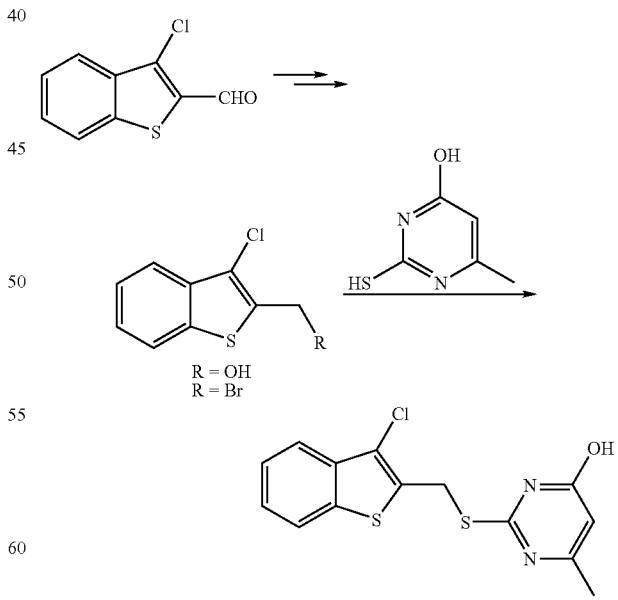

To a solution of sodium borohydride (231 mg, 6.1 mmol) in absolute ethanol (10 mL) was added a solution of 3-chloro-1-benzothiophen-2-carbaldehyde (1.0 g, 5.1 mmol) in absolute ethanol (5 mL) at 0° C. The mixture was stirred for 2 hours at room temperature. Water was added and extracted 3 times with ethyl acetate. The combined organic phase was washed with brine and dried over sodium sulfate. After evaporation of the solvent, (3-chloro-1-benzothiophen-2-yl)methanol was obtained as an orange pale solid (944 mg, 94% yield) and used for next step without further purification; $^1$H NMR (400 MHz, CDCl$_3$): δ 2.17 (bs, 1H), 4.99 (s, 2H), 7.37-7.47 (m, 2H), 7.78-7.82 (m, 2H).

To a solution of (3-chloro-1-benzothiophen-2-yl)methanol (480 mg, 2.4 mmol) in anhydrous diethyl ether (8 mL) was added dropwise a solution of phosphorus tribromide (230 µL, 2.4 mmol) in anhydrous diethyl ether (2 mL) at 0° C. The mixture was stirred for 3 hours at room temperature. Water was added and extracted 3 times with ethyl acetate. The combined organic phase was washed with brine and dried over magnesium sulfate. After evaporation of the solvent, 2-(bromomethyl)-3-chloro-1-benzothiophene was obtained as a pink pale solid (537 mg, 85% yield) and used for the next step without further purification; $^1$H NMR (400 MHz, CDCl$_3$): δ 4.81 (s, 2H), 7.40-7.48 (m, 2H), 7.76-7.82 (m, 2H).

6-methyl-2-sulfanylpyrimidin-4-ol (148 mg, 1.0 mmol) was dissolved in absolute ethanol (8 mL), then triethylamine (180 µL, 1.3 mmol) and 2-(bromomethyl)-3-chloro-1-benzothiophene (300 mg, 1.2 mmol) were added. The mixture was stirred overnight at room temperature. The precipitate was filtered, washed with ethanol and water and then diethyl ether, and dried in vacuo to afford to 2-{[(3-chloro-1-benzothiophen-2-yl)methyl]sulfanyl}-6-methylpyrimidin-4-ol (195 mg, 58% yield); $^1$H NMR (400 MHz, DMSO-d$_6$): δ 2.27 (s, 3H), 4.72 (s, 2H), 5.69 (s, 1H), 6.07 (bs, 1H), 7.43-7.53 (m, 2H), 7.73-7.76 (m, 1H), 7.97-8.00 (m, 114), 12.29 (bs, 1H); LRMS (ES$^+$) m/z 323 (100%, M+1), 325 (35%, M+3).

Example 22

2-{[(3,5-dichloropyridin-4-yl)methyl]sulfanyl}-6-methylpyrimidin-4-ol

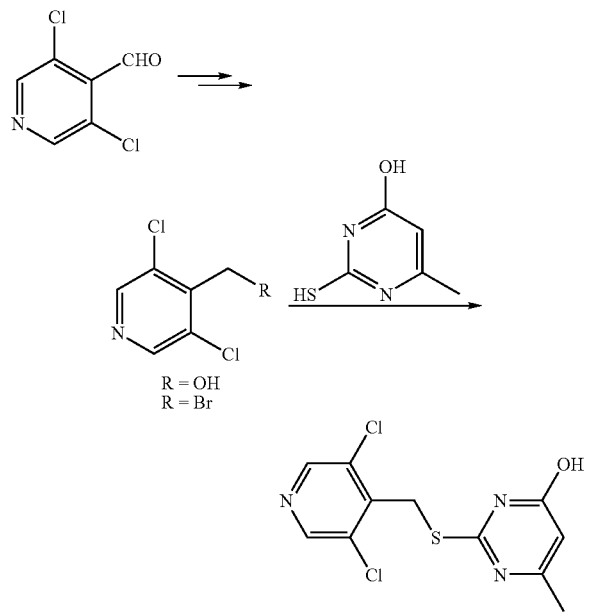

To a solution of sodium borohydride (322 mg, 8.5 mmol) in anhydrous methanol (10 mL) was added a solution of 3,5-dichloropyridine-4-carbaldehyde (1.0 g, 5.7 mmol) in anhydrous methanol (5 mL) at 0° C. The mixture was stirred for 3 hours at room temperature. Water was added and extracted 3 times with ethyl acetate. The organic phase was washed with brine and dried over sodium sulfate. After evaporation of the solvent, (3,5-dichloropyridin-4-yl)methanol was obtained (940 mg, 93% yield) and used for the next step without further purification; $^1$H NMR (400 MHz, CDCl$_3$): δ 2.23 (t, J=7.1 Hz, 1H), 4.94 (d, J=7.1 Hz, 2H), 8.52 (s, 2H).

To a solution of (3,5-dichloropyridin-4-yl)methanol (470 mg, 2.6 mmol) in anhydrous chloroform (10 mL) was added dropwise a solution of phosphorus tribromide (250 µL, 2.6 mmol) in anhydrous chloroform (2 mL) at 0° C. The mixture was stirred for 1.5 hours at room temperature. The solid was filtered and washed with dichloromethane to afford 4-(bromomethyl)-3,5-dichloropyridine (471 mg, 75% yield), which was used for next step without further purification; $^1$H NMR (400 MHz, MeOD$_4$): δ 4.76 (s, 2H), 8.63 (s, 2H).

6-methyl-2-sulfanylpyrimidin-4-ol (134 mg, 940 µmol) was dissolved in absolute ethanol (10 mL), then triethylamine (200 µL, 1.4 mmol) and 4-(bromomethyl)-3,5-dichloropyridine (250 mg, 1.0 mmol) were added. The mixture was stirred for 2 hours at room temperature. The solid was removed by filtration, and filtrate was evaporated. The residue was triturated in diethyl ether, filtered, washed with water plus diethyl ether, and then dried in vacuo to afford to 2-{[(3,5-dichloropyridin-4-yl)methyl]sulfanyl}-6-methylpyrimidin-4-ol (56 mg, 20% yield); $^1$H NMR (400 MHz, DMSO-d$_6$): δ 2.23 (s, 3H), 4.69 (s, 2H), 6.10 (bs, 1H), 8.66 (s, 2H); LRMS (ES$^+$) m/z 302 (100%, M+1), 304 (70%, M+3).

Example 23

2-{[(2-chloro-3-hydroxyphenyl)methyl]sulfanyl}-6-methylpyrimidin-4-ol

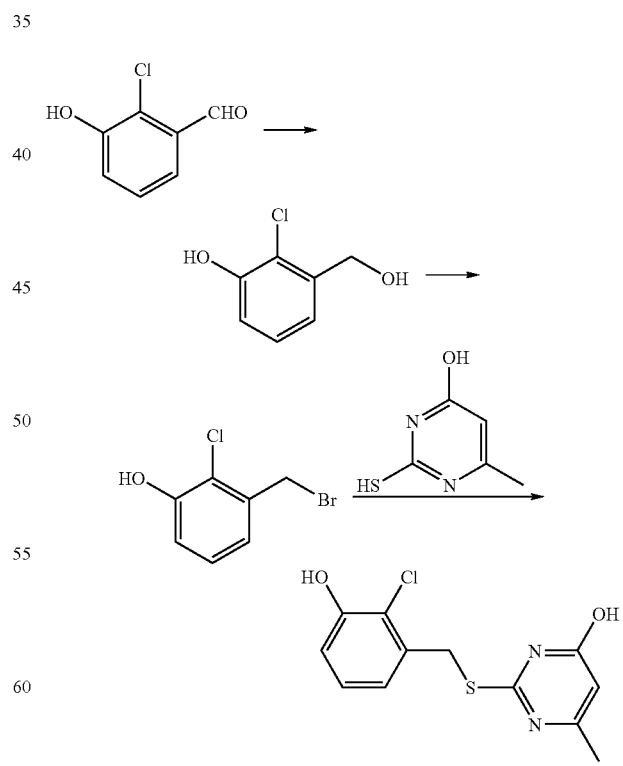

To a solution of sodium borohydride (724 mg, 19.2 mmol) in anhydrous methanol (10 mL) was added a solution of 2-chloro-3-hydroxybenzaldehyde (1.0 g, 6.4 mmol) in anhydrous methanol (5 mL) at 0° C. The mixture was stirred for 3 hours at room temperature. Water was added and extracted 3 times with ethyl acetate. The combined organic phase was washed with brine and dried over sodium sulfate. After evaporation of the solvent, 2-chloro-3-(hydroxymethyl)phenol was obtained (710 mg, 70% yield) and used for next step without further purification; $^1$H NMR (400 MHz, DMSO-$d_6$): δ 4.51 (d, J=5.8 Hz, 2H), 5.28 (t, J=5.8 Hz, 1H), 6.84-6.87 (m, 1H), 6.96-6.99 (m, 1H), 7.12 (t, J=7.8 Hz, 1H), 10.02 (s, 1H).

To a solution of 2-chloro-3-(hydroxymethyl)phenol (400 mg, 2.5 mmol) in anhydrous chloroform (8 mL) was added dropwise a solution of phosphorus tribromide (240 μL, 2.5 mmol) in anhydrous chloroform (2 mL) at 0° C. The mixture was stirred for 2 hours at room temperature. Water was added and extracted 3 times with dichloromethane. The combined organic phase was washed with brine and dried over magnesium sulfate. After evaporation of the solvent, 3-(bromomethyl)-2-chlorophenol was obtained (373 mg, 67% yield) and used for next step without further purification; $^1$H NMR (400 MHz, DMSO-$d_6$): δ 4.70 (s, 2H), 6.94-6.97 (m, 1H), 7.02-7.04 (m, 1H), 7.13 (t, J=7.8 Hz, 1H), 10.32 (bs, 1H).

6-methyl-2-sulfanylpyrimidin-4-ol (152 mg, 1.1 mmol) was dissolved in absolute ethanol (8 mL), then triethylamine (140 μL, 1.0 mmol) and 3-(bromomethyl)-2-chlorophenol (200 mg, 0.9 mmol) were added. The mixture was stirred overnight at room temperature. The solid was removed by filtration, and the filtrate was evaporated. The residue was dissolved in DCM and purified on silica gel using 10% DCM/MeOH to afford 2-{[(2-chloro-3-hydroxyphenyl)methyl]sulfanyl}-6-methylpyrimidin-4-ol (87 mg, 37% yield); $^1$H NMR (400 MHz, DMSO-$d_6$): δ 2.22 (s, 3H), 4.11 (bs, 1H), 4.44 (s, 2H), 5.99 (bs, 1H), 6.88-6.91 (m, 1H), 7.01-7.10 (m, 2H), 10.24 (bs, 1H); LRMS (ES$^+$) m/z 283 (100%, M+1), 285 (50%, M+3).

Example 24

2-{[(2-chloro-3-nitrophenyl)methyl]sulfanyl}-6-methylpyrimidin-4-ol

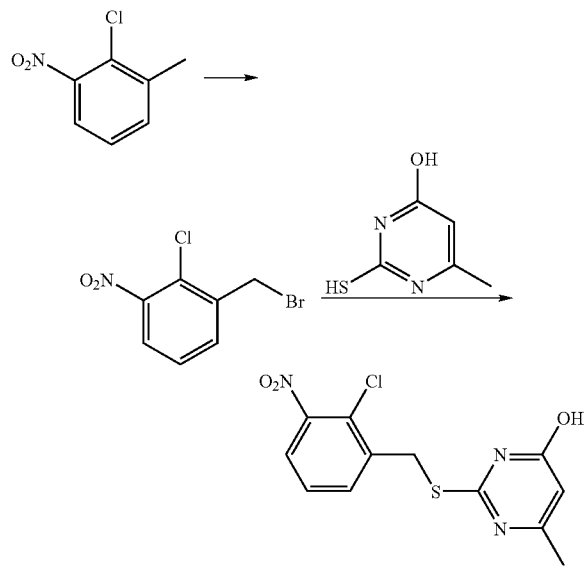

2-chloro-1-methyl-3-nitrobenzene (1 g, 5.8 mmol) was dissolved in CCl$_4$ (10 mL), then N-bromosuccinimide (2.28 g, 12.8 mmol) and benzoyl peroxide (846 mg, 3.5 mmol) were added. The mixture was stirred overnight at reflux. The solid was removed by filtration, and the filtrate was washed with water and dried over sodium sulfate. After evaporation of the solvent, the residue was dissolved in DCM and purified on silica gel using 30% hexane/AcOEt to afford 1-(bromomethyl)-2-chloro-3-nitrobenzene (686 mg, 47% yield); $^1$H NMR (400 MHz, CDCl$_3$): δ 4.64 (s, 2H), 7.42 (t, J=7.9 Hz, 1H), 7.67 (dd, J=1.6 Hz, J=7.9 Hz, 1H), 7.75 (dd, J=1.6 Hz, J=7.9 Hz, 1H).

6-methyl-2-sulfanylpyrimidin-4-ol (200 mg, 1.4 mmol) was dissolved in absolute ethanol (15 mL), then triethylamine (230 μL, 1.7 mmol) and 1-(bromomethyl)-2-chloro-3-nitrobenzene (350 mg, 1.4 mmol) were added. The mixture was stirred overnight at room temperature. The solid was filtered, washed with methanol, and then dried in vacuo to afford 2-{[(2-chloro-3-nitrophenyl)methyl]sulfanyl}-6-methylpyrimidin-4-ol as white solid (277 mg, 64% yield); $^1$H NMR (400 MHz, DMSO-$d_6$): δ 2.23 (s, 3H), 4.56 (s, 2H), 6.00 (bs, 1H), 7.56 (t, J=7.9 Hz, 1H), 7.95 (d, J=8.2 Hz, 2H); LRMS (ES$^+$) m/z 312 (100%, M+1), 314 (45%, M+3).

Example 25

2-{[(3-amino-2-chlorophenyl)methyl]sulfanyl}-6-methylpyrimidin-4-ol

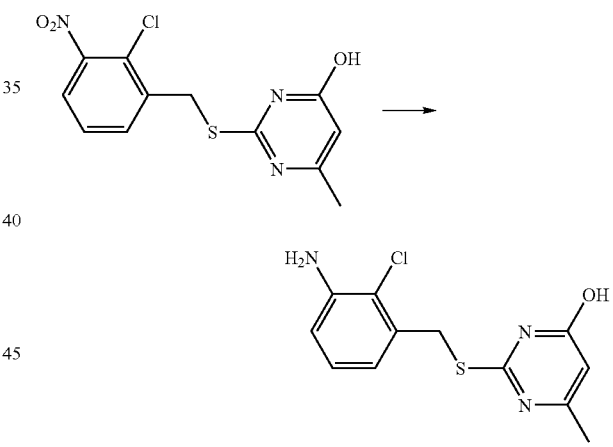

2-{[(2-chloro-3-nitrophenyl)methyl]sulfanyl}-6-methylpyrimidin-4-ol (150 mg, 481 mmol) was dissolved in 1:1 EtOH/DCM (6 mL). Hydrazine hydrate (224 mL, 7.2 mmol) and catalytic amount of Ni-Raney solution in water were added. The mixture was stirred overnight at room temperature. The solid material was filtered on Celite and washed with methanol and ethyl acetate. The filtrate was evaporated. The residue was dissolved in DCM and purified on silica gel using 10% DCM/MeOH to afford 2-{[(3-amino-2-chlorophenyl)methyl]sulfanyl}-6-methylpyrimidin-4-ol (10 mg, 7% yield); $^1$H NMR (400 MHz, DMSO-$d_6$): δ 2.21 (s, 3H), 4.39 (s, 2H), 5.41 (s, 2H), 5.98 (bs, 1H), 6.70-6.75 (m, 2H), 6.95 (t, J=7.7 Hz, 1H); LRMS (ES$^+$) m/z 282 (100%, M+1), 284 (35%, M+3).

Example 26

2-{[(3-chloropyridin-4-yl)methyl]sulfanyl}-6-methylpyrimidin-4-ol hydrochloride

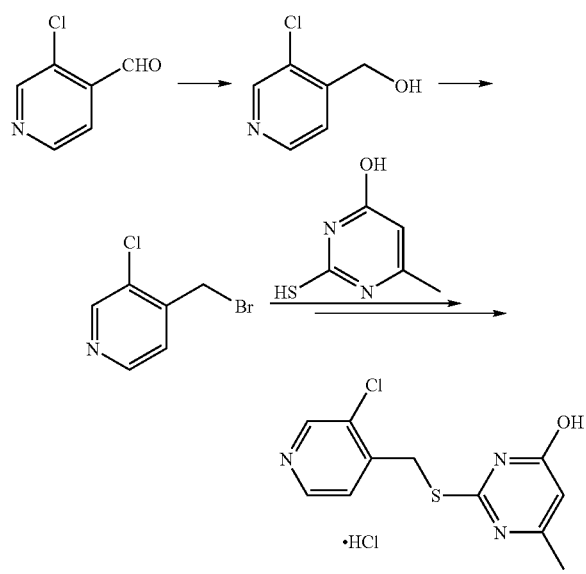

To a solution of sodium borohydride (601 mg, 15.9 mmol) in anhydrous methanol (25 mL) was added a solution of 3-chloropyridine-4-carbaldehyde (1.5 g, 10.6 mmol) in anhydrous methanol (5 mL) at 0° C. The mixture was stirred for 1 hour at room temperature. Water was added and extracted 3 times with ethyl acetate. The combined organic phase was washed with brine and dried over sodium sulfate. After evaporation of the solvent, (3-chloropyridin-4-yl)methanol was obtained as a white solid (1.4 g, 90% yield) and used for next step without further purification; $^1$H NMR (400 MHz, CDCl$_3$): δ 2.41 (t, J=5.9 Hz, 1H), 4.83 (dd, J=0.8 Hz, J=5.9 Hz, 2H), 7.52-7.55 (m, 1H), 8.51 (m, 2H).

To a solution of (3-chloropyridin-4-yl)methanol (700 mg, 4.9 mmol) in anhydrous chloroform (15 mL) was added dropwise a solution of phosphorus tribromide (460 µL, 4.9 mmol) in anhydrous chloroform (5 mL) at 0° C. The mixture was stirred for 8 hours at room temperature. The solid was filtered and washed with dichloromethane to afford crude 4-(bromomethyl)-3-chloropyridine, which was used for the next step without further purification; $^1$H NMR (400 MHz, MeOd$_4$): δ 4.95 (s, 2H), 8.21 (d, J=6.0 Hz, 1H), 8.30 (d, J=6.0 Hz, 1H), 9.09 (s, 1H).

6-methyl-2-sulfanylpyrimidin-4-ol (242 mg, 1.7 mmol) was dissolved in absolute ethanol (10 mL), then triethylamine (350 µL, 2.5 mmol) and 4-(bromomethyl)-3-chloropyridine (350 mg, 1.7 mmol) in absolute ethanol (5 mL) were added. The mixture was stirred overnight at room temperature. The solid was removed by filtration, and the filtrate was evaporated. The residue was triturated in diethyl ether, filtered, washed with water plus diethyl ether, and then dried in vacuo to afford to 2-{[(3-chloropyridin-4-yl)methyl]sulfanyl}-6-methylpyrimidin-4-ol (158 mg, 35% yield); $^1$H NMR (400 MHz, DMSO-d$_6$): δ 2.20 (s, 3H), 4.46 (s, 2H), 6.03 (bs, 1H), 7.63 (d, J=5.0 Hz, 1H), 8.47 (d, J=5.0 Hz, 1H), 8.63 (s, 1H); LRMS (ES$^+$) m/z 268 (100%, M+1), 270 (65%, M+3).

2-{[(3-chloropyridin-4-yl)methyl]sulfanyl}-6-methylpyrimidin-4-ol (100 mg, 373 mol) was stirred in methanol (10 mL) and a solution of 4 N HCl in dioxane (140 µL, 560 mmol) was added dropwise at 0° C. The mixture was stirred for 1.5 hours at room temperature. The solvent was removed, and the residue was washed 3 times with diethyl ether and dried in vacuo to afford to 2-{[(3-chloropyridin-4-yl)methyl]sulfanyl}-6-methylpyrimidin-4-ol hydrochloride (103 mg, 91% yield); $^1$H NMR (400 MHz, DMSO-d$_6$): δ 2.19 (s, 3H), 4.48 (s, 2H), 6.07 (bs, 1H), 7.76 (d, J=5.1 Hz, 1H), 8.53 (d, J=5.1 Hz, 1H), 8.74 (s, 1H); LRMS (ES$^+$) m/z 268 (100%, M+1), 270 (65%, M+3).

Example 27

6-methyl-2-{[(2,3,6-trichlorophenyl)methyl]sulfanyl}pyrimidin-4-ol

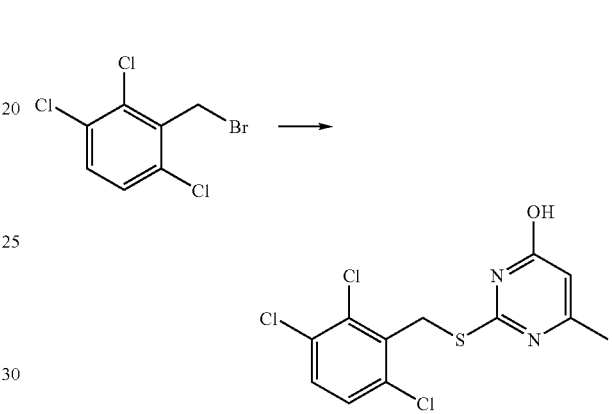

In a 100 mL round bottom flask, 2-(bromomethyl)-1,3,4-trichlorobenzene (550 mg, 2.0 mmol), 6-methyl-2-sulfanylpyrimidin-4-ol (250 mg, 2.0 mmol), and potassium carbonate (306 mg, 2.2 mmol) were mixed in DMF (10 mL). The reaction mixture was stirred at room temperature for 2 hours. Water (50 mL) was added. The mixture was filtered and washed with water and ethyl acetate to provide the title compound as a white solid (450 mg, 70% yield); $^1$H NMR (400 MHz, DMSO-d$_6$): δ 2.11 (s, 3H), 5.43 (s, 2H), 5.89 (s, 1H), 6.57 (br, 1H), 7.56 (d, 1H), 7.71 (d, 1H); M+ 318, 320.

Example 28

2-{[(2-chloro-6-methoxyphenyl)methyl]sulfanyl}-6-methylpyrimidin-4-ol

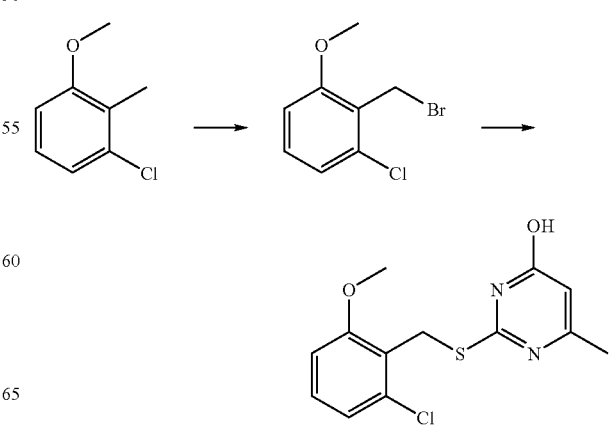

In a 250 mL round bottom flask, 1-chloro-3-methoxy-2-methylbenzene (5.0 g, 31.9 mmol) was dissolved in CCl$_4$ (50 mL). To the solution, 1-bromopyrrolidine-2,5-dione (5.8 g, 32.6 mmol) and benzoyl benzenecarboperoxoate (70 mg) were added in sequence. The resulting mixture was refluxed for 4 hours and left at room temperature overnight. The mixture was filtered. The filtrate was evaporated to provide crude product of 2-(bromomethyl)-1-chloro-3-methoxybenzene as a colorless liquid, which was used for next step without further purification.

2-(bromomethyl)-1-chloro-3-methoxybenzene (470 mg, 2 mmol), 6-methyl-2-sulfanylpyrimidin-4-ol (270 mg, 1.9 mmol), and potassium carbonate (263 mg, 1.9 mmol) were mixed in DMF (10 mL). The mixture was stirred at room temperature for 2 hours. To the mixture, water (100 mL) was added. The suspension was filtered and washed with water and ethyl acetate to provide pure titled product (400 mg, 70% yield); $^1$H NMR (400 MHz, DMSO-d$_6$): δ 2.20 (s, 3H), 3.82 (s, 3H), 4.50 (s, 2H), 6.00 (s, 1H), 7.05 (m, 2H), 7.31 (t, 1H); M+ 297.

Example 29

2-{[(2-chloro-4-nitrophenyl)methyl]sulfanyl}-6-methylpyrimidin-4-ol

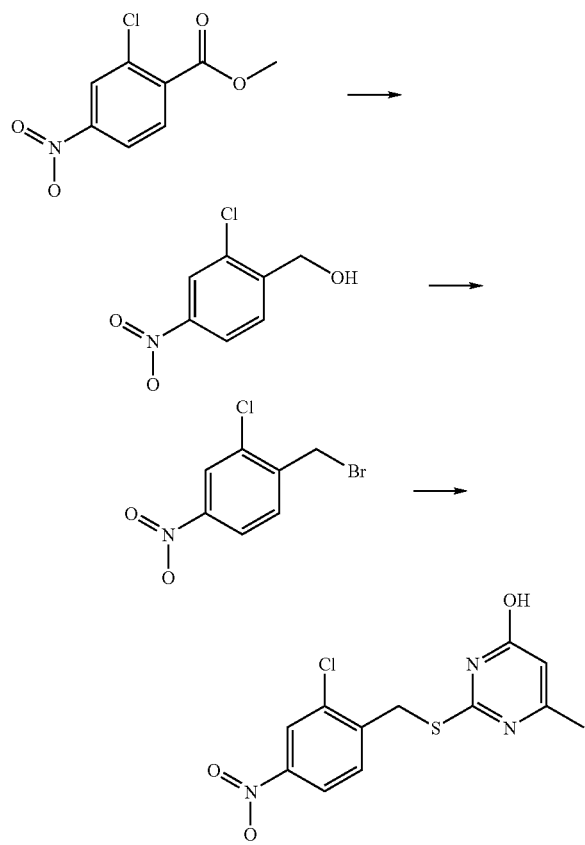

In a 250 mL round bottom flask, methyl 2-chloro-4-nitrobenzoate (5 g, 23 mmol) was dissolved in anhydrous dichloromethane (100 mL). The solution was cooled to −78° C. under nitrogen. Bis(2-methylpropyl)alumane (35 mL, 35 mmol, 1 M in hexane) was added dropwise. The mixture was stirred at −78° C. for 4 hours and quenched by addition of water (5 mL). The resulting mixture was warmed up to room temperature in 20 minutes. Na$_2$SO$_4$ (15 g) was added. After 10 minutes, the mixture was filtered. The filtrate was evaporated to provide (2-chloro-4-nitrophenyl)methanol (95% yield).

(2-chloro-4-nitrophenyl)methanol (707 mg, 3.73 mmol) was dissolved in dichloromethane (15 mL) at 0° C. under nitrogen. Tribromophosphane (0.7 mL, 7.46 mmol) was added dropwise. The resulting mixture was stirred at room temperature overnight. The reaction was quenched by addition of 10% NaHCO$_3$ solution (2 mL). After 10 minutes, Na$_2$SO$_4$ (15 g) was added. The solvent was filtered and evaporated to provide 1-(bromomethyl)-2-chloro-4-nitrobenzene, which was used without further purification.

1-(bromomethyl)-2-chloro-4-nitrobenzene, 6-methyl-2-sulfanylpyrimidin-4-ol (425 mg, 3 mmol), and potassium carbonate (420 mg, 3 mmol) were mixed in DMF (10 mL). The mixture was stirred at room temperature for 2 hours. To the mixture, water (100 mL) was added. The suspension was filtered and washed with water and ethyl acetate to provide pure titled product (500 mg, 54% yield); $^1$H NMR (400 MHz, DMSO-d$_6$): δ 2.20 (s, 3H), 4.55 (s, 2H), 6.03 (s, 1H), 7.92 (d, 1H), 8.19 (d, 1H), 8.31 (s, 1H); M+ 312.

Example 30

6-methyl-2-[(quinolin-3-ylmethyl)sulfanyl]pyrimidin-4-ol

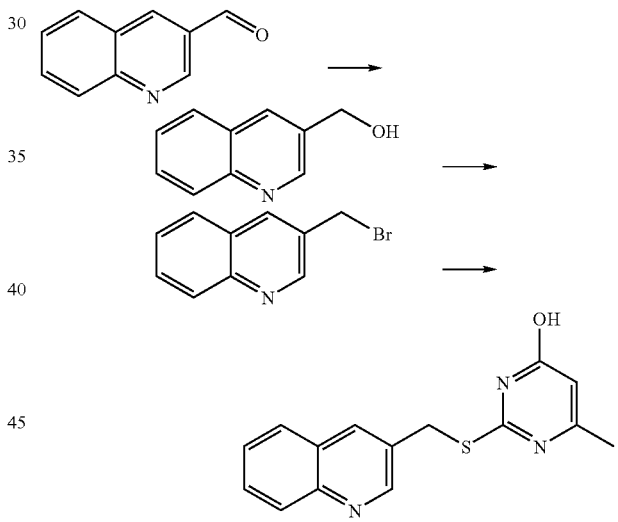

In a 250 mL round bottom flask, quinoline-3-carbaldehyde (1.57 g, 10 mmol) was dissolved anhydrous ethanol (20 mL). The solution was cooled to 0° C. under nitrogen. NaBH$_4$ (420 mg, 11 mmol) was added in one portion. The mixture was stirred at room temperature for 2 hours, and quenched by addition of water (3 mL). Na$_2$SO$_4$ (15 g) was added. After 10 minutes, the mixture was filtered. The filtrate was evaporated to provide quinolin-3-ylmethanol.

Quinolin-3-ylmethanol was dissolved dichloromethane (15 mL) at 0° C. under nitrogen. Tribromophosphane (2.15 mL, 22 mmol) was added dropwise. The resulting mixture was stirred at room temperature overnight. The reaction was quenched by addition of 10% NaHCO$_3$ solution (5 mL). After 10 minutes, Na$_2$SO$_4$ (30 g) was added. The solvent was filtered and evaporated to provide 3-(bromomethyl)quinoline, which was used without further purification.

3-(bromomethyl)quinoline, 6-methyl-2-sulfanylpyrimidin-4-ol (853 mg, 6 mmol) and triethylamine (1 mL, 7 mmol)

were mixed in ethanol (50 mL). The mixture was stirred at room temperature for 2 hours. After evaporation, water (100 mL) was added. The suspension was filtered and washed with water and ethyl acetate to provide pure titled product (1.7 g, 99% yield); $^1$H NMR (400 MHz, DMSO-$d_6$): δ 2.21 (s, 3H), 4.54 (s, 2H), 6.01 (s, 1H), 7.58 (m, 1H), 7.70 (m, 1H), 7.94 (m, 2H), 8.35 (s, 1H), 8.96 (s, 1H); M+ 284.

Example 31

2-{[(2-chloropyridin-3-yl)methyl]sulfanyl}-6-methylpyrimidin-4-ol hydrochloride

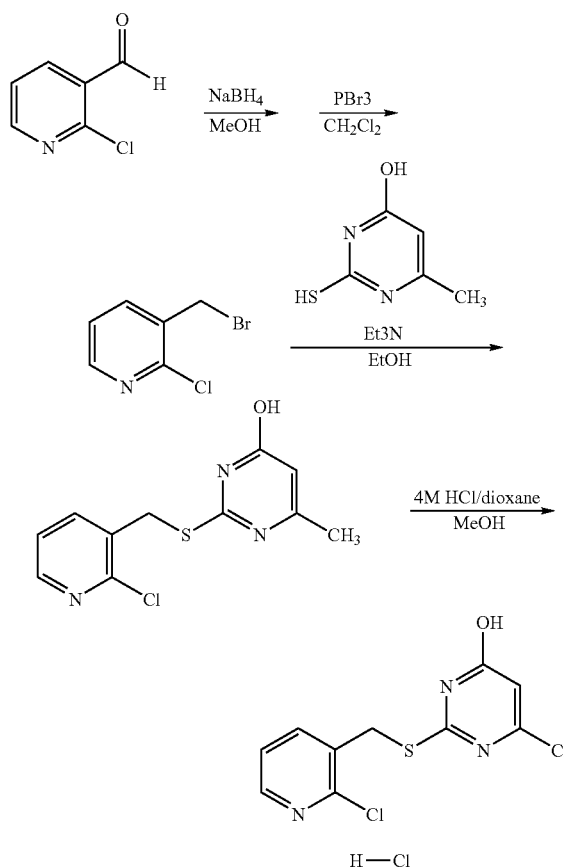

To a 0° C. solution of 2-chloropyridine-3-carbaldehyde (2.0 g, 14.1 mmol) in anhydrous methanol (80 mL) was added sodium borohydride (550 mg, 14.5 mmol). The reaction mixture was stirred at room temperature for 3 hours. Saturated ammonium chloride solution (20 mL) was added. The resultant mixture was extracted with dichloromethane (3×20 mL). The organic extracts were combined, dried over MgSO$_4$, filtered, evaporated, and dried in vacuo, affording (2-chloropyridin-3-yl)methanol (800 mg, 40% yield). The product was used without further purification.

To a solution of (2-chloropyridin-3-yl)methanol (800 mg, 5.6 mmol) in anhydrous dichloromethane (50 mL) was added dropwise phosphorus tribromide (1.0 mL, 11.2 mmol). The mixture was stirred at room temperature overnight. Dichloromethane was evaporated. Water (20 mL) was added. The mixture was treated slowly with a saturated aqueous sodium bicarbonate solution. The mixture was extracted with dichloromethane (3×20 mL). The organic extracts were combined, dried over MgSO$_4$, filtered, evaporated, and dried in vacuo, affording 3-(bromomethyl)-2-chloropyridine (1.0 g, 80% yield). The product was used without further purification.

A mixture of 3-(bromomethyl)-2-chloropyridine (1.0 g, 4.8 mmol), 6-methyl-2-sulfanylpyrimidin-4-ol (570 mg, 4.0 mmol), and triethylamine (1.4 mL, 10.0 mmol) in absolute ethanol (20 mL) was stirred at room temperature overnight. The product was recovered by filtration, washed with EtOH (15 mL), diethyl ether (3×15 mL), water (3×30 mL), and hexanes (3×15 mL). The solid material was dried in vacuo, affording the 2-{[(2-chloropyridin-3-yl)methyl]sulfanyl}-6-methylpyrimidin-4-ol (400 mg, 31% yield). The product was used without further purification.

To a solution of 2-{[(2-chloropyridin-3-yl)methyl]sulfanyl}-6-methylpyrimidin-4-ol (400 mg, 1.5 mmol) in MeOH (5 mL) was added 4 M HCl/dioxane (2 mL, 8.0 mmol). The mixture was evaporated and dried in vacuo, affording the title compound (416 mg, 91% yield); $^1$H NMR (400 MHz, DMSO-$d_6$): δ 2.20 (s, 3H), 4.42 (s, 2H), 6.05 (s, 1H), 7.39 (td, 1H, J=2.7 Hz, 7.4 Hz), 8.05 (dd, 1H, J=2.0 Hz, 7.6 Hz), 8.30 (dd, 1H, J=2.0 Hz, 6.7 Hz); M− 266.

Example 32

2-{[(4-chloroquinolin-3-yl)methyl]sulfanyl}-6-methylpyrimidin-4-ol hydrochloride

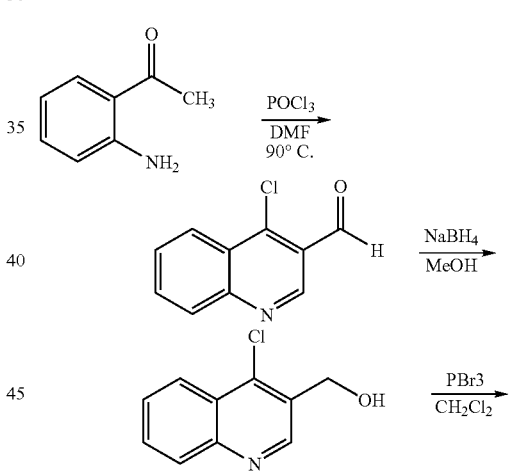

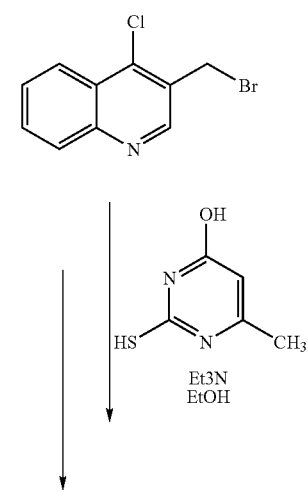

-continued

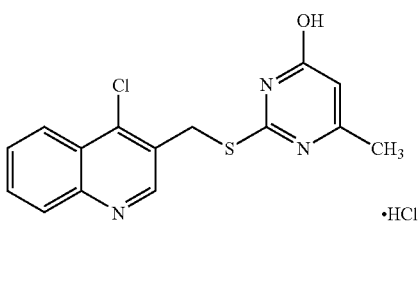

To a 0° C. solution of 1-(2-aminophenyl)ethan-1-one (2.0 g, 14.8 mmol) in anhydrous DMF (10 mL) was added dropwise phosphorus oxychloride (5.5 mL, 59.2 mmol). The reaction mixture was stirred at room temperature for 1 hour and at 90° C. for 3 hours. After cooling to room temperature, the mixture was poured in a mixture of ice/water/NH₄OAc to neutralize. The mixture was stirred at room temperature overnight. The product was recovered by filtration and washed with water (2×20 mL). The solid material was dissolved in ethyl acetate (100 mL). The solution was dried over MgSO₄, filtered, evaporated, and dried in vacuo, affording 4-chloroquinoline-3-carbaldehyde (1.2 g, 43% yield). The product was used without further purification.

To a 0° C. solution of 4-chloroquinoline-3-carbaldehyde (1.2 g, 6.3 mmol) in anhydrous methanol (20 mL) was added sodium borohydride (250 mg, 6.6 mmol). The reaction mixture was stirred at room temperature for 3 hours. Saturated ammonium chloride solution (20 mL) was added. The resultant mixture was extracted with dichloromethane (2×20 mL). The organic extracts were combined, dried over MgSO₄, filtered, evaporated, and dried in vacuo, affording (4-chloroquinolin-3-yl)methanol (1.0 g, 85% yield). The product was used without further purification.

To a solution of (4-chloroquinolin-3-yl)methanol (1.0 mg, 5.2 mmol) in anhydrous dichloromethane (50 mL) was added dropwise phosphorus tribromide (1.0 mL, 11.2 mmol). The mixture was stirred at room temperature for 3 hours. Dichloromethane was evaporated. Water (20 mL) was added. The mixture was treated slowly with a saturated aqueous sodium bicarbonate solution. The mixture was extracted with dichloromethane (2×30 mL). The organic extracts were combined, dried over MgSO₄, filtered, evaporated, and dried in vacuo, affording 3-(bromomethyl)-4-chloroquinoline (982 mg, 74% yield). The product was used without further purification.

A mixture of 3-(bromomethyl)-4-chloroquinoline (982 mg, 3.8 mmol), 6-methyl-2-sulfanylpyrimidin-4-ol (450 mg, 3.2 mmol), and triethylamine (1.3 mL, 9.5 mmol) in absolute ethanol (20 mL) was stirred at room temperature overnight. The solvent was evaporated to dryness and co-evaporated with EtOAc (20 mL). The product was suspended in water (200 mL). The product was recovered by filtration and washed with water (3×200 mL), diethyl ether (1×50 mL), and hexanes (2×50 mL). The solid material was dried in vacuo, affording the title compound (951 mg, 79% yield); ¹H NMR (400 MHz, DMSO-d₆): δ 2.22 (s, 3H), 4.65 (s, 2H), 6.02 (s (br), 1H), 7.75 (td, 1H, J=1.4 Hz, 6.8 Hz), 7.83 (td, 1H, J=1.4 Hz, 6.8 Hz), 8.05 (dd, 1H, J=0.6 Hz, 7.6 Hz), 8.20 (dd, 1H, J=0.6 Hz, 8.4 Hz), 9.10 (s, 1H); M+ 318.

Example 33

2-{[(3,5-dichloropyridin-4-yl)methyl]sulfanyl}-6-methylpyrimidin-4-ol hydrochloride

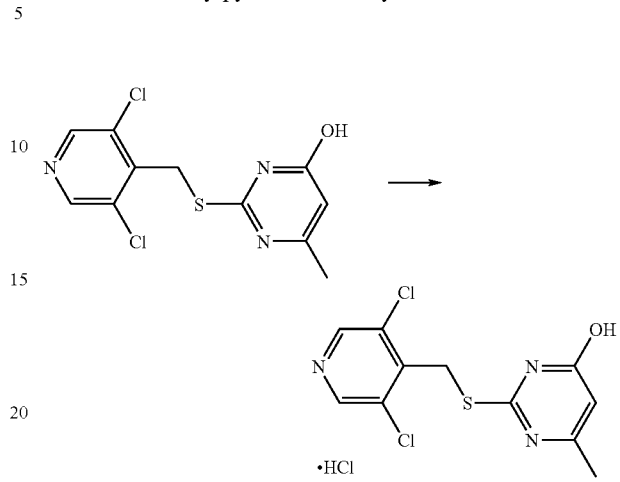

2-{[(3,5-dichloropyridin-4-yl)methyl]sulfanyl}-6-methylpyrimidin-4-ol (200 mg, 662 μmol) was stirred in methanol (20 mL) and a solution of 4 N HCl in dioxane (250 μL, 993 mmol) was added dropwise at 0° C. The mixture was stirred for 30 minutes at room temperature (clear solution). The solvent was removed, and the residue was washed 3 times with diethyl ether and dried in vacuo to afford 2-{[(3,5-dichloropyridin-4-yl)methyl]sulfanyl}-6-methylpyrimidin-4-ol hydrochloride (164 mg, 73% yield); ¹H NMR (400 MHz, DMSO-d₆): δ 2.24 (s, 3H), 4.69 (s, 2H), 6.13 (s, 1H), 8.67 (s, 2H); LRMS (ES⁺) m/z 302 (100%, M+1), 304 (70%, M+3).

Example 34

2-{[(3,5-difluoro-4-yl)methyl]sulfanyl}-6-methylpyrimidin-4-ol

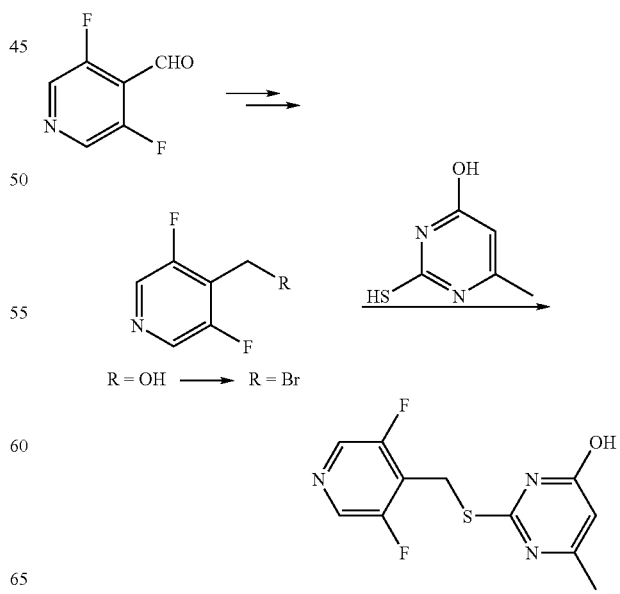

To a solution of sodium borohydride (198 mg, 5.2 mmol) in anhydrous methanol (8 mL) was added a solution of 3,5-difluoropyridine-4-carbaldehyde (0.5 g, 3.5 mmol) in anhydrous methanol (2 mL) at 0° C. The mixture was stirred for 6 hours at room temperature. Water was added, and the mixture was extracted 3 times with ethyl acetate. The organic phase was washed with brine and dried over sodium sulfate. After evaporation of the solvent, (3,5-difluoropyridin-4-yl)methanol was obtained and used in the next step without purification; $^1$H NMR (400 MHz, CDCl$_3$): δ 2.25 (bs, 1H), 4.85 (s, 2H), 8.36 (s, 2H).

To a solution of (3,5-difluoropyridin-4-yl)methanol (3.5 mmol) in anhydrous chloroform (15 mL) was added dropwise a solution of phosphorus tribromide (330 μL, 3.5 mmol) in anhydrous chloroform (5 mL) at 0° C. The mixture was stirred for 6 hours at room temperature. Water was added, and the reaction was extracted 3 times with dichloromethane. The combined organic phases were washed with brine and dried over magnesium sulfate. After evaporation of the solvent, 4-(bromomethyl)-3,5-difluoropyridine was obtained as pale yellow solid (600 mg, 83% yield for 2 steps) and used in the next step without purification; $^1$H NMR (400 MHz, MeOd$_4$): δ 4.59 (s, 2H), 8.42 (s, 2H).

6-methyl-2-sulfanylpyrimidin-4-ol (227 mg, 1.6 mmol) was dissolved in absolute ethanol (20 mL), then triethylamine (335 μL, 2.4 mmol) and 4-(bromomethyl)-3,5-difluoropyridine (350 mg, 1.7 mmol) were added. The mixture was stirred overnight at room temperature. The solvent was removed by evaporation. The residue was triturated in methanol, filtered, washed with water plus diethyl ether, and then dried in vacuo to afford to 2-{[(3,5-difluoropyridin-4-yl)methyl]sulfanyl}-6-methylpyrimidin-4-ol (179 mg, 42% yield); $^1$H NMR (400 MHz, DMSO-d$_6$): δ 2.15 (s, 3H), 4.45 (s, 2H), 6.01 (bs, 1H), 8.49 (s, 2H); LRMS (ES$^+$) m/z 270 (100%, M+1).

Example 35

2-{[(3-fluoro-4-yl)methyl]sulfanyl}-6-methylpyrimidin-4-ol

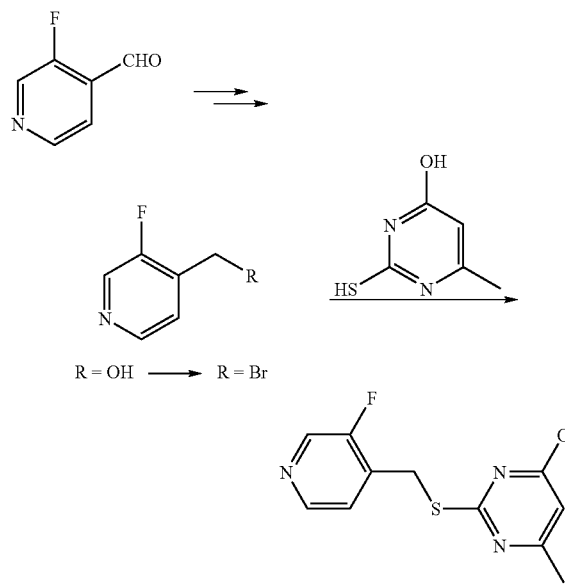

To a solution of sodium borohydride (454 mg, 12.0 mmol) in anhydrous methanol (15 mL) was added a solution of 3-fluoropyridine-4-carbaldehyde (1.0 g, 8.0 mmol) in anhydrous methanol (5 mL) at 0° C. The mixture was stirred overnight at room temperature. Water was added and extracted 3 times with ethyl acetate. The combined organic phase was washed with brine and dried over sodium sulfate. After evaporation of the solvent, (3-fluoropyridin-4-yl)methanol was obtained and used in the next step without purification; $^1$H NMR (400 MHz, CDCl$_3$): δ 2.25 (bs, 1H), 4.85 (d, J=5.7 Hz, 2H), 7.50 (t, J=5.2 Hz, 1H) 8.38-8.43 (m, 2H).

To a solution of (3-fluoropyridin-4-yl)methanol (910 mg, 7.2 mmol) in anhydrous chloroform (25 mL) was added dropwise a solution of phosphorus tribromide (675 μL, 7.2 mmol) in anhydrous chloroform (10 mL) at 0° C. The mixture was stirred for 3 hours at room temperature. Water was added and extracted 3 times with dichloromethane. The organic phase was washed with brine and dried over magnesium sulfate. After evaporation of the solvent, 4-(bromomethyl)-3-fluoropyridine was obtained (260 mg, 19% yield) and used in the next step without further purification; $^1$H NMR (400 MHz, MeOd$_4$): δ 0.81 (s, 2H), 8.25 (t, J=6.4 Hz, 1H). 8.76 (d, J=5.9 Hz, 1H), 9.05 (d, J=3.5 Hz, 1H).

6-methyl-2-sulfanylpyrimidin-4-ol (152 mg, 1.1 mmol) was dissolved in absolute ethanol (20 mL), then triethylamine (200 μL, 1.4 mmol) and 4-(bromomethyl)-3-fluoropyridine (260 mg, 1.4 mmol) were added. The mixture was stirred over the weekend at room temperature. The solid was removed by filtration and washed with methanol. The filtrate was evaporated, and the residue was triturated in methanol, filtered, washed with water and diethyl ether, and then dried in vacuo to afford to 2-{[(3-fluoropyridin-4-yl)methyl]sulfanyl}-6-methylpyrimidin-4-ol (14 mg, 7% yield); $^1$H NMR (400 MHz, DMSO-d$_6$): δ 2.18 (s, 3H), 4.41 (s, 2H), 6.00 (bs, 1H), 7.58 (t, J=5.7 Hz, 1H), 8.37 (dd, J=0.8 Hz, J=4.9 Hz, 1H), 8.53 (d, J=1.8 Hz, 1H); LRMS (ES$^+$) m/z 252 (100%, M+1).

Example 36

2-{[(2-fluoropyridin-3-yl)methyl]sulfanyl}-6-methylpyrimidin-4-ol

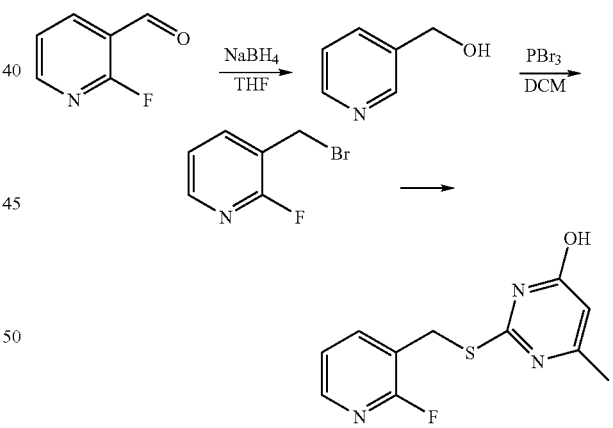

In a 250 mL round bottom flask, 2-fluoropyridine-3-carbaldehyde (2.5 g, 20 mmol) was dissolved in anhydrous ethanol (20 mL). The solution was cooled to 0° C. under nitrogen. NaBH$_4$ (1.5 g, 40 mmol) was added in one portion. The mixture was stirred at room temperature for 2 hours and quenched by addition of water (5 mL). Na$_2$SO$_4$ (20 g) was added. After 10 minutes, the mixture was filtered. The filtrate was evaporated to provide (2-fluoropyridin-3-yl)methanol.

The crude (2-fluoropyridin-3-yl)methanol was dissolved in dichloromethane (30 mL) at 0° C. under nitrogen. Phosphorus tribromide (4.2 mL, 42 mmol) was added dropwise. The resulting mixture was stirred at room temperature overnight. The reaction was quenched by addition of 10% NaHCO$_3$ solution (5 mL). After 10 minutes, Na$_2$SO$_4$ (30 g)

was added. The solvent was filtered and evaporated to provide 3-(bromomethyl)-2-fluoropyridine, which was used without further purification.

3-(bromomethyl)-2-fluoropyridine, 6-methyl-2-sulfanylpyrimidin-4-ol (1.42 g, 10 mmol) and triethylamine (1.54 mL, 11 mmol) were mixed in ethanol (50 mL). The mixture was stirred at room temperature for 2 hours. After evaporation, water (100 mL) was added. The suspension was filtered and washed with water and ethyl acetate to provide pure titled product (1.8 g, 72% yield); $^1$H NMR (400 MHz, DMSO-d$_6$): δ 2.17 (s, 3H), 4.35 (s, 2H), 6.00 (br, 1H), 7.28 (m, 1H), 8.05 (m, 1H), 8.11 (m, 1H); M+ 252.

Example 37

2-{[(2,6-dichlorophenyl)methane]sulfinyl}-6-methylpyrimidin-4-ol

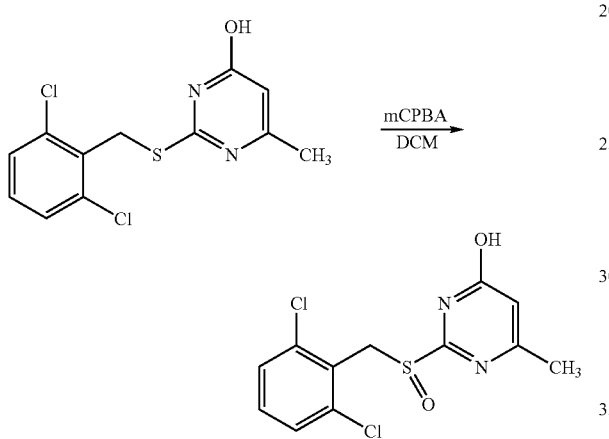

In a 100 mL round bottom flask, 2-{[(2,6-dichlorophenyl)methyl]sulfanyl}-6-methylpyrimidin-4-ol (301 mg, 1.0 mmol) was suspended in DCM (10 mL). 3-chlorobenzene-1-carboperoxoic acid (2580 mg, 1.1 mmol) was added. The resulting mixture was stirred at room temperature for 1 hour. 10% Na$_2$SO$_3$ solution (5 mL) was added. After 20 minutes, Na$_2$SO$_4$ (20 g) was added. The solution was filtered and evaporated. The crude product was purified by column chromatography (0 to 5% methanol in DCM) to provide 2-{[(2,6-dichlorophenyl)methane]sulfinyl}-6-methylpyrimidin-4-ol (130 mg, 41% yield); $^1$H NMR (400 MHz, DMSO-d$_6$): δ 2.11 (s, 3H), 4.53 (s, 2H), 6.03 (s, 1H), 7.38 (t, 1H), 7.50 (d, 2H); M+ 317.

Example 38

2-{[(2,6-dichlorophenyl)methane]sulfonyl}-6-methylpyrimidin-4-ol

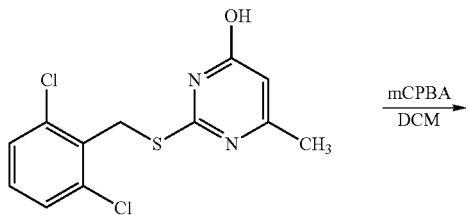

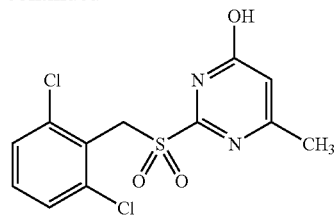

In a 100 mL round bottom flask, 2-{[(2,6-dichlorophenyl)methyl]sulfanyl}-6-methylpyrimidin-4-ol (301 mg, 1.0 mmol) was suspended in DCM (10 mL). 3-chlorobenzene-1-carboperoxoic acid (2580 mg, 1.1 mmol) was added. The resulting mixture was stirred at room temperature for 1 hour. 10% Na$_2$SO$_3$ solution (5 mL) was added. After 20 minutes, Na$_2$SO$_4$ (20 g) was added. The solution was filtered and evaporated. The crude product was purified by column chromatography (0 to 5% methanol in DCM) to provide 2-{[(2,6-dichlorophenyl)methane]sulfonyl}-6-methylpyrimidin-4-ol (15 mg) as a by-product (5% yield); $^1$H NMR (400 MHz, DMSO-d$_6$): δ 2.11 (s, 3H), 4.50 (s, 2H), 6.03 (s, 1H), 7.38 (t, 1H), 7.50 (d, 21-1); M+ 333.

Example 39

2-{[(2-chloro-6-hydroxyphenyl)methyl]sulfanyl}-6-methylpyrimidin-4-ol

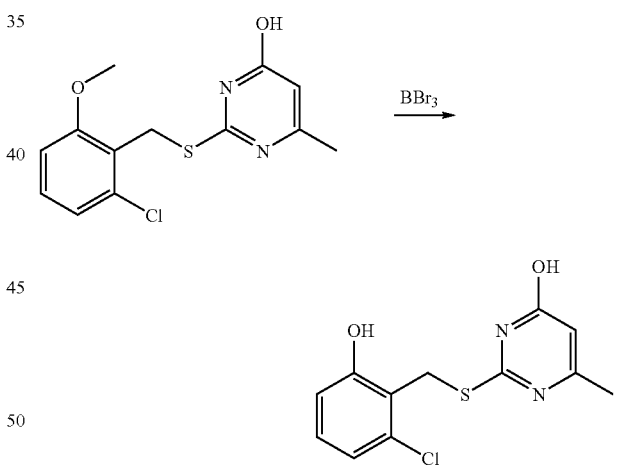

In a 250 mL round bottom flask, 2-{[(2-chloro-6-methoxyphenyl)methyl]sulfanyl}-6-methylpyrimidin-4-ol (200 mg, 0.67 mmol) was dissolved in DCM (10 mL). BBr$_3$ (1.42 mL, 1.42 mmol) was added dropwise. The resulting mixture was stirred at room temperature overnight. Water (5 mL) was added, followed by Na$_2$SO$_4$ (20 g) and DCM (100 mL) after 5 minutes. The solution was filtered and evaporated. The crude product was purified by column chromatography to provide the title compound as a white solid (180 mg, 95% yield); $^1$H NMR (400 MHz, DMSO-d$_6$): δ 2.06 (s, 3H), 4.48 (s, 2H), 6.02 (br, 1H), 6.83 (d, 1H), 6.93 (d, 1H), 7.15 (t, 1H), 10.44 (br, 1H); M+ 283.

Example 40

2-{[(3-chloro-2H-indazol-2-yl)methyl]sulfanyl}-6-methylpyrimidin-4-ol

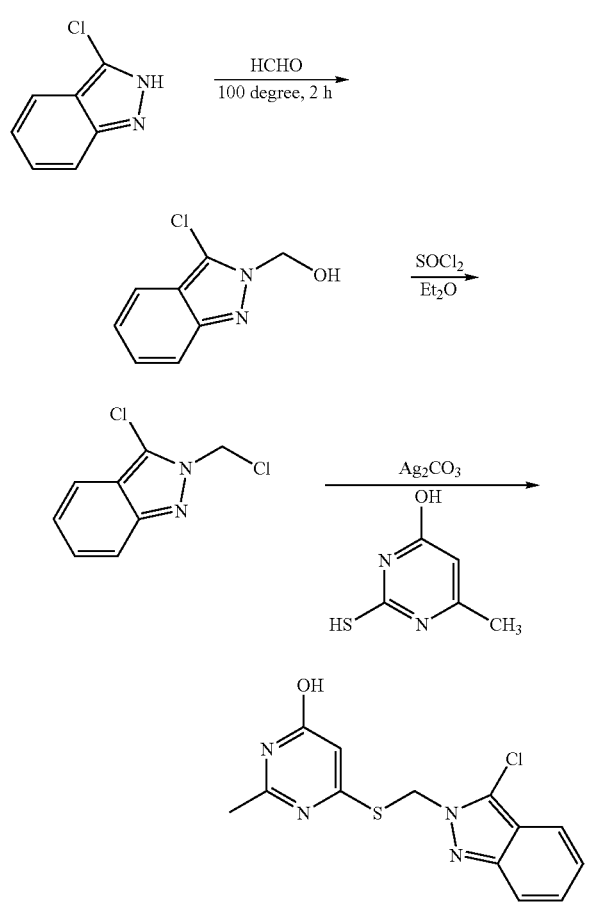

In a 250 mL round bottom flask, 3-chloro-2H-indazole (1.95 g, 10 mmol), 30% HCHO (2 mL, 20 mmol) were mixed in water (10 mL). The reaction mixture was refluxed for 2 hours. After cooling down to room temperature, the solid was filtered, washed with water, and dried under vacuum to provide (3-chloro-2H-indazol-2-yl)methanol (1.82 g, 99% yield).

(3-chloro-2H-indazol-2-yl)methanol was dissolved in SOCl₂ (10 mL). The mixture was stirred at room temperature for 3 hours and evaporated to provide crude 3-chloro-2-(chloromethyl)-2H-indazole as a HCl salt.

3-chloro-2-(chloromethyl)-2H-indazole hydrochloride (285 mg, 1.0 mmol), 6-methyl-2-sulfanylpyrimidin-4-ol (142 mg, 1.0 mmol), and silver carbonate (550 mg, 2.0 mmol) were mixed in acetone (20 mL). The mixture was stirred at room temperature overnight. The solid was filtered. The solution was evaporated, and the crude product was purified by column chromatography to provide the titled final product (15 mg, 5% yield); $^1$H NMR (400 MHz, DMSO-$d_6$): δ 2.34 (s, 3H), 6.05 (s, 1H), 6.22 (s, 2H), 7.25 (t, 1H), 7.48 (t, 1H), 7.67 (d, 1H), 7.74 (s, 1H); M+ 307.

Example 41

6-methyl-2-[(quinolin-4-ylmethyl)sulfanyl]pyrimidin-4-ol

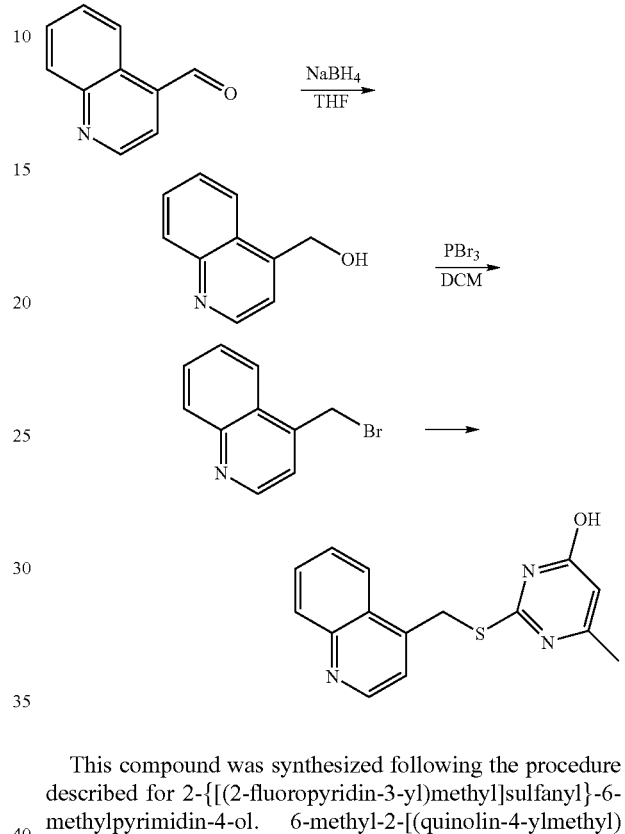

This compound was synthesized following the procedure described for 2-{[(2-fluoropyridin-3-yl)methyl]sulfanyl}-6-methylpyrimidin-4-ol. 6-methyl-2-[(quinolin-4-ylmethyl)sulfanyl]pyrimidin-4-ol was obtained as a white solid (1.2 g, 45% overall yield); $^1$H NMR (400 MHz, DMSO-$d_6$): δ 2.21 (s, 3H), 4.54 (s, 2H), 6.01 (s, 1H), 7.58 (m, 1H), 7.70 (m, 1H), 7.94 (m, 2H), 8.35 (s, 1H), 8.96 (s, 1H); M+ 284.

Example 42

2-[(isoquinolin-4-ylmethyl)sulfanyl]-6-methylpyrimidin-4-ol hydrochloride

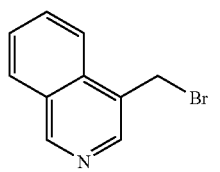

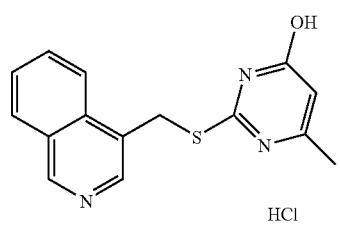

This compound was synthesized following the procedure described for 2-{[(2-fluoropyridin-3-yl)methyl]sulfanyl}-6-methylpyrimidin-4-ol. 2-[(isoquinolin-4-ylmethyl)sulfanyl]-6-methylpyrimidin-4-ol hydrochloride was obtained as a white solid (800 mg, 45% overall yield); $^1$H NMR (400 MHz, DMSO-$d_6$): δ 2.26 (s, 3H), 4.85 (s, 2H), 6.04 (s, 1H), 7.70 (t, 1H), 7.84 (t, 1H), 8.17 (m, 2H), 8.64 (s, 1H), 9.24 (s, 1H); M+ 284.

Example 43

2-{[(3-chlorothiophen-2-yl)methyl]sulfanyl}-6-methylpyrimidin-4-ol

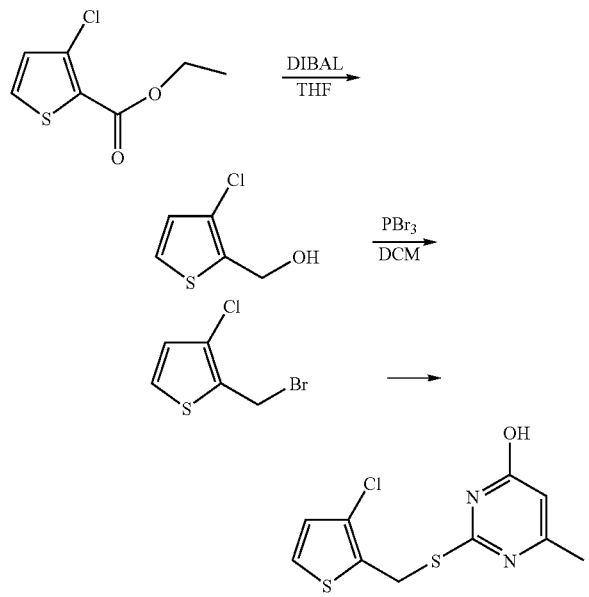

This compound was synthesized following the procedure described for 2-{[(2-chloro-4-nitrophenyl)methyl]sulfanyl}-6-methylpyrimidin-4-ol. 2-{[(3-chlorothiophen-2-yl)methyl]sulfanyl}-6-methylpyrimidin-4-ol was obtained as a white solid (750 mg, 30% overall yield); $^1$H NMR (400 MHz, DMSO-$d_6$): δ 2.06 (s, 3H), 4.53 (s, 2H), 6.04 (s, 1H), 7.01 (d, 1H), 7.53 (d, 1H); M+ 273.

Example 44

2-{[(5-fluoropyridin-3-yl)methyl]sulfanyl}-6-methylpyrimidin-4-ol hydrochloride

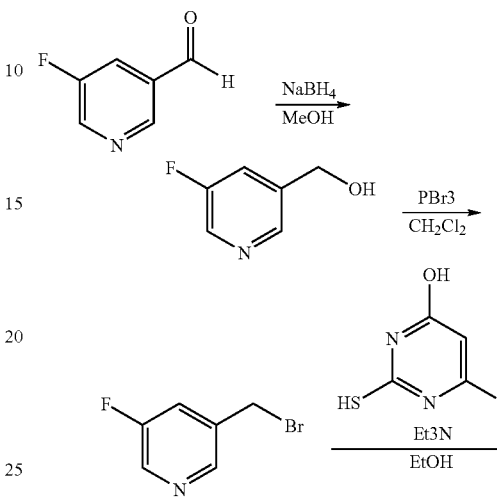

To a 0° C. solution of 5-fluoropyridine-3-carbaldehyde (500 mg, 4.0 mmol) in anhydrous methanol (20 mL) was added sodium borohydride (150 mg, 4.0 mmol). The reaction mixture was stirred at room temperature for 3 hours. Saturated ammonium chloride solution (20 mL) was added. The resultant mixture was extracted with EtOAc (3×20 mL). The organic extracts were combined, dried over MgSO$_4$, filtered, evaporated, and dried in vacuo, affording (5-fluoropyridin-3-yl)methanol (430 mg, 85% yield). The product was used without further purification.

To a solution of (5-fluoropyridin-3-yl)methanol (430 mg, 3.4 mmol) in anhydrous dichloromethane (30 mL) was added dropwise phosphorus tribromide (650 μL, 6.8 mmol). The mixture was stirred at room temperature overnight. Dichloromethane was evaporated. The residue was dried in vacuo, affording 3-(bromomethyl)-5-fluoropyridine hydrobromide. The product was used without further purification.

A mixture of 3-(bromomethyl)-5-fluoropyridine hydrobromide (3.4 mmol), 6-methyl-2-sulfanylpyrimidin-4-ol (370 mg, 2.6 mmol), and triethylamine (1.7 mL, 12.0 mmol) in absolute ethanol (40 mL) was stirred at room temperature overnight. The solid material was removed by filtration. The filtrate was recovered, evaporated, co-evaporated with EtOAc (20 mL), and then dried in vacuo. The solid residue was treated with water (100 mL). The solid product was recovered by filtration, washed with water (1×20 mL) and diethyl ether (2×20 mL), and then dried in vacuo, affording the 2-{[(5-fluoropyridin-3-yl)methyl]sulfanyl}-6-methylpyrimidin-4-ol (200 mg, 23% yield); $^1$H NMR (400 MHz, DMSO-d$_6$): δ 2.21 (s, 3H), 4.41 (s, 2H), 6.02 (s (br), 1H), 7.80 (m, 1H), 8.05 (dd, 1H, J=2.0 Hz, 7.6 Hz), 8.46 (d, 1H, J=2.7 Hz), 8.54 (t, 1H, J=1.6 Hz); M+ 252. The product was used without further purification.

To a mixture of 2-{[(5-fluoropyridin-3-yl)methyl]sulfanyl}-6-methylpyrimidin-4-ol (185 mg, 0.74 mmol) in MeOH (2 mL) was added 4 M HCl/dioxane (1 mL, 4.0 mmol). The mixture was evaporated and dried in vacuo, affording the title compound (213 mg, 99% yield); $^1$H NMR (400 MHz, DMSO-d$_6$): δ 2.22 (s, 3H), 4.43 (s, 2H), 6.09 (s, 1H), 7.96 (td, 1H, J=2.7 Hz, 7.4 Hz), 8.57 (d, 1H, J=2.5 Hz), 8.62 (t, 1H, J=1.6 Hz); M+ 252.

Example 45

2-{[(2,5-dichlorothiophen-3-yl)methyl]sulfanyl}-6-methylpyrimidin-4-ol

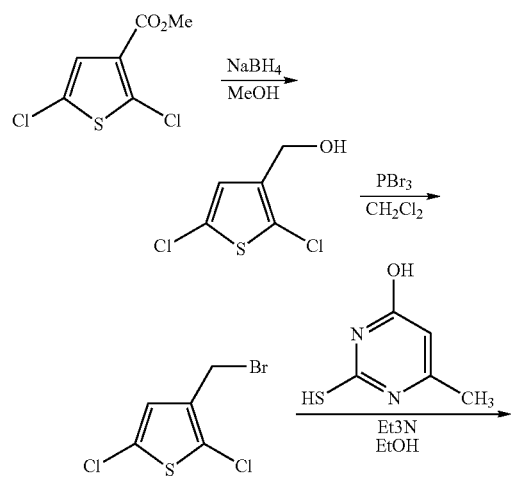

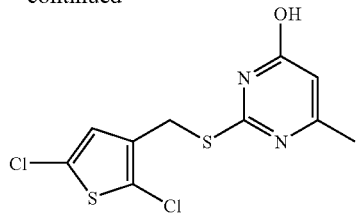

To a 0° C. solution of methyl 2,5-dichlorothiophene-3-carboxylate (1.5 g, 7.1 mmol) in anhydrous methanol (50 mL) was added sodium borohydride (1.35 g, 35.7 mmol). The reaction mixture was stirred at room temperature overnight. After cooling to 0° C., a saturated ammonium chloride solution (50 mL) was added. The resultant mixture was extracted with DCM (3×50 mL). The organic extracts were combined, dried over MgSO$_4$, filtered, evaporated, and dried in vacuo. The product was purified by flash chromatography (0-15% EtOAc/hexanes), affording (2,5-dichlorothiophen-3-yl)methanol (286 mg, 22% yield).

To a solution of (2,5-dichlorothiophen-3-yl)methanol (280 mg, 1.5 mmol) in anhydrous dichloromethane (15 mL) was added dropwise phosphorus tribromide (285 µL, 3.0 mmol). The mixture was stirred at room temperature for 3 hours. Dichloromethane was evaporated. The residue was treated with a saturated sodium bicarbonate solution until no more gas evolved. The resultant mixture was extracted with EtOAc (3×20 mL). The organic extracts were combined, dried over MgSO$_4$, filtered, evaporated, and dried in vacuo, affording 3-(bromomethyl)-2,5-dichlorothiophene (125 mg, 34% yield). The product was used without further purification.

A mixture of 3-(bromomethyl)-2,5-dichlorothiophene (125 mg, 0.51 mmol), 6-methyl-2-sulfanylpyrimidin-4-ol (60 mg, 0.42 mmol), and triethylamine (180 µL, 1.3 mmol) in absolute ethanol (5 mL) was stirred at room temperature overnight. The mixture was recovered and evaporated. The solid residue was treated with water (100 mL). The solid product was recovered by filtration, washed with water (1×15 mL), diethyl ether (2×15 mL), and hexanes (2×15 mL), and then dried in vacuo, affording 2-{[(2,5-dichlorothiophen-3-yl)methyl]sulfanyl}-6-methylpyrimidin-4-ol (91 mg, 71% yield); $^1$H NMR (400 MHz, DMSO-d$_6$): δ 2.21 (s, 3H), 4.27 (s, 2H), 6.02 (s (br), 1H), 7.17 (s 1H); M+ 308.

Example 46

2-({[2-chloro-6-(4-ethylpiperazin-1-yl)phenyl]methyl}sulfanyl)-6-methylpyrimidin-4-ol dihydrochloride

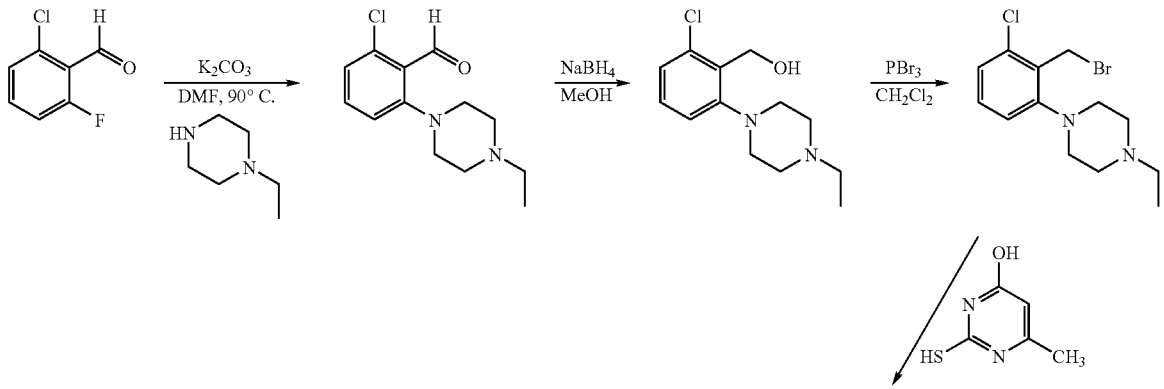

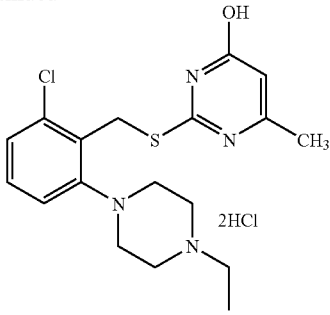

A mixture of 2-chloro-6-fluorobenzaldehyde (5.0 g, 31.5 mmol), 1-ethylpiperazine (8.0 mL, 63.0 mmol), and potassium carbonate (5.0 g, 36.2 mmol) in anhydrous DMF (30 mL) was stirred at 90° C. overnight. DMF was evaporated. The viscous mixture was poured in water (200 mL). The mixture was extracted with diethyl ether (3×100 mL). The organic extracts were combined, dried over MgSO$_4$, filtered, evaporated, and dried in vacuo, affording 2-chloro-6-(4-ethylpiperazin-1-yl)benzaldehyde (7.4 g, 93% yield). The product was used without further purification.

To a 0° C. solution of 2-chloro-6-(4-ethylpiperazin-1-yl)benzaldehyde (7.4 g, 29.4 mmol) in anhydrous methanol (150 mL) was added sodium borohydride (1.7 g, 44 mmol). The reaction mixture was stirred at 0° C. for 0.5 hour and at room temperature overnight. After cooling to 0° C., a saturated ammonium chloride solution (200 mL) was added. The resultant mixture was extracted with DCM (3×100 mL) and EtOAc (1×100 mL). The organic extracts were combined, dried over MgSO$_4$, filtered, evaporated, and dried in vacuo, affording [2-chloro-6-(4-ethylpiperazin-1-yl)phenyl]methanol (6.3 g, 84% yield). The product was used without further purification.

To a solution of [2-chloro-6-(4-ethylpiperazin-1-yl)phenyl]methanol (6.31 g, 24.8 mmol) in anhydrous dichloromethane (200 mL) was added dropwise phosphorus tribromide (5 mL, 52.7 mmol). The mixture was stirred at room temperature for 3 hours. Dichloromethane was evaporated. The residue was dried in vacuo, affording 1-[2-(bromomethyl)-3-chlorophenyl]-4-ethylpiperazine. The product was used without further purification.

A mixture of 1-[2-(bromomethyl)-3-chlorophenyl]-4-ethylpiperazine (24.8 mmol), 6-methyl-2-sulfanylpyrimidin-4-ol (2.35 g, 16.5 mmol), and triethylamine (17 mL, 124 mmol) in absolute ethanol (300 mL) was stirred at room temperature overnight. The solid material was removed by filtration. The filtrate was recovered and evaporated. The solid residue was treated with water (500 mL). The mixture was extracted with DCM (3×200 mL) and EtOAc (1×200 mL). The organic extracts were combined, dried over MgSO$_4$, filtered, evaporated, and dried in vacuo. The crude product was purified by flash chromatography (0-20% MeOH/DCM and 0-15% MeOH/DCM), affording 2-({[2-chloro-6-(4-ethylpiperazin-1-yl)phenyl]methyl}sulfanyl)-6-methylpyrimidin-4-ol (505 mg, 5% yield); $^1$H NMR (400 MHz, DMSO-d$_6$): δ 1.00 (t, 3H, J=7.2 Hz), 2.24 (s, 3H), 2.85 (m, 2H), 2.50 (m, 4H), 2.87 (m, 4H), 4.67 (s, 2H), 6.02 (s, 1H), 7.22 (m, 2H), 7.32 (t, 1H, J=8.0 Hz); M+ 379.

To a mixture of 2-({[2-chloro-6-(4-ethylpiperazin-1-yl)phenyl]methyl}sulfanyl)-6-methylpyrimidin-4-ol (500 mg, 1.3 mmol) in MeOH (10 mL) was added 4 M HCl/dioxane (2 mL, 8 mmol). The mixture was stirred for 15 minutes, evaporated, and dried in vacuo, affording the title compound (575 mg, 98% yield); $^1$H NMR (400 MHz, DMSO-d$_6$): δ 1.26 (t, 3H, J=7.2 Hz), 2.24 (s, 3H), 3.15 (m, 6H), 3.22 (d, 2H, J=11.3 Hz), 3.49 (d, 2H, J=11.7 Hz), 4.67 (s, 2H), 6.11 (s, 1H), 7.19 (dd, 1H, J=1.2 Hz, 7.8 Hz), 7.29 (dd, 1H, J=1.2 Hz, 7.8 Hz), 7.34 (t, 1H, J=8.0 Hz); M+ 379.

Example 47

6-methyl-2-{[(1-methyl-1H-benzimidazol-2-yl)methyl]sulfanyl}pyrimidin-4-ol dihydrochloride

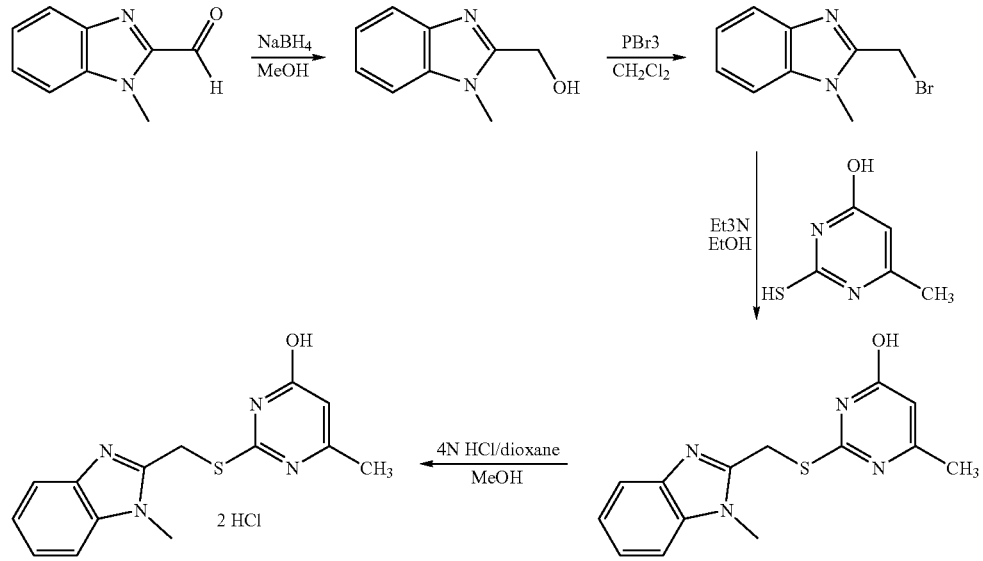

To a 0° C. solution of 1-methyl-1H-benzimidazole-2-carbaldehyde (1.1 g, 6.8 mmol) in anhydrous methanol (50 mL) was added sodium borohydride (350 mg, 9.3 mmol). The reaction mixture was stirred at room temperature for 5 hours. Saturated ammonium chloride solution (20 mL) was added. Methanol was evaporated. The resultant mixture was extracted with EtOAc (3×50 mL) and $CH_2Cl_2$ (1×50 mL). The organic extracts were combined, dried over $MgSO_4$, filtered, evaporated, and dried in vacuo. (1-methyl-1H-benzimidazol-2-yl)methanol was obtained (1.1 g, 99% yield). The product was used without further purification.

To a solution of (1-methyl-1H-benzimidazol-2-yl)methanol (1.1 g, 6.8 mmol) in anhydrous dichloromethane (60 mL) was added dropwise phosphorus tribromide (1.3 mL, 14.0 mmol). The mixture was stirred at room temperature overnight. Dichloromethane was evaporated. The residue was dried in vacuo, affording 2-(bromomethyl)-1-methyl-1H-benzimidazole hydrobromide. The product was used without further purification.

A mixture of 2-(bromomethyl)-1-methyl-benzimidazole hydrobromide (6.8 mmol), 6-methyl-2-sulfanylpyrimidin-4-ol (740 mg, 5.2 mmol), and triethylamine (4 mL, 28.7 mmol) in absolute ethanol (30 mL) was stirred at room temperature overnight. The mixture was recovered, evaporated, and then co-evaporated with EtOAc (20 mL). The solid residue was treated with water (200 mL). The solid product was recovered by filtration, washed with water (2×20 mL), diethyl ether (2×20 mL), and hexanes (2×20 mL), and then dried in vacuo, affording 6-methyl-2-{[(1-methyl-1H-benzimidazol-2-yl)methyl]sulfanyl}pyrimidin-4-ol (1.3 g, 90% yield); $^1$H NMR (400 MHz, DMSO-$d_6$): δ 2.18 (s, 3H), 3.83 (s, 3H), 4.70 (s, 2H), 6.02 (s, 1H), 7.19 (m, 2H), 7.53 (m, 2H); M+ 287. The product was used without further purification.

To a mixture of 6-methyl-2-{[(1-methyl-1H-1benzimidazol-2-yl)methyl]sulfanyl}pyrimidin-4-ol (428 mg, 1.5 mmol) in MeOH (3 mL) was added 4 M HCl/dioxane (2 mL, 8.0 mmol). The mixture became clear and a solid precipitated. The solid material was recovered by filtration and dried in vacuo, affording the title compound (533 mg, 99% yield); $^1$H NMR (400 MHz, DMSO-$d_6$): δ 2.11 (s, 3H), 3.56 (s, 3H), 4.14 (s, 2H), 6.14 (s, 1H), 7.61 (m, 2H), 7.80 (m, 1H), 7.98 (m, 1H); M+ 287.

Example 48

2-{[(3,5-dimethyl-1,2-oxazol-4-yl)methyl]sulfanyl}-6-methylpyrimidin-4-ol

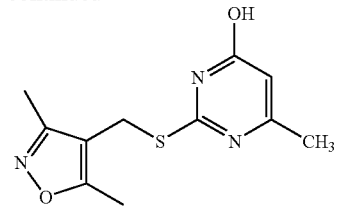

To a 0° C. solution of 3,5-dimethyl-1,2-oxazole-4-carbaldehyde (1.0 g, 8.0 mmol) in anhydrous methanol (60 mL) was added sodium borohydride (450 mg, 12.0 mmol). The reaction mixture was stirred at room temperature overnight. Water (50 mL) was added and methanol was evaporated. The resultant mixture was extracted with EtOAc (1×50 mL) and $CH_2Cl_2$ (3×50 mL). The organic extracts were combined, dried over $MgSO_4$, filtered, evaporated, and dried in vacuo, affording (3,5-dimethyl-1,2-oxazol-4-yl)methanol (805 mg, 79% yield). The product was used without further purification.

To a solution of (3,5-dimethyl-1,2-oxazol-4-yl)methanol (805 mg, 6.3 mmol) in anhydrous dichloromethane (60 mL) was added dropwise phosphorus tribromide (1.2 mL, 12.6 mmol). The mixture was stirred at room temperature for 3 hours. Dichloromethane was evaporated, and the residue was dried in vacuo, affording 4-(bromomethyl)-3,5-dimethyl-1,2-oxazole. The product was used without further purification.

A mixture of 4-(bromomethyl)-3,5-dimethyl-1,2-oxazole (6.3 mmol), 6-methyl-2-sulfanylpyrimidin-4-ol (611 mg, 4.3 mmol), and triethylamine (5 mL, 36.0 mmol) in absolute ethanol (25 mL) was stirred at room temperature overnight. The solid material was removed by filtration. The filtrate was recovered, evaporated, and co-evaporated with EtOAc (20 mL). The solid residue was treated with water (200 mL). The solid product was recovered by filtration, washed with water (2×20 mL), diethyl ether (2×20 mL), and hexanes (2×20 mL), and then dried in vacuo, affording the title compound (783 mg, 72% yield); $^1$H NMR (400 MHz, DMSO-$d_6$): δ 2.19 (m, 6H), 2.40 (s, 3H), 4.16 (s, 2H), 5.99 (s (br), 1H); M+ 252.

Example 49

2-{[(5-bromo-2-chlorophenyl)methyl]sulfanyl}-6-methylpyrimidin-4-ol

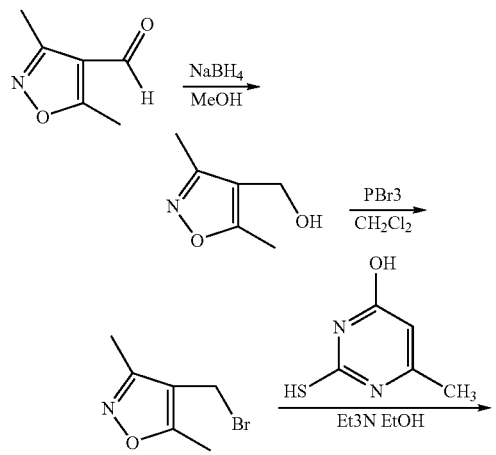

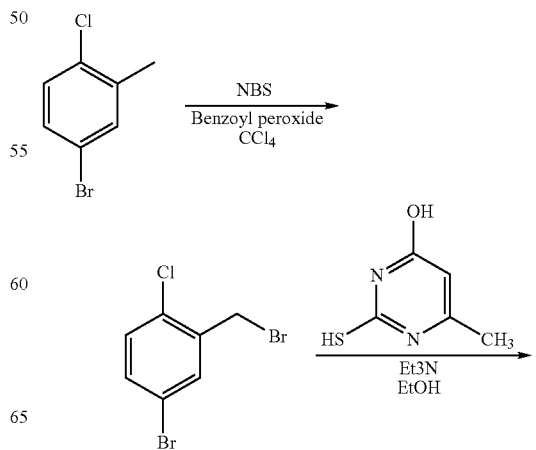

A mixture of 4-bromo-1-chloro-2-methylbenzene (5.0 g, 24.0 mmol), N-bromosuccinimide (4.4 g, 25.0 mmol), and benzoyl peroxide (700 mg, 2.9 mmol) in anhydrous carbon tetrachloride (85 mL) was stirred at reflux for 4 hours. Dichloromethane (50 mL) was added. The mixture was extracted with 1 N NaOH (1×150 mL) and brine (1×150 mL). The organic extract was recovered, dried over MgSO$_4$, filtered, evaporated, and dried in vacuo. The crude product was purified by flash chromatography (0-5% EtOAc/hexanes), affording 4-bromo-2-(bromomethyl)-1-chlorobenzene (4.76 g, 70% yield). The product was used without further purification.

A mixture of 4-bromo-2-(bromomethyl)-1-chlorobenzene (4.76 g. 16.7 mmol), 6-methyl-2-sulfanylpyrimidin-4-ol (1.83 g, 12.9 mmol), and triethylamine (5 mL, 36.0 mmol) in absolute ethanol (200 mL) was stirred at room temperature overnight. The reaction mixture was evaporated to dryness. The solid residue was treated with water (500 mL). The solid product was recovered by filtration, washed with water (2×50 mL), diethyl ether (3×50 mL), and hexanes (3×50 mL), and then dried in vacuo, affording the title compound (3.23 g, 56% yield); $^1$H NMR (400 MHz, DMSO-d$_6$): δ 2.21 (s, 3H), 4.39 (s, 2H), 6.00 (s (br), 1H), 7.41 (d, 1H, J=8.4 Hz), 7.53 (dd, 1H, J=2.3 Hz, 8.4 Hz), 7.86 (d, 1H, J=2.0 Hz); M+ 347.

Example 50

6-methyl-2-[(quinoxalin-6-ylmethyl)sulfanyl]pyrimidin-4-ol dihydrochloride

A mixture of 6-methylquinoxaline (2.0 g, 13.9 mmol), N-bromosuccinimide (3.0 g, 16.9 mmol), and benzoyl peroxide (411 mg, 1.7 mmol) in anhydrous carbon tetrachloride (50 mL) was stirred at reflux for 2 days. Dichloromethane (50 mL) was added after cooling to room temperature. The mixture was extracted with 1 N NaOH (1×100 mL) and brine (1×100 mL). The organic extract was recovered, dried over MgSO$_4$, filtered, evaporated, and dried in vacuo. The crude product was purified by flash chromatography (0-30% EtOAc/hexanes), affording 6-(bromomethyl)quinoxaline (1.10 g, 35% yield).

A mixture of 6-(bromomethyl)quinoxaline (900 mg, 4.0 mmol), 6-methyl-2-sulfanylpyrimidin-4-ol (440 mg, 3.1 mmol), and triethylamine (1.1 mL, 7.8 mmol) in absolute ethanol (20 mL) was stirred at room temperature overnight. The reaction mixture was evaporated and then co-evaporated with EtOAc. The solid residue was treated with water (100 mL). The solid product was recovered by filtration, washed with water (2×20 mL), diethyl ether (3×20 mL), and hexanes (3×20 mL), and then dried in vacuo, affording 6-methyl-2-[(quinoxalin-6-ylmethyl)sulfanyl]pyrimidin-4-ol (658 mg, 75% yield). The product was used without further purification.

To a mixture of 6-methyl-2-[(quinoxalin-6-ylmethyl)sulfanyl]pyrimidin-4-ol (650 mg, 2.3 mmol) in MeOH (3 mL) was added 4 M HCl/dioxane (3 mL, 12.0 mmol). The mixture became clear, and a solid precipitated. The solid material was recovered by filtration, washed with diethyl ether (2×20 mL), and dried in vacuo, affording the title compound (797 mg, 97% yield); $^1$H NMR (400 MHz, DMSO-d$_6$): δ 2.25 (s, 3H), 4.66 (s, 2H), 6.11 (s, 1H), 7.94 (dd, 1H, J=2.0 Hz, 8.6 Hz), 8.07 (d, 1H, J=8.6 Hz), 8.16 (d, 1H, J=1.7 Hz), 8.94 (m, 2H); M+ 285.

Example 51

6-methyl-2-[(1,3-thiazol-5-ylmethyl)sulfanyl]pyrimidin-4-ol

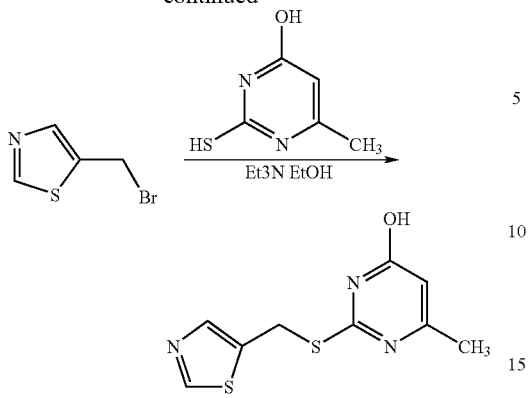

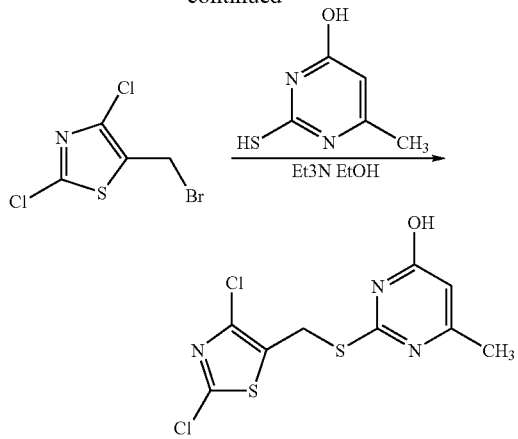

To a 0° C. solution of 1,3-thiazole-5-carbaldehyde (1.0 g, 8.8 mmol) in anhydrous methanol (65 mL) was added sodium borohydride (500 mg, 13.3 mmol). The reaction mixture was stirred at room temperature overnight. A solution of saturated ammonium chloride (60 mL) was added. The resultant mixture was extracted with EtOAc (2×60 mL) and CH$_2$Cl$_2$ (2×60 mL). The organic extracts were combined, dried over MgSO$_4$, filtered, evaporated, and dried in vacuo, affording 1,3-thiazol-5-ylmethanol (500 mg, 50%). The product was used without further purification.

To a solution of 1,3-thiazol-5-ylmethanol (500 mg, 4.3 mmol) in anhydrous dichloromethane (40 mL) was added dropwise phosphorus tribromide (850 mL, 9.0 mmol). The mixture was stirred at room temperature overnight. The solvent was evaporated. The residue was dried in vacuo, affording 5-(bromomethyl)-1,3-thiazole. The product was used without further purification.

A mixture of 5-(bromomethyl)-1,3-thiazole (4.3 mmol), 6-methyl-2-sulfanylpyrimidin-4-ol (427 mg, 3.0 mmol), and triethylamine (1.7 mL, 12.0 mmol) in absolute ethanol (20 mL) was stirred at room temperature overnight. The mixture was evaporated and then co-evaporated with EtOAc (20 mL). The solid residue was treated with water (100 mL). The solid product was recovered by filtration, washed with water (2×20 mL), diethyl ether (2×20 mL), and hexanes (2×20 mL), and then dried in vacuo. The crude product was purified by flash chromatography (0-5% MeOH/CH$_2$Cl$_2$), affording the title compound (28 mg, 4% yield); $^1$H NMR (400 MHz, DMSO-d$_6$): δ 2.09 (s, 3H), 4.64 (s, 2H), 4.16 (s, 2H), 6.02 (s (br), 1H), 7.87 (d, 1H, J=0.8 Hz), 8.94 (s, 1H); M+ 240.

Example 52

2-{[(2,4-dichloro-1,3-thiazol-5-yl)methyl]sulfanyl}-6-methylpyrimidin-4-ol

To a 0° C. solution of 2,4-dichloro-1,3-thiazole-5-carbaldehyde (1.0 g, 5.5 mmol) in anhydrous methanol (45 mL) was added sodium borohydride (340 mg, 9.0 mmol). The reaction mixture was stirred at room temperature overnight. Water (50 mL) was added and the methanol was evaporated. The resultant mixture was extracted with EtOAc (2×50 mL). The organic extracts were combined, dried over MgSO$_4$, filtered, evaporated, and dried in vacuo, to afford (2,4-dichloro-1,3-thiazol-5-yl)methanol (850 mg, 84% yield). The product was used without further purification.

To a solution of (2,4-dichloro-1,3-thiazol-5-yl)methanol (850 mg, 4.6 mmol) in anhydrous dichloromethane (40 mL) was added dropwise phosphorus tribromide (850 μL, 9.2 mmol). The mixture was stirred at room temperature for 3 hours. The solvent was evaporated. The residue was dried in vacuo, affording 5-(bromomethyl)-2,4-dichloro-1,3-thiazole. The product was used without further purification.

A mixture of 5-(bromomethyl)-2,4-dichloro-1,3-thiazole, 6-methyl-2-sulfanylpyrimidin-4-ol (500 mg, 3.5 mmol), and triethylamine (2.5 mL, 18.0 mmol) in absolute ethanol (20 mL) was stirred at room temperature overnight. The solid material was removed by filtration. The filtrate was evaporated and then co-evaporated with EtOAc (20 mL). The solid residue was treated with water (100 mL). The solid product was recovered by filtration, washed with water (2×20 mL), diethyl ether (2×20 mL), and hexanes (2×20 mL), and then dried in vacuo. The crude product was purified by flash chromatography (0-5% MeOH/CH$_2$Cl$_2$), affording the title compound (778 mg, 72% yield); $^1$H NMR (400 MHz, DMSO-d$_6$): δ 2.27 (s, 3H), 4.46 (s, 2H), 6.09 (s (br), 1H); M+ 310.

Example 53

2-{[(1-ethyl-1H-imidazol-2-yl)methyl]sulfanyl}-6-methylpyrimidin-4-ol dihydrochloride

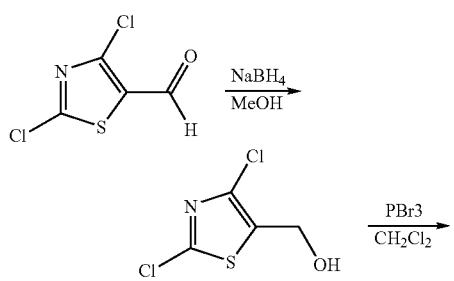

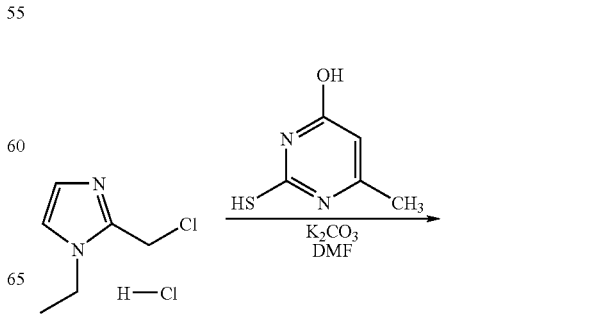

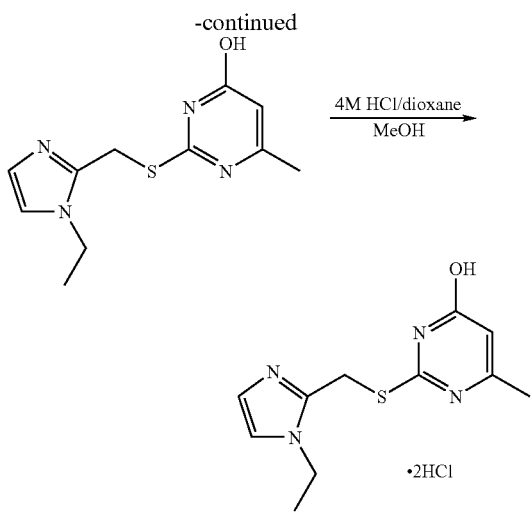

A mixture of 2-(chloromethyl)-1-ethyl-1H-imidazol-1-ium chloride (1.0 g, 5.5 mmol), 6-methyl-2-sulfanylpyrimidin-4-ol (650 mg, 4.6 mmol), and potassium carbonate (2.0 g, 14.4 mmol) in anhydrous DMF (10 mL) was stirred at room temperature overnight. The reaction mixture was evaporated under reduced pressure. The solid residue was treated with dichloromethane (20 mL) and brine (60 mL). The aqueous layer was recovered and evaporated. The residue was purified by flash chromatography (0-20% MeOH/CH$_2$Cl$_2$), affording 2-{[(1-ethyl-1H-imidazol-2-yl)methyl]sulfanyl}-6-methylpyrimidin-4-ol (244 mg, 21% yield); $^1$H NMR (400 MHz, DMSO-d$_6$): δ 1.27 (t, 3H, J=7.2 Hz), 2.17 (s, 3H), 4.00 (m, 2H), 4.50 (s, 2H), 6.00 (s, 1H), 6.81 (s, 1H), 7.15 (s, 1H); M+ 251. The product was used without further purification.

To a mixture of 2-{[(1-ethyl-1H-imidazol-2-yl)methyl]sulfanyl}-6-methylpyrimidin-4-ol (215 mg, 0.86 mmol) in MeOH (3 mL) was added 4 M HCl/dioxane (2 mL, 8.0 mmol). The mixture became clear, and a solid precipitated. The solvent was evaporated. The solid product was dried in vacuo, affording the title compound (275 mg, 99% yield); $^1$H NMR (400 MHz, DMSO-d$_6$): δ 1.38 (t, 3H, J=7.2 Hz), 2.16 (s, 3H), 4.29 (m, 2H), 4.73 (s, 2H), 6.17 (s, 1H), 7.61 (d, 1H, J=2.0 Hz), 7.15 (d, 1H, J=2.0 Hz); M+ 251.

Example 54

2-[({2-chloro-4-[(diethylamino)methyl]phenyl}methyl)sulfanyl]-6-methylpyrimidin-4-ol A mixture of 2-chloro-5-methylbenzoic acid (4.0 g, 23.4 mmol) in methanol (50 mL) and a few drops of concentrated sulfuric acid were stirred at reflux for 5 hours. After cooling to room temperature, methanol was evaporated. The residue was dissolved in ethyl acetate (50 mL). The solution was extracted with saturated NaHCO$_3$ (3×50 mL). The organic layer was dried over MgSO$_4$, filtered, evaporated, and dried in vacuo, affording methyl 2-chloro-5-methylbenzoate (3.07 g, 71% yield). The product was used without further purification.

A mixture of methyl 2-chloro-5-methylbenzoate (3.0 g, 16.2 mmol), N-bromosuccinimide (3.0 g, 17.0 mmol), and benzoyl peroxide (catalytic) in anhydrous carbon tetrachloride (50 mL) was stirred at reflux overnight. Dichloromethane (50 mL) was added after cooling to room temperature. The mixture was extracted with 1 N NaOH (2×100 mL). The organic layer was recovered, dried over MgSO$_4$, filtered, evaporated, and dried in vacuo, affording methyl 5-(bromomethyl)-2-chlorobenzoate (4.06 g, 95% yield). The product was used without further purification.

A mixture of 5-(bromomethyl)-2-chlorobenzoate (4.0 g, 15.6 mmol), diethylamine (5 mL, 48.1 mmol), and potassium carbonate (4.3 g, 31.2 mmol) in acetone (60 mL) was stirred at room temperature for 2 days. The solid material was removed by filtration. The filtrate was recovered, evaporated, and dried in vacuo, affording methyl 2-chloro-5-[(diethylamino)methyl]benzoate (3.97 g, 99% yield). The product was used without further purification.

To a solution of methyl 2-chloro-5-[(diethylamino)methyl]benzoate (3.97 g, 15.5 mmol) in anhydrous THF (100 mL) was added a solution of diisobutylaluminium hydride (1 M in toluene, 35 mL, 35 mmol). The reaction mixture was stirred at room temperature for 90 minutes. A Rochelle's salt solution (200 mL) and dichloromethane (200 mL) were added. The resultant mixture was stirred at room temperature for 2 hours. The organic layer was recovered, dried over MgSO$_4$, filtered, evaporated, and dried in vacuo, affording {2-chloro-5-[(diethylamino)methyl]phenyl}methanol (3.0 mg, 85% yield). The product was used without further purification.

To a solution of {2-chloro-5-[(diethylamino)methyl]phenyl}methanol (3.0 g, 13.2 mmol) in anhydrous dichloromethane (80 mL) was added dropwise phosphorus tribromide (2.5 mL, 26.4 mmol). The mixture was stirred at room temperature overnight. The solvent was evaporated. The residue was dried in vacuo, affording {[3-(bromomethyl)-4-chlorophenyl]methyl}diethylamine. The product was used without further purification.

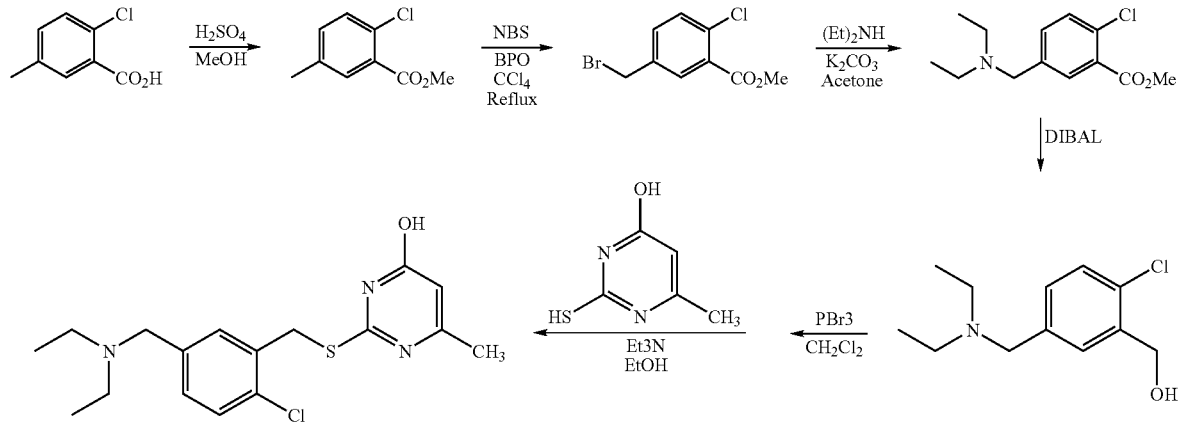

A mixture of {[3-(bromomethyl)-4-chlorophenyl]methyl}diethylamine (13.2 mmol), 6-methyl-2-sulfanylpyrimidin-4-ol (1.07 g, 7.5 mmol), and triethylamine (8 mL, 57.4 mmol) in absolute ethanol (50 mL) was stirred at room temperature overnight. The mixture was evaporated and then co-evaporated with EtOAc (20 mL). The solid residue was treated with water (100 mL). The solution was extracted with dichloromethane (5×100 mL). The organic extracts were combined, dried over MgSO$_4$, filtered, evaporated, and dried in vacuo. The crude product was purified by flash chromatography (0-15% MeOH/CH$_2$Cl$_2$), affording the title compound (932 mg, 39% yield); $^1$H NMR (400 MHz, DMSO-d$_6$): δ 1.11 (t, 6H, J=6.8 Hz), 2.21 (s, 3H), 2.86 (m, 4H), 4.09 (s (br), 2H), 4.45 (s, 2H), 6.01 (s (br), 1H), 7.45 (m, 1H), 7.52 (m, 1H), 7.72 (s, 1H); M+ 352.

Example 55

2-{[(2-chloroquinolin-3-yl)methyl]sulfanyl}-6-methylpyrimidin-4-ol

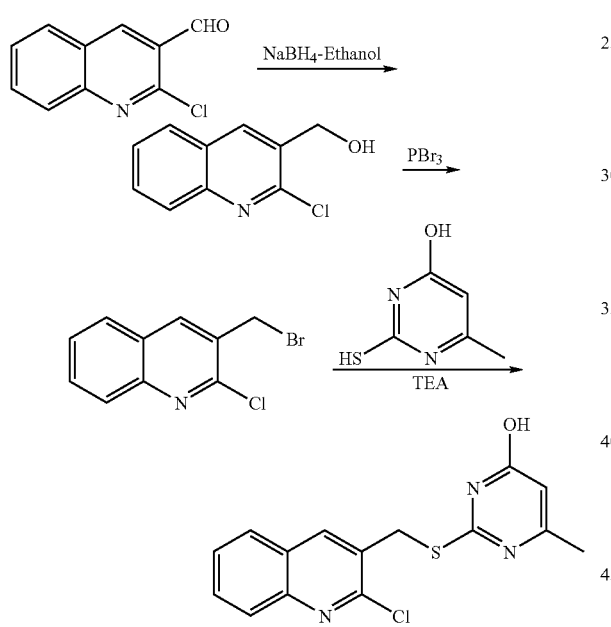

To a solution of 2-chloroquinoline-3-carbaldehyde (1.0 g, 5.21 mmol) in anhydrous ethanol (20 mL) at 0° C., was added sodium borohydride (0.197 g, 5.21 mmol). The reaction mixture was stirred at the same temperature for 1 hour. After completion of the reaction, as monitored by TLC and HPLC, the reaction mixture was quenched with water. The solvent was evaporated, and the crude residue was extracted with dichloromethane. The organic layer was washed with water and brine and dried over anhydrous sodium sulfate to provide the (2-chloroquinolin-3-yl)methanol as a white solid (0.96 g, 95% yield); M+ 193.64.

To a solution of (2-chloroquinolin-3-yl)methanol (0.96 g, 4.95 mmol) in anhydrous chloroform at 0° C. was added phosphorous tribromide (1.34 g, 4.95 mmol). After stirring at room temperature for 2 hours, the solvent was evaporated to provide 3-(bromomethyl)-2-chloroquinoline (1.27 g), which was used in the next step without purification.

To a mixture of 6-methyl-2-sulfanylpyrimidin-4-ol (0.492 g, 3.46 mmol) and 3-(bromomethyl)-2-chloroquinoline (1.27 g, 4.95 mmol) in anhydrous ethanol (30 mL) at room temperature was added triethylamine (1.50 g, 14.85 mmol). The reaction mixture was stirred at room temperature overnight. The solvent was evaporated to dryness and water (50 mL) was added. The mixture was sonicated, and a white solid precipitated out. The product was filtered, washed with water, washed with ether, and then dried in vacuo to provide 2-{[(2-chloroquinolin-3-yl)methyl]sulfanyl}-6-methylpyrimidin-4-ol as a white solid (1.03 g, 66% yield); $^1$H NMR (400 MHz, DMSO-d$_6$): δ 2.24 (s, 3H), 4.57 (s, 2H), 6.00 (bs, 1H), 7.61 (t, 1H), 7.78 (t, 1H), 7.79 (d, J=10.8 Hz, 1H), 8.01 (d, J=10.8 Hz, 1H), 8.67 (s, 1H); M+ 317.8.

Example 56

2-{[(2,6-dichloropyridin-3-yl)methyl]sulfanyl}-6-methylpyrimidin-4-ol

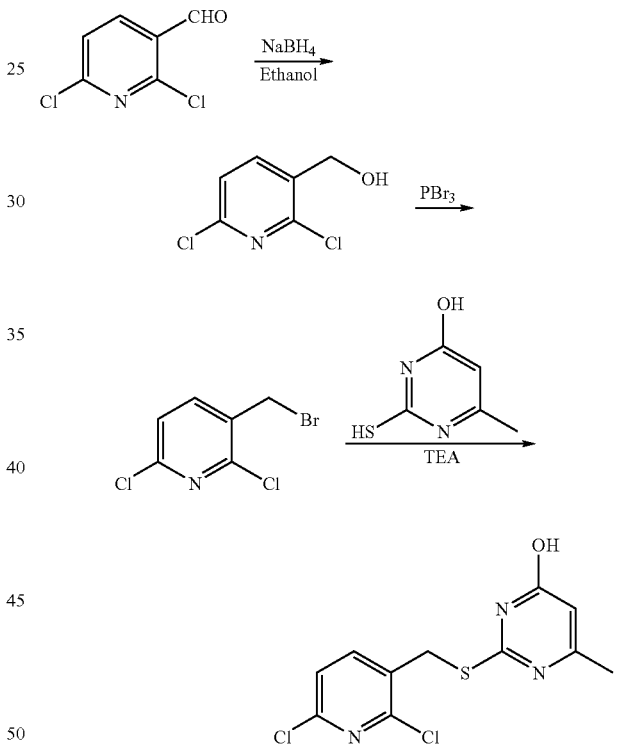

The title compound was prepared following the procedure described for Example 55 using 2,6-dichloropyridine-3-carbaldehyde to provide (2,6-dichloropyridin-3-yl)methanol; $^1$H NMR (400 MHz, DMSO-d$_6$): δ 4.51 (s, 2H), 5.65 (m, 1H), 7.51 (d, J=8.1 Hz, 1H), 8.01 (d, J=8.1 Hz, 1H); M+ 178.5.

The crude (2,6-dichloropyridin-3-yl)methanol was converted to 3-(bromomethyl)-2,6-dichloropyridine, which was then reacted with 6-methyl-2-sulfanylpyrimidin-4-ol in the presence of triethylamine to provide 2-{[(2,6-dichloropyridin-3-yl)methyl]sulfanyl}-6-methylpyrimidin-4-ol as a white solid (0.822 g, 82% yield); $^1$H NMR (400 MHz, DMSO-d$_6$): δ 2.15 (s, 3H), 4.36 (s, 2H), 5.95 (bs, 1H), 7.40 (d, J=8.0 Hz, 1H), 8.01 (d, J=8.0 Hz, 1H); M+ 302.5.

Example 57

2-[(isoquinolin-5-ylmethyl)sulfanyl]-6-methylpyrimidin-4-ol

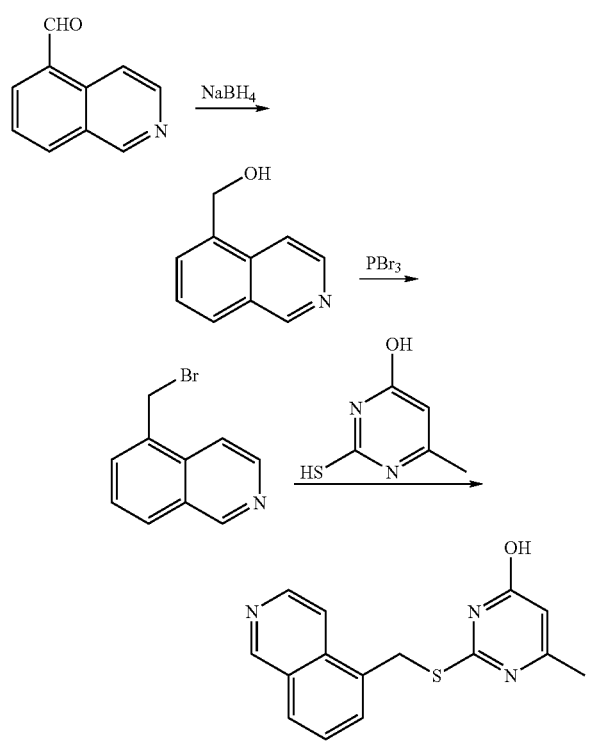

The title compound was prepared by following the procedure described for Example 55 using isoquinoline-5-carbaldehyde to provide isoquinolin-5-ylmethanol. Isoquinolin-5-ylmethanol provided 5-(bromomethyl)isoquinoline, which was then reacted with 6-methyl-2-sulfanylpyrimidin-4-ol to provide 2-[(isoquinolin-5-ylmethyl)sulfanyl]-6-methylpyrimidin-4-ol as a white solid (0.96 g, 75% yield); $^1$H NMR (400 MHz, DMSO-$d_6$): δ 2.22 (s, 3H), 4.84 (s, 2H), 5.99 (bs, 114), 7.60 (t, J=8.21 Hz, 15.16, 1H), 7.90 (d, J=8.0 Hz, 1H), 8.01 (d, J=7.2 Hz, 1H), 8.05 (d, J=8.3 Hz, 1H), 8.53 (d, J=5.8 Hz, 1H), 9.30 (s, 11-1); M+ 283.4.

Example 58

2-{[(6-chloropyridin-3-yl)methyl]sulfanyl}-6-methylpyrimidin-4-ol

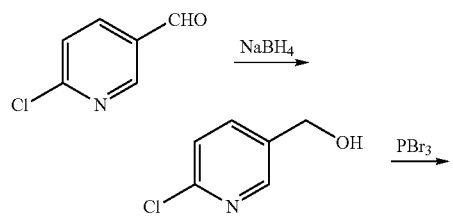

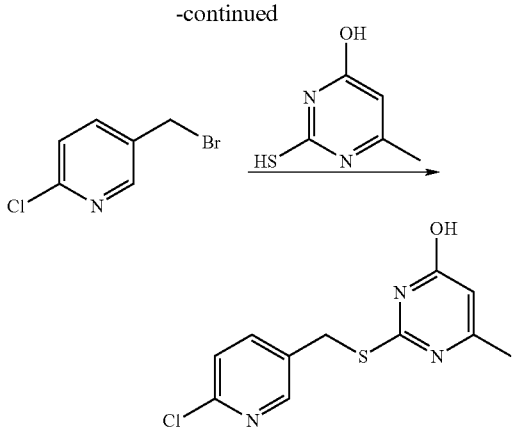

The title compound was prepared by following the procedure described for Example 55 from 6-chloropyridine-3-carbaldehyde to provide (6-chloropyridin-3-yl)methanol, which was converted to 5-(bromomethyl)-2-chloropyridine. The reaction of 6-methyl-2-sulfanylpyrimidin-4-ol with 5-(bromomethyl)-2-chloropyridine provided 2-{[(6-chloropyridin-3-yl)methyl]sulfanyl}-6-methylpyrimidin-4-ol (0.82 g, 62% yield); $^1$H NMR (400 MHz, DMSO-$d_6$): δ 2.17 (s, 3H), 4.33 (s, 2H), 5.99 (bs, 1H), 7.46 (d, J=8.3 Hz, 1H), 7.90 (d, J=8.3 Hz, 1H), 8.45 (s, 1H), 9.30 (s, 1H); M+ 268.2.

Example 59

2-{[(6-methoxypyridin-3-yl)methyl]sulfanyl}-6-methylpyrimidin-4-ol

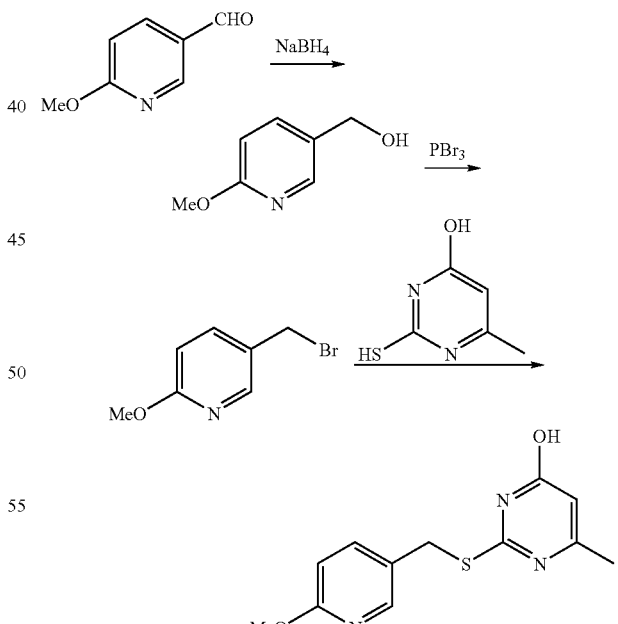

The title compound was prepared by following the procedure described for Example 55 using 6-methoxypyridine-3-carbaldehyde to provide (6-methoxypyridin-3-yl)methanol, which was converted to 5-(bromomethyl)-2-methoxypyridine. The reaction of 5-(bromomethyl)-2-methoxypyridine and 6-methyl-2-sulfanylpyrimidin-4-ol provided 2-{[(6- methoxypyridin-3-yl)methyl]sulfanyl}-6-methylpyrimidin-4-ol as a white solid (0.975 g, 75% yield); $^1$H NMR (400 MHz, DMSO-$d_6$): δ 2.19 (s, 3H), 3.79 (s, 3H), 4.29 (s, 2H), 5.99 (bs, 1H), 6.74 (d, J=8.3 Hz, 1H), 7.72 (d, J=8.3 Hz, 1H), 8.19 (s, 1H); M+ 263.87.

Example 60

6-methyl-2-{[(1-methyl-1H-pyrazol-5-yl)methyl]sulfanyl}pyrimidin-4-ol

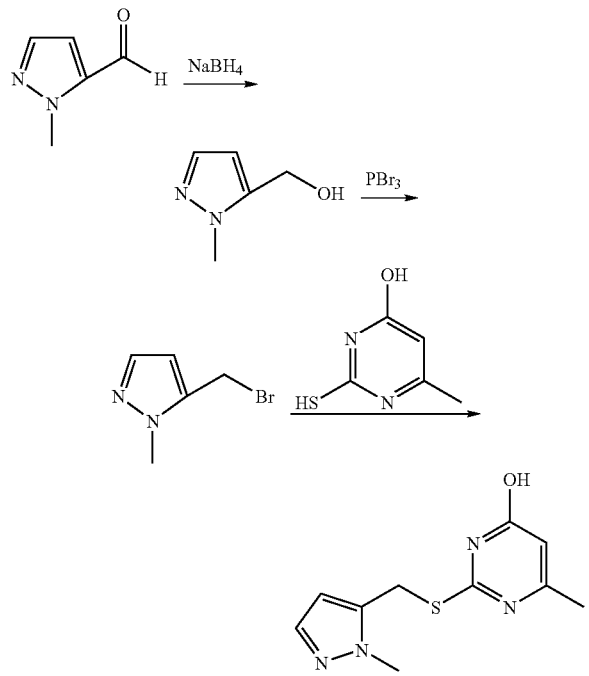

The title compound was prepared by following the procedure described for Example 55 from 1-methyl-1H-pyrazole-5-carbaldehyde to provide (1-methyl-1H-pyrazol-5-yl)methanol, which gave 5-(bromomethyl)-1-methyl-1H-pyrazole upon reaction with phosphorous tribromide. The reaction of 5-(bromomethyl)-1-methyl-1H-pyrazole and 6-methyl-2-sulfanylpyrimidin-4-ol provided 6-methyl-2-{[(1-methyl-1H-pyrazol-5-yl)methyl]sulfanyl}pyrimidin-4-ol as a white solid (0.742 g, 55% yield); $^1$H NMR (400 MHz, DMSO-$d_6$): δ 2.21 (s, 3H), 3.82 (s, 3H), 4.47 (s, 2H), 6.04 (bs, 1H), 6.23 (d, J=1.7 Hz, 1H), 7.29 (d, J=1.7 Hz, 1H), 8.19 (s, 1H); M+ 236.3.

Example 61

2-{[(2,3-dichloropyridin-4-yl)methyl]sulfanyl}-6-methylpyrimidin-4-ol

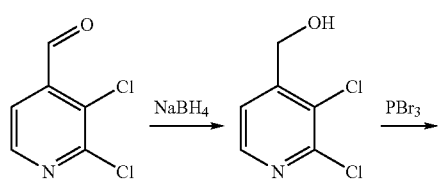

-continued

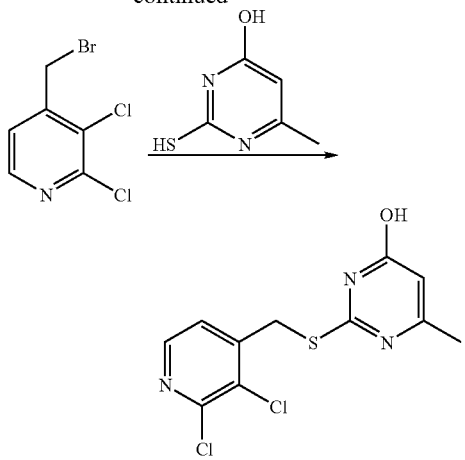

The title compound was prepared by following the procedure described for Example 55 from 2,3-dichloropyridine-4-carbaldehyde to provide (2,3-dichloropyridin-4-yl)methanol; $^1$H NMR (400 MHz, DMSO-$d_6$): δ 4.60 (d, J=5.7 Hz, 2H), 5.80 (t, J=4.6, 11.3 Hz, 1H), 7.59 (d, J=4.7 Hz, 1H), 8.38 (d, J=4.7 Hz, 1H); M+ 177.8.

(2,3-dichloropyridin-4-yl)methanol was converted to 4-(bromomethyl)-2,3-dichloropyridine. The reaction of 4-(bromomethyl)-2,3-dichloropyridine and 6-methyl-2-sulfanylpyrimidin-4-ol provided 2-{[(2,3-dichloropyridin-4-yl)methyl]sulfanyl}-6-methylpyrimidin-4-ol as a white solid (0.98 g, 78% yield); $^1$H NMR (400 MHz, DMSO-$d_6$): δ 2.21 (s, 3H), 3.82 (s, 3H), 4.47 (s, 2H), 6.04 (bs, 1H), 7.68 (d, J=4.7 Hz, 1H), 8.32 (d, J=4.7 Hz, 1H); M+ 302.2.

Example 62

2-[({6-chloroimidazo[2,1-b][1,3]thiazol-5-yl}methyl)sulfanyl]-6-methylpyrimidin-4-ol

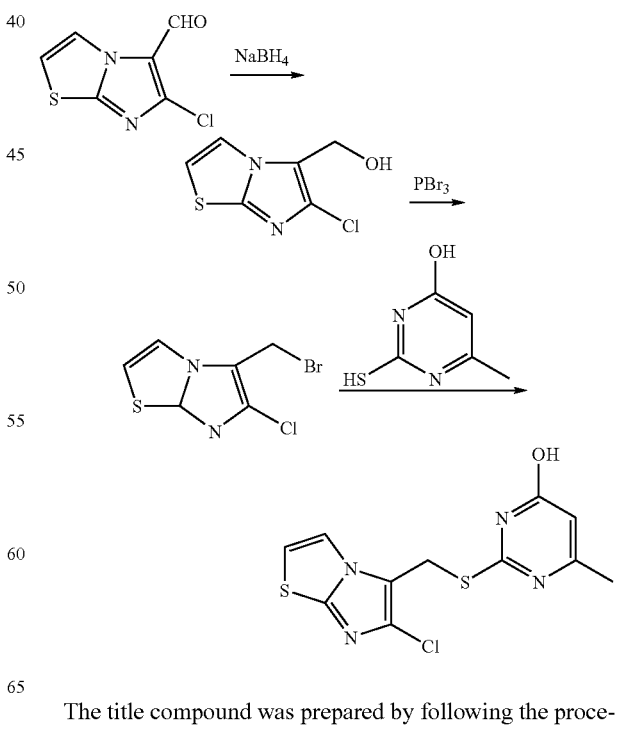

The title compound was prepared by following the procedure described for Example 55, whereby 6-chloroimidazo[2, 1-b][1,3]thiazole-5-carbaldehyde provided {6-chloroimidazo[2,1-b][1,3]thiazol-5-yl}methanol; $^1$H NMR (400 MHz, DMSO-d$_6$): δ 4.62 (d, J=5.2 Hz, 2H), 5.38 (t, J=5.4, 10.9 Hz, 1H), 7.38 (d, J=4.7 Hz, 1H), 7.91 (d, J=4.7 Hz, 1H); M+ 188.7.

{6-chloroimidazo[2,1-b][1,3]thiazol-5-yl}methanol was converted to 5-(bromomethyl)-6-chloroimidazo[2,1-b][1,3]thiazole, which was then reacted with 6-methyl-2-sulfanylpyrimidin-4-ol to give the title compound as a white solid (0.27 g, 22% yield); $^1$H NMR (400 MHz, DMSO-d$_6$): δ 2.21 (s, 3H), 4.67 (s, 2H), 6.04 (bs, 1H), 7.42 (d, J=4.7 Hz, 1H), 8.02 (d, J=4.7 Hz, 1H); M+ 312.8.

Example 63

6-methyl-2-({[5-(pyridin-3-yl)pyridin-3-yl]methyl}sulfanyl)pyrimidin-4-ol

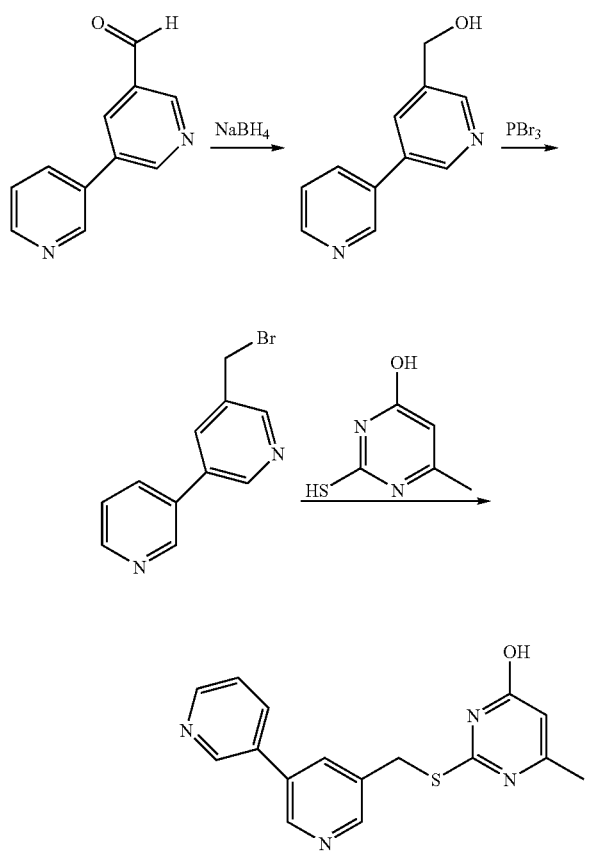

The title compound was prepared by following the procedure described for Example 55. 5-(pyridin-3-yl)pyridine-3-carbaldehyde provided [5-(pyridin-3-yl)pyridin-3-yl]methanol, which was reacted with phosphorus tribromide to give 3-(bromomethyl)-5-(pyridin-3-yl)pyridine. The reaction of 3-(bromomethyl)-5-(pyridin-3-yl)pyridine with 6-methyl-2-sulfanylpyrimidin-4-ol gave 6-methyl-2-({[5-(pyridin-3-yl)pyridin-3-yl]methyl}sulfanyl)pyrimidin-4-ol as a white solid (0.18 g, 15% yield); $^1$H NMR (400 MHz, DMSO-d$_6$): δ 2.21 (s, 3H), 4.45 (s, 2H), 6.04 (bs, 1H), 7.54 (m, 1H), 8.24 (d, J=4.7 Hz, 1H), 8.30 (s, 1H), 8.63 (d, J=4.7 Hz, 1H), 8.64 (s, 1H), 8.83 (s, 1H), 8.93 (s, 1H); M+ 310.1.

Example 64

2-{[(2,4-dichloropyridin-3-yl)methyl]sulfanyl}-6-methylpyrimidin-4-ol

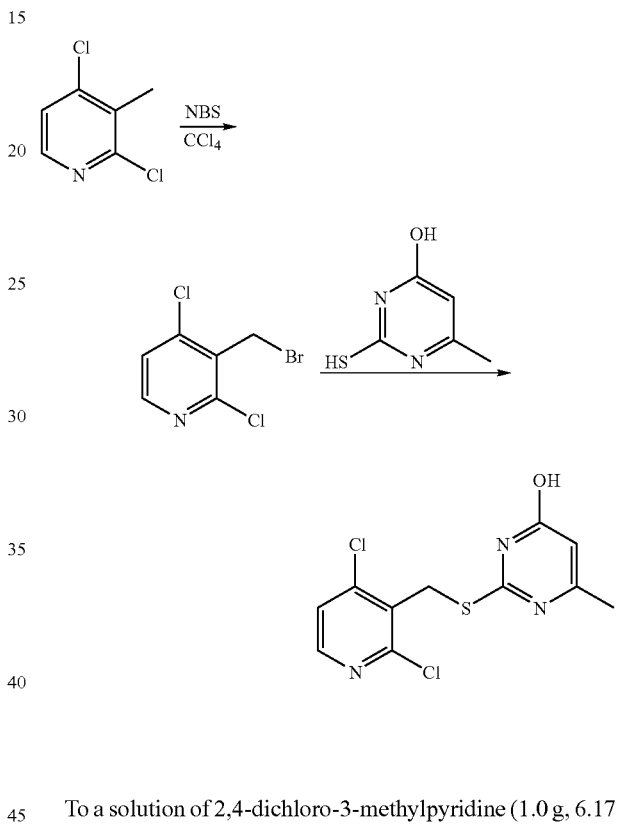

To a solution of 2,4-dichloro-3-methylpyridine (1.0 g, 6.17 mmol) in carbon tetrachloride (25 mL) was added NBS (1.09 g, 6.17 mmol) and a catalytic amount of benzoyl peroxide (0.15 g, 0.617 mmol). The reaction mixture was heated to reflux for 4 hours, and then cooled to room temperature and filtered. The filtrate was evaporated to afford 3-(bromomethyl)-2,4-dichloropyridine as a syrup (1.41 g, 95% yield), which was used in the next reaction without any further purification.

To a solution of 3-(bromomethyl)-2,4-dichloropyridine (1.41 g, 5.86 mmol) in anhydrous ethanol (20 mL) was added 6-methyl-2-sulfanylpyrimidin-4-ol (0.58 g, 4.09 mmol) and triethylamine (0.65 g, 6.43 mmol). The reaction mixture was stirred at room temperature overnight. The solvent was evaporated, and water was added to precipitate the product. The white solid was filtered and washed with water and ether to provide 2-{[(2,4-dichloropyridin-3-yl)methyl]sulfanyl}-6-methylpyrimidin-4-ol as a white solid (0.795 g, 45% yield); $^1$H NMR (400 MHz, DMSO-d$_6$): δ 2.23 (s, 3H), 2.31 (s, 3H), 4.68 (s, 2H), 6.04 (bs, 1H), 7.67 (d, J=5.3 Hz, 1H), 8.35 (d, J=5.3 Hz, 1H); M+ 302.3.

Example 65

6-methyl-2-[(quinolin-2-ylmethyl)sulfanyl]pyrimidin-4-ol hydrochloride

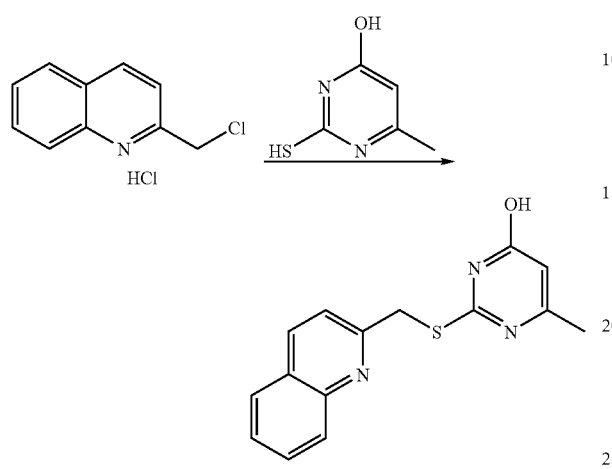

A mixture of 2-(chloromethyl)quinoline hydrochloride (1.0 g, 4.67 mmol) and 6-methyl-2-sulfanylpyrimidin-4-ol (0.46 g, 3.26 mmol) and K$_2$CO$_3$ (1.28 g, 9.34 mmol) in DMF (25 mL) was stirred overnight at room temperature. The solvent was filtered and evaporated to provide the crude product. Water was added to the crude reaction mixture to precipitate the product, which was then filtered and washed with water and ether to provide the titled product as a beige solid (0.68 g, 52% yield); $^1$H NMR (400 MHz, DMSO-d$_6$): δ 2.09 (s, 3H), 2.31 (s, 3H), 4.95 (s, 2H), 6.04 (bs, 1H), 7.87 (t, J=7.8, 15.0 Hz, 1H), 8.08 (m, 2H), 8.26 (d, J=8.1 Hz, 1H), 8.48 (d, J=8.2 Hz, 1H), 9.00 (d, J=8.2 Hz, 1H); M+ 283.3.

Example 66

6-methyl-2-({[2-(piperidin-1-yl)quinolin-3-yl]methyl}sulfanyl)pyrimidin-4-ol

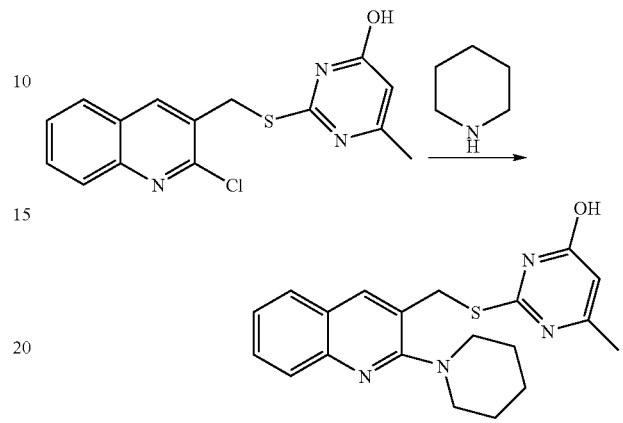

A mixture of 2-{[(2-chloroquinolin-3-yl)methyl]sulfanyl}-6-methylpyrimidin-4-ol (0.5 g, 1.57 mmol) and piperidine (1.33 g, 15.7 mmol) in DMSO was heated overnight at 90° C. Water was then added, and the product was extracted in dichloromethane and back washed with water. The organic layer was separated, dried, and evaporated to provide the titled product as a beige solid (0.35 g, 61% yield); $^1$H NMR (400 MHz, DMSO-d$_6$): δ 2.09 (s, 3H), 2.31 (s, 3H), 4.95 (s, 2H), 6.04 (bs, 1H), 7.87 (t, J=7.8, 15.0 Hz, 1H), 8.08 9 m, 2H), 8.26 (d, J=8.1 Hz, 1H), 8.48 (d, J=8.2 Hz, 1H), 9.00 (d, J=8.2 Hz, 1H); M+ 366.5.

Example 67

2-({[2-chloro-4-(4-ethylpiperazin-1-yl)phenyl]methyl}sulfanyl)-6-methylpyrimidin-4-ol

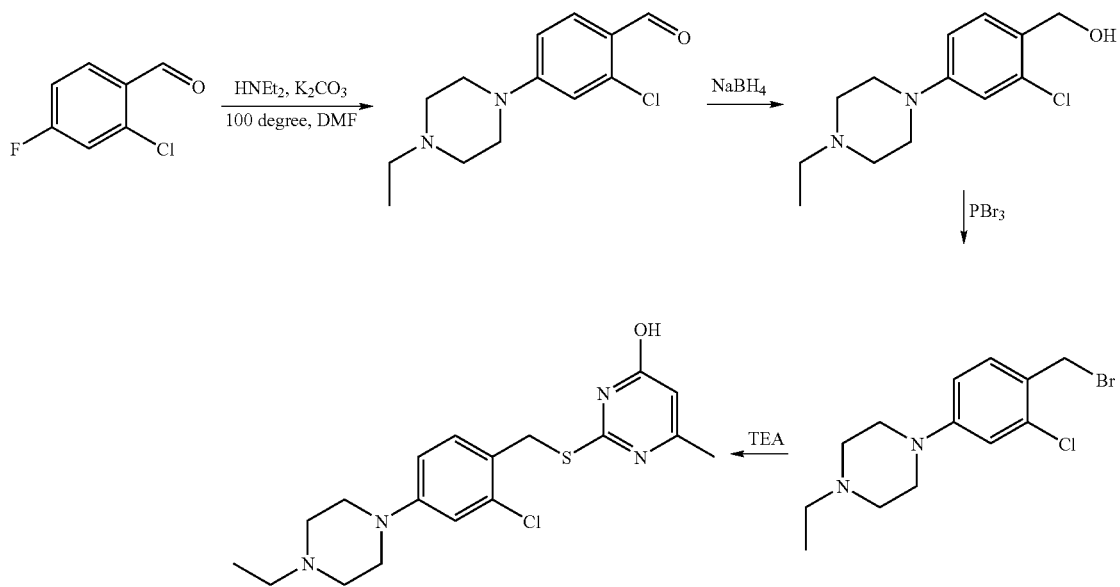

In a 250 mL round bottom flask, 2-chloro-4-fluorobenzaldehyde (3.15 g, 20 mmol), 1-ethylpiperazine (2.8 mL, 22 mmol), and potassium carbonate (2.76 g, 20 mmol) were dissolved in anhydrous DMF (20 mL). The mixture was heated at 100° C. for 4 hours. DMF was evaporated under vacuum. The crude product was partitioned between water (100 mL) and DCM (150 mL). The organic phase was separated, washed with water, dried over Na₂SO₄, and evaporated to provide nearly pure 2-chloro-4-(4-ethylpiperazin-1-yl)benzaldehyde.

The crude 2-chloro-4-(4-ethylpiperazin-1-yl)benzaldehyde was dissolved in anhydrous ethanol (20 mL). The solution was cooled to 0° C. under nitrogen, and NaBH₄ (1.52 g, 40 mmol) was added in one portion. The mixture was stirred at room temperature for 2 hours and quenched by addition of water (5 mL). Na₂SO₄ (20 g) was then added. After 10 minutes, the mixture was filtered. The filtrate was evaporated to provide [2-chloro-4-(4-ethylpiperazin-1-yl)phenyl]methanol.

[2-chloro-4-(4-ethylpiperazin-1-yl)phenyl]methanol was dissolved in dichloromethane (30 mL) at 0° C. under nitrogen. Phosphorus tribromide (4.2 mL, 42 mmol) was added dropwise. The resulting mixture was stirred at room temperature for 2 hours. The reaction was quenched by addition of 10% NaHCO₃ solution (5 mL). After 10 minutes, Na₂SO₄ (30 g) was added. The solvent was filtered and evaporated to provide 1-[4-(bromomethyl)-3-chlorophenyl]-4-ethylpiperazine, which was used without further purification.

1-[4-(bromomethyl)-3-chlorophenyl]-4-ethylpiperazine, 6-methyl-2-sulfanylpyrimidin-4-ol (1.42 g, 10 mmol) and triethylamine (2.8 mL, 20 mmol) were mixed in ethanol (50 mL). The mixture was stirred at room temperature for 2 hours. After evaporation, water (100 mL) was added. The suspension was filtered and washed with water and ethyl acetate to provide crude product, which was further purified by CombiFlash to yield a white solid (400 mg, 5% overall yield); ¹H NMR (400 MHz, DMSO-d₆): δ 1.16 (t, 3H), 2.20 (s, 3H), 2.48 (q, 4H), 3.06 (q, 4H), 4.35 (s, 2H), 5.98 (br, 1H), 6.88 (d, 1H), 7.00 (s, 1H), 7.42 (d, 1H); M+ 379.

Example 68

3-chloro-2-{[(4-hydroxy-6-methylpyrimidin-2-yl)sulfanyl]methyl}benzonitrile

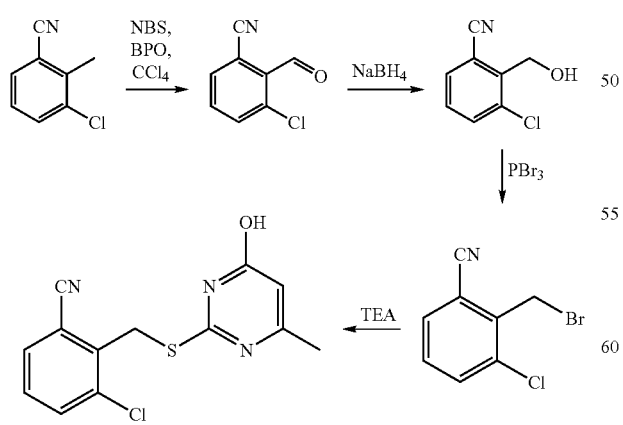

The title compound was prepared by following the procedure described for Example 55 from 3-chloro-2-methylbenzonitrile to provide the title compound as a white solid (800 mg, 40% yield); ¹H NMR (400 MHz, DMSO-d₆): δ 2.25 (s, 3H), 4.66 (s, 2H), 6.03 (br, 1H), 7.50 (m, 1H), 7.85 (d, 2H); M+ 292.

Example 69

3-chloro-N,N-diethyl-2-{[(4-hydroxy-6-methylpyrimidin-2-yl)sulfanyl]methyl}benzene-1-carboximidamide

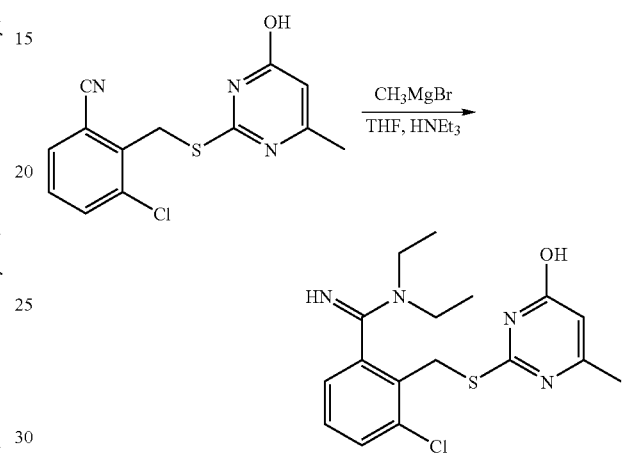

In a 100 mL round bottom flask, diethylamine (0.31 mL, 3.0 mmol) was added into the solution of MeMgBr (0.90 mL, 3 mmol) in THF (20 mL). The resulting mixture was stirred at 40° C. for 1 hour, followed by addition of 3-chloro-2-{[(4-hydroxy-6-methylpyrimidin-2-yl)sulfanyl]methyl}benzonitrile (292 mg, 1.0 mmol). After another 1.5 hours, the solvent was removed under vacuum. The crude product was purified by CombiFlash (0 to 20% MeOH in DCM) to provide the title compound as a grey-yellow solid (200 mg, 68% yield); ¹H NMR (400 MHz, DMSO-d₆): δ 1.17 (t, 6H), 2.28 (s, 3H), 3.31 (q, 4H), 4.60-4.80 (m, 2H), 6.03 (br, 1H), 7.57 (m, 2H), 7.88 (d, 1H); M+ 365.

Example 70

2-{[(4-amino-2-chlorophenyl)methyl]sulfanyl}-6-methylpyrimidin-4-ol

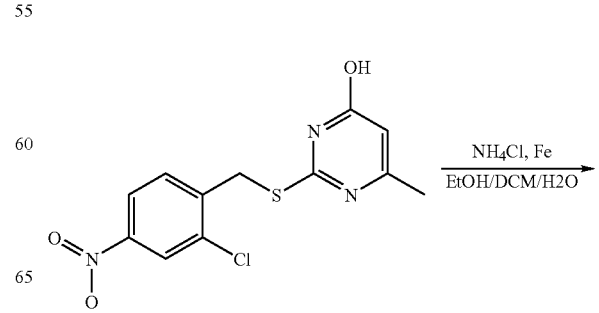

-continued

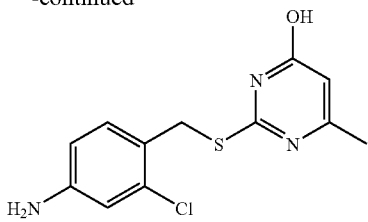

2-{[(2-chloro-4-nitrophenyl)methyl]sulfanyl}-6-methylpyrimidin-4-ol (282 mg, 1.0 mmol) was dissolved in DCM/EtOH/H$_2$O (20 mL/20 mL/10 mL). Iron (550 mg, 10 mmol) and NH$_4$Cl (540 mg, 10 mmol) were added. The mixture was stirred at room temperature for 3 hours. DCM (200 mL) was added to extract the product. The organic phase was dried over MgSO$_4$ and evaporated. The crude product was purified by CombiFlash (0 to 8% MeOH/DCM) to provide the title compound as a yellow solid (100 mg, 35% yield); $^1$H NMR (400 MHz, DMSO-d$_6$): δ 2.22 (s, 3H), 4.37 (s, 2H), 5.95 (br, 1H), 6.65 (d, 1H), 6.92 (s, 1H), 7.38 (d, 1H); M+ 282.

Example 71

2-({[2-chloro-4-(diethylamino)phenyl]methyl}sulfanyl)-6-methylpyrimidin-4-ol

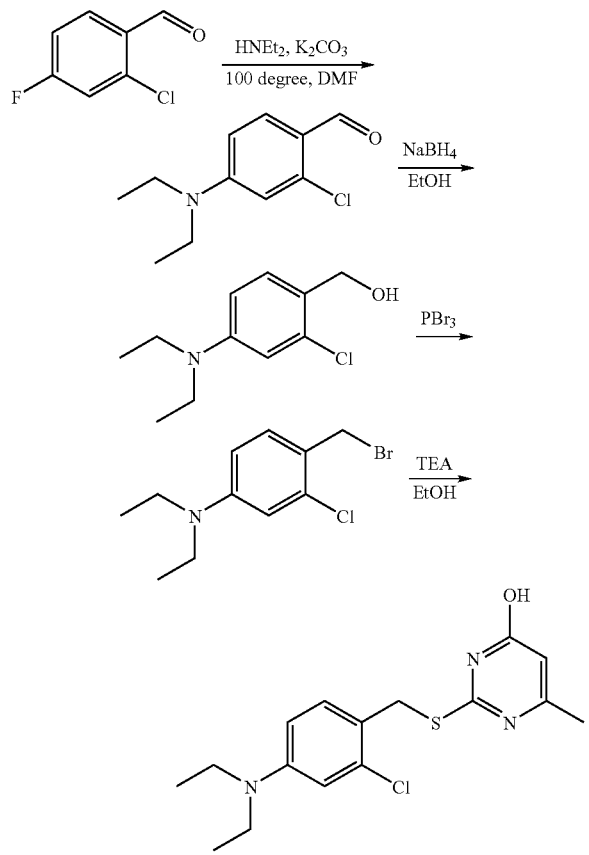

The title compound was prepared by following the procedure described for Example 67 by reacting 2-chloro-4-fluorobenzaldehyde with diethylamine, which provided a white solid (400 mg, 5% overall yield); $^1$H NMR (400 MHz, DMSO-d$_6$): δ 1.07 (t, 6H), 2.22 (s, 3H), 3.28 (q, 4H), 4.36 (s, 2H), 5.99 (br, 1H), 6.56 (d, 1H), 6.64 (s, 1H), 7.32 (d, 1H); M+ 338.

Example 72

6-methyl-2-{[(2-methylpyridin-3-yl)methyl]sulfanyl}pyrimidin-4-ol

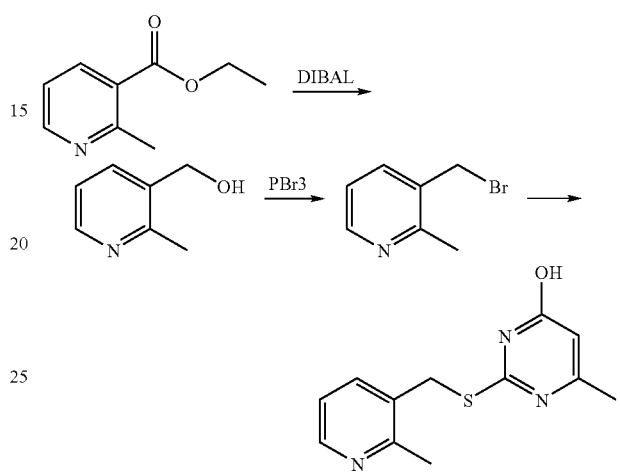

The title compound was prepared by following the procedure described for Example 67 from ethyl 2-methylpyridine-3-carboxylate but with DIBAL as the reducing agent. The desired compound was obtained as a white solid (640 mg, 88% yield); $^1$H NMR (400 MHz, DMSO-d$_6$): δ 2.21 (s, 3H), 2.55 (s, 3H), 4.40 (s, 2H), 6.03 (br, 1H), 7.19 (m, 1H), 7.80 (d, 1H), 8.34 (d, 1H); M+ 248.

Example 73

6-methyl-2-{[(5-methyl-1,3-thiazol-2-yl)methyl]sulfanyl}pyrimidin-4-ol

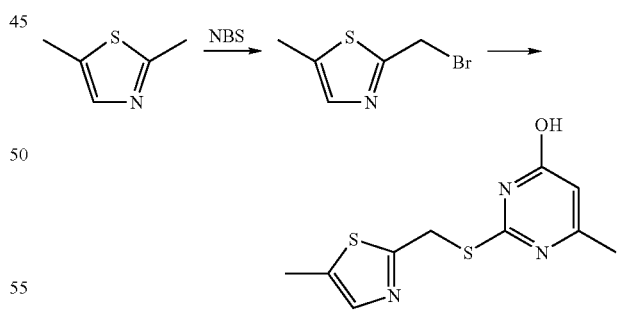

To CCl$_4$ (100 mL) in a 250 mL round bottom flask were added 2,5-dimethyl-1,3-thiazole (1.7 g, 15 mmol), 1-bromopyrrolidine-2,5-dione (2.94 g, 16.5 mmol), and benzoyl benzenecarboperoxoate (180 mg, 0.75 mmol). The reaction mixture was heated at 80° C. for 4 hours. The solvent was then removed under vacuum. The crude product was dissolved in ethanol (30 mL). 6-methyl-2-sulfanylpyrimidin-4-ol (700 mg, 5 mmol) and triethylamine (1.4 mL) were added, and the mixture was stirred at room temperature for 2 hours. After removal of the solvent, the crude product was purified by column chromatography (0-8% methanol in DCM) to provide the title compound as a white solid (480 mg, 40% yield); $^1$H NMR (400 MHz, DMSO-d$_6$): δ 2.25 (s, 3H), 2.50 (s, 3H), 4.56 (s, 2H), 6.03 (br, 1H), 7.55 (s, 1H); M+ 254.

Example 74

2-[({6-chloroimidazo[1,2-a]pyridin-2-yl}methyl)sulfanyl]-6-methylpyrimidin-4-ol

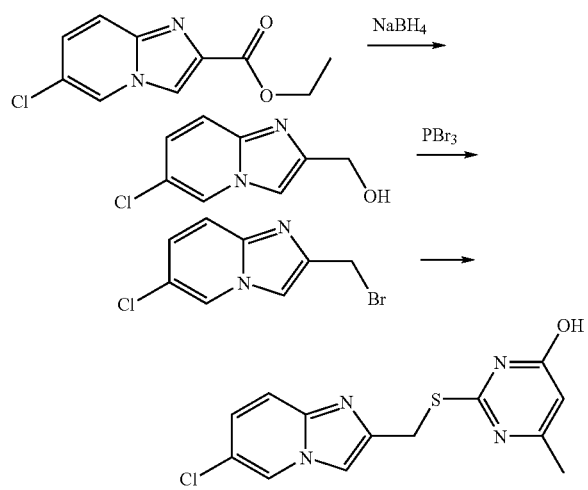

The title compound was prepared by following the procedure described for Example 67 from ethyl 6-chloroimidazo[1,2-a]pyridine-2-carboxylate, which provided a white solid (410 mg, 45% yield); $^1$H NMR (400 MHz, DMSO-d$_6$): δ 2.23 (s, 3H), 4.48 (s, 2H), 6.02 (br, 1H), 7.27 (d, 1H), 7.53 (d, 1H), 7.88 (s, 1H), 8.81 (s, 1H); M+ 308.

Example 75

6-methyl-2-{[(2-methyl-1,3-thiazol-5-yl)methyl]sulfanyl}pyrimidin-4-ol

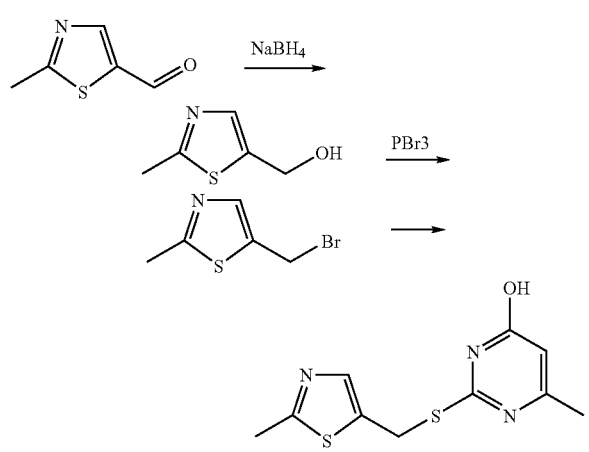

The title compound was prepared by following the procedure described for Example 67 from 2-methyl-1,3-thiazole-5-carbaldehyde, which provided a white solid (150 mg, 15% yield); $^1$H NMR (400 MHz, DMSO-d$_6$): δ 2.25 (s, 3H), 2.56 (s, 3H), 4.56 (s, 2H), 6.00 (br, 1H), 7.44 (s, 1H); M+ 254.

Example 76

6-methyl-2-{[(2-methyl-1,3-oxazol-4-yl)methyl]sulfanyl}pyrimidin-4-ol

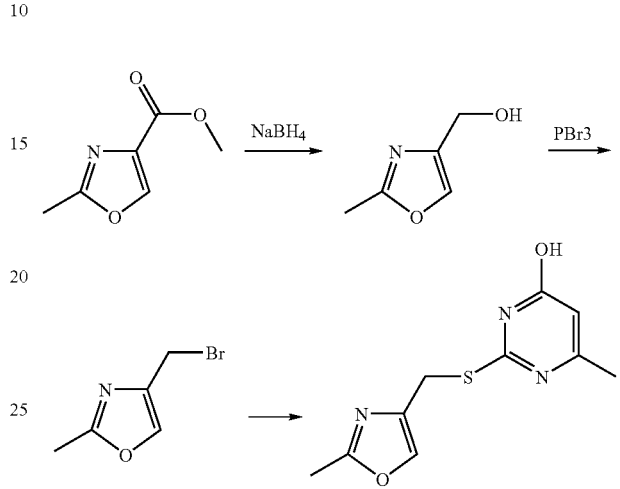

The title compound was prepared by following the procedure described for Example 67 from methyl 2-methyl-1,3-oxazole-4-carboxylate, which provided a white solid (90 mg, 10% yield); $^1$H NMR (400 MHz, DMSO-d$_6$): δ 2.20 (s, 3H), 2.36 (s, 3H), 4.20 (s, 2H), 6.00 (br, 1H), 7.85 (s, 1H); M+ 238.

Example 77

2-{[(1,5-dimethyl-1H-pyrazol-4-yl)methyl]sulfanyl}-6-methylpyrimidin-4-ol

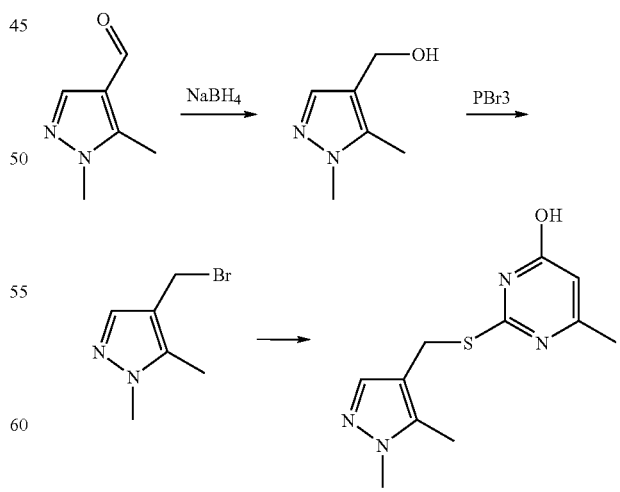

The title compound was prepared by following the procedure described for Example 67 from 1,5-dimethyl-1H-pyrazole-4-carbaldehyde, which provided a white solid (15 mg, 2% yield); ¹H NMR (400 MHz, DMSO-d₆): δ 2.21 (s, 3H), 2.23 (s, 3H), 3.68 (s, 3H), 4.18 (s, 2H), 5.99 (br, 1H), 7.32 (s, 1H); M+ 251.

Example 78

2-{[(1-ethyl-1H-imidazol-5-yl)methyl]sulfanyl}-6-methylpyrimidin-4-ol

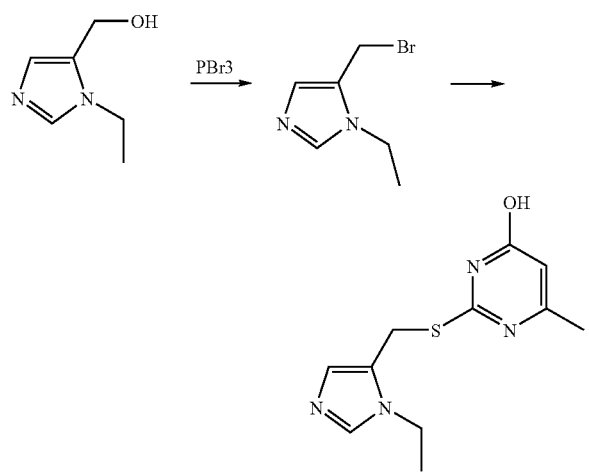

To a solution of (1-ethyl-1H-imidazol-5-yl)methanol (631 mg, 5.0 mmol) in dichloromethane (20 mL) was added dropwise tribromophosphane (0.94 mL, 10.0 mmol). The resulting mixture was stirred at room temperature for 6 hours. After evaporation, the crude 5-(bromomethyl)-1-ethyl-1H-imidazole was dissolved in cold ethanol (30 mL), and 6-methyl-2-sulfanylpyrimidin-4-ol (700 mg, 5 mmol) and triethylamine (2.8 mL, 20 mmol) were added. After 2 hours, the solvent was evaporated, and the residue was purified by chromatography (4% methanol in dichloromethane) to provide a white solid (150 mg, 12% yield); ¹H NMR (400 MHz, DMSO-d₆): δ 1.33 (t, 3H), 2.22 (s, 3H), 4.02 (q, 2H), 4.46 (s, 2H), 6.03 (br, 1H), 6.88 (s, 1H), 7.64 (s, 1H); M+ 251.

Example 79

2-{[(5-chloro-1-methyl-1H-imidazol-2-yl)methyl]sulfanyl}-6-methylpyrimidin-4-ol

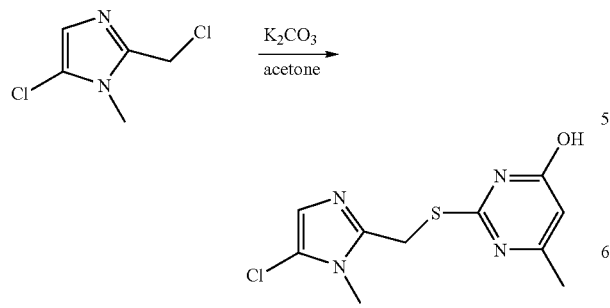

5-chloro-2-(chloromethyl)-1-methyl-1H-imidazole hydrochloride (1.0 g, 5.0 mmol), potassium carbonate (1.65 g, 12 mmol), and 6-methyl-2-sulfanylpyrimidin-4-ol (560 mg, 4.0 mmol) were mixed in acetone (20 mL). The mixture was stirred at room temperature overnight. Acetone was then removed under reduced pressure. The crude solid was purified by column chromatography to provide the title compound as a white solid (850 mg, 79% yield); ¹H NMR (400 MHz, DMSO-d₆): δ 2.20 (s, 3H), 3.60 (s, 3H), 4.51 (s, 2H), 6.04 (br, 1H), 6.93 (s, 1H); M+ 271.

Example 80

6-methyl-2-({[1-(propan-2-yl)-1H-imidazol-5-yl]methyl}sulfanyl)pyrimidin-4-ol

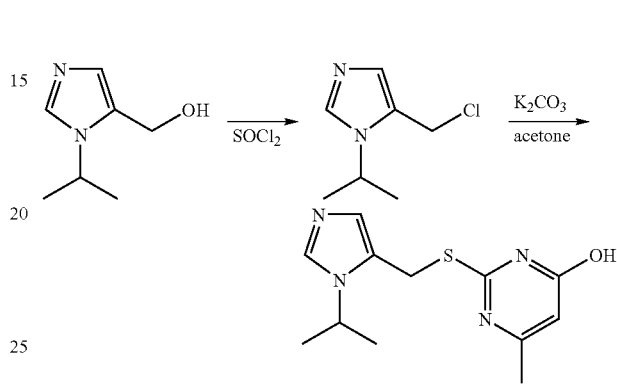

[1-(propan-2-yl)-1H-imidazol-5-yl]methanol (255 mg, 1.8 mmol) was dissolved in SOCl₂ (2 mL) and diethyl ether (10 mL). After 3 hours, the solvents were evaporated. To the solid was added potassium carbonate (414 mg, 3 mmol), 6-methyl-2-sulfanylpyrimidin-4-ol (200 mg, 1.4 mmol), and acetone (20 mL). The resulting mixture was stirred at room temperature overnight. Acetone was evaporated, and the crude solid was purified by column chromatography to provide the title compound as a white solid (150 mg, 32% yield); ¹H NMR (400 MHz, DMSO-d₆): δ 1.51 (m, 6H), 2.27 (s, 3H), 4.53 (m, 1H), 4.92 (s, 2H), 6.01 (br, 1H), 6.99 (s, 1H), 7.83 (s, 1H); M+ 265.

Example 81

2-{[(1,2-dimethyl-1H-imidazol-4-yl)methyl]sulfanyl}-6-methylpyrimidin-4-ol

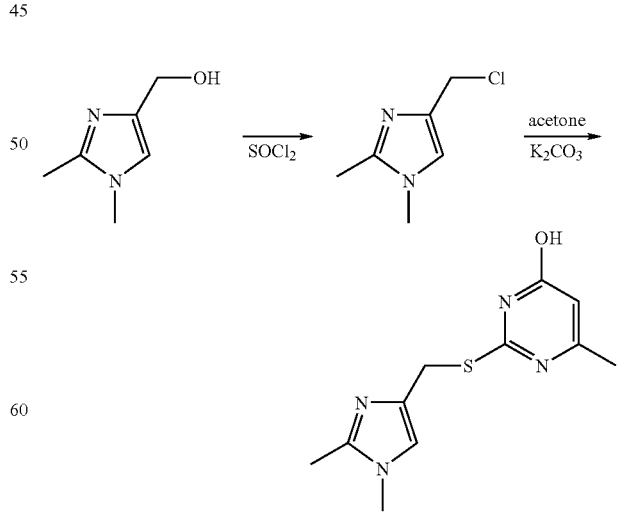

The title compound was prepared by following the procedure described for Example 80 from (1,2-dimethyl-1H-imidazol-4-yl)methanol, which provided a white solid (150 mg, 12% yield); ¹H NMR (400 MHz, CD₃OD): δ 2.14 (s, 3H), 2.22 (s, 3H), 3.69 (s, 3H), 4.57 (s, 2H), 6.01 (s, 1H), 7.56 (s, 1H); M+ 251.

Example 82

2-({imidazo[1,2-a]pyridin-2-ylmethyl}sulfanyl)-6-methylpyrimidin-4-ol hydrochloride

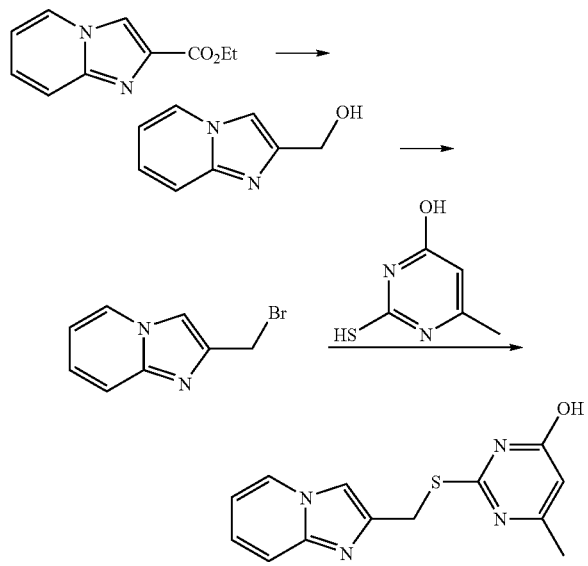

Ethyl imidazo[1,2-a]pyridine-2-carboxylate (1.5 g, 7.9 mmol) was dissolved in diethyl ether (30 mL) and dichloromethane (20 mL). Lithium aluminum hydride (450 mg, 11.8 mmol) was added at 0° C., and the mixture was stirred 3 hours at room temperature. The reaction was quenched with an aqueous solution of sodium hydroxide and extracted 5 times with ethyl acetate. The combined organic phase was washed with brine and dried over sodium sulfate. After evaporation of the solvent, imidazo[1,2-a]pyridin-2-ylmethanol was obtained as a yellow oil (527 mg, 45% yield) and used in the next step without purification; ¹H NMR (400 MHz, CDCl₃): δ 4.86 (s, 2H), 6.76-6.80 (m, 1H), 7.15-7.20 (m, 1H), 7.55-7.58 (m, 2H), 8.09 (d, J=6.8 Hz, 1H).

To a solution of imidazo[1,2-a]pyridin-2-ylmethanol (1.0 g, 6.7 mmol) in anhydrous dichloromethane (25 mL) was added dropwise a solution of phosphorus tribromide (640 µL, 6.7 mmol) in anhydrous dichloromethane (5 mL) at 0° C. The mixture was stirred for 5 hours at room temperature. The mixture was evaporated and crude 2-(bromomethyl)imidazo[1,2-a]pyridine was used in the next step without purification.

6-methyl-2-sulfanylpyrimidin-4-ol (638 mg, 4.5 mmol) was dissolved in anhydrous DMF (20 mL), then potassium carbonate (1.86 g, 13.5 mmol) and 2-(bromomethyl)imidazo[1,2-a]pyridine (1.42 g, 6.7 mmol) were added. The mixture was stirred overnight at room temperature. The solid was removed by filtration and washed with methanol, where the filtrate was evaporated. The residue was dissolved in DCM/MeOH and purified on silica gel using 12% DCM/MeOH to afford 2-({imidazo[1,2-a]pyridin-2-ylmethyl}sulfanyl)-6-methylpyrimidin-4-ol as a white solid (631 mg, 52% yield); ¹H NMR (400 MHz, DMSO-d₆): δ 2.21 (s, 3H), 4.46 (s, 2H), 5.99 (bs, 1H), 6.84 (dt, J=1.7 Hz, J=6.7 Hz, 1H), 7.17-7.22 (m, 1H), 7.45 (dd, J=9.0 Hz, J=0.8 Hz, 1H), 7.86 (s, 1H), 8.46-8.49 (m, 1H); LRMS (ES⁺) m/z 273 (60%, M+1).

2-({imidazo[1,2-a]pyridin-2-ylmethyl}sulfanyl)-6-methylpyrimidin-4-ol (100 mg, 367 µmol) was stirred in methanol (10 mL), and a solution of 4 N HCl in dioxane (140 µL, 551 µmol) was added dropwise at 0° C. The mixture was stirred for 1 hour at room temperature. The solvent was removed by evaporation, and the residue was triturated with diethyl ether and dried in vacuo to afford to 2-({imidazo[1,2-a]pyridin-2-ylmethyl}sulfanyl)-6-methylpyrimidin-4-ol hydrochloride (118 mg, 100% yield); ¹H NMR (400 MHz, DMSO-d₆): δ 2.25 (s, 3H), 4.62 (s, 2H), 6.11 (s, 1H), 6.84 (dt, J=2.1 Hz, J=6.4 Hz, 1H), 7.88-7.94 (m, 2H), 8.30 (s, 1H), 8.88 (d, J=6.8 Hz, 1H); LRMS (ES⁺) m/z 273 (100%, M+1).

Example 83

2-{[(3-bromo-2-chlorophenyl)methyl]sulfanyl}-6-methylpyrimidin-4-ol

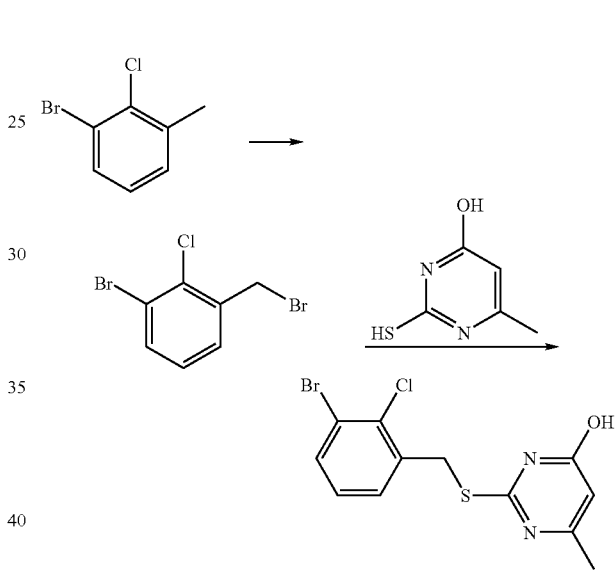

1-bromo-2-chloro-3-methylbenzene (10 g, 48.7 mmol) was dissolved in CCl₄ (100 mL), and then N-bromosuccinimide (13.0 g, 73.0 mmol) and benzoyl peroxide (5.9 g, 24.3 mmol) were added. The mixture was stirred for 2 hours at reflux. The solid was removed by filtration, and the filtrate was washed with water and dried over sodium sulfate. After evaporation of the solvent, the residue was dissolved in DCM and purified on silica gel using 10% hexane/AcOEt to afford 1-bromo-3-(bromomethyl)-2-chlorobenzene (6.36 g, 46% yield); ¹H NMR (400 MHz, CDCl₃): δ 4.62 (s, 2H), 7.12 (t, J=7.8 Hz, 1H), 7.39 (dd, J=1.6 Hz, J=7.6 Hz, 1H), 7.60 (dd, J=1.6 Hz, J=8.0 Hz, 1H).

6-methyl-2-sulfanylpyrimidin-4-ol (1.21 g, 8.5 mmol) was dissolved in anhydrous DMF (50 mL), and then potassium carbonate (1.76 g, 12.7 mmol) and 1-bromo-3-(bromomethyl)-2-chlorobenzene (3.13 g, 11.0 mmol) in anhydrous DMF (10 mL) were added. The mixture was stirred overnight at room temperature. The solid was filtered, washed with water plus diethyl ether, and dried in vacuo to afford to 2-{[(3-bromo-2-chlorophenyl)methyl]sulfanyl}-6-methylpyrimidin-4-ol (2.28 g, 78% yield); ¹H NMR (400 MHz, DMSO-d₆): δ 2.03 (s, 3H), 4.39 (s, 2H), 5.67 (s, 1H), 7.17 (t, J=7.9 Hz, 1H), 7.63 (d, J=7.9 Hz, 2H); LRMS (ES⁺) m/z 345 (75%, M+1), 347 (100%, M+3), 349 (30%, M+5).

Example 84

3-chloro-N,N-diethyl-4-{[(4-hydroxy-6-methylpyrimidin-2-yl)sulfanyl]methyl}benzene-1-carboximidamide dihydrochloride

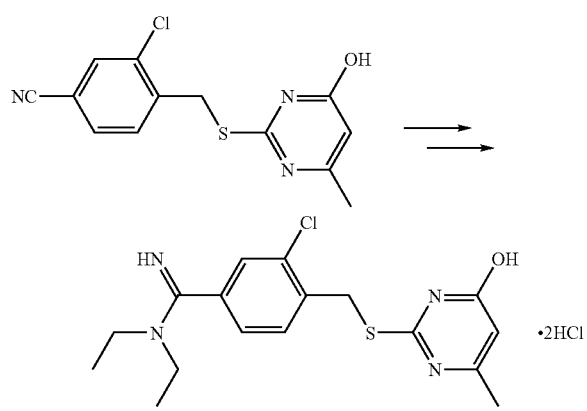

To a solution of 3.0 M methyl magnesium bromide in diethyl ether (1.3 mL, 3.86 mmol) dissolved in anhydrous THF (4 mL) was added diethyl amine in anhydrous THF (1 mL).

The mixture was stirred for 15 minutes at 40° C. Then, 3-chloro-4-{[(4-hydroxy-6-methylpyrimidin-2-yl)sulfanyl]methyl}benzonitrile (375 mg, 1.3 mmol) was added and stirred at 40° C. for 3.5 hours. The solvent was evaporated, and the residue was dissolved in DCM and purified on silica gel using 20% DCM/MeOH to afford 3-chloro-N,N-diethyl-4-{[(4-hydroxy-6-methylpyrimidin-2-yl)sulfanyl]methyl}benzene-1-carboximidamide (111 mg, 15% yield); $^1$H NMR (400 MHz, DMSO-$d_6$): δ 1.15 (t, J=7.9 Hz, 6H), 2.21 (s, 3H), 2.90 (q, J=7.2 Hz, 4H), 4.51 (s, 2H), 6.0 (bs, 1H), 7.51-7.54 (m, 1H), 7.81-7.84 (m, 2H); LRMS (ES$^+$) m/z 365 (100%, M+1).

3-chloro-N,N-diethyl-4-{[(4-hydroxy-6-methylpyrimidin-2-yl)sulfanyl]methyl}benzene-1-carboximidamide (83 mg, 227 μmol) was stirred in methanol (10 mL), and a solution of 4 N HCl in dioxane (170 μL, 681 μmol) was added dropwise at 0° C. The mixture was stirred for 1.5 hours at room temperature. The solvent was removed by evaporation, and the residue was triturated with diethyl ether and dried in vacuo to afford to 3-chloro-N,N-diethyl-4-{[(4-hydroxy-6-methylpyrimidin-2-yl)sulfanyl]methyl}benzene-1-carboximidamide dihydrochloride (80 mg, 81% yield); $^1$H NMR (400 MHz, DMSO-$d_6$): δ 1.15 (t, J=7.2 Hz, 6H), 2.21 (s, 3H), 2.84-2.93 (m, 4H), 4.51 (s, 2H), 6.04 (bs, 1H), 7.51-7.54 (m, 1H), 7.81-7.84 (m, 2H); LRMS (ES$^+$) m/z 365 (100%, M+1).

Example 85

6-methyl-2-{[(1-methyl-1H-imidazol-5-yl)methyl]sulfanyl}pyrimidin-4-ol hydrochloride

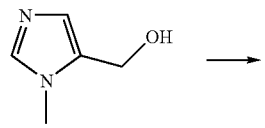

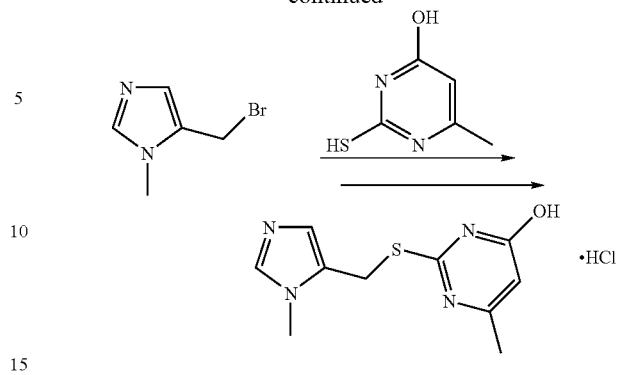

To a solution of (1-methyl-1H-imidazol-5-yl)methanol (1.0 g, 8.9 mmol) in anhydrous dichloromethane (40 mL) was added dropwise a solution of phosphorus tribromide (840 μL, 8.9 mmol) in anhydrous dichloromethane (5 mL) at 0° C. The mixture was stirred overnight at room temperature. The mixture was evaporated, and crude 5-(bromomethyl)-1-methyl-1H-imidazole was used in the next step without purification.

6-methyl-2-sulfanylpyrimidin-4-ol (846 mg, 5.9 mmol) was dissolved in anhydrous DMF (40 mL), then potassium carbonate (2.46 g, 17.8 mmol) and 5-(bromomethyl)-1-methyl-1H-imidazole (1.56 g, 8.9 mmol) were added. The mixture was stirred for 4 hours at room temperature. The solid was removed by filtration, washed with methanol, and the filtrate was evaporated. The residue was dissolved in DCM/MeOH and purified on silica gel using 10% DCM in MeOH to afford 6-methyl-2-{[(1-methyl-1H-imidazol-5-yl)methyl]sulfanyl}pyrimidin-4-ol (589 mg, 42% yield for 2 steps); $^1$H NMR (400 MHz, DMSO-$d_6$): δ 2.22 (s, 3H), 3.61 (s, 3H), 4.44 (s, 2H), 6.02 (s, 1H), 6.88 (s, 1H), 7.56 (s, 1H); LRMS (ES$^+$) m/z 237 (100%, M+1).

6-methyl-2-{[(1-methyl-1H-imidazol-5-yl)methyl]sulfanyl}pyrimidin-4-ol, (252 mg, 1.1 mmol) was stirred in methanol (30 mL), and a solution of 4N HCl in dioxane (400 μL, 1.6 mmol) was added dropwise at 0° C. The mixture was stirred for 1 hour at room temperature. The solvent was removed by evaporation, and the residue was triturated with diethyl ether and dried in vacuo to afford to 6-methyl-2-{[(1-methyl-1H-imidazol-5-yl)methyl]sulfanyl}pyrimidin-4-ol hydrochloride (281 mg, 96% yield); $^1$H NMR (400 MHz, DMSO-$d_6$): δ 2.24 (s, 3H), 3.88 (s, 3H), 4.50 (s, 2H), 6.15 (bs, 1H), 7.65 (s, 1H), 9.09 (s, 1H); LRMS (ES) m/z 237 (70%, M+1).

Example 86

6-methyl-2-[(1,3-thiazol-4-ylmethyl)sulfanyl]pyrimidin-4-ol hydrochloride

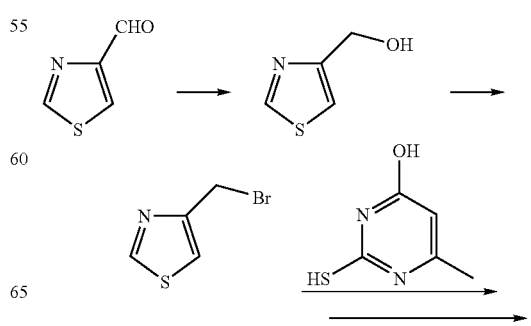

-continued

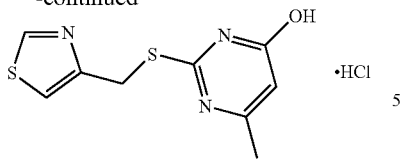

·HCl

To a solution of sodium borohydride (502 mg, 13.3 mmol) in methanol (20 mL) was added a solution of 1,3-thiazole-4-carbaldehyde (1.0 g, 8.8 mmol) in methanol (5 mL) at 0° C. The mixture was stirred for 2 hours at room temperature. The solvent was evaporated, water was added, and the mixture was extracted 3 times with ethyl acetate. The combined organic phase was washed with brine and dried over sodium sulfate. After evaporation of the solvent, 1,3-thiazole-4-ylmethanol was obtained as a yellow oil (596 mg, 58% yield) and used in the next step without purification; $^1$H NMR (400 MHz, CDCl$_3$): δ 2.67 (bs, 1H), 4.85 (d, J=5.9 Hz, 2H), 728 (s, 1H), 8.81 (s, 1H).

To a solution of 1,3-thiazole-4-ylmethanol (596 mg, 5.2 mmol) in anhydrous dichloromethane (25 mL) was added dropwise a solution of phosphorus tribromide (490 µL, 5.2 mmol) in anhydrous dichloromethane (5 mL) at 0° C. The mixture was stirred for 3.5 hours at room temperature. The mixture was evaporated, and the crude 4-(bromomethyl)-1,3-thiazole was used in the next step without purification.

6-methyl-2-sulfanylpyrimidin-4-ol (491 mg, 3.4 mmol) was dissolved in anhydrous DMF (25 mL), then potassium carbonate (1.43 g, 10.3 mmol) and 4-(bromomethyl)-1,3-thiazole (922 mg, 5.2 mmol) were added. The mixture was stirred for 4 hours at room temperature. The solid was removed by filtration and washed with methanol, and the filtrate was evaporated. The residue was dissolved in DCM/MeOH and purified on silica gel using 10% DCM in MeOH to afford to 6-methyl-2-[(1,3-thiazol-4-ylmethyl)sulfanyl]pyrimidin-4-ol (268 mg, 32% yield for 2 steps); $^1$H NMR (400 MHz, DMSO-d$_6$): δ 2.21 (s, 3H), 4.53 (s, 2H), 6.00 (bs, 1H), 7.63 (d, J=2.0 Hz, 1H), 9.06 (d, J=2.0 Hz, 1H).

6-methyl-2-[(1,3-thiazol-4-ylmethyl)sulfanyl]pyrimidin-4-ol, (247 mg, 1.0 mmol) was stirred in methanol (30 mL), and a solution of 4 N HCl in dioxane (390 µL, 1.5 mmol) was added dropwise at 0° C. The mixture was stirred for 1 hour at room temperature. The solvent was removed by evaporation, and the residue was triturated with diethyl ether and dried in vacuo to afford to 6-methyl-2-[(1,3-thiazol-4-ylmethyl)sulfanyl]pyrimidin-4-ol hydrochloride (260 mg, 92% yield); $^1$H NMR (400 MHz, DMSO-d$_6$): δ 2.27 (s, 3H), 4.58 (s, 2H), 6.19 (s, 1H), 7.73 (d, J=2.0 Hz, 1H), 9.14 (d, J=2.0 Hz, 1H); LRMS (ES$^+$) m/z 240 (100%, M+1).

Example 87

6-methyl-2-[(1H-pyrazol-1-ylmethyl)sulfanyl]pyrimidin-4-ol

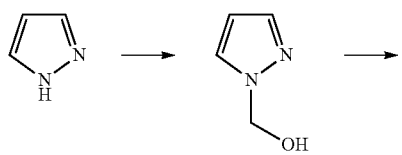

-continued

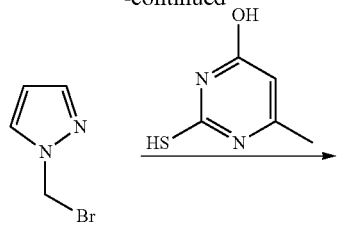

To a solution of 1H-pyrazole (3.0 g, 44.1 mmol) in ethanol (45 mL) was added an aqueous solution of formaldehyde (37%, 36 mL, 441 mmol) at room temperature. The mixture was stirred overnight at 45° C., then the solvent was evaporated to afford crude 1H-pyrazol-1-ylmethanol, which was used in the next step without purification.

To a solution of 1H-pyrazol-1-ylmethanol (4.33 mg, 44.1 mmol) in anhydrous dichloromethane (130 mL) was added dropwise a solution of phosphorus tribromide (4.2 mL, 44.1 mmol) in anhydrous dichloromethane (20 mL) at 0° C. The mixture was stirred for 2.5 hours at room temperature. The mixture was evaporated, and the crude 1-(bromomethyl)-1H-pyrazole was used in the next step without purification.

6-methyl-2-sulfanylpyrimidin-4-ol (3.1 g, 22.1 mmol) was dissolved in anhydrous DMF (150 mL), then potassium carbonate (9.1 g, 66.2 mmol) and 1-(bromomethyl)-1H-pyrazole (7.10 mg, 44.1 mmol) were added. The mixture was stirred overnight at room temperature. The solid was removed by filtration and washed with methanol, and the filtrate was evaporated. The residue was dissolved in DCM/MeOH and purified on silica gel using 10% DCM in MeOH to afford 6-methyl-2-[(1H-pyrazol-1-ylmethyl)sulfanyl]pyrimidin-4-ol (365 mg, 7% yield for 3 steps); $^1$H NMR (400 MHz, DMSO-d$_6$): δ 2.26 (s, 3H), 5.93 (s, 2H), 6.11 (bs, 1H), 6.25 (t, J=2.1 Hz, 1H), 7.50 (d, J=1.4 Hz, 1H). 7.88 (d, J=2.0 Hz, 1H); LRMS (ES$^+$) m/z 223 (100%, M+1).

Example 88

2-{[(5-chloro-1,3-dimethyl-1H-pyrazol-4-yl)methyl]sulfanyl}-6-methylpyrimidin-4-ol dihydrochloride

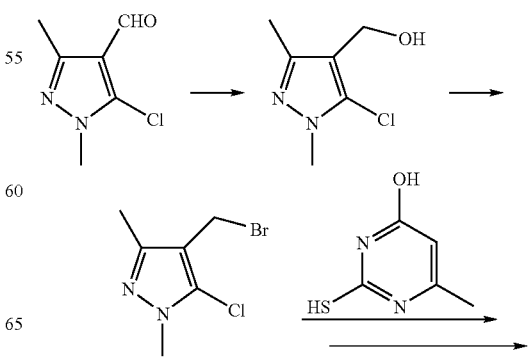

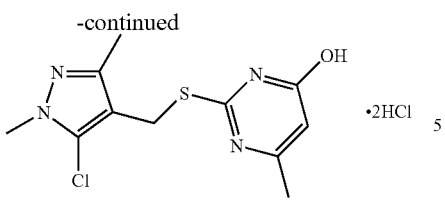

To a solution of sodium borohydride (358 mg, 9.5 mmol) in methanol (15 mL) was added a solution of 5-chloro-1,3-dimethyl-1H-pyrazole-4-carbaldehyde (1.0 g, 6.3 mmol) in methanol (5 mL) at 0° C. The mixture was stirred overnight at room temperature. The solvent was evaporated, water was added, and the mixture was extracted 3 times with ethyl acetate. The combined organic phase was washed with brine and dried over sodium sulfate. After evaporation of the solvent, (5-chloro-1,3-dimethyl-1H-pyrazol-4-yl)methanol was obtained as a white solid (690 mg, 68% yield) and used in the next step without further purification; $^1$H NMR (400 MHz, CDCl$_3$): δ 1.53 (t, J=5.5 Hz, 1H), 2.28 (s, 3H), 3.77 (s, 3H), 4.49 (d, J=5.5 Hz, 2H).

To a solution of (5-chloro-1,3-dimethyl-1H-pyrazol-4-yl)methanol (750 mg, 4.6 mmol) in anhydrous dichloromethane (35 mL) was added dropwise a solution of phosphorus tribromide (450 µL, 4.6 mmol) in anhydrous dichloromethane (5 mL) at 0° C. The mixture was stirred overnight at room temperature. The mixture was then evaporated, and crude 4-(bromomethyl)-5-chloro-1,3-dimethyl-1H-pyrazole was used in the next step without purification.

6-methyl-2-sulfanylpyrimidin-4-ol (437 mg, 3.0 mmol) was dissolved in anhydrous DMF (25 mL), then potassium carbonate (1.27 g, 9.2 mmol) and crude 4-(bromomethyl)-5-chloro-1,3-dimethyl-1H-pyrazole (1.03 g, 4.6 mmol) were added. The mixture was stirred for 3 hours at room temperature. The solid was removed by filtration and washed with methanol, and the filtrate was evaporated. The residue was dissolved in DCM/MeOH and purified on silica gel using 10% DCM/MeOH to afford 2-{[(5-chloro-1,3-dimethyl-1H-pyrazol-4-yl)methyl]sulfanyl}-6-methylpyrimidin-4-ol (190 mg, 22% yield for 2 steps); $^1$H NMR (400 MHz, DMSO-d$_6$): δ 2.17 (s, 3H), 2.20 (s, 3H), 3.70 (s, 3H), 4.20 (s, 2H), 5.76 (bs, 1H); LRMS (ES$^+$) m/z 285 (80%, M+1), 287 (30%, M+3).

2-{[(5-chloro-1,3-dimethyl-1H-pyrazol-4-yl)methyl]sulfanyl}-6-methylpyrimidin-4-ol, (150 mg, 527 mmol) was stirred in methanol (30 mL) and a solution of 4 N HCl in dioxane (395 µL, 1.6 mmol) was added dropwise at 0° C. The mixture was stirred for 30 minutes at room temperature. The solvent was removed by evaporation, and the residue was triturated with diethyl ether and dried in vacuo to afford 2-{[(5-chloro-1,3-dimethyl-1H-pyrazol-4-yl)methyl]sulfanyl}-6-methylpyrimidin-4-ol dihydrochloride (143 mg, 76% yield); $^1$H NMR (400 MHz, DMSO-d$_6$): δ 2.18 (s, 3H), 2.23 (s, 3H), 3.70 (s, 3H), 4.21 (s, 2H), 6.09 (s, 1H); LRMS (ES$^+$) m/z 285 (40%, M+1), 287 (15%, M+3).

Example 89

2-{[(1-ethyl-4H-pyrazol-3-yl)methyl]sulfanyl}-6-methylpyrimidin-4-ol hydrochloride

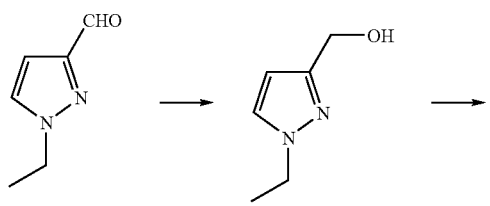

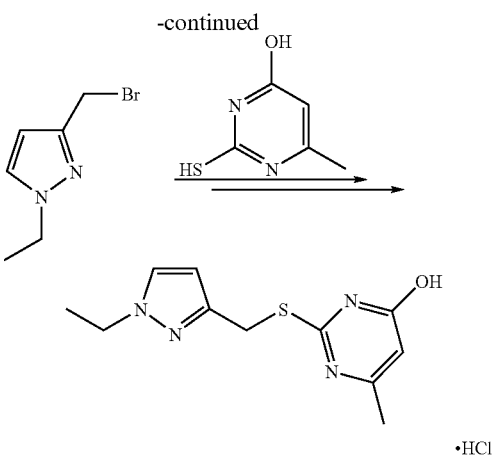

To a solution of sodium borohydride (457 mg, 12.1 mmol) in methanol (20 mL) was added a solution of 1-ethyl-1H-pyrazole-3-carbaldehyde (1.0 g, 8.1 mmol) in methanol (10 mL) at 0° C. The mixture was stirred overnight at room temperature. The solvent was evaporated, water was added, and the mixture was extracted 3 times with ethyl acetate. The organic phase was washed with brine and dried over sodium sulfate. After evaporation of the solvent (1-ethyl-1H-pyrazol-3-yl)methanol was obtained (394 mg, 41% yield) and used in the next step without purification; $^1$H NMR (400 MHz, CDCl$_3$): δ 1.48 (t, J=7.3 Hz, 3H), 2.07 (t, J=5.9 Hz, 1H), 4.15 (q, J=7.3 Hz, 2H), 4.69 (d, J=5.9 Hz, 2H), 6.23 (d, J=2.3 Hz, 1H), 7.35 (d, J=2.2 Hz, 1H).

To a solution of (1-ethyl-1H-pyrazol-3-yl)methanol (394 mg, 3.1 mmol) in anhydrous dichloromethane (25 mL) was added dropwise a solution of phosphorus tribromide (295 µL, 3.1 mmol) in anhydrous dichloromethane (5 mL) at 0° C. The mixture was stirred for 3 hours at room temperature. The mixture was then evaporated, and crude 3-(bromomethyl)-1-ethyl-1H-pyrazole was used in the next step without purification.

6-methyl-2-sulfanylpyrimidin-4-ol (341 mg, 2.4 mmol) was dissolved in anhydrous DMF (20 mL), then potassium carbonate (995 mg, 7.2 mmol) and 3-(bromomethyl)-1-ethyl-1H-pyrazole (590 mg, 3.1 mmol) were added. The mixture was stirred for 2.5 hours at room temperature. The solid was removed by filtration and washed with methanol, and the filtrate was evaporated. The residue was dissolved in DCM/MeOH and purified on silica gel using 8% DCM in MeOH to afford 2-{[(1-ethyl-1H-pyrazol-3-yl)methyl]sulfanyl}-6-methylpyrimidin-4-ol (235 mg, 39% yield for 2 steps); $^1$H NMR (400 MHz, DMSO-d$_6$): δ 1.34 (t, J=7.2 Hz, 3H), 2.20 (s, 3H), 4.07 (q, J=7.3 Hz, 2H), 4.32 (s, 2H), 5.99 (bs, 1H), 6.19 (d, J=2.2 Hz, 1H), 7.63 (d, J=2.2 Hz, 1H); LRMS (ES$^+$) m/z 251 (100%, M+1).

2-{[(1-ethyl-1H-pyrazol-3-yl)methyl]sulfanyl}-6-methylpyrimidin-4-ol (221 mg, 881 µmol) was stirred in methanol (30 mL) and a solution of 4 N HCl in dioxane (330 µL, 1.3 mmol) was added dropwise at 0° C. The mixture was stirred for 30 minutes at room temperature. The solvent was removed by evaporation, and the residue was triturated with diethyl ether and dried in vacuo to afford 2-{[(1-ethyl-1H-pyrazol-3-yl)methyl]sulfanyl}-6-methylpyrimidin-4-ol hydrochloride (243 mg, 96% yield); $^1$H NMR (400 MHz, DMSO-d$_6$): δ 1.34 (t, J=7.3 Hz, 3H), 2.25 (s, 3H), 4.08 (q, J=7.3 Hz, 2H), 4.36 (s, 2H), 6.13 (s, 1H), 6.22 (d, J=2.2 Hz, 1H), 7.66 (d, J=2.2 Hz, 1H); LRMS (ES) m/z 251 (75%, M+1).

Example 90

2-{[(3,5-dimethyl-1H-pyrazol-1-yl)methyl]sulfanyl}-6-methylpyrimidin-4-ol

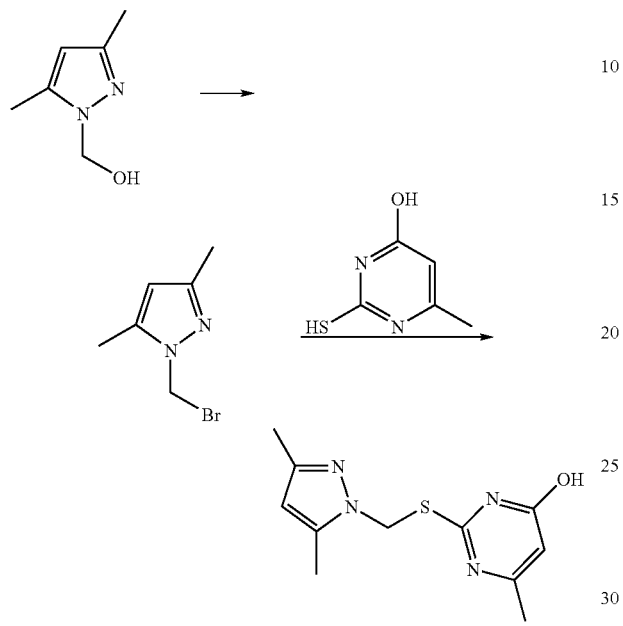

To a solution of (3,5-dimethyl-1H-pyrazol-1-yl)methanol (2.0 g, 15.8 mmol) in anhydrous dichloromethane (50 mL) was added dropwise a solution of phosphorus tribromide (1.5 mL, 15.8 mmol) in anhydrous dichloromethane (10 mL) at 0° C. The mixture was stirred for 3 hours at room temperature. The mixture was then evaporated, and crude 1-(bromomethyl)-3,5-dimethyl-1H-pyrazole was used in the next step without purification.

6-methyl-2-sulfanylpyrimidin-4-ol (1.2 g, 8.8 mmol) was dissolved in anhydrous DMF (50 mL), then potassium carbonate (3.6 g, 26.3 mmol) and 1-(bromomethyl)-3,5-dimethyl-1H-pyrazole (3.0 g, 15.8 mmol) were added. The mixture was stirred overnight at room temperature. The solid was removed by filtration and washed with methanol, and the filtrate was evaporated. The residue was dissolved in DCM/MeOH and purified on silica gel using 10% DCM in MeOH to afford 2-{[(3,5-dimethyl-1H-pyrazol-1-yl)methyl]sulfanyl)-6-methylpyrimidin-4-ol (218 mg, 10% yield for 2 steps); $^1$H NMR (400 MHz, DMSO-$d_6$) δ 2.12 (s, 3H), 2.22 (s, 3H), 2.30 (s, 3H), 5.81 (s, 2H), 5.83 (s, 6.07 (bs, 1H); LRMS (ES$^+$) m/z 251 (50%, M+1).

Example 91

2-{[(1,2-dimethyl-1H-imidazol-5-yl)methyl]sulfanyl}-6-methylpyrimidin-4-ol hydrochloride

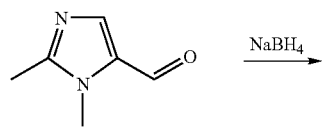

To a solution of sodium borohydride (457 mg, 12.1 mmol) in methanol (25 mL) was added a solution of 1,2-dimethyl-1H-imidazole-5-carbaldehyde (1.0 g, 8.1 mmol) in methanol (10 mL) at 0° C. The mixture was stirred overnight at room temperature. The solvent was evaporated, and crude (1,2-dimethyl-1H-imidazol-5-yl)methanol was obtained and used in the next step without purification; $^1$H NMR (400 MHz, DMSO-$d_6$): δ 2.22 (s, 3H), 3.45 (s, 3H), 4.34 (s, 2H), 5.05 (bs, 1H), 6.57 (s, 1H).

To a solution of (1,2-dimethyl-1H-imidazol-5-yl)methanol (1.02 g, 8.1 mmol) in anhydrous dichloromethane (30 mL) was added dropwise a solution of phosphorus tribromide (760 μL, 8.1 mmol) in anhydrous dichloromethane (10 mL) at 0° C. The mixture was stirred for 2.5 hours at room temperature. The mixture was then evaporated, and crude 5-(bromomethyl)-1,2-dimethyl-1H-imidazole was used in the next step without purification.

6-methyl-2-sulfanylpyrimidin-4-ol (764 mg, 5.4 mmol) was dissolved in anhydrous DMF (30 mL), then potassium carbonate (2.23 g, 16.1 mmol) and 5-(bromomethyl)-1,2-dimethyl-1H-imidazole (1.52 g, 8.1 mmol) were added. The mixture was stirred overnight at room temperature. The solid was removed by filtration and washed with methanol, and the filtrate was evaporated. The residue was dissolved in DCM/MeOH and purified on silica gel using 20% DCM in MeOH to afford 2-{[(1,2-dimethyl-1H-imidazol-5-yl)methyl]sulfanyl}-6-methylpyrimidin-4-ol (279 mg, 21% yield for 3 steps); $^1$H NMR (400 MHz, DMSO-$d_6$): δ 2.20 (s, 3H), 2.24 (s, 3H), 3.46 (s, 3H), 4.40 (s, 2H), 5.99 (s, 1H), 6.72 (s, 1H); LRMS (ES$^+$) m/z 251 (50%, M+1).

2-{[(1,2-dimethyl-1H-imidazol-5-yl)methyl]sulfanyl}-6-methylpyrimidin-4-ol (390 mg, 1.6 mmol) was stirred in methanol (50 mL), and a solution of 4 N HCl in dioxane (580 μL, 2.3 mmol) was added dropwise at 0° C. The mixture was stirred for 30 minutes at room temperature. The solvent was removed by evaporation, and the residue was triturated with diethyl ether and dried in vacuo to afford 2-{[(1,2-dimethyl-1H-imidazol-5-yl)methyl]sulfanyl}-6-methylpyrimidin-4-ol hydrochloride (412 mg, 92% yield); $^1$H NMR (400 MHz, DMSO-d$_6$): δ 2.23 (s, 3H), 2.55 (s, 3H), 3.68 (s, 3H), 4.48 (s, 2H), 6.12 (s, 1H), 7.51 (s, 1H); LRMS (ES$^+$) m/z 251 (100%, M+1).

Example 92

6-methyl-2-{[(2-methyl-1,3-thiazol-4-yl)methyl]sulfanyl}pyrimidin-4-ol hydrochloride

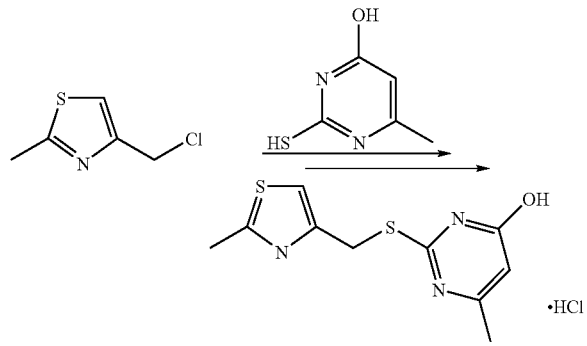

6-methyl-2-sulfanylpyrimidin-4-ol (772 mg, 5.4 mmol) was dissolved in anhydrous DMF (30 mL), then potassium carbonate (2.25 g, 16.3 mmol) and 4-(chloromethyl)-2-methyl-1,3-thiazole (1.50 g, 8.1 mmol) were added. The mixture was stirred overnight at room temperature. The solid was removed by filtration and washed with methanol, and the filtrate was evaporated. The residue was dissolved in DCM/MeOH and purified on silica gel using 10% DCM in MeOH to afford 6-methyl-2-{[(2-methyl-1,3-thiazol-4-yl)methyl]sulfanyl}pyrimidin-4-ol (244 mg, 18% yield); $^1$H NMR (400 MHz, DMSO-d$_6$): δ 2.18 (s, 3H), 2.59 (s, 3H), 4.40 (s, 2H), 5.98 (bs, 1H), 7.36 (s, 1H); LRMS (ES$^+$) m/z 254 (80%, M+1).

6-methyl-2-{[(2-methyl-1,3-thiazol-4-yl)methyl]sulfanyl}pyrimidin-4-ol (200 mg, 790 μmol) was stirred in methanol (25 mL), and a solution of 4 N HCl in dioxane (300 μL, 1.2 mmol) was added dropwise at 0° C. The mixture was stirred for 30 minutes at room temperature. The solvent was removed by evaporation, and the residue was triturated with diethyl ether and dried in vacuo to afford 6-methyl-2-{[(2-methyl-1,3-thiazol-4-yl)methyl]sulfanyl}pyrimidin-4-ol hydrochloride (230 mg, 100% yield); $^1$H NMR (400 MHz, DMSO-d$_6$): δ 2.22 (s, 3H), 2.64 (s, 3H), 4.44 (s, 2H), 6.10 (bs, 1H), 7.46 (s, 1H); LRMS (ES$^+$) m/z 254 (100%, M+1).

Example 93

6-methyl-2-({[1-(propane-2-yl)-1H-benzimidazol-2-yl]methyl}sulfanyl)pyrimidin-4-ol hydrochloride

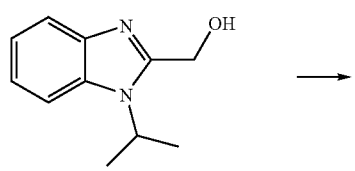

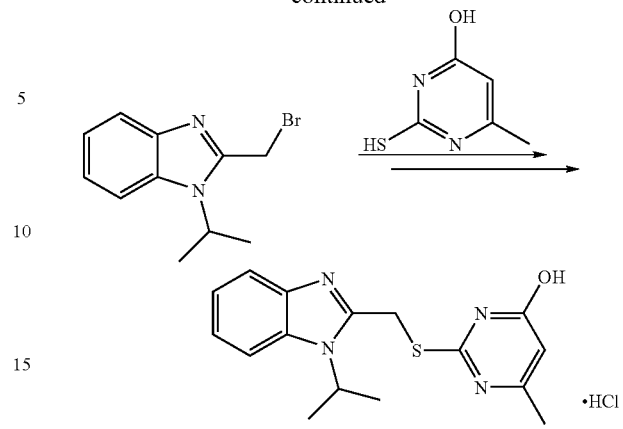

To a solution of [1-(propan-2-yl)-1H-benzimidazol-2-yl]methanol (1.5 g, 7.9 mmol) in anhydrous dichloromethane (30 mL) was added dropwise a solution of phosphorus tribromide (750 μL, 7.9 mmol) in anhydrous dichloromethane (5 mL) at 0° C. The mixture was stirred for 1.5 hours at room temperature. The mixture was then evaporated, and the crude 2-(bromomethyl)-1-(propan-2-yl)-1H-benzimidazole was used in the next step without purification.

6-methyl-2-sulfanylpyrimidin-4-ol (746 mg, 5.2 mmol) was dissolved in anhydrous DMF (30 mL), then potassium carbonate (2.18 g, 15.8 mmol) and 2-(bromomethyl)-1-(propan-2-yl)-1H-benzimidazole (1.99 g, 7.9 mmol) were added. The mixture was stirred overnight at room temperature. The solid was removed by filtration and washed with methanol, and the filtrate was evaporated. The residue was dissolved in DCM/MeOH and purified on silica gel using 12% DCM in MeOH to afford 6-methyl-2-({[1-(propane-2-yl)-1H-benzimidazol-2-yl]methyl}sulfanyl)pyrimidin-4-ol (1.01 g, 41% yield for 2 steps); $^1$H NMR (400 MHz, DMSO-d$_6$): δ 1.55 (s, 3H), 1.56 (s, 3H), 2.20 (s, 3H), 4.76 (s, 2H), 4.84-4.92 (m, 1H), 6.06 (bs, 1H), 7.13-7.20 (m, 2H), 7.54-7.57 (m, 1H), 7.68-7.71 (m, 1H); LRMS (ES$^+$) m/z 315 (100%, M+1).

6-methyl-2-({[1-(propane-2-yl)-1H-benzimidazol-2-yl]methyl}sulfanyl)pyrimidin-4-ol (500 mg, 1.6 mmol) was stirred in methanol (50 mL) and a solution of 4 N HCl in dioxane (600 μL, 2.4 mmol) was added dropwise at 0° C. The mixture was stirred for 1 hour at room temperature. The solvent was removed by evaporation, and the residue was triturated with diethyl ether and dried in vacuo to afford 6-methyl-2-({[1-(propane-2-yl)-1H-benzimidazol-2-yl]methyl}sulfanyl)pyrimidin-4-ol hydrochloride (560 mg, 100% yield); $^1$H NMR (400 MHz, DMSO-d$_6$): δ 1.68 (s, 3H), 1.70 (s, 3H), 2.14 (s, 3H), 5.01 (s, 2H), 5.21-5.28 (m, 1H), 6.20 (s, 1H), 7.54-7.61 (m, 2H), 7.84-7.87 (m, 1H), 8.16-8.19 (m, 1H); LRMS (ES$^+$) m/z 315 (100%, M+1).

Example 94

2-{[(4-chloro-1,3-thiazol-5-yl)methyl]sulfanyl}-6-methylpyrimidin-4-ol

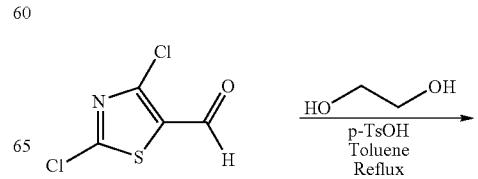

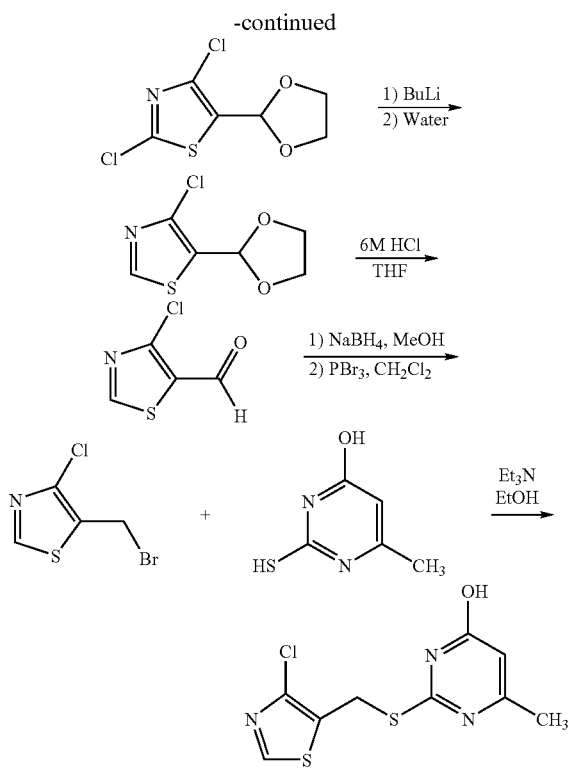

In a round bottom flask equipped with a Dean-Stark trap was charged ethylene glycol (2.3 mL, 41.1 mmol), 2,4-dichloro-1,3-thiazole-5-carbaldehyde (2.5 g, 13.7 mmol), and toluene (35 mL). To this solution was added 4-methyl-benzene-1-sulfonic acid hydrate (210 mg, 1.1 mmol). The reaction mixture was stirred at reflux overnight. After cooling to room temperature, the solution was poured in 10% sodium carbonate solution (50 mL). The mixture was extracted with EtOAc (2×35 mL). The organic extracts were combined, dried over MgSO$_4$, filtered, evaporated, and dried in vacuo, affording 2,4-dichloro-5-(1,3-dioxolan-2-yl)-1,3-thiazole (2.9 g, 93% yield). The product was used without further purification.

To a –78° C. solution of 2,4-dichloro-5-(1,3-dioxolan-2-yl)-1,3-thiazole (2.9 g, 12.7 mmol) in anhydrous THF (60 mL) was added a solution of butyl lithium (2.5 M in hexanes, 8 mL, 20 mmol). The reaction mixture was stirred at –78° C. for 1.5 hours. The reaction mixture was then quenched with brine (50 mL). The mixture was extracted with EtOAc (3×50 mL). The organic extracts were combined, dried over MgSO$_4$, filtered, evaporated, and dried in vacuo, affording 4-chloro-5-(1,3-dioxolan-2-yl)-1,3-thiazole (2.1 g, 87% yield). The product was used without further purification.

To a solution of 4-chloro-5-(1,3-dioxolan-2-yl)-1,3-thiazole (2.1 g, 11.1 mmol) in THF (25 mL) was added 6N HCl (5 mL). The solution was stirred at room temperature for 2 hours. The solution was poured into brine (50 mL). The mixture was extracted with EtOAc (2×50 mL). The organic extracts were combined, dried over MgSO$_4$, filtered, evaporated, and dried in vacuo, affording 4-chloro-1,3-thiazole-5-carbaldehyde (1.4 g, 86% yield). The product was used without further purification.

To a 0° C. solution of 4-chloro-1,3-thiazole-5-carbaldehyde (1.4 g, 9.5 mmol) in anhydrous methanol (100 mL) was added sodium borohydride (570 mg, 15.2 mmol). The reaction mixture was stirred at room temperature for 3 hours. Water (20 mL) was added. MeOH was evaporated. The resultant residue was extracted with EtOAc (1×20 mL) and 2-butanol (1×20 mL). The organic extracts were combined, dried over MgSO$_4$, filtered, evaporated, and dried in vacuo, affording (4-chloro-1,3-thiazol-5-yl)methanol (1.3 g, 91% yield). The product was used without further purification.

To a solution of (4-chloro-1,3-thiazol-5-yl)methanol (1.2 g, 8.4 mmol) in anhydrous dichloromethane (50 mL) was added tribromophosphane (850 μL, 9.0 mmol). The mixture was stirred at room temperature for 2 hours. Dichloromethane was evaporated. The residue was dried in vacuo, affording 5-(bromomethyl)-4-chloro-1,3-thiazole. The crude product was used without further purification.

A mixture of 5-(bromomethyl)-4-chloro-1,3-thiazole (8.4 mmol), 6-methyl-2-sulfanylpyrimidin-4-ol (850 mg, 6.0 mmol), and triethylamine (3.5 mL, 25 mmol) in absolute ethanol (45 mL) was stirred at room temperature overnight. The mixture was evaporated to dryness and then co-evaporated with EtOAc (20 mL). The residue was treated with water (100 mL). The solid material was recovered by filtration and washed with water (3×25 mL), diethyl ether (2×25 mL), and hexanes (2×25 mL). The solid material was dried in vacuo. The crude product was purified by flash chromatography (0-4% MeOH/DCM), affording the title compound (491 mg, 31% yield); $^1$H NMR (400 MHz, DMSO-d$_6$): δ 2.15 (s, 3H), 4.62 (s, 2H), 6.05 (s, 1H), 8.82 (s, 1H); M+ 274.

Example 95

6-methyl-2-{[(4-methyl-1,3-thiazol-5-yl)methyl]sulfanyl}pyrimidin-4-ol hydrochloride

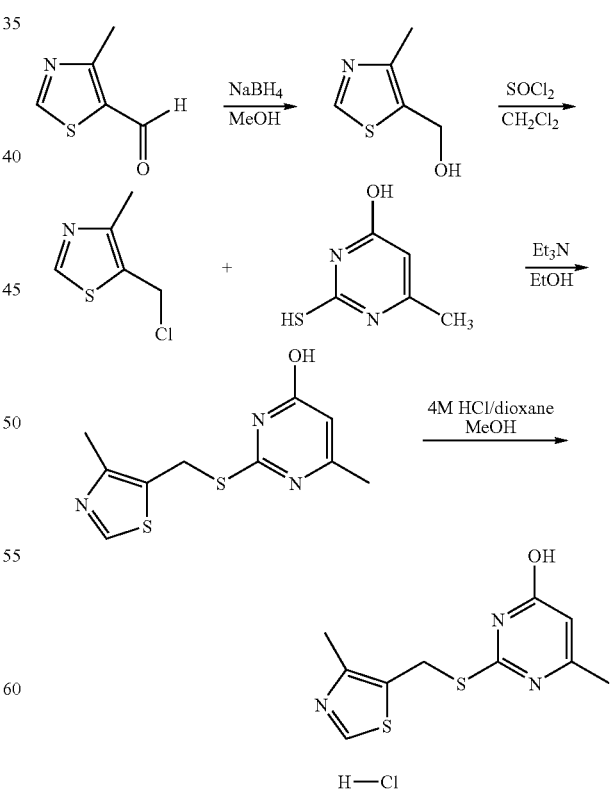

To a 0° C. solution of 4-methyl-1,3-thiazole-5-carbaldehyde (1.5 g, 11.8 mmol) in anhydrous methanol (100 mL) was added sodium borohydride (670 mg, 17.7 mmol). The reaction mixture was stirred at room temperature for 3 hours. Water (30 mL) was added. The mixture was then evaporated. The resultant residue was treated with EtOAc (50 mL). The mixture was extracted with water (50 mL). The organic layer was dried over MgSO$_4$, filtered, evaporated, and dried in vacuo, affording (4-methyl-1,3-thiazol-5-yl)methanol (1.4 g, 92% yield). The product was used without further purification.

To a solution of (4-methyl-1,3-thiazol-5-yl)methanol (1.4 g, 11.0 mmol) in anhydrous dichloromethane (75 mL) was added thionyl chloride (4 mL). The mixture was stirred at room temperature overnight. Dichloromethane was evaporated. The residue was co-evaporated with toluene (2×20 mL) and then dried in vacuo, affording 5-(chloromethyl)-4-methyl-1,3-thiazole. The product was used without further purification.

A mixture of 5-(chloromethyl)-4-methyl-1,3-thiazole (887 mg, 4.9 mmol), 6-methyl-2-sulfanylpyrimidin-4-ol (600 mg, 4.2 mmol), and potassium carbonate (2.1 g, 15 mmol) in acetone (30 mL) was stirred at room temperature overnight. The solid material was removed by filtration. The filtrate was recovered and evaporated, co-evaporated with EtOAc (20 mL) and dried in vacuo. The solid residue was treated with diethyl ether (30 mL). The solid product was recovered by filtration, washed with diethyl ether (2×15 mL) and hexanes (1×15 mL), and dried in vacuo, affording 6-methyl-2-{[(4-methyl-1,3-thiazol-5-yl)methyl]sulfanyl}pyrimidin-4-ol (1.0 g, 93% yield); $^1$H NMR (400 MHz, DMSO-d$_6$): δ 1.91 (s, 3H), 2.34 (s, 3H), 4.31 (s, 2H), 5.32 (s, 1H), 8.73 (s, 1H); M+ 254. The product was used without further purification.

To a mixture of 6-methyl-2-{[(4-methyl-1,3-thiazol-5-yl)methyl]sulfanyl}pyrimidin-4-ol (500 mg, 2.0 mmol) in MeOH (5 mL) was added 4 M HCl/dioxane (2 mL, 8.0 mmol). The solution was evaporated and dried in vacuo, affording the title compound (213 mg, 99% yield); $^1$H NMR (400 MHz, DMSO-d$_6$): δ 2.26 (s, 3H), 2.44 (s, 3H), 4.58 (s, 2H), 6.08 (s, 1H), 9.10 (s, 1H); M+ 254.

Example 96

2-{[(5-chloro-1-methyl-1H-imidazol-4-yl)methyl]sulfanyl}-6-methylpyrimidin-4-ol hydrochloride

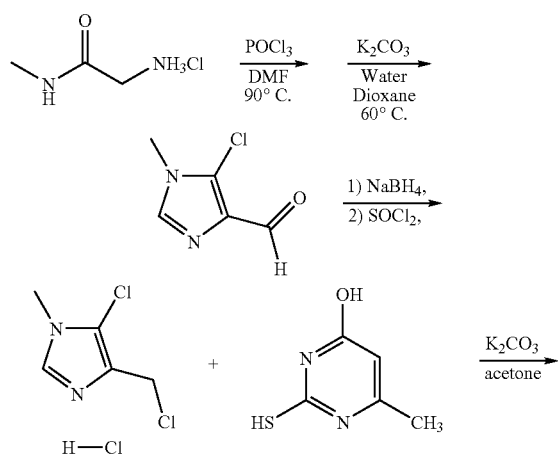

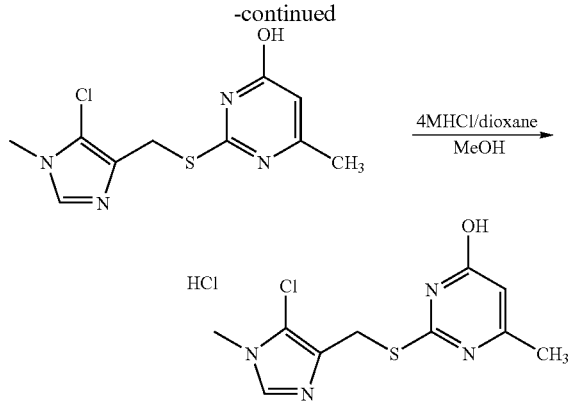

Phosphoryl trichloride (1 mL, 11 mmol) was added slowly to a 0° C. solution of DMF (22 mL), followed by 2-amino-N-methylacetamide hydrochloride (2.5 g, 20 mmol). The mixture was warmed at room temperature and stirred at 60° C. before phosphoryl trichloride (35 mL, 390 mmol) was added slowly. The solution was stirred at 90° C. overnight. After cooling to room temperature, the mixture was poured into ice/water (500 mL). Solid sodium carbonate was added until pH 6-7 was reached. The mixture was extracted with DCM (4×150 mL). The organic extracts were combined, dried over MgSO$_4$, filtered, evaporated, and dried in vacuo. The residue was dissolved in water (10 mL) and 1,4-dioxane (20 mL) before potassium carbonate (10 g, 72.3 mmol) was added. The mixture was stirred at 60° C. for 4 hours. The mixture was evaporated to dryness. The residue was treated with 50% EtOAc/Et$_2$O (250 mL). The solid was removed by filtration. The filtrate was recovered, evaporated, and dried in vacuo, affording 5-chloro-1-methyl-1H-imidazole-4-carbaldehyde (476 mg, 23% yield). The product was used without further purification.

To a 0° C. solution of 5-chloro-1-methyl-1H-imidazole-4-carbaldehyde (475 mg, 3.3 mmol) in anhydrous methanol (50 mL) was added sodium borohydride (190 mg, 5.0 mmol). The reaction mixture was stirred at room temperature for 4 hours. Water (25 mL) was added. The mixture was evaporated. The resultant residue was treated with EtOAc (20 mL). The mixture was extracted with water (5 mL). The organic extract was dried over MgSO$_4$, filtered, evaporated, and dried in vacuo, affording (5-chloro-1-methyl-1H-imidazol-4-yl)methanol (397 mg, 82% yield). The product was used without further purification.

To a solution of (5-chloro-1-methyl-1H-imidazol-4-yl)methanol (397 mg, 2.7 mmol) in anhydrous dichloromethane (20 mL) was added thionyl chloride (1 mL). The mixture was stirred at room temperature for 2 hours. Dichloromethane was evaporated and then co-evaporated with toluene (2×10 mL). The residue was dried in vacuo, affording 5-chloro-4-(chloromethyl)-1-methyl-1H-imidazole hydrochloride (550 mg, 99% yield). The product was used without further purification.

A mixture of 5-chloro-4-(chloromethyl)-1-methyl-1H-imidazole hydrochloride (463 mg, 2.3 mmol), 6-methyl-2-sulfanylpyrimidin-4-ol (213 mg, 1.5 mmol), and potassium carbonate (1.1 g, 8.0 mmol) in acetone (15 mL) was stirred at room temperature overnight. The solid material was removed by filtration and washed with 50% acetone/MeOH (2×15 mL). The filtrate was recovered and evaporated. The crude product was purified by flash chromatography (0-10% MeOH/DCM and 0-6% MeOH/DCM), affording 2-{[(5-chloro-1-methyl-1H-imidazol-4-yl)methyl]sulfanyl}-6-methylpyrimidin-4-ol (1.0 g, 93% yield); $^1$H NMR (400 MHz, DMSO-d$_6$): δ 2.17 (s, 3H), 3.53 (s, 3H), 4.25 (s, 2H), 5.97 (s, 1H), 7.70 (s, 1H); M+271. The product was used without further purification.

To a mixture of 2-{[(5-chloro-1-methyl-1H-imidazol-4-yl)methyl]sulfanyl}-6-methylpyrimidin-4-ol (50 mg, 0.18 mmol) in MeOH (2 mL) was added 4 M HCl/dioxane (500 µL, 2.0 mmol). The solution was evaporated and dried in vacuo, affording the title compound (55 mg, 99% yield); $^1$H NMR (400 MHz, DMSO-d$_6$): δ 2.23 (s, 3H), 3.75 (s, 3H), 4.45 (s, 2H), 6.08 (s, 1H), 9.13 (s, 1H); M+ 271.

Example 97

2-{[(1-ethyl-4-methyl-1H-imidazol-5-yl)methyl]sulfanyl}-6-methylpyrimidin-4-ol hydrochloride

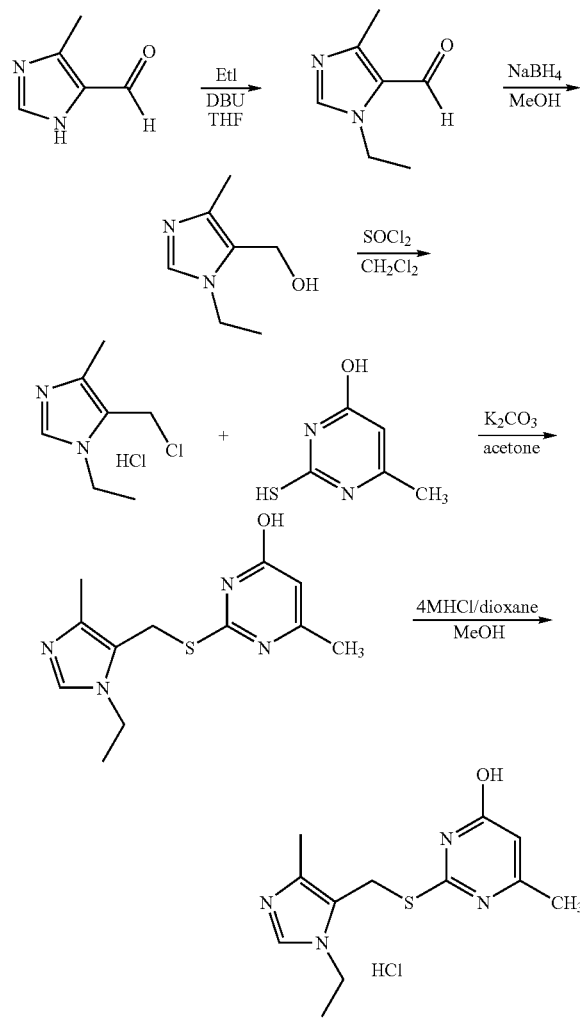

To 4-methyl-1H-imidazole-5-carbaldehyde (5.0 g, 45.4 mmol) in anhydrous THF (50 mL) was added diaza(1,3)bicyclo[5.4.0]undecane (DBU, 6.8 mL, 45.4 mmol), and iodoethane (3.4 mL, 45.4 mmol). The mixture was stirred at room temperature overnight. Water (50 mL) was added before the THF was evaporated. The mixture was extracted with EtOAc (1×50 mL) and 2-butanol (2×50 mL). The organic extracts were combined, dried over MgSO$_4$, filtered, evaporated, and dried in vacuo. The crude product was purified by flash chromatography (0-1% MeOH/DCM), affording 1-ethyl-4-methyl-1H-imidazole-5-carbaldehyde (806 mg, 13% yield).

To a 0° C. solution of 1-ethyl-4-methyl-1H-imidazole-5-carbaldehyde (806 mg, 5.8 mmol) in anhydrous methanol (55 mL) was added sodium borohydride (500 mg, 13.2 mmol). The reaction mixture was stirred at room temperature overnight. Water (30 mL) was added. The mixture was evaporated. The resultant residue was treated with EtOAc (50 mL). The solution was dried over MgSO$_4$, filtered, evaporated, and dried in vacuo, affording (1-ethyl-4-methyl-1H-imidazol-5-yl)methanol (754 mg, 93% yield). The product was used without further purification.

To (1-ethyl-4-methyl-1H-imidazol-5-yl)methanol (754 mg, 5.4 mmol) in anhydrous dichloromethane (35 mL) was added thionyl chloride (2 mL). The mixture was stirred at room temperature overnight. Dichloromethane was evaporated and then co-evaporated with toluene (2×15 mL). The residue was dried in vacuo, affording 5-(chloromethyl)-1-ethyl-4-methyl-1H-imidazole hydrochloride (1.0 g, 95% yield). The product was used without further purification.

A mixture of 5-(chloromethyl)-1-ethyl-4-methyl-1H-imidazole hydrochloride (1.0 g, 5.1 mmol), 6-methyl-2-sulfanylpyrimidin-4-ol (500 mg, 3.5 mmol), and potassium carbonate (1.2 g, 9.0 mmol) in acetone (25 mL) was stirred at room temperature overnight. The solid material was removed by filtration. The filtrate was recovered and evaporated. The crude product was purified by flash chromatography (0-6% MeOH/DCM), affording 2-{[(1-ethyl-4-methyl-1H-imidazol-5-yl)methyl]sulfanyl}-6-methyl-pyrimidin-4-ol (428 mg, 46% yield); $^1$H NMR (400 MHz, DMSO-d$_6$): δ 1.31 (t, 3H, J=6.7 Hz), 2.11 (s, 3H), 2.22 (s, 3H), 3.95 (m, 2H), 4.48 (s, 2H), 6.02 (s, 1H), 7.54 (s, 1H); M+ 266. The product was used without further purification.

To a mixture of 2-{[(1-ethyl-4-methyl-1H-imidazol-5-yl)methyl]sulfanyl}-6-methylpyrimidin-4-ol (160 mg, 0.60 mmol) in MeOH (2 mL) was added 4 M HCl/dioxane (800 µL, 3.2 mmol). The solution was evaporated and dried in vacuo, affording the title compound (178 mg, 99% yield); $^1$H NMR (400 MHz, DMSO-d$_6$): δ 1.44 (t, 3H, J=6.7 Hz), 2.22 (s, 3H), 2.37 (s, 3H), 4.24 (m, 2H), 4.56 (s, 2H), 6.12 (s, 1H), 9.09 (s, 1H); M+ 266.

Example 98

2-{[(1-ethyl-5-methyl-1H-imidazol-4-yl)methyl]sulfanyl}-6-methylpyrimidin-4-ol hydrochloride

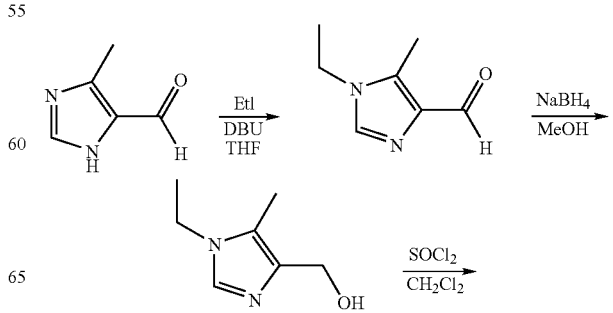

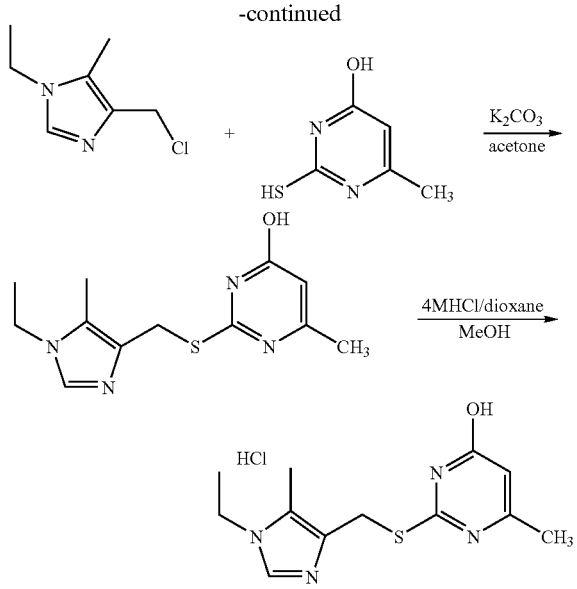

To a solution of 4-methyl-1H-imidazole-5-carbaldehyde (5.0 g, 45.4 mmol) in anhydrous THF (50 mL) was added diaza(1,3)bicyclo[5.4.0]undecane (DBU, 6.8 mL, 45.4 mmol) and iodoethane (3.4 mL, 45.4 mmol). The reaction mixture was stirred at room temperature overnight. Water (50 mL) was added before THF was evaporated. The mixture was extracted with EtOAc (1×50 mL) and 2-butanol (2×50 mL). The organic extracts were combined, dried over $MgSO_4$, filtered, evaporated, and dried in vacuo. The crude product was purified by flash chromatography (0-1% MeOH/DCM), affording 1-ethyl-5-methyl-1H-imidazole-4-carbaldehyde (730 mg, 12% yield).

To a 0° C. solution of 1-ethyl-5-methyl-1H-imidazole-4-carbaldehyde (700 mg, 5.1 mmol) in anhydrous methanol (75 mL) was added sodium borohydride (380 mg, 10.0 mmol). The reaction mixture was stirred at room temperature for 2 hours. Water (20 mL) was added. The mixture was evaporated. The resultant residue was treated with EtOAc (30 mL) and water (5 mL). The mixture was dried over $MgSO_4$, filtered, evaporated, and dried in vacuo, affording (1-ethyl-5-methyl-1H-imidazol-4-yl)methanol (350 mg, 49% yield). The product was used without further purification.

To a solution of (1-ethyl-5-methyl-1H-imidazol-4-yl)methanol (340 mg, 2.4 mmol) in anhydrous dichloromethane (20 mL) was added thionyl chloride (900 µL). The mixture was stirred at room temperature for 4 hours. Dichloromethane was evaporated, and the mixture was then co-evaporated with toluene (20 mL). The residue was dried in vacuo, affording 4-(chloromethyl)-1-ethyl-5-methyl-1H-imidazole hydrochloride (450 mg, 96% yield). The product was used without further purification.

A mixture of 4-(chloromethyl)-1-ethyl-5-methyl-1H-imidazole hydrochloride (450 mg, 2.3 mmol), 6-methyl-2-sulfanylpyrimidin-4-ol (215 mg, 1.5 mmol), and potassium carbonate (720 mg, 5.2 mmol) in acetone (15 mL) was stirred at room temperature for 3 days. The solid material was removed by filtration. The filtrate was recovered and evaporated. The crude product was purified by flash chromatography (0-6% MeOH/DCM), affording 2-{[(1-ethyl-5-methyl-1H-imidazol-4-yl)methyl]sulfanyl}-6-methylpyrimidin-4-ol (128 mg, 32% yield); $^1$H NMR (400 MHz, DMSO-$d_6$): δ 1.26 (t, 3H, J=6.7 Hz), 2.18 (m, 6H), 3.86 (m, 2H), 4.26 (s, 2H), 5.95 (s, 1H), 7.55 (s, 11-1); M+ 266. The product was used without further purification.

To a mixture of 2-{[(1-ethyl-5-methyl-1H-imidazol-4-yl)methyl]sulfanyl}-6-methylpyrimidin-4-ol (60 mg, 0.23 mmol) in MeOH (2 mL) was added 4 M HCl/dioxane (500 µL, 2.0 mmol). The mixture was filtered to remove particles in suspension. The solution was evaporated and dried in vacuo, affording the title compound (68 mg, 99% yield); $^1$H NMR (400 MHz, DMSO-$d_6$): δ 1.38 (t, 3H, J=6.7 Hz), 2.23 (s, 3H), 2.38 (s, 3H), 4.09 (m, 2H), 4.44 (s, 2H), 6.09 (s, 1H), 9.04 (s, 1H); M+ 266.

Example 99

6-methyl-2-({[4-methyl-1-(propan-2-yl)-1H-imidazol-5-yl]methyl}sulfanyl)pyrimidin-4-ol hydrochloride

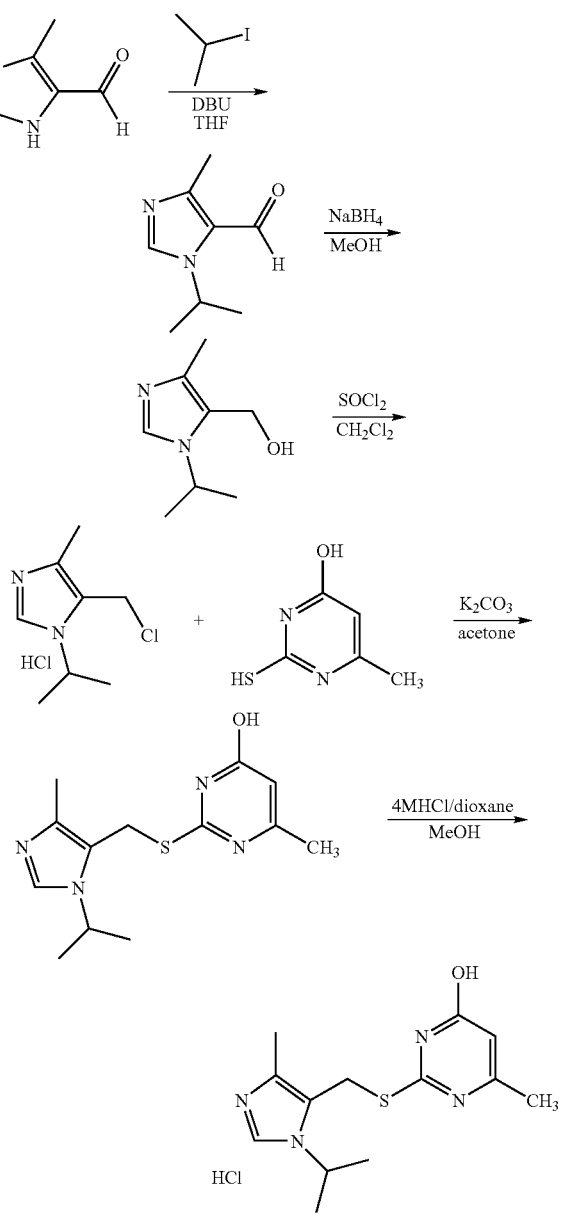

To a solution of 4-methyl-1H-imidazole-5-carbaldehyde (5.0 g, 45.4 mmol) in anhydrous THF (50 mL) was added diaza(1,3)bicyclo[5.4.0]undecane (DBU, 6.8 mL, 45.4 mmol) and 2-iodopropane (4.5 mL, 45.4 mmol). The reaction mixture was stirred at room temperature overnight. Water (50 mL) was added. The mixture was extracted with EtOAc (1×50 mL) and 2-butanol (2×50 mL). The organic extracts were combined, dried over MgSO$_4$, filtered, evaporated, and dried in vacuo. The crude product was purified by flash chromatography (0-2% MeOH/DCM), affording 4-methyl-1-(propan-2-yl)-1H-imidazole-5-carbaldehyde (691 mg, 10% yield).

To a 0° C. solution of 4-methyl-1-(propan-2-yl)-1H-imidazole-5-carbaldehyde (924 mg, 6.1 mmol) in anhydrous methanol (75 mL) was added sodium borohydride (425 mg, 11.2 mmol). The reaction mixture was stirred at room temperature for 3 hours. Water (20 mL) was added. Methanol was evaporated. The resultant mixture was extracted with EtOAc (1×20 mL) and 2-butanol (2×20 mL). The solution was dried over MgSO$_4$, filtered, evaporated, and dried in vacuo, affording [4-methyl-1-(propan-2-yl)-1H-imidazol-5-yl]methanol (703 mg, 75% yield). The product was used without further purification.

To a solution of [4-methyl-1-(propan-2-yl)-1H-imidazol-5-yl]methanol (703 mg, 4.6 mmol) in anhydrous dichloromethane (40 mL) was added thionyl chloride (1.7 mL). The mixture was stirred at room temperature overnight. Dichloromethane was evaporated, and then the mixture was co-evaporated with toluene (1×20 mL). The residue was dried in vacuo, affording 5-(chloromethyl)-4-methyl-1-(propan-2-yl)-1H-imidazole hydrochloride (824 mg, 86% yield). The product was used without further purification.

A mixture of 5-(chloromethyl)-4-methyl-1-(propan-2-yl)-1H-imidazole hydrochloride (824 g, 3.9 mmol), 6-methyl-2-sulfanylpyrimidin-4-ol (970 mg, 7.0 mmol), and potassium carbonate (1.2 g, 9.0 mmol) in acetone (30 mL) was stirred at room temperature for 2 days. The solid material was removed by filtration. The filtrate was recovered and evaporated. The crude product was purified by flash chromatography (0-8% MeOH/DCM), affording 6-methyl-2-({[4-methyl-1-(propan-2-yl)-1H-imidazol-5-yl]methyl}-sulfanyl)pyrimidin-4-ol (215 mg, 28% yield); $^1$H NMR (400 MHz, DMSO-d$_6$): δ 1.36 (d, 3H, J=6.7 Hz), 2.09 (s, 3H), 2.19 (s, 3H), 4.31 (m, 1H), 4.45 (s, 2H), 6.00 (s, 1H), 7.66 (s, 1H); M+ 279. The product was used without further purification.

To a mixture of 6-methyl-2-({[4-methyl-1-(propan-2-yl)-1H-imidazol-5-yl]methyl}-sulfanyl)pyrimidin-4-ol (200 mg, 0.72 mmol) in MeOH (3 mL) was added 4 M HCl/dioxane (1 mL, 4.0 mmol). The mixture was filtered to remove particles in suspension. The solution was evaporated and dried in vacuo, affording the title compound (208 mg, 92% yield); $^1$H NMR (400 MHz, DMSO-d$_6$): δ 1.49 (d, 3H, J=6.7 Hz), 2.23 (s, 3H), 2.36 (s, 3H), 4.60 (s, 2H), 4.75 (m, 1H), 6.10 (s, 1H), 9.24 (s, 1H); M+ 279.

Example 100

2-{[(2,4-dichloropyridin-3-yl)methyl]sulfanyl}-6-(trifluoromethyl)pyrimidin-4-ol

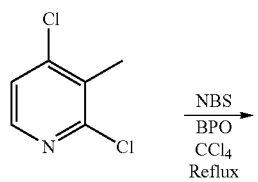

To a solution 2,4-dichloro-3-methylpyridine (2.0 g, 12.3 mmol) in anhydrous carbon tetrachloride (50 mL) was added recrystallized 1-bromopyrrolidine-2,5-dione (2.25 g, 12.6 mmol) and benzoyl benzenecarboperoxoate (400 mg, 1.6 mmol). The mixture was stirred at reflux for 2 hours. After cooling to room temperature, the solid material was removed by filtration and washed with carbon tetrachloride (2×10 mL). The filtrate was recovered and evaporated. The solid product was dried in vacuo, affording 3-(bromomethyl)-2,4-dichloropyridine (2.9 g, 99% yield). The product was used without further purification.

A mixture of 3-(bromomethyl)-2,4-dichloropyridine (2.9 g, 12.3 mmol), 2-sulfanyl-6-(trifluoromethyl)pyrimidin-4-ol (1.2 g, 6.1 mmol), and triethylamine (1.3 mL, 9.3 mmol) in absolute ethanol (25 mL) was stirred at room temperature overnight. The mixture was evaporated to dryness. The residue was dissolved in EtOAc (80 mL). The solution was extracted with water (3×50 mL) and 1 N NaOH (1×50 mL). The organic layer was recovered, dried over MgSO$_4$, filtered, evaporated, and dried in vacuo. The crude product was purified by flash chromatography (0-5% MeOH/DCM), affording the title compound (475 mg, 22% yield); $^1$H NMR (400 MHz, DMSO-d$_6$): δ 4.75 (s, 2H), 6.72 (s, 1H), 7.69 (d, 1H, J=5.3 Hz), 8.36 (d, 1H, J=5.3 Hz); M+ 357.

Example 101

6-methyl-2-({[4-(propan-2-yl)-1,3-thiazol-5-yl]methyl}sulfanyl)pyrimidin-4-ol

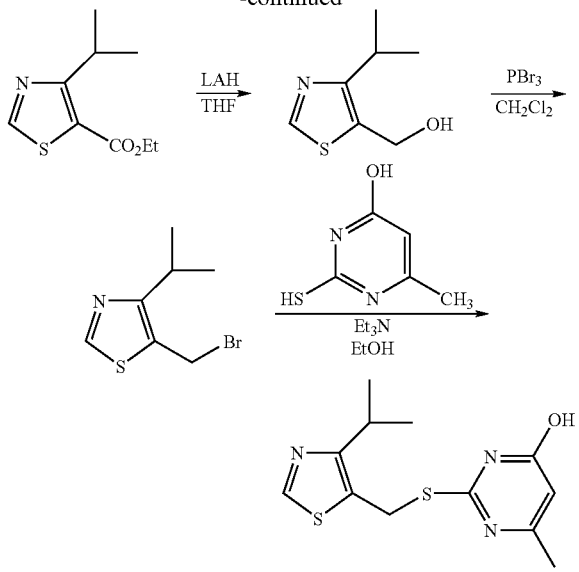

To a 0° C. solution of ethyl 4-methyl-3-oxopentanoate (5.0 mL, 31 mmol) in water (20 mL) was added bromine (16 mL, 31.3 mmol) via syringe pump (0.5 hour). The mixture was stirred at 0° C. for 0.5 hour. The solution was extracted with EtOAc (3×20 mL). The organic extracts were combined, extracted with brine (2×60 mL), dried over MgSO$_4$, filtered, evaporated, and dried in vacuo, affording ethyl 2-bromo-4-methyl-3-oxopentanoate (6.0 g, 82% yield). The product was used without further purification.

To a refluxing solution of thiourea (1.9 g, 25.6 mmol) in absolute ethanol (20 mL) was added ethyl 2-bromo-4-methyl-3-oxopentanoate (6.0 g, 25.3 mmol). The solution was stirred at reflux for another 1.5 hours. After cooling to room temperature, the solution was poured in ice/water (100 mL). The mixture was neutralized with concentrated NH$_4$OH. The solid material was recovered by filtration, washed with water (2×20 mL) and hexanes (2×20 mL), and dried in vacuo, affording ethyl 2-amino-4-(propan-2-yl)-1,3-thiazole-5-carboxylate (3.6 g, 66% yield). The product was used without further purification.

To a 0° C. solution of ethyl 2-amino-4-(propan-2-yl)-1,3-thiazole-5-carboxylate (3.6 g, 16.7 mmol) in anhydrous THF (60 mL) was added boron trifluoride diethyl etherate (3.0 mL, 23.9 mmol). After 15 minutes of stirring at 0° C., tert-butyl nitrite (10 mL, 84 mmol) was added. The mixture was stirred at 0° C. for 4 hours before more tert-butyl nitrite (10 mL, 84 mmol) was added. The mixture was stirred at 0° C. for 1 hour before a solution of sodium hypophosphonate (6.2 g, 70.1 mmol) in water (20 mL) was added. The mixture was stirred at 0° C. for 2 hours and at room temperature overnight. The solution was basified to pH 9-10 with 5N NaOH and was extracted with EtOAc (3×60 mL). The organic extracts were combined, extracted with brine (1×100 mL), dried over MgSO$_4$, filtered, evaporated, and dried in vacuo, affording ethyl 4-(propan-2-yl)-1,3-thiazole-5-carboxylate (2.1 g, 63% yield). The product was used without further purification.

To a 0° C. mixture of lithium aluminum hydride (300 mg, 7.9 mmol) in anhydrous THF (10 mL) was slowly added a solution of ethyl 4-(propan-2-yl)-1,3-thiazole-5-carboxylate (1.06 g, 6.1 mmol) in anhydrous THF (10 mL). The reaction mixture was stirred at room temperature for 1.5 hours. After cooling to 0° C., water (20 mL) and EtOAc (40 mL) were added. The mixture was stirred for 30 minutes. The solid material was removed by filtration. The organic layer was recovered. The aqueous layer was extracted with EtOAc (2×20 mL). The combined organic extracts were dried over MgSO$_4$, filtered, evaporated, and dried in vacuo, affording [4-(propan-2-yl)-1,3-thiazol-5-yl]methanol (802 mg, 96% yield). The product was used without further purification.

To a solution of [4-(propan-2-yl)-1,3-thiazol-5-yl]methanol (800 mg, 5.1 mmol) in anhydrous dichloromethane (35 mL) was added tribromophosphane (520 µL, 5.5 mmol). The mixture was stirred at room temperature for 1.5 hours. Dichloromethane was evaporated. The residue was dried in vacuo, affording 5-(bromomethyl)-4-(propan-2-yl)-1,3-thiazole. The crude product was used without further purification.

A mixture of 5-(bromomethyl)-4-(propan-2-yl)-1,3-thiazole (5.1 mmol), 6-methyl-2-sulfanylpyrimidin-4-ol (510 mg, 3.6 mmol), and triethylamine (2.2 mL, 15.8 mmol) in absolute ethanol (30 mL) was stirred at room temperature overnight. The mixture was evaporated to dryness and then co-evaporated with EtOAc (20 mL). The residue was treated with water (100 mL). The solid material was recovered by filtration and washed with water (2×20 mL), diethyl ether (2×20 mL), and hexanes (2×20 mL). The solid material was dried in vacuo, affording the title compound (565 mg, 56% yield); $^1$H NMR (400 MHz, DMSO-d$_6$): δ 1.20 (d, 6H, J=6.8 Hz), 2.24 (s, 3H), 3.27 (m, 1H), 4.61 (s, 2H), 6.03 (s, 1H), 8.84 (s, 1H); M+ 282.

Example 102

2-{[(3-chloro-5-ethylpyridin-4-yl)methyl]sulfanyl}-6-methylpyrimidin-4-ol

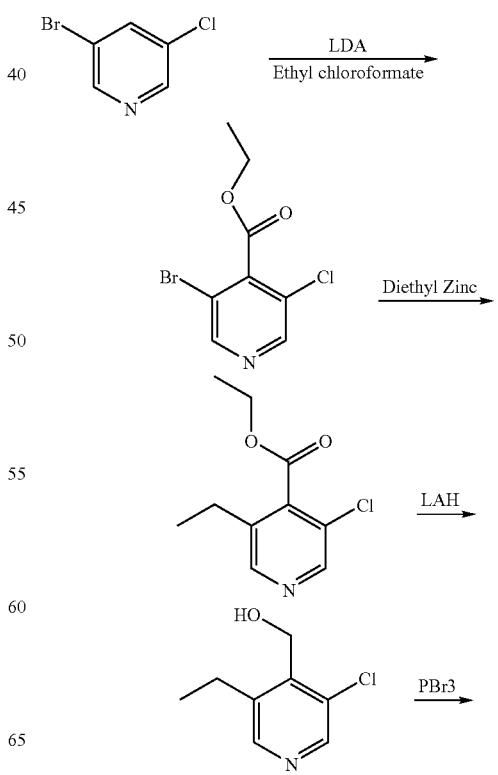

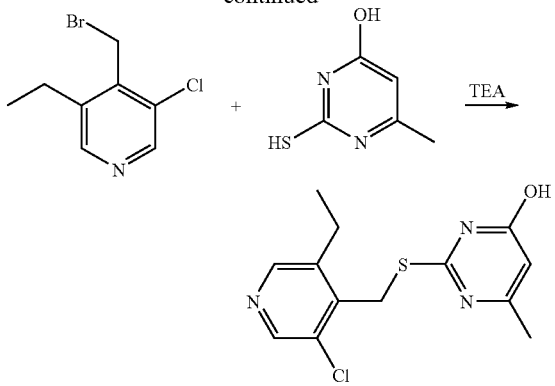

To a solution of LDA (2 M solution in THF/heptane/ethylbenzene, 2.78 g, 12.97 mL, 25.95 mmol) in anhydrous THF (20 mL) under nitrogen atmosphere cooled to −78° C. was added a solution of the 3-bromo-5-chloropyridine (5.0 g, 25.98 mmol) in anhydrous THF (40 mL) at −78° C. The reaction mixture was allowed to stir at the same temperature for 45 minutes. Then, a solution of chloro(ethoxy)methanone (28.19 g, 259.7 mmol) was added slowly over 15 minutes. After stirring for 20 minutes, the reaction mixture was quenched with saturated NaHCO$_3$ solution. The reaction mixture was extracted into ethyl acetate (3×100 mL), and the combined organic layer was washed with water and brine. The organic layer was separated, dried over anhydrous sodium sulfate, and filtered. The filtrate was evaporated, and the residue was purified through CombiFlash using 0-10% ethyl acetate in hexane to provide ethyl 3-bromo-5-chloropyridine-4-carboxylate as a pale yellow oil (5.84 g, 85% yield); $^1$H NMR (400 MHz, DMSO-d$_6$): δ 1.35 (t, 3H), 4.45 (q, 2H), 8.82 (s, 1H), 8.87 (s, 1H); M+ 265.5.

To a solution of ethyl 3-bromo-5-chloropyridine-4-carboxylate (5.84 g, 22.08 mmol) in anhydrous dioxane (40 mL) at room temperature was added (1,1'-bis(diphenylphosphino) ferrocene)dichloropalladium (II) (323 mg, 0.441 mmol). Then, diethylzinc (2.72 g, 18 mL, 22.09 mmol, 15% solution in toluene) was added dropwise and the reaction was heated at 70° C. for 45 minutes. The reaction mixture was cooled to room temperature and then was quenched with MeOH. The resulting mixture was extracted with ethyl acetate (2×100 mL), and the organic layer was washed with water, 0.1 N HCl, and brine. The organic layer was then dried over anhydrous sodium sulfate and filtered. The filtrate was evaporated, and the residue was purified by CombiFlash using 0-30% ethyl acetate and hexane to provide ethyl 5-chloro-3-ethylpyridine-4-carboxylate as a pale yellow oil (2.59 g, 55% yield); $^1$H NMR (400 MHz, CDCl$_3$): δ 1.25 (t, 3H), 1.45 (t, 3H), 2.65 (q, 2H), 4.47 (q, 2H), 8.41 (s, 1H), 8.49 (s, 1H); M+ 214.5.

To a suspension of lithium aluminum hydride (LAH, 0.920 g, 24.24 mmol) in anhydrous THF (20 mL) at 0° C. was added dropwise a solution of ethyl 5-chloro-3-ethylpyridine-4-carboxylate (2.59 g, 12.12 mmol) in THF (30 mL). After stirring for 1 hour, the reaction mixture was slowly quenched with 15% aqueous NaOH and then water. Ethyl acetate was added, and the mixture was stirred for 10 minutes. The white precipitate was filtered off and washed with ethyl acetate (2×50 mL). The combined organic layer was dried over anhydrous sodium sulfate and filtered. The filtrate was evaporated to provide (3-chloro-5-ethylpyridin-4-yl)methanol as a thick oil (1.83 g, 88% yield) and used for the next step without any further purification; M+ 166.5.

To a solution of (3-chloro-5-ethylpyridin-4-yl)methanol (1.83 g, 10.66 mmol) in anhydrous chloroform (40 mL) was added dropwise tribromophosphane (2.91 g, 1.01 mL, 10.75 mmol) at 0° C. The reaction mixture was allowed to stir overnight at room temperature. The solvent was evaporated to provide crude 4-(bromomethyl)-3-chloro-5-ethylpyridine, which was used in the next step without further purification.

To a mixture of crude 4-(bromomethyl)-3-chloro-5-ethylpyridine (2.5 g, 10.66 mmol) and 6-methyl-2-sulfanylpyrimidin-4-ol (0.985 g, 6.92 mmol) in anhdrous ethanol (50 mL) at 0° C. was added triethylamine (3.77 g, 37.31 mmol). The reaction mixture was allowed to stir at room temperature overnight. The solvent was evaporated to provide a crude residue. Ether was added to precipitate the triethylamine hydrochloride salt. The solid was filtered and washed with ether several times. The combined ether fraction was evaporated to provide a crude residue, which was purified by Combiflash using 0-10% MeOH:dichloromethane. This provided 2-{[(3-chloro-5-ethylpyridin-4-yl)methyl]sulfanyl}-6-methylpyrimidin-4-ol as a white solid (1.33 g, 42.2% yield); $^1$H NMR (400 MHz, CDCl$_3$): δ 1.19 (t, 3H), 2.24 (s, 3H), 2.84 (q, 2H), 4.59 (s, 2H), 6.00 (bs, 1H), 8.41 (s, 1H), 8.50 (s, 1H); M+ 296.1.

Example 103

2-{[(3-chloro-5-ethylpyridin-4-yl)methyl]sulfanyl}-6-(trifluoromethyl)pyrimidin-4-ol

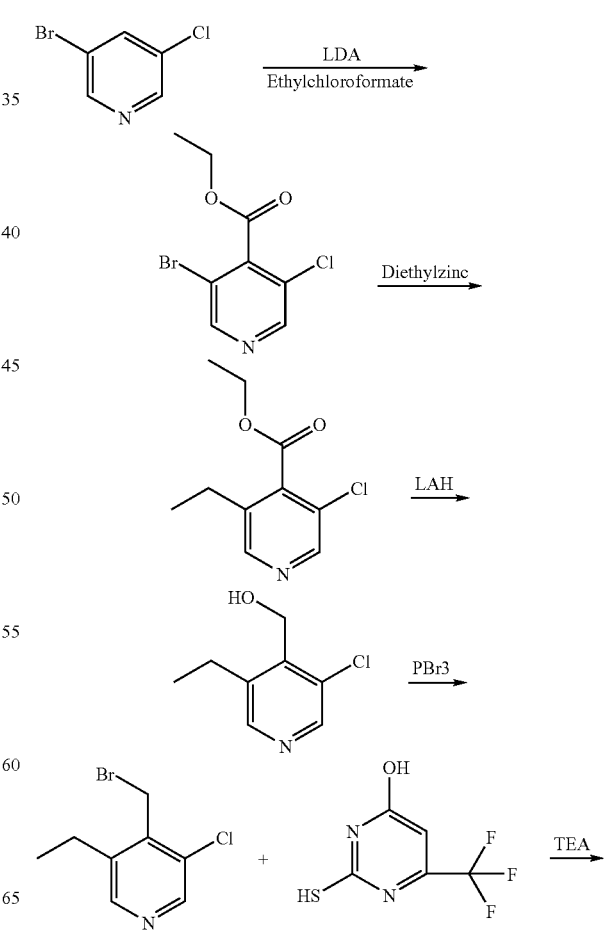

-continued

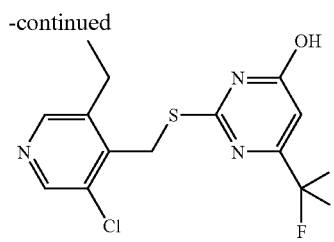

To a solution of LDA (2 M solution in THF/heptane/ethylbenzene, 2.78 g, 12.97 mL, 25.95 mmol) in anhydrous THF (20 mL) under nitrogen atmosphere and cooled to −78° C. was added a solution of 3-bromo-5-chloropyridine (5.0 g, 25.98 mmol) in anhydrous THF (40 mL) at −78° C. The reaction mixture was allowed to stir at the same temperature for 45 minutes. Then, a solution of chloro(ethoxy)methanone (28.19 g, 259.7 mmol) was added slowly over 15 minutes. After stirring for 20 minutes, the reaction mixture was quenched with saturated NaHCO$_3$ solution. The mixture was extracted into ethyl acetate (3×100 mL), and the combined organic layers were washed with water and brine. The separated organic layer was dried over anhydrous sodium sulfate and filtered. The filtrate was evaporated, and the residue was purified through CombiFlash using 0-10% ethyl acetate in hexane to provide ethyl 3-bromo-5-chloropyridine-4-carboxylate as pale yellow oil (5.84 g, 85% yield); $^1$H NMR (400 MHz, DMSO-d$_o$): δ 1.35 (t, 3H), 4.45 (q, 2H), 8.82 (s, 1H), 8.87 (s, 1H); M+ 265.5.

To a solution of ethyl 3-bromo-5-chloropyridine-4-carboxylate (5.84 g, 22.08 mmol) in anhydrous dioxane (40 mL) at room temperature was added (1,1'-bis(diphenylphosphino)ferrocene)dichloropalladium (II) (323 mg, 0.441 mmol). Then, diethylzinc (2.72 g, 18 mL, 22.09 mmol, 15% solution in toluene) was added dropwise and the reaction was heated at 70° C. for 45 minutes. The mixture was cooled to room temperature, quenched with MeOH, and extracted with ethyl acetate (2×100 mL). The organic layer was washed with water, 0.1 N HCl, and brine, and then dried over anhydrous sodium sulfate. The filtered solution was evaporated, and the residue was purified by CombiFlash using 0-30% ethyl acetate in hexane to provide ethyl 5-chloro-3-ethylpyridine-4-carboxylate as a pale yellow oil (2.59 g, 55% yield); $^1$H NMR (400 MHz, CDCl$_3$): δ 1.25 (t, 3H), 1.45 (t, 3H), 2.65 (q, 2H), 4.47 (q, 2H), 8.41 (s, 1H), 8.49 (s, 1H); M+ 214.5.

To a suspension of LAH (0.92 g, 24.24 mmol) in anhydrous THF (20 mL) at 0° C. was added dropwise a solution of 5-chloro-3-ethylpyridine-4-carboxylate (2.59 g, 12.12 mmol) in THF (30 mL). After stirring for 1 hour, the reaction mixture was slowly quenched with 15% NaOH and then diluted with water. Ethyl acetate was added, the mixture was stirred for 10 minutes, and the precipitated white solid was filtered off. The solid was washed with ethyl acetate (2×50 mL). The combined organic layer was separated, dried over anhydrous sodium sulfate, and filtered. The filtrate was evaporated to provide (3-chloro-5-ethylpyridin-4-yl)methanol as a thick oil (1.83 g, 88% yield), which was used for the next step without any further purification; M+ 166.5.

To a solution of (3-chloro-5-ethylpyridin-4-yl)methanol (1.83 g, 10.66 mmol) in anhydrous chloroform (40 mL) was added dropwise tribromophosphane (2.91 g, 1.01 mL, 10.75 mmol) at 0° C. The reaction mixture was allowed to stir overnight at room temperature. The solvent was then evaporated to provide crude 4-(bromomethyl)-3-chloro-5-ethylpyridine, which was used for the next step without any further purification.

To a mixture of crude 4-(bromomethyl)-3-chloro-5-ethylpyridine (2.5 g, 10.66 mmol), 2-sulfanyl-6-(trifluoromethyl)pyrimidin-4-ol (1.35 g, 6.92 mmol) in anhydrous ethanol (50 mL) at 0° C. was added triethylamine (3.77 g, 37.31 mmol). The reaction mixture was allowed to stir overnight at room temperature. The solvent was evaporated to provide a crude residue. Ether was added to precipitate the triethylamine hydrochloride salt. The solid was filtered and washed with ether several times. The combined ether layers were evaporated to provide a crude residue, which was purified by Combiflash using 0-10% MeOH in dichloromethane to provide 2-{[(3-chloro-5-ethylpyridin-4-yl)methyl]sulfanyl}-6-(trifluoromethyl)pyrimidin-4-ol as a white solid (1.5 g, 40% yield); $^1$H NMR (400 MHz, CDCl$_3$): δ 1.17 (t, 3H), 2.24 (s, 3H), 2.84 (q, 2H), 4.65 (s, 2H), 6.72 (s, 1H), 8.41 (s, 1H), 8.50 (s, 1H); M+ 350.1

Example 104

2-{[(3,5-diethylpyridin-4-yl)methyl]sulfanyl}-6-methylpyrimidin-4-ol

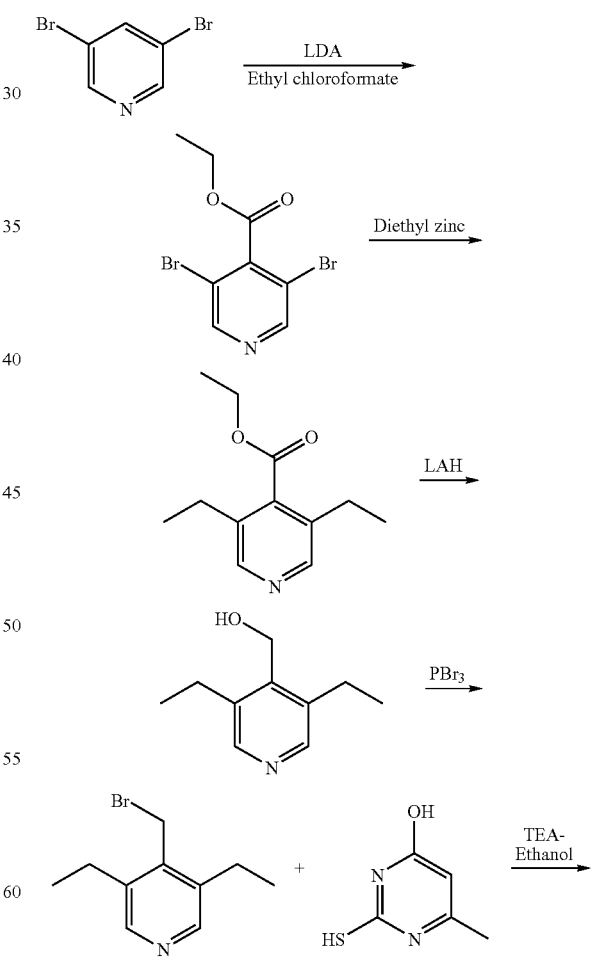

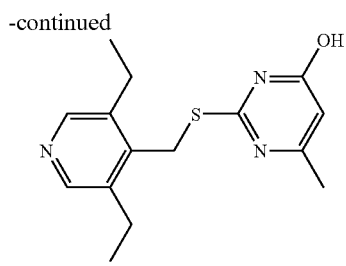

To a solution of LDA (2 M solution in THF/heptane/ethylbenzene) (2.26 g, 10.54 mL, 21.06 mmol) in anhydrous THF (20 mL) under nitrogen atmosphere cooled to −78° C. was added a solution of the 3,5-dibromopyridine (5.0 g, 21.10 mmol) in anhydrous THF (40 mL) at −78° C. The reaction mixture was allowed to stir at the same temperature for 45 minutes. Then, a solution of chloro(ethoxy)methanone (22.90 g, 211.02 mmol) was added slowly over 15 minutes. After stirring for 20 minutes, the reaction mixture was quenched with saturated aqueous $NaHCO_3$. The mixture was extracted with ethyl acetate (3×100 mL), and the combined organic layer was washed with water and brine. The organic layer was dried over anhydrous sodium sulfate and filtered. The filtrate was evaporated, and the residue was purified through CombiFlash using 0-10% ethyl acetate in hexane to provide ethyl 3,5-dibromopyridine-4-carboxylate as pale yellow oil (5.98 g, 92% yield); $^1$H NMR (400 MHz, DMSO-$d_6$): δ1.43 (t, 3H), 4.49 (q, 2H), 8.67 (s, 2H); M+ 307.9.

To a solution of ethyl 3,5-dibromopyridine-4-carboxylate (5.98 g, 19.35 mmol) in anhydrous dioxane (40 mL) was added at room temperature (1,1'-bis(diphenylphosphino)ferrocene)dichloropalladium (II) (424 mg, 0.580 mmol). Diethylzinc (3.58 g, 23.8 mL, 28.95 mmol, 15% solution in toluene) was then added dropwise. The reaction mixture was heated at 70° C. for 45 minutes, then cooled to room temperature and quenched with MeOH. The resulting mixture was extracted with ethyl acetate (2×100 mL), washed with water, 0.1 N HCl, and brine. The organic layer was dried over anhydrous sodium sulfate and filtered. The filtrate was evaporated, and the residue was purified by CombiFlash using 0-30% ethyl acetate in hexane to provide ethyl 3,5-diethylpyridine-4-carboxylate as a pale yellow oil (2.2 g, 54.8% yield); $^1$H NMR (400 MHz, CDCl$_3$): δ 1.23 (t, 6H), 1.40 (t, 3H), 2.64 (q, 4H), 4.44 (q, 2H), 8.36 (s, 2H), M+ 208.5; M+ 180.2.

To a suspension of LAH (0.805 g, 21.22 mmol) in anhydrous THF (20 mL) at 0° C. was added a dropwise a solution of ethyl 3,5-diethylpyridine-4-carboxylate (2.20 g, 10.61 mmol) in THF (30 mL). After stirring for 1 hour, the reaction mixture was slowly quenched with 15% NaOH solution and then diluted with water. Ethyl acetate was added, the mixture was stirred for 10 minutes, and the precipitated white solid was filtered off. The solid was washed with ethyl acetate (2×50 mL). The combined organic layers were dried over anhydrous sodium sulfate and filtered. The filtrate was evaporated to provide (3,5-diethylpyridin-4-yl)methanol as a thick oil (1.50 g, 86% yield) which was used for the next step without any further purification; $^1$H NMR (400 MHz, DMSO-$d_6$): δ 1.15 (t, 6H), 2.70 (q, 4H), 4.50 (s, 2H), 5.06 (bs, 1H), 8.22 (s, 2H), M+ 208.5; M+ 166.2.

To a solution of (3,5-diethylpyridin-4-yl)methanol (1.50 g, 9.07 mmol) in anhydrous chloroform (40 mL) at 0° C. was added dropwise tribromophosphane (2.48 g, 0.861 mL, 9.16 mmol). The reaction mixture was allowed to stir overnight at room temperature. The solvent was evaporated to provide crude 4-(bromomethyl)-3,5-diethylpyridine, which was used for the next step without any further purification; M+ 229.2.

To a mixture of crude 4-(bromomethyl)-3,5-diethylpyridine (2.07 g, 9.07 mmol) and 6-methyl-2-sulfanylpyrimidin-4-ol (0.838 g, 5.89 mmol) in anhydrous ethanol (50 mL) at 0° C. was added triethylamine (3.21 g, 4.42 mL 31.75 mmol), and the reaction mixture was allowed to stir at room temperature overnight. The solvent was evaporated to provide a crude residue. Ether was added to precipitate the triethylamine hydrobromide salt. The solid was filtered and washed with ether several times. The combined ether layers were evaporated, and the crude residue was purified by Combiflash using 0-10% MeOH in dichloromethane to provide 2-{[(3,5-diethylpyridin-4-yl)methyl]sulfanyl}-6-methylpyrimidin-4-ol as a white solid; $^1$H NMR (400 MHz, DMSO-$d_6$): δ 1.23 (t, 6H), 1.40 (t, 3H), 2.64 (q, 4H), 4.44 (q, 2H), 8.36 (s, 2H); M+1 290.4.

Example 105

2-{[(3,5-diethylpyridin-4-yl)methyl]sulfanyl}-6-(trifluoromethyl)pyrimidin-4-ol

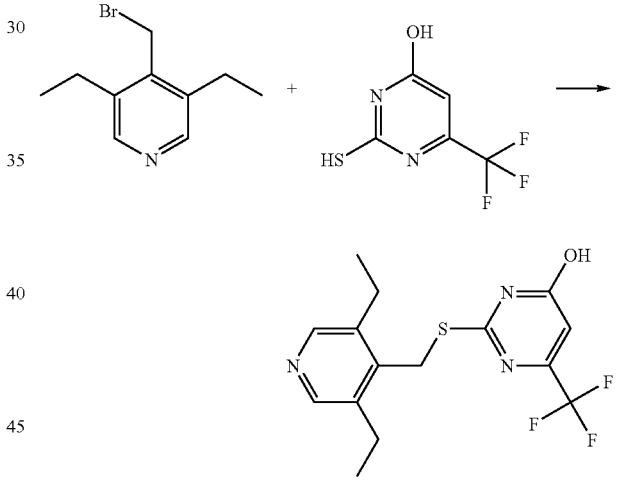

To a mixture of crude 4-(bromomethyl)-3,5-diethylpyridine and 2-sulfanyl-6-(trifluoromethyl)pyrimidin-4-ol (0.838 g, 5.89 mmol) in anhydrous ethanol (50 mL) at 0° C. was added triethylamine (3.21 g, 4.42 mL, 31.75 mmol). The reaction mixture was allowed to stir at room temperature overnight. The solvent was evaporated to provide a crude residue. Ether was added to precipitate the triethylamine hydrobromide salt. The solid was filtered and washed with ether several times. The combined ether layers were evaporated, and the crude residue was purified by Combiflash using 0-10% MeOH in dichloromethane to provide 2-{[(3,5-diethylpyridin-4-yl)methyl]sulfanyl}-6-methylpyrimidin-4-ol and 2-{[(3-ethylpyridin-4-yl)methyl]sulfanyl}-6-methylpyrimidin-4-ol as a white solid; $^1$H NMR (400 MHz, DMSO-$d_6$): δ 1.19 (t, 6H), 2.64 (q, 4H), 4.55 (s, 2H), 6.70 (s, 1H), 8.30 (s, 2H); M+1 344.4.

Example 106

6-methyl-2-({[1-(2-methylpropyl)-1H-imidazol-5-yl]methyl}sulfanyl)pyrimidin-4-ol

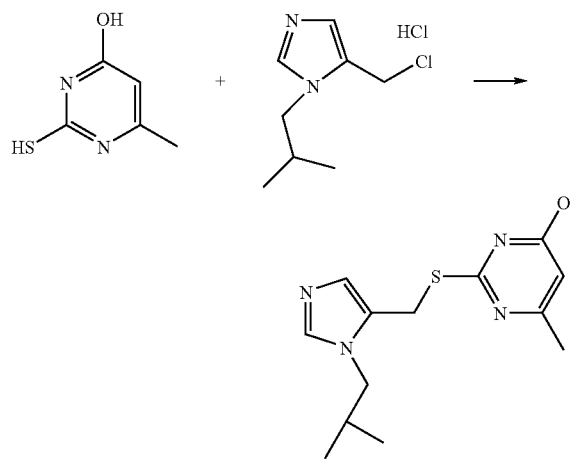

To a solution of 5-(chloromethyl)-1-(2-methylpropyl)-1H-imidazole hydrochloride (1.0 g, 4.89 mmol), 6-methyl-2-sulfanylpyrimidin-4-ol (0.546 g, 3.84 mmol), and potassium carbonate (0.677 g, 4.90 mmol) was added. The reaction mixture was stirred at room temperature overnight. Potassium carbonate was filtered, and the solvent was evaporated, affording the title compound as a white solid (1.09 g, 82% yield); $^1$H NMR (400 MHz, DMSO-$d_6$): δ 0.82 (d, J=6.6 Hz, 6H), 2.01 (m, 1H), 2.21 (s, 3H), 3.75 (d, J=7.6 Hz, 2H), 4.47 (s, 2H), 6.03 (bs, 1H), 6.88 (s, 1H), 7.58 (s, 1H); M+1 279.3.

Example 107

2-[({3-chloroimidazo[1,2-a]pyridin-2-yl}methyl)sulfanyl]-6-methylpyrimidin-4-ol

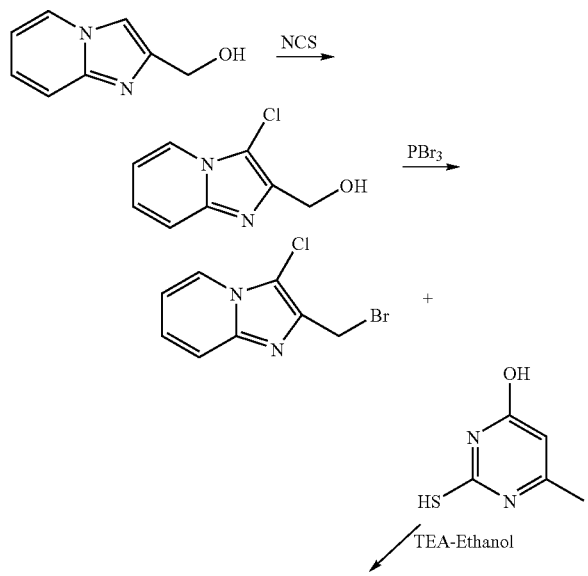

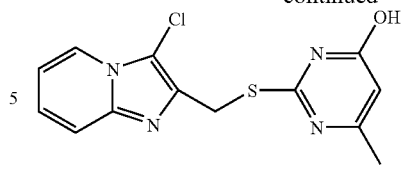

To a solution of imidazo[1,2-a]pyridin-2-ylmethanol (1.0 g, 6.75 mmol) in anhydrous DMF was added 1-chloropyrrolidine-2,5-dione (0.898 g, 6.75 mmol) at room temperature. The reaction mixture was allowed to stir for 2 hours. The solvent was evaporated, and the residue was purified by CombiFlash using dichloromethane and methanol (0-10%) to provide {3-chloroimidazo[1,2-a]pyridin-2-yl}methanol as a grey solid (0.799 g, 65% yield); M+1 183.2.

To a solution of {3-chloroimidazo[1,2-a]pyridin-2-yl}methanol (0.799 g, 4.39 mmol) in anhydrous chloroform (25 mL) at 0° C. was added tribromophosphane (1.20 g, 0.41 mL, 4.43 mmol), and the reaction mixture was allowed to stir at room temperature overnight. The solvent was evaporated to provide the crude 2-(bromomethyl)-3-chloroimidazo[1,2-a]pyridine, which was used for the next step without any further purification; M+1 246.2.

To a mixture of 2-(bromomethyl)-3-chloroimidazo[1,2-a]pyridine (1.07 g, 5.87 mmol) and 6-methyl-2-sulfanylpyrimidin-4-ol (0.539 g, 3.82 mmol) in anhydrous ethanol (30 mL) at 0° C. was added triethylamine (2.08 g, 2.86 mL, 20.57 mmol), and the reaction mixture was stirred overnight at room temperature. The solvent was evaporated to dryness, and water was added to precipitate the product. The crude product was purified by column chromatography using dichloromethane and methanol (0-10%) to provide 2-[({3-chloroimidazo[1,2-a]pyridin-2-yl}methyl)sulfanyl]-6-methylpyrimidin-4-ol; $^1$H NMR (400 MHz, DMSO-$d_6$): δ 2.18 (s, 3H), 4.52 (s, 2H), 6.03 (bs, 1H), 7.07 (t, 1H), 7.35 (t, 1H), 7.59 (d, 1H), 8.30 (d, 1H); M+1 279.3.

Example 108

4-chloro-2-{[(3,5-dichloropyridin-4-yl)methyl]sulfanyl}-6-methylpyrimidine

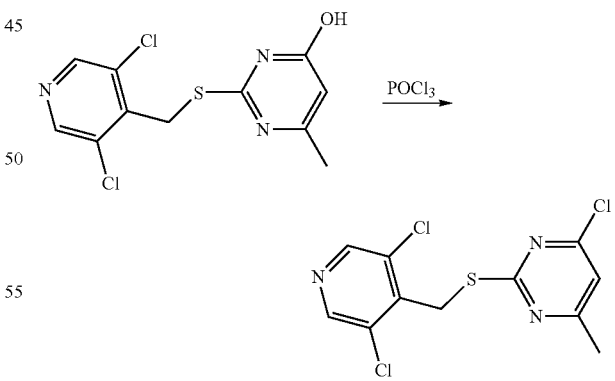

A mixture of 2-{[(3,5-dichloropyridin-4-yl)methyl]sulfanyl}-6-methylpyrimidin-4-ol (2.0 g, 6.62 mmol) and phosphoryl trichloride (20 mL) was heated at 75° C. for 1 hour. The solvent was evaporated, and the crude residue was extracted into ethyl acetate (2×100 mL). The organic layer was washed with 10% sodium bicarbonate solution and brine. The organic layer was separated, dried over anhydrous sodium sulfate, and filtered. The solvent was evaporated, and the residue was purified by CombiFlash using 0-5% methanol in dichloromethane to provide 4-chloro-2-{[(3,5-dichloropyridin-4-yl)methyl]sulfanyl}-6-methylpyrimidine as a white solid (1.01 g, 47.1% yield); ¹H NMR (400 MHz, DMSO-d₆): δ 2.45 (s, 3H), 4.70 s, 2H), 7.40 (s, 1H), 8.66 (d, 2H); M+1 321.2.

Example 109

2-{[(4-chloro-1-methyl-1H-imidazol-5-yl)methyl]sulfanyl}-6-methylpyrimidin-4-ol

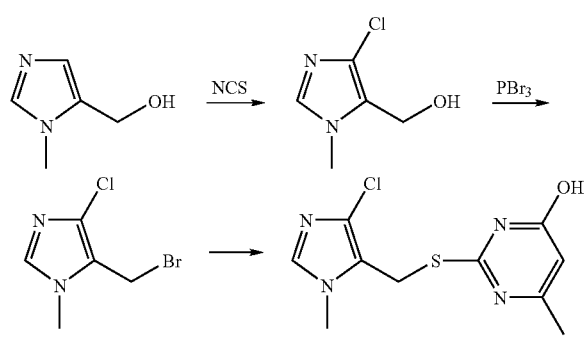

To the solution of (1-methyl-1H-imidazol-5-yl)methanol (1.14 g, 10 mmol) in dioxane (50 mL), in a 250 mL round bottom flask, was added 1-chloropyrrolidine-2,5-dione (1.38 g, 10 mmol). The resulting mixture was stirred at room temperature overnight. Dioxane was removed under vacuum to provide (4-chloro-1-methyl-1H-imidazol-5-yl)methanol. The crude (4-chloro-1-methyl-1H-imidazol-5-yl)methanol was dissolved in 40 mL of chloroform, followed by addition of tribromophosphane (1.9 mL, 20 mmol). The resulting mixture was stirred at room temperature overnight. The solvent was evaporated to provide 5-(bromomethyl)-4-chloro-1-methyl-1H-imidazole.

5-(bromomethyl)-4-chloro-1-methyl-1H-imidazole was dissolved in DMF (20 mL). Potassium carbonate (3 g) and 6-methyl-2-sulfanylpyrimidin-4-ol (1.4 g, 10 mmol) were added. The new mixture was stirred at room temperature for 2 hours. DMF was removed under vacuum. The crude compound was purified by column chromatography to provide 2-{[(4-chloro-1-methyl-1H-imidazol-5-yl)methyl]sulfanyl}-6-methylpyrimidin-4-ol as the major product (350 mg, 13% overall yield); ¹H NMR (400 MHz, DMSO-d₆): δ 2.19 (s, 3H), 3.72 (s, 3H), 4.59 (s, 2H), 6.00 (bs, 1H), 7.59 (s, 1H); M+ 271.

Example 110

2-({[2-chloro-1-(propan-2-yl)-1H-imidazol-5-yl]methyl}sulfanyl)-6-methylpyrimidin-4-ol

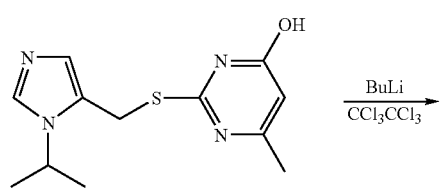

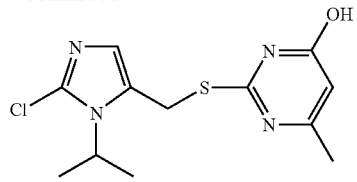

In a 250 mL round bottom flask, 6-methyl-2-({[1-(propan-2-yl)-1H-imidazol-5-yl]methyl}sulfanyl)pyrimidin-4-ol (260 mg, 1.0 mmol) was dissolved in THF (20 mL) at −78° C. BuLi (0.88 mL, 2.2 mmol) was added dropwise. After 1 hour, hexachloroethane (360 mg, 1.5 mmol) was added. The resulting mixture was stirred at 0° C. for 2 hours. A few drops of methanol were added to quench the reaction. Then, the solvent as removed under vacuum, and the crude was purified by column chromatography to provide the title compound as a white solid (200 mg, 87% yield); ¹H NMR (400 MHz, CD₃OD): δ 1.45 (d, 6H), 2.20 (s, 3H), 4.46 (s, 2H), 4.62 (m, 1H), 6.02 (bs, 1H), 6.84 (s, 1H); M+ 299.

Example 111

2-{[(2-chloro-1-ethyl-1H-imidazol-5-yl)methyl]sulfanyl}-6-methylpyrimidin-4-ol

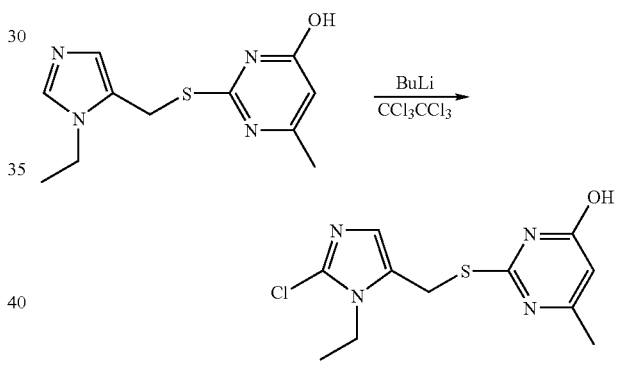

2-{[(2-chloro-1-ethyl-1H-imidazol-5-yl)methyl]sulfanyl}-6-methylpyrimidin-4-ol was synthesized from 2-{[(1-ethyl-1H-imidazol-5-yl)methyl]sulfanyl}-6-methylpyrimidin-4-ol following the procedure described for Example 110 to provide a pale white solid (120 mg, 24% yield); ¹H NMR (400 MHz, DMSO-d₆): δ 1.38 (t, 3H), 2.23 (s, 3H), 4.00 (q, 2H), 4.42 (s, 2H), 4.54 (m, 1H), 6.05 (bs, 1H), 6.93 (s, 1H); M+ 285.

Example 112

2-{[(3-ethyl-5-methyl-1,2-oxazol-4-yl)methyl]sulfanyl}-6-methylpyrimidin-4-ol

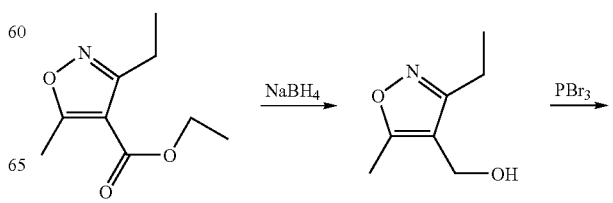

189
-continued

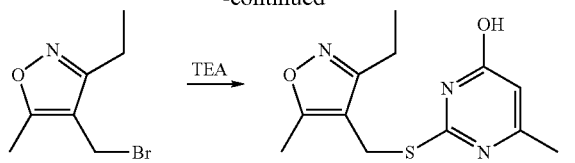

In a 250 mL round bottom flask, ethyl 3-ethyl-5-methyl-1,2-oxazole-4-carboxylate (1.83 g, 10 mmol) was dissolved in ethanol (20 mL). NaBH$_4$ (760 mg, 20 mmol) was added in one portion. The resulting mixture was stirred at room temperature overnight. The reaction was quenched by slow addition of water (2 mL). After 10 minutes, the solvent was evaporated, and the crude material was purified by column chromatography to provide 3-ethyl-5-methyl-1,2-oxazol-4-yl)methanol (700 mg, 55% yield).

3-ethyl-5-methyl-1,2-oxazol-4-yl)methanol (280 mg, 2 mmol) and tribromophosphane (0.38 mL, 4 mmol) were dissolved in dichloromethane (15 mL). The mixture was stirred at room temperature for 4 hours. The solvent was evaporated, and the crude material was dissolved in ethanol (10 mL). Triethylamine (1.4 mL, 10 mmol) and 6-methyl-2-sulfanylpyrimidin-4-ol (280 mg, 2 mmol) were added. The mixture was stirred at room temperature for 3 hours. Ethanol was evaporated. The crude compound was purified by column chromatography to provide the title compound (150 mg, 28% yield); $^1$H NMR (400 MHz, DMSO-d$_6$): δ 1.27 (t, 3H), 2.26 (s, 3H), 2.45 (s, 3H), 2.73 (q, 2H), 4.30 (s, 2H), 4.62 (m, 1H), 6.00 (br, 1H); M+ 266.

Example 113

2-{[(1-cyclopentyl-1H-imidazol-5-yl)methyl]sulfanyl}-6-methylpyrimidin-4-ol

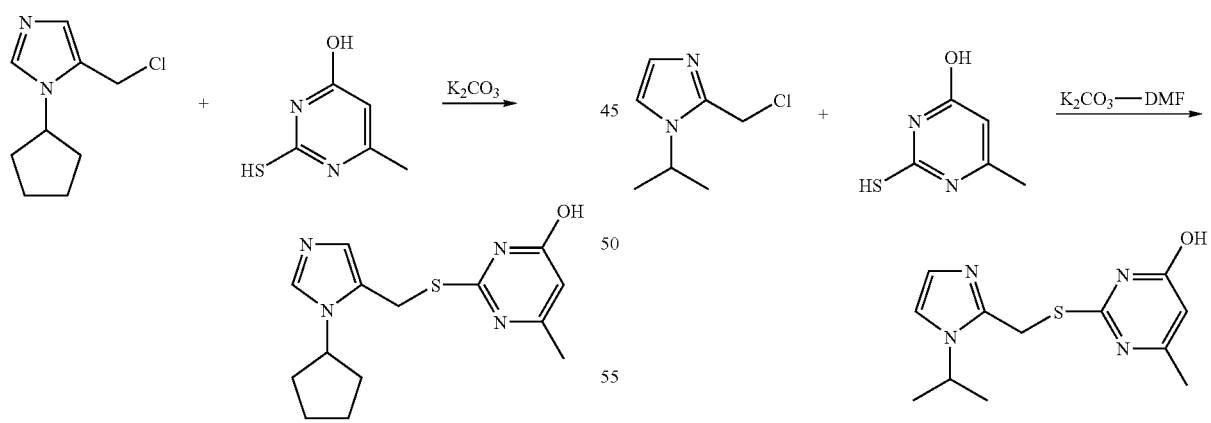

This example was synthesized from 5-(chloromethyl)-1-cyclopentyl-1H-imidazole and 6-methyl-2-sulfanylpyrimidin-4-ol following the general procedure as shown in the last step of Example 109 to provide 2-{[(1-cyclopentyl-1H-imidazol-5-yl)methyl]sulfanyl}-6-methylpyrimidin-4-ol as a white solid (700 mg, 50% yield); $^1$H NMR (400 MHz, DMSO-d$_6$): δ 1.61 (m, 2H), 1.79 (m, 4H), 2.10 (m, 2H), 2.21 (s, 3H), 4.48 (s, 2H), 4.54 (m, 1H), 6.02 (br, 1H), 6.88 (s, 1H), 7.73 (s, 1H); M+ 291.

190
Example 114

6-methyl-2-{[(1-methyl-1H-imidazol-4-yl)methyl]sulfanyl}pyrimidin-4-ol

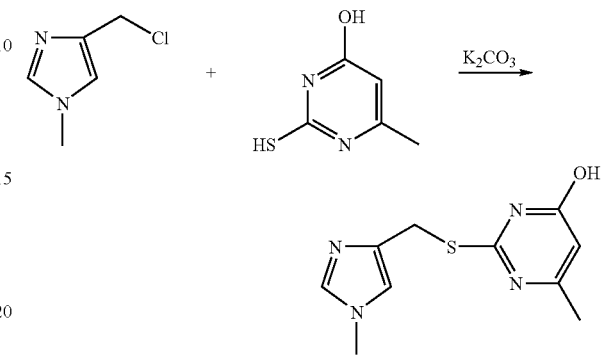

This example was synthesized from 4-(chloromethyl)-1-methyl-1H-imidazole and 6-methyl-2-sulfanylpyrimidin-4-ol following the general procedure as shown in the last step of Example 109. This provided the title compound as a white solid (260 mg, 60% yield); $^1$H NMR (400 MHz, DMSO-d$_6$): δ 2.19 (s, 3H), 3.60 (s, 3H), 4.24 (s, 2H), 5.97 (bs, 1H), 7.06 (s, 1H), 7.52 (s, 1H); M+ 237.

Example 115

6-methyl-2-({[1-(propan-2-yl)-1H-imidazol-2-yl]methyl}sulfanyl)pyrimidin-4-ol

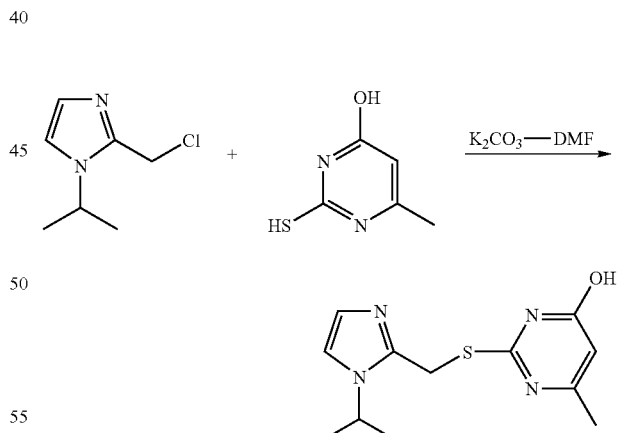

This example was synthesized from 2-(chloromethyl)-1-(propan-2-yl)-1H-imidazole and 6-methyl-2-sulfanylpyrimidin-4-ol following the general procedure as shown in the last step of Example 109. This provided the title compound as a pale white solid (1.0 g, 72% yield); $^1$H NMR (400 MHz, DMSO-d$_6$): δ 1.33 (m, 6H), 2.18 (s, 3H), 4.52 (s, 2H), 4.54 (m, 1H), 4.54 (m, 1H), 6.00 (br, 1H), 6.83 (s, 1H), 7.26 (s, 1H); M+ 265.

Example 116

2-({[2,4-dichloro-1-(propan-2-yl)-1H-imidazol-5-yl]methyl}sulfanyl)-6-methylpyrimidin-4-ol

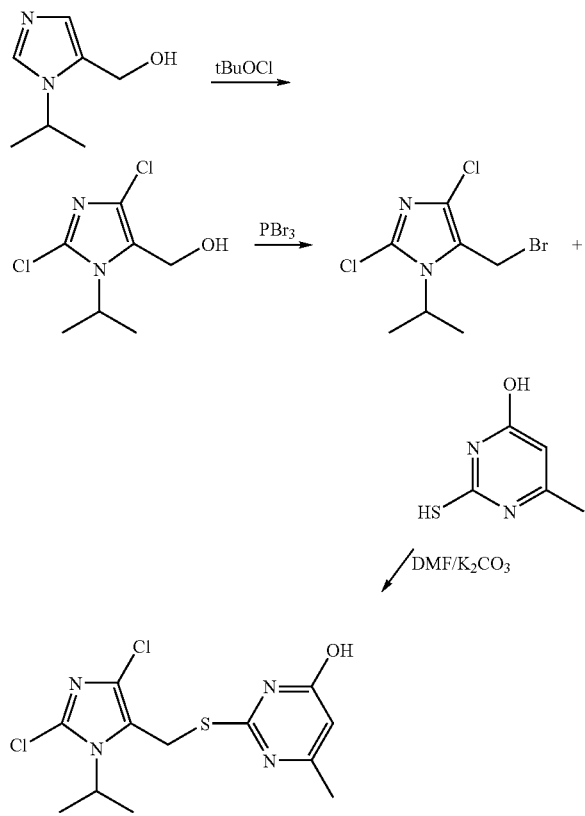

To the solution of [1-(propan-2-yl)-1H-imidazol-5-yl]methanol (1.41 g, 10 mmol) in DMF (50 mL) in a 250 mL round bottom flask, tBuOCl (2.1 mL, 25 mmol) was added dropwise at 0° C. The resulting mixture was stirred at room temperature overnight in the dark. DMF was removed under vacuum. The crude product was purified by column chromatography to provide a semi-solid [2,4-dichloro-1-(propan-2-yl)-1H-imidazol-5-yl]methanol.

[2,4-dichloro-1-(propan-2-yl)-1H-imidazol-5-yl]methanol was dissolved in chloroform (40 mL), followed by addition of $PBr_3$ (1.9 mL, 20 mmol). The resulting mixture was stirred at room temperature overnight. The solvent was evaporated and the crude mixture was dissolved in DMF (20 mL). Potassium carbonate (3 g) and 6-methyl-2-sulfanylpyrimidin-4-ol (1.4 g, 10 mmol) were added. The mixture was then stirred at room temperature for 2 hours. DMF was removed under vacuum and the crude residue was purified by column chromatography to provide 2-({[2,4-dichloro-1-(propan-2-yl)-1H-imidazol-5-yl]methyl}sulfanyl)-6-methylpyrimidin-4-ol (700 mg, 21% overall yield); $^1$H NMR (400 MHz, $CD_3OD$): δ 1.59 (d, 6H), 2.24 (s, 3H), 4.56 (s, 2H), 4.59 (m, 1H), 6.03 (bs, 1H); M+ 333.

Example 117

2-{[(2,4-dichloro-1-ethyl-1H-imidazol-5-yl)methyl]sulfanyl}-6-methylpyrimidin-4-ol

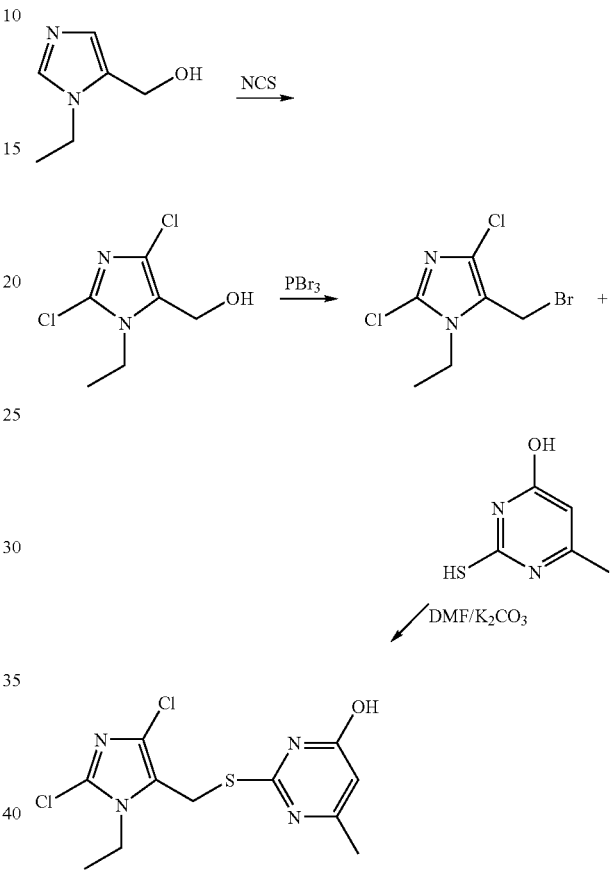

To the solution of (1-ethyl-1H-imidazol-5-yl)methanol (1.26 g, 10 mmol) in dioxane (50 mL) in a 250 mL round bottom flask, was added NCS (1.38 g, 10 mmol). The resulting mixture was stirred at room temperature overnight. Dioxane was removed under vacuum. The crude (2,4-dichloro-1-ethyl-1H-imidazol-5-yl)methanol was dissolved in chloroform (40 mL), followed by addition of $PBr_3$ (1.9 mL, 20 mmol). The resulting mixture was stirred at room temperature overnight. The solvent was evaporated. The crude 5-(bromomethyl)-2,4-dichloro-1-ethyl-1H-imidazole was dissolved in DMF (20 mL). Potassium carbonate (3 g) and 6-methyl-2-sulfanylpyrimidin-4-ol (1.4 g, 10 mmol) were added. The new mixture was stirred at room temperature for 2 hours. DMF was removed under vacuum. The crude product was purified by column chromatography to provide 2-{[(2,4-dichloro-1-ethyl-1H-imidazol-5-yl)methyl]sulfanyl}-6-methylpyrimidin-4-ol (100 mg, 3% overall yield); $^1$H NMR (400 MHz, $CDCl_3$): δ 1.38 (t, 3H), 2.25 (s, 3H), 4.02 (q, 2H), 4.57 (s, 2H), 4.59 (m, 1H), 6.03 (br, 1H); M+ 319.

Example 118

2-{[(4-chloro-1-ethyl-1H-imidazol-5-yl)methyl]sulfanyl}-6-methylpyrimidin-4-ol

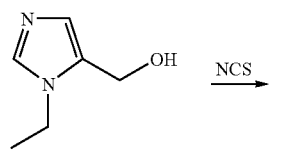

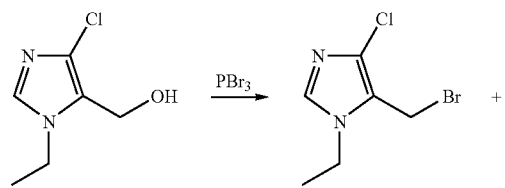

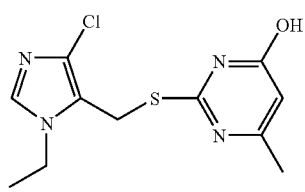

To the solution of (1-ethyl-1H-imidazol-5-yl)methanol (1.26 g, 10 mmol) in dioxane (50 mL) in a 250 mL round bottom flask, was added NCS (1.38 g, 10 mmol). The resulting mixture was stirred at room temperature overnight. Dioxane was removed under vacuum, and the crude solid was dissolved in chloroform (40 mL), followed by addition of PBr₃ (1.9 mL, 20 mmol). The resulting mixture was stirred at room temperature overnight. The solvent was then evaporated. The crude 5-(bromomethyl)-4-chloro-1-ethyl-1H-imidazole was dissolved in DMF (20 mL). Potassium carbonate (3 g) and 6-methyl-2-sulfanylpyrimidin-4-ol (1.4 g, 10 mmol) were added. The mixture was stirred at room temperature for 2 hours. DMF was removed under vacuum, and the residue was purified by column chromatography to provide 2-{[(4-chloro-1-ethyl-1H-imidazol-5-yl)methyl]sulfanyl}-6-methylpyrimidin-4-ol (100 mg, 3% overall yield); ¹H NMR (400 MHz, CD₃OD): δ 1.41 (t, 3H), 2.29 (s, 3H), 4.12 (q, 1H), 4.60 (s, 2H), 4.59 (m, 1H), 6.01 (br, 1H), 7.66 (s, 1H); M+ 285.

Example 119

2-{[(2-chloro-1-methyl-1H-imidazol-5-yl)methyl]sulfanyl}-6-methylpyrimidin-4-ol

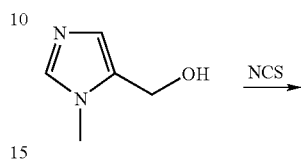

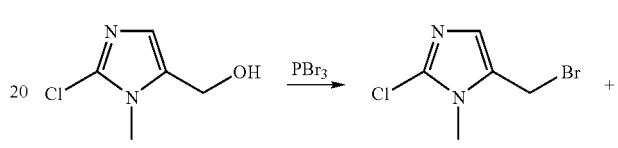

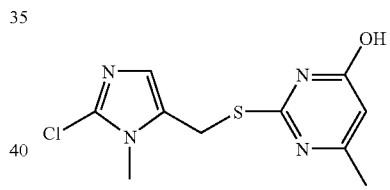

To the solution of (1-methyl-1H-imidazol-5-yl)methanol (570 mg, 5 mmol) in dioxane (50 mL) in a 250 mL round bottom flask, was added NCS (815 mg, 6 mmol). The resulting mixture was stirred at room temperature overnight. Dioxane was removed under vacuum. The crude (4-chloro-1-ethyl-1H-imidazol-5-yl)methanol was dissolved in chloroform (40 mL), followed by addition of PBr₃ (1.2 mL, 12.8 mmol). The resulting mixture was stirred at room temperature overnight. The solvent was evaporated to provide 5-(bromomethyl)-2-chloro-1-ethyl-1H-imidazole, which was then dissolved DMF (20 mL). Potassium carbonate (2 g) and 6-methyl-2-sulfanylpyrimidin-4-ol (700 mg, 5 mmol) were added. The mixture was stirred at room temperature for 2 hours. DMF was removed under vacuum. The crude was purified by column chromatography to provide 2-{[(2-chloro-1-methyl-1H-imidazol-5-yl)methyl]sulfanyl}-6-methylpyrimidin-4-ol (210 mg, 15% overall yield); ¹H NMR (400 MHz, CDCl₃): δ 2.30 (s, 3H), 3.59 (s, 3H), 4.45 (s, 2H), 6.08 (bs, 1H), 6.94 (s, 1H); M+ 271.

Example 120

2-{[(3,5-dichloropyridin-4-yl)methyl]sulfanyl}-6-(trifluoromethyl)pyrimidin-4-ol

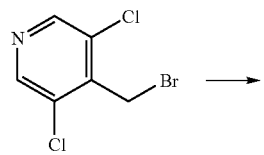

-continued

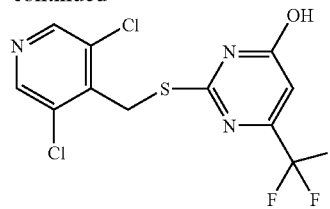

This example was synthesized from 2-sulfanyl-6-(trifluoromethyl)pyrimidin-4-ol and 4-(bromomethyl)-3,5-dichloropyridine by following general procedure as described in the last step of Example 22. The title compound was obtained as a white solid (660 mg, 37% yield); $^1$H NMR (400 MHz, DMSO-d$_6$): δ 4.72 (s, 2H), 6.69 (br, 1H), 8.64 (s, 2H); M+ 356.

Example 121

2-{[(4-chloro-1H-pyrazol-3-yl)methyl]sulfanyl}-6-methylpyrimidin-4-ol

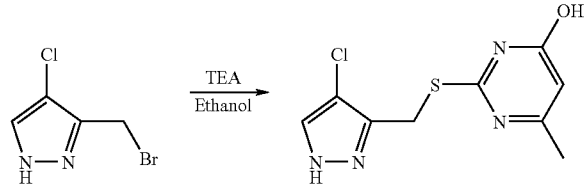 [SMILES: Clc1c[nH]nc1CBr ; Cc1cc(O)nc(SCc2n[nH]cc2Cl)n1]

This example was synthesized from 3-(bromomethyl)-4-chloro-1H-pyrazole and 6-methyl-2-sulfanylpyrimidin-4-ol following general procedure as described in the last step of Example 22. The title compound was obtained as a white solid (500 mg, 20% yield); $^1$H NMR (400 MHz, DMSO-d$_6$): δ 2.21 (s, 3H), 3.17 (s, 1H), 4.40 (s, 2H), 6.00 (bs, 1H), 7.93 (s, 1H); M+ 257.

Example 122

6-methyl-2-[({2-methylimidazo[1,2-a]pyridin-3-yl}methyl)sulfanyl]pyrimidin-4-ol

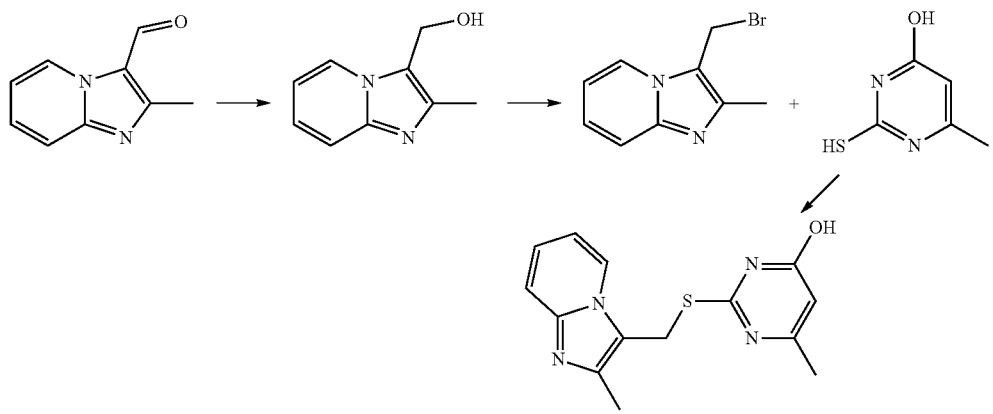

To a solution of sodium borohydride (531 mg, 14.0 mmol) in methanol (30 mL) was added a solution of 2-methylimidazo[1,2-a]pyridine-3-carbaldehyde (1.5 g, 9.4 mmol) in methanol (5 mL) at 0° C. The mixture was stirred for 2 hours at room temperature. The solvent was evaporated, water was added, and the mixture was extracted 3 times with ethyl acetate. The organic phase was washed with brine and dried over sodium sulfate. After evaporation of the solvent, {2-methylimidazo[1,2-a]pyridin-3-yl}methanol was obtained (914 mg, 59% yield) and used in the next step without further purification; $^1$H NMR (400 MHz, DMSO-d$_6$): δ 2.31 (s, 3H), 4.74 (d, J=5.4 Hz, 2H), 5.06 (t, J=5.4 Hz, 1H), 6.86 (dt, J=6.8 Hz, J=1.3 Hz, 1H), 7.16-7.21 (m, 1H), 7.42 (td, J=9.0 Hz, J=1.2 Hz, 1H), 8.28 (td, J=6.8 Hz, J=1.2 Hz, 1H).

To a solution of {2-methylimidazo[1,2-a]pyridin-3-yl}methanol (914 mg, 5.5 mmol) in anhydrous dichloromethane (25 mL) was added dropwise a solution of tribromophosphane (520 µL, 5.5 mmol) in anhydrous dichloromethane (10 mL) at 0° C. The mixture was stirred for 1.5 hours at room temperature. The mixture was evaporated, and crude 3-(bromomethyl)-2-methylimidazo[1,2-a]pyridine was used in the next step without further purification.

6-methyl-2-sulfanylpyrimidin-4-ol (522 mg, 3.7 mmol) was dissolved in anhydrous DMF (20 mL), then were added potassium carbonate (1.52 g, 11.0 mmol) and 3-(bromomethyl)-2-methylimidazo[1,2-a]pyridine (5.5 mmol) in DMF (10 mL). The mixture was stirred overnight at room temperature. The solid was removed by filtration washed with methanol, and the filtrate was evaporated. The residue was dissolved in DCM/MeOH and purified on silica gel using 4-12% DCM/MeOH to afford 6-methyl-2-[({2-methylimidazo[1,2-a]pyridin-3-yl}methyl)sulfanyl]pyrimidin-4-ol (165 mg, 16% yield); ¹H NMR (400 MHz, DMSO-d₆): δ 2.23 (s, 3H), 2.42 (s, 3H), 4.84 (s, 2H), 6.01 (s, 1H), 6.94 (dt, J=6.8 Hz, J=1.4 Hz, 1H), 7.21-7.26 (m, 1H), 7.47 (td, J=9.0 Hz, J=1.0 Hz, 1H), 8.43 (td, J=6.8 Hz, J=1.2 Hz, 1H); LRMS (ES⁺) m/z 287 (80%, M+1).

Example 123

2-[({2-chloroimidazo[1,2-a]pyridin-3-yl}methyl)sulfanyl]-6-methylpyrimidin-4-ol

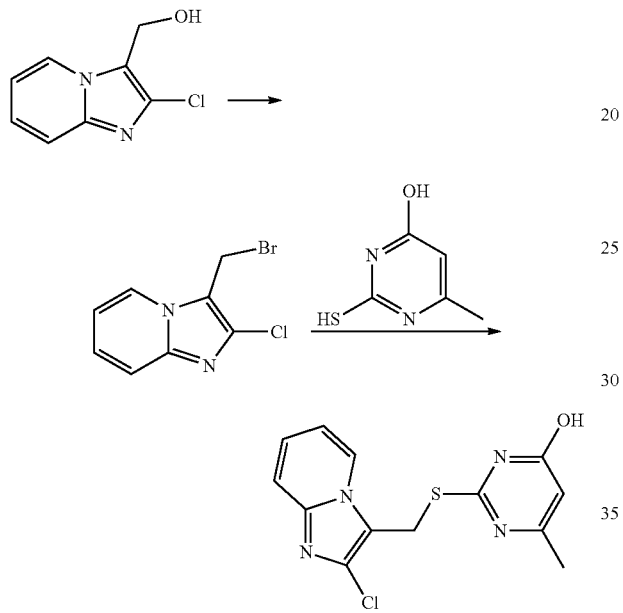

To a solution of {2-chloroimidazo[1,2-a]pyridin-3-yl}methanol (1.0 g, 5.5 mmol) in anhydrous dichloromethane (25 mL) was added dropwise a solution of tribromophosphane (520 μL, 5.5 mmol) in anhydrous dichloromethane (5 mL) at 0° C. The mixture was stirred for 3 hours at room temperature. The mixture was evaporated, and crude 3-(bromomethyl)-2-chloroimidazo[1,2-a]pyridine was used in the next step without further purification.

6-methyl-2-sulfanylpyrimidin-4-ol (600 mg, 4.2 mmol) was dissolved in anhydrous DMF (20 mL), and then potassium carbonate (1.75 g, 12.7 mmol) and 3-(bromomethyl)-2-chloroimidazo[1,2-a]pyridine (5.5 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 0-12% DCM/MeOH to afford the title compound (165 mg, 15% yield); ¹H NMR (400 MHz, DMSO-d₆): δ 2.22 (s, 3H), 4.85 (s, 2H), 6.03 (bs, 1H), 7.10 (t, J=6.7 Hz, 1H), 7.39 (t, J=7.0 Hz, 1H), 7.57 (d, J=9.0 Hz, 1H), 8.59 (d, J=6.8 Hz, 1H); LRMS (ES⁺) m/z 307 (85%, M+1).

Example 124

2-{[(1-ethyl-1H-pyrazol-5-yl)methyl]sulfanyl}-6-methylpyrimidin-4-ol hydrochloride

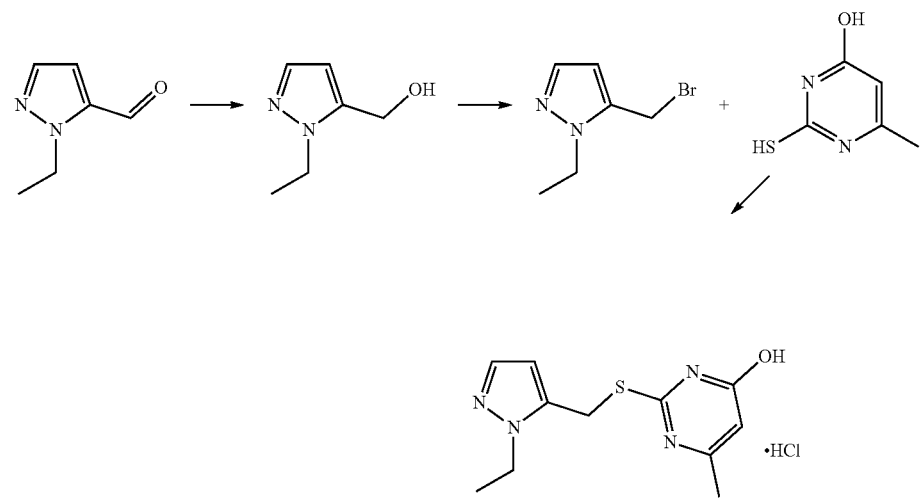

To a solution of sodium borohydride (686 mg, 18.1 mmol) in methanol (40 mL) was added a solution of 1-ethyl-1H-pyrazole-5-carbaldehyde (1.5 g, 12.1 mmol) in methanol (10 mL) at 0° C. The mixture was stirred for 2.5 hours at room temperature. The solvent was evaporated, water was added, and the mixture was extracted 3 times with ethyl acetate. The combined organic phases were washed with brine and dried over sodium sulfate. After evaporation of solvent, (1-ethyl-1H-pyrazol-5-yl)methanol was obtained as a colorless oil (1.07 g, 70% yield) and used in the next step without further purification; $^1$H NMR (400 MHz, DMSO-d$_6$): δ 1.31 (t, J=7.2 Hz, 3H), 4.10 (q, J=7.2 Hz, 2H), 4.49 (d, J=5.5 Hz, 2H), 5.25 (t, J=5.5 Hz, 1H), 6.12 (d, J=1.5 Hz, 1H), 7.31 (d, J=1.5 Hz, 1H).

To a solution of (1-ethyl-1H-pyrazol-5-yl)methanol (1.07 mg, 8.5 mmol) in anhydrous dichloromethane (35 mL) was dropwise added a solution of tribromophosphane (800 μL, 8.5 mmol) in anhydrous dichloromethane (5 mL) at 0° C. The mixture was stirred for 1.5 hours at room temperature. The mixture was evaporated, and crude 5-(bromomethyl)-1-ethyl-1H-pyrazole was used in the next step without further purification.

6-methyl-2-sulfanylpyrimidin-4-ol (927 mg, 6.5 mmol) was dissolved in anhydrous DMF (30 mL), then potassium carbonate (2.70 g, 19.6 mmol) and 5-(bromomethyl)-1-ethyl-1H-pyrazole (8.5 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 10% DCM/MeOH to afford 2-{[(1-ethyl-1H-pyrazol-5-yl)methyl]sulfanyl}-6-methylpyrimidin-4-ol (265 mg, 16% yield for 2 steps); $^1$H NMR (400 MHz, DMSO-d$_6$): δ 1.32 (t, J=7.0 Hz, 3H), 2.21 (s, 3H), 4.15 (q, J=7.2 Hz, 2H), 4.50 (s, 2H), 6.04 (bs, 1H), 6.22 (d, J=1.7 Hz, 1H), 7.33 (d, J=1.7 Hz, 1H).

2-{[(1-ethyl-1H-pyrazol-5-yl)methyl]sulfanyl}-6-methylpyrimidin-4-ol (150 mg, 600 μmol) was stirred in methanol (20 mL) and a solution of 4 N HCl in dioxane (225 μL, 900 μmol) was added dropwise at 0° C. The mixture was stirred for 30 minutes at room temperature. The solvent was removed by evaporation, and the residue was triturated with diethyl ether and dried in vacuo to afford 2-{[(1-ethyl-1H-pyrazol-5-yl)methyl]sulfanyl}-6-methylpyrimidin-4-ol hydrochloride (170 mg, 100% yield); $^1$H NMR (400 MHz, DMSO-d$_6$): δ 1.30 (t, J=7.0 Hz, 3H), 2.21 (s, 3H), 4.15 (q, J=7.0 Hz, 2H), 4.50 (s, 2H), 6.11 (s, 1H), 6.25 (d, J=1.7 Hz, 1H), 7.37 (d, J=1.7 Hz, 1H); LRMS (ES$^+$) m/z 251 (50%, M+1).

Example 125

2-{[(1-cyclohexyl-1H-imidazol-5-yl)methyl]sulfanyl}-6-methylpyrimidin-4-ol hydrochloride

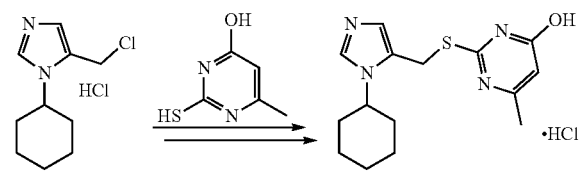

6-methyl-2-sulfanylpyrimidin-4-ol (1.1 g, 7.7 mmol) was dissolved in anhydrous DMF (40 mL), then potassium carbonate (3.19 g, 23.1 mmol) and 5-(chloromethyl)-1-cyclohexyl-1H-imidazole hydrochloride (8.5 mmol) in DMF (10 mL) were added. The mixture was stirred for 3.5 hours at room temperature. The solid was removed by filtration and washed with methanol, and the filtrate was evaporated. The residue was dissolved in DCM/MeOH and purified on silica gel using 12% DCM/MeOH to afford 2-{[(1-cyclohexyl-1H-imidazol-5-yl)methyl]sulfanyl)-6-methylpyrimidin-4-ol (770 mg, 44% yield); $^1$H NMR (500 MHz, DMSO-d$_6$): δ 1.17-1.30 (m, 2H), 1.62-1.67 (m, 4H), 1.77-1.81 (m, 2H), 1.92-1.95 (m, 2H), 2.23 (s, 3H). 3.92-3.96 (m, 1H), 4.51 (s, 2H), 6.03 (s, 1H), 6.85 (s, 1H), 7.75 (s, 1H).

2-{[(1-cyclohexyl-1H-imidazol-5-yl)methyl]sulfanyl)-6-methylpyrimidin-4-ol (300 mg, 986 μmol) was stirred in methanol (30 mL), and a solution of 4 N HCl in dioxane (370 μL, 1.5 mmol) was added dropwise at 0° C. The mixture was stirred for 30 minutes at room temperature. The solvent was removed by evaporation, and the residue was triturated with diethyl ether and dried in vacuo to afford 2-{[(1-cyclohexyl-1H-imidazol-5-yl)methyl]sulfanyl)-6-methylpyrimidin-4-ol hydrochloride (330 mg, 98% yield); $^1$H NMR (500 MHz, DMSO-d$_6$): δ 1.15-2.05 (m, 10H), 2.22 (s, 3H). 4.28-4.36 (m, 1H), 4.58 (s, 2H), 6.14 (s, 1H), 7.64 (s, 1H), 9.32 (s, 1H); LRMS (ES$^+$) m/z 305 (100%, M+1).

Example 126

2-{[(5-chloro-1H-pyrazol-1-yl)methyl]sulfanyl}-6-methylpyrimidin-4-ol

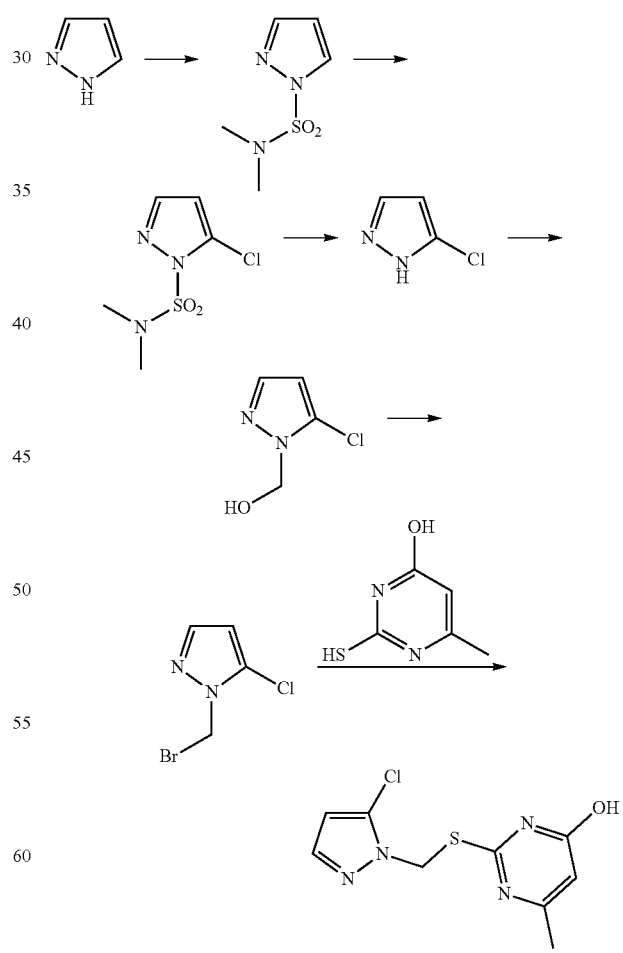

To a solution of sodium hydride (5.2 g, 130 mmol, 60% in mineral oil) in anhydrous THF (50 mL) was added a solution of 1H-pyrazole (5.92 g, 87 mmol) in anhydrous THF (100 mL) at 0° C. The mixture was stirred for 30 minutes at room temperature. Dimethylsulfamoyl chloride (13.9 mL, 130 mmol) was added at 0° C., and then the mixture was stirred for 1.5 hours at room temperature. Water was added, and the mixture was extracted 3 times with ethyl acetate. The organic phase was washed with brine and dried over sodium sulfate. After evaporation of the solvent, the oil was passed through a short silica gel column using 20% hexane/ethyl acetate as a solvent. N,N-dimethyl-1H-pyrazole-1-sulfonamide was obtained as a yellow oil and used in the next step without further purification.

N,N-dimethyl-1H-pyrazole-1-sulfonamide (8.89 g, 50.8 mmol) was dissolved in anhydrous THF (250 mL). The solution was cooled at −78° C., a solution of n-butyl lithium (32.6 mL, 81.4 mmol, 2.5 M in hexane) was added dropwise, and then the mixture was stirred for 45 minutes. A solution of hexachloroethane (18.0 g, 76.3 mmol) in anhydrous THF (20 mL) was added dropwise at −78° C., and the reaction stirred for 1.5 hours. Water was added, and the mixture was extracted 5 times with dichloromethane. The combined organic phases were washed with brine and then dried over magnesium sulfate. After evaporation of the solvent, 5-chloro-N,N-dimethyl-1H-pyrazole-1-sulfonamide was obtained and used in the next step without further purification.

5-chloro-N,N-dimethyl-1H-pyrazole-1-sulfonamide (8.9 g, 50.8 mmol) was dissolved in anhydrous dichloromethane (40 mL), TFA (80 mL, 1016 mmol) was added at 0° C., and the mixture was stirred at room temperature for 2 days. The mixture was partially evaporated, hexane was added, and the solid was filtered and then rinsed with hexane. The filtrate was evaporated, and the crude 5-chloro-1H-pyrazole was used in the next step without further purification.

5-chloro-1H-pyrazole (50.8 mmol) was dissolved in ethanol (55 mL). A solution of formalin (15.2 g, 508 mmol, 37%) was added at room temperature, and the mixture was heated at 45° C. overnight. The reaction mixture was evaporated and dried under vacuum, and the residue was triturated in methanol. The solid was filtered and rinsed with methanol. The filtrate was evaporated, and crude (5-chloro-1H-pyrazol-1-yl)methanol was obtained and used in the next step without further purification.

To a solution of (5-chloro-1H-pyrazol-1-yl)methanol (50.8 mmol) in anhydrous dichloromethane (130 mL) was added dropwise a solution of tribromophosphane (4.8 mL, 50.8 mmol) in anhydrous dichloromethane (20 mL) at 0° C. The mixture was stirred for 2.5 hours at room temperature. The mixture was evaporated, and crude 1-(bromomethyl)-5-chloro-1H-pyrazole was used in the next step without further purification.

6-methyl-2-sulfanylpyrimidin-4-ol (4.8 g, 33.9 mmol) was dissolved in anhydrous DMF (180 mL), then potassium carbonate (14.0 g, 102 mmol) and 1-(bromomethyl)-5-chloro-1H-pyrazole (8.5 mmol) in DMF (20 mL) were added. The mixture was stirred overnight at room temperature. The solid was removed by filtration and washed with methanol, and the filtrate was evaporated. The residue was dissolved in DCM/MeOH and purified on silica gel using 3-10% DCM/MeOH to afford 2-{[(5-chloro-1H-pyrazol-1-yl)methyl]suflanyl}-6-methylpyrimidin-4-ol (88 mg, 1.0% yield for 6 steps); $^1$H NMR (400 MHz, DMSO-$d_6$): δ 2.24 (s, 3H), 5.85 (s, 2H), 6.10 (bs, 1H), 6.30 (d, J=2.3 Hz, 1H), 7.93 (s, 1H); LRMS (ES$^+$) m/z 257 (45%, M+1), 259 (15%, M+3).

Example 127

2-({[4-chloro-2-(propan-2-yl)pyridin-3-yl]methyl}sulfanyl)-6-methylpyrimidin-4-ol hydrochloride

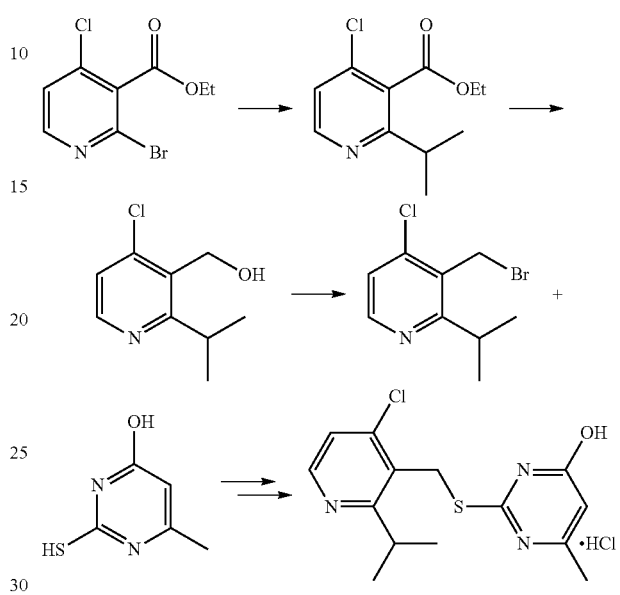

Ethyl 2-bromo-4-chloropyridine-3-carboxylate (1 g, 3.78 mmol) was dissolved in anhydrous dioxane (30 mL). A solution of diisopropyl zinc (4.5 mL, 4.54 mmol, 1.0 M in toluene) was added dropwise, followed with (1,1'-bis(diphenylphosphino)ferrocene)dichloropalladium (44 mg, 60 µmol). The mixture was heated at 40° C. overnight, and water followed with 1 N HCl was added. The reaction mixture was extracted 3 times with ethyl acetate, and the combined organic phases were washed with brine and dried over sodium sulfate. After evaporation, the residue was dissolved in DCM and purified on silica gel using 0-15% hexane/ethyl acetate to afford ethyl 4-chloro-2-(propan-2-yl)pyridine-3-carboxylate (428 mg, 50% yield).

Lithium aluminum hydride (226 mg, 5.96 mmol) was stirred in anhydrous THF (30 mL). A solution of 4-chloro-2-(propan-2-yl)pyridine-3-carboxylate (904 mg, 3.97 mmol) in anhydrous THF (5 mL) was added at 0° C., and the reaction mixture was stirred at room temperature for 3 hours. The reaction was quenched with an aqueous solution of sodium hydroxide and extracted 5 times with ethyl acetate. The combined organic phase was washed with brine and dried over sodium sulfate. After evaporation of the solvent, [4-chloro-2-(propan-2-yl)pyridin-3-yl]methanol was obtained as an oil (735 mg, 100% yield) and used in the next step without further purification.

To a solution of [4-chloro-2-(propan-2-yl)pyridin-3-yl]methanol (735 mg, 3.97 mmol) in anhydrous dichloromethane (20 mL) was added dropwise a solution of tribromophosphane (375 µL, 3.97 mmol) in anhydrous dichloromethane (10 mL) at 0° C. The mixture was stirred for 1.5 hours at room temperature. The mixture was then evaporated and the crude 3-(bromomethyl)-4-chloro-2-(propan-2-yl)pyridine was used in the next step without further purification.

6-methyl-2-sulfanylpyrimidin-4-ol (434 mg, 3.0 mmol) was dissolved in anhydrous DMF (15 mL), and then potassium carbonate (1.27 g, 9.2 mmol) and 3-(bromomethyl)-4-chloro-2-(propan-2-yl)pyridine (4.0 mmol) in DMF (5 mL) were added. The mixture was stirred overnight at room temperature. The solid was removed by filtration and washed with methanol, and the filtrate was evaporated. The residue was dissolved in DCM/MeOH and purified on silica gel using 5-10% DCM/MeOH to afford 2-({[4-chloro-2-(propan-2-yl)pyridin-3-yl]methyl}sulfanyl)-6-methylpyrimidin-4-ol (239 mg, 25% yield for 2 steps); $^1$H NMR (400 MHz, DMSO-$d_6$): δ 1.20 (d, J=6.7 Hz, 6H), 2.23 (bs, 3H), 3.50-3.57 (m, 1H), 4.65 (s, 2H), 6.00 (bs, 1H), 7.43 (d, J=5.2 Hz, 1H), 8.45 (d, J=5.2 Hz, 1H).

2-({[4-chloro-2-(propan-2-yl)pyridin-3-yl]methyl}sulfanyl)-6-methylpyrimidin-4-ol (176 mg, 570 μmol) was stirred in methanol (20 mL), and a solution of 4 N HCl in dioxane (215 μL, 855 μmol) was added dropwise at 0° C. The mixture was stirred for 30 minutes at room temperature. The solvent was removed by evaporation, and the residue was triturated with diethyl ether and dried in vacuo to afford 2-({[4-chloro-2-(propan-2-yl)pyridin-3-yl]methyl}sulfanyl)-6-methylpyrimidin-4-ol hydrochloride (200 mg, 100% yield); $^1$H NMR (400 MHz, DMSO-$d_6$): δ 1.28 (d, J=6.7 Hz, 6H), 2.26 (s, 3H), 3.56-3.68 (m, 1H), 4.70 (s, 2H), 6.14 (s, 1H), 7.69 (d, J=5.5 Hz, 1H), 8.55 (d, J=5.5 Hz, 1H); LRMS (ES$^+$) m/z 310 (15%, M+1).

Example 128

2-{[(4-chloro-1-methyl-1H-pyrazol-3-yl)methyl]sulfanyl}-6-(trifluoromethyl)pyrimidin-4-ol hydrochloride

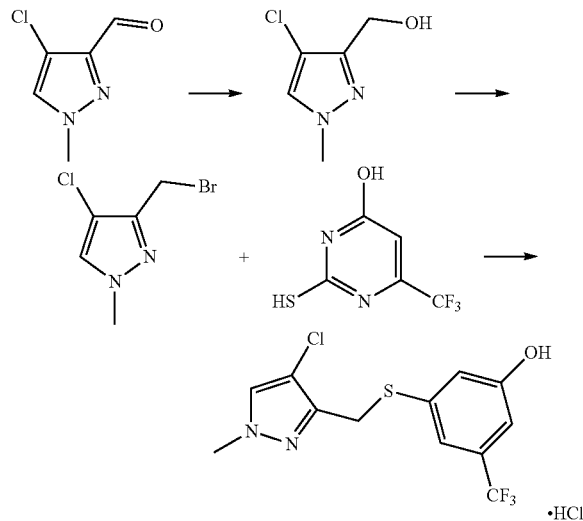

To a solution of sodium borohydride (393 mg, 10.4 mmol) in methanol (25 mL) was added a solution of 4-chloro-1-methyl-1H-pyrazole-3-carbaldehyde (1.0 g, 6.9 mmol) in methanol (10 mL) at 0° C. The mixture was stirred for 4 hours at room temperature. The solvent was evaporated, water was added, and the mixture was extracted 3 times with ethyl acetate. The combined organic phases were washed with brine and dried over sodium sulfate. After evaporation of the solvent, (4-chloro-1-methyl-1H-pyrazol-3-yl)methanol was obtained as a yellow oil (680 mg, 67% yield) and used in the next step without further purification; $^1$H NMR (400 MHz, DMSO-$d_6$): δ 3.77 (s, 3H), 4.34 (d, J=5.6 Hz, 2H), 5.03 (s, J=5.6 Hz, 1H), 7.85 (s, 1H).

To a solution of (4-chloro-1-methyl-1H-pyrazol-3-yl)methanol (680 mg, 4.7 mmol) in anhydrous dichloromethane (25 mL) was added dropwise a solution of tribromophosphane (450 μL, 4.7 mmol) in anhydrous dichloromethane (5 mL) at 0° C. The mixture was stirred for 1 hour at room temperature and then was evaporated to yield 3-(bromomethyl)-4-chloro-1-methyl-1H-pyrazole, which was used in the next step without further purification.

2-sulfanyl-6-(trifluoromethyl)pyrimidin-4-ol (721 mg, 3.7 mmol) was dissolved in anhydrous DMF (20 mL), and then potassium carbonate (1.53 g, 11.0 mmol) and 3-(bromomethyl)-4-chloro-1-methyl-1H-pyrazole (4.7 mmol) were added. The mixture was stirred overnight at room temperature. The solid was removed by filtration and washed with methanol, and the filtrate was evaporated. The residue was dissolved in DCM/MeOH and purified on silica gel using 4-10% DCM/MeOH to afford 2-{[(4-chloro-1-methyl-1H-pyrazol-3-yl)methyl]sulfanyl}-6-(trifluoromethyl)pyrimidin-4-ol (135 mg, 11% yield for 2 steps); $^1$H NMR (400 MHz, DMSO-$d_6$): δ 3.78 (s, 3H), 4.39 (s, 2H), 6.66 (s, 1H), 7.93 (s, 1H).

2-{[(4-chloro-1-methyl-1H-pyrazol-3-yl)methyl]sulfanyl}-6-(trifluoromethyl)pyrimidin-4-ol (120 mg, 370 μmol) was stirred in methanol (15 mL) and a solution of 4 N HCl in dioxane (140 μL, 554 μmol) was added dropwise at 0° C. The mixture was stirred for 30 minutes at room temperature. The solvent was removed by evaporation, and the residue was triturated with diethyl ether and dried in vacuo to afford 2-{[(4-chloro-1-methyl-1H-pyrazol-3-yl)methyl]sulfanyl}-6-(trifluoromethyl)pyrimidin-4-ol hydrochloride (85 mg, 63% yield); $^1$H NMR (400 MHz, DMSO-$d_6$): δ 3.78 (s, 3H), 4.39 (s, 2H), 6.66 (s, 1H), 7.94 (s, 1H); LRMS (ES$^+$) m/z 325 (10%, M+1).

Example 129

2-{[(4-chloro-2-ethylpyridin-3-yl)methyl]sulfanyl}-6-methylpyrimidin-4-ol hydrochloride

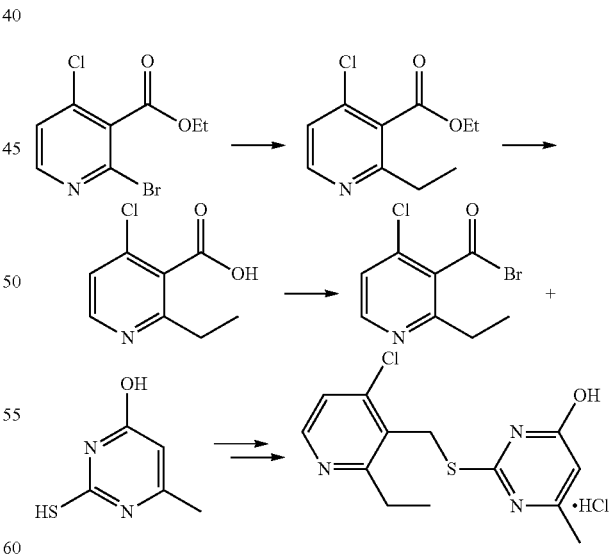

Ethyl 2-bromo-4-chloropyridine-3-carboxylate (1.5 g, 5.7 mmol) was dissolved in anhydrous dioxane (45 mL). A solution of diethyl zinc (4.6 mL, 5.1 mmol, 1.1 M in toluene) was added dropwise, and then was added (1,1'-bis(diphenylphosphino)ferrocene)dichloropalladium (62 mg, 85 μmol). The mixture was heated at 40° C. overnight, and then water plus 1

N HCl were added. The reaction mixture was extracted 3 times with ethyl acetate. The combined organic phase was washed with brine and dried over sodium sulfate. After evaporation, the residue was dissolved in DCM and purified on silica gel using 0-15% hexane/ethyl acetate to afford ethyl 4-chloro-2-ethylpyridine-3-carboxylate (687 mg, 57% yield).

Lithium aluminum hydride (234 mg, 6.2 mmol) was stirred in anhydrous THF (30 mL). A solution of ethyl 4-chloro-2-ethylpyridine-3-carboxylate (878 mg, 4.1 mmol) in anhydrous THF (5 mL) was added at 0° C., and the reaction mixture was stirred at room temperature for 1.5 hours. The reaction was quenched with an aqueous solution of sodium hydroxide and extracted 5 times with ethyl acetate. The combined organic phase was washed with brine and dried over sodium sulfate. After evaporation of the solvent, (4-chloro-2-ethylpyridin-3-yl)methanol was obtained as an oil (601 mg, 85% yield) and used in the next step without further purification.

To a solution of (4-chloro-2-ethylpyridin-3-yl)methanol (601 mg, 3.5 mmol) in anhydrous dichloromethane (20 mL) was added dropwise a solution of tribromophosphane (330 µL, 3.5 mmol) in anhydrous dichloromethane (10 mL) at 0° C. The mixture was stirred for 2.5 hours at room temperature. The mixture was evaporated, and crude 3-(bromomethyl)-4-chloro-2-ethylpyridine was used in the next step without further purification.

6-methyl-2-sulfanylpyrimidin-4-ol (382 mg, 2.7 mmol) was dissolved in anhydrous DMF (15 mL), and then potassium carbonate (1.12 g, 8.1 mmol) and 3-(bromomethyl)-4-chloro-2-ethylpyridine (3.5 mmol) in DMF (10 mL) were added. The mixture was stirred for 2.5 hours at room temperature. The solid was removed by filtration and washed with methanol, and the filtrate was evaporated. The residue was dissolved in DCM/MeOH and purified on silica gel using 5-10% DCM/MeOH to afford 2-{[(4-chloro-2-ethylpyridin-3-yl)methyl]sulfanyl}-6-methylpyrimidin-4-ol (100 mg, 13% yield for 2 steps); $^1$H NMR (400 MHz, DMSO-d$_6$): δ 1.22 (t, J=7.4 Hz, 3H), 2.24 (s, 3H), 2.97 (q, J=7.4 Hz, 2H), 4.62 (s, 2H), 6.07 (bs, 1H), 7.44 (d, J=5.3 Hz, 1H), 8.40 (d, J=5.3 Hz, 1H).

2-{[(4-chloro-2-ethylpyridin-3-yl)methyl]sulfanyl}-6-methylpyrimidin-4-ol (260 mg, 879 µmol) was stirred in methanol (30 mL) and a solution of 4 N HCl in dioxane (330 µL, 1.32 mmol) was added dropwise at 0° C. The mixture was stirred for 30 minutes at room temperature. The solvent was removed by evaporation, and the residue was triturated with diethyl ether and dried in vacuo to afford 2-{[(4-chloro-2-ethylpyridin-3-yl)methyl]sulfanyl}-6-methylpyrimidin-4-ol hydrochloride (292 mg, 100% yield); $^1$H NMR (400 MHz, DMSO-d$_6$) δ 1.27 (t, J=7.4 Hz, 3H), 2.25 (s, 3H), 3.15-3.21 (m, 2H), 4.69 (s, 2H), 6.12 (s, 1H), 7.87 (d, J=5.9 Hz, 1H), 8.61 (d, J=5.9 Hz, 1H); LRMS (ES$^+$) m/z 296 (20%, M+1).

Example 130

2-{[(2,4-diethylpyridin-3-yl)methyl]sulfanyl-6-methylpyrimidin-4-ol hydrochloride

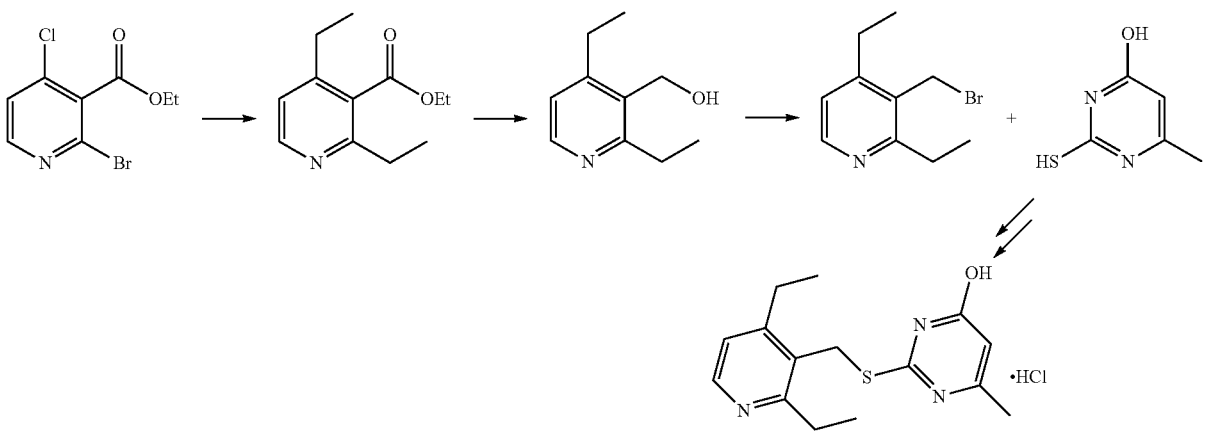

Ethyl 2-bromo-4-chloropyridine-3-carboxylate (2.0 g, 7.6 mmol) was dissolved in anhydrous dioxane (55 mL). A solution of diethyl zinc (6.9 mL, 7.6 mmol, 1.1 M in toluene) was added dropwise, and then was added (1,1'-bis(diphenylphosphino)ferrocene)dichloropalladium (83 mg, 113 µmol). The mixture was heated at 70° C. for 6 hours, and water followed by 1 N HCl was added. The mixture was extracted 3 times with ethyl acetate, and the combined organic phases were washed with brine and dried over sodium sulfate. After evaporation, the residue was dissolved in DCM and purified on silica gel using 0-20% hexane/ethyl acetate to afford ethyl 2,4-diethylpyridine-3-carboxylate (720 mg, 46% yield).

Lithium aluminum hydride (410 mg, 10.8 mmol) was stirred in anhydrous THF (45 mL). A solution of ethyl 2,4-diethylpyridine-3-carboxylate (1.50 g, 7.2 mmol) in anhydrous THF (10 mL) was added at 0° C., and then stirred at room temperature for 2 hours. The reaction was quenched with an aqueous solution of sodium hydroxide and extracted 5 times with ethyl acetate. The combined organic phase was washed with brine and dried over sodium sulfate. After evaporation of the solvent, (2,4-diethylpyridin-3-yl)methanol was obtained as an oil (1.17 g, 98% yield) and used in the next step without further purification.

To a solution of (2,4-diethylpyridin-3-yl)methanol (1.17 g, 7.1 mmol) in anhydrous dichloromethane (35 mL) was added dropwise a solution of tribromophosphane (670 µL, 7.1 mmol) in anhydrous dichloromethane (10 mL) at 0° C. The mixture was stirred for 1 hour at room temperature. The mixture was evaporated, and crude 3-(bromomethyl)-2,4-diethylpyridine was used in the next step without further purification.

6-methyl-2-sulfanylpyrimidin-4-ol (839 mg, 5.9 mmol) was dissolved in anhydrous DMF (30 mL), and then potassium carbonate (2.45 g, 17.7 mmol) and 3-(bromomethyl)-2,4-diethylpyridine (7.1 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 3-10% DCM/MeOH to afford 2-{[(2,4-diethylpyridin-3-yl)methyl]sulfanyl-6-methylpyrimidin-4-ol (966 mg, 56% yield for 2 steps); $^1$H NMR (400 MHz, DMSO-$d_6$): δ 1.14-1.22 (m, 6H), 2.22 (s, 3H), 2.68 (q, J=7.5 Hz, 2H), 2.82 (q, J=7.5 Hz, 2H), 4.48 (s, 2H), 6.05 (bs, 1H), 7.08 (d, J=5.1 Hz, 1H), 8.32 (d, J=5.1 Hz, 1H).

2-{[(2,4-diethylpyridin-3-yl)methyl]sulfanyl-6-methylpyrimidin-4-ol (430 mg, 1.5 mmol) was stirred in methanol (65 mL) and a solution of 4 N HCl in dioxane (560 μL, 2.22 mmol) was added dropwise at 0° C. The mixture was stirred for 15 minutes at room temperature. The solvent was removed by evaporation, and the residue was triturated with diethyl ether and dried in vacuo to afford 2-{[(2,4-diethylpyridin-3-yl)methyl]sulfanyl-6-methylpyrimidin-4-ol hydrochloride (466 mg, 96% yield); $^1$H NMR (400 MHz, DMSO-$d_6$): δ 1.25-1.35 (m, 6H), 2.24 (s, 3H), 2.97 (q, J=7.6 Hz, 2H), 3.18 (q, J=7.6 Hz, 2H), 4.67 (s, 2H), 6.14 (s, 1H), 7.82 (d, J=6.1 Hz, 1H), 8.67 (d, J=6.1 Hz, 1H); LRMS (ES$^+$) m/z 290 (35%, M+1).

Example 131

2-{[(4-chloro-2-ethylpyridin-3-yl)methyl]sulfanyl}-6-(trifluoromethyl)pyrimidin-4-ol hydrochloride

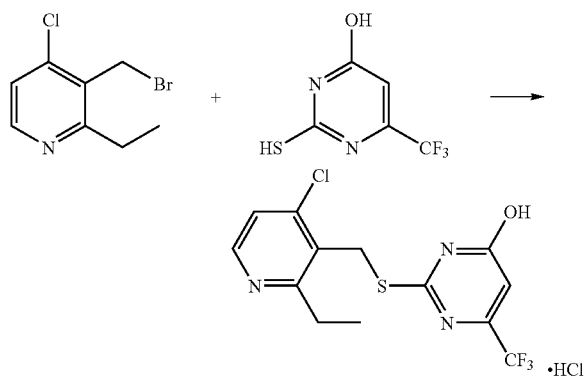

2-sulfanyl-6-(trifluoromethyl)pyrimidin-4-ol (884 mg, 4.5 mmol) was dissolved in anhydrous DMF (30 mL), and then potassium carbonate (1.87 g, 13.5 mmol) and 3-(bromomethyl)-4-chloro-2-ethylpyridine (5.4 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 3-10% DCM/MeOH to afford 2-{[(4-chloro-2-ethylpyridin-3-yl)methyl]sulfanyl}-6-(trifluoromethyl)pyrimidin-4-ol (391 mg, 25% yield for 2 steps); $^1$H NMR (400 MHz, DMSO-$d_6$): δ 1.19 (t, J=7.4 Hz, 3H), 2.93 (q, J=7.4 Hz, 2H), 4.66 (s, 2H), 6.69 (s, 1H), 7.43 (d, J=5.3 Hz, 1H), 8.40 (d, J=5.3 Hz, 1H).

2-{[(4-chloro-2-ethylpyridin-3-yl)methyl]sulfanyl}-6-(trifluoromethyl)pyrimidin-4-ol (165 mg, 472 μmol) was stirred in methanol (20 mL) and a solution of 4 N HCl in dioxane (180 μL, 708 μmol) was added dropwise at 0° C. The mixture was stirred for 30 minutes at room temperature. The solvent was removed by evaporation, and the residue was triturated with diethyl ether and dried in vacuo to afford 2-{[(4-chloro-2-ethylpyridin-3-yl)methyl]sulfanyl}-6-(trifluoromethyl)pyrimidin-4-ol hydrochloride (160 mg, 88% yield); $^1$H NMR (400 MHz, DMSO-$d_6$): δ 1.21 (t, J=7.4 Hz, 3H), 3.05 (q, J=7.4 Hz, 2H), 4.69 (s, 2H), 6.71 (s, 1H), 7.71 (d, J=5.7 Hz, 1H), 8.53 (d, J=5.7 Hz, 1H); LRMS (ES$^+$) m/z 350 (100%, M+1).

Example 132

2-{[(2-ethylpyridin-3-yl)methyl]sulfanyl)-6-(trifluoromethyl)pyrimidin-4-ol hydrochloride

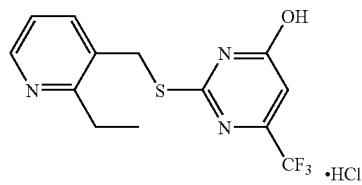

2-{[(2-ethylpyridin-3-yl)methyl]sulfanyl)-6-(trifluoromethyl)pyrimidin-4-ol (245 mg) was isolated during the purification of 2-{[(4-chloro-2-ethylpyridin-3-yl)methyl]sulfanyl}-6-(trifluoromethyl)pyrimidin-4-ol in Example 131; $^1$H NMR (400 MHz, DMSO-$d_6$): δ 1.21 (t, J=7.4 Hz, 3H), 2.83 (q, J=7.4 Hz, 2H), 4.44 (s, 2H), 6.62 (s, 1H), 7.14 (q, J=4.8 Hz, J=2.9 Hz, 1H), 7.76 (q, J=5.9 Hz, J=1.8 Hz, 1H), 8.39 (q, J=2.9 Hz, J=1.8 Hz 1H); LRMS (ES$^+$) m/z 316 (100%, M+1).

2-{[(2-ethylpyridin-3-yl)methyl]sulfanyl)-6-(trifluoromethyl)pyrimidin-4-ol (218 mg, 694 μmol) was stirred in methanol (30 mL), and a solution of 4 N HCl in dioxane (260 μL, 1.04 mmol) was dropwise added at 0° C. The mixture was stirred for 30 minutes at room temperature. The solvent was removed by evaporation, and the residue was triturated with diethyl ether and dried in vacuo to afford 2-{[(2-ethylpyridin-3-yl)methyl]sulfanyl)-6-(trifluoromethyl)pyrimidin-4-ol hydrochloride (225 mg, 92% yield); $^1$H NMR (400 MHz, DMSO-$d_6$): δ 1.28 (t, J=7.6 Hz, 3H), 3.11-3.17 (m, 2H), 4.58 (s, 2H), 6.65 (s, 1H), 7.77 (q, J=5.9 Hz, J=1.8 Hz, 1H), 8.49 (d, J=7.8 Hz, 1H), 8.39 (d, J=5.5 Hz 1H).

Example 133

2-{[(2,4-diethylpyridin-3-yl)methyl]sulfanyl}-6-(trifluoromethyl)pyrimidin-4-ol hydrochloride

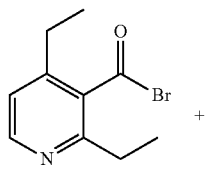

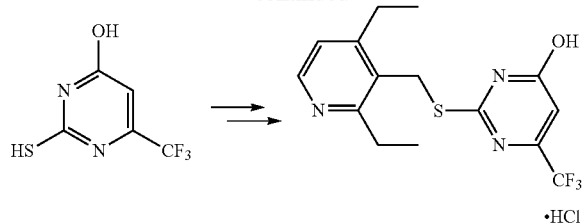

2-sulfanyl-6-(trifluoromethyl)pyrimidin-4-ol (592 mg, 3.0 mmol) was dissolved in anhydrous DMF (25 mL), and then potassium carbonate (1.25 g, 9.0 mmol) and 3-(bromomethyl)-2,4-diethylpyridine (3.6 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 3-12% DCM/MeOH to afford 2-{[(2,4-diethylpyridin-3-yl)methyl]sulfanyl}-6-(trifluoromethyl)pyrimidin-4-ol (860 mg, 69% yield for 2 steps); $^1$H NMR (400 MHz, DMSO-$d_6$): δ 1.13-1.20 (m, 6H), 2.67 (q, J=7.5 Hz, 2H), 2.81 (q, J=7.5 Hz, 2H), 4.54 (s, 2H), 6.67 (s, 1H), 7.10 (d, J=5.1 Hz, 1H), 8.34 (d, J=5.1 Hz, 1H).

2-{[(2,4-diethylpyridin-3-yl)methyl]sulfanyl}-6-(trifluoromethyl)pyrimidin-4-ol (500 mg, 1.5 mmol) was stirred in methanol (60 mL), and a solution of 4 N HCl in dioxane (550 μL, 2.2 mmol) was added dropwise at 0° C. The mixture was stirred for 10 minutes at room temperature. The solvent was removed by evaporation, and the residue was triturated with diethyl ether and dried in vacuo to afford 2-{[(2,4-diethylpyridin-3-yl)methyl]sulfanyl}-6-(trifluoromethyl)pyrimidin-4-ol hydrochloride (530 mg, 95% yield); $^1$H NMR (400 MHz, DMSO-$d_6$): δ 1.21-1.29 (m, 6H), 2.93 (q, J=7.5 Hz, 2H), 3.11-3.17 (m, 2H), 4.69 (s, 2H), 6.74 (s, 1H), 7.79 (d, J=6.1 Hz, 1H), 8.65 (d, J=6.1 Hz, 1H); LRMS (ES$^+$) m/z 344 (100%, M+1).

Example 134

2-{[(4-ethyl-1-methyl-1H-pyrazol-3-yl)methyl]sulfanyl}-6-methylpyrimidin-4-ol hydrochloride

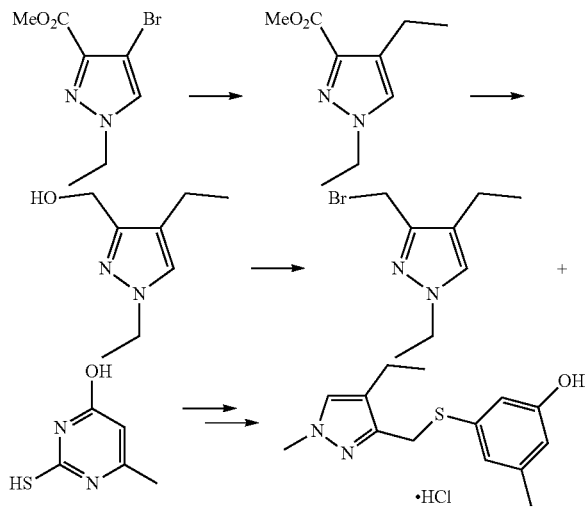

Methyl 4-bromo-1-ethyl-1H-pyrazole-3-carboxylate (2.5 g, 11.4 mmol) was dissolved in anhydrous dioxane (90 mL). A solution of diethyl zinc (10.4 mL, 11.4 mmol, 1.1 M in toluene) was added dropwise, and then was added (1,1'-bis(diphenylphosphino)ferrocene)dichloropalladium (125 mg, 171 μmol). The mixture was heated at 75° C. overnight, and water plus 1 N HCl were added. The mixture was extracted 3 times with ethyl acetate, and the combined organic phases were washed with brine and dried over sodium sulfate. After evaporation, the residue was dissolved in DCM and purified on silica gel using 0-30% hexane/ethyl acetate to afford methyl 1,4-diethyl-1H-pyrazole-3-carboxylate (912 mg, 48% yield).

Lithium aluminum hydride (433 mg, 11.4 mmol) was stirred in anhydrous THF (50 mL). A solution of methyl 1,4-diethyl-1H-pyrazole-3-carboxylate (1.28 g, 7.6 mmol) in anhydrous THF (10 mL) was added at 0° C., and then stirred at room temperature for 1.5 hours. The reaction was quenched with an aqueous solution of sodium hydroxide and extracted 5 times with ethyl acetate. The combined organic phase was washed with brine and dried over sodium sulfate. After evaporation of the solvent, (1,4-diethyl-1H-pyrazol-3-yl)methanol was obtained (710 mg, 65% yield) and used in the next step without further purification.

To a solution of (1,4-diethyl-1H-pyrazol-3-yl)methanol (710 mg, 5.1 mmol) in anhydrous dichloromethane (30 mL) was dropwise added a solution of tribromophosphane (480 μL, 5.1 mmol) in anhydrous dichloromethane (5 mL) at 0° C. The mixture was stirred for 1 hour at room temperature. The mixture was evaporated, and crude 3-(bromomethyl)-1,4-diethyl-1H-pyrazole was used in the next step without further purification.

6-methyl-2-sulfanylpyrimidin-4-ol (604 mg, 4.2 mmol) was dissolved in anhydrous DMF (30 mL), and then potassium carbonate (1.76 g, 12.8 mmol) and 3-(bromomethyl)-1,4-diethyl-1H-pyrazole (5.1 mmol) were added. The mixture was stirred overnight at room temperature. The solid was removed by filtration and washed with methanol, and the filtrate was evaporated. The residue was dissolved in DCM/MeOH and purified on silica gel using 4-12% DCM/MeOH to afford 2-{[(4-ethyl-1-methyl-1H-pyrazol-3-yl)methyl]sulfanyl}-6-methylpyrimidin-4-ol (454 mg, 41% yield for 2 steps); $^1$H NMR (400 MHz, DMSO-$d_6$): δ 1.07 (t, J=7.4 Hz, 3H), 2.17 (s, 3H), 2.37 (q, J=7.4 Hz, 2H), 3.70 (s, 3H), 4.29 (s, 2H), 6.00 (s, 1H), 7.41 (s, 1H).

2-{[(4-ethyl-1-methyl-1H-pyrazol-3-yl)methyl]sulfanyl}-6-methylpyrimidin-4-ol (129 mg, 488 μmol) was stirred in methanol (20 mL), and a solution of 4 N HCl in dioxane (190 μL, 732 μmol) was added dropwise at 0° C. The mixture was stirred for 15 minutes at room temperature. The solvent was removed by evaporation, and the residue was triturated with diethyl ether and dried in vacuo to afford 2-{[(4-ethyl-1-methyl-1H-pyrazol-3-yl)methyl]sulfanyl}-6-methylpyrimidin-4-ol hydrochloride (113 mg, 77% yield); $^1$H NMR (400 MHz, DMSO-$d_6$): δ 1.10 (t, J=7.6 Hz, 3H), 2.24 (s, 3H), 2.41 (q, J=7.0 Hz, J=0.4 Hz, 2H), 3.75 (s, 3H), 4.35 (s, 2H), 6.12 (s, 1H), 7.48 (s, 1H); LRMS (ES$^+$) m/z 265 (40%, M+1).

Example 135

6-methyl-2-({[4-(trifluoromethyl)pyridin-3-yl]methyl}sulfanyl)pyrimidin-4-ol hydrochloride

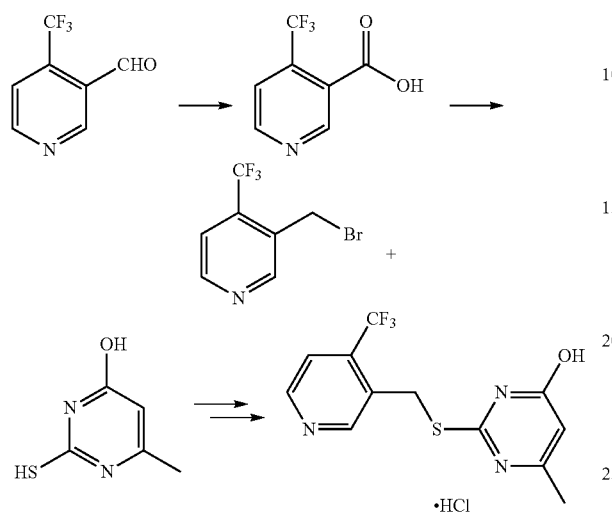

To a solution of sodium borohydride (324 mg, 8.6 mmol) in methanol (20 mL) was added a solution of 4-(trifluoromethyl)pyridine-3-carbaldehyde (1.0 g, 5.7 mmol) in methanol (10 mL) at 0° C. The mixture was stirred for 1.5 hours at room temperature. The solvent was evaporated, water was added, and the mixture was extracted 3 times with ethyl acetate. The combined organic phases were washed with brine and dried over sodium sulfate. After evaporation of the solvent, [4-(trifluoromethyl)pyridin-3-yl]methanol was obtained as an oil (980 mg, 97% yield) and used in the next step without further purification.

To a solution of [4-(trifluoromethyl)pyridin-3-yl]methanol (980 mg, 5.5 mmol) in anhydrous dichloromethane (35 mL) was added dropwise a solution of tribromophosphane (530 µL, 5.5 mmol) in anhydrous dichloromethane (5 mL) at 0° C. The mixture was stirred for 2 hours at room temperature. The mixture was evaporated, and crude 3-(bromomethyl)-4-(trifluoromethyl)pyridine was used in the next step without further purification.

6-methyl-2-sulfanylpyrimidin-4-ol (604 mg, 4.2 mmol) was dissolved in anhydrous DMF (30 mL), and then potassium carbonate (1.76 g, 12.8 mmol) and 3-(bromomethyl)-4-(trifluoromethyl)pyridine (5.5 mmol) in DMF (10 mL) were added. The mixture was stirred overnight at room temperature. The solid was removed by filtration and washed with methanol, and the filtrate was evaporated. The residue was dissolved in DCM/MeOH and purified on silica gel using 12% DCM/MeOH to afford 6-methyl-2-({[4-(trifluoromethyl)pyridin-3-yl]methyl}sulfanyl)pyrimidin-4-ol (349 mg, 21% yield for 2 steps); $^1$H NMR (400 MHz, DMSO-d$_6$): δ 2.22 (s, 3H), 4.59 (s, 2H), 6.07 (bs, 1H), 7.75 (d, J=5.3 Hz, 1H), 8.76 (d, J=5.1 Hz, 1H), 9.02 (s, 1H).

6-methyl-2-({[4-(trifluoromethyl)pyridin-3-yl]methyl}sulfanyl)pyrimidin-4-ol, (150 mg, 498 µmol) was stirred in methanol (20 mL) and a solution of 4 N HCl in dioxane (190 µL, 747 µmol) was added dropwise at 0° C. The mixture was stirred for 15 minutes at room temperature. The solvent was removed by evaporation, and the residue was triturated with diethyl ether and dried in vacuo to afford 6-methyl-2-({[4-(trifluoromethyl)pyridin-3-yl]methyl}sulfanyl)pyrimidin-4-ol hydrochloride (147 mg, 88% yield); $^1$H NMR (400 MHz, DMSO-d$_6$) δ 2.23 (s, 3H), 4.60 (s, 2H), 6.11 (s, 1H), 7.78 (d, J=5.1 Hz, 1H), 8.78 (d, J=5.1 Hz, 1H), 9.04 (s, 1H); LRMS (ES$^+$) m/z 302 (100%, M+1).

Example 136

2-{[(3,5-dichloropyridin-4-yl)methyl]sulfanyl}-6-methylpyrimidin-4-amine

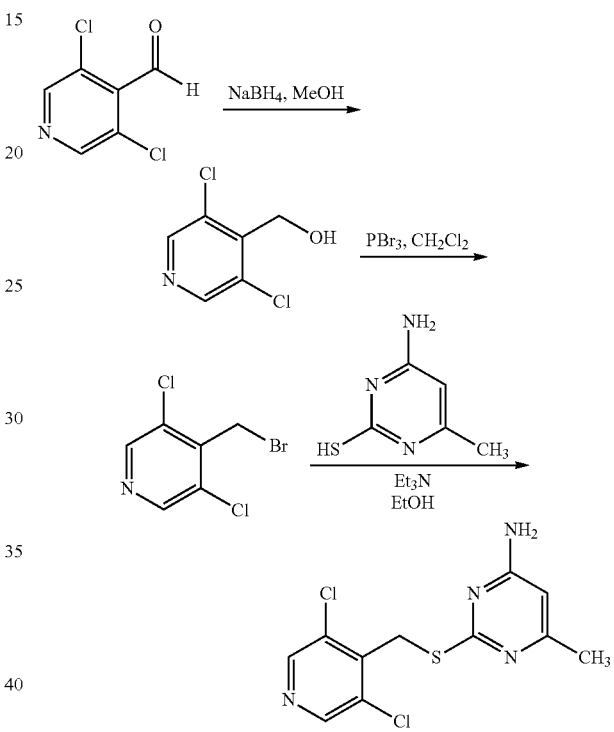

To a 0° C. solution of 3,5-dichloropyridine-4-carbaldehyde (7.0 g, 40 mmol) in anhydrous methanol (500 mL) was added sodium borohydride (2.3 g, 60 mmol). The reaction mixture was stirred at room temperature for 3 hours. Water (150 mL) was added and MeOH was evaporated. The mixture was extracted with ethyl acetate (2×100 mL) and 2-butanol (1×100 mL). The organic extracts were combined, dried over MgSO$_4$, filtered, evaporated, and dried in vacuo, affording (3,5-dichloropyridin-4-yl)methanol (6.4 g, 90% yield), which was used without further purification.

To a solution of (3,5-dichloropyridin-4-yl)methanol (1.9 g, 10.7 mmol) in anhydrous dichloromethane (75 mL) was added tribromophosphane (1.1 mL, 11.5 mmol). The mixture was stirred at room temperature for 1.5 hours. Dichloromethane was evaporated, and the mixture was co-evaporated with toluene (2×20 mL). The residue was dried in vacuo, affording 4-(bromomethyl)-3,5-dichloropyridine hydrobromide (2.9 g, 98% yield), which was used without further purification.

A mixture of 4-(bromomethyl)-3,5-dichloropyridine hydrobromide (2.9 g, 10.5 mmol), 4-amino-6-methylpyrimidine-2-thiol (1.0 g, 7.1 mmol), and triethylamine (3 mL, 21.5 mmol) in absolute EtOH (80 mL) was stirred at room temperature overnight. The mixture was evaporated, co-evaporated with EtOAc (20 mL), and dried in vacuo. The solid residue was treated with water (150 mL). The solid product was recovered by filtration, washed with water (2×25 mL), diethyl ether (2×25 mL), and hexanes (2×25 mL), and dried in vacuo, affording the title compound (1.9 g, 92% yield); $^1$H NMR (400 MHz, DMSO-$d_6$): δ 2.29 (s, 3H), 4.78 (s, 2H), 6.29 (s, 1H), 8.45 (s (br), 2H), 8.69 (s, 2H); M+ 302.

Example 137

2-{[(3,5-dichloropyridin-4-yl)methyl]sulfanyl}-4-methylpyrimidine

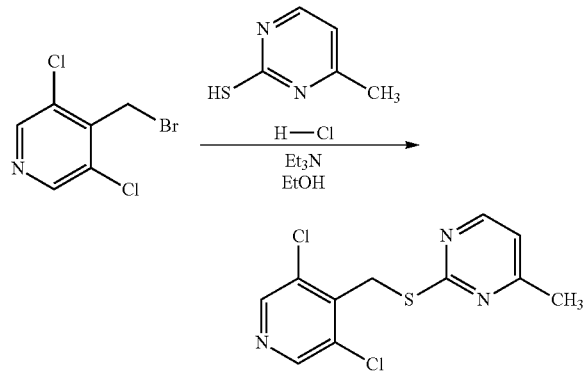

A mixture of 4-(bromomethyl)-3,5-dichloropyridine hydrobromide (1.3 g, 5.0 mmol), 4-methylpyrimidine-2-thiol hydrochloride (543 mg, 3.3 mmol), and triethylamine (1.8 mL, 12.9 mmol) in absolute EtOH (35 mL) was stirred at room temperature overnight. The mixture was evaporated, co-evaporated with EtOAc (10 mL), and dried in vacuo. The solid residue was treated with water (75 mL). The mixture was extracted with 50% ethyl acetate/Et$_2$O (75 mL). The organic extract was extracted with brine (2×75 mL), dried over MgSO$_4$, filtered, evaporated, and dried in vacuo. The crude product was purified by flash chromatography (0-4% MeOH/CH$_2$Cl$_2$), affording the title compound (800 mg, 85% yield); $^1$H NMR (400 MHz, DMSO-$d_6$): δ 2.45 (s, 3H), 4.70 (s, 2H), 7.17 (d, 1H, J=5.1 Hz), 8.54 (d, 1H, J=5.1 Hz), 8.67 (s, 2H); M+ 287.

Example 138

N-(2-{[(3,5-dichloropyridin-4-yl)methyl]sulfanyl}-6-methylpyrimidin-4-yl)acetamide

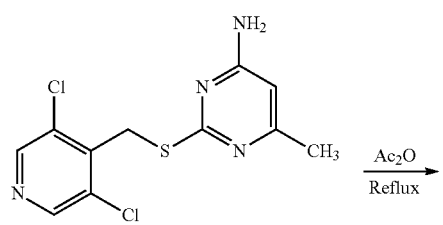

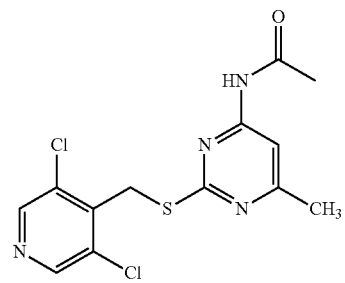

A mixture of 2-{[(3,5-dichloropyridin-4-yl)methyl]sulfanyl}-6-methylpyrimidin-4-amine (500 mg, 1.7 mmol) in acetic anhydride (10 mL) was stirred at reflux overnight. After cooling to room temperature, the mixture was neutralized slowly with a saturated solution of NaHCO$_3$ (aq.) until pH 7-8 was reached. The mixture was extracted with ethyl acetate (2×25 mL). The organic extracts were combined, dried over MgSO$_4$, filtered, evaporated, and dried in vacuo. The crude product was purified by flash chromatography (0-3% MeOH/CH$_2$Cl$_2$), affording the title compound (136 mg, 23% yield); $^1$H NMR (400 MHz, DMSO-$d_6$): δ 2.11 (s, 3H), 2.51 (s, 3H), 4.70 (s, 2H), 7.70 (s, 1H), 8.67 (s, 2H), 10.87 (s (br), 1H); M+ 287.

Example 139

2-{[(2-ethylpyridin-3-yl)methyl]sulfanyl}-6-methylpyrimidin-4-ol hydrochloride

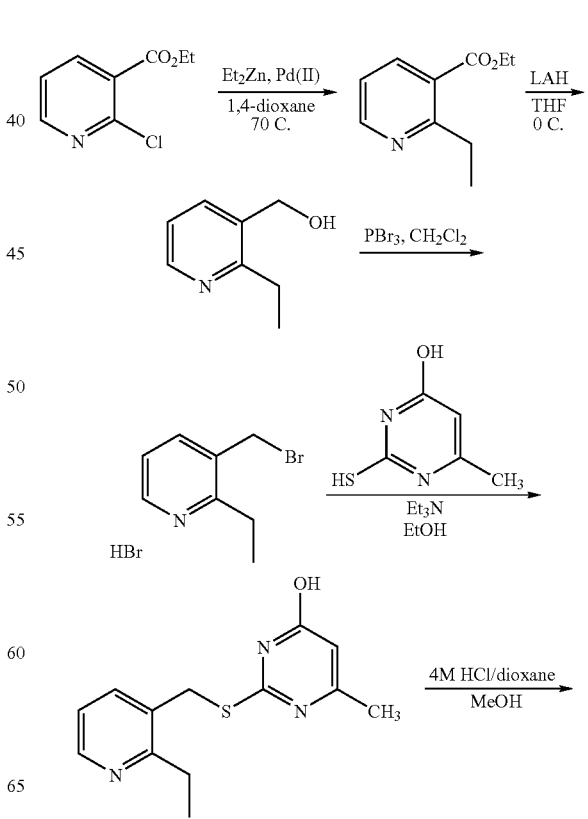

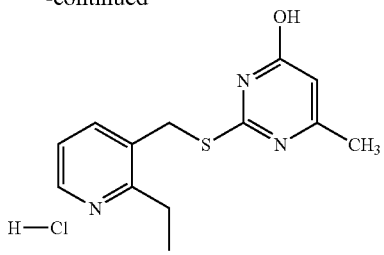

To a solution of ethyl 2-chloropyridine-3-carboxylate (15 g, 81 mmol) in anhydrous 1,4-dioxane (150 mL) at room temperature was added (1,1'-bis(diphenylphosphino)ferrocene)dichloropalladium (II) (1.3 g, 1.6 mmol) followed by a diethylzinc solution (75 mL, 83 mmol, 1.1 M solution in toluene). The mixture was stirred at 70° C. for 1 hour. After cooling to room temperature, the reaction was quenched with MeOH. Ethyl acetate (200 mL) was added. The mixture was extracted with 0.2 N HCl (200 mL). The organic layer was recovered. The pH of the aqueous phase was brought around 6 with 2 N NaOH. The mixture was extracted with EtOAc (1×100 mL). The combined organic extracts were dried over MgSO$_4$, filtered, evaporated, and dried in vacuo. The crude product was purified by flash chromatography (0-20% ethyl acetate/hexane), affording ethyl 2-ethylpyridine-3-carboxylate (8.8 g, 61% yield)

To a 0° C. mixture of lithium aluminum hydride (2.0 g, 53 mmol) in anhydrous THF (100 mL) was slowly added a solution of ethyl 2-ethylpyridine-3-carboxylate (4.8 g, 26.8 mmol) in anhydrous THF (30 mL). The reaction mixture was stirred at 0° C. for 1.5 hours. The reaction was quenched with 5 N NaOH. Water (200 mL) and EtOAc (200 mL) were added. The mixture was stirred for 30 minutes. The solid material was removed by filtration. The organic layer was recovered. The aqueous layer was extracted with EtOAc (2×100 mL). The combined organic extracts were dried over MgSO$_4$, filtered, evaporated, and dried in vacuo, affording (2-ethylpyridin-3-yl)methanol (3.1 g, 84% yield), which was used without further purification.

To a solution (2-ethylpyridin-3-yl)methanol (3.0 g, 21.9 mmol) in anhydrous dichloromethane (150 mL) was added tribromophosphane (2.3 mL, 24.2 mmol). The mixture was stirred at room temperature overnight. Dichloromethane was evaporated. The residue was dried in vacuo, affording 3-(bromomethyl)-2-ethylpyridine, which was used without further purification.

To a 0° C. mixture of 3-(bromomethyl)-2-ethylpyridine (21.9 mmol) and 6-methyl-2-sulfanylpyrimidin-4-ol (2.0 g, 14 mmol) in absolute ethanol (200 mL) was added triethylamine (11 mL, 79 mmol). The mixture was stirred at room temperature overnight. Diethyl ether (300 mL) was added to the clear solution. The precipitate was removed by filtration. The filtrate was recovered, evaporated, and co-evaporated with EtOAc (1×100 mL). The residue was treated with water (300 mL). The solid material was recovered by filtration, washed with water (3×50 mL), diethyl ether (2×50 mL), and hexanes (1×50 mL), and dried in vacuo, affording 2-{[(2-ethylpyridin-3-yl)methyl]sulfanyl}-6-methylpyrimidin-4-ol (1.9 g, 52% yield), which was used without further purification.

To a 0° C. mixture of 2-{[(2-ethylpyridin-3-yl)methyl]sulfanyl}-6-methylpyrimidin-4-ol (1.0 g, 3.8 mmol) in MeOH (15 mL) was added 4 M HCl/dioxane (4 mL, 16 mmol). The solution was evaporated and dried in vacuo, affording the title compound (1.1 g, 97% yield); $^1$H NMR (500 MHz, DMSO-d$_6$): δ 1.35 (t, 3H, J=7.5 Hz), 2.21 (s, 3H), 3.22 (m, 2H), 4.59 (s, 2H), 6.12 (s, 1H), 7.88 (t, 1H, J=7.5 Hz), 8.69 (m, 2H); M+ 262.

Example 140

2-{[(3-ethyl-5-fluoropyridin-4-yl)methyl]sulfanyl}-6-methylpyrimidin-4-ol

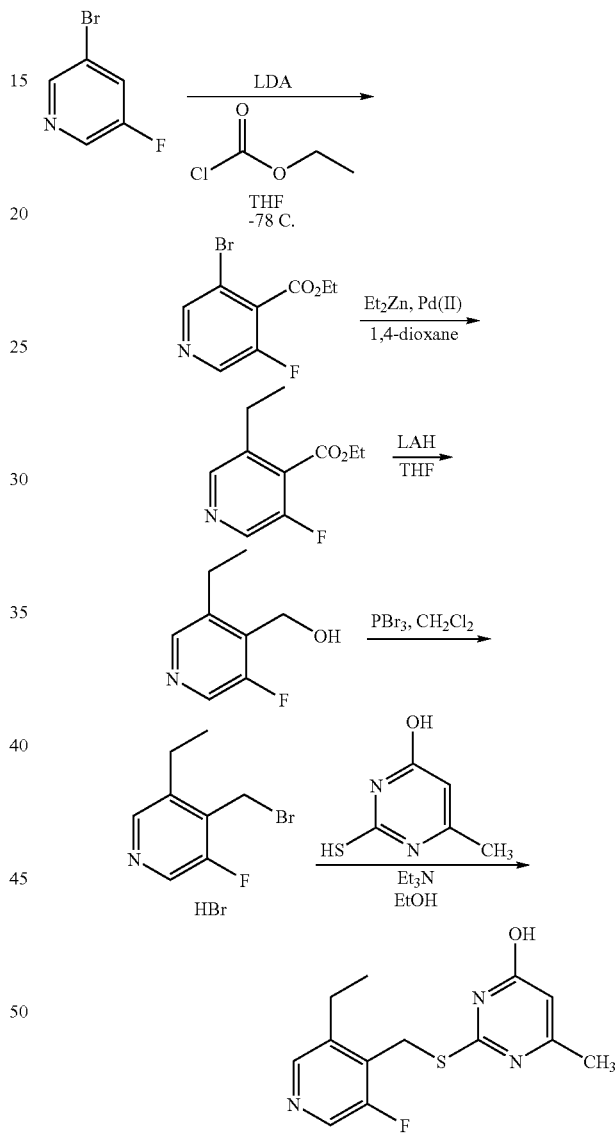

To a −78° C. solution of LDA (2 M solution in heptane/THF, 14.2 mL, 28.4 mmol) in anhydrous THF (45 mL) was added a solution of the 3-bromo-5-fluoropyridine (5.0 g, 28.4 mmol) in anhydrous THF (20 mL). The reaction mixture was stirred at −78° C. for 45 minutes. Then, a solution of ethyl chloroformate (24 mL, 284 mmol) was added slowly over 10 minutes. After stirring for 20 minutes, the reaction mixture was quenched with a saturated solution of NaHCO$_3$. The mixture was extracted into ethyl acetate (3×100 mL). The combined organic extracts were extracted with water (2×200 mL), dried over MgSO$_4$, filtered, evaporated, and dried in vacuo, affording ethyl 3-bromo-5-fluoropyridine-4-carboxylate (4.8 g, 69% yield). The product was used without further purification.

To a solution of ethyl 3-bromo-5-fluoropyridine-4-carboxylate (4.8 g, 20 mmol) in anhydrous 1,4-dioxane (30 mL) at room temperature was added (1,1'-bis(diphenylphosphino)ferrocene)dichloropalladium (II) (325 mg, 0.43 mmol), followed by a diethylzinc solution (22 mL, 20 mmol, 1.1 M solution in toluene). The mixture was stirred at 70° C. for 45 minutes. After cooling to room temperature, the reaction was quenched with MeOH. Ethyl acetate (100 mL) was added. The mixture was extracted with 0.1 N HCl (200 mL). The organic layer was recovered. The pH of the aqueous phase was brought to 6 with 2 N NaOH. The mixture was extracted with EtOAc (1×100 mL). The combined organic extracts were dried over MgSO$_4$, filtered, evaporated, and dried in vacuo. The crude product was purified by flash chromatography (0-20% ethyl acetate/hexane), affording ethyl 3-ethyl-5-fluoropyridine-4-carboxylate (2.0 g, 51% yield)

To a 0° C. mixture of lithium aluminum hydride (760 mg, 10.1 mmol) in anhydrous THF (60 mL) was slowly added a solution of ethyl 3-ethyl-5-fluoropyridine-4-carboxylate (2.00 g, 10.1 mmol) in anhydrous THF (25 mL). The reaction mixture was stirred at 0° C. for 2 hours. The reaction was quenched with 5N NaOH. Water (100 mL) and EtOAc (100 mL) were added. The mixture was stirred for 30 minutes. The solid material was removed by filtration. The organic layer was recovered. The aqueous layer was extracted with EtOAc (1×100 mL). The combined organic extracts were dried over MgSO$_4$, filtered, evaporated and dried in vacuo, affording (3-ethyl-5-fluoropyridin-4-yl)methanol (1.5 g, 95% yield). The product was used without further purification.

To a solution of (3-ethyl-5-fluoropyridin-4-yl)methanol (1.5 g, 9.7 mmol) in anhydrous dichloromethane (75 mL) was added tribromophosphane (1 mL, 10.5 mmol). The mixture was stirred at room temperature overnight. Dichloromethane was evaporated. The residue was dried in vacuo, affording 4-(bromomethyl)-3-ethyl-5-fluoropyridine hydrobromide. The crude product was used without further purification.

A mixture of 4-(bromomethyl)-3-ethyl-5-fluoropyridine hydrobromide (9.7 mmol), 6-methyl-2-sulfanylpyrimidin-4-ol (1.7 g, 12 mmol), and triethylamine (3.5 mL, 25 mmol) in absolute ethanol (100 mL) was stirred at overnight room temperature. The mixture was evaporated. Water (100 mL) and EtOAc (100 mL) were added. The organic layer was recovered, dried over MgSO$_4$, filtered, evaporated, and dried in vacuo. The crude mixture was purified by flash chromatography (0-5% MeOH/CH$_2$Cl$_2$), affording the title compound (250 mg, 9% yield); $^1$H NMR (500 MHz, DMSO-d$_6$): δ 1.21 (t, 3H, J=7.5 Hz), 2.23 (s, 3H), 2.83 (q, 2H, J=7.5 Hz), 4.51 (s, 2H), 6.07 (s, 1H), 8.33 (s, 1H), 8.41 (s, 1H); M+ 280.

Example 141

2-{[(3-ethylpyridin-4-yl)methyl]sulfanyl}-6-methylpyrimidin-4-ol hydrochloride

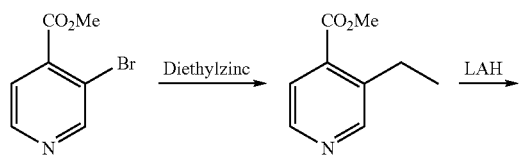

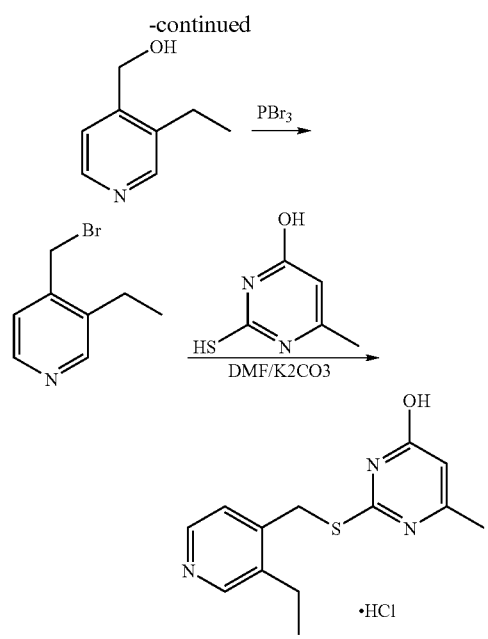

Methyl 3-bromopyridine-4-carboxylate (5 g, 23.1 mmol) was dissolved in anhydrous dioxane (150 mL). A solution of diethyl zinc (18.9 mL, 20.8 mmol, 1.1 M in toluene) was added dropwise and then was added catalyst ((1,1'-bis(diphenylphosphino)ferrocene)dichloropalladium (254 mg, 347 μmol). The mixture was heated at 70° C. for 3.5 hours and then water followed with 1 N HCl was added. The mixture was extracted 3 times with ethyl acetate. The combined organic phase was washed with brine and dried over sodium sulfate. After evaporation, the residue was dissolved in DCM and purified on silica gel using 0-20% hexane/ethyl acetate to afford methyl 3-ethylpyridine-4-carboxylate (730 mg, 19% yield).

Lithium aluminum hydride (956 mg, 5.8 mmol) was stirred in anhydrous THF (40 mL). A solution of methyl 3-ethylpyridine-4-carboxylate (904 mg, 3.97 mmol) in anhydrous THF (10 mL) was added at 0° C., and then stirred at room temperature for 1 hour. The reaction was quenched with an aqueous solution of sodium hydroxide and extracted 5 times with ethyl acetate. The organic phase was washed with brine and dried over sodium sulfate. After evaporation of the solvent, (3-ethylpyridin-4-yl)methanol was obtained as a yellow oil (770 mg, 97% yield) and used in the next step without further purification.

To a solution of (3-ethylpyridin-4-yl)methanol (5.8 mmol) in anhydrous dichloromethane (40 mL) was added dropwise a solution of phosphorus tribromide (546 μL, 5.8 mmol) in anhydrous dichloromethane (40 mL) at 0° C. The mixture was stirred for 2 hours at room temperature. The mixture was evaporated, and crude 4-(bromomethyl)-3-ethylpyridine was used in the next step without further purification.

6-methyl-2-sulfanylpyrimidin-4-ol (686 mg, 4.8 mmol) was dissolved in anhydrous DMF (30 mL), and then potassium carbonate (2.0 g, 14.5 mmol) and 4-(bromomethyl)-3-ethylpyridine (5.8 mmol) in DMF (10 mL) were added. The mixture was stirred for 2.5 hours at room temperature. The solid was removed by filtration and washed with methanol, and the filtrate was evaporated. The residue was dissolved in DCM/MeOH and purified on silica gel using 3-12% DCM/MeOH to afford 2-{[(3-ethylpyridin-4-yl)methyl]sulfanyl}-6-methylpyrimidin-4-ol (88 mg, 6% yield for 3 steps).

2-{[(3-ethylpyridin-4-yl)methyl]sulfanyl}-6-methylpyrimidin-4-ol (100 mg, 383 μmol) was stirred in methanol (20 mL) and a solution of 4 N HCl in dioxane (145 μL, 574 μmol) was added dropwise at 0° C. The mixture was stirred for 15 minutes at room temperature. The solvent was removed by evaporation, and the residue was triturated with diethyl ether and dried in vacuo to afford 2-{[(3-ethylpyridin-4-yl)methyl] sulfanyl)-6-methylpyrimidin-4-ol hydrochloride (110 mg, 97% yield); ¹H NMR (400 MHz, DMSO-d₆): δ 1.28 (t, J=7.5 Hz, 3H), 2.15 (s, 3H), 2.98 (q, J=7.5 Hz, 2H), 4.62 (s, 2H), 6.08 (s, 1H), 8.12 (d, J=6.0 Hz, 1H), 8.70 (d, J=6.0 Hz, 1H), 8.77 (s, 1H); LRMS (ES⁺) m/z 262 (100%, M+1).

Example 142

2-{[(3-ethylpyridin-4-yl)methyl]sulfanyl}-6-(trifluoromethyl)pyrimidin-4-ol

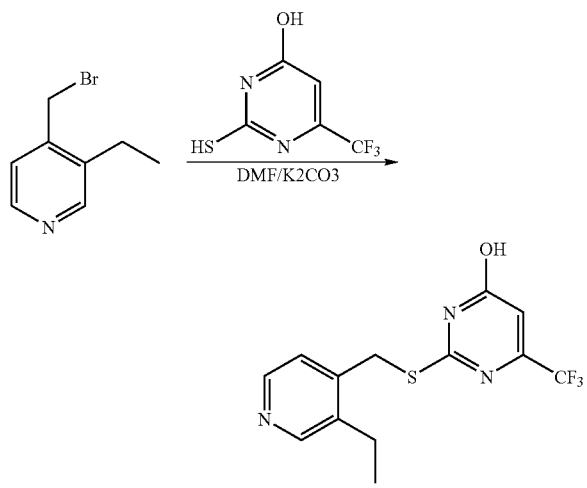

2-sulfanyl-6-(trifluoromethyl)pyrimidin-4-ol (1.56 g, 8.0 mmol) was dissolved in anhydrous DMF (50 mL), and then potassium carbonate (3.3 g, 23.9 mmol) and 4-(bromomethyl)-3-ethylpyridine (10.3 mmol) in DMF (10 mL) were added. The reaction mixture was stirred overnight at room temperature. The solid was removed by filtration and washed with methanol, and the filtrate was evaporated. The residue was dissolved in DCM/MeOH and purified on silica gel using 3-12% DCM/MeOH to afford 2-{[(3-ethylpyridin-4-yl)methyl]sulfanyl}-6-(trifluoromethyl)pyrimidin-4-ol (357 mg, 14% yield for 3 steps); ¹H NMR (500 MHz, DMSO-d₆): δ 1.21 (t, J=7.5 Hz, 3H), 2.75 (q, J=7.5 Hz, 2H), 4.46 (s, 2H), 6.65 (s, 1H), 7.41 (d, J=5.1 Hz, 1H), 8.34 (d, J=5.0 Hz, 1H), 8.42 (s, 1H); LRMS (ES⁺) m/z 316 (100%, M+1).

Example 143

2-{[(4-chloro-1-methyl-1H-pyrazol-3-yl)methyl)sulfanyl}-6-methylpyrimidin-4-ol

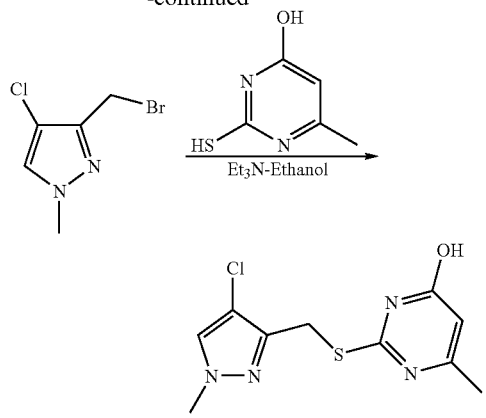

To a solution of 4-chloro-1-methyl-1H-pyrazole-3-carbaldehyde (10.0 g, 69.2 mmol) in methanol (190 mL) was added sodium borohydride (3.93 g, 104 mmol) at 0° C. The mixture was stirred for 2 hours at room temperature and quenched with water. The solvent was evaporated, water was added, and the mixture was extracted 3 times with ethyl acetate. The combined organic phase was washed with brine and dried over sodium sulfate. After evaporation of the solvent, (4-chloro-1-methyl-1H-pyrazol-3-yl)methanol was obtained (9.04 g, 90% yield) and used in the next step without further purification; ¹H NMR (500 MHz, DMSO-d₆): δ 3.77 (s, 3H), 4.35 (d, J=5.5 Hz, 2H), 5.03 (t, J=5.5 Hz, 1H), 7.84 (s, 1H).

To a solution of (4-chloro-1-methyl-1H-pyrazol-3-yl)methanol (9.0 g, 61.7 mmol) in anhydrous dichloromethane (240 mL) was added dropwise a solution of phosphorus tribromide (5.0 mL, 67.8 mmol) in anhydrous dichloromethane (10 mL) at 0° C. The mixture was stirred for 2 hours at room temperature. The mixture was evaporated, and crude 3-(bromomethyl)-4-chloro-1-methyl-1H-pyrazole was used in the next step without further purification.

To a solution of 3-(bromomethyl)-4-chloro-1-methyl-1H-pyrazole (61.7 mmol) in absolute ethanol (250 mL) was added 6-methyl-2-sulfanylpyrimidin-4-ol (5.84 g, 41.1 mmol) and triethylamine (23.0 mL, 165 mmol) at 0° C. The mixture was stirred at room temperature overnight. The white solid was filtered and washed with diethyl ether (300-500 mL). The filtrate was recovered, and the solvent was evaporated. The residue triturated in water, filtered, and washed with water (3×300 mL) and then DCM (50 mL). The solid was died under vacuum overnight. 2-{[(4-chloro-1-methyl-1H-pyrazol-3-yl)methyl)sulfanyl}-6-methylpyrimidin-4-ol was obtained as a white solid (5.48 g, 49% yield for 2 steps); ¹H NMR (400 MHz, DMSO-d₆): δ 2.20 (bs, 3H), 3.78 (s, 3H), 4.35 (s, 2H), 6.05 (bs, 1H), 7.92 (s, 1H); LRMS (ES⁺) m/z 271 (100%, M+1); 273 (35%, M+3).

Example 144

2-{[(5-ethylpyridin-3-yl)methyl]sulfanyl}-6-methylpyrimidin-4-ol hydrochloride

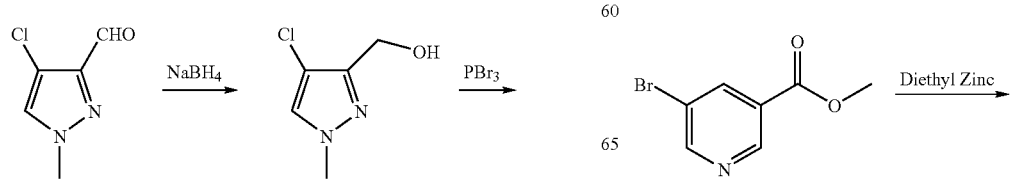

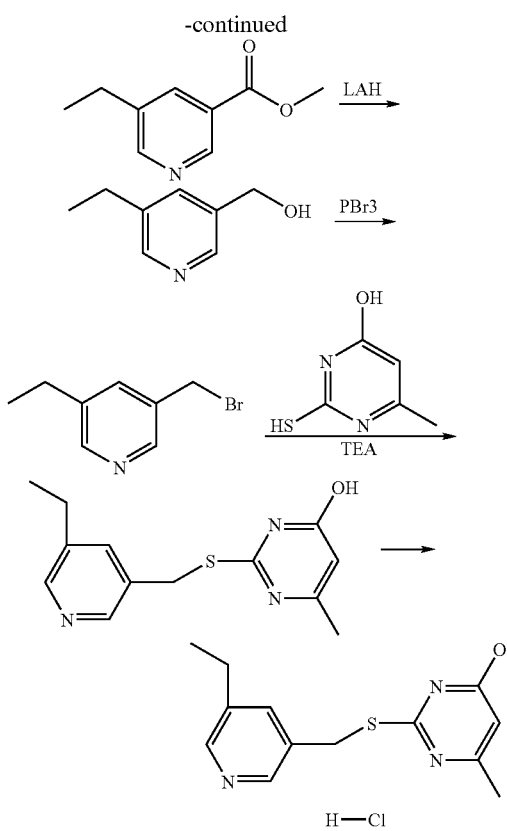

To a solution of methyl 5-bromopyridine-3-carboxylate (10.0 g, 46.29 mmol) in anhydrous dioxane (100 mL) at room temperature was added (1,1'-bis(diphenylphosphino)ferrocene)dichloropalladium (II) (677 mg, 0.925 mmol). Then, diethylzinc (5.71 g, 38 mL, 46.29 mmol, 15% solution in toluene) was added dropwise. The reaction mixture was heated at 70° C. for 45 minutes, then cooled to room temperature and quenched with MeOH. The mixture was extracted with ethyl acetate (2×250 mL) and washed with water, 0.1 N HCl, and brine. The organic layer was dried over anhydrous sodium sulfate and filtered. The filtrate was evaporated, and the residue was purified by CombiFlash using 0-30% ethyl acetate and hexane to provide methyl 5-ethylpyridine-3-carboxylate as a yellow oil (4.20 g, 55% yield); $^1$H NMR (400 MHz, CDCl$_3$): δ 1. (t, 3H), 1.45 (t, 3H), 2.78 (q, 2H), 3.99 (s, 3H), 8.15 (s, 1H), 8.65 (s, 1H), 8.89 (s, 1H); M+ 165.1.

To a suspension of LAH (1.92 g, 50.85 mmol) in anhydrous THF 40 mL at 0° C. was added dropwise a solution of methyl 5-ethylpyridine-3-carboxylate (4.20 g, 25.42 mmol) in THF (50 mL). After stirring for 1 hour, the reaction mixture was slowly quenched with 15% NaOH and then diluted with water. Ethyl acetate was added, the reaction mixture was stirred for 10 minutes, and the precipitate was filtered off. The solid was washed with ethyl acetate (3×100 mL). The filtrate was dried over anhydrous sodium sulfate, filtered, and evaporated to provide (5-ethylpyridin-3-yl)methanol as a thick oil (3.31 g, 95% yield), which was used in the next step without any further purification; M+ 137.18.

To a solution of (5-ethylpyridin-3-yl)methanol (3.31 g, 24.12 mmol) in anhydrous chloroform (50 mL) at 0° C. was added tribromophosphane (7.18 g, 2.49 mL, 26.54 mmol) dropwise. The reaction mixture was allowed to stir overnight at room temperature. The solvent was evaporated to provide crude 3-(bromomethyl)-5-ethylpyridine (4.82 g, 100% yield), which was used in the next step without any further purification.

To a mixture of 3-(bromomethyl)-5-ethylpyridine (4.82 g, 24.08 mmol), 6-methyl-2-sulfanylpyrimidin-4-ol (2.22 g, 15.65 mmol) in anhydrous ethanol (100 mL) at 0° C. was added triethylamine (9.74 g, 13.41 mL, 96.35 mmol). The reaction mixture was allowed to stir at room temperature overnight. The solvent was evaporated to provide a crude residue. Ether was added to precipitate the triethylamine hydrobromide salt. The solid was filtered and was washed with ether several times. The solvent was evaporated to provide a crude residue, which was purified by combiflash using 0-10% MeOH: dichloromethane. 2-{[(5-ethylpyridin-3-yl)methyl]sulfanyl}-6-methylpyrimidin-4-ol was obtained as a white solid (2.83 g, 45% yield); $^1$H NMR (400 MHz, DMSO-d$_6$): δ 1.14 (t, 3H), 2.21 (s, 3H), 2.61 (q, 2H), 4.35 (s, 2H), 6.00 (bs, 1H), 7.69 (s, 1H), 8.31 (s, 1H) 8.45 (s, 1H); M+ 261.5.

2-{[(5-ethylpyridin-3-yl)methyl]sulfanyl}-6-methylpyrimidin-4-ol (1.0 g, 3.82 mmol) was stirred in methanol (10 mL), and a solution of 4 N HCl in dioxane (2.86 mL, 11.47 mmol) was added dropwise at 0° C. The mixture was stirred for 5 minutes at 0° C. Anhydrous ether (25 mL) was added to precipitate the salt, which was filtered and washed with anhydrous ether to provide 2-{[(5-ethylpyridin-3-yl)methyl]sulfanyl}-6-methylpyrimidin-4-ol hydrochloride as a white solid (1.08 g, 95% yield); $^1$H NMR (400 MHz, DMSO-d$_6$): δ 1.23 (t, 3H), 2.23 (s, 3H), 2.81 (q, 2H), 4.49 (s, 2H), 6.09 (bs, 1H), 8.69 (s, 1H), 8.73 (s, 1H), 8.89 (s, 1H); M+ 261.5.

Example 145

6-methyl-2-({[2-(trifluoromethyl)pyridin-3-yl]methyl}sulfanyl)pyrimidin-4-ol

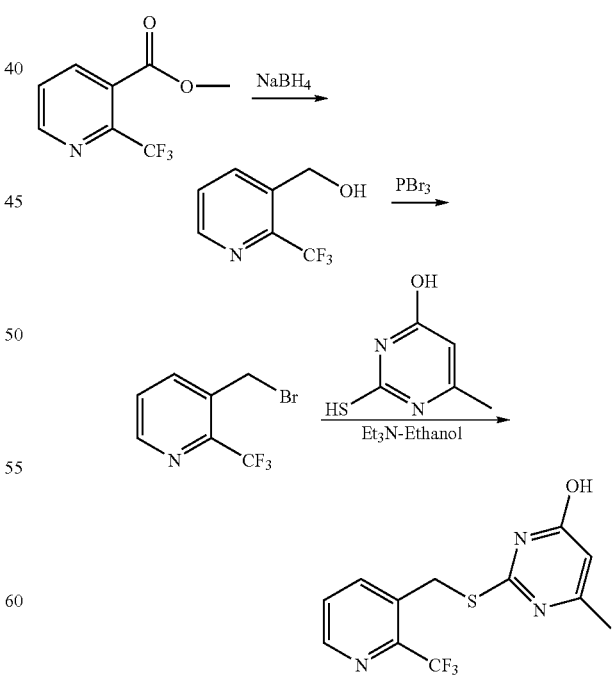

To a suspension of sodium borohydride (0.24 g, 6.32 mmol) in anhydrous THF (40 mL) at 0° C. was added dropwise a solution of methyl 2-(trifluoromethyl)pyridine-3-carboxylate (650 mg, 3.16 mmol) in THF (50 mL). After stirring for 1 hour, the reaction mixture was slowly quenched with 15% NaOH and then diluted with water. Ethyl acetate was added, the reaction mixture was stirred for 10 minutes, and the precipitated white solid was filtered off. The solid was washed with ethyl acetate (3×100 mL). The organic layer was separated, dried over anhydrous sodium sulfate, and filtered. The filtrate was evaporated to provide [2-(trifluoromethyl)pyridin-3-yl]methanol as a thick oil (0.505 g, 90% yield), which was used for the next step without any further purification; M+ 177.1.

To a solution of [2-(trifluoromethyl)pyridin-3-yl]methanol (0.505 g, 5.5 mmol) in anhydrous dichloromethane (25 mL) was added dropwise a solution of tribromophosphane (0.848 g, 3.13 mmol) in anhydrous dichloromethane (10 mL) at 0° C. The mixture was stirred for 1.5 hours at room temperature. The mixture was evaporated, and the crude 3-(bromomethyl)-2-(trifluoromethyl)pyridine was used in the next step without further purification.

To a mixture of crude 3-(bromomethyl)-2-(trifluoromethyl)pyridine (0.684 g, 2.84 mmol), 6-methyl-2-sulfanylpyrimidin-4-ol (0.242 g, 1.70 mmol) in anhydrous ethanol (100 mL) at 0° C. was added triethylamine (1.14 g, 1.57 mL, 11.36 mmol). The reaction mixture was allowed to stir at room temperature overnight. The solvent was evaporated, and ether was added to the precipitated triethylamine hydrobromide salt. The solid was filtered and washed with ether several times. The solvent was evaporated to provide a crude residue, which was purified by Combiflash using 0-10% MeOH:dichloromethane. 6-methyl-2-({[2-(trifluoromethyl)pyridin-3-yl]methyl}sulfanyl)pyrimidin-4-ol was obtained as a white solid (0.438 g, 51% yield); $^1$H NMR (400 MHz, DMSO-d$_6$): δ 1.14 (t, 3H), 2.21 (s, 3H), 2.61 (q, 2H), 4.35 (s, 2H), 6.00 (bs, 1H), 7.69 (s, 1H), 8.31 (s, 1H) 8.45 (s, 1H); M+ 301.5.

Example 146

2-{[(2,4-dimethylpyridin-3-yl)methyl]sulfanyl}-6-methylpyrimidin-4-ol

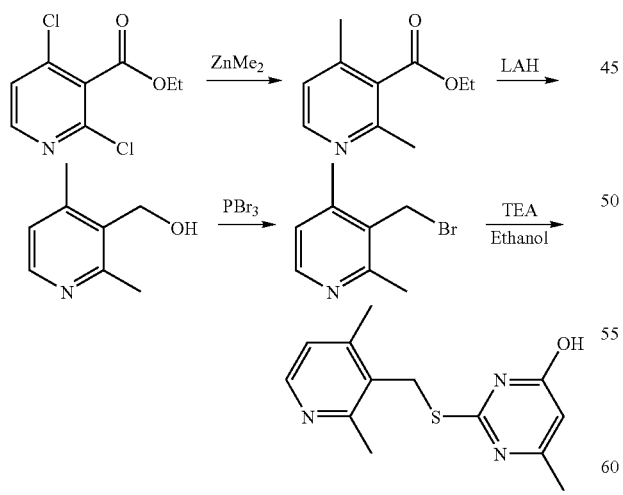

To the solution of ethyl 2,4-dichloropyridine-3-carboxylate (3.3 g, 15 mmol) in dioxane (100 mL) in a 500 mL round bottom flask was added dimethylzinc (22 mL, 1.0 M in hexane) and (1,1'-bis(diphenylphosphino)ferrocene)dichloropalladium (II) dichloromethane complex (300 mg, 0.4 mmol). The resulting mixture was heated at 70° C. for 8 hours. After cooling, the reaction was quenched by addition of methanol (10 mL). The mixture was poured into water (500 mL) and extracted with dichloromethane (3×200 mL). The combined organic layer was evaporated, and the crude residue was filtered through a silica pad (5 cm) with 20% ethyl acetate in hexane (200 mL). After evaporation, the oily ethyl 2,4-dimethylpyridine-3-carboxylate was used in the next step without further purification.

To the suspension of LAH (0.95 g, 25 mmol) in THF (100 mL), ethyl 2,4-dimethylpyridine-3-carboxylate (1.5 g, 8.4 mmol) was added dropwise as a solution in THF (10 mL) at 0° C. After 30 minutes, the reaction was quenched by addition of acetone/water and then more water (100 mL) was added. The mixture was extracted with DCM (3×100 mL), dried over magnesium sulfate, and evaporated to provide (2,4-dimethylpyridin-3-yl)methanol, which was used in the next step without any further purification.

(2,4-dimethylpyridin-3-yl)methanol was dissolved in dichloromethane (100 mL). Tribromophosphane (1.5 mL, 16 mmol) was added slowly. After 2 hours, the mixture was evaporated to dryness. The crude solid was dissolved in cold ethanol (100 mL), and 6-methyl-2-sulfanylpyrimidin-4-ol (1.13 g, 8.0 mmol) and triethylamine (4.5 mL, 32 mmol) were added. The resulting mixture was stirred at room temperature for 3 hours. The solvent was evaporated, and the crude solid was washed with THF (200 mL). After evaporation of solvent, the crude was purified by CombiFlash (0-6% MeOH in DCM) to provide 2-{[(2,4-dimethylpyridin-3-yl)methyl]sulfanyl}-6-methylpyrimidin-4-ol (2.5 g, 64% yield); $^1$H NMR (500 MHz, DMSO-d$_6$): δ 2.23 (s, 3H), 2.68 (s, 3H), 2.84 (s, 3H), 4.62 (s, 2H), 6.05 (br, 1H), 7.71 (s, 1H), 8.62 (s, 1H); M+ 232.

Example 147

2-{[(3-chloro-5-methylpyridin-4-yl)methyl]sulfanyl}-6-methylpyrimidin-4-ol

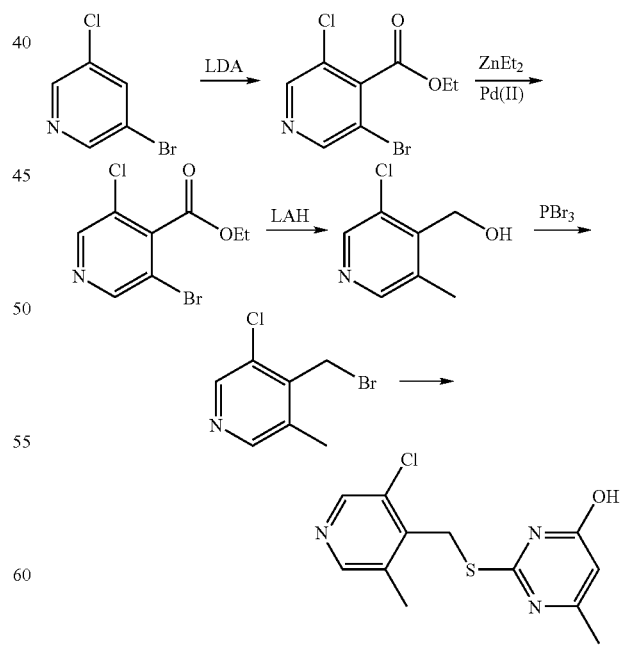

3-bromo-5-chloropyridine (25 g, 130 mmol) in THF (50 mL) was added slowly to a solution of LDA (140 mmol) in THF (250 mL) at −78° C. over 10 minutes. After stirring for 30 minutes, ethyl chloroformate (26 mL, 260 mmol) in THF (30 mL) was added in portions over 5 minutes. After 10 more minutes, the reaction mixture was poured into cold 10% aqueous NaHCO₃ (500 mL). The mixture was extracted with ethyl acetate (2×250 mL). The organic layer was dried over MgSO₄ and evaporated. The crude solid was filtered through a silica pad with hexane (500 mL). The filtrate was evaporated to provide pure ethyl 3-bromo-5-chloropyridine-4-carboxylate (28 g, 80% yield).

To the solution of ethyl 3-bromo-5-chloropyridine-4-carboxylate (28 g, 105 mmol) in dioxane (300 mL) in a 1 L round bottom flask was added dimethylzinc (105 mL, 1.0 M in hexane) and (1,1'-bis(diphenylphosphino)ferrocene)dichloropalladium(II) dichloromethane complex (1.3 g, 1.6 mmol). The resulting mixture was heated at 60° C. for 20 hours. After cooling, the reaction mixture was poured into cold water (500 mL) and extracted with dichloromethane (3×200 mL). After evaporation of the solvent, the crude product was filtered through a silica pad (10 cm) with 20% ethyl acetate in hexane (400 mL), and the solvent was evaporated. The oily ethyl 3-chloro-5-methylpyridine-4-carboxylate (20 g, 90% yield) was used in the next step without further purification.

To the suspension of LAH (2.3 g, 60 mmol) in THF (100 mL) at 0° C. was added dropwise ethyl 3-chloro-5-methylpyridine-3-carboxylate (5 g, 20 mmol) as a solution in THF (10 mL). After 30 minutes, the reaction was quenched by addition of acetone/water and more water (100 mL) was added. The mixture was extracted with DCM (2×100 mL), dried over magnesium sulfate, and then filtered. Tribromophosphane, (2.1 mL, 22 mmol) was added slowly to the filtrate. After 2 hours, the mixture was evaporated to dryness and the crude bromide was dissolved in cold ethanol (100 mL).

6-methyl-2-sulfanylpyrimidin-4-ol (2.15 g, 15 mmol) and triethylamine (11.2 mL, 80 mmol) were then added to the crude bromide. The resulting mixture was stirred at room temperature for 3 hours. The solvent was evaporated, and the crude solid was washed with THF (200 mL). The filtrate was evaporated, and the crude material was purified by CombiFlash (0~6% MeOH in DCM) to provide 2-{[(3-chloro-5-methylpyridin-4-yl)methyl]sulfanyl}-6-methylpyrimidin-4-ol as a white solid (2.65 g, 63% yield); ¹H NMR (500 MHz, DMSO-d₆): δ 2.42 (s, 3H), 2.53 (s, 3H), 4.57 (s, 2H), 6.05 (bs, 1H), 8.39 (s, 1H), 8.50 (s, 1H); M+ 282.

Example 148

2-{[(3-chloro-5-methylpyridin-4-yl)methyl]sulfanyl}-6-(trifluoromethyl)pyrimidin-4-ol

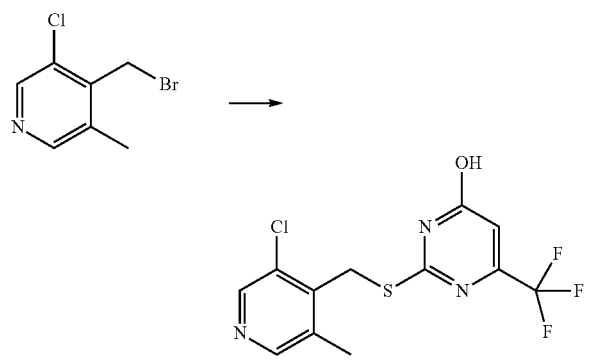

2-{[(3-chloro-5-methylpyridin-4-yl)methyl]sulfanyl}-6-(trifluoromethyl)pyrimidin-4-ol was synthesized from 3-bromo-5-chloropyridine and 2-sulfanyl-6-(trifluoromethyl)pyrimidin-4-ol by following the procedure provided for the last step in Example 22. A white solid was obtained (1.5 g, 32% yield); ¹H NMR (500 MHz, DMSO-d₆): δ 2.42 (s, 3H), 2.50 (s, 3H), 4.61 (s, 2H), 6.71 (bs, 1H), 8.40 (s, 1H), 8.50 (s, 1H); M+ 336.

Example 149

6-methyl-2-{[(1-methyl-1H-1,2,3-benzotriazol-5-yl)methyl]sulfanyl}pyrimidin-4-ol

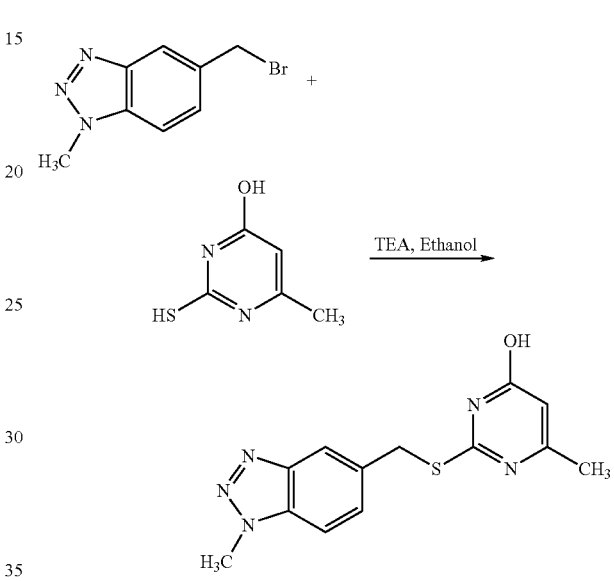

To a mixture of 5-(bromomethyl)-1-methyl-1H-1,2,3-benzotriazole (1.0 g, 4.22 mmol) and 6-methyl-2-sulfanylpyrimidin-4-ol (0.404 g, 2.87 mmol) in anhydrous ethanol (50 mL) at 0° C. was added triethylamine (0.894 g, 8.84 mmol). Then, the reaction mixture was allowed to stir at room temperature overnight. The solvent was evaporated to provide a crude residue. Ether was added to precipitate the triethylamine hydrochloride salt. The solid was filtered and washed with ether several times. The solvent was evaporated to provide a crude residue, which was purified by Combiflash using 0-10% methanol:dichloromethane to provide 6-methyl-2-{[(1-methyl-1H-1,2,3-benzotriazol-5-yl)methyl]sulfanyl}pyrimidin-4-ol as a white solid (953 mg, 75% yield); ¹H NMR (400 MHz, DMSO-d₆): δ 2.21 (s, 3H), 4.28 (s, 2H), 4.55 (s, 3H), 6.04 (bs, 1H), 7.62 (d, J=8.7 Hz, 1H), 7.80 (d, J=8.7 Hz, 1H), 8.07 (s, 1H); M+ 287.5.

Example 150

6-methyl-2-[({6-methylimidazo[1,2-a]pyridin-3-yl}methyl)sulfanyl]pyrimidin-4-ol

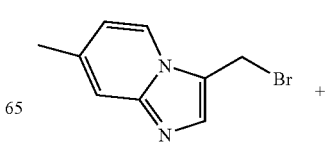

-continued

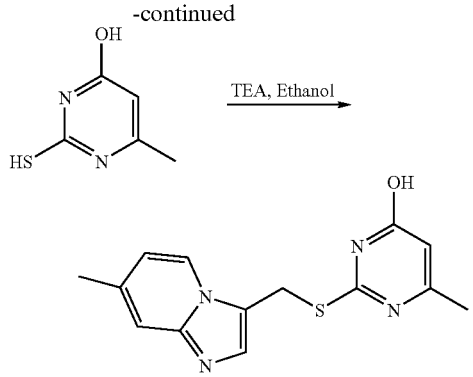

To a mixture of 3-(bromomethyl)-7-methylimidazo[1,2-a]pyridine (1.0 g, 4.44 mmol), 6-methyl-2-sulfanylpyrimidin-4-ol (0.407 g, 2.88 mmol) in anhydrous ethanol (50 mL) at 0° C. was added triethylamine (0.898 g, 8.88 mmol). Then, the reaction mixture was allowed to stir at room temperature overnight. The solvent was evaporated to provide a crude residue. Ether was added to precipitate the triethylamine hydrochloride salt. The solid was filtered and washed with ether several times. The solvent was evaporated to provide a crude residue, which was purified by Combiflash using 0-10% methanol:dichloromethane to provide 6-methyl-2-[({6-methylimidazo[1,2-a]pyridin-3-yl}methyl)sulfanyl]pyrimidin-4-ol as a white solid (826 mg, 65% yield); $^1$H NMR (400 MHz, DMSO-$d_6$): δ 2.25 (s, 3H), 2.31 (s, 3H), 4.79 (s, 2H), 6.04 (bs, 1H), 7.15 (d, J=8.0 Hz, 1H), 7.51 (d, J=8.0 Hz, 1H), 7.54 (s, 1H), 8.32 (s, 1H); M+ 286.5.

Example 151

6-methyl-2-[(pyrimidin-2-ylmethyl)sulfanyl]pyrimidin-4-ol dihydrochloride

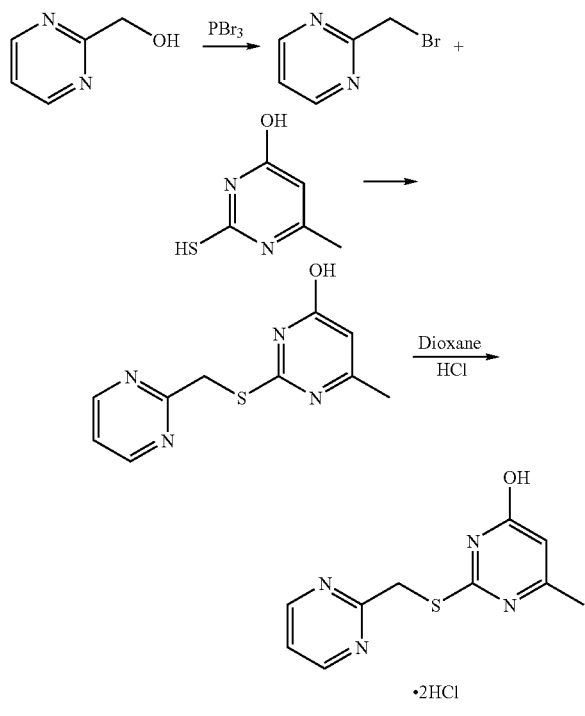

To a solution of pyrimidin-2-ylmethanol (1 g, 9.1 mmol) in anhydrous dichloromethane (40 mL) added was dropwise a solution of tribromophosphane (860 µL, 9.1 mmol) in anhydrous dichloromethane (5 mL) at 0° C. The mixture was stirred overnight at room temperature, and then solvent was evaporated to provide crude 2-(bromomethyl)pyrimidine, which was used in the next step without further purification; $^1$H NMR (400 MHz, DMSO-$d_6$): δ 4.68 (s, 2H), 7.46 (t, J=4.9 Hz, 1H), 8.84 (d, J=4.9 Hz, 2H).

6-methyl-2-sulfanylpyrimidin-4-ol (867 mg, 6.1 mmol) was dissolved in absolute ethanol (130 mL), and then triethylamine (3.75 mL, 27.3 mmol) and 2-(bromomethyl)pyrimidine (1.57 g, 9.1 mmol) were added. The mixture was stirred overnight at room temperature. The solid was removed by filtration, and the filtrate was evaporated. The residue was triturated in water, filtered, and washed with water followed with diethyl ether. The solid was then dissolved in DCM and purified on silica gel using 10% DCM/MeOH to afford 6-methyl-2-[(pyrimidin-2-ylmethyl)sulfanyl]pyrimidin-4-ol (326 mg, 23% yield); $^1$H NMR (400 MHz, DMSO-$d_6$): δ 2.13 (s, 3H), 4.67 (s, 2H), 6.02 (bs, 1H), 7.42 (t, J=4.9 Hz, 1H), 8.78 (d, J=4.9 Hz, 2H); LRMS (ES$^+$) m/z 235 (100%, M+1).

6-methyl-2-[(pyrimidin-2-ylmethyl)sulfanyl]pyrimidin-4-ol (100 mg, 427 µmol) was stirred in methanol (10 mL), and a solution of 4 N HCl in dioxane (320 µL, 1.28 mmol) was added dropwise at 0° C. The mixture was stirred for 20 minutes at room temperature. The solvent was removed by evaporation, and the residue was triturated with diethyl ether, filtered, washed with ether, and dried in vacuo to afford 6-methyl-2-[(pyrimidin-2-ylmethyl)sulfanyl]pyrimidin-4-ol dihydrochloride (105 mg, 80% yield); $^1$H NMR (400 MHz, DMSO-$d_6$): δ 2.15 (s, 3H), 4.68 (s, 2H), 6.05 (bs, 1H), 7.44 (t, J=4.9 Hz, 1H), 8.79 (d, J=4.9 Hz, 2H); LRMS (ES$^+$) m/z 235 (100%, M+1).

Example 152

2-({[6-(4-ethylpiperazin-1-yl)pyridin-3-yl]methyl}sulfanyl)-6-methylpyrimidin-4-ol

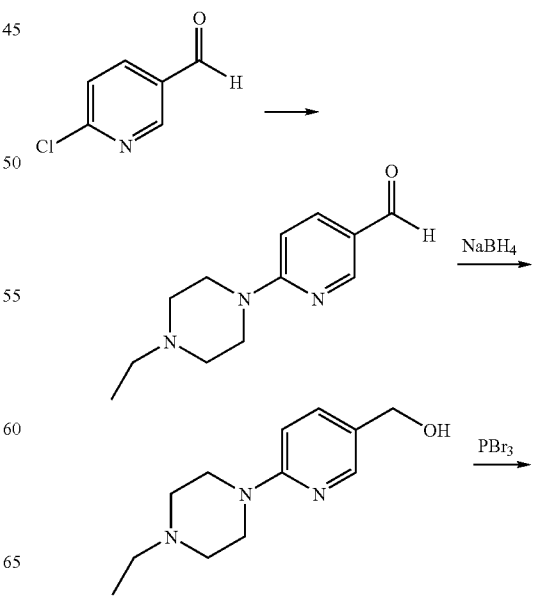

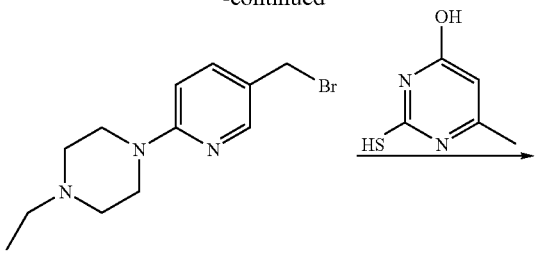

4H), 4.23 (s, 2H), 6.01 (bs, 1H), 6.78 (d, J=8.8 Hz, 1H), 7.58 (d, J=8.8 Hz, 1H), 8.14 (s, 1H); LRMS (ES⁺) m/z 345.6.

Example 153

2-({[2-chloro-6-(4-ethylpiperazin-1-yl)pyridin-3-yl]methyl}sulfanyl)-6-methylpyrimidin-4-ol and 2-({[6-chloro-2-(4-ethylpiperazin-1-yl)pyridin-3-yl]methyl}sulfanyl)-6-methylpyrimidin-4-ol

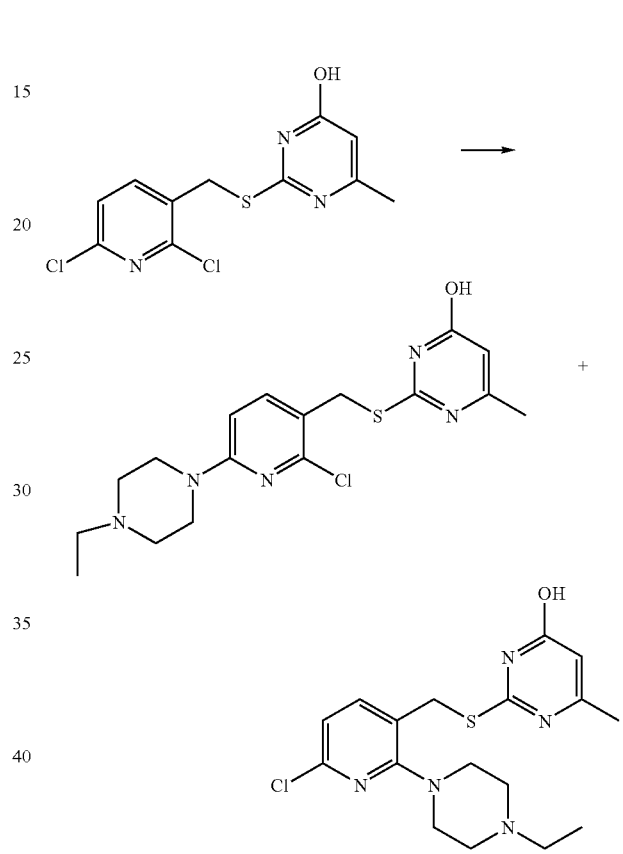

6-chloropyridine-3-carbaldehyde (5.0 g, 35.32 mmol) and 1-ethylpiperazine (20.16 g, 176.60 mmol, 22.42 mL) were heated overnight in a mixture of DMF/water (1:1, 40 mL) at 100° C. The reaction mixture was extracted with ethyl acetate (2×100 mL). The organic layer was dried over anhydrous sodium sulfate and filtered. The filtrate was evaporated to dryness to provide 6-(4-ethylpiperazin-1-yl)pyridine-3-carbaldehyde, which was used in the next reaction without any further purification (6.91 g, 89% yield); ¹H NMR (400 MHz, DMSO-d₆): δ 0.99 (t, 3H), 2.31 (q, 2H), 2.39 (m, 4H), 3.66 (m, 4H), 6.91 (d, J=9.2 Hz, 1H), 7.82 (d, J=9.2 Hz, 1H), 8.55 (s, 1H), 9.7 (s, 1H); LRMS (ES) m/z 219.8.

To a solution of 6-(4-ethylpiperazin-1-yl)pyridine-3-carbaldehyde (6.9 g, 31.46 mmol) in anhydrous ethanol (80 mL) was added at 0° C. sodium borohydride (2.38 g, 62.93 mmol). The reaction mixture was stirred at room temperature for 1 hour and then quenched with water. The solvent was evaporated, and the mixture was extracted with ethyl acetate (2×200 mL). The organic layer was separated, dried over anhydrous sodium sulfate, and filtered. The filtrate was evaporated to provide [6-(4-ethylpiperazin-1-yl)pyridin-3-yl]methanol as a syrup (6.61 g, 95% yield); ¹H NMR (400 MHz, DMSO-d₆): δ 0.99 (t, 3H), 2.31 (q, 2H), 2.39 (m, 4H), 3.42 (m, 4H), 4.32 (s, 2H), 4.98 (s, 1H), 6.78 (d, J=8.6 Hz, 1H), 7.82 (d, J=8.6 Hz, 1H), 8.01 (s, 1H); LRMS (ES⁺) m/z 221.3.

To a solution of [6-(4-ethylpiperazin-1-yl)pyridin-3-yl]methanol (3.0 g, 13.55 mmol) in anhydrous chloroform was added at 0° C. tribromophosphane (4.03 g, 14.91 mmol). The reaction mixture was allowed to stir at room temperature for 3 hours. The solvent was evaporated to provide 1-[5-(bromomethyl)pyridin-2-yl]-4-ethylpiperazine (3.85 g), which was used in the next step without any further purification.

To a suspension of 1-[5-(bromomethyl)pyridin-2-yl]-4-ethylpiperazine (3.85 g, 13.54 mmol) and 6-methyl-2-sulfanylpyrimidin-4-ol (1.25 g, 8.86 mmol) in anhydrous ethanol at 0° C. was added triethylamine (5.47 g, 54.18 mmol). The reaction mixture was stirred overnight at room temperature. The solvent was evaporated, and the residue was purified by column chromatography using 0-15% methanol:dichloromethane to provide (2-({[6-(4-ethylpiperazin-1-yl)pyridin-3-yl]methyl}sulfanyl)-6-methylpyrimidin-4-ol as a white solid (1.82 g, 39% yield); ¹H NMR (400 MHz, DMSO-d₆): δ 0.99 (t, 3H), 2.18 (s, 3H), 2.31 (q, 2H), 2.56 (m, 4H), 3.42 (m, 4H), 4.23 (s, 2H), 6.01 (bs, 1H), 6.78 (d, J=8.8 Hz, 1H), 7.58 (d, J=8.8 Hz, 1H), 8.14 (s, 1H); LRMS (ES⁺) m/z 345.6.

A mixture of 2-{[(2,6-dichloropyridin-3-yl)methyl]sulfanyl}-6-methylpyrimidin-4-ol (2.0 g, 6.61 mmol) and 1-ethylpiperazine (3.77 g, 26.88 mmol) was heated in DMSO (20 mL) at 90° C. overnight. After cooling, the mixture was extracted with ethyl acetate (2×100 mL). The organic layer was separated and washed with water and brine. The organic layer was dried over anhydrous sodium sulfate and filtered. The filtrate was evaporated to dryness and purified by CombiFlash chromatography using 0-20% dichloromethane:methanol to provide 2-({[2-chloro-6-(4-ethylpiperazin-1-yl)pyridin-3-yl]methyl}sulfanyl)-6-methylpyrimidin-4-ol (¹H NMR (400 MHz, DMSO-d₆): δ 1.02 (t, 3H), 2.18 (s, 3H), 2.31 (q, 2H), 2.56 (m, 4H), 3.42 (m, 4H), 4.30 (s, 2H), 6.01 (bs, 1H), 6.78 (d, J=8.4 Hz, 1H), 7.72 (d, J=8.4 Hz, 1H), LRMS (ES⁺) m/z 379.8) and 2-({[6-chloro-2-(4-ethylpiperazin-1-yl)pyridin-3-yl]methyl}sulfanyl)-6-methylpyrimidin-4-ol (¹H NMR (400 MHz, DMSO-d₆): δ 0.99 (t, 3H), 2.21 (s, 3H), 2.31 (q, 2H), 2.56 (m, 4H), 3.42 (m, 4H), 4.37 (s, 2H), 6.01 (bs, 1H), 7.06 (d, J=7.7 Hz, 1H), 7.77 (d, J=7.7 Hz, 1H), LRMS (ES⁺) m/z 379.8) as a white solid (1.73 g, 3:1 ratio, 69% yield).

Example 154

6-methyl-2-[(pyrimidin-5-ylmethyl)sulfanyl]pyrimidin-4-ol

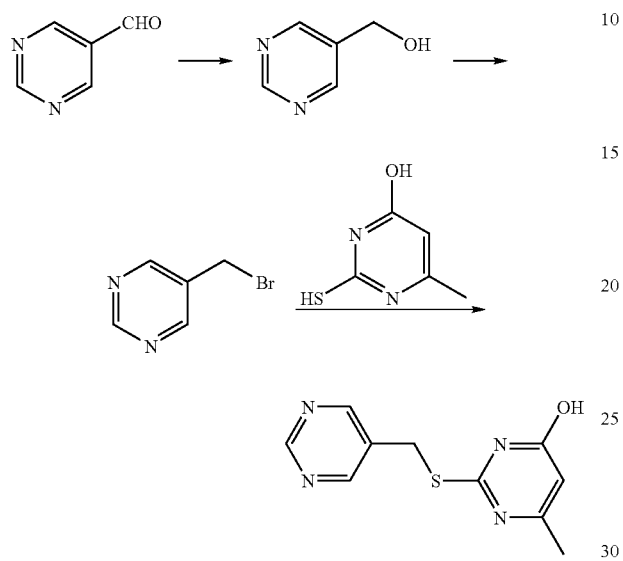

To a solution of sodium borohydride (525 mg, 13.9 mmol) in anhydrous methanol (25 mL) was added a solution of pyrimidine-5-carbaldehyde (1.0 g, 9.2 mmol) in anhydrous methanol (5 mL) at 0° C. The mixture was stirred for 2.5 hours at room temperature. Water was added, and the mixture was extracted 3 times with ethyl acetate. The organic phase was washed with brine and dried over sodium sulfate. After evaporation of the solvent, pyrimidin-5-ylmethanol was obtained (300 mg, 29% yield) and used in the next step without further purification; $^1$H NMR (400 MHz, CDCl$_3$): δ 4.79 (s, 2H), 8.77 (s, 2H), 9.17 (s, 1H).

To a solution of pyrimidin-5-ylmethanol (560 mg, 5.1 mmol) in anhydrous chloroform (20 mL) was added dropwise a solution of tribromophosphane (480 μL, 5.1 mmol) in anhydrous chloroform (5 mL) at 0° C. The mixture was stirred overnight at room temperature. The mixture was evaporated, and crude 5-(bromomethyl)pyrimidine was used in the next step without further purification; $^1$H NMR (400 MHz, DMSO-d$_6$): δ 4.76 (s, 2H), 8.92 (s, 2H), 9.14 (s, 1H).

6-methyl-2-sulfanylpyrimidin-4-ol (483 mg, 3.4 mmol) was dissolved in absolute ethanol (70 mL), and triethylamine (1.4 mL, 10.2 mmol) and 5-(bromomethyl)pyrimidine (882 mg, 5.1 mmol) were added. The mixture was stirred overnight at room temperature. The solid was filtered. The filtrate was evaporated. The residue was triturated in water, filtered, and washed with water followed with diethyl ether. The solid was dissolved in DCM and purified on silica gel using 10% DCM/MeOH to afford 6-methyl-2-[(pyrimidin-5-ylmethyl)sulfanyl]pyrimidin-4-ol (12 mg, 2% yield); $^1$H NMR (400 MHz, DMSO-d$_6$): δ 2.19 (s, 3H), 4.34 (s, 2H), 6.02 (bs, 1H), 8.88 (s, 2H), 9.05 (s, 1H); LRMS (ES) m/z 235 (100%, M+1).

Example 155

2-{[(3,5-diethyl-1,2-oxazol-4-yl)methyl]sulfanyl}-6-methylpyrimidin-4-ol

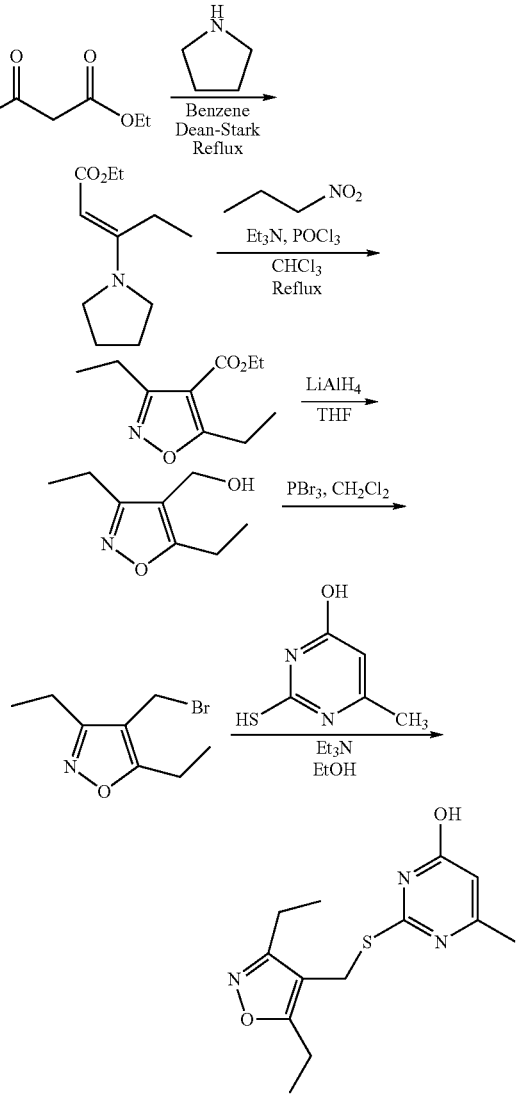

Ethyl 3-oxopentanoate (2.5 mL, 17.6 mmole) and pyrrolidine (1.4 mL, 17.1 mmole) were dissolved in benzene and added to a 100 mL flask fitted with a Dean-Stark water separator. The reaction was stirred at reflux for 3 hours. After cooling to room temperature, the solvent was evaporated under reduced pressure and the product was dried in vacuo, affording ethyl 3-(pyrrolidin-1-yl)pent-2-enoate (3.4 g, 98% yield). The product was used without further purification.

To a 0° C. solution of 3-(pyrrolidin-1-yl)pent-2-enoate (3.4 g, 17.2 mmol), 1-nitropropane (2.0 mL, 22.2 mmol), and triethylamine (7.5 mL, 53.4 mmol) in anhydrous chloroform (20 mL) was added a solution of phosphoryl trichloride (4.0 mL, 42.9 mmol) in anhydrous chloroform (6 mL) via syringe pump (1 hour). The reaction mixture was allowed to warm to room temperature and stirred overnight. The mixture was then stirred at reflux for 1 hour. After cooling to room temperature, the mixture was extracted with water (3×20 mL), 2

N HCl (2×20 mL), and brine (1×20 mL). The organic layer was recovered, dried over MgSO₄, filtered, evaporated, and dried in vacuo. The crude product was purified by flash chromatography (0-15% ethyl acetate/hexane), affording ethyl 3,5-diethyl-1,2-oxazole-4-carboxylate (830 mg, 25%).

To a 0° C. mixture of LAH (270 mg, 7.1 mmol) in anhydrous THF (10 mL) was slowly added a solution of ethyl 3,5-diethyl-1,2-oxazole-4-carboxylate (826 mg, 4.7 mmol) in anhydrous THF (10 mL). The mixture was stirred at 0° C. for 5 hours, and the mixture was then quenched with 5 N NaOH. Water (50 mL) and EtOAc (50 mL) were added. The mixture was stirred for 30 minutes. The solids were filtered, and the organic layer was recovered. The aqueous layer was extracted with EtOAc (1×50 mL). The combined organic extracts were washed with brine (1×200 mL), dried over MgSO₄, filtered, evaporated, and dried in vacuo, affording (3,5-diethyl-1,2-oxazol-4-yl)methanol (710 mg, 97% yield), which was used without further purification.

To a solution of (3,5-diethyl-1,2-oxazol-4-yl)methanol (710 mg, 4.6 mmol) in anhydrous DCM (30 mL) was added tribromophosphane (465 µL, 4.9 mmol). The mixture was stirred at room temperature for 5 hours, and then DCM was evaporated. The residue was dried in vacuo, affording 4-(bromomethyl)-3,5-diethyl-1,2-oxazole, which was used without further purification.

A mixture of 4-(bromomethyl)-3,5-diethyl-1,2-oxazole (4.6 mmol), 6-methyl-2-sulfanylpyrimidin-4-ol (440 mg, 3.3 mmol), and triethylamine (1.3 mL, 9.3 mmol) in absolute ethanol (35 mL) was stirred at room temperature overnight. The mixture was evaporated. The residue was treated with water (50 mL). The solid material was removed by filtration. The solid was washed with diethyl ether (3×25 mL). The filtrate was recovered, extracted with water (2×75 mL), dried over MgSO₄, filtered, evaporated, and dried in vacuo, affording the title compound (220 mg, 30% yield); ¹H NMR (400 MHz, DMSO-d₆): δ 1.18 (m, 6H), 2.21 (s, 3H), 2.65 (m, 2H), 2.83 (m, 2H), 4.22 (s, 2H), 6.02 (s, 1H); M+ 280.

Example 156

2-[({2-chloro-6-[(diethylamino)methyl]phenyl}methyl)sulfanyl]-6-methylpyrimidin-4-ol

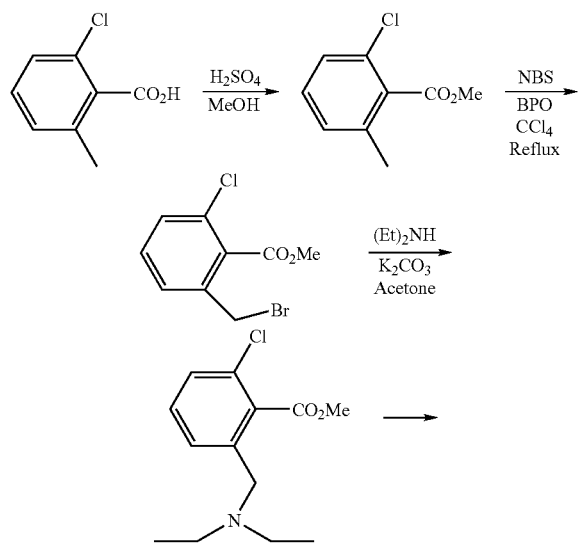

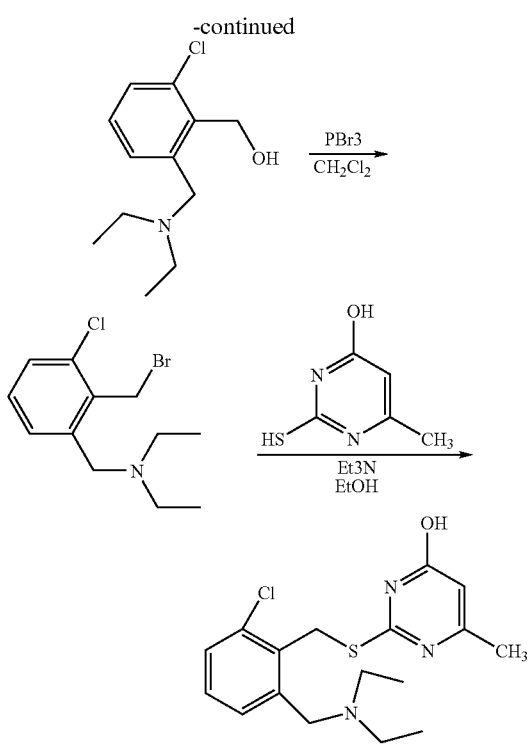

A mixture of 2-chloro-6-methylbenzoic acid (4.0 g, 23.4 mmol) in methanol (50 mL) and a few drops of concentrated sulfuric acid were stirred at reflux for 5 hours. After cooling to room temperature, methanol was evaporated, and the residue was dissolved in ethyl acetate (50 mL). The solution was extracted with saturated NaHCO₃ (3×50 mL). The organic layer was dried over MgSO₄, filtered, evaporated, and dried in vacuo, affording methyl 2-chloro-6-methylbenzoate (3.07 g, 71% yield). The product was used without further purification.

A mixture of methyl 2-chloro-6-methylbenzoate (3.0 g, 16.2 mmol), N-bromosuccinimide (3.0 g, 17.0 mmol), and benzoyl peroxide (catalytic) in anhydrous carbon tetrachloride (50 mL) was stirred at reflux overnight. Dichloromethane (50 mL) was added after cooling to room temperature. The mixture was extracted with 1 N NaOH (2×100 mL). The organic layer was recovered, dried over MgSO₄, filtered, and evaporated, and the residue was dried in vacuo, affording methyl 2-(bromomethyl)-6-chlorobenzoate (4.06 g, 95% yield), which was used without further purification.

A mixture of methyl 2-(bromomethyl)-6-chlorobenzoate (4.0 g, 15.6 mmol), diethylamine (5 mL, 48.1 mmol), and potassium carbonate (4.3 g, 31.2 mmol) in acetone (60 mL) was stirred at room temperature for 2 days. The solid material was removed by filtration. The filtrate was recovered, evaporated, and dried in vacuo, affording methyl 2-chloro-6-[(diethylamino)methyl]benzoate (3.97 g, 99% yield), which was used without further purification.

To methyl 2-chloro-6-[(diethylamino)methyl]benzoate (3.97 g, 15.5 mmol) in anhydrous THF (100 mL) was added a solution of diisobutylaluminium hydride (1 M in toluene, 35 mL, 35 mmol). The reaction mixture was stirred at room temperature for 90 minutes. A Rochelle's salt solution (200 mL) and dichloromethane (200 mL) were added. The mixture was stirred at room temperature for 2 hours. The organic layer was recovered, dried over MgSO₄, filtered, evaporated, and dried in vacuo, affording {2-chloro-6-[(diethylamino)methyl]phenyl}methanol (3.0 mg, 85% yield), which was used without further purification.

To {2-chloro-6-[(diethylamino)methyl]phenyl}methanol (3.0 g, 13.2 mmol) in anhydrous dichloromethane (80 mL) was added dropwise tribromophosphane (2.5 mL, 26.4 mmol). The mixture was stirred at room temperature overnight. The solvent was evaporated, and the residue was dried in vacuo, affording {[2-(bromomethyl)-3-chlorophenyl]methyl}diethylamine. The product was used without further purification.

A mixture of {[2-(bromomethyl)-3-chlorophenyl]methyl}diethylamine (13.2 mmol), 6-methyl-2-sulfanylpyrimidin-4-ol (1.07 g, 7.5 mmol), and triethylamine (8 mL, 57.4 mmol) in absolute ethanol (50 mL) was stirred at room temperature overnight. The mixture was evaporated and then co-evaporated with EtOAc (20 mL). The solid residue was treated with water (100 mL), and the solution was extracted with dichloromethane (5×100 mL). The organic extracts were combined, dried over MgSO$_4$, filtered, evaporated, and dried in vacuo. The crude product was purified by flash chromatography (0-15% MeOH/CH$_2$Cl$_2$), affording 2-[({2-chloro-6-[(diethylamino)methyl]phenyl}methyl)sulfanyl]-6-methylpyrimidin-4-ol (932 mg, 39% yield); $^1$H NMR (400 MHz, DMSO-d$_6$): δ 0.96 (t, 6H, J=6.8 Hz), 2.21 (s, 3H), 2.86 (m, 4H), 4.69 (s, 2H), 6.01 (s 1H), 7.35 (m, 1H), 7.42 (m, 1H); M+ 352.

Example 157

2-{[(3,5-dichloropyridin-4-yl)methyl]sulfanyl}-5-methylpyrimidin-4-ol

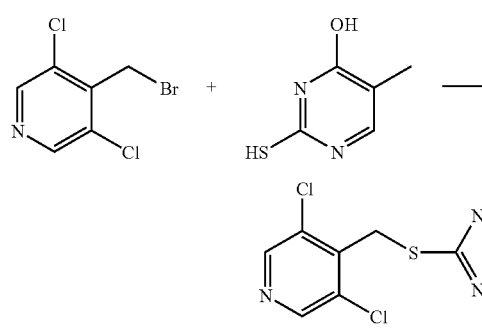

To a mixture of 4-(bromomethyl)-3,5-dichloropyridine (1.0 g, 4.15 mmol) and 5-methyl-2-sulfanylpyrimidin-4-ol (0.38 g, 2.69 mmol) in anhydrous ethanol (25 mL) at 0° C. was added triethylamine (1.67 g, 16.6 mmol). The reaction mixture was stirred at room temperature overnight. The solvent was evaporated, water was added, and the mixture was sonicated and then filtered. The solid was washed with water and hexane to provide 2-{[(3,5-dichloropyridin-4-yl)methyl]sulfanyl}-5-methylpyrimidin-4-ol (0.817 g, 65% yield); $^1$H NMR (400 MHz, DMSO-d$_6$): δ 1.90 (s, 3H), 4.66 (s, 2H), 7.99 (s 1H), 8.66 (s, 2H); M+ 302.5.

Example 158

2-{[(3,5-dichloropyridin-4-yl)methyl]sulfanyl}-6-methylpyrimidine-4-thiol

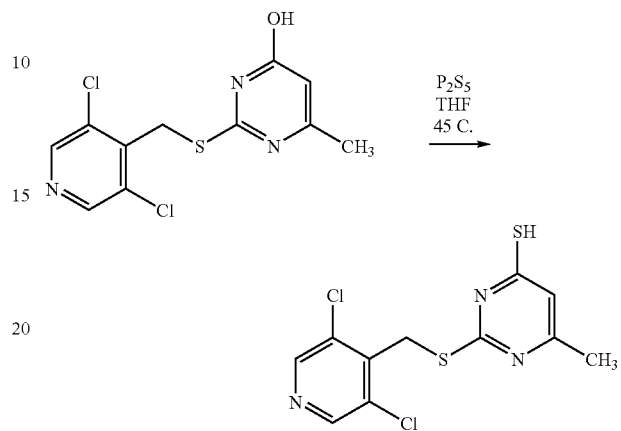

A mixture of 2-{[(3,5-dichloropyridin-4-yl)methyl]sulfanyl}-6-methylpyrimidin-4-ol (500 mg, 1.6 mmol) and phosphorous pentasulfide (756 mg, 1.7 mmol) in anhydrous THF (15 mL) was stirred at 45° C. overnight. More phosphorous pentasulfide (377 mg, 0.85 mmol) was added, and the mixture was stirred at 45° C. overnight. The solid was removed by filtration, and the recovered filtrate was evaporated. The crude product was purified by flash chromatography (0-10% MeOH/DCM). The recovered solid was triturated with 25% Et$_2$O/hexanes. The solid material was recovered by filtration and dried in vacuo, affording the title compound (88 mg, 17% yield); $^1$H NMR (500 MHz, DMSO-d$_6$): δ2.13 (s, 3H), 4.60 (s, 2H), 6.90 (s, 1H), 8.62 (s, 2H); M+ 319.

Example 159

2-{[(3,5-dichloropyridin-4-yl)(hydrogenio)methyl]sulfanyl}-6-(trifluoromethyl)pyrimidin-4-ol

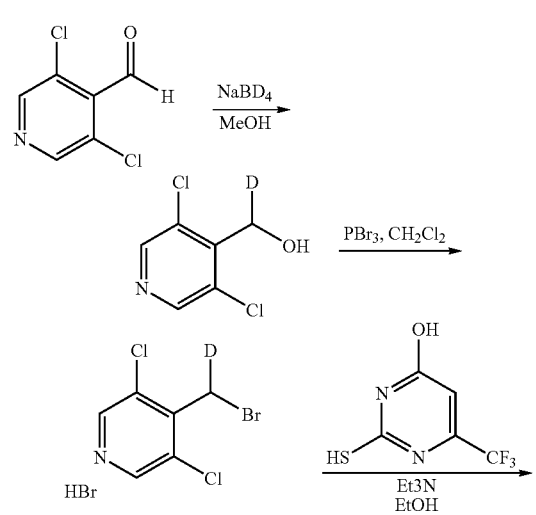

-continued

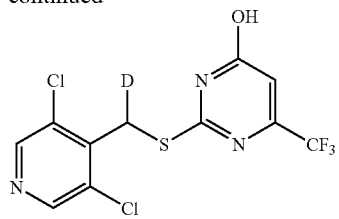

To a 0° C. solution of 3,5-dichloropyridine-4-carbaldehyde (1.0 g, 5.7 mmol) in anhydrous methanol (20 mL) was added sodium borodeuteride (500 mg, 11.9 mmol). The reaction mixture was stirred at room temperature for 1.5 hours. Water (20 mL) was added, and MeOH was evaporated. The resultant mixture was extracted with EtOAc (3×20 mL). The organic extracts were combined, dried over MgSO₄, filtered, evaporated, and dried in vacuo, affording (3,5-dichloropyridin-4-yl)(hydrogenio)methanol (800 mg, 78% yield). The product was used without further purification.

To a solution of (3,5-dichloropyridin-4-yl)(hydrogenio) methanol (800 mg, 4.5 mmol) in anhydrous dichloromethane (30 mL) was added tribromophosphane (475 μL, 5.0 mmol). The mixture was stirred at room temperature overnight. Dichloromethane was evaporated, and the residue was dried in vacuo, affording 4-[bromo(hydrogenio)methyl]-3,5-dichloropyridine hydrobromide. The crude product was used without further purification.

To a 0° C. mixture of 4-[bromo(hydrogenio)methyl]-3,5-dichloropyridine hydrobromide (4.5 mmol) and 2-sulfanyl-6-(trifluoromethyl)pyrimidin-4-ol (588 mg, 3.0 mmol) in absolute ethanol (40 mL) was added triethylamine (2.1 mL, 15 mmol). The mixture was stirred at room temperature overnight. The solid precipitate was removed by filtration. Diethyl ether (200 mL) was added to the filtrate. The precipitate was removed by filtration. The filtrate was evaporated, co-evaporated with EtOAc (25 mL), and dried in vacuo. The residue was treated with water (200 mL). The solid material was recovered by filtration and washed with water (3×25 mL) and hexanes (3×25 mL). The solid material was dried in vacuo, affording the title compound (728 mg, 68% yield); ¹H NMR (400 MHz, DMSO-d₆): δ 4.74 (s, 1H), 6.72 (s, 1H), 8.67 (s, 1H), 13.55 (s (br), 1H); M– 356.

Example 160

6-methyl-2-[(quinoxalin-2-ylmethyl)sulfanyl]pyrimidin-4-ol dihydrochloride

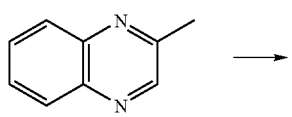

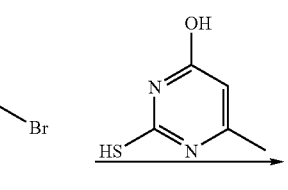

-continued

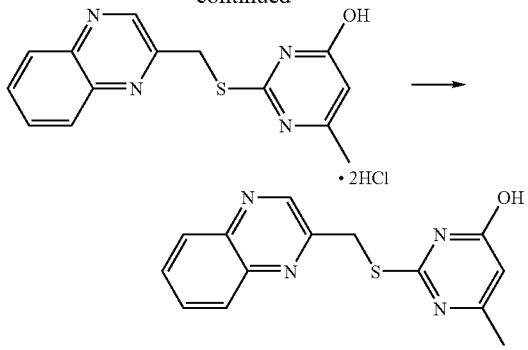

2-methylquinoxaline (1 g, 6.9 mmol) was dissolved in CCl₄ (15 mL), and then 1-bromopyrrolidine-2,5-dione (1.8 g, 10.4 mmol) and benzoyl benzenecarboperoxoate (1.0 g, 4.2 mmol) were added. The mixture was stirred overnight at reflux. The solids were removed by filtration. The filtrate was washed with brine and dried over sodium sulfate. After evaporation of the solvent, the residue was dissolved in DCM and purified on silica gel using 40% hexane/AcOEt to afford 2-(bromomethyl)quinoxaline (714 mg, 46% yield); ¹H NMR (400 MHz, DMSO-d₆): δ 4.94 (s, 2H), 7.84-7.90 (m, 2H), 8.04-8.11 (m, 2H), 9.09 (s, 1H).

6-methyl-2-sulfanylpyrimidin-4-ol (245 mg, 1.7 mmol) was dissolved in anhydrous DMF (10 mL), and then were added potassium carbonate (357 mg, 2.6 mmol) and 2-(bromomethyl)quinoxaline (500 mg, 2.2 mmol) in anhydrous DMF (5 mL). The mixture was stirred over a weekend at room temperature. The solvent was removed by evaporation, and the residue was dissolved in DCM and purified on silica gel using 10% DCM/MeOH to afford 6-methyl-2-[(quinoxalin-2-ylmethyl)sulfanyl]pyrimidin-4-ol (363 mg, 57% yield); ¹H NMR (400 MHz, DMSO-d₆): δ 2.17 (s, 3H), 4.72 (s, 2H), 6.01 (bs, 1H), 7.81-7.88 (m, 2H), 8.03-8.11 (m, 2H), 9.10 (s, 1H); LRMS (ES⁺) m/z 285 (100%, M+1).

6-methyl-2-[(quinoxalin-2-ylmethyl)sulfanyl]pyrimidin-4-ol (250 mg, 879 μmol) was stirred in methanol (25 mL) and a solution of 4 N HCl in dioxane (660 μL, 2.63 mmol) was added dropwise at 0° C. The mixture was stirred for 20 minutes at room temperature. The solvent was removed by evaporation, and the residue was triturated with diethyl ether, filtered, washed with ether, and dried in vacuo to afford 6-methyl-2-[(quinoxalin-2-ylmethyl)sulfanyl]pyrimidin-4-ol dihydrochloride (289 mg, 92% yield); ¹H NMR (400 MHz, DMSO-d₆): δ 2.20 (s, 3H), 4.74 (s, 2H), 6.10 (s, 1H), 7.82-7.89 (m, 2H), 8.03-8.11 (m, 2H), 9.12 (s, 1H); LRMS (ES⁺) m/z 285 (100%, M+1).

Example 161

2-{[(3-chloro-5-methylpyridin-4-yl)methyl]sulfanyl}-6-methylpyrimidin-4-yl acetate

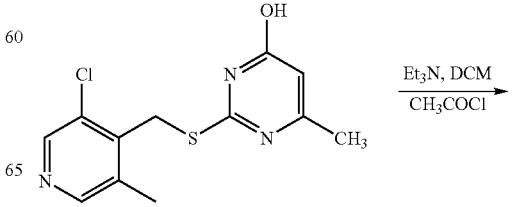

-continued

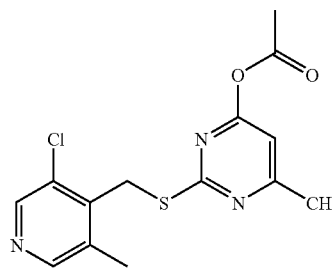

In a 250 mL round bottom flask, 2-{[(3-chloro-5-methylpyridin-4-yl)methyl]sulfanyl}-6-methylpyrimidin-4-ol (565 mg, 2.0 mmol) was dissolved in dichloromethane (25 mL). Acetyl chloride (0.21 mL, 3.0 mmol) was added, followed by triethylamine (0.42 mL, 3.0 mmol). After 30 minutes, the reaction mixture was evaporated. The crude product was purified by column chromatography (0–35% ethyl acetate/hexane) to provide 2-{[(3-chloro-5-methylpyridin-4-yl)methyl]sulfanyl}-6-methylpyrimidin-4-yl acetate as a white solid (500 mg, 77% yield); $^1$H NMR (500 MHz, CDCl$_3$): δ 2.35 (s, 3H), 2.45 (s, 3H), 2.52 (s, 3H), 4.57 (s, 2H), 6.73 (s, 1H), 8.29 (s, 1H), 8.44 (s, 1H); M+ 324.

Example 162

2-{[(3,5-dichloropyridin-4-yl)methane]sulfinyl}-6-(trifluoromethyl)pyrimidin-4-ol

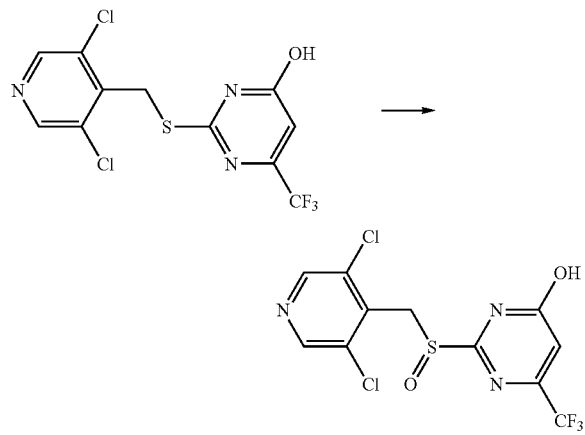

2-{[(3,5-dichloropyridin-4-yl)methyl]sulfanyl}-6-(trifluoromethyl)pyrimidin-4-ol (300 mg, 840 μmol) was dissolved in anhydrous dichloromethane (10 mL). A solution of 3-chlorobenzene-1-carboperoxoic acid (208 mg, 927 μmol, 77%) in anhydrous dichloromethane (5 mL) was added portionwise at 0° C. over 10 minutes. The mixture was stirred overnight, and the white solid was filtered, rinsed with dichloromethane, and dried in vacuo to afford pure 2-{[(3,5-dichloropyridin-4-yl)methane]sulfinyl}-6-(trifluoromethyl)pyrimidin-4-ol (187 mg, 60% yield); $^1$H NMR (500 MHz, DMSO-d$_6$): δ 4.73 (s, 2H), 7.26 (s, 1H), 8.65 (s, 2H); LRMS (ES$^+$) m/z 372 (80%, M+1), 374 (70%, M+3).

Example 163

2-{[(4-ethyl-1,3-thiazol-5-yl)methyl]sulfanyl}-6-methylpyrimidin-4-ol

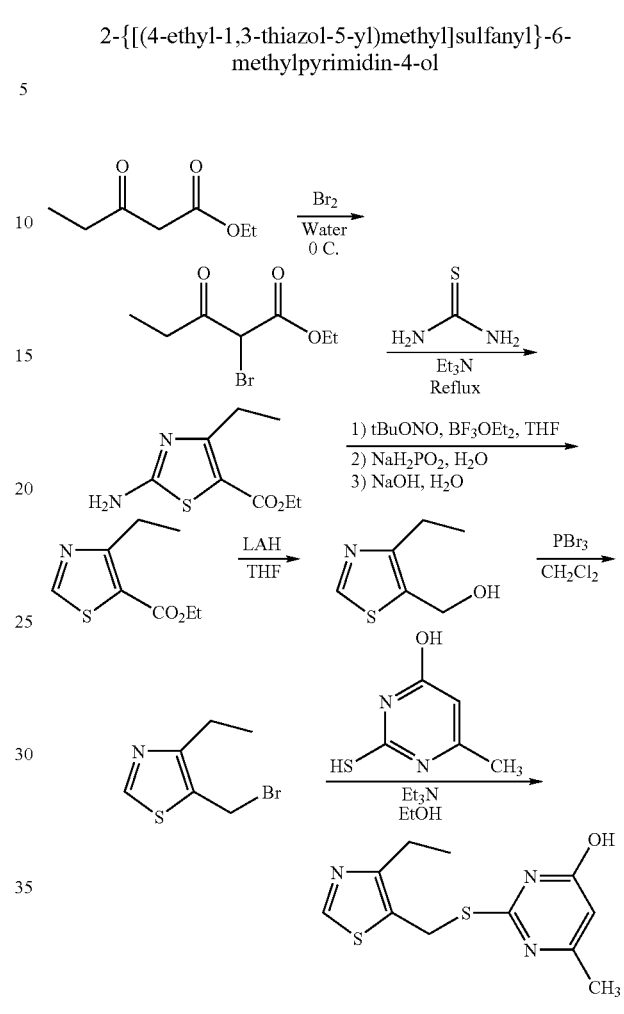

To a 0° C. solution of ethyl 3-oxopentanoate (5.0 mL, 34.7 mmol) in water (30 mL) was added bromine (1.8 mL, 35.0 mmol) via syringe pump (0.5 hour). The mixture was stirred at 0° C. for 0.5 hour. The solution was extracted with EtOAc (2×35 mL). The organic extracts were combined, dried over MgSO$_4$, filtered, evaporated, and dried in vacuo, affording ethyl 2-bromo-3-oxopentanoate (7.3 g, 94% yield). The product was used without further purification.

To a refluxing solution of thiourea (2.6 g, 34.3 mmol) in absolute ethanol (30 mL) was slowly added at reflux ethyl 2-bromo-3-oxopentanoate (7.3 g, 32.7 mmol). The solution was stirred at reflux for 1.5 hours. After cooling to room temperature, the solution was poured in ice/water (150 mL). The mixture was neutralized with concentrated NH$_4$OH. The solid material was recovered by filtration, washed with water (2×50 mL) and hexanes (3×50 mL), and dried in vacuo, affording ethyl 2-amino-4-ethyl-1,3-thiazole-5-carboxylate (6.8 g, 94% yield). The product was used without further purification.

To a 0° C. solution of ethyl 2-amino-4-ethyl-1,3-thiazole-5-carboxylate (2.6 g, 13.0 mmol) in anhydrous THF (40 mL) was added boron trifluoride diethyl etherate (2.0 mL, 16.5 mmol). After 15 minutes of stirring at 0° C., tert-butyl nitrite (7 mL, 59 mmol) was added. The mixture was stirred at 0° C. for 3 hours, and then an aqueous solution of sodium hypophosphonate (4.1 g, 47 mmol, 15 mL) was added. The mixture was stirred at 0° C. for 2 hours and at room temperature overnight. The solution was basified to pH 8-9 with 5 N NaOH and then was extracted with EtOAc (3×75 mL). The organic extracts were combined, dried over MgSO$_4$, filtered, evaporated, and dried in vacuo, affording ethyl 4-ethyl-1,3-thiazole-5-carboxylate (1.91 g, 80% yield). The product was used without further purification.

To a 0° C. mixture of lithium aluminum hydride (800 mg, 21.0 mmol) in anhydrous THF (30 mL) was slowly added a solution of ethyl 4-ethyl-1,3-thiazole-5-carboxylate (1.91 g, 10.3 mmol) in anhydrous THF (50 mL). The reaction mixture was stirred at 0° C. for 1.5 hours. The reaction was quenched with 5 N NaOH. Water (150 mL) and EtOAc (150 mL) were added. The mixture was stirred for 30 minutes. The solid material was removed by filtration. The organic layer was recovered. The aqueous layer was extracted with EtOAc (1×100 mL). The combined organic extracts were back extracted with brine (2×200 mL), dried over MgSO$_4$, filtered, evaporated, and dried in vacuo, affording (4-ethyl-1,3-thiazol-5-yl)methanol (1.05 g, 71% yield). The product was used without further purification.

To a solution of (4-ethyl-1,3-thiazol-5-yl)methanol (1.0 g, 7.0 mmol) in anhydrous dichloromethane (50 mL) was added tribromophosphane (725 µL, 7.6 mmol). The mixture was stirred at room temperature for 2 hours. Dichloromethane was evaporated. The residue was dried in vacuo, affording 5-(bromomethyl)-4-ethyl-1,3-thiazole. The crude product was used without further purification.

A mixture of 5-(bromomethyl)-4-ethyl-1,3-thiazole (7.0 mmol), 6-methyl-2-sulfanylpyrimidin-4-ol (700 mg, 4.9 mmol), and triethylamine (3.0 mL, 21.5 mmol) in absolute ethanol (70 mL) was stirred at room temperature overnight. The mixture was evaporated, and the residue was treated with 50% diethyl ether/acetone (100 mL). The solid material was removed by filtration. The filtrate was recovered and evaporated. The crude product was purified by flash chromatography (0-10% MeOH/CH$_2$Cl$_2$). The column was repeated 4 times, affording the title compound (132 mg, 10% yield); $^1$H NMR (500 MHz, DMSO-d$_6$): δ 1.19 (t, 2H, J=7.5 Hz), 2.801 (m, 2H, J=7.5 Hz), 4.55 (s, 2H), 6.05 (s, 1H), 8.85 (s, 1H); M+ 268.

Example 164

2-{[(4-ethyl-1,3-thiazol-5-yl)methyl]sulfanyl}-6-(trifluoromethyl)pyrimidin-4-ol To a 0° C. solution of ethyl 3-oxopentanoate (5.0 mL, 34.7 mmol) in water (30 mL) was added bromine (1.8 mL, 35.0 mmol) via syringe pump addition (0.5 h). The mixture was stirred at 0° C. for 0.5 hour. The solution was extracted with EtOAc (2×35 mL). The organic extracts were combined, dried over MgSO$_4$, filtered, evaporated, and dried in vacuo, affording ethyl 2-bromo-3-oxopentanoate (7.3 g, 94% yield). The product was used without further purification.

To a refluxing solution of thiourea (2.6 g, 34.3 mmol) in absolute ethanol (30 mL) was added ethyl 2-bromo-3-oxopentanoate (7.3 g, 32.7 mmol) always keeping the mixture at reflux. The solution was stirred at reflux for another 1.5 hours. After cooling to room temperature, the solution was poured in ice/water (150 mL). The mixture was neutralized with concentrated NH$_4$OH. The solid material was recovered by filtration, washed with water (2×50 mL) and hexanes (3×50 mL), and dried in vacuo, affording ethyl 2-amino-4-ethyl-1,3-thiazole-5-carboxylate (6.8 g, 94% yield). The product was used without further purification.

To a 0° C. solution of ethyl 2-amino-4-ethyl-1,3-thiazole-5-carboxylate (4.0 g, 18.2 mmol) in anhydrous THF (65 mL) was added boron trifluoride diethyl etherate (3.2 mL, 25.5 mmol). After 15 minutes of stirring at 0° C. was added tert-butyl nitrite (10 mL, 84 mmol). The mixture was stirred at 0° C. for 3 hours before a solution of sodium hypophosphonate (6.4 g, 73 mmol) in water (20 mL) was added. The mixture was stirred at 0° C. for 2 hours and at room temperature overnight. The solution was basified to pH 8-9 with 5 N NaOH and was extracted with EtOAc (3×75 mL). The organic extracts were combined, dried over MgSO$_4$, filtered, evaporated, and dried in vacuo, affording ethyl 4-ethyl-1,3-thiazole-5-carboxylate (3.19 g, 85% yield). The product was used without further purification.

To a 0° C. mixture of lithium aluminum hydride (1.2 g, 31.2 mmol) in anhydrous THF (30 mL) was slowly added a solution of ethyl 4-ethyl-1,3-thiazole-5-carboxylate (3.19 g, 15.6 mmol) in anhydrous THF (40 mL). The reaction mixture was stirred at 0° C. for 1.5 hours. The reaction was quenched with 5 N NaOH. Water (100 mL) and EtOAc (100 mL) were added. The mixture was stirred for 30 minutes. The solid material was removed by filtration. The organic layer was recovered. The aqueous layer was extracted with EtOAc (1×100 mL). The combined organic extracts were dried over MgSO$_4$, filtered, evaporated, and dried in vacuo, affording (4-ethyl-1,3-

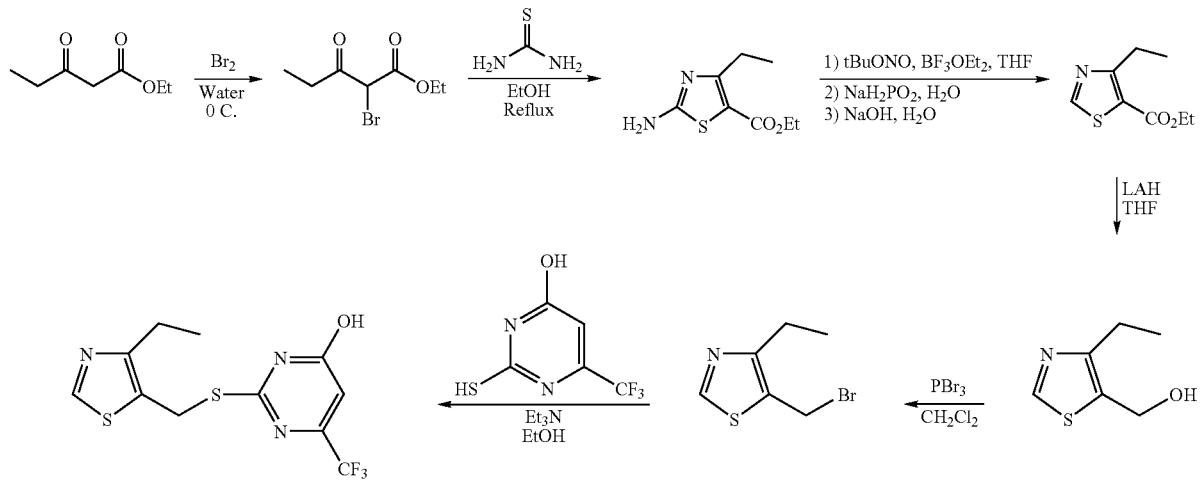

thiazol-5-yl)methanol (1.77 g, 79% yield). The product was used without further purification.

To a solution of (4-ethyl-1,3-thiazol-5-yl)methanol (740 mg, 5.2 mmol) in anhydrous dichloromethane (35 mL) was added tribromophosphane (550 μL, 5.7 mmol). The mixture was stirred at room temperature for 2 hours. Dichloromethane was evaporated. The residue was dried in vacuo, affording 5-(bromomethyl)-4-ethyl-1,3-thiazole. The crude product was used without further purification.

A mixture of 5-(bromomethyl)-4-ethyl-1,3-thiazole (5.2 mmol), 2-sulfanyl-6-(trifluoromethyl)pyrimidin-4-ol (700 mg, 3.6 mmol), and triethylamine (1.5 mL, 11 mmol) in absolute ethanol (40 mL) was stirred at room temperature overnight. The mixture was evaporated. The residue was treated with diethyl ether (100 mL). The solid material was removed by filtration. The filtrate was recovered and evaporated. The crude product was purified by flash chromatography (0-4% MeOH/CH$_2$Cl$_2$), affording the title compound (900 mg, 78% yield); $^1$H NMR (500 MHz, DMSO-d$_6$): δ 1.19 (t, 2H, J=7.5 Hz), 2.76 (m, 2H, J=7.5 Hz), 4.65 (s, 2H), 6.65 (s, 1H), 8.88 (s, 1H); M+ 322.

Example 165

2-{[(3,5-dimethylpyridin-4-yl)methyl]sulfanyl}-6-methylpyrimidin-4-ol hydrochloride

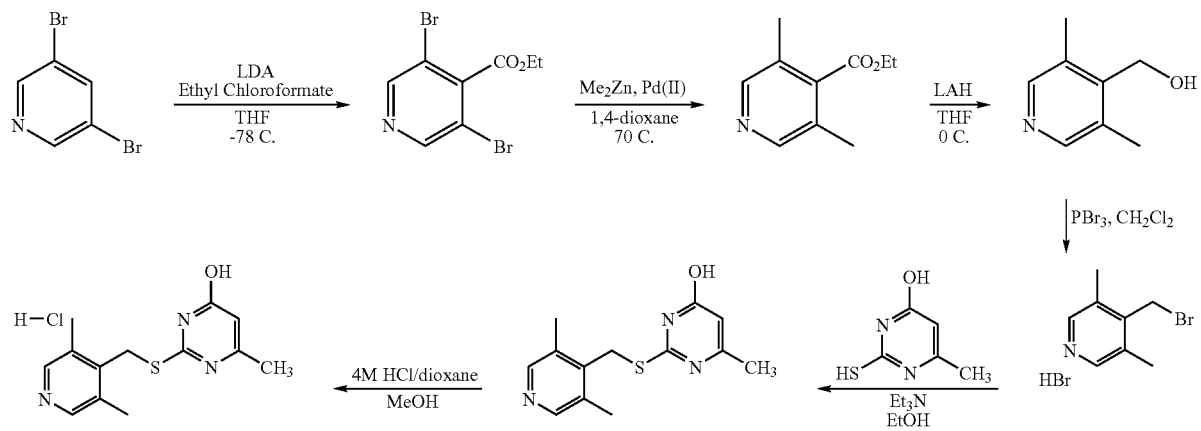

To a −78° C. solution of LDA (64 mL, 128 mmol, 2 M solution) in anhydrous THF (100 mL) was added a solution of 3,5-dibromopyridine (28 g, 118 mmol) in anhydrous THF (100 mL). The reaction mixture was stirred at −78° C. for 45 minutes. Then, a solution of ethyl chloroformate (100 mL, 105 mmol) was added slowly over 15 minutes. After stirring for 15 minutes, the reaction mixture was quenched with a saturated solution of NaHCO$_3$ (250 mL). The mixture was extracted into ethyl acetate (3×150 mL). The combined organic extracts were extracted with brine (2×400 mL), dried over MgSO$_4$, filtered, evaporated, and dried in vacuo. The crude product was purified by flash chromatography (0-20% ethyl acetate/hexane), affording ethyl 3,5-dibromopyridine-4-carboxylate (33 g, 91% yield).

To a solution of ethyl 3,5-dibromopyridine-4-carboxylate (20.0 g, 64.7 mmol) in anhydrous 1,4-dioxane (40 mL) at room temperature was added (1,1'-bis(diphenylphosphino) ferrocene dichloro palladium (II) (1.0 g. 1.3 mmol) followed by a dimethylzinc solution (35 mL, 70 mmol, 2 M solution in toluene). The mixture was stirred at 70° C. overnight. After cooling to room temperature, the reaction was quenched with MeOH and ethyl acetate (200 mL) was added. The mixture was extracted with 0.2 N HCl (200 mL). The organic layer was recovered. The pH of the aqueous phase was brought to 6 with 2 N NaOH. The mixture was extracted with EtOAc (2×100 mL). The combined organic extracts were dried over MgSO$_4$, filtered, evaporated, and dried in vacuo. The crude product was purified by flash chromatography (0-20% ethyl acetate/hexane), affording ethyl 3,5-dimethylpyridine-4-carboxylate (4.77 g, 41% yield).

To a 0° C. mixture of lithium aluminum hydride (2.0 g, 53 mmol) in anhydrous THF (100 mL) was slowly added a solution of ethyl 3,5-dimethylpyridine-4-carboxylate (4.77 g, 26.6 mmol) in anhydrous THF (30 mL). The reaction mixture was stirred at 0° C. for 1.5 hours. The reaction was quenched with 5 N NaOH. Water (100 mL) and EtOAc (100 mL) were added. The mixture was stirred for 30 minutes. The solid material was removed by filtration. The organic layer was recovered. The aqueous layer was extracted with EtOAc (2×50 mL). The combined organic extracts were dried over MgSO$_4$, filtered, evaporated, and dried in vacuo, affording (3,5-dimethylpyridin-4-yl)methanol (2.55 g, 70% yield). The product was used without further purification.

To a solution of (3,5-dimethylpyridin-4-yl)methanol (2.55 g, 18.6 mmol) in anhydrous dichloromethane (130 mL) was added tribromophosphane (2.0 mL, 21.1 mmol). The mixture was stirred at room temperature for 5 hours. Dichloromethane was evaporated. The residue was dried in vacuo, affording 4-(bromomethyl)-3,5-dimethylpyridine. The crude product was used without further purification.

To a 0° C. mixture of 4-(bromomethyl)-3,5-dimethylpyridine (18.6 mmol) and 6-methyl-2-sulfanylpyrimidin-4-ol (1.7 g, 12 mmol) in absolute ethanol (170 mL) was added triethylamine (8 mL, 57.4 mmol). The mixture was stirred at room temperature overnight. The solid precipitate was removed by filtration. Diethyl ether (300 mL) was added to the filtrate. The precipitate was removed by filtration. The filtrate was recovered, evaporated, and co-evaporated with EtOAc (1×50 mL). The residue was treated with water (300 mL). The solid material was recovered by filtration, washed with water (4×30 mL), diethyl ether (3×30 mL) and hexanes (2×30 mL), and dried in vacuo, affording 2-{[(3,5-dimethylpyridin-4-yl)methyl]sulfanyl}-6-methylpyrimidin-4-ol (1.78 g, 57% yield). The product was used without further purification.

To a 0° C. mixture of 2-{[(3,5-dimethylpyridin-4-yl)methyl]sulfanyl}-6-methylpyrimidin-4-ol (1.1 g, 3.8 mmol) in MeOH (15 mL) was added 4M HCl/dioxane (4 mL, 16 mmol). The solution was evaporated and dried in vacuo, affording the title compound (1.1 g, 97% yield); $^1$H NMR (500 MHz, DMSO-$d_6$): δ 2.23 (s, 3H), 2.56 (s, 6H), 4.65 (m, 2H), 4.44 (s, 2H), 6.15 (s, 1H), 8.69 (s, 1H); M+ 262.

Example 166

2-{[(4-acetyl-1,3-thiazol-5-yl)methyl]sulfanyl}-6-(trifluoromethyl)pyrimidin-4-ol

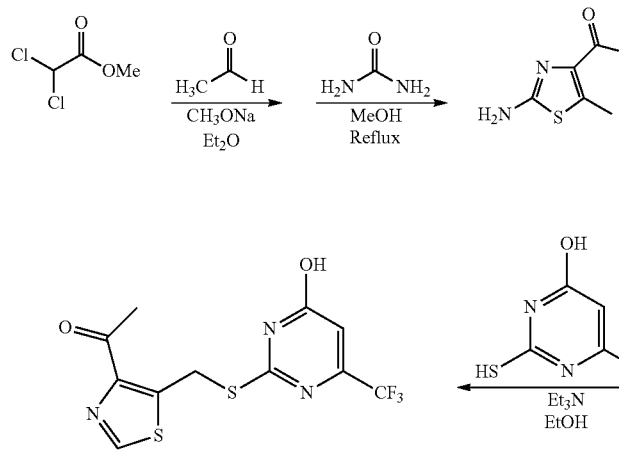

Sodium methoxide (25% wt solution, 50 mL) was added slowly to a 0° C. solution of methyl 2,2-dichloroacetate (25 mL, 261 mmol) and acetaldehyde (15 mL, 267 mmol) in 200 mL diethyl ether. The mixture was stirred at 0° C. for 1 hour. Water (100 mL) was added, and the organic layer was recovered. The aqueous phase was extracted with diethyl ether (2×100 mL). The organic extracts were combined, washed with brine (2×200 mL), dried over MgSO$_4$, filtered, evaporated, and dried in vacuo. The crude oil (29 g) was dissolved in MeOH (250 mL), and thiourea (15.5 g, 190 mmol) was added. The solution was stirred at reflux for 4 hours. After cooling to room temperature, the solvent was evaporated. The oily residue was dissolved in MeOH (50 mL). The solution was poured into ice/water (500 mL). The pH was brought to approximately 8-9 with concentrated ammonium hydroxide. The yellow solid material was recovered by filtration, washed with water (3×50 mL) and hexanes (3×50 mL), and dried in vacuo, affording methyl 2-amino-5-methyl-1,3-thiazole-4-carboxylate (11.7 g, 26%) as a yellow solid. The product was used without further purification.

To a solution of tert-butyl nitrite (24 mL, 202 mmol) in 1,4-dioxane (180 mL) was added a mixture of methyl 2-amino-5-methyl-1,3-thiazole-4-carboxylate (6.83 g, 40.0 mmol) in 1,4-dioxane (70 mL). The solution was stirred at 60° C. for 1 hour. After cooling to room temperature, the solvent was evaporated. The crude oil was purified by flash chromatography (0-20% EtOAc/hexanes), affording methyl 5-methyl-1,3-thiazole-4-carboxylate (3.95 g, 63%). The product was used for the next step without any further purification.

To a −78° C. solution of methyl 5-methyl-1,3-thiazole-4-carboxylate (3.95 g, 25.3 mmol) in DCM (85 mL) was added a solution of diisobutylaluminum hydride (1M in toluene, 27 mL, 27 mmol). The mixture was stirred at −78° C. for 2 hours. More diisobutylaluminum hydride (1M in toluene, 8 mL, 8 mmol) was added. The mixture was stirred at −78° C. for another 2 hours. The reaction was quenched with a Rochelle's salt solution (400 mL), and additional DCM (200 mL) was added. The mixture was stirred vigorously until the layers were well separated. The organic layer was recovered, dried over MgSO$_4$, filtered, evaporated, and dried in vacuo, affording 5-methyl-1,3-thiazole-4-carbaldehyde (2.4 g, 75%). The product was used for the next step without further purification.

To a 0° C. solution of 5-methyl-1,3-thiazole-4-carbaldehyde (1.0 g, 79 mmol) in anhydrous THF (30 mL) was added a solution of methyl magnesium bromide (3M in diethyl ether; 6 mL, 18 mmol). The reaction mixture was stirred at room temperature for 2 hours, and the mixture was then quenched with a saturated solution of ammonium chloride (20 mL). The mixture was extracted with EtOAc (3×30 mL). The organic extracts were combined, dried over MgSO$_4$, filtered, evaporated, and dried in vacuo, affording 1-(5-methyl-1,3-thiazol-4-yl)ethan-1-ol (1.0 g, 63%). The product was used without further purification.

To a solution of 1-(5-methyl-1,3-thiazol-4-yl)ethan-1-ol (1.0 g, 7.0 mmol) in anhydrous carbon tetrachloride (50 mL) was added recrystallized 1-bromopyrrolidine-2,5-dione (1.4 g, 7.7 mmol) and benzoyl benzenecarboperoxoate (170 mg, 0.7 mmol). The mixture was stirred at reflux for 5 hours. After cooling to room temperature, the solid material was removed by filtration. The filtrate was recovered and evaporated. The residue was dried in vacuo, affording 1-[5-(bromomethyl)-1,3-thiazol-4-yl]ethan-1-one (615 mg, 40%). The product was used for the next step without further purification.

To a mixture of 1-[5-(bromomethyl)-1,3-thiazol-4-yl]ethan-1-one (615 mg, 2.8 mmol) and 2-sulfanyl-6-(trifluoromethyl)pyrimidin-4-ol (255 mg, 1.3 mmol) in absolute ethanol (25 mL) at 0° C. was added triethylamine (725 µL, 5.2 mmol). The mixture was stirred at room temperature for 4 hours. The mixture was evaporated, and the solid residue was treated with diethyl ether (50 mL). The solid salts were removed by filtration. The filtrate was recovered and evaporated. The crude product was purified by flash chromatography (0-10% MeOH/CH$_2$Cl$_2$ and 0-5% MeOH/CH$_2$Cl$_2$), affording 2-{[(4-acetyl-1,3-thiazol-5-yl)methyl]sulfanyl}-6-(trifluoromethyl)pyrimidin-4-ol (150 mg, 34%); $^1$H NMR (500 MHz, DMSO-$d_6$): δ 2.71 (s, 3H), 4.82 (s, 2H), 6.58 (s, 1H), 8.99 (s, 1H); M+ 336.

Example 167

2-{[(4-ethenyl-1,3-thiazol-5-yl)methyl]sulfanyl}-6-(trifluoromethyl)pyrimidin-4-ol

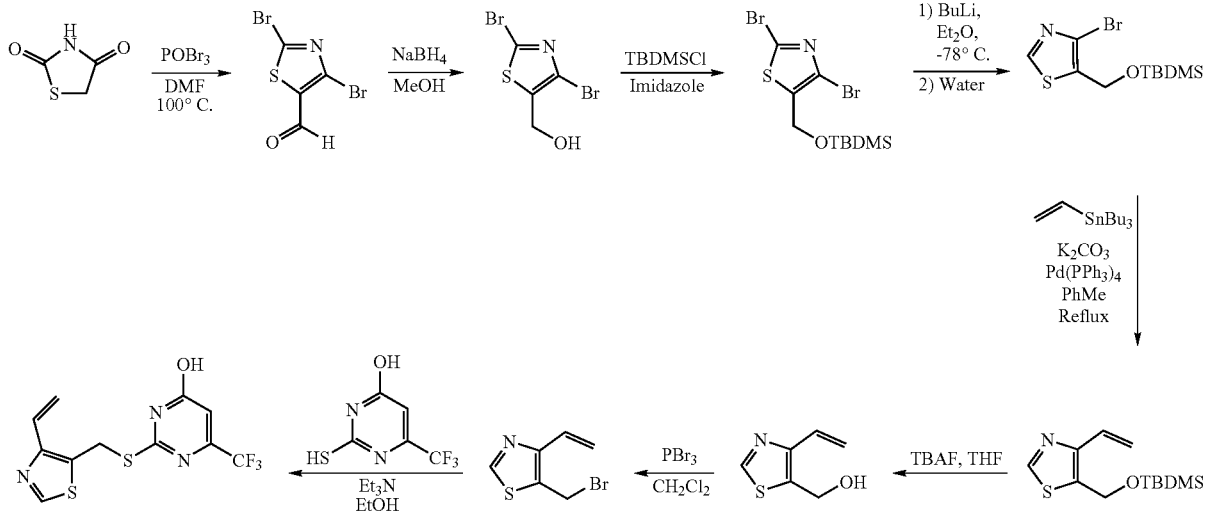

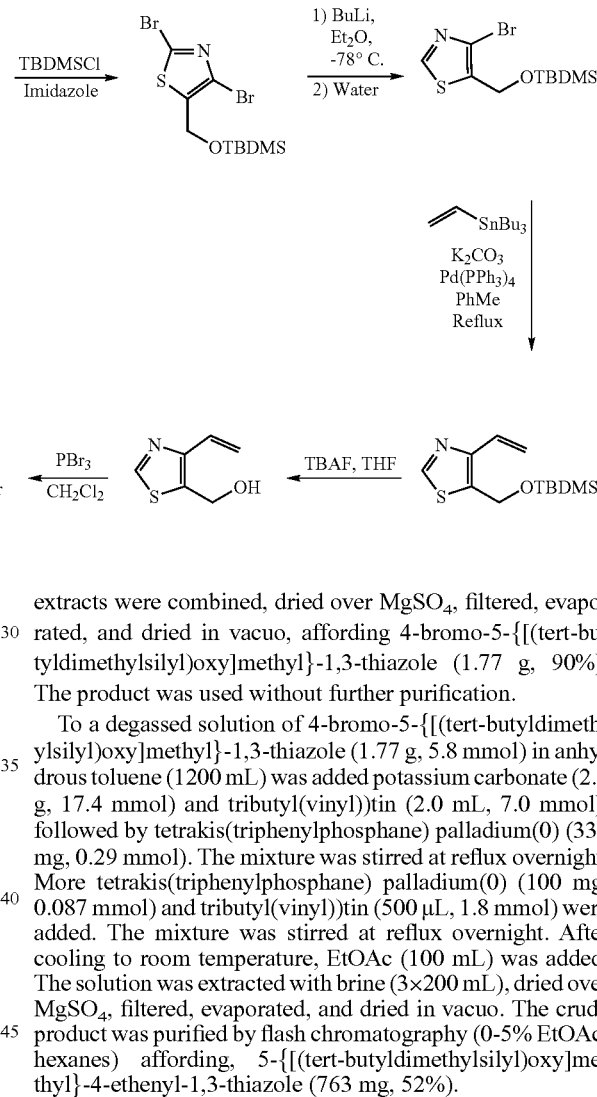

To a mixture of 1,3-thiazolidine-2,4-dione (3.56 g, 30 mmol) and phosphoroyl tribromide (43.0 g, 150 mL) was added DMF (2.56, 34.0 mmol). The mixture was stirred at 75° C. for 1 hour and at 100° C. overnight. The crude black mixture was poured into ice/water (500 mL). The mixture was extracted with DCM (5×300 mL). The organic extracts were combined, washed with brine (2×100 mL), dried over MgSO$_4$, filtered, evaporated, and dried in vacuo. The crude product was triturated with hexanes (250 mL). The solid material was recovered by filtration, washed with hexanes (2×20 mL) and dried in vacuo, affording 2,4-dibromo-1,3-thiazole-5-carbaldehyde (3.38 g, 41%). The product was used without further purification.

To a 0° C. solution of 2,4-dibromo-1,3-thiazole-5-carbaldehyde (3.38 g, 12.3 mmol) in anhydrous methanol (130 mL) was added sodium borohydride (600 mg, 15.9 mmol). The reaction mixture was stirred at room temperature for 3 hours. Water (100 mL) was added, and the mixture was evaporated. The resultant residue was extracted with EtOAc (3×100 mL). The organic extracts were combined, washed with brine (2×100 mL), dried over MgSO$_4$, filtered, evaporated, and dried in vacuo, affording (2,4-dibromo-1,3-thiazol-5-yl)methanol (2.64 g, 77%). The product was used without further purification.

To a solution of (2,4-dibromo-1,3-thiazol-5-yl)methanol (2.64 g, 9.6 mmol) and imidazole (1.6 g, 24 mmol) in DMF (15 mL) was added a solution of tert-butyl(chloro)dimethylsilane (1.7 g, 11.5 mmol) in DMF (15 mL). The reaction mixture was stirred at room temperature overnight. The reaction mixture was poured in water (400 mL), and the resultant mixture was extracted with EtOAc (3×50 mL). The organic extracts were combined, extracted with brine (2×150 mL), dried over MgSO$_4$, filtered, evaporated, and dried in vacuo, affording 2,4-dibromo-5-{[(tert-butyldimethylsilyl)oxy]methyl}-1,3-thiazole (3.44 g, 93%). The product was used without further purification.

To a −78° C. solution of 2,4-dibromo-5-{[(tert-butyldimethylsilyl)oxy]methyl}-1,3-thiazole (2.44 g, 6.3 mmol) in anhydrous diethyl ether (120 mL) was added a solution of n-butyl lithium (2.5M in hexanes, 2.5 mL, 6.3 mmol). The reaction mixture was stirred at −78° C. for 1 hour. Water (75 mL) was added, and the mixture was warmed to room temperature then extracted with EtOAc (3×75 mL). The organic extracts were combined, dried over MgSO$_4$, filtered, evaporated, and dried in vacuo, affording 4-bromo-5-{[(tert-butyldimethylsilyl)oxy]methyl}-1,3-thiazole (1.77 g, 90%). The product was used without further purification.

To a degassed solution of 4-bromo-5-{[(tert-butyldimethylsilyl)oxy]methyl}-1,3-thiazole (1.77 g, 5.8 mmol) in anhydrous toluene (1200 mL) was added potassium carbonate (2.4 g, 17.4 mmol) and tributyl(vinyl))tin (2.0 mL, 7.0 mmol), followed by tetrakis(triphenylphosphane) palladium(0) (335 mg, 0.29 mmol). The mixture was stirred at reflux overnight. More tetrakis(triphenylphosphane) palladium(0) (100 mg. 0.087 mmol) and tributyl(vinyl))tin (500 µL, 1.8 mmol) were added. The mixture was stirred at reflux overnight. After cooling to room temperature, EtOAc (100 mL) was added. The solution was extracted with brine (3×200 mL), dried over MgSO$_4$, filtered, evaporated, and dried in vacuo. The crude product was purified by flash chromatography (0-5% EtOAc/hexanes) affording, 5-{[(tert-butyldimethylsilyl)oxy]methyl}-4-ethenyl-1,3-thiazole (763 mg, 52%).

A solution of 5-{[(tert-butyldimethylsilyl)oxy]methyl}-4-ethenyl-1,3-thiazole (763 mg, 3.0 mmol) and a tetrabutylammonium fluoride solution (1M in THF; 4 mL, 4.0 mmol) in anhydrous THF (30 mL) was stirred at room temperature for 1.5 hours. The solvent was evaporated, and the residue was treated with EtOAc (50 mL). The solution was extracted with water (3×50 mL) and brine (1×50 mL), dried over MgSO$_4$, filtered, and evaporated. The residue was dried in vacuo, affording (4-ethenyl-1,3-thiazol-5-yl)methanol (370 mg, 87%). The product was used without further purification.

To a solution of (4-ethenyl-1,3-thiazol-5-yl)methanol (370 mg, 2.6 mmol) in anhydrous dichloromethane (20 mL) was added dropwise tribromophosphane (275 uL, 2.9 mmol). The mixture was stirred at room temperature for 3 hours. Dichloromethane was evaporated, and the residue was dried in vacuo to afford 5-(bromomethyl)-4-ethenyl-1,3-thiazole hydrobromide. The product was used without further purification.

To a 0° C. mixture of 5-(bromomethyl)-4-ethenyl-1,3-thiazole hydrobromide (2.6 mmol) and 2-sulfanyl-6-(trifluoromethyl)pyrimidin-4-ol (275 mg, 1.4 mmol) in absolute ethanol (15 mL) was added triethylamine (1.5 mL, 10.8 mmol). The mixture was stirred at room temperature overnight. The solution was evaporated, and the residue was treated with diethyl ether (100 mL). The solid material was removed by filtration. The filtrate was evaporated, and the crude product was purified by flash chromatography (0-5% MeOH/DCM), affording 2-{[(4-ethenyl-1,3-thiazol-5-yl)methyl]sulfanyl}-6-(trifluoromethyl)pyrimidin-4-ol (270 mg, 60%); $^1$H NMR (500 MHz, DMSO-$d_6$): δ 4.75 (s, 2H), 5.42 (dd, 1H, J=2.3 Hz, 10.8 Hz), 6.06 (dd, 1H, J=2.3 Hz, 16.9 Hz), 6.68 (s, 1H), 8.95 (s, 1H); M+ 320.

Example 168

2-({[4-(1-hydroxyethyl)-1,3-thiazol-5-yl]methyl}sulfanyl)-6-(trifluoromethyl)pyrimidin-4-ol

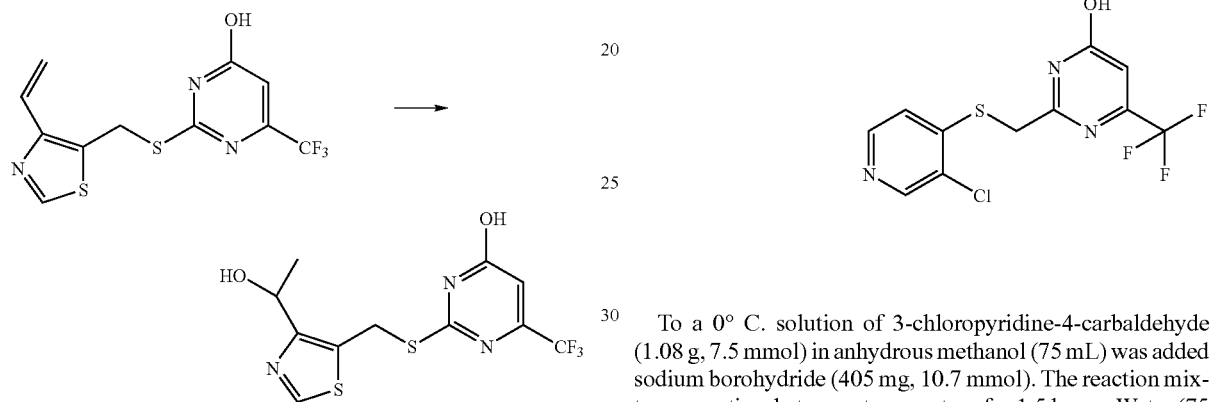

To a solution of 2-{[(4-ethenyl-1,3-thiazol-5-yl)methyl]sulfanyl}-6-(trifluoromethyl)pyrimidin-4-ol (see Example 167; 130 mg, 0.41 mmol) in anhydrous THF 5 mL was added borane-THF solution (1M in THF; 5.0 mL, 5.0 mmol). The mixture was stirred at room temperature for 24 hours. After cooling to 0° C., hydrogen peroxide (30%, 1.8 mL, 18 mmol) was added to the reaction mixture, followed by 10N NaOH (1.0 mL, 10 mmol). The reaction mixture was stirred for 1.5 hours, and water (25 mL) was added. The reaction mixture was extracted with ethyl acetate (3×25 mL). The organic layers were combined, dried over MgSO$_4$, filtered, and evaporated to provide the crude product, which was purified by combiflash using 0 to 15% MeOH:CH$_2$Cl$_2$ to provide 2-({[4-(1-hydroxyethyl)-1,3-thiazol-5-yl]methyl}sulfanyl)-6-(trifluoromethyl)pyrimidin-4-ol (3.0 mg). $^1$H NMR (500 MHz, DMSO-$d_6$): δ 1.41 (d, 3H), 4.77 (q, 2H), 5.06 (m, 1H), 6.55 (s, 1H), 8.85 (s, 1H); M+ 338.

Example 169

2-{[(3-chloropyridin-4-yl)methyl]sulfanyl}-6-(trifluoromethyl)pyrimidin-4-ol

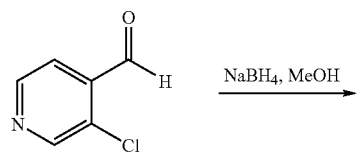

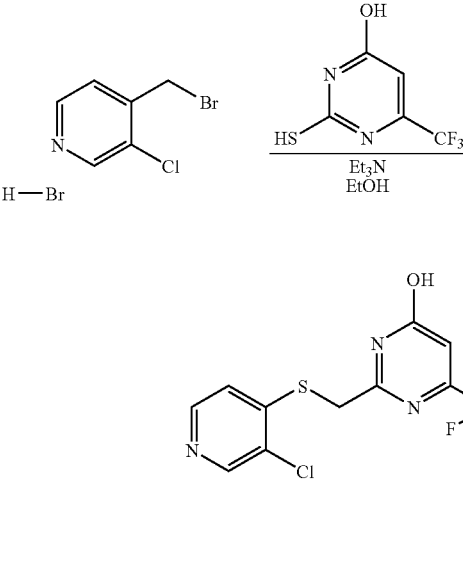

To a 0° C. solution of 3-chloropyridine-4-carbaldehyde (1.08 g, 7.5 mmol) in anhydrous methanol (75 mL) was added sodium borohydride (405 mg, 10.7 mmol). The reaction mixture was stirred at room temperature for 1.5 hours. Water (75 mL) was added, and the reaction mixture was evaporated. The resultant residue was extracted with EtOAc (3×50 mL). The organic extracts were combined, washed with brine (2×100 mL), dried over MgSO$_4$, filtered, evaporated, and dried in vacuo, affording (3-chloropyridin-4-yl)methanol (1.0 g, 96%). The product was used in the next step without further purification.

To a solution of (3-chloropyridin-4-yl)methanol (1.0 g, 7.2 mmol) in anhydrous dichloromethane (35 mL) was added dropwise tribromophosphane (750 uL, 7.9 mmol). The mixture was stirred at room temperature for 5 hours. Dichloromethane was evaporated, and the residue was dried in vacuo, affording 4-(bromomethyl)-3-chloropyridine hydrobromide. The product was used for the next step without further purification.

To a 0° C. mixture of 4-(bromomethyl)-3-chloropyridine hydrobromide (7.2 mmol) and 2-sulfanyl-6-(trifluoromethyl)pyrimidin-4-ol (922 mg, 4.7 mmol) in absolute ethanol (40 mL) was added triethylamine (4.0 mL, 28.7 mmol). The mixture was stirred at room temperature overnight. The solid material was removed by filtration. Diethyl ether (2×50 mL) was used to wash the recovered solid. The solid material was removed by filtration. The filtrate was evaporated to dryness and then co-evaporated with ethyl acetate (1×25 mL). The solid residue was treated with water (100 mL). The solid product was recovered by filtration, washed with water (2×30 mL), diethyl ether (1×30 mL), and hexanes (2×30 mL), and was dried in vacuo to afford 2-{[(3-chloropyridin-4-yl)methyl]sulfanyl}-6-(trifluoromethyl)pyrimidin-4-ol (822 mg, 54%); $^1$H NMR (500 MHz, DMSO-$d_6$): δ 4.50 (s, 2H), 6.66 (s, 1H), 7.58 (d, 1H, J=4.9 Hz), 8.47 (d, 1H, J=4.9 Hz), 8.64 (s, 1H); M+ 322.

Example 170

2-{[(4-methyl-1,3-thiazol-5-yl)methyl]sulfanyl}-6-(trifluoromethyl)pyrimidin-4-ol

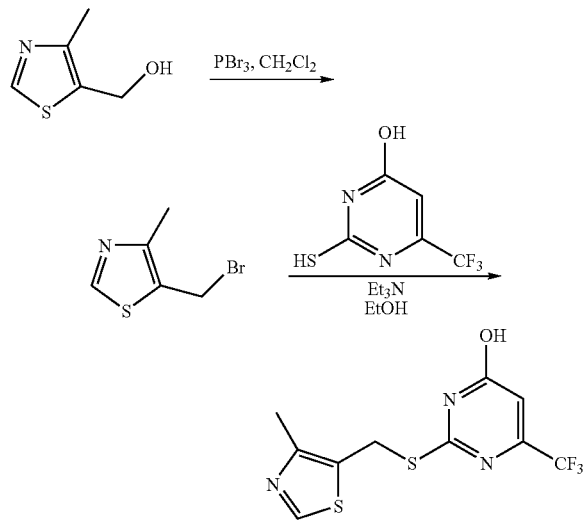

To a solution of (4-methyl-1,3-thiazol-5-yl)methanol (2.5 g, 19.4 mmol) in anhydrous dichloromethane (100 mL) was added dropwise tribromophosphane (2.00 mL, 21.3 mmol). The mixture was stirred at room temperature for 3.5 hours. Dichloromethane was evaporated, and the residue was then dried in vacuo, affording 5-(bromomethyl)-4-methyl-1,3-thiazole hydrobromide. The product was used for the next step without further purification.

To a 0° C. mixture of 5-(bromomethyl)-4-methyl-1,3-thiazole hydrobromide (19.4 mmol) and 2-sulfanyl-6-(trifluoromethyl)pyrimidin-4-ol (2.47 g, 12.6 mmol) in absolute ethanol (100 mL) was added triethylamine (8.00 mL, 57.4 mmol). The mixture was stirred at room temperature for 2 days. The solid material was removed by filtration and washed with diethyl ether (100 mL). The filtrate was evaporated to dryness and then co-evaporated with ethyl acetate (1×50 mL). The solid residue was treated with water (100 mL), and the mixture was stirred for 30 minutes. The solid product was recovered by filtration, washed with water (2×25 mL), diethyl ether (2×25 mL), and hexanes (2×25 mL), and then dried in vacuo to afford 2-{[(4-methyl-1,3-thiazol-5-yl)methyl]sulfanyl}-6-(trifluoromethyl)pyrimidin-4-ol (1.76 g, 45%); $^1$H NMR (500 MHz, DMSO-d$_6$): δ 2.39 (s, 3H), 4.61 (s, 2H), 6.65 (s, 1H), 8.86 (s, 1H); M+ 308.

Example 171

2-{[(3-chloro-5-methoxypyridin-4-yl)methyl]sulfanyl}-6-(trifluoromethyl)pyrimidin-4-ol

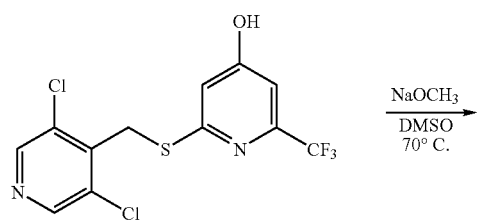

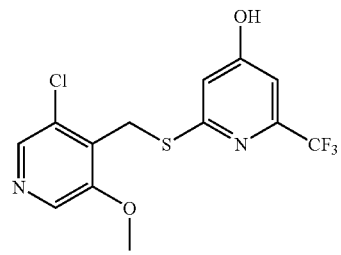

A mixture of 2-{[(3,5-dichloropyridin-4-yl)methyl]sulfanyl}-6-(trifluoromethyl)-pyrimidin-4-ol (see, e.g., Example 120; 1.0 g, 2.8 mmol) and a sodium methoxide solution (25% wt., 2.6 mL) in dimethyl sulfoxide (10 mL) was stirred at 70° C. overnight. Water (100 mL) was added, and the pH of the mixture was adjusted to around 6 with 2N HCl. The mixture was extracted with EtOAc (3×75 mL). The organic extracts were combined, dried over MgSO$_4$, filtered, evaporated, and dried in vacuo to afford 2-{[(3-chloro-5-methoxypyridin-4-yl)methyl]sulfanyl}-6-(trifluoromethyl)pyrimidin-4-ol (912 mg, 93%); $^1$H NMR (500 MHz, DMSO-d$_6$): δ 3.97 (s, 3H), 4.59 (s, 2H), 6.68 (s (br), 1H), 8.32 (s, 1H), 8.39 (s, 1H); M+ 352.

Example 172

2-{[(3-chloro-5-hydroxypyridin-4-yl)methyl]sulfanyl}-6-(trifluoromethyl)pyrimidin-4-ol

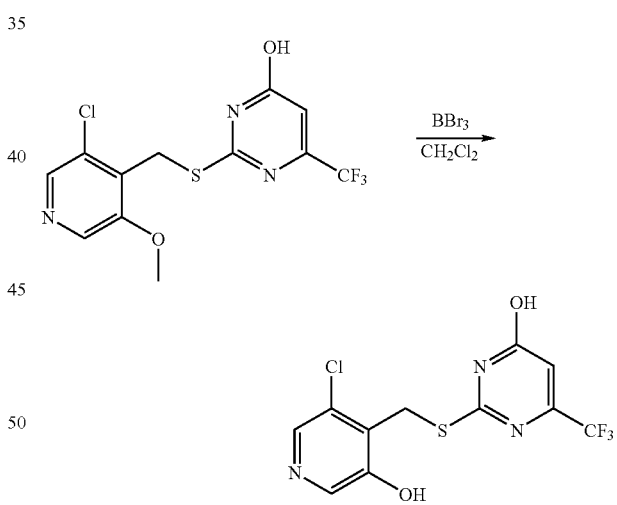

A mixture of 2-{[(3-chloro-5-hydroxypyridin-4-yl)methyl]sulfanyl}-6-(trifluoromethyl)pyrimidin-4-ol (800 mg, 2.3 mmol) and tribromoborane (2.2 mL, 23 mmol) in anhydrous dichloromethane (50 mL) was stirred at reflux for 3 days. The mixture was poured into ice/water (100 mL). The mixture was extracted with dichloromethane (3×50 mL). The organic extracts were combined, extracted with NaHCO$_3$ (sat) (1×200 mL) and brine (1×200 mL), dried over MgSO$_4$, filtered, evaporated and dried in vacuo. The crude product was purified by flash chromatography (0-60% EtOAc/CH$_2$Cl$_2$) and (0-20% i-PrOH/CH$_2$Cl$_2$), affording 2-{[(3-chloro-5-hydroxypyridin-4-yl)methyl]sulfanyl}-6-(trifluoromethyl)pyrimidin-4-ol (35 mg, 4.5%); $^1$H NMR (500 MHz, DMSO-$d_6$): δ 4.56 (s, 2H), 6.60 (s, 1H), 8.15 (s, 2H); M+ 338.

Example 173

2-{[(4-ethyl-1,3-thiazol-5-yl)dihydrogeniomethyl]sulfanyl}-6-(trifluoromethyl)pyrimidin-4-ol

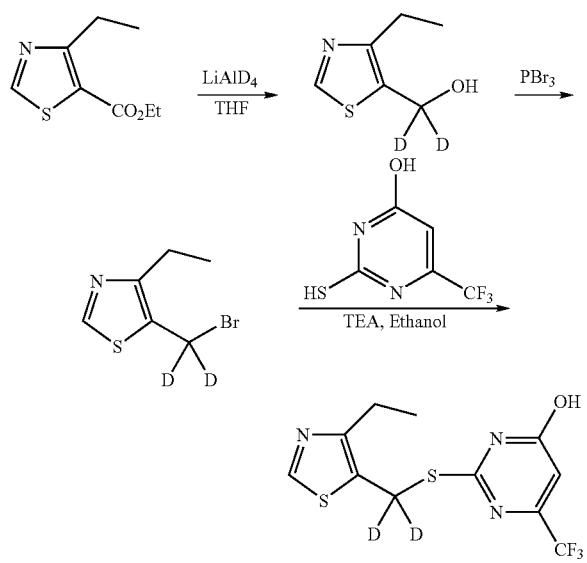

To a 0° C. suspension of lithium aluminum deuteride (1.44 g, 34.30 mmol) in anhydrous THF (30 mL) was slowly added a solution of ethyl 4-ethyl-1,3-thiazole-5-carboxylate (3.19 g, 17.21 mmol) in anhydrous THF (40 mL). The reaction mixture was stirred at 0° C. for 2 hours. The reaction was quenched with 0.1N NaOH via slow dropwise addition. Water (100 mL) and EtOAc (200 mL) were added. The mixture was stirred for 30 minutes. The solid material was removed by filtration, and the organic layer was recovered. The aqueous layer was extracted with EtOAc (2×100 mL). The combined organic extracts were dried over $MgSO_4$, filtered, evaporated, and dried in vacuo, affording 5-[dihydrogenio(hydroxy)methyl]-4-ethyl-1,3-thiazole (1.95 g, 77.3%). The product was used for the next step without further purification.

To a solution of 5-[dihydrogenio(hydroxy)methyl]-4-ethyl-1,3-thiazole (1.95 g, 13.4 mmol) in anhydrous dichloromethane (40 mL) was added tribromophosphane (4.36 g, 1.51 mL, 16.10 mmol). The mixture was stirred at room temperature for 2 hours, and the dichloromethane was evaporated. The residue was dried in vacuo, affording 5-(bromodihydrogeniomethyl)-4-ethyl-1,3-thiazole. The crude product was used without further purification.

To a mixture of 5-(bromodihydrogeniomethyl)-4-ethyl-1,3-thiazole (2.79 g, 13.42 mmol), 2-sulfanyl-6-(trifluoromethyl)pyrimidin-4-ol (1.84 g, 9.38 mmol) and ethanol (60 mL) at 0° C. was added triethylamine (7.5 mL, 53.6 mmol). The reaction mixture was stirred at room temperature overnight. The mixture was evaporated to dryness. The residue was treated with THF (100 mL), and the solid material was removed by filtration. The filtrate was recovered and evaporated. The crude product was purified by flash chromatography (0-10% MeOH/$CH_2Cl_2$), affording 2-{[(4-ethyl-1,3-thiazol-5-yl)dihydrogeniomethyl]sulfanyl}-6-(trifluoromethyl)pyrimidin-4-ol (2.2 g, 72%); $^1$H NMR (500 MHz, DMSO-$d_6$): δ 1.19 (t, 2H, J=7.5 Hz), 2.76 (m, 2H, J=7.5 Hz), 6.62 (s, 1H), 8.87 (s, 1H); M+ 324.

Example 174

5-bromo-2-{[(4-ethyl-1,3-thiazol-5-yl)methyl]sulfanyl}-6-(trifluoromethyl)pyrimidin-4-ol

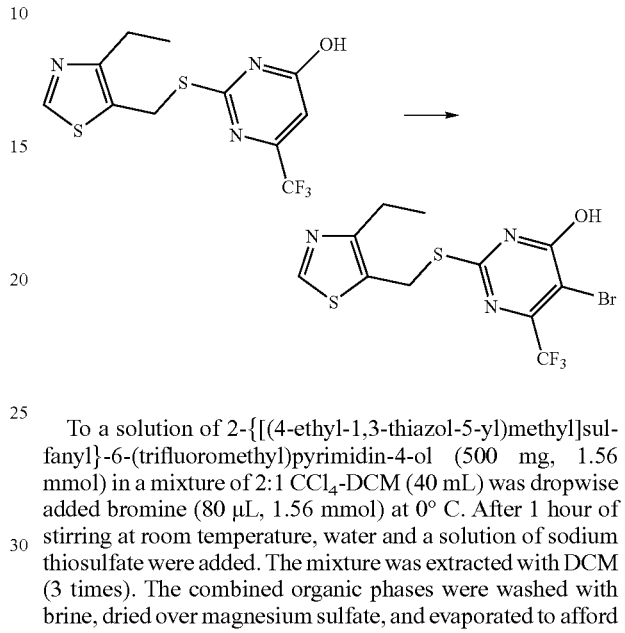

To a solution of 2-{[(4-ethyl-1,3-thiazol-5-yl)methyl]sulfanyl}-6-(trifluoromethyl)pyrimidin-4-ol (500 mg, 1.56 mmol) in a mixture of 2:1 $CCl_4$-DCM (40 mL) was dropwise added bromine (80 μL, 1.56 mmol) at 0° C. After 1 hour of stirring at room temperature, water and a solution of sodium thiosulfate were added. The mixture was extracted with DCM (3 times). The combined organic phases were washed with brine, dried over magnesium sulfate, and evaporated to afford a crude oil. The residue was dissolved in DCM and purified on silica gel using DCM/MeOH (0 to 15%) to provide 5-bromo-2-{[(4-ethyl-1,3-thiazol-5-yl)methyl]sulfanyl}-6-(trifluoromethyl)pyrimidin-4-ol as a white solid (72 mg, 12% yield). $^1$H NMR (500 MHz, DMSO-$d_6$): δ 1.17 (t, J=7.4 Hz, 3H), 2.75 (q, J=7.4 Hz, 2H), 4.64 (s, 2H), 8.87 (s, 1H). LRMS ($ES^+$) m/z 402 (50%, M+2), 400 (50%, M).

Example 175

2-{[(4-ethyl-1,3-thiazol-5-yl)methane]sulfinyl}-6-(trifluoromethyl)pyrimidin-4-ol

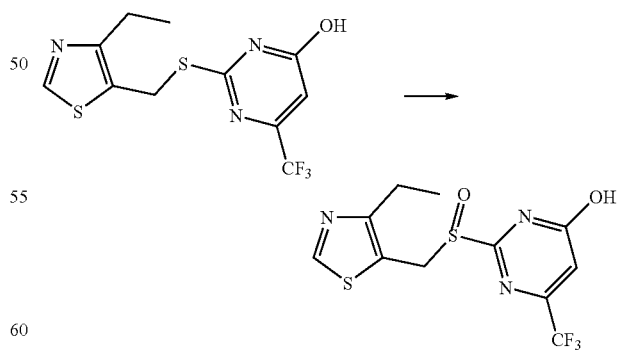

To a solution of 2-{[(4-ethyl-1,3-thiazol-5-yl)methyl]sulfanyl}-6-(trifluoromethyl)pyrimidin-4-ol (200 mg, 622 mmol) in DCM (10 mL) was added dropwise a solution of sodium hypochlorite (2 mL, chlorine ≥4%, Aldrich) at 0° C. After 3 hours of stirring at room temperature, water was added. The mixture was extracted with DCM (3 times). The combined organic phases were washed with brine, dried over magnesium sulfate, and evaporated to afford a crude oil. The residue was dissolved in DCM and purified on silica gel using DCM/MeOH (0 to 20%) to provide 2-{[(4-ethyl-1,3-thiazol-5-yl)methane]sulfinyl}-6-(trifluoromethyl)pyrimidin-4-ol (22 mg, 10% yield). $^1$H NMR (500 MHz, MeOH-d$_4$): δ 1.19 (t, J=7.6 Hz, 3H), 2.70 (m, 2H), 4.62 (d, J=14.6 Hz, 1H), 4.74 (d, J=14.6 Hz, 1H), 6.49 (s, 1H), 8.83 (s, 1H). LRMS (ES$^-$) m/z 336 (10%, M−1).

Example 176

4-ethyl-5-({[4-methoxy-6-(trifluoromethyl)pyrimidin-2-yl]sulfanyl}methyl)-1,3-thiazole

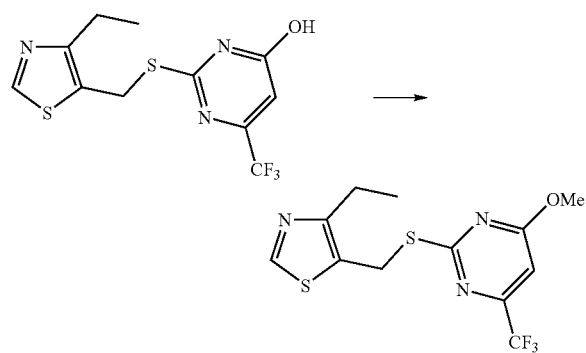

To a solution of 2-{[(4-ethyl-1,3-thiazol-5-yl)methyl]sulfanyl}-6-(trifluoromethyl)pyrimidin-4-ol (500 mg, 1.56 mmol) in anhydrous methanol (10 mL) was added dropwise a solution of 30% sodium methoxide in methanol (310 μL, 1.71 mmol) at 0° C. The mixture was heated to 65° C. for 1 hour. Iodomethane (220 μL, 3.43 mmol) was added at room temperature, and the reaction was heated overnight at 65° C. The solvent was evaporated, and the residue was extracted three times with dichloromethane/water. The combined organic phases were washed with brine, dried over magnesium sulfate, and evaporated to afford a crude oil. The residue was dissolved in DCM and purified on silica gel using DCM/MeOH (0 to 10%) to afford 4-ethyl-5-({[4-methoxy-6-(trifluoromethyl)pyrimidin-2-yl]sulfanyl}methyl)-1,3-thiazole (315 mg, 60% yield). $^1$H NMR (500 MHz, MeOH-d$_4$): δ 1.21 (t, J=7.5 Hz, 3H), 2.79 (q, J=7.5 Hz, 2H), 3.40 (s, 3H), 4.74 (s, 2H), 6.76 (s, 1H), 8.89 (s, 1H). LRMS (ES) m/z 336 (100%, M+1).

Example 177

Determination of Analgesic Effect in an Experimental Model of Neuropathic Pain

The analgesic effect of a representative number of the compounds of the invention was determined using the procedures described hereafter.

Adult, male Sprague-Dawley rats were obtained from Charles River Laboratories (Wilmington, Mass.) and housed under standard conditions at the Institut Armand-Frappier (Laval, QC). Food and water were provided to experimental animals ad libitum, and rats weighed 175-200 grams at the time of assessment.

Compounds were prepared for intraperitoneal administration by dissolving them in a vehicle of hydroxypropyl methylcellulose (Sigma, St-Louis, Mo.); total volume of solution administered to rats was 10 ml/kg.

Neuropathic pain was induced in rats via spared nerve injury (SNI) of the left sciatic nerve in accordance with the procedure described by Decosterd & Woolf (*Pain* 2000; 87(2):149-58). Briefly, under isoflurane anesthesia, the sciatic nerve was exposed by dissection at the level of lower thigh, and a lesion of two of the three terminal branches of the nerve (tibial and common peroneal nerves) were performed leaving the remaining sural nerve intact. The incision was closed-up using simple suturing, and the rats allowed to recover.

Alternatively, neuropathic pain was induced in rats via chronic constriction injury (CCI) of the left sciatic nerve with the procedure described by Bennett & Xie (*Pain* 1988; 33(1): 87-107). Briefly, under isoflurane anaesthesia, the sciatic nerve was exposed by dissection at the level of the lower thigh and four loose ligatures (USP 4/0, Braun Melsaugen, FRG) were implanted around the nerve—with due attention not to interrupt the epineural circulation. The incision was closed-up using simple suturing, and the rats allowed to recover.

After approximately two weeks, a stable allodynia to blunt mechanical stimuli was identified in the hind paw ipsilateral to the SNI or CCI, manifested as a reduction of 50% withdrawal threshold, and identified using the Von Frey technique, as described by Chaplan et al. (*J. Neurosci. Methods* 1994; 53(1):55-63), or the Hargreaves method, as described by Hargreaves et al. (*Pain* 1988; 32(1):77-88). Rats were considered to be fully neuropathic upon displaying a 50% withdrawal threshold of ≤3.5 grams consistently over the course of 72 hours.

Compounds were administered to neuropathic rats via acute local delivery in the intraperitoneal space or by oral gavage.

Compounds of the invention that demonstrated efficacy in this assay include:

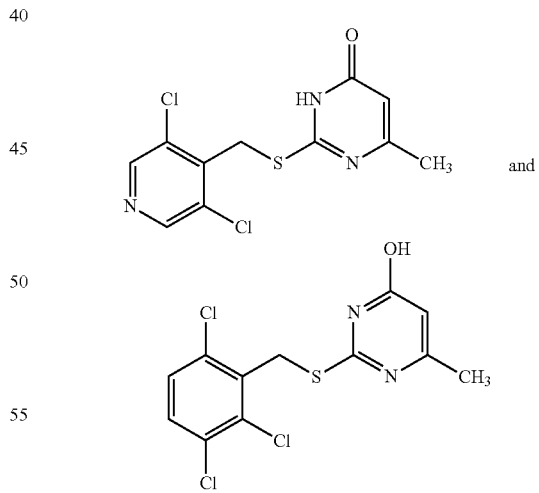

Table 1 presents the peak efficacy of several representative compounds in rats rendered neuropathic via the SNI Model, in terms of 50% withdrawal threshold. Data are presented as mean efficacy±standard error of the mean. Note that in all cases the peak efficacy shown for the compounds was significantly different from the 50% withdrawal threshold of neuropathic rats administered vehicle control (p<0.05, as assessed by repeated-measures ANOVA).

TABLE 1

| IUPAC name | Peak 50% withdrawal threshold (g) |
| --- | --- |
| 6-methyl-2-{[(2,3,6-trichlorophenyl)methyl]sulfanyl}pyrimidin-4-ol | 6.24 ± 1.48 |
| 2-{[(3,5-dichloropyridin-4-yl)methyl]sulfanyl}-6-methylpyrimidin-4-ol | 9.13 ± 1.60 |
| 2-{[(3-chloro-5-ethylpyridin-4-yl)methyl]sulfanyl}-6-methylpyrimidin-4-ol | 8.73 ± 1.75 |
| 2-{[(2,4-dichloropyridin-3-yl)methyl]sulfanyl}-6-methylpyrimidin-4-ol | 7.74 ± 2.13 |
| 2-{[(3,5-diethylpyridin-4-yl)methyl]sulfanyl}-6-(trifluoromethyl)pyrimidin-4-ol | 6.04 ± 1.17 |
| 2-{[(3,5-dichloropyridin-4-yl)methyl]sulfanyl}-6-(trifluoromethyl)pyrimidin-4-ol | 5.77 ± 1.01 |

Table 2 presents the peak efficacy of several representative compounds in rats rendered neuropathic via the CCI model, in terms of 50% withdrawal threshold. Data are presented as mean efficacy±standard error of the mean. Note that in all cases the peak efficacy shown for the compounds was significantly different from the 50% withdrawal threshold of neuropathic rats administered vehicle control ($p<0.05$, as assessed by repeated-measures ANOVA).

TABLE 2

| IUPAC name | Peak 50% withdrawal threshold (s) |
| --- | --- |
| 2-{[(3,5-dichloropyridin-4-yl)methyl]sulfanyl}-6-methylpyrimidin-4-ol | 14.49 ± 1.24 |
| 2-{[(4-chloro-1-methyl-1H-pyrazol-3-yl)methyl]sulfanyl}-6-methylpyrimidin-4-ol | 11.98 ± 1.71 |
| 2-{[(2-ethylpyridin-3-yl)methyl]sulfanyl}-6-methylpyrimidin-4-ol | 10.46 ± 1.16 |
| 2-{[(4-ethyl-1,3-thiazol-5-yl)methyl]sulfanyl}-6-(trifluoromethyl)pyrimidin-4-ol | 10.45 ± 0.47 |
| 2-{[(3,5-dichloropyridin-4-yl)methyl]sulfanyl}-6-(trifluoromethyl)pyrimidin-4-ol | 11.7 ± 1.43 |

Example 178

Determination of Anti-Convulsant Effect in an Experimental Psychomotor Seizure Model of Partial Epilepsy (Minimal Clonic Seizure Test)

The anti-convulsant effect of a representative number of the compounds of the invention was determined using the procedures described hereafter.

Adult mice are pretreated with 100 mg/kg of test compound, acutely administered intraperitoneally. At varying times (15, 30, 60, 120 and 240 minutes post-treatment), animals are challenged with sufficient current (32 mA, 6 Hz, for 3 seconds) delivered through corneal electrodes to elicit a psychomotor seizure. Untreated mice will display seizures characterized by a minimal clonic phase followed by stereotyped, automatistic behaviors similar to the aura of human patients with partial seizures. Animals not displaying this behavior are considered protected (Barton et al., *Epilepsy Res.* 2001; 47(3):217-27). Results are expressed as the number of animal protected out of the number of animal tested over time.

Compounds of the invention that demonstrated efficacy in this assay include:

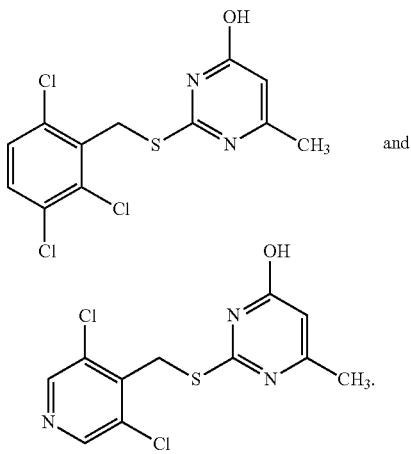

and

Table 3 presents the peak protection of representative compounds in mice subjected to the Minimal Clonic Seizure model. Data are presented as number of protected animals out of number of tested animals over time.

TABLE 3

| IUPAC name | Protected Animals/tested animals | | | | |
| --- | --- | --- | --- | --- | --- |
| | 15 minutes | 30 minutes | 60 minutes | 120 minutes | 240 minutes |
| 6-methyl-2-{[(2,3,6-trichlorophenyl)methyl]sulfanyl}pyrimidin-4-ol | 1/4 | 3/4 | 2/4 | 1/4 | 0/4 |
| 2-{[(3,5-dichloropyridin-4-yl)methyl]sulfanyl}-6-methylpyrimidin-4-ol | 3/4 | 3/4 | 3/4 | 1/4 | 0/4 |

It should also be noted that for in vivo medicinal uses, potency is not the only factor to be considered to estimate the suitability of a compound as a pharmaceutical agent. Other factors such as toxicity and bioavailability also determine the suitability of a compound as a pharmaceutical agent. Toxicity and bioavailability can also be tested in any assay system known to the skilled artisan.

The present invention is not to be limited in scope by the specific embodiments disclosed in the examples, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

Other embodiments are in the claims.

What is claimed is:

1. A compound having the structure of a formula selected from the group consisting of:

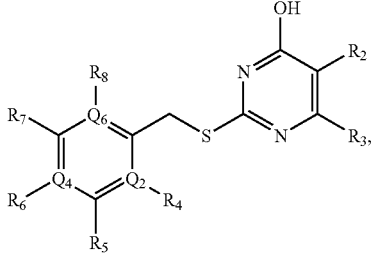
(Ia-2)

including other tautomers, stereoisomers, E/Z stereoisomers, prodrugs, and pharmaceutically acceptable salts thereof, wherein:

$R_2$ is —H, -D, —$CF_3$, —$C_1$-$C_5$ alkyl, —$C_2$-$C_5$ alkenyl, —$C_2$-$C_5$ alkynyl, or —CN;

$R_3$ is —$CF_3$, —$C_1$-$C_5$ alkyl, —$C_2$-$C_5$ alkenyl, —$C_2$-$C_5$ alkynyl, or —CN;

$R_4$, $R_6$, and $R_8$ are each, independently, absent —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, and $R_5$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle, provided that the resulting ring system is not unsubstituted imidazo[1,2-a]pyridine, 5- or 6-chloro-imidazo[1,2-a]pyridine, 8-substituted quinoline, 2- or 4-chloro-quinoline, or 4-hydroxy-1,3-quinazoline;

each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle; and $Q_2$, $Q_4$, and $Q_6$ are each, independently, N, $N^+$—$O^-$, or C, wherein $Q_2$, $Q_4$, and $Q_6$ are not simultaneously C; wherein, (a) when each of $R_5$, $R_6$, $R_7$, and $R_8$ is H, $Q_2$ is N, and each of $Q_4$ and $Q_6$ is C, $R_3$ is not —$CF_3$, —$C_1$-$C_3$ alkyl, or difluorobenzyl, (b) when each of $R_4$, $R_5$, $R_6$, and $R_7$ is H, $Q_6$ is N, and each of $Q_2$ and $Q_4$ is C, $R_3$ is not —$CF_3$, —$C_1$-$C_3$ alkyl, or difluorobenzyl, and (c) when each of $R_4$, $R_5$, $R_7$, and $R_8$ is H, $Q_4$ is N, and each of $Q_2$ and $Q_6$ is C, $R_3$ is not —$CH_3$, —$CH_2CH_2CH_3$, or difluorobenzyl;

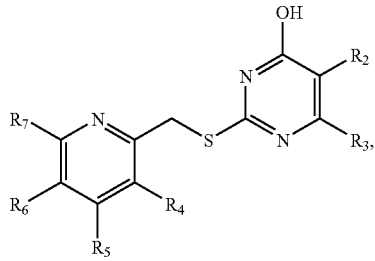
(Ia-3)

including other tautomers, stereoisomers, E/Z stereoisomers, prodrugs, and pharmaceutically acceptable salts thereof, wherein:

$R_2$ is —H, -D, —$CF_3$, —$C_1$-$C_5$ alkyl, —$C_2$-$C_5$ alkenyl, —$C_2$-$C_5$ alkynyl, or —CN;

$R_3$ is —$CF_3$, —$C_1$-$C_5$ alkyl, —$C_2$-$C_5$ alkenyl, —$C_2$-$C_5$ alkynyl, or —CN;

$R_4$, $R_5$, $R_6$, and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, together with the carbon atoms to which each is attached, join to form a 5- to 6-membered aromatic or non aromatic carbocycle or heterocycle, provided that the resulting ring system is not 8-substituted quinoline or 4-chloro-quinoline; and each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle, wherein, when each of $R_4$, $R_5$, $R_6$, and $R_7$ is H, $R_3$ is not —$CF_3$, —$C_1$-$C_3$ alkyl, or difluorobenzyl;

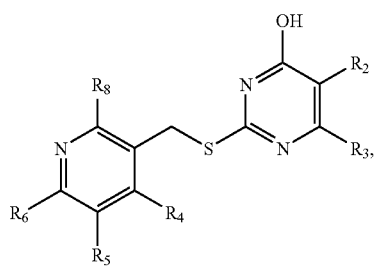
(Ia-4)

including other tautomers, stereoisomers, E/Z stereoisomers, prodrugs, and pharmaceutically acceptable salts thereof, wherein:

$R_2$ is —H, -D, —$CF_3$, —$C_1$-$C_5$ alkyl, —$C_2$-$C_5$ alkenyl, —$C_2$-$C_5$ alkynyl, or —CN;

$R_3$ is —$CF_3$, —$C_1$-$C_5$ alkyl, —$C_2$-$C_5$ alkenyl, —$C_2$-$C_5$ alkynyl, or —CN;

$R_4$, $R_5$, $R_6$, and $R_8$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₅ and R₆, together with the carbon atoms to which each is attached, join to form a 5- to 6-membered aromatic or non aromatic carbocycle or heterocycle, provided that the resulting ring system is not 8-substituted quinoline or 2- or 4-chloro-quinoline; and each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-C₅ alkynyl, or two Z, together with the atom to which each is attached, join to form a 3- to 7-membered aromatic or non aromatic heterocycle, wherein, (a) when each of R₅ and R₆ is H, R₄ is chloro, and R₈ is H or chloro, R₃ is not —CF₃ or —C₁-C₃ alkyl, and (b) when each of R₄, R₅, R₆, and R₈ is H, R₃ is not —CF₃ or —C₁-C₃ alkyl;

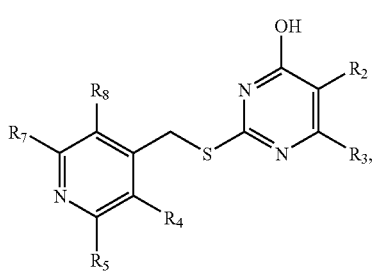

(Ia-5)

including other tautomers, stereoisomers, E/Z stereoisomers, prodrugs, and pharmaceutically acceptable salts thereof, wherein:

R₂ is —H, -D, —CF₃, —C₁-C₅ alkyl, —C₂-C₅ alkenyl, —C₂-C₅ alkynyl, or —CN;

R₃ is —CF₃, —C₁-C₅ alkyl, —C₂-C₅ alkenyl, —C₂-C₅ alkynyl, or —CN;

R₄, R₅, R₇, and R₈ are each, independently, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₇ and R₈, together with the carbon atoms to which each is attached, join to form a 5- to 6-membered aromatic or non aromatic carbocycle or heterocycle, provided that the resulting ring system is not 8-substituted quinoline or 2- or 4-chloro-quinoline; and each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-C₅ alkynyl, or two Z, together with the atom to which each is attached, join to form a 3- to 7-membered aromatic or non aromatic heterocycle, wherein, when each of R₄, R₅, R₇, and R₈ is H, R₃ is not —CH₃, —CH₂CH₂CH₃, or difluorobenzyl;

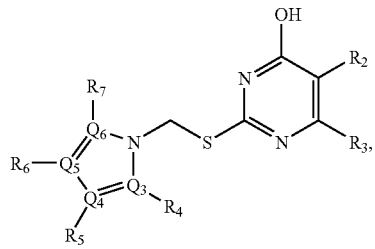

(Ia-6)

including other tautomers, stereoisomers, E/Z stereoisomers, prodrugs, and pharmaceutically acceptable salts thereof, wherein:

R₂ is —H, -D, —CF₃, —C₁-C₅ alkyl, —C₂-C₅ alkenyl, —C₂-C₅ alkynyl, or —CN;

R₃ is —CF₃, —C₁-C₅ alkyl, —C₂-C₅ alkenyl, —C₂-C₅ alkynyl, or —CN;

R₄, R₅, R₆, and R₇, are each, independently, absent, —H, -D, —OH, halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)₂, —C(NH)N(Z)₂, —C(O)Z, —OC(O)Z, —OC(O)OZ, —OC(O)N(Z)₂, —C(O)N(Z)₂, —C(O)OZ, —SZ, —SOZ, —S(O)₂Z, —NHC(O)Z, —NHS(O)₂Z, —NHC(NH)N(Z)₂, —NZC(NH)N(Z)₂, —NHC(NCN)N(Z)₂, or —NZC(NCN)N(Z)₂, or R₄ and R₅, or R₅ and R₆, or R₆ and R₇, together with the atoms to which each is attached, join to form a 5- to 6-membered aromatic or non aromatic carbocycle or heterocycle, provided that the resulting ring system is not unsubstituted imidazo[1,2-a]pyridine, 5- or 6-chloro-imidazo[1,2-a]pyridine, or substituted or unsubstituted benzimidazole;

each Z is, independently, —H, —C₁-C₅ alkyl, —C₃-C₇ cycloalkyl, —C₆ aryl, —C₇-C₉ arylalkyl, 3 to 7-membered aromatic or non aromatic heterocycle, —C₂-C₅ alkenyl, or —C₂-C₅ alkynyl, or two Z, together with the atom to which each is attached, join to form a 3- to 7-membered aromatic or non aromatic heterocycle; and Q₃, Q₄, Q₅, and Q₆ are each, independently, N, N⁺—O⁻, or C;

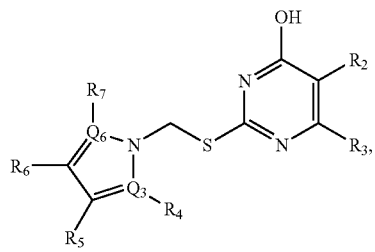

(Ia-7)

including other tautomers, stereoisomers, E/Z stereoisomers, prodrugs, and pharmaceutically acceptable salts thereof, wherein:

R₂ is —H, -D, —CF₃, —C₁-C₅ alkyl, —C₂-C₅ alkenyl, —C₂-C₅ alkynyl, or —CN;

R₃ is —CF₃, —C₁-C₅ alkyl, —C₂-C₅ alkenyl, —C₂-C₅ alkynyl, or —CN;

R₄ and R₇, are each, independently, absent, —H, -D, —OH, -halogen, —CN, —NO₂, —C₁-C₅ alkyl, —C₃-C₆ cycloalkyl, —C₆ aryl, —C₇-C₉ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, and $R_5$ and $R_6$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, together with the atoms to which each is attached, join to form a 5- to 6-membered aromatic or non aromatic carbocycle or heterocycle;

each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle; and $Q_3$ and $Q_6$ are each, independently, N, N$^+$—O$^-$, or C;

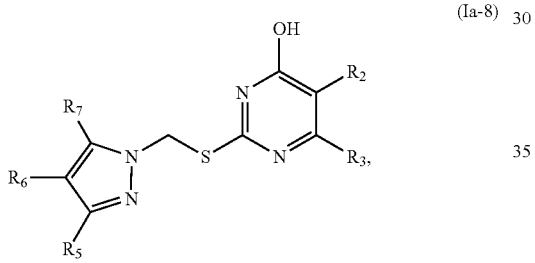

(Ia-8)

including other tautomers, stereoisomers, E/Z stereoisomers, prodrugs, and pharmaceutically acceptable salts thereof, wherein:

$R_2$ is —H, -D, —CF$_3$, —C$_1$-C$_5$ alkyl, —C$_2$-C$_5$ alkenyl, —C$_2$-C$_5$ alkynyl, or —CN;

$R_3$ is —CF$_3$, —C$_1$-C$_5$ alkyl, —C$_2$-C$_5$ alkenyl, —C$_2$-C$_5$ alkynyl, or —CN;

$R_5$, $R_6$, and $R_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or $R_4$ and $R_5$, or $R_5$ and $R_6$, or $R_6$ and $R_7$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

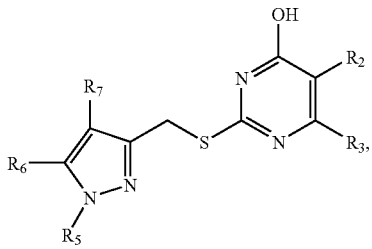

(Ia-9)

including other tautomers, stereoisomers, E/Z stereoisomers, prodrugs, and pharmaceutically acceptable salts thereof, wherein:

$R_2$ is —H, -D, —CF$_3$, —C$_1$-C$_5$ alkyl, —C$_2$-C$_5$ alkenyl, —C$_2$-C$_5$ alkynyl, or —CN;

$R_3$ is —CF$_3$, —C$_1$-C$_5$ alkyl, —C$_2$-C$_5$ alkenyl, —C$_2$-C$_5$ alkynyl, or —CN;

$R_5$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

$R_6$ and $R_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or $R_5$ and $R_6$, or $R_6$ and $R_7$, together with the atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

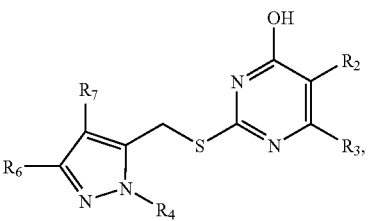

(Ia-10)

including other tautomers, stereoisomers, E/Z stereoisomers, prodrugs, and pharmaceutically acceptable salts thereof, wherein:

$R_2$ is —H, -D, —CF$_3$, —C$_1$-C$_5$ alkyl, —C$_2$-C$_5$ alkenyl, —C$_2$-C$_5$ alkynyl, or —CN;

$R_3$ is —CF$_3$, —C$_1$-C$_5$ alkyl, —C$_2$-C$_5$ alkenyl, —C$_2$-C$_5$ alkynyl, or —CN;

$R_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_6$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_6$ and R$_7$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

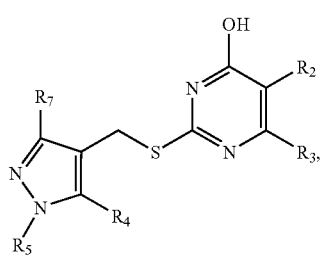

(Ia-11)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_5$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_4$ and R$_5$, together with the atoms to which each is attached, join to form a 5- to 6-membered aromatic or non aromatic heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

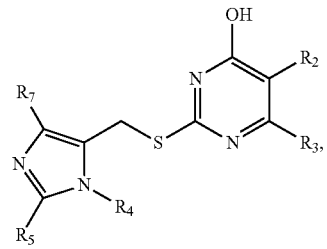

(Ia-12)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_4$, R$_5$ and R$_7$ are each, independently, —H, -D, —OH, halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_4$ and R$_5$, together with the carbon atoms to which each is attached, join to form a 5- to 6-membered aromatic or non aromatic carbocycle or heterocycle, provided that the resulting ring system is not unsubstituted imidazo[1,2-a]pyridine or 5- or 6-chloro-imidazo[1,2-a]pyridine; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

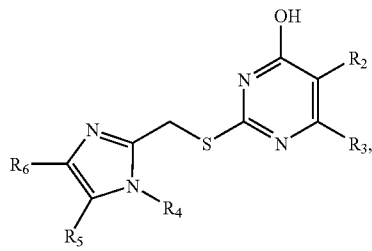

(Ia-13)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_5$ and R$_6$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N (Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_4$ and R$_5$, or R$_5$ and R$_6$, together with the carbon atoms to which each is attached, join to form a 5- to 6-membered aromatic or non aromatic carbocycle or heterocycle wherein R$_5$ is not —NO$_2$ when R$_6$ is —H, and provided that the resulting ring system is not substituted or unsubstituted benzimidazole, unsubstituted imidazo[1,2-a]pyridine, or 5- or 6-chloro-imidazo[1,2-a]pyridine; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

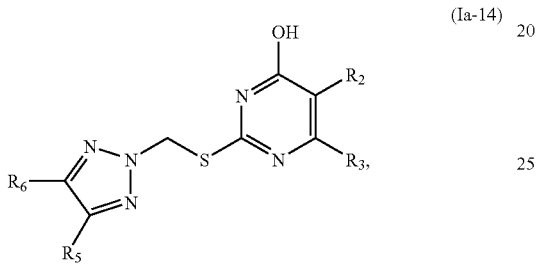

(Ia-14)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_5$ and R$_6$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$, or R$_5$ and R$_6$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle;

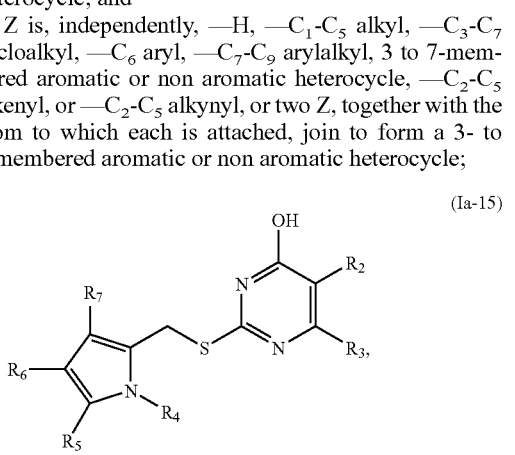

(Ia-15)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_4$ is —H, —OH, —CN, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —N(Z)$_2$, —C(NH)N(Z)$_2$, —C(O)Z, —C(O)N(Z)$_2$, —C(O)OZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$;

R$_5$, R$_6$, and R$_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_5$ and R$_6$, or R$_6$ and R$_7$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a3- to 7-membered aromatic or non aromatic heterocycle;

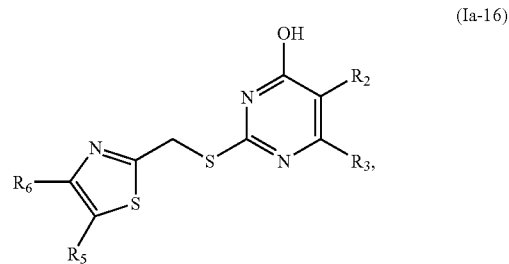

(Ia-16)

including other tautomers, stereoisomers, E/Z stereoisomers, prodrugs, and pharmaceutically acceptable salts thereof, wherein:

R$_2$ is —H, -D, —CF$_3$, —C$_1$-C$_5$ alkyl, —C$_2$-C$_5$ alkenyl, —C$_2$-C$_5$ alkynyl, or —CN;

R$_3$ is —CF$_3$, —C$_1$-C$_5$ alkyl, —C$_2$-C$_5$ alkenyl, —C$_2$-C$_5$ alkynyl, or —CN;

R$_5$ and R$_6$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or R$_5$ and R$_6$, together with the carbon atoms to which each is attached, join to form a 5- to 6-membered aromatic or non aromatic carbocycle or heterocycle provided that the resulting ring system is not unsubstituted benzothiazole; and each Z is, independently, —H, —$C_1$-$C_6$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle;

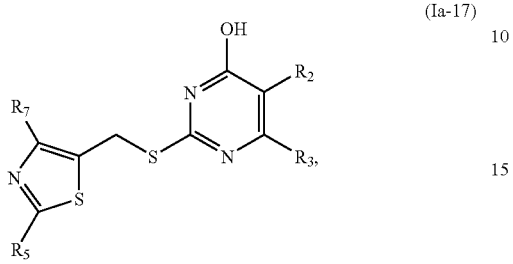

(Ia-17)

including other tautomers, stereoisomers, E/Z stereoisomers, prodrugs, and pharmaceutically acceptable salts thereof, wherein:
$R_2$ is —H, -D, —$CF_3$, —$C_1$-$C_5$ alkyl, —$C_2$-$C_5$ alkenyl, —$C_2$-$C_5$ alkynyl, or —CN;
$R_3$ is —$CF_3$, —$C_1$-$C_5$ alkyl, —$C_2$-$C_5$ alkenyl, alkynyl, or —CN;
$R_5$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and
each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle;

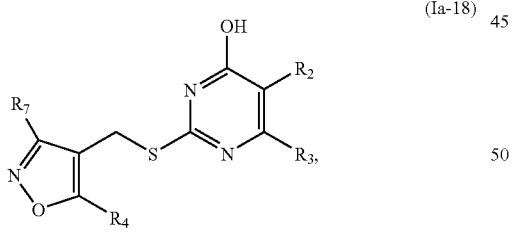

(Ia-18)

including other tautomers, stereoisomers, E/Z stereoisomers, prodrugs, and pharmaceutically acceptable salts thereof, wherein:
$R_2$ is —H, -D, —$CF_3$, —$C_1$-$C_5$ alkyl, —$C_2$-$C_5$ alkenyl, —$C_2$-$C_5$ alkynyl, or —CN;
$R_3$ is $CF_3$, —$C_1$-$C_5$ alkyl, —$C_2$-$C_5$ alkenyl, —$C_2$-$C_5$ alkynyl, or —CN;
$R_4$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and
each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle;

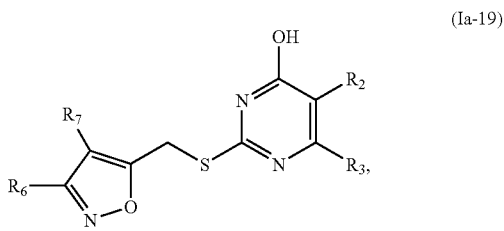

(Ia-19)

including other tautomers, stereoisomers, E/Z stereoisomers, prodrugs, and pharmaceutically acceptable salts thereof, wherein:
$R_2$ is —H, -D, —$CF_3$, —$C_1$-$C_5$ alkyl, —$C_2$-$C_5$ alkenyl, —$C_2$-$C_5$ alkynyl, or —CN;
$R_3$ is —$CF_3$, —$C_1$-$C_5$ alkyl, —$C_2$-$C_5$ alkenyl, —$C_2$-$C_5$ alkynyl, or —CN;
$R_6$ and $R_7$ are each, independently, —H, -D, —OH, -halogen, —CN, —$NO_2$, —$C_1$-$C_5$ alkyl, —$C_3$-$C_6$ cycloalkyl, —$C_6$ aryl, —$C_7$-$C_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or $R_6$ and $R_7$, together with the carbon atoms to which each is attached, join to form a 5- to 6-membered aromatic or non aromatic carbocycle or heterocycle; and
each Z is, independently, —H, —$C_1$-$C_5$ alkyl, —$C_3$-$C_7$ cycloalkyl, —$C_6$ aryl, —$C_7$-$C_9$ arylalkyl, 3 to 7-membered aromatic or non aromatic heterocycle, —$C_2$-$C_5$ alkenyl, or —$C_2$-$C_5$ alkynyl, or two Z, together with the atom to which each is attached, join to form a 3- to 7-membered aromatic or non aromatic heterocycle;

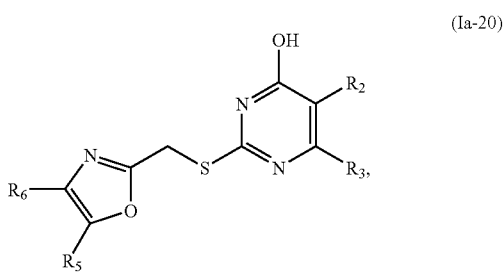

(Ia-20)

including other tautomers, stereoisomers, E/Z stereoisomers, prodrugs, and pharmaceutically acceptable salts thereof, wherein:
$R_2$ is —H, -D, —$CF_3$, —$C_1$-$C_5$ alkyl, —$C_2$-$C_5$ alkenyl, —$C_2$-$C_5$ alkynyl, or —CN;
$R_3$ is —$CF_3$, —$C_1$-$C_5$ alkyl, —$C_2$-$C_5$ alkenyl, —$C_2$-$C_5$ alkynyl, or —CN;

$R_5$ and $R_6$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or $R_5$ and $R_6$, together with the carbon atoms to which each is attached, join to form a 5- to 6-membered aromatic or non aromatic carbocycle or heterocycle; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle; and

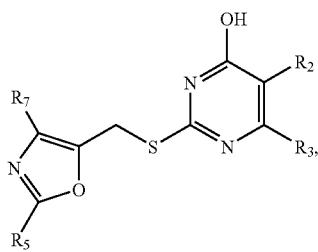

(Ia-21)

including other tautomers, stereoisomers, E/Z stereoisomers, prodrugs, and pharmaceutically acceptable salts thereof, wherein:

$R_2$ is —H, -D, —CF$_3$, —C$_1$-C$_5$ alkyl, —C$_2$-C$_5$ alkenyl, —C$_2$-C$_5$ alkynyl, or —CN;

$R_3$ is —CF$_3$, —C$_1$-C$_5$ alkyl, —C$_2$-C$_5$ alkenyl, —C$_2$-C$_5$ alkynyl, or —CN;

$R_5$ and $R_7$ are each, independently, —H, -D, —OH, -halogen, —CN, —NO$_2$, —C$_1$-C$_5$ alkyl, —C$_3$-C$_6$ cycloalkyl, —C$_6$ aryl, —C$_7$-C$_9$ arylalkyl, 3 to 7-membered aromatic or non aromatic heterocycle, —OZ, —N(Z)$_2$, —C(NH)N(Z)$_2$, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, or —NZC(NCN)N(Z)$_2$; and each Z is, independently, —H, —C$_1$-C$_5$ alkyl, —C$_3$-C$_7$ cycloalkyl, —C$_6$ aryl, —C$_7$-C$_9$ arylalkyl, 3 to 7-membered aromatic or non aromatic heterocycle, —C$_2$-C$_5$ alkenyl, or —C$_2$-C$_5$ alkynyl, or two Z, together with the atom to which each is attached, join to form a 3- to 7-membered aromatic or non aromatic heterocycle.

2. A compound having the following structure:

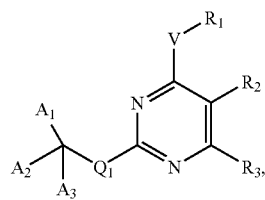

(Ia)

and its tautomer

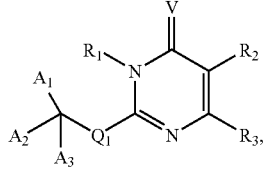

(Ib)

including other tautomers, stereoisomers, E/Z stereoisomers, prodrugs, and pharmaceutically acceptable salts thereof, wherein:

$Q_1$ is —S—, —SO—, —SO$_2$—, —CH$_2$CH$_2$—, —CH=CH—, —OCH$_2$—, —SCH$_2$—, —SOCH$_2$—, or —SO$_2$CH$_2$—;

V is O, S, NH, or NZ, or N-terminal linked amino acid, or halogen when $R_1$ is absent;

$R_1$ is absent, —H, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, —(CR$_{2A}$R$_{2B}$)$_{r3}$PO(OZ)$_2$, or C-terminal linked amino acid;

each $R_{1A}$, $R_{1B}$, $R_{2A}$, and $R_{2B}$ is, independently, H or C$_{1-5}$ alkyl;

Z is either —H or —CH$_3$;

each n is 1 or 2;

each r2 is an integer between 1-3;

each r3 is an integer between 0-2;

$R_2$ is —H, -D, —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$R_3$ is —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$A_1$ and $A_2$ are each, independently, —H, -D, -halogen, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, or —C$_7$-C$_{14}$ arylalkyl;

$A_3$ is an aromatic heterocyclic ring selected from the group consisting of:

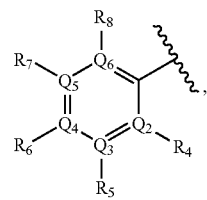

(Fragment A-1)

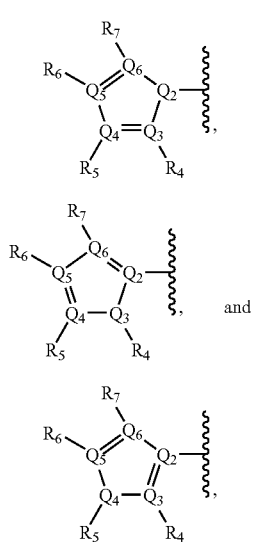

(Fragment A-2)

(Fragment A-3) and (Fragment A-4)

$Q_2$, $Q_5$, and $Q_6$ are each, independently, N, $N^+$—$O^-$, or C; $Q_3$ and $Q_4$ are each, independently, N, $N^+$—$O^-$, C, O, or S, wherein only one of $Q_3$ and $Q_4$ can be O or S;

wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and $R_4$, $R_5$, $R_6$, $R_7$, and $R_8$ are each, independently, absent, —H, -D, —OH, —$O^-$, -halogen, —CN, —$NO_2$, —SH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle, provided that the resulting ring system is not substituted or unsubstituted benzimidazole, unsubstituted benzothiazole, unsubstituted imidazo[1,2-a]pyridine, 5- or 6-chloro-imidazo[1,2-a]pyridine, unsubstituted quinoline, 8-substituted quinoline, unsubstituted quinoxaline, 2- or 4-chloro-quinoline, or 4-hydroxy-1,3-quinazoline, wherein when $A_3$ is unsubstituted pyridine-2-yl, and $A_1$ and $A_2$ are each —H, $R_3$ is not —OH, —$CF_3$, —$C_1$-$C_3$ alkyl, phenyl, difluorobenzyl, or —NHC(O)CH$_3$;

wherein when $A_3$ is unsubstituted pyridine-4-yl, and $A_1$ and $A_2$ are each —H, $R_3$ is not —OH, —$CH_3$, $CH_2CH_2CH_3$, or difluorobenzyl;

wherein when $A_3$ is unsubstituted, 6-chloro, or 2,6-dichloro pyridine-3-yl, and $A_1$ and $A_2$ are each —H, $R_3$ is not —OH, —$CF_3$, —$C_1$-$C_3$ alkyl, phenyl, or —NHC(O)CH$_3$;

wherein when $A_3$ is substituted or unsubstituted pyrazol-1-yl, $R_3$ is not —OH;

wherein $A_3$ is not 4-$NO_2$-imidazol-2-yl; and provided that (a) $R_1$ is —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, or —(CR$_{2A}$R$_{2B}$)$_{r3}$PO(OZ)$_2$;

(b) $R_2$ is —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

c) $R_3$ is —OZ, —C(NH)N(Z)$_2$, O(CH$_2$)$_n$OZ, —C(O)Z, —OC(O)Z, —OC(O)OZ, —OC(O)N(Z)$_2$, C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$; or (d) at least one of $R_4$, $R_5$, $R_6$, $R_7$, and $R_8$ is —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$.

3. A compound having the following structure

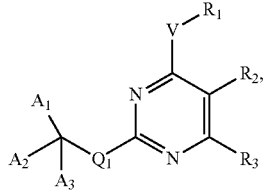
(Ia)

and its tautomer

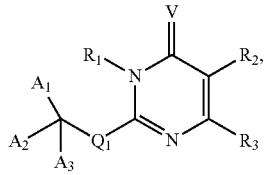
(Ib)

including other tautomers, stereoisomers, E/Z stereoisomers, prodrugs, and pharmaceutically acceptable salts thereof, wherein:

$Q_1$ is —S—, —SO—, —$SO_2$—, —$CH_2CH_2$—, —CH=CH—, —$OCH_2$—, —$SCH_2$—, —$SOCH_2$—, or —$SO_2CH_2$—;

V is O, S, NH, or NZ, or N-terminal linked amino acid, or halogen when $R_1$ is absent;

$R_1$ is absent, —H, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, —(CR$_{2A}$R$_{2B}$)$_{r3}$PO(OZ)$_2$, or C-terminal linked amino acid;

each $R_{1A}$, $R_{1B}$, $R_{2A}$, and $R_{2B}$ is, independently, H or $C_{1-5}$ alkyl;

each Z is, independently, —H, —$C_1$-$C_8$ alkyl, —$C_4$-$C_{12}$ alkcycloalkyl, —$C_3$-$C_9$ alkheterocyclyl, wherein the heterocyclyl is 3 to 9 membered, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —$C_2$-$C_8$ alkenyl, or —$C_2$-$C_8$ alkynyl, or two Z, together with the atom(s) to which each is attached, join to form a 3- to 7-membered aromatic or non aromatic heterocycle;

each n is 1 or 2;

each r2 is an integer between 1-3;

each r3 is an integer between 0-2;

R$_2$ is —H, -D, —OH, -halogen, —CN, —NO$_2$, —SH, —CF$_3$, —C$_1$-C$_3$ alkyl, —C$_2$-C$_8$ alkenyl, —C$_2$-C$_8$ alkynyl, C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

R$_3$ is —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

A$_1$ and A$_2$ are each, independently, —H, -D, -halogen, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, or —C$_7$-C$_{14}$ arylalkyl;

A$_3$ is an aromatic heterocyclic ring selected from the group consisting of:

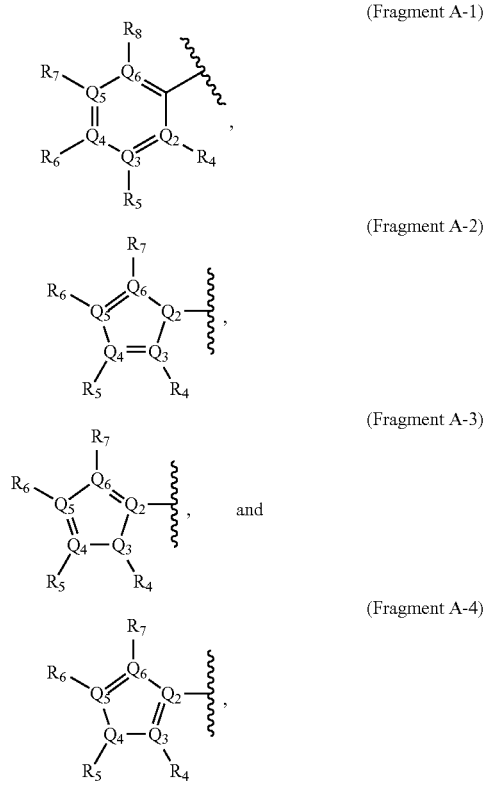

Q$_2$, Q$_5$, and Q$_6$ are each, independently, N, N$^+$—O$^-$, or C;
Q$_3$ and Q$_4$ are each, independently, N, N$^+$—O$^-$, C, O, or S, wherein only one of Q$_3$ and Q$_4$ can be O or S;
wherein Q$_2$, Q$_3$, Q$_4$, Q$_5$, and Q$_6$ simultaneously are C only if R$_4$ and R$_5$, R$_5$ and R$_6$, R$_6$ and R$_7$, or R$_7$ and R$_8$, together with the atoms to which each is attached, loin to form a 5- to 6-membered aromatic or non aromatic heterocyclyl; and R$_4$, R$_5$, R$_6$, R$_7$, and R$_8$ are each, independently, absent, —H, -D, —OH, —O$^-$, -halogen, —CN, —NO$_2$, —SH, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or R$_4$ and R$_5$, or R$_5$ and R$_6$, or R$_6$ and R$_7$, or R$_7$ and R$_8$, together with the atoms to which each is attached, join to form a 5- to 6-membered aromatic or non aromatic carbocycle or heterocycle provided that the resulting ring system is not substituted or unsubstituted benzimidazole, unsubstituted benzothiazole, unsubstituted imidazo[1,2-a]pyridine, 5- or 6-chloro-imidazo[1,2-a]pyridine, indole when R$_2$ is C(O)OCH$_2$CH$_3$ unsubstituted quinoline, 8-substituted quinoline, unsubstituted quinoxaline, 2- or 4-chloroquinoline, or 4-hydroxy-1,3-quinazoline, wherein when A$_3$ is unsubstituted pyridine-2-yl, and A$_1$ and A$_2$ are each —H, R$_3$ is not —OH, —CF$_3$, —C$_1$-C$_3$ alkyl, phenyl, difluorobenzyl, —NHC(O)furan, —NHC(O)CH$_3$, or —NHC(O)CH$_2$CH$_3$;

wherein when A$_3$ is unsubstituted pyridine-4-yl, and A$_1$ and A$_2$ are each —H, R$_3$ is not —OH, —CH$_3$, CH$_2$CH$_2$CH$_3$, or difluorobenzyl;

wherein when A$_3$ is unsubstituted, 6-chloro, or 2,6-dichloro pyridine-3-yl, and A$_1$ and A$_2$ are each —H, R$_3$ is not —OH, —CF$_3$, —C$_1$-C$_3$ alkyl, phenyl, —C(O)OCH$_2$CH$_3$, or —NHC(O)CH$_3$;

wherein when A$_3$ is substituted or unsubstituted pyrazol-1-yl, R$_3$ is not —OH;

wherein A$_3$ is not 4-NO$_2$-imidazol-2-yl; and provided that (a) R$_1$ is —C(O)N(Z)$_2$, —(CR$_{1A}$R$_{1B}$)$_{r2}$OPO(OZ)$_2$, or —(CR$_{2A}$R$_{2B}$)$_{r3}$PO(OZ)$_2$;

(b) R$_2$ is —N(Z)$_2$, —C(NH)N(Z)$_2$, —OC(O)N(Z)$_2$, —C(O)N(Z)$_2$, —S(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

c) R$_3$ is —C(NH)N(Z)$_2$, —OC(O)N(Z)$_2$, —C(O)N(Z)$_2$, —NHC(NH)N(Z)$_2$, —NZC(NH)N(Z)$_2$, —NHC(NCN)N(Z)$_2$, —NZC(NCN)N(Z)$_2$, or —PO(OZ)$_2$; or (d) at least one of R$_4$, R$_5$, R$_6$, R$_7$, and R$_8$ is —N(Z)$_2$, —C(NH)N(Z)$_2$, —OC(O)N(Z)$_2$, —C(O)N(Z)$_2$, —NHC(NH)N(Z)$_2$, —NZC(NH)N(Z)$_2$, —NHC(NCN)N(Z)$_2$, —NZC(NCN)N(Z)$_2$, or —PO(OZ)$_2$; and provided that two Z, together with the atom to which each is attached, join to form a 5-, 6-, or 7-membered non aromatic heterocycle.

4. A compound having the following structure:

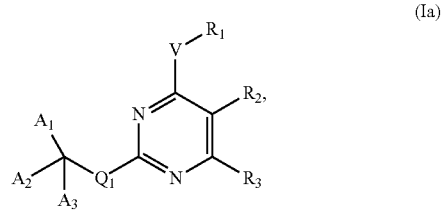

(Ia)

and its tautomer

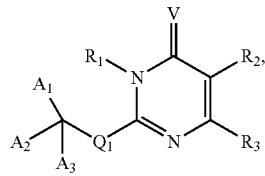 (Ib)

including other tautomers, stereoisomers, E/Z stereoisomers, prodrugs, and pharmaceutically acceptable salts thereof, wherein:

$Q_1$ is —S—, —SO—, —SO$_2$—, —CH$_2$CH$_2$—, —CH═CH—, —OCH$_2$—, —SCH$_2$—, —SOCH$_2$—, or —SO$_2$CH$_2$—;

V is O, S, NH, or NZ, or N-terminal linked amino acid, or halogen when $R_1$ is absent;

$R_1$ is absent, —H, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, —(CR$_{2A}$R$_{2B}$)$_{r3}$PO(OZ)$_2$, or C-terminal linked amino acid;

each $R_{1A}$, $R_{1B}$, $R_{2A}$, and $R_{2B}$ is, independently, H or C$_{1-5}$ alkyl;

each Z is, independently, —H, —C$_1$-C$_8$ alkyl, —C$_4$-C$_{12}$alkcycloalkyl, —C$_3$-C$_9$ alkheterocyclyl, wherein the heterocyclyl is 3 to 9 membered, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —C$_2$-C$_8$ alkenyl, or —C$_2$-C$_8$ alkynyl, or two Z, together with the atom(s) to which each is attached, join to form a 3- to 7-membered aromatic or non aromatic heterocycle;

each n is 1 or 2;

each r2 is an integer between 1-3;

each r3 is an integer between 0-2;

$R_2$ is —H, -D, —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9 membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$R_3$ is —OH, -halogen, —CN, —NO$_2$, —SH, —CF$_3$, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$A_1$ and $A_2$ are each, independently, —H, -D, -halogen, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, or —C$_7$-C$_{14}$ arylalkyl;

$A_3$ is an aromatic heterocyclic ring selected from the group consisting of:

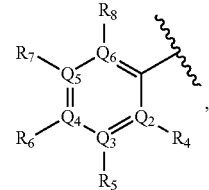 (Fragment A-1)

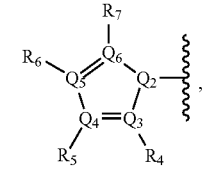 (Fragment A-2)

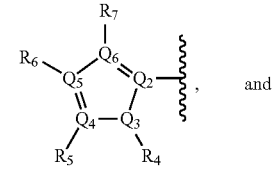 (Fragment A-3)

and

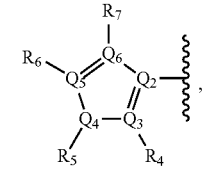 (Fragment A-4)

$Q_2$, $Q_5$, and $Q_6$ are each, independently, N, N$^+$—O$^-$, or C;

$Q_3$ and $Q_4$ are each, independently, N, N$^+$—O$^-$, C, O, or S, wherein only one of $Q_3$ and $Q_4$ can be O or S;

wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and $R_4$, $R_5$, $R_6$, $R_7$, and $R_8$ are each, independently, absent, —H, -D, —OH, —O$^-$, -halogen, —CN, —NO$_2$, —SH, —C$_1$-C$_8$ alkyl, —C$_2$-C$_8$ alkenyl, —C$_2$-C$_8$ alkynyl, —C$_3$-C$_{12}$ cycloalkyl, —C$_6$-C$_{12}$ aryl, —C$_7$-C$_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle provided that the resulting ring system is not substituted or unsubstituted benzimidazole, unsubstituted benzothiazole, unsubstituted imidazo[1,2-a]pyridine, 5- or 6-chloro-imidazo[1,2-a]pyridine, indole when $R_2$ is C(O)OCH$_2$CH$_3$ unsubstituted quinoline, 8-substituted quinoline, unsubstituted quinoxaline, 2- or 4-chloroquinoline, or 4-hydroxy-1,3-quinazoline, wherein when $A_3$ is unsubstituted pyridine-2-yl, and $A_1$ and $A_2$ are each —H, $R_3$ is not —OH, —CF$_3$, —C$_1$-C$_3$ alkyl, phenyl, difluorobenzyl, —NHC(O)furan, —NHC(O)CH$_3$, or —NHC(O)CH$_2$CH$_3$;

wherein when $A_3$ is unsubstituted pyridine-4-yl, and $A_1$ and $A_2$ are each —H, $R_3$ is not —OH, —CH$_3$, —CH$_2$CH$_2$CH$_3$, or difluorobenzyl;

wherein when $A_3$ is unsubstituted, 6-chloro, or 2,6-dichloro pyridine-3-yl, and $A_1$ and $A_2$ are each —H, $R_3$ is not —OH, —$CF_3$, —$C_1$-$C_3$ alkyl, phenyl, —C(O)OCH$_2$CH$_3$, or —NHC(O)CH$_3$;

wherein when $A_3$ is substituted or unsubstituted pyrazol-1-yl, $R_3$ is not —OH;

wherein $A_3$ is not 4-NO$_2$-imidazol-2-yl; and provided that
(a) $R_1$ is —C(O)N(Z)$_2$, —(CR$_{1A}$R$_{1B}$)$_{r2}$OPO(OZ)$_2$, or —(CR$_{2A}$R$_{2B}$)$_{r3}$PO(OZ)$_2$;
(b) $R_2$ is —N(Z)$_2$, —C(NH)N(Z)$_2$, —OC(O)N(Z)$_2$, —C(O)N(Z)$_2$, —S(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;
c) $R_3$ is —C(NH)N(Z)$_2$, —OC(O)N(Z)$_2$, —C(O)N(Z)$_2$, —NHC(NH)N(Z)$_2$, —NZC(NH)N(Z)$_2$, —NHC(NCN)N(Z)$_2$, —NZC(NCN)N(Z)$_2$, or —PO(OZ)$_2$; or
(d) at least one of $R_4$, $R_5$, $R_6$, $R_7$, and $R_8$ is —N(Z)$_2$, —C(NH)N(Z)$_2$, —OC(O)N(Z)$_2$, —C(O)N(Z)$_2$, —NHC(NH)N(Z)$_2$, —NZC(NH)N(Z)$_2$, —NHC(NCN)N(Z)$_2$, —NZC(NCN)N(Z)$_2$, or —PO(OZ)$_2$; and provided that two Z, together with the atom to which each is attached, join to form a 3- to 7-membered aromatic or non aromatic heterocycle, wherein the heterocycle is substituted with any of the substituent groups described herein for $R_4$-$R_8$.

5. A compound having the following structure:

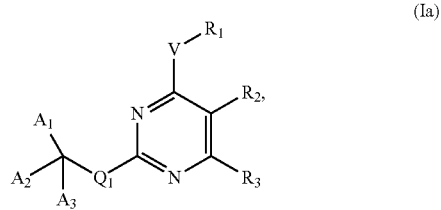

(Ia)

and its tautomer

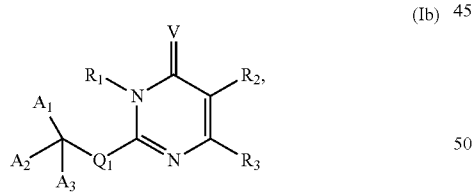

(Ib)

including other tautomers, stereoisomers, E/Z stereoisomers, prodrugs, and pharmaceutically acceptable salts thereof, wherein:

$Q_1$ is —S—, —SO—, —SO$_2$—, —CH$_2$CH$_2$—, —CH=CH—, —OCH$_2$—, —SCH$_2$—, —SOCH$_2$—, or —SO$_2$CH$_2$—;

V is O, S, NH, or NZ, or N-terminal linked amino acid, or halogen when $R_1$ is absent;

$R_1$ is absent, —H, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, —(CR$_{2A}$R$_{2B}$)$_{r3}$PO(OZ)$_2$, or C-terminal linked amino acid;

each Z is, independently, —H, —$C_1$-$C_8$ alkyl, —$C_4$-$C_{12}$ alkcycloalkyl, —$C_3$-$C_9$ alkheterocyclyl, wherein the heterocyclyl is 3 to 9 membered, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —$C_2$-$C_8$ alkenyl, or —$C_2$-$C_8$ alkynyl, or two Z, together with the atom(s) to which each is attached, join to form a 3- to 7-membered aromatic or non aromatic heterocycle;

each n is 1 or 2;

each r2 is an integer between 1-3;

each r3 is an integer between 0-2;

$R_2$ is —H, -D, —OH, -halogen, —CN, —NO$_2$, —SH, —CF$_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$R_3$ is —OH, -halogen, —CN, —NO$_2$, —SH, —CF$_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$A_1$ and $A_2$ are each, independently, —H, -D, -halogen, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, or —$C_7$-$C_{14}$ arylalkyl;

$A_3$ is an aromatic heterocyclic ring selected from the group consisting of:

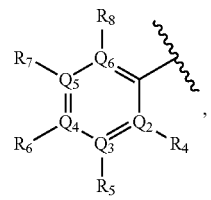

(Fragment A-1)

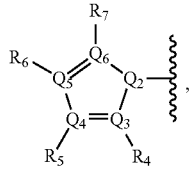

(Fragment A-2)

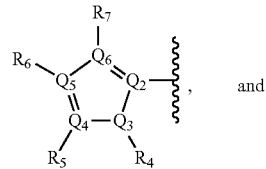

(Fragment A-3)

and

-continued

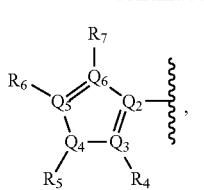

(Fragment A-4)

$Q_2$, $Q_5$, and $Q_6$ are each, independently, N, $N^+$—$O^-$, or C;
$Q_3$ and $Q_4$ are each, independently, N, $N^+$—$O^-$, C, O, or S, wherein only one of $Q_3$ and $Q_4$ can be O or S;
wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and
$R_4$, $R_5$, $R_6$, $R_7$, and $R_8$ are each, independently, absent, —H, -D, —OH, —$O^-$, -halogen, —CN, —$NO_2$, —SH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —$N(Z)_2$, —$C(NH)N(Z)_2$, —$O(CH_2)_n$OZ, —C(O)Z, —OC(O)Z, —OC(O)OZ, —OC(O)N(Z)_2$, —$C(O)N(Z)_2$, —C(O)OZ, —SZ, —SOZ, —$S(O)_2Z$, —NHC(O)Z, —NHS(O)_2Z$, —NHC(NH)N(Z)_2$, —NZC(NH)N(Z)_2$, —NHC(NCN)N(Z)_2$, —NZC(NCN)N(Z)_2$, —PO(OZ)_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle provided that the resulting ring system is not substituted benzimidazole, 5- or 6-chloro-imidazo[1,2-a]pyridine, 8-substituted quinoline, 2- or 4-chloro-quinoline, or 4-hydroxy-1,3-quinazoline;
wherein said compound comprises a carbocycle or heterocycle formed by combining $R_4$ and $R_5$, or $R_6$ and $R_7$, or $R_7$ and $R_8$ with the atoms to which each is attached; and
wherein the carbocycle or the heterocycle formed by $R_4$ and $R_5$, $R_5$ and $R_6$, $R_6$ and $R_7$, or $R_7$ and $R_8$, is substituted with 1, 2, 3, 4, 5, 6, or 7 substituents.

6. The compound of claim 5, wherein the heterocycle formed by $R_4$ and $R_5$, $R_5$ and $R_6$, $R_6$ and $R_7$, or $R_7$ and $R_8$, is substituted with an amino group.

7. A compound having the following structure:

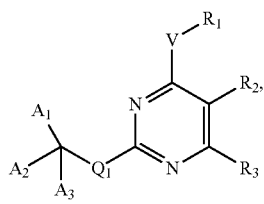

(Ia)

and its tautomer

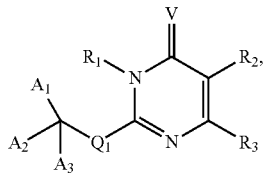

(Ib)

including other tautomers, stereoisomers, E/Z stereoisomers, prodrugs, and pharmaceutically acceptable salts thereof, wherein:

$Q_1$ is —S—, —SO—, —$SO_2$—, —$CH_2CH_2$—, —CH=CH—, —$OCH_2$—, —$SCH_2$—, —$SOCH_2$—, or —$SO_2CH_2$—;

V is O, S, NH, or NZ, or N-terminal linked amino acid, or halogen when $R_1$ is absent;

$R_1$ is absent, —H, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, —$(CH_2)_nOZ$, —C(O)Z, —C(O)OZ, —C(O)NHZ, —$C(O)N(Z)_2$, —$(CR_{1A}R_{1B})_{r2}OPO(OZ)_2$, —$(CR_{2A}R_{2B})_{r3}PO(OZ)_2$, or C-terminal linked amino acid;

each $R_{1A}$, $R_{1B}$, $R_{2A}$, and $R_{2B}$ is, independently, H or $C_{1-5}$ alkyl;

each Z is, independently, —H, —$C_{1-3}$ alkyl, or two Z combine to form a 5-, 6-, or 7-membered ring each n is 1 or 2;

each r2 is an integer between 1-3;

each r3 is an integer between 0-2;

$R_2$ is —H, -D, —OH, -halogen, —CN, —$NO_2$, —SH, —$CF_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —$N(Z)_2$, —$C(NH)N(Z)_2$, —$O(CH_2)_nOZ$, —C(O)Z, —OC(O)Z, —OC(O)OZ, —OC(O)N(Z)_2$, —$C(O)N(Z)_2$, —C(O)OZ, —SZ, —SOZ, —$S(O)_2Z$, —NHC(O)Z, —NHS(O)_2Z$, —NHC(NH)N(Z)_2$, —NZC(NH)N(Z)_2$, —NHC(NCN)N(Z)_2$, —NZC(NCN)N(Z)_2$, or —$PO(OZ)_2$;

$R_3$ is —OH, -halogen, —CN, —$NO_2$, —SH, —$CF_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —$C(NH)N(Z)_2$, —$O(CH_2)_nOZ$, —C(O)Z, —OC(O)Z, —OC(O)OZ, —OC(O)N(Z)_2$, —$C(O)N(Z)_2$, —C(O)OZ, —SZ, —SOZ, —$S(O)_2Z$, —NHC(O)Z, —NHS(O)_2Z$, —NHC(NH)N(Z)_2$, —NZC(NH)N(Z)_2$, —NHC(NCN)N(Z)_2$, —NZC(NCN)N(Z)_2$, or —$PO(OZ)_2$;

$A_1$ and $A_2$ are each, independently, —H, -D, -halogen, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, or —$C_7$-$C_{14}$ arylalkyl;

$A_3$ is an aromatic heterocyclic ring selected from the group consisting of:

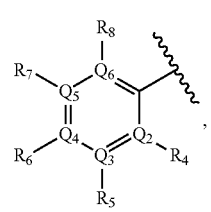

(Fragment A-1)

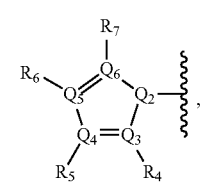

(Fragment A-2)

-continued

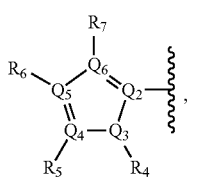
(Fragment A-3)

and

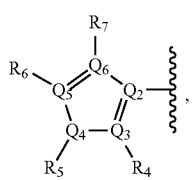
(Fragment A-4)

$Q_2$, $Q_5$, and $Q_6$ are each, independently, N, $N^+$—$O^-$, or C;
$Q_3$ and $Q_4$ are each, independently, N, $N^+$—$O^-$, C, O, or S, wherein only one of $Q_3$ and $Q_4$ can be O or S;
wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and
$R_4$, $R_5$, $R_6$, $R_7$, and $R_8$ are each, independently, absent, —H, -D, —OH, —$O^-$, -halogen, —CN, —$NO_2$, —SH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle provided that the resulting ring system is not substituted or unsubstituted benzimidazole, unsubstituted benzothiazole, unsubstituted imidazo[1,2-a]pyridine, 5- or 6-chloro-imidazo[1,2-a]pyridine, indole when $R_2$ is C(O)OCH$_2$CH$_3$ unsubstituted quinoline, 8-substituted quinoline, unsubstituted quinoxaline, 2- or 4-chloro-quinoline, or 4-hydroxy-1,3-quinazoline,
wherein when $A_3$ is unsubstituted pyridine-2-yl, and $A_1$ and $A_2$ are each —H, $R_3$ is not —OH, —$CF_3$, —$C_1$-$C_3$ alkyl, phenyl, difluorobenzyl, —NHC(O)CH$_3$, or —NHC(O)CH$_2$CH$_3$;
wherein when $A_3$ is unsubstituted pyridine-4-yl, and $A_1$ and $A_2$ are each —H, $R_3$ is not —OH, —CH$_3$, —CH$_2$CH$_2$CH$_3$, or difluorobenzyl;
wherein when $A_3$ is unsubstituted, 6-chloro, or 2,6-dichloro pyridine-3-yl, and $A_1$ and $A_2$ are each —H, $R_3$ is not —OH, —$CF_3$, —$C_1$-$C_3$ alkyl, phenyl, —C(O)OCH$_2$CH$_3$, or —NHC(O)CH$_3$;
wherein when $A_3$ is substituted or unsubstituted pyrazol-1-yl, $R_3$ is not —OH;
wherein $A_3$ is not 4-$NO_2$-imidazol-2-yl; and
provided that
(a) $R_1$ is —(CH$_2$)$_n$OZ, —C(O)Z, —C(O)OZ, —C(O)NHZ, —C(O)N(Z)$_2$, —(CR$_{1A}$R$_{1B}$)$_{r2}$OPO(OZ)$_2$, or —(CR$_{2A}$R$_{2B}$)$_{r3}$PO(OZ)$_2$;
(b) $R_2$ is —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

c) $R_3$ is —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$; or (d) at least one of $R_4$, $R_5$, $R_6$, $R_7$, and $R_8$ is —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$.

8. The compound of claim 7, wherein each Z is, independently, —H, —CH$_3$, or —CH$_2$CH$_3$.

9. The compound of claim 7, wherein both Z are either —H or —CH$_3$.

10. The compound of claim 7, wherein two Z, together with the atom to which each is attached, join to form a 5-, 6-, or 7-membered non aromatic heterocycle.

11. A compound selected from the group consisting of:

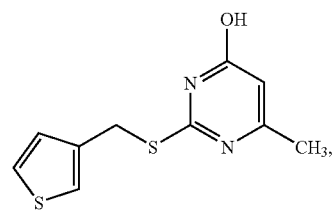

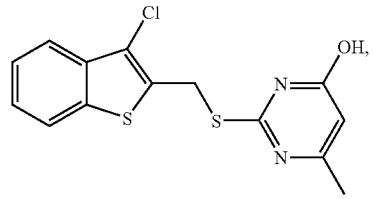

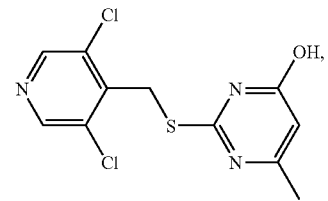

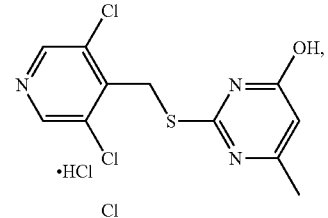

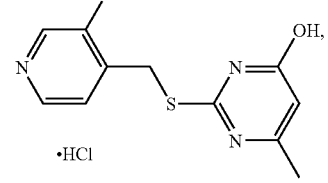

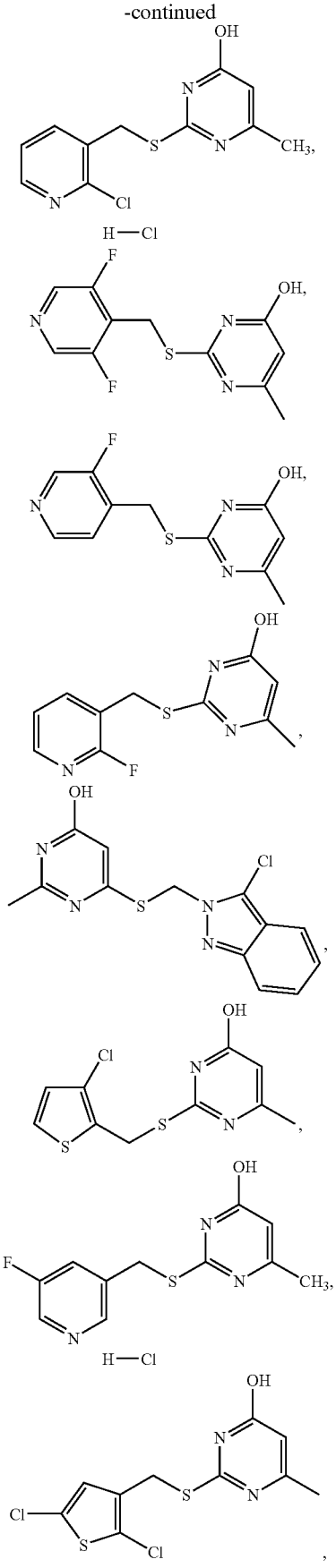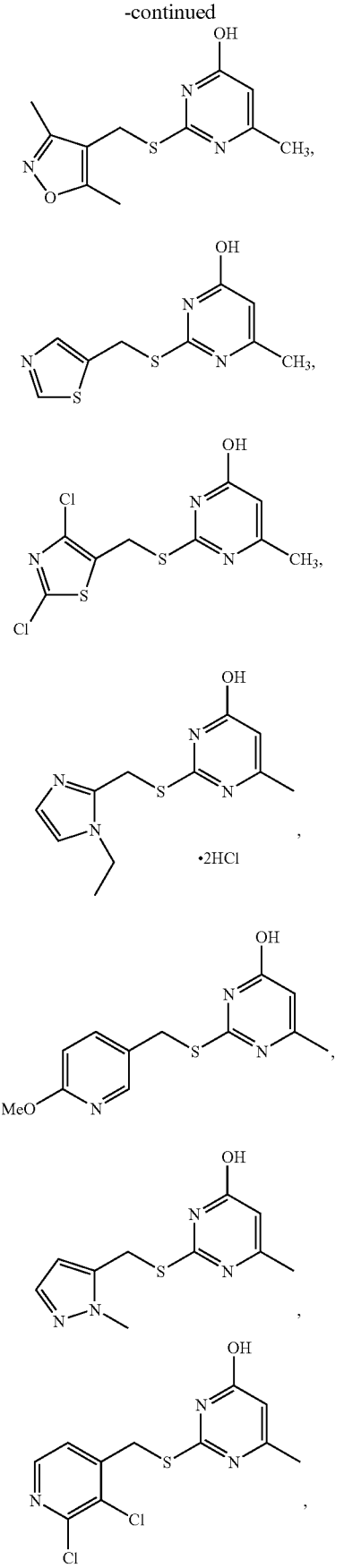

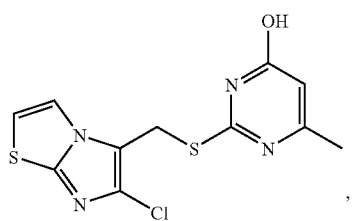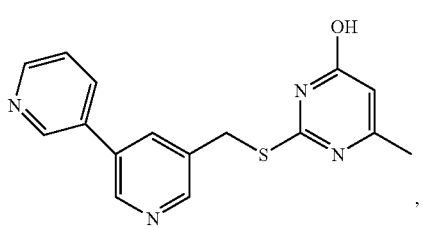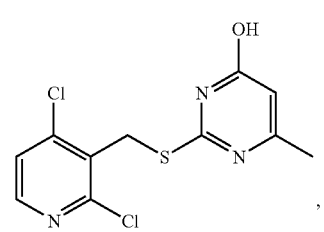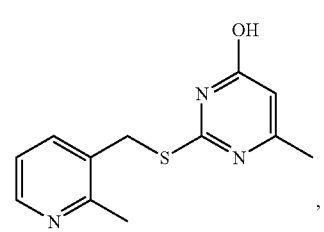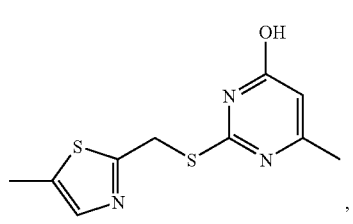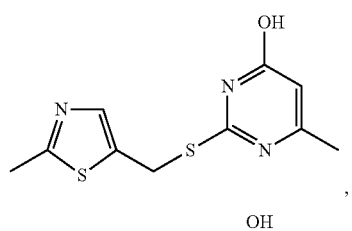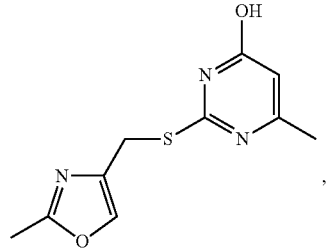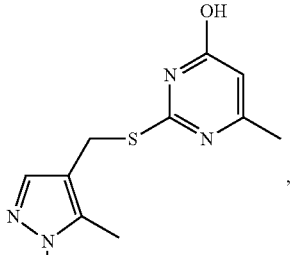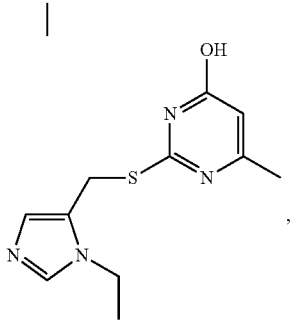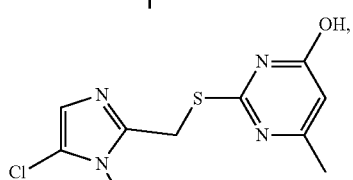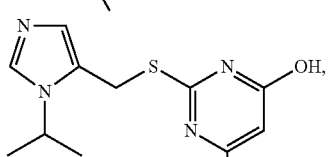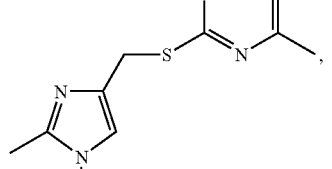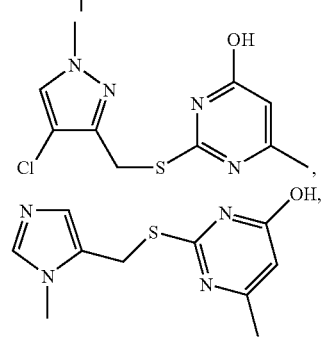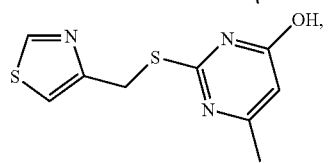

-continued
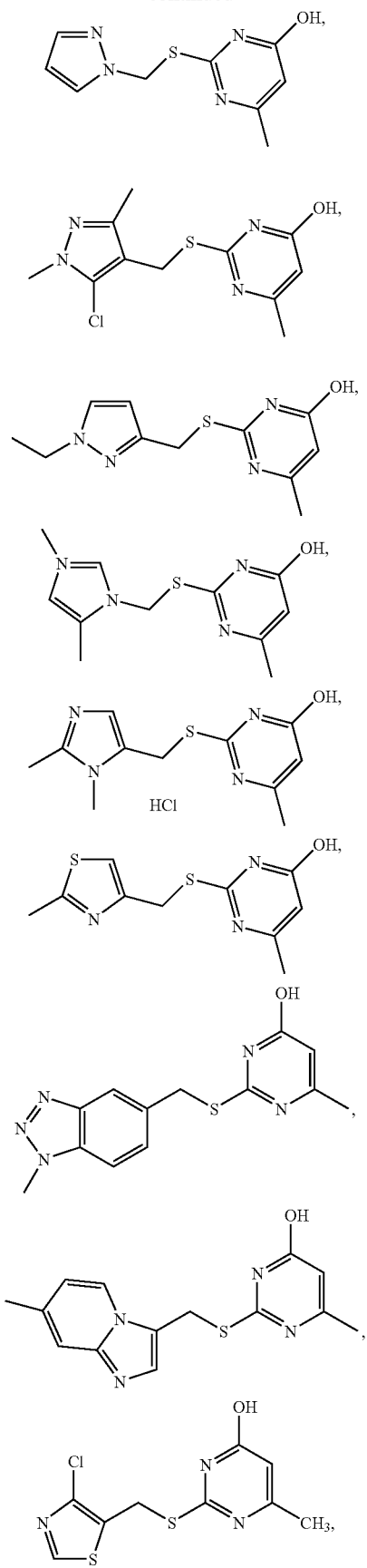
-continued
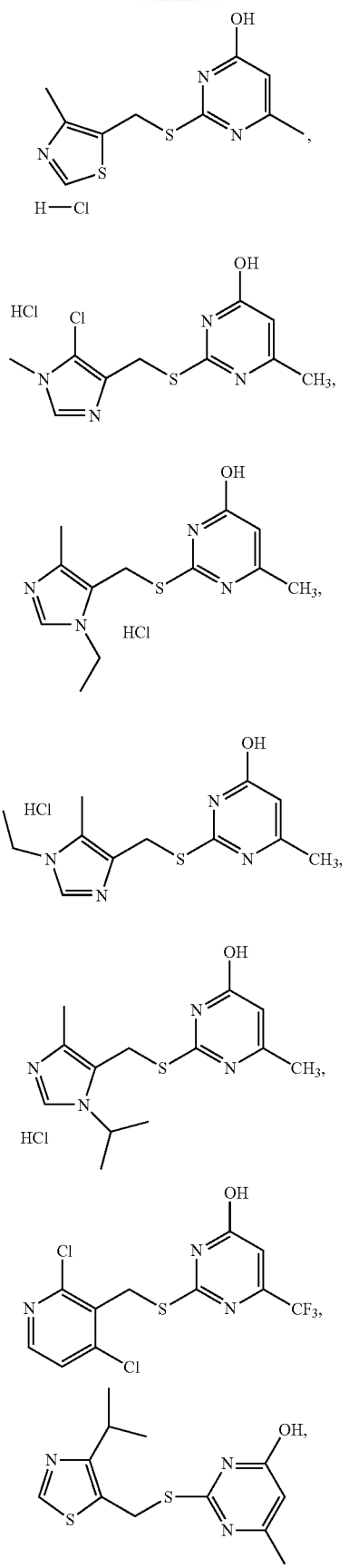

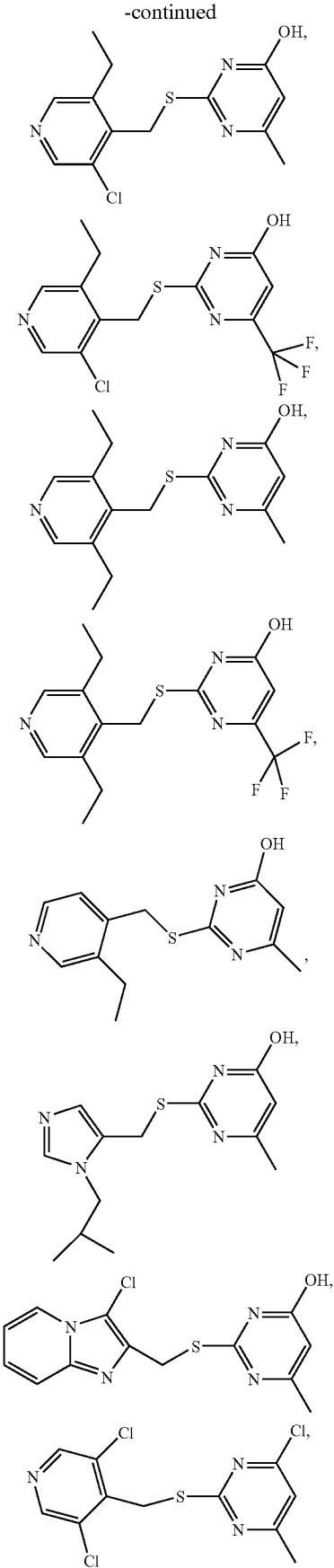
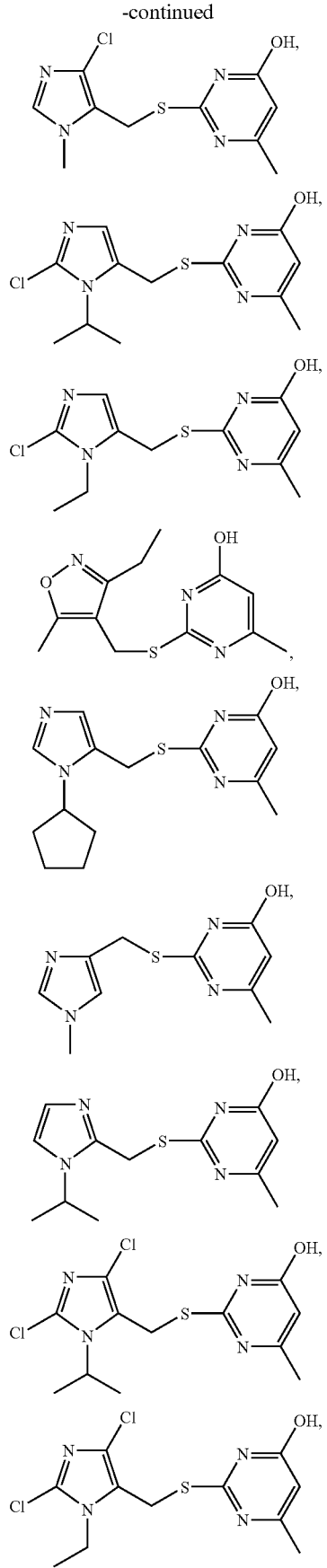

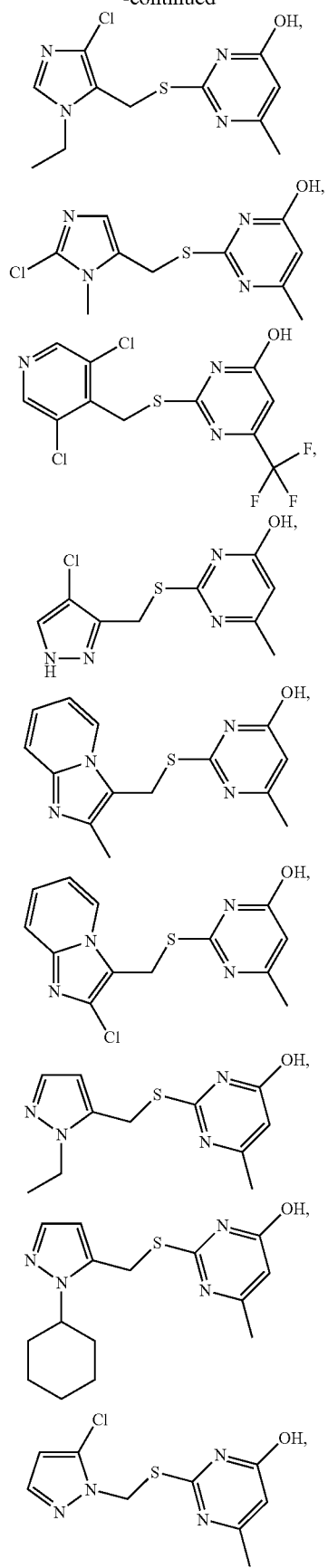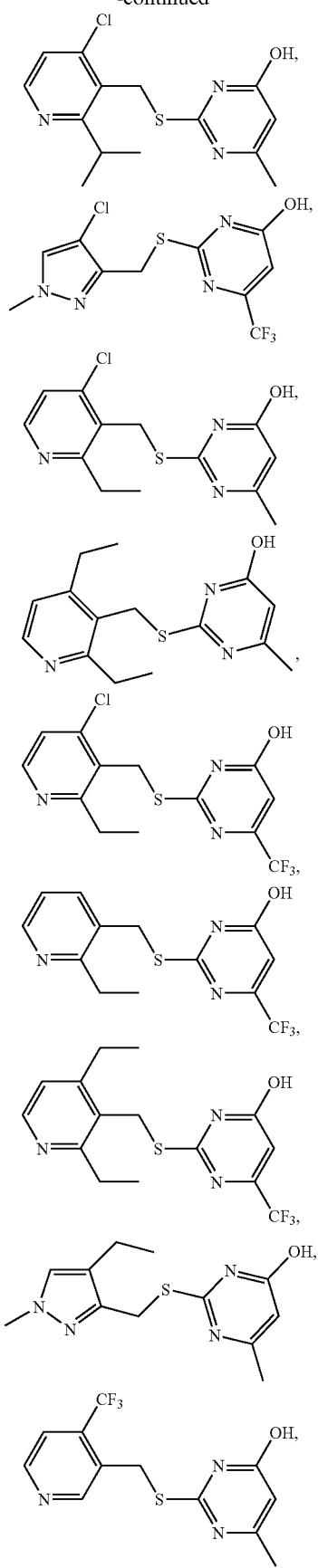

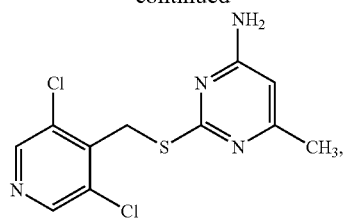
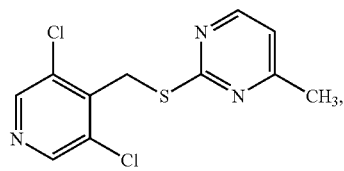
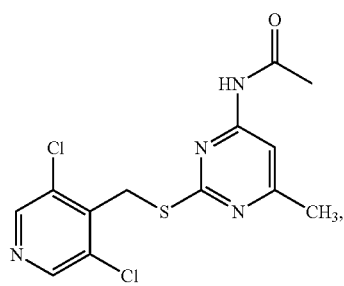
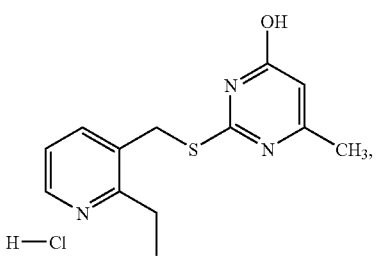
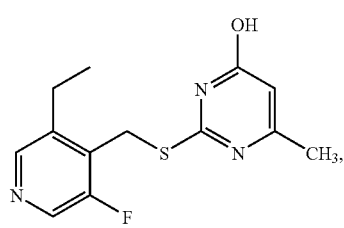
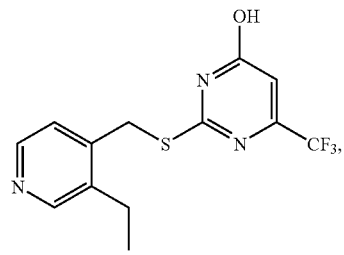
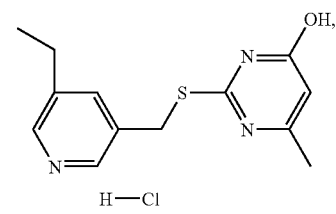
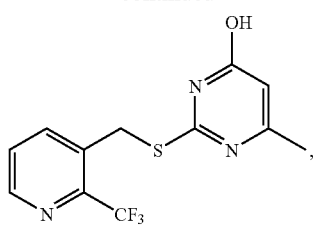
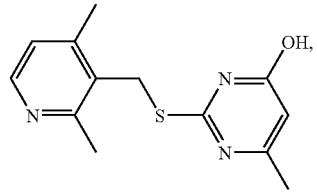
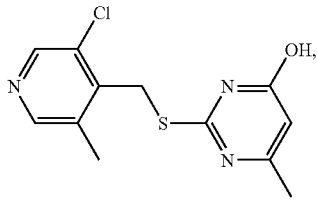
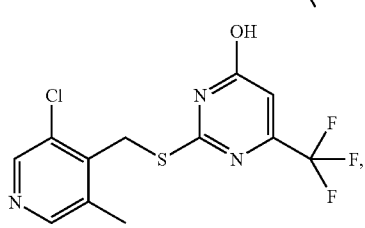
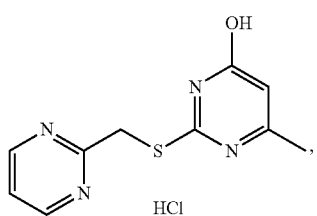
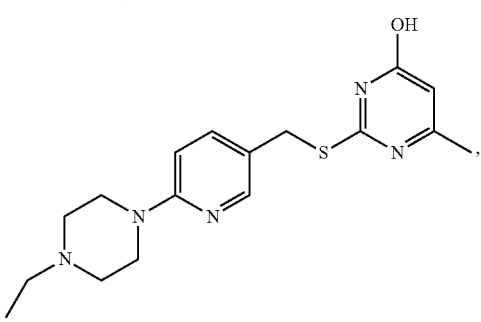
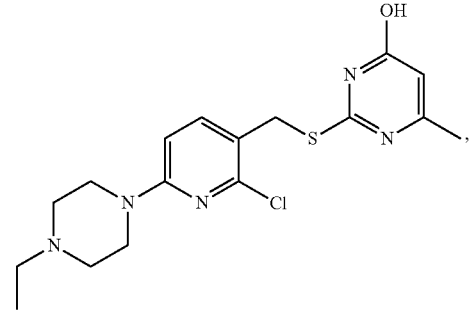

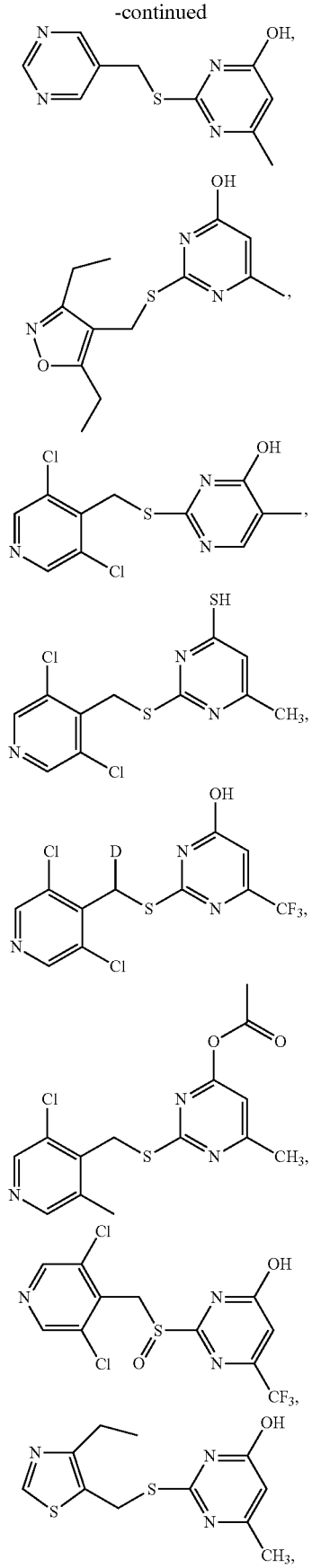
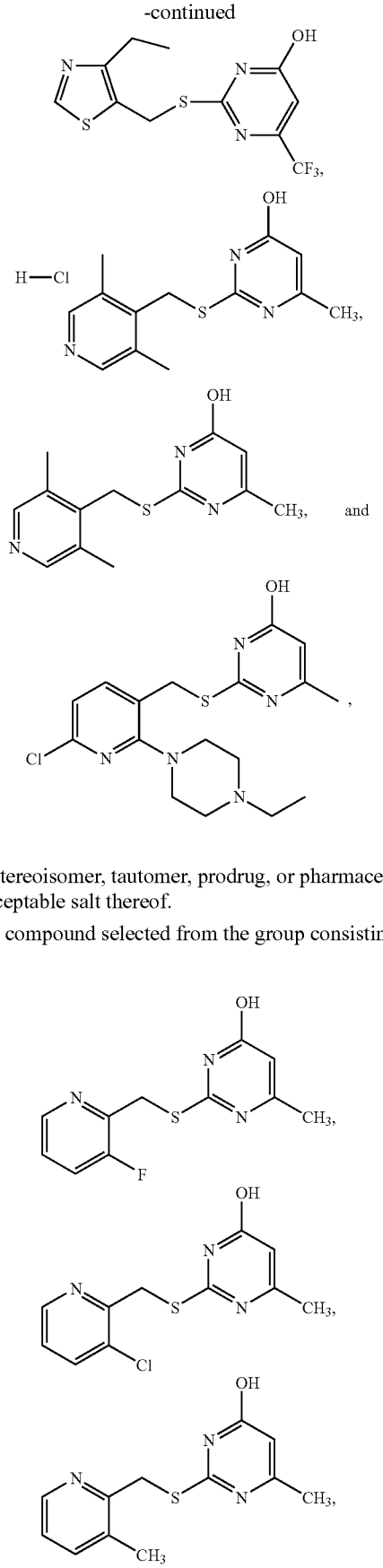
or a stereoisomer, tautomer, prodrug, or pharmaceutically acceptable salt thereof.
12. A compound selected from the group consisting of:

-continued
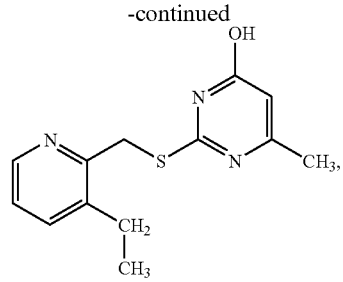
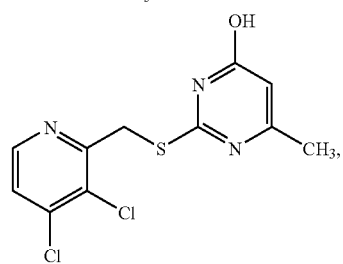
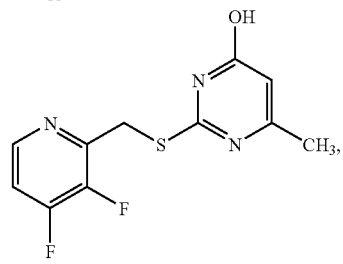
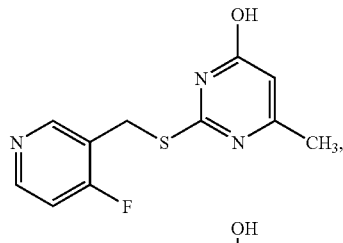
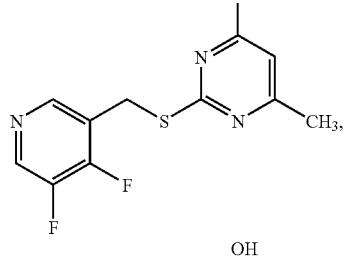
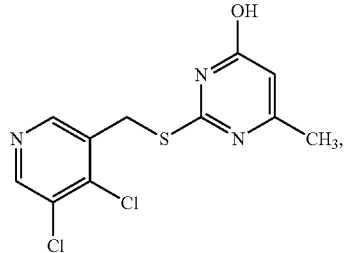
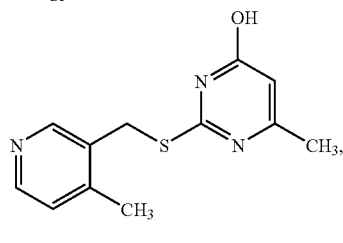
-continued
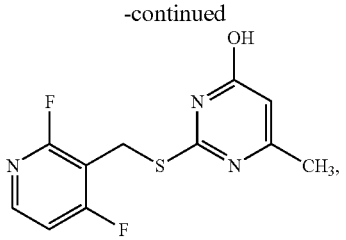
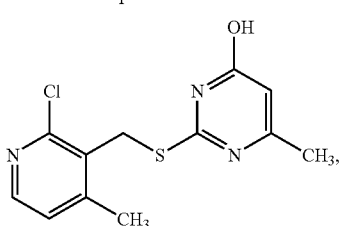
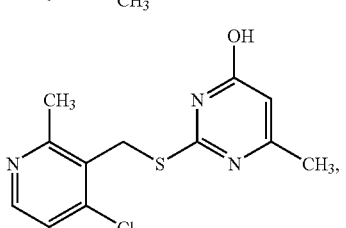
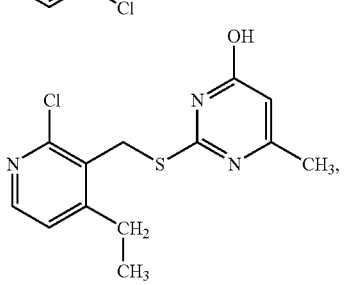
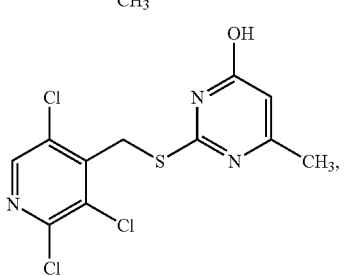
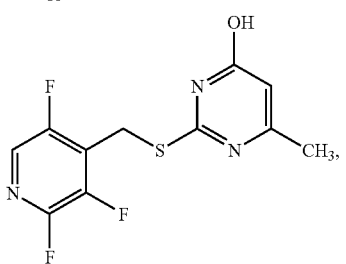
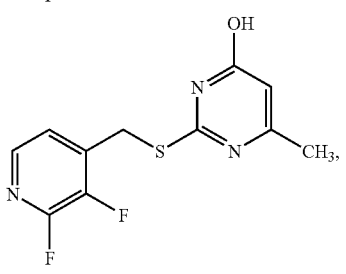

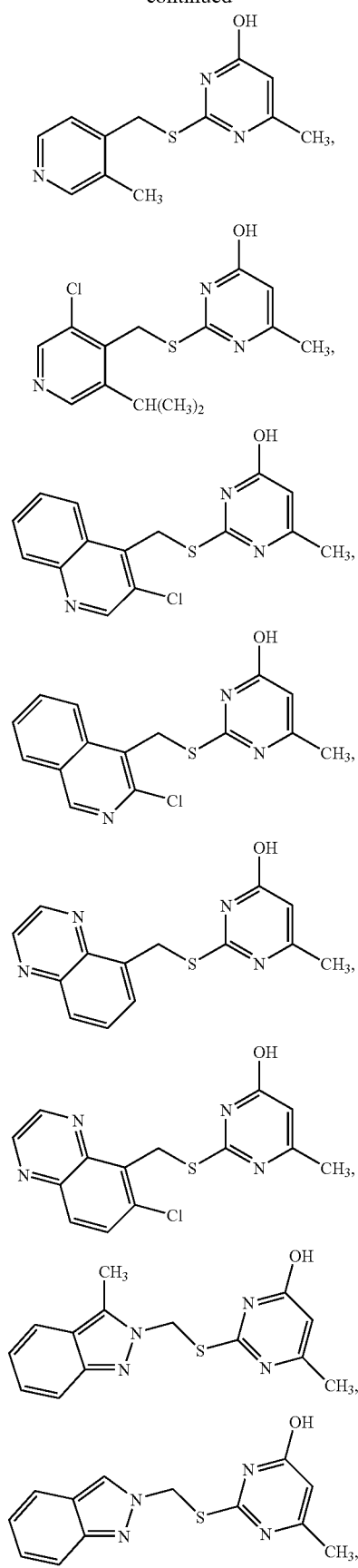
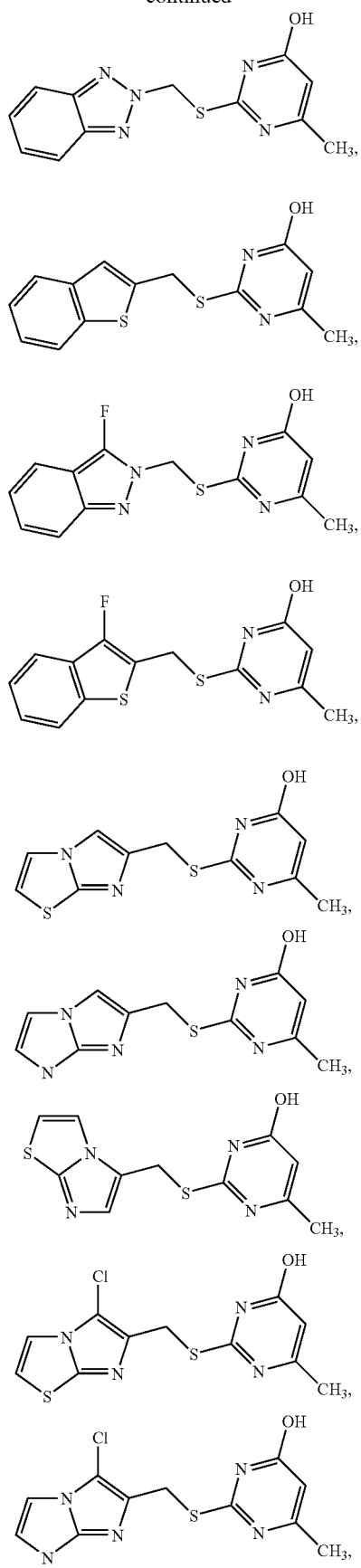

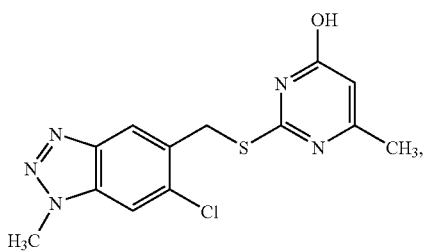
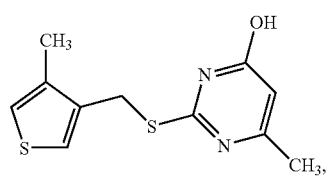
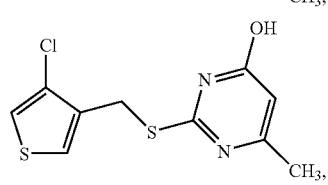
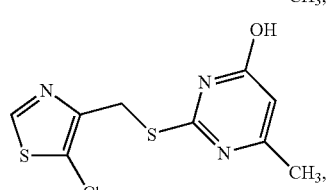
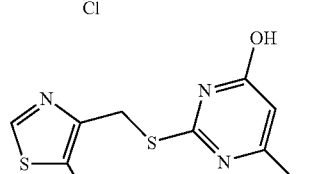
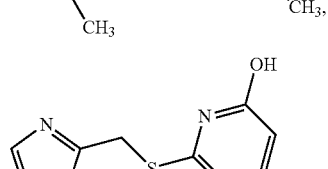
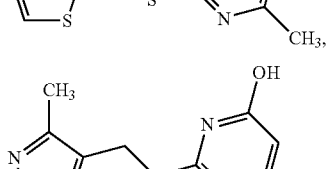
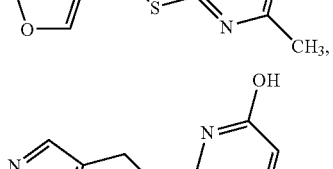
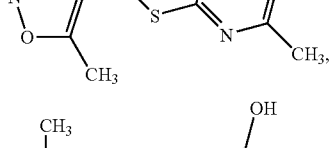
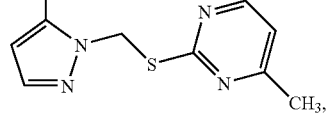
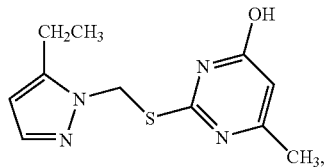
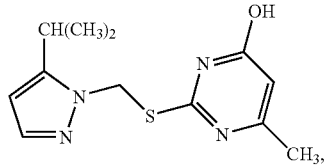
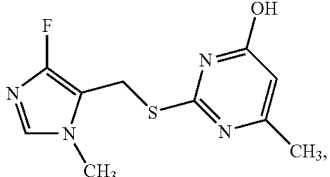
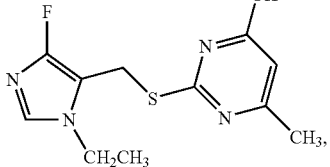
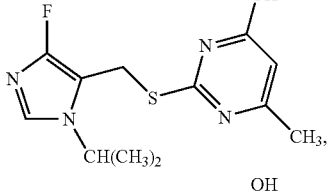
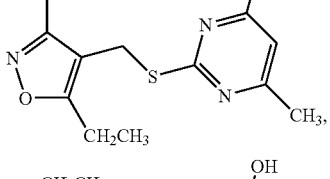
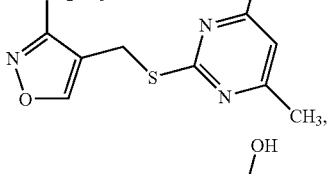
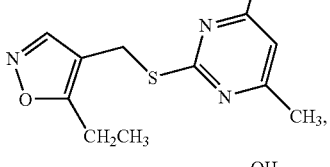
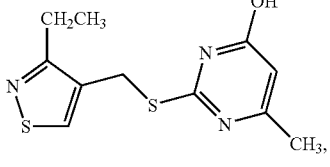

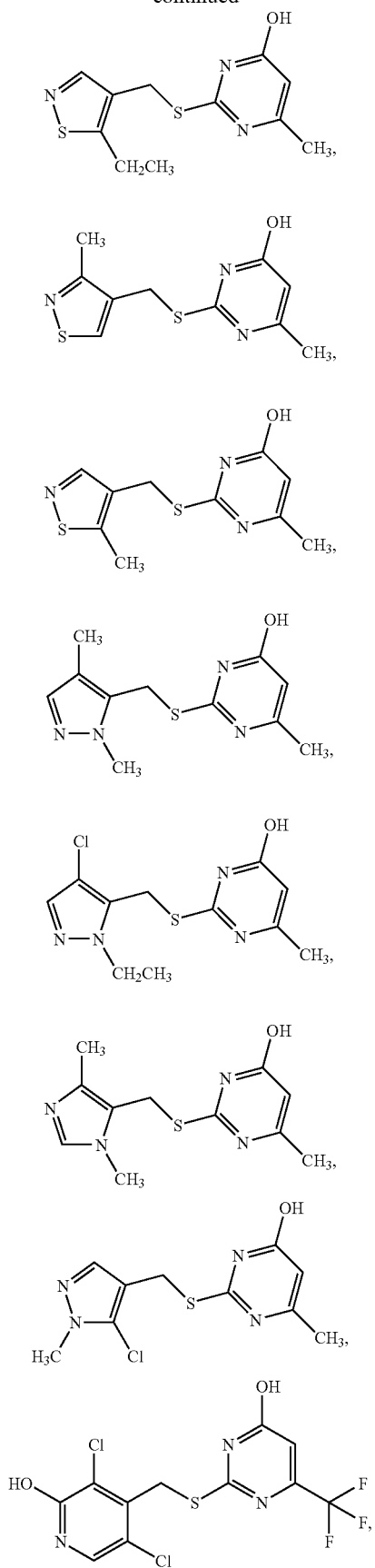
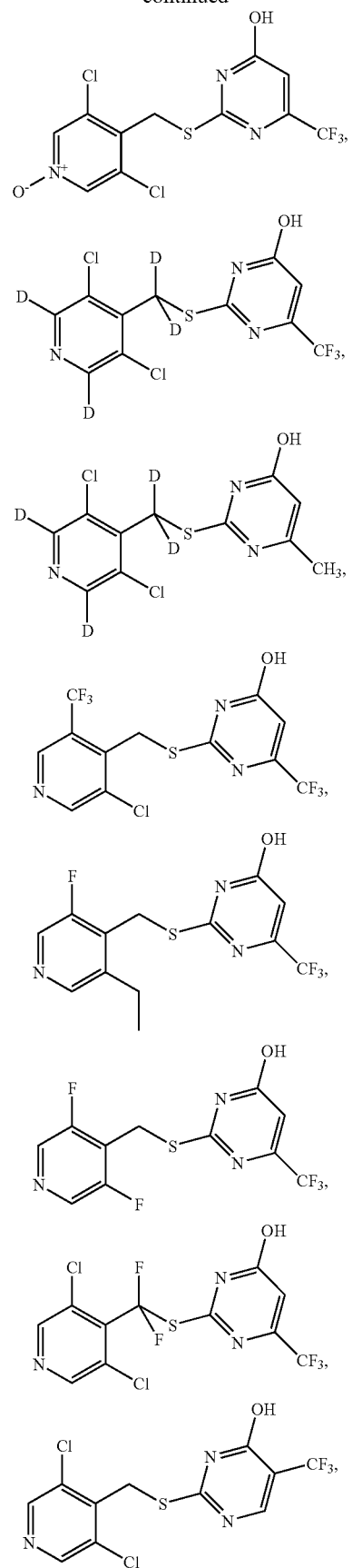

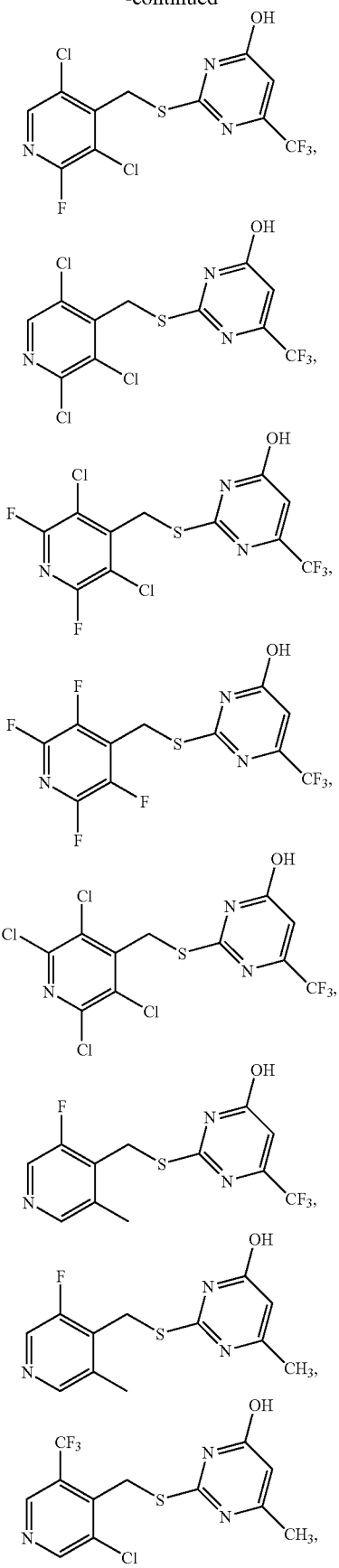
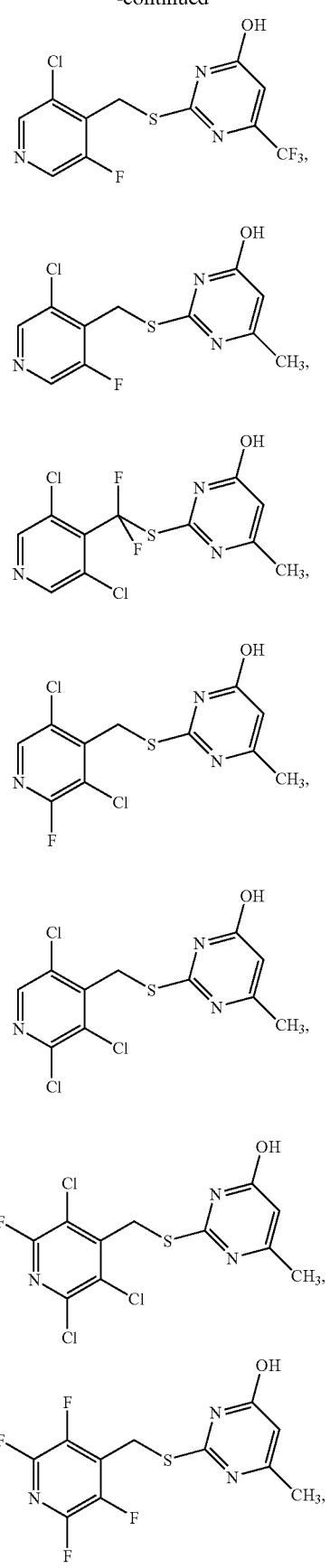

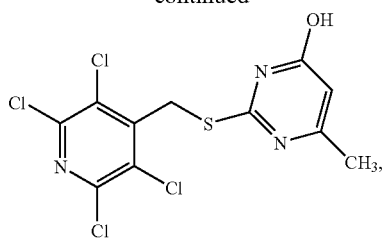
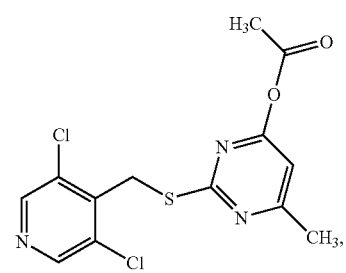
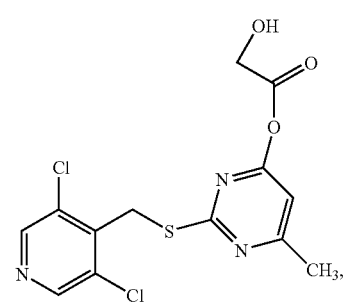
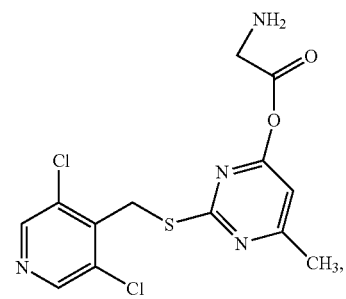
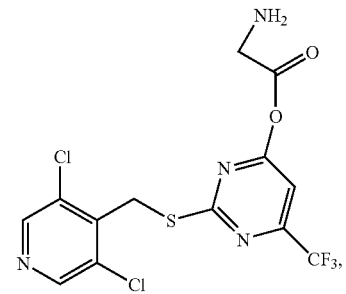
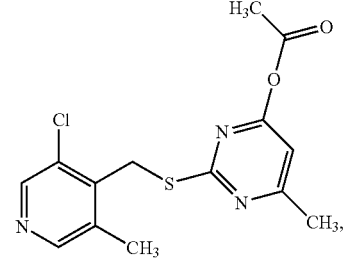
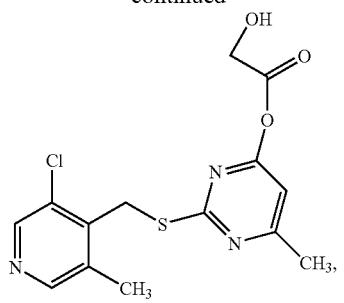
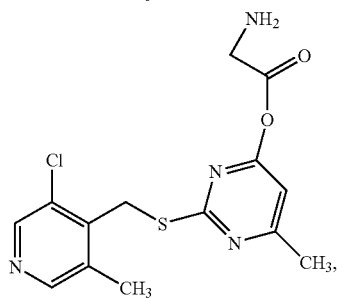
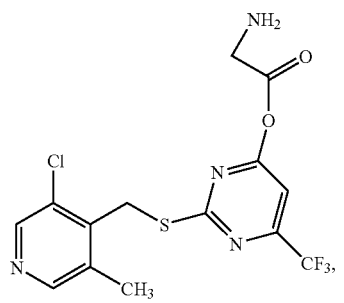
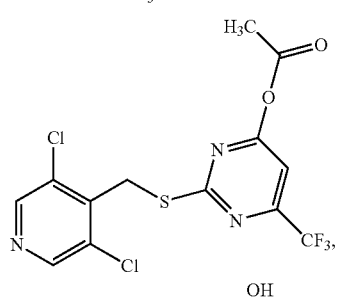
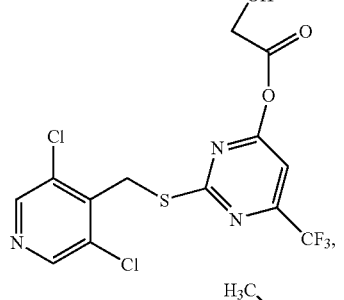
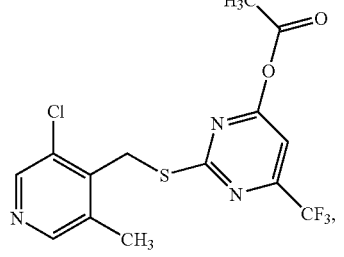

311
-continued
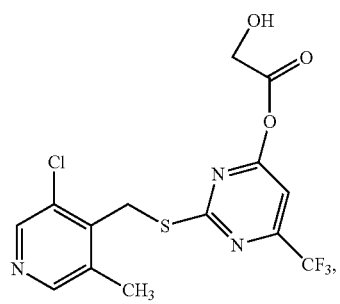
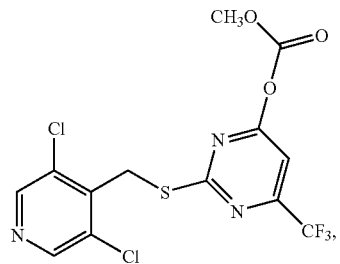
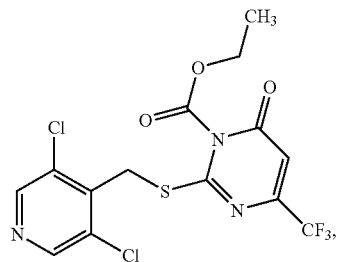
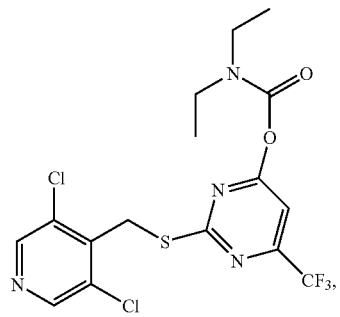
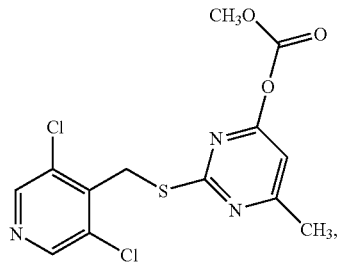
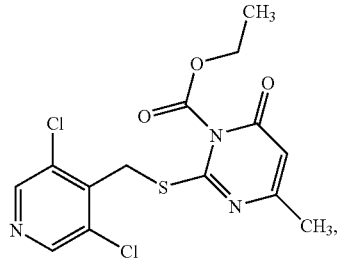
312
-continued
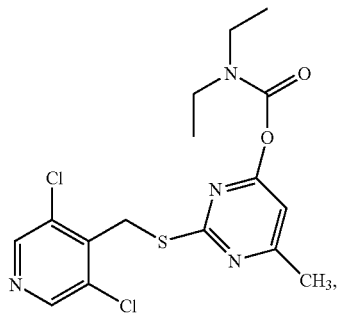
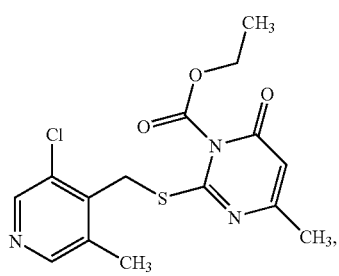
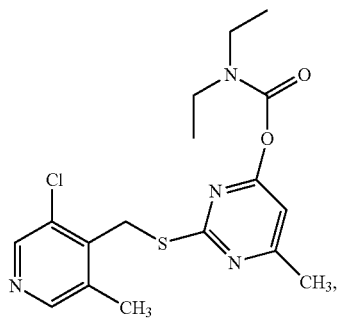
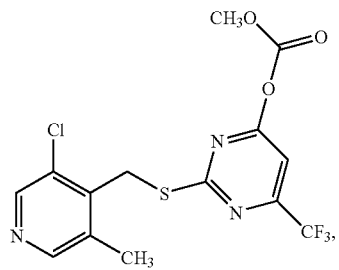
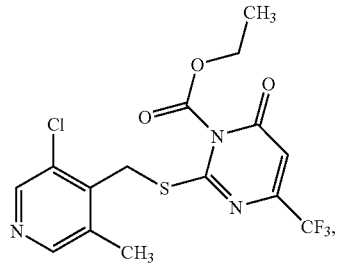

313
-continued
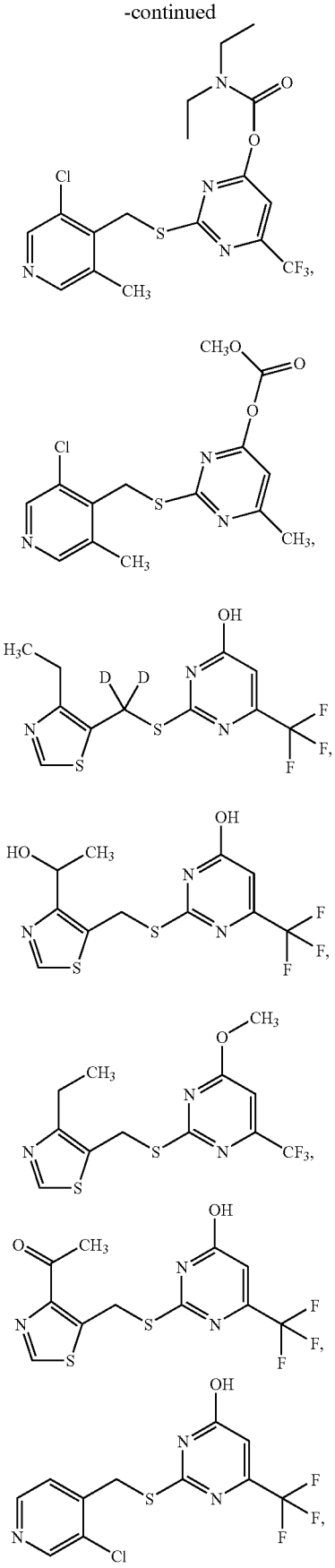
314
-continued
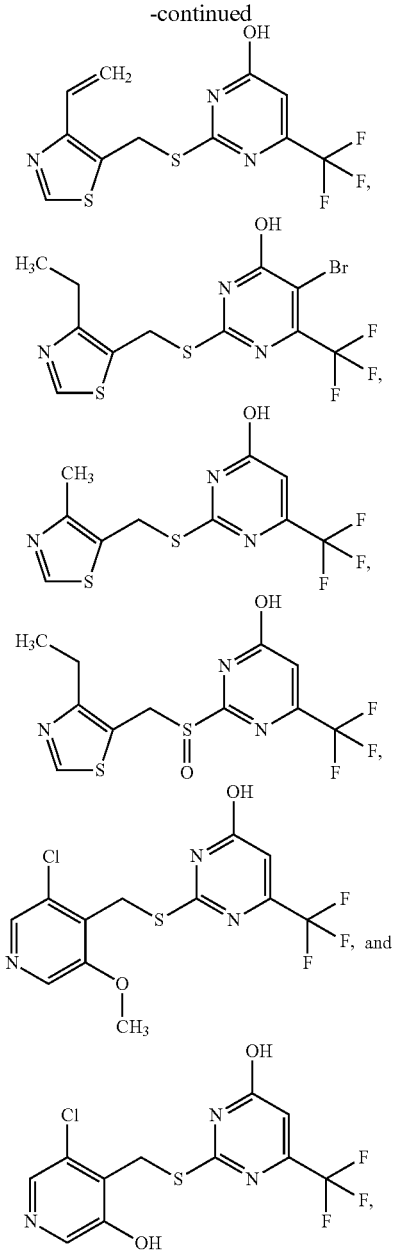
or a stereoisomer, tautomer, prodrug, or pharmaceutically acceptable salt thereof.
13. A composition comprising a pharmaceutically acceptable carrier or vehicle and an effective amount of a compound having the following structure:
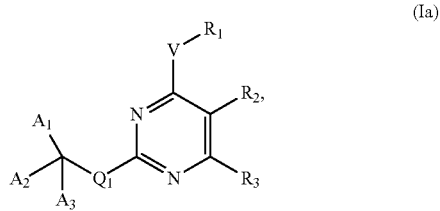
(Ia)

and its tautomer

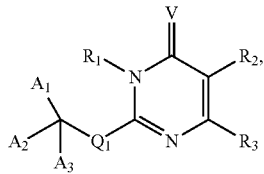
(Ib)

including other tautomers, stereoisomers, E/Z stereoisomers, prodrugs, and pharmaceutically acceptable salts thereof, wherein:

$Q_1$ is —S—, —SO—, —$SO_2$—, —$CH_2CH_2$—, —CH=CH—, —$OCH_2$—, —$SCH_2$—, —$SOCH_2$—, or —$SO_2CH_2$—;

V is O, S, NH, or NZ, or N-terminal linked amino acid, or halogen when $R_1$ is absent;

$R_1$ is absent, —H, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, —$(CH_2)_n$OZ, —C(O)Z, —C(O)OZ, —C(O)NHZ, —C(O)N(Z)$_2$, —$(CR_{1A}R_{1B})_{r2}$OPO$(OZ)_2$, —$(CR_{2A}R_{2B})_{r3}$PO$(OZ)_2$, or C-terminal linked amino acid;

each $R_{1A}$, $R_{1B}$, $R_{2A}$, and $R_{2B}$ is, independently, H or $C_{1-5}$ alkyl;

each Z is, independently, —H, —$C_1$-$C_8$ alkyl, —$C_4$-$C_{12}$ alkcycloalkyl, —$C_3$-$C_9$ alkheterocyclyl, wherein the heterocyclyl is 3 to 9 membered, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —$C_2$-$C_8$ alkenyl, or —$C_2$-$C_8$ alkynyl, or two Z, together with the atom(s) to which each is attached, loin to form a 3- to 7-membered aromatic or non aromatic heterocycle;

each n is 1 or 2;

each r2 is an integer between 1-3;

each r3 is an integer between 0-2;

$R_2$ is —H, -D, —OH, -halogen, —CN, —$NO_2$, —SH, —$CF_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$R_3$ is —OH, -halogen, —CN, —$NO_2$, —SH, —$CF_3$, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, or —PO(OZ)$_2$;

$A_1$ and $A_2$ are each, independently, —H, -D, -halogen, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, or —$C_7$-$C_{14}$ arylalkyl;

$A_3$ is an aromatic heterocyclic ring selected from the group consisting of:

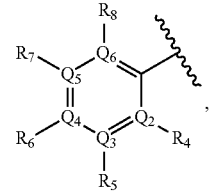
(Fragment A-1)

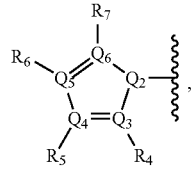
(Fragment A-2)

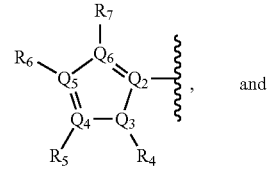
(Fragment A-3)

and

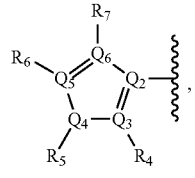
(Fragment A-4)

$Q_2$, $Q_5$, and $Q_6$ are each, independently, N, N$^+$—O$^-$, or C;

$Q_3$ and $Q_4$ are each, independently, N, N$^+$—O$^-$, C, O, or S, wherein only one of $Q_3$ and $Q_4$ can be O or S;

wherein $Q_2$, $Q_3$, $Q_4$, $Q_5$, and $Q_6$ simultaneously are C only if $R_4$ and $R_5$, $R_5$ and $R_6$, $R_6$ and $R_7$, or $R_7$ and $R_8$, together with the atoms to which each is attached, join to form a 5- to 6-membered aromatic or non aromatic heterocyclyl; and $R_4$, $R_5$, $R_6$, $R_7$, and $R_8$ are each, independently, absent, —H, -D, —OH, —O$^-$, -halogen, —CN, —$NO_2$, —SH, —$C_1$-$C_8$ alkyl, —$C_2$-$C_8$ alkenyl, —$C_2$-$C_8$ alkynyl, —$C_3$-$C_{12}$ cycloalkyl, —$C_6$-$C_{12}$ aryl, —$C_7$-$C_{14}$ arylalkyl, 3 to 9-membered aromatic or non aromatic heterocyclyl, —OZ, —N(Z)$_2$, —C(NH)N(Z)$_2$, —O(CH$_2$)$_n$OZ, —C(O)Z, —OC(O)Z, —OC(O)OZ, —OC(O)N(Z)$_2$, —C(O)N(Z)$_2$, —C(O)OZ, —SZ, —SOZ, —S(O)$_2$Z, —NHC(O)Z, —NHS(O)$_2$Z, —NHC(NH)N(Z)$_2$, —NZC(NH)N(Z)$_2$, —NHC(NCN)N(Z)$_2$, —NZC(NCN)N(Z)$_2$, —PO(OZ)$_2$, or $R_4$ and $R_5$, or $R_5$ and $R_6$, or $R_6$ and $R_7$, or $R_7$ and $R_8$, together with the atoms to which each is attached, join to form a 5- to 6-membered aromatic or non aromatic carbocycle or heterocycle provided that the resulting ring system is not substituted or unsubstituted benzimidazole, unsubstituted benzothiazole, unsubstituted imidazo[1,2-a]pyridine, 5- or 6-chloro-imidazo[1,2-a]pyridine, indole when $R_2$ is C(O)OCH$_2$CH$_3$ unsubstituted quinoline, 8-substituted quinoline, unsubstituted quinoxaline, 2- or 4-chloroquinoline, or 4-hydroxy-1,3-quinazoline, wherein when $A_3$ is unsubstituted pyridine-2-yl, and $A_1$ and $A_2$ are each —H, $R_3$ is not —OH, —$CF_3$, —$C_1$-$C_3$ alkyl, phenyl, difluorobenzyl, —NHC(O)furan, —NHC(O)CH$_3$, or —NHC(O)CH$_2$CH$_3$;

wherein when $A_3$ is unsubstituted pyridine-4-yl, and $A_1$ and $A_2$ are each —H, $R_3$ is not —OH, —CH$_3$, —CH$_2$CH$_2$CH$_3$, or difluorobenzyl;

wherein when $A_3$ is unsubstituted, 6-chloro, or 2,6-dichloro pyridine-3-yl, and $A_1$ and $A_2$ are each —H, $R_3$ is not —OH, —CF$_3$, —C$_1$-C$_3$ alkyl, phenyl, —C(O)OCH$_2$CH$_3$, or —NHC(O)CH$_3$;

wherein when $A_3$ is substituted or unsubstituted pyrazol-1-yl, $R_3$ is not —OH; and wherein $A_3$ is not 4-NO$_2$-imidazol-2-yl.

\* \* \* \* \*